United States Patent
Calderwood et al.

(10) Patent No.: US 9,029,409 B2
(45) Date of Patent: May 12, 2015

(54) ISOXAZOLINES AS THERAPEUTIC AGENTS

(75) Inventors: David J. Calderwood, Framingham, MA (US); Eric C. Breinlinger, Charlton, MA (US); Steven L. Swann, San Diego, CA (US); Venkata Srikanth Chitty, Hyderabad (IN); Subramanya Seetharama Shastry Hosahalli, Karnataka (IN); Subhendu Mukherjee, W. Bengal (IN); Siva Sanjeeva Rao Thunuguntla, Andhra Pradesh (IN)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/460,158

(22) Filed: Apr. 30, 2012

(65) Prior Publication Data
US 2013/0023526 A1   Jan. 24, 2013

(30) Foreign Application Priority Data

Apr. 30, 2011 (IN) .......................... 1272/DEL/2011

(51) Int. Cl.
| | | |
|---|---|---|
| A01N 43/80 | (2006.01) | |
| A61K 31/42 | (2006.01) | |
| C07D 261/02 | (2006.01) | |
| C07D 413/14 | (2006.01) | |
| C07D 413/04 | (2006.01) | |
| C07D 413/12 | (2006.01) | |

(52) U.S. Cl.
CPC ............ C07D 413/14 (2013.01); C07D 413/04 (2013.01); C07D 413/12 (2013.01)

(58) Field of Classification Search
None
See application file for complete search history.

(56) References Cited

U.S. PATENT DOCUMENTS

| | | | |
|---|---|---|---|
| 7,125,870 B2 * | 10/2006 | Xue et al. .................... | 514/235.2 |
| 7,166,609 B2 * | 1/2007 | Klingler et al. ............... | 514/256 |
| 7,662,972 B2 | 2/2010 | Mita et al. | |
| 8,093,272 B2 | 1/2012 | Sundermann et al. | |
| 8,288,393 B2 | 10/2012 | Iwata et al. | |
| 2004/0067985 A1 | 4/2004 | Haviv et al. | |
| 2005/0004111 A1 * | 1/2005 | Klingler et al. ............. | 514/227.5 |
| 2006/0173021 A1 | 8/2006 | Sun et al. | |
| 2007/0037974 A1 | 2/2007 | Brotherton-Pleiss et al. | |
| 2007/0066617 A1 | 3/2007 | Mita et al. | |
| 2007/0129369 A1 | 6/2007 | Sundermann et al. | |
| 2007/0155739 A1 * | 7/2007 | Sucholeiki et al. ........ | 514/230.5 |
| 2007/0259874 A1 | 11/2007 | Palle et al. | |
| 2009/0143410 A1 * | 6/2009 | Patel ............ | 514/256 |
| 2009/0312330 A1 | 12/2009 | Mita et al. | |
| 2010/0279999 A1 | 11/2010 | Renold et al. | |
| 2011/0124858 A1 | 5/2011 | Iwata et al. | |
| 2012/0015980 A1 | 1/2012 | Fischer et al. | |

FOREIGN PATENT DOCUMENTS

| | | |
|---|---|---|
| EC | SP003448 A | 5/2000 |
| EP | 2186804 A1 | 5/2010 |
| GB | 2481118 A | 12/2011 |
| WO | 00/63204 A2 | 10/2000 |
| WO | WO-2004014370 A2 | 2/2004 |
| WO | 2004041788 A1 | 5/2004 |
| WO | WO-2004043349 A2 | 5/2004 |
| WO | 2005085216 A1 | 9/2005 |
| WO | WO-2005110971 A1 | 11/2005 |
| WO | WO-2007069773 A1 | 6/2007 |
| WO | WO-2007070606 A2 | 6/2007 |
| WO | 2007079162 A1 | 7/2007 |
| WO | 2007123855 A2 | 11/2007 |
| WO | WO-2008154528 A2 | 12/2008 |
| WO | 2009016498 A1 | 2/2009 |
| WO | WO-2009022746 A1 | 2/2009 |
| WO | 2009036328 A2 | 3/2009 |
| WO | 2009058299 A1 | 5/2009 |
| WO | WO-2009080250 A2 | 7/2009 |
| WO | WO-2009112275 A1 | 9/2009 |
| WO | 2010010187 A1 | 1/2010 |
| WO | WO-2010020522 A1 | 2/2010 |
| WO | 2010045190 A1 | 4/2010 |
| WO | 2010045191 A2 | 4/2010 |
| WO | WO-2010051188 A1 | 5/2010 |
| WO | WO-2010070068 A2 | 6/2010 |
| WO | WO-2010084067 A2 | 7/2010 |

(Continued)

OTHER PUBLICATIONS

Milinkevich et al., "Synthesis of 5-(Thiazol-5-yl)-4,5-dihydroisoxazoles from 3-Chloropentane-2,4-dione," *J. Combinatorial Chem.*, 10(4):521-525 (2008).

(Continued)

*Primary Examiner* — Jeffrey S. Lundgren
*Assistant Examiner* — Stephanie Springer
(74) *Attorney, Agent, or Firm* — McCarter & English, LLP; Elizabeth A. Hanley; Yu Lu

(57) ABSTRACT

The present invention provides compound of Formula (I)

Formula (I)

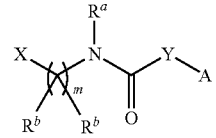

biologically active metabolites, pro-drugs, isomers, stereoisomers, solvates, hydrates and pharmaceutically acceptable salts thereof wherein the variables are defined herein. The compounds of the invention are useful for treating immunological conditions.

17 Claims, No Drawings

(56) References Cited

FOREIGN PATENT DOCUMENTS

| WO | WO-2010112545 A1 | 10/2010 |
| WO | WO-2010116282 A1 | 10/2010 |
| WO | WO-2010142801 A1 | 12/2010 |
| WO | WO-2011067272 A1 | 6/2011 |
| WO | 2011/157733 A2 | 12/2011 |
| WO | 2011157654 A1 | 12/2011 |
| WO | 2012/107533 A1 | 8/2012 |

OTHER PUBLICATIONS

CAS Registry No. 1014106-64-9; STN entry date : Apr. 13, 2008 N-cyclohexyl-5-[4,5-dihydro-5-methyl-3-(3-pyridinyl)-5-isoxazolyl]-4-methyl-2-thiazolecarboxamide.

CAS Registry No. 958986-08-8; STN entry date: Dec. 20, 2007 N-cyclohexyl-5-[4-dihydro-5-methyl-3-(nitrophenyl)-5-isoxazolyl]-4-methyl-2-thiazolecarboxamide.

* cited by examiner

ISOXAZOLINES AS THERAPEUTIC AGENTS

CROSS REFERENCE TO PRIOR APPLICATION

This application claims priority to Indian Provisional Application Serial No. 1272/DEL/2011 filed on Apr. 30, 2011, the contents of which are incorporated herein.

BACKGROUND OF THE INVENTION

Matrix metalloproteinases (MMPs) are a family of structurally related zinc-containing enzymes that have been reported to mediate the breakdown of connective tissue in normal physiological processes such as embryonic development, reproduction and tissue remodeling as well as pathological conditions such as rheumatoid arthritis (RA), osteoarthritis (OA), osteoporosis, atherosclerosis and tumor metastasis. MMP family comprises of more than 20 members in human including collagenases (MMP-1, MMP-8, MMP-13), gelatinases (MMP-2, MMP-9), stromelysins (MMP-3, MMP-10, MMP-11), matrilysins (MMP-7, MMP-26), membrane-type (MMP-14, MMP-15, MMP-16, MMP-17, MMP-24, MMP-25), as well as metalloelastases (MMP-12, MMP-19, MMP-20, MMP-22, MMP-23) (*Nat Rev Drug Discov.*, 2007, 6, 480-98).

The most significant members of the MMP family with respect to OA pathology are the collagenases (MMP-1, -8, and -13) which are responsible for type II collagen breakdown (*Nat Rev Drug Discov* 2007, 6, 480-98; *Semin Cell Dev Biol*, 2008, 19, 61-8). In recent years, increasing evidence suggests that MMP-13 is the main collagenase responsible for degradation of type II collagen in OA. MMP-13 is not found in normal adult tissues but is specifically expressed in the articular cartilage of OA patients (*J Rheumato.*, 11996, 23, 590-5; *J Clin Invest* 1996, 97, 2011-9; *J Clin Inves.*, t1996, 97, 761-8; *J Clin Invest.*, 1997, 99, 1534-45). Analysis of human OA cartilage shows a correlation between presence of MMP-13 and MMP-specific collagen cleavage products with disease severity (*Arthritis Rheum.*, 1983, 26, 63-8; *J Rheumatol.*, 2005, 32, 876-86). In vitro data demonstrate that MMP-13 selective inhibitors prevent cytokine-induced collagen loss in human and bovine cartilage ex-plant cultures (*Arthritis Rheum*. 2009, 60, 2008-18; *J Biol Chem* 2007 282, 27781-91).

Preclinical models of OA have elevated MMP-13 expression and MMP-13-induced collagen cleavage products in cartilage, synovial fluid, and urine which have been shown to correlate with disease progression (*Osteoarthritis Cartilage* 2005 13, 139-45; *Arthritis Rheum.*, 1998 41, 877-90). Transgenic mice expressing active human MMP-13 through a cartilage-specific promoter demonstrate pathological changes in articular cartilage of the mouse joints similar to those observed in human OA (*J Clin Invest.*, 2001 107, 35-44; *Arthritis Rheum.*, 2003 48, 1077). In contrast, MMP-13 deficient mice show significantly reduced cartilage degradation as compared to the wild-type following destabilization of the medial meniscus (*Arthritis Rheum.*, 2009 60, 3723-33). Lastly, an orally active MMP-13 selective inhibitor was chondroprotective in rat medial meniscus tear (MMT), rabbit and dog anterior cruciate ligament/medial menisectomy models of OA (*Arthritis Rheum.*, 2009 60, 2008-18; *J Biol. Chem.*, 2007 282, 27781-91, *Arthritis Rheum.*, 2010 62, 3006-15). Taken together, these data indicate that MMP-13 plays an important role in development and progression of the OA in preclinical models and that selective inhibition of MMP-13 can halt breakdown of cartilage thereby preventing joint destruction.

The catalytic zinc domain in MMPs has been the primary focus of inhibitor design. The modification of substrates by introducing zinc chelating groups has generated potent inhibitors such as peptide hydroxamates and thiol-containing peptides (*Drug Discov Today*, 2007 12, 640-6). Over the last 10-15 years, many non-selective MMP inhibitors have advanced to Phase II clinical trials in treatment of diseases such as cancer, rheumatoid arthritis and OA. However, none of these inhibitors have advanced to late stage trials due to a number of significant challenges: A) Highly variable pharmacokinetics and often poor oral bioavailability. B) All of these non-selective inhibitors target the zinc-binding site which is common to all matrix metalloproteinases. The clinical utility of non-selective MMP inhibitors has been restricted by dose-dependent musculoskeletal effects in humans [joint stiffness, inflammation, pain in arms and shoulders termed "musculoskeletal syndrome" (MSS)] (*Arthritis Res Ther.*, 2007 9, R109). No specific MMP has been implicated in MSS and it is believed that non-selective inhibition of multiple MMPs is the primary cause of this toxicity. Although no specific MMP has been implicated in MSS, there is substantial evidence that MMP-13 does not play a major role in development of MSS. Clinical data from humans with mis-sense mutation of MMP13 are characterized by defective growth and modeling of vertebrae and long bones and do not exhibit signs of MSS (*J Clin Invest.*, 2005 115, 2832-42). Preclinical data from mice deficient of MMP-13 also demonstrate growth defects but no histological signs of fibrodysplasia (MSS) (*Development*, 2004 131, 5883-95). Finally, a 2-week rat model of fibrodysplasia (MSS) study has shown that animals dosed with a highly selective MMP-13 inhibitor do not develop histological signs of fibrodysplasia as compared to animals dosed with a pan-MMP inhibitor (*Arthritis Rheum.*, 2009 60, 2008-18); (*J Biol Chem* 2007 282, 27781-91).

Hence, there continues to be a need to find new selective MMP-13 inhibitors with an acceptable therapeutic window making them clinically attractive in the treatment of diseases.

SUMMARY OF THE INVENTION

In one embodiment the invention provides a compound of Formula (I)

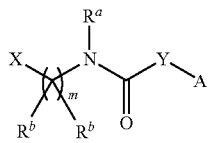

Formula (I)

biologically active metabolites, pro-drugs, isomers, stereoisomers, solvates, hydrates and pharmaceutically acceptable salts thereof wherein A is

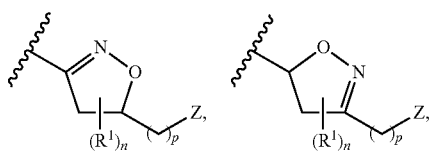

-continued

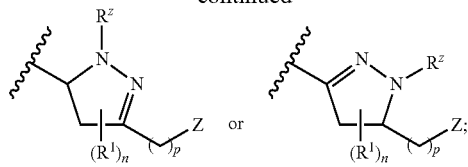

X is an optionally substituted ring system which is aromatic, partly aromatic or non-aromatic having one or more fused ring systems;

Y is optionally substituted heteroaryl;

Z is —C(O)NR$^c$R$^d$, —C(O)OCH$_3$, —NR$^c$R$^d$, optionally substituted (C$_1$-C$_6$)alkyl, optionally substituted (C$_3$-C$_6$)cycloalkyl, optionally substituted aryl, optionally substituted heteroaryl or optionally substituted heterocyclyl;

R$^a$ is independently H, optionally substituted (C$_1$-C$_3$)alkyl or optionally substituted (C$_3$-C$_6$)cycloalkyl;

R$^b$ is independently H, CF$_3$, optionally substituted (C$_1$-C$_3$) alkyl or optionally substituted (C$_3$-C$_6$)cycloalkyl;

R$^c$ is H and R$^d$ is H or optionally substituted (C$_1$-C$_6$)alkyl; or

R$^c$ and R$^d$, together with the nitrogen atom to which they are attached, form a 5- or 6-membered saturated or unsaturated, aromatic or nonaromatic heterocyclic ring system;

R$^1$ is independently H, OR$^a$, Br, Cl, F, optionally substituted (C$_1$-C$_3$)alkyl or optionally substituted (C$_3$-C$_6$)cycloalkyl;

R$^z$ is H, optionally substituted (C$_1$-C$_3$)alkyl or optionally substituted (C$_3$-C$_6$)cycloalkyl;

m is 0, 1 or 2;

n is 0, 1, 2 or 3; and p is 0, 1, 2 or 3;

provided that when Y is pyridinyl it is not substituted by optionally substituted phenyl.

In another embodiment the invention provides a compound according to the previous embodiment wherein X is optionally substituted naphthyl, optionally substituted phenyl, optionally substituted azaindolyl, optionally substituted benzo[1,4]oxazin-3-onyl, optionally substituted benzo[b]thienyl, optionally substituted benzimidazolyl, optionally substituted benzo[1,3]dioxolyl, optionally substituted benzofuranyl, optionally substituted benzoxazolyl, optionally substituted benzothiazolyl, optionally substituted benzothiadiazolyl, optionally substituted benzoxadiazolyl, optionally substituted 2,3-dihydrobenzo[1,4]dioxinyl, optionally substituted 2,3-dihydrobenzo furanyl, optionally substituted furanyl, optionally substituted imidazolyl, optionally substituted imidazopyridinyl, optionally substituted indolyl, optionally substituted indazolyl, optionally substituted isoxazolyl, optionally substituted isothiazolyl, optionally substituted oxadiazolyl, optionally substituted oxazolyl, optionally substituted purinyl, optionally substituted pyranyl, optionally substituted pyrazinonyl, optionally substituted pyrazinyl, optionally substituted pyrazolyl, optionally substituted pyridazinyl, optionally substituted pyridazinonyl, optionally substituted pyridinyl, optionally substituted pyridonyl, optionally substituted pyrimidinonyl, optionally substituted pyrimidinyl, optionally substituted pyrrolyl, optionally substituted pyrrolo[2,3-d]pyrimidinyl, optionally substituted pyrazolo[3,4-d]pyrimidinyl, optionally substituted 1H-quinoxalin-2-only, optionally substituted quinolinyl, optionally substituted quinazolinyl, optionally substituted triazolyl, optionally substituted thiazolyl, optionally substituted tetrazolyl, optionally substituted thiadiazolyl, or optionally substituted thienyl.

In another embodiment the invention provides a compound according to any of the foregoing embodiments wherein Y is optionally substituted furanyl, optionally substituted imidazolyl, optionally substituted isoxazolyl, optionally substituted isothiazolyl, optionally substituted oxazolyl, optionally substituted pyrazolyl, optionally substituted pyridazinyl, optionally substituted pyridazinonyl, optionally substituted pyridinyl, optionally substituted pyrimidinyl, optionally substituted pyrrolyl, optionally substituted thienyl, optionally substituted triazinyl, or optionally substituted 1,2,4-triazolyl.

In another embodiment the invention provides a compound according to any of the foregoing embodiments wherein Z is —C(O)NH$_2$, —C(O)-optionally substituted morpholinyl, —C(O)-optionally substituted pyrrolidinyl, —C(O)—N(H)CH$_2$CH$_2$OH, optionally substituted (C$_3$-C$_6$)cycloalkyl, optionally substituted azaindolyl, optionally substituted azepinyl, optionally substituted azetidinyl, optionally substituted benzo[b]thienyl, optionally substituted benzimidazolyl, optionally substituted benzofuranyl, optionally substituted benzoxazolyl, optionally substituted benzothiazolyl, optionally substituted benzothiadiazolyl, optionally substituted benzoxadiazolyl, optionally substituted 1,4-dioxanyl, optionally substituted furanyl, optionally substituted imidazolyl, optionally substituted imidazopyridinyl, optionally substituted indolinyl, optionally substituted indolyl, optionally substituted indazolyl, optionally substituted isoindolinyl, optionally substituted isoxazolyl, optionally substituted isothiazolyl, optionally substituted morpholinyl, optionally substituted naphthyl, optionally substituted oxadiazolyl, optionally substituted phenyl, optionally substituted oxazolyl, optionally substituted piperazinyl, optionally substituted piperidinyl, optionally substituted purinyl, optionally substituted pyranyl, optionally substituted pyrazinyl, optionally substituted pyrazolyl, optionally substituted pyrazolo[3,4-b]pyridinyl, optionally substituted N-methylpyrazonyl, optionally substituted pyridazinyl, optionally substituted pyrazinonyl, optionally substituted pyridazinonyl, optionally substituted pyridinyl, optionally substituted pyridonyl, optionally substituted pyrimidinonyl, optionally substituted N-methylpyridazonyl, optionally substituted N—(C$_1$-C$_6$) alkylpyridonyl, optionally substituted pyrimidinyl, optionally substituted N—(C$_1$-C$_6$)alkylpyrimidonyl, optionally substituted pyrrolidinyl, optionally substituted pyrrolyl, optionally substituted pyrrolo[2,3-d]pyrimidinyl, optionally substituted pyrazolo[3,4-d]pyrimidinyl, optionally substituted quinolinyl, optionally substituted quinazolinyl, optionally substituted quinucludinyl, optionally substituted tetrahydrofuranyl, optionally substituted tetrahydroindolyl, optionally substituted tetrahydropyranyl, optionally substituted thiomorpholinyl, optionally substituted triazolyl, optionally substituted thiazolyl, optionally substituted tetrazolyl, optionally substituted thiadiazolyl, or optionally substituted thienyl, optionally substituted thiomorpholinyl, or optionally substituted tropanyl.

In another embodiment the invention provides a compound according to any of the foregoing embodiments wherein X is optionally substituted naphthyl, optionally substituted phenyl, optionally substituted azaindolyl, optionally substituted benzo[1,4]oxazin-3-onyl, optionally substituted benzo[b]thienyl, optionally substituted benzimidazolyl, optionally substituted benzo[1,3]dioxolyl, optionally substituted benzofuranyl, optionally substituted benzoxazolyl, optionally substituted benzothiazolyl, optionally substituted benzothiadiazolyl, optionally substituted benzoxadiazolyl, optionally substituted 2,3-dihydrobenzo[1,4]dioxinyl, optionally substituted 2,3-dihydrobenzo furanyl, optionally substituted furanyl, optionally substituted imidazolyl, optionally substituted imidazopyridinyl, optionally substituted indolyl, optionally substituted indazolyl, optionally substituted isoxazolyl, optionally substituted isothiazolyl, optionally substituted oxadiazolyl, optionally substituted oxazolyl, optionally substituted purinyl, optionally substituted pyranyl, optionally substituted pyrazinonyl, optionally substituted pyrazinyl, optionally substituted pyrazolyl, optionally substituted pyridazinyl, optionally substituted pyridazinonyl, optionally substituted pyridazinonyl, optionally substituted pyridinyl, optionally substituted pyridonyl, optionally substituted pyrimidinonyl, optionally substituted pyrimidinyl, optionally substituted pyrrolyl, optionally substituted pyrrolo[2,3-d]pyrimidinyl, optionally substituted pyrazolo[3,4-d]pyrimidinyl, optionally substituted 1H-quinoxalin-2-only, optionally substituted quinolinyl, optionally substituted quinazolinyl, optionally substituted triazolyl, optionally substituted thiazolyl, optionally substituted tetrazolyl, optionally substituted thiadiazolyl, or optionally substituted thienyl;

Y is optionally substituted furanyl, optionally substituted imidazolyl, optionally substituted isoxazolyl, optionally substituted isothiazolyl, optionally substituted oxazolyl, optionally substituted pyrazolyl, optionally substituted pyridazinonyl, optionally substituted pyridazinyl, optionally substituted pyridinyl, optionally substituted pyrimidinyl, optionally substituted pyrrolyl, optionally substituted thienyl, optionally substituted triazinyl, or optionally substituted 1,2,4-triazolyl; and Z is —C(O)NH$_2$, —C(O)-optionally substituted morpholinyl, —C(O)-optionally substituted pyrrolidinyl, —C(O)—N(H)CH$_2$CH$_2$OH, optionally substituted ($C_3$-$C_6$)cycloalkyl, optionally substituted azaindolyl, optionally substituted azepinyl, optionally substituted azetidinyl, optionally substituted benzo[b]thienyl, optionally substituted benzimidazolyl, optionally substituted benzofuranyl, optionally substituted benzoxazolyl, optionally substituted benzothiazolyl, optionally substituted benzothiadiazolyl, optionally substituted benzoxadiazolyl, optionally substituted 1,4-dioxanyl, optionally substituted furanyl, optionally substituted imidazolyl, optionally substituted imidazopyridinyl, optionally substituted indolinyl, optionally substituted indolyl, optionally substituted indazolyl, optionally substituted isoindolinyl, optionally substituted isoxazolyl, optionally substituted isothiazolyl, optionally substituted morpholinyl, optionally substituted naphthyl, optionally substituted oxadiazolyl, optionally substituted phenyl, optionally substituted oxazolyl, optionally substituted piperazinyl, optionally substituted piperidinyl, optionally substituted purinyl, optionally substituted pyranyl, optionally substituted pyrazinyl, optionally substituted pyrazolyl, optionally substituted pyrazolo[3,4-b]pyridinyl, optionally substituted N-methylpyrazonyl, optionally substituted pyridazinyl, optionally substituted pyrazinonyl, optionally substituted pyridazinonyl, optionally substituted pyridinyl, optionally substituted pyridonyl, optionally substituted pyrimidinonyl, optionally substituted N-methylpyridazonyl, optionally substituted N—($C_1$-$C_6$)alkylpyridonyl, optionally substituted pyrimidinyl, optionally substituted N—($C_1$-$C_6$)alkylpyrimidonyl, optionally substituted pyrrolidinyl, optionally substituted pyrrolyl, optionally substituted pyrrolo[2,3-d]pyrimidinyl, optionally substituted pyrazolo[3,4-d]pyrimidinyl, optionally substituted quinolinyl, optionally substituted quinazolinyl, optionally substituted quinucludinyl, optionally substituted tetrahydrofuranyl, optionally substituted tetrahydroindolyl, optionally substituted tetrahydropyranyl, optionally substituted thiomorpholinyl, optionally substituted triazolyl, optionally substituted thiazolyl, optionally substituted tetrazolyl, optionally substituted thiadiazolyl, or optionally substituted thienyl, optionally substituted thiomorpholinyl, or optionally substituted tropanyl.

In another embodiment the invention provides a compound according to any of the foregoing embodiments wherein X is optionally substituted naphthyl, optionally substituted phenyl, optionally substituted benzo[1,4]oxazin-3-onyl, optionally substituted benzoxazolyl, optionally substituted 2,3-dihydrobenzo[1,4]dioxinyl, optionally substituted 2,3-dihydrobenzo furanyl, optionally substituted furanyl, optionally substituted imidazolyl, optionally substituted isoxazolyl, optionally substituted isothiazolyl, optionally substituted oxadiazolyl, optionally substituted oxazolyl, optionally substituted pyrazinyl, optionally substituted pyrazolyl, optionally substituted pyrazinonyl, optionally substituted pyridazinonyl, optionally substituted pyridinyl, optionally substituted pyridonyl, optionally substituted pyrimidinonyl, optionally substituted pyrimidinyl, optionally substituted pyrrolyl, optionally substituted triazolyl, optionally substituted thiazolyl, optionally substituted tetrazolyl, or optionally substituted thienyl.

In another embodiment the invention provides a compound according to any of the foregoing embodiments wherein Z is optionally substituted ($C_3$-$C_6$)cycloalkyl, optionally substituted azetidinyl, optionally substituted 1,4-dioxanyl, optionally substituted imidazolyl, optionally substituted isothiazolyl, optionally substituted morpholinyl, optionally substituted phenyl, optionally substituted piperazinyl, optionally substituted piperidinyl, optionally substituted purinyl, optionally substituted pyranyl, optionally substituted pyrazinyl, optionally substituted pyrazolyl, optionally substituted pyrazolo[3,4-b]pyridinyl, optionally substituted pyridazinyl, optionally substituted pyridazinonyl, optionally substituted pyridinyl, optionally substituted pyridonyl, optionally substituted pyrimidinyl, optionally substituted pyrrolidinyl, optionally substituted pyrrolyl, optionally substituted tetrahydropyranyl, optionally substituted triazolyl, optionally substituted thiazolyl, optionally substituted tetrazolyl, optionally substituted thiadiazolyl, optionally substituted thienyl, or optionally substituted thiomorpholinyl.

In another embodiment the invention provides a compound according to any of the foregoing embodiments wherein X is optionally substituted phenyl, optionally substituted benzo[1,4]oxazin-3-onyl, optionally substituted benzoxazolyl, optionally substituted 2,3-dihydrobenzo[1,4]dioxinyl, optionally substituted 2,3-dihydrobenzo furanyl, optionally substituted pyrazinonyl, optionally substituted pyridazinonyl, optionally substituted pyridinyl, optionally substituted pyridonyl, optionally substituted pyrimidinonyl, optionally substituted pyrimidinyl, optionally substituted pyrrolyl, or optionally substituted thienyl.

In another embodiment the invention provides a compound according to any of the foregoing embodiments wherein Z is optionally substituted ($C_3$-$C_6$)cycloalkyl, optionally substituted azetidinyl, optionally substituted 1,4-dioxanyl, optionally substituted morpholinyl, optionally substituted phenyl, optionally substituted piperazinyl, optionally substituted piperidinyl, optionally substituted pyrazinyl, optionally substituted pyrazolyl, optionally substituted pyridazinyl, optionally substituted pyridazinonyl optionally substituted pyridonyl, optionally substituted pyridinyl, optionally substituted pyrimidinyl, optionally substituted pyrrolidinyl, optionally substituted tetrahydropyranyl, optionally substituted triazolyl, optionally substituted tetrazolyl, optionally substituted thiadiazolyl, optionally substituted thienyl, or optionally substituted thiomorpholinyl.

In another embodiment the invention provides a compound according to any of the foregoing embodiments wherein A is In another embodiment the invention provides a compound according to any of the foregoing embodiments wherein m is 1, 2 or 3.

In another embodiment the invention provides a compound according to any of the foregoing embodiments wherein n is 0 or 1.

In another embodiment the invention provides a compound according to any of the foregoing embodiments wherein p is 0.

In another embodiment the invention provides a compound according to any of the foregoing embodiments wherein X is optionally substituted phenyl, optionally substituted benzo[1,4]oxazin-3-only, optionally substituted benzoxazolyl, optionally substituted 2,3-dihydrobenzo[1,4]dioxinyl, optionally substituted 2,3-dihydrobenzo furanyl, optionally substituted pyrazinonyl, optionally substituted pyridazinonyl, optionally substituted pyridinyl, optionally substituted pyridonyl, or optionally substituted pyrimidinonyl.

In another embodiment the invention provides a compound according to any of the foregoing embodiments wherein X is optionally substituted with one or more substituents independently selected from the group consisting of Br, Cl, F, $CF_3$, CN, $COR^b$, COOH, $OCF_3$, OH, —$N(R^c)(R^d)$, —$NO_2$, optionally substituted ($C_1$-$C_6$)alkyl, optionally substituted ($C_1$-$C_6$)alkoxy, —$S(O)R^d$, or —$S(O)_2(R^d)$; wherein $R^d$ is independently H, optionally substituted ($C_1$-$C_3$)alkyl or optionally substituted ($C_3$-$C_6$)cycloalkyl;

$R^d$ is H, —$C(O)R^b$, optionally substituted ($C_1$-$C_6$)alkyl, optionally substituted ($C_3$-$C_6$)cycloalkyl, optionally substituted azetidinyl, or optionally substituted pyrrolidinyl.

In another embodiment the invention provides a compound according to any of the foregoing embodiments wherein Y is optionally substituted imidazolyl, optionally substituted pyrazolyl, optionally substituted pyridazinyl, optionally substituted pyridazinonyl, optionally substituted pyridinyl, optionally substituted pyridonyl, optionally substituted pyrimidinyl or optionally substituted triazinyl.

In another embodiment the invention provides a compound according to any of the foregoing embodiments wherein Z is optionally substituted ($C_3$-$C_6$)cycloalkyl, optionally substituted azetidinyl, optionally substituted 1,4-dioxanyl, optionally substituted morpholinyl, optionally substituted phenyl, optionally substituted piperidinyl, optionally substituted pyrazinonyl, optionally substituted pyrazinyl, optionally substituted pyrazolyl, optionally substituted pyridazinyl, optionally substituted pyridazinonyl optionally substituted pyridinyl, optionally substituted pyridonyl, optionally substituted pyrimidinonyl, optionally substituted pyrimidinyl, optionally substituted tetrahydropyranyl, optionally substituted tetrazolyl, optionally substituted thiadiazolyl, optionally substituted thienyl, or optionally substituted thiomorpholinyl.

In another embodiment the invention provides a compound according to any of the foregoing embodiments wherein Z is optionally substituted by one or more substituents independently selected from Br, Cl, F, $CF_3$, CN, —$COR^f$, —$C(O)CH_2N(R^c)(R^e)$, —$CON(R^c)(R^e)$, $COOR^e$, —$N(R^c)(R^e)$, —$N(R^d)C(O)OR^a$—, —$N(R^c)C(O)R^e$, —$N(R^c)C(O)N(R^c)(R^e)$, —$N(R^c)S(O)_2R^e$, —$N(R^c)S(O)_2N(R^c)(R^e)$, —$NO_2$, oxo, —OH, —$S(O)R^e$, —$S(O)_2(R^e)$, optionally substituted ($C_1$-$C_6$)alkyl, optionally substituted ($C_1$-$C_6$)alkoxy, optionally substituted ($C_3$-$C_6$)cycloalkyl, —$(C(R^b)_2)_rR^f$; wherein $R^b$ is independently H, $CF_3$, optionally substituted ($C_1$-$C_3$) alkyl or optionally substituted ($C_3$-$C_6$)cycloalkyl; or $(R^b)_2$, together with the carbon atom to which it is attached, can form a 3- to 6-membered cycloalkyl $R^e$ is H, —$C(O)R^c$, optionally substituted ($C_1$-$C_6$)alkyl, optionally substituted ($C_3$-$C_6$)cycloalkyl, optionally substituted heteroaryl or optionally substituted heterocyclyl; or $R^c$ and $R^e$ together with the atom to which they are attached can form an optionally substituted heterocycle;

$R^f$ is H, Br, Cl, F, $CF_3$, CN, $OCF_3$, —$COR^e$, —$C(O)CH_2N(R^c)(R^e)$, —$CON(R^c)(R^e)$, $COOR^e$, —$N(R^c)(R^e)$, —$N(R^c)C(O)R^e$, —$N(R^c)C(O)N(R^c)(R^e)$, —$N(R^c)S(O)_2R^e$, —$NO_2$, oxo, optionally substituted ($C_1$-$C_6$)alkyl, optionally substituted ($C_3$-$C_6$)cycloalkyl, $OR^c$, —$S(R^c)$, —$S(R^e)$, —$S(O)R_c$—$S(O)R^e$, —$S(O)_2(R^c)$, —$S(O)_2(R^e)$, —$S(O)_2N(R^c)(R^e)$, optionally substituted azetidinyl, optionally substituted 1,4-dioxanyl, optionally substituted imidazolyl, optionally substituted isoxazolyl, optionally substituted morpholinyl, optionally substituted oxazolyl, optionally substituted oxadiazolyl, optionally substituted piperazinyl, optionally substituted piperidinyl, optionally substituted pyrazolyl, optionally substituted pyridinyl, optionally substituted pyrimidinyl, optionally substituted tetrazolyl, optionally substituted thienyl, optionally substituted thiomorpholinyl or optionally substituted triazolyl; and r is 0, 1 or 2;

provided that r is not 0 when $R^f$ is $OCF_3$, $OR^c$, —$S(R^c)$, —$S(R^e)$, —$S(O)R^c$, —$S(O)R^e$, —$S(O)_2(R^c)$, —$S(O)_2(R^e)$, or —$S(O)_2N(R^c)(R^e)$.

In another embodiment the invention provides a compound according to any of the foregoing embodiments wherein Z is optionally substituted by one or more substituents independently selected from Br, Cl, F, $CF_3$, CN, —C(O)OH, —C(O)$OCH_3$, —C(O)$CH_3$, —C(O)$CH_2OC(O)CH_3$, —C(O)C($CH_3$)$_3$, —C(O)C(H)($CH_3$)$_2$, —C(O)$CH_2CN$, —C(O)$CH_2OH$, —C(O)$CH_2OCH_3$, —C(O)$CH_2CH_2N(CH_3)_2$, —C(O)C($CH_3$)$_2$OH, —C(O)OC($CH_3$)$_3$, —C(O)N(H)$CH_2CH_3$, —C(O)$CH_2N(CH_3)_2$, —C(O)$CH_2N(H)S(O)_2CH_3$, —C(O)$CH_2N(H)C(O)CH_3$, —C(O)$CH_2N(H)C(O)N(H)CH_3$, —C(O)$CH_2OCH_3$, —C(O)$CH_2S(O)_2CH_3$, —C(O)$NH_2$, —C(O)N($CH_3$)$_2$, —C(O)N(H)$CH_3$, —C(O)N(H)$CH_2CH_3$, —C(O)N(H)CH($CH_3$)$_2$, —C(O)N(H)$CH_2CH_2OH$, —C(O)N(H)-isoxazolyl, —C(O)N(H)thiazolyl, —C(O)N($CH_3$)$CH_2CH_2OH$, —C(O)-cyclopropyl, —C(O)-cyclobutyl, —$OCH_3$, —$OCH_2CH_2OH$, —OC($CH_3$)$_3$, —$NH_2$, —N(H)C(O)$CH_3$—, —N(H)C(O)$CH_2OH$, —N(H)C(O)$CH_2CN$, —N(H)C(O)C($CH_3$)$_2$OH, —N(H)C(O)C(H)(OH)$CH_3$, —N(H)C(O)$CH_2N(CH_3)_2$, —N(H)C(O)$CH_2N(H)CH_3$, —N(H)C(O)(OH)$CH_3$, —N($R^c$)C(O)N($R^c$)($R^e$), —N(H)C(O)N($CH_3$)$_2$, —N(H)C(O)N(H)$CH_3$—N(H)C(O)N(H)$CH_2CH_2OH$, —N(H)C(O)N(H)C(H)($CH_2OH$)$_2$, —N(H)C(O)N($CH_3$)$CH_2CH_2OH$, —N(H)C(O)N($CH_3$)$CH_2C(H)(OH)CH_2OH$, —N(H)C(O)O($CH_3$)$_3$, —N(H)S(O)$_2NH_2$, —N(H)S(O)$_2CH_3$, —N($R^c$)S(O)$_2N(R^c)(R^e)$, —$NO_2$, oxo, —OH, —S(O)$CH_3$, —S(O)$CH_2CH_3$, —S(O)$CH_2CH_2CH_3$, —S(O)$_2C(H)(CH_3)_2$, —S(O)$_2$ cyclopropyl, —S(O)$_2$-optionally substituted imidazolyl, —S(O)$_2$-optionally substituted isoxazolyl, —$CH_2C(O)N(H)CH_3$, —$CH_2OCH_3$, —$CH_2OH$, —$CH_2CH_2OH$, —$CH_2OS(O)_2$-optionally substituted phenyl, —C($CH_3$)$OH$, —C(H)($CH_2$)$_2OH$, —$CH_2NH_2$, —$CH_2N(CH_3)_2$, —$CH_2N(H)C(O)CH_3$, —$CH_2N(H)C(O)C(H)(OH)CH_3$, —$CH_2N(H)C(O)CH_2CN$, —$CH_2N(H)C(O)CH_2OH$, —$CH_2N(H)C(O)C(CH_3)_2OH$, —$CH_2N(H)C(O)N(H)CH_3$, —$CH_2N(H)C(O)N(CH_3)_2$, —CH$_2$S(O)$_2$CH$_3$, optionally substituted (C$_1$-C$_6$)alkyl, optionally substituted (C$_1$-C$_6$)alkoxy, optionally substituted morpholinyl, optionally substituted piperidinyl, optionally substituted (C$_3$-C$_6$)cycloalkyl, and —(C(R$^b$)$_2$)$_r$R$^f$; wherein R$^b$ is independently H, CF$_3$, optionally substituted (C$_1$-C$_3$) alkyl or optionally substituted (C$_3$-C$_6$)cycloalkyl; or (R$^b$)$_2$, together with the carbon atom to which it is attached, can form a 3- to 6-membered cycloalkyl R$^e$ is H, —C(O)R$^c$, optionally substituted (C$_1$-C$_6$)alkyl, optionally substituted (C$_3$-C$_6$)cycloalkyl, optionally substituted heteroaryl or optionally substituted heterocyclyl; or R$^c$ and R$^e$ together with the atom to which they are attached can form an optionally substituted heterocycle;

R$^f$ is H, Br, Cl, F, CF$_3$, CN, OCF$_3$, —COR$^e$, —C(O)CH$_2$N(R$^c$)(R$^e$), —CON(R$^c$)(R$^e$), COOR$^e$, —N(R$^c$)(R$^e$), —N(R$^c$)C(O)R$^e$, —N(R$^c$)C(O)N(R$^c$)(R$^e$), —N(R$^c$)S(O)$_2$R$^e$, —NO$_2$, oxo, optionally substituted (C$_1$-C$_6$)alkyl, optionally substituted (C$_3$-C$_6$)cycloalkyl, OR$^c$, —S(R$^c$), —S(R$^e$), —S(O)R$^c$, —S(O)R$_c$—S(O)$_2$(R$^c$), —S(O)$_2$(R$^e$), —S(O)$_2$N(R$^c$)(R$^e$), optionally substituted azetidinyl, optionally substituted 1,4-dioxanyl, optionally substituted imidazolyl, optionally substituted isoxazolyl, optionally substituted morpholinyl, optionally substituted 1,2,4-oxadiazolyl, optionally substituted oxazolyl, optionally substituted oxadiazolyl, optionally substituted piperazinyl, optionally substituted piperidinyl, optionally substituted pyrazolyl, optionally substituted pyridazinyl, optionally substituted pyridinyl, optionally substituted pyrimidinyl, optionally substituted pyrrolidinyl, optionally substituted tetrazolyl, optionally substituted thienyl, optionally substituted thiomorpholinyl or optionally substituted triazolyl; and r is 0, 1 or 2;

provided that r is not 0 when R$^f$ is OCF$_3$, OR$^c$, —S(R$^c$), —S(R$^e$), —S(O)R$^c$, —S(O)R$^e$, —S(O)$_2$(R$^c$), —S(O)$_2$(R$^e$), or —S(O)$_2$N(R$^c$)(R$^e$).

In another embodiment the invention provides a compound according to any of the foregoing embodiments wherein Z is optionally substituted by one or more substituents independently selected from Br, Cl, F, CF$_3$, CH$_3$, CN, —C(O)OH, —C(O)OCH$_3$, —C(O)CH$_3$, —C(O)CH$_2$OC(O)CH$_3$, —C(O)C(CH$_3$)$_3$, —C(O)C(H)(CH$_3$)$_2$, —C(O)CH$_2$CN, —C(O)CH$_2$OH, —C(O)CH$_2$OCH$_3$, —C(O)CH$_2$CH$_2$N(CH$_3$)$_2$, —C(O)C(CH$_3$)$_2$OH, —C(O)OC(CH$_3$)$_3$, —C(O)N(H)CH$_2$CH$_3$, —C(O)CH$_2$N(CH$_3$)$_2$, —C(O)CH$_2$N(H)S(O)$_2$CH$_3$, —C(O)CH$_2$N(H)C(O)CH$_3$, —C(O)CH$_2$N(H)C(O)N(H)CH$_3$, —C(O)CH$_2$OCH$_3$, —C(O)CH$_2$S(O)$_2$CH$_3$, —C(O)NH$_2$, —C(O)N(CH$_3$)$_2$, —C(O)N(H)CH$_3$, —C(O)N(H)CH$_2$CH$_3$, —C(O)N(H)CH(CH$_3$)$_2$, —C(O)N(H)CH$_2$CH$_2$OH, —C(O)N(H)-isoxazolyl, —C(O)N(H)thiazolyl, —C(O)N(CH$_3$)CH$_2$CH$_2$OH, —C(O)-cyclopropyl, —C(O)-cyclobutyl, —OCH$_3$, —OCH$_2$CH$_2$OH, —OC(CH$_3$)$_3$, —NH$_2$, —N(H)C(O)CH$_3$—, —N(H)C(O)CH$_2$OH, —N(H)C(O)CH$_2$CN, —N(H)C(O)C(CH$_3$)$_2$OH, —N(H)C(O)C(H)(OH)CH$_3$, —N(H)C(O)CH$_2$N(CH$_3$)$_2$, —N(H)C(O)CH$_2$N(H)CH$_3$, —N(H)C(O)(OH)CH$_3$, —N(R$^c$)C(O)N(R$^c$)(R$^e$), —N(H)C(O)N(CH$_3$)$_2$, —N(H)C(O)N(H)CH$_3$—N(H)C(O)N(H)CH$_2$CH$_2$OH, —N(H)C(O)N(H)C(H)(CH$_2$OH)$_2$, —N(H)C(O)N(CH$_3$)CH$_2$CH$_2$OH, —N(H)C(O)N(CH$_3$)CH$_2$C(H)(OH)CH$_2$OH, —N(H)C(O)O(CH$_3$)$_3$, —N(H)S(O)$_2$NH$_2$, —N(H)S(O)$_2$CH$_3$, —N(R$^c$)S(O)$_2$N(R$^c$)(R$^e$), —NO$_{2,1,2,4}$-oxadiazolyl, oxo, —OH, —S(O)CH$_3$, —S(O)CH$_2$CH$_3$, —S(O)CH$_2$CH$_2$CH$_3$, —S(O)$_2$C(H)(CH$_3$)$_2$, —S(O)$_2$cyclopropyl, —S(O)$_2$-optionally substituted imidazolyl, —S(O)$_2$-optionally substituted isoxazolyl, —S(O)$_2$CN, —CH$_2$C(O)N(H)CH$_3$, —CH$_2$OCH$_3$, —CH$_2$OH, —CH$_2$CH$_2$OH, —CH$_2$OS(O)$_2$-optionally substituted phenyl, —C(CH$_3$)OH, —C(H)(CH$_2$)$_2$OH, —CH$_2$NH$_2$, —CH$_2$N(CH$_3$)$_2$, —CH$_2$N(H)C(O)CH$_3$, —CH$_2$N(H)C(O)C(H)(OH)CH$_3$, —CH$_2$N(H)C(O)CH$_2$CN, —CH$_2$N(H)C(O)CH$_2$OH, —CH$_2$N(H)C(O)C(CH$_3$)$_2$OH, —CH$_2$N(H)C(O)N(H)CH$_3$, —CH$_2$N(H)C(O)N(CH$_3$)$_2$, —CH$_2$S(O)$_2$CH$_3$, —CH$_2$-morpholinyl, —CH$_2$-thiomorpholinyl, optionally substituted morpholinyl, optionally substituted oxadiazolyl, optionally substituted oxazolyl, optionally substituted piperidinyl, and optionally substituted (C$_3$-C$_6$)cycloalkyl wherein R$^e$ is H, —C(O)R$_c$, optionally substituted (C$_1$-C$_6$) alkyl, optionally substituted (C$_3$-C$_6$)cycloalkyl, optionally substituted azetidinyl, optionally substituted morpholinyl, optionally substituted piperidinyl, or optionally substituted pyrrolidinyl.

In another embodiment the invention provides a compound according to any of the foregoing embodiments wherein Y is optionally substituted by one or more substituents independently selected from the group consisting of CF$_3$, CN, —COH, —COOH, NO$_2$, —N(R$^a$)$_2$, —N(R$^a$)C(O)N(R$^a$)$_2$, —C(O)N(R$^a$)$_2$, —S(O)R$^a$, —S(O)$_2$R$^a$, halogen, optionally substituted (C$_1$-C$_6$)alkyl, optionally substituted (C$_1$-C$_6$) alkoxy, optionally substituted aryl, optionally substituted heteroaryl, and optionally substituted heterocyclyl.

In another embodiment the invention provides a compound according to any of the foregoing embodiments wherein X is optionally substituted phenyl, optionally substituted benzo[1,4]oxazin-3-onyl, optionally substituted benzoxazolyl, optionally substituted 2,3-dihydrobenzo[1,4]dioxinyl, optionally substituted 2,3-dihydrobenzo furanyl, optionally substituted pyrazinonyl, optionally substituted pyridazinonyl, optionally substituted pyridazinyl, or optionally substituted pyridinyl;

Y is optionally substituted pyrimidinyl; and

Z is optionally substituted cyclohexyl, optionally substituted 1,4-dioxanyl, optionally substituted pyridonyl, or optionally substituted pyridinyl.

In another embodiment the invention provides a compound wherein the compound is 6-(5-(1-Acetylpiperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-(methylsulfonyl)piperidin-4-yl)-4,5-dihydroisoxazol-3-yl)pyrimidine-4-carboxamide;

N-(4-fluoro-3-methoxybenzyl)-6-(5-(1-(2-hydroxyacetyl)piperidin-4-yl)-4,5-dihydroisoxazol-3-yl)-2-methylpyrimidine-4-carboxamide;

N-(4-fluoro-3-methoxybenzyl)-6-((S)-5-((2S,5S)-5-(hydroxymethyl)-1,4-dioxan-2-yl)-4,5-dihydro-isoxazol-3-yl)-2-methylpyrimidine-4-carboxamide;

N-(4-fluoro-3-methoxybenzyl)-6-((R)-5-((2S,5S)-5-(hydroxymethyl)-1,4-dioxan-2-yl)-4,5-dihydro-isoxazol-3-yl)-2-methylpyrimidine-4-carboxamide;

N-(4-Fluoro-3-methoxybenzyl)-6-((S)-5-((2R,5R)-5-(hydroxymethyl)-1,4-dioxan-2-yl)-4,5-dihydro-isoxazol-3-yl)-2-methylpyrimidine-4-carboxamide;

N-(4-fluoro-3-methoxybenzyl)-6-((R)-5-((2R,5R)-5-(hydroxymethyl)-1,4-dioxan-2-yl)-4,5-dihydro-isoxazol-3-yl)-2-methylpyrimidine-4-carboxamide;

6-(5-(4-Carbamoylphenyl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(morpholine-4-carbonyl)-4,5-dihydroisoxazol-3-yl)pyrimidine-4-carboxamide;

N-(4-fluoro-3-methoxybenzyl)-6-(5-(2-(2-hydroxypropan-2-yl)pyridin-4-yl)-4,5-dihydroisoxazol-3-yl)-2-methylpyrimidine-4-carboxamide;

6-(5-(2H-tetrazol-5-yl)-4,5-dihydroisoxazol-3-yl)-N-(4-fluoro-3-methoxybenzyl)-2-methylpyrimidine-4-carboxamide;
N-(4-fluoro-3-methoxybenzyl)-2-methyl-6-(5-(piperidin-4-yl)-4,5-dihydroisoxazol-3-yl)pyrimidine-4-carboxamide hydrochloride;
6-(5-(1-(ethylcarbamoyl)piperidin-4-yl)-4,5-dihydroisoxazol-3-yl)-N-(4-fluoro-3-methoxybenzyl)-2-methylpyrimidine-4-carboxamide;
6-(5-(1-(cyclopropanecarbonyl)piperidin-4-yl)-4,5-dihydroisoxazol-3-yl)-N-(4-fluoro-3-methoxybenzyl)-2-methylpyrimidine-4-carboxamide;
6-(5-(1-(2-acetamidoacetyl)piperidin-4-yl)-4,5-dihydroisoxazol-3-yl)-N-(4-fluoro-3-methoxybenzyl)-2-methylpyrimidine-4-carboxamide;
6-(5-(1-(2-cyanoacetyl)piperidin-4-yl)-4,5-dihydroisoxazol-3-yl)-N-(4-fluoro-3-methoxybenzyl)-2-methylpyrimidine-4-carboxamide;
N-(4-fluoro-3-methoxybenzyl)-2-methyl-6-(5-(1-(2-(methylsulfonyl)acetyl)piperidin-4-yl)-4,5-dihydroisoxazol-3-yl)pyrimidine-4-carboxamide;
N-(4-fluoro-3-methoxybenzyl)-6-(5-(1-(2-hydroxy ethyl carbamoyl)piperidin-4-yl)-4,5-dihydroisoxazol-3-yl)-2-methylpyrimidine-4-carboxamide;
N-(4-fluoro-3-methoxybenzyl)-6-(5-(1-(isoxazol-3-ylcarbamoyl)piperidin-4-yl)-4,5-dihydroisoxazol-3-yl)-2-methylpyrimidine-4-carboxamide;
N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide;
N-(4-fluoro-3-methoxybenzyl)-6-((R)-5-((2R,5R)-5-(hydroxymethyl)-1,4-dioxan-2-yl)-4,5-dihydroisoxazol-3-yl)-2-methylpyrimidine-4-carboxamide;
N-(4-fluoro-3-methoxybenzyl)-2-methyl-6-(5-(1-(methylcarbamoyl)piperidin-4-yl)-4,5-dihydroisoxazol-3-yl)pyrimidine-4-carboxamide;
6-((S)-5-((2R,5R)-5-(cyanomethyl)-1,4-dioxan-2-yl)-4,5-dihydroisoxazol-3-yl)-N-(4-fluoro-3-methoxybenzyl)-2-methylpyrimidine-4-carboxamide;
N-(4-fluoro-3-methoxybenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;
(2S,5R)-5-((S)-3-(6-((4-fluoro-3-methoxybenzyl)carbamoyl)-2-methylpyrimidin-4-yl)-4,5-dihydroisoxazol-5-yl)-1,4-dioxane-2-carboxylic acid;
N-(4-fluoro-3-methoxybenzyl)-2-methyl-6-(5-(morpholinomethyl)-4,5-dihydroisoxazol-3-yl)pyrimidine-4-carboxamide;
6-((S)-5-((2R,5S)-5-Carbamoyl-1,4-dioxan-2-yl)-4,5-dihydroisoxazol-3-yl)-N-(4-fluoro-3-methoxybenzyl)-2-methylpyrimidine-4-carboxamide;
6-(5-(1H-imidazol-4-yl)-4,5-dihydroisoxazol-3-yl)-N-(4-fluoro-3-methoxybenzyl)-2-methylpyrimidine-4-carboxamide;
6-(5-(4-(2-hydroxyethoxy)phenyl)-5-methyl-4,5-dihydroisoxazol-3-yl)-N-(4-methoxybenzyl)-2-methylpyrimidine-4-carboxamide 2,2,2-trifluoroacetate;
6-(5-(4-(2-hydroxyethoxy)phenyl)-4,5-dihydroisoxazol-3-yl)-N-(4-methoxybenzyl)-2-methylpyrimidine-4-carboxamide;
N-(4-methoxybenzyl)-2-methyl-6-(5-phenyl-4,5-dihydroisoxazol-3-yl)pyrimidine-4-carboxamide;
6-(5-(4-(hydroxymethyl)phenyl)-5-methyl-4,5-dihydroisoxazol-3-yl)-N-(4-methoxybenzyl)-2-methylpyrimidine-4-carboxamide;
N-(4-methoxybenzyl)-6-(5-(4-methoxyphenyl)-4,5-dihydroisoxazol-3-yl)-2-methylpyrimidine-4-carboxamide;
N-(4-methoxybenzyl)-2-methyl-6-(5-(4-morpholinophenyl)-4,5-dihydroisoxazol-3-yl)pyrimidine-4-carboxamide;
N-(4-methoxybenzyl)-2-methyl-6-(5-(4-(piperidin-1-yl)phenyl)-4,5-dihydroisoxazol-3-yl)pyrimidine-4-carboxamide;
6-(5-(4-(diethylamino)phenyl)-4,5-dihydroisoxazol-3-yl)-N-(4-methoxybenzyl)-2-methylpyrimidine-4-carboxamide;
6-(5-(3-(2-hydroxyethoxy)phenyl)-4,5-dihydroisoxazol-3-yl)-N-(4-nethoxybenzyl)-2-methylpyrimidine-4-carboxamide;
N-(4-methoxybenzyl)-2-methyl-6-(5-(pyridin-2-yl)-4,5-dihydroisoxazol-3-yl)pyrimidine-4-carboxamide;
6-(5-cyclohexyl-4,5-dihydroisoxazol-3-yl)-N-(4-methoxybenzyl)-2-methylpyrimidine-4-carboxamide;
6-(5-cyclohexyl-4,5-dihydroisoxazol-3-yl)-N-(4-methoxybenzyl)-2-methylpyrimidine-4-carboxamide;
6-(5-(4-(hydroxymethyl)phenyl)-4,5-dihydroisoxazol-3-yl)-N-(4-nethoxybenzyl)-2-methylpyrimidine-4-carboxamide;
6-(5-(4-carbamoylphenyl)-4,5-dihydroisoxazol-3-yl)-N-(4-methoxybenzyl)-2-methylpyrimidine-4-carboxamide;
6-(5-cyclohexyl-4,5-dihydroisoxazol-3-yl)-N-(4-fluoro-3-methoxybenzyl)-2-methylpyrimidine-4-carboxamide;
6-(5-(1-acetylpiperidin-4-yl)-4,5-dihydroisoxazol-3-yl)-N-(4-methoxybenzyl)-2-methylpyrimidine-4-carboxamide;
N-(4-fluoro-3-methoxybenzyl)-2-methyl-6-(5-(pyridin-2-yl)-4,5-dihydroisoxazol-3-yl)pyrimidine-4-carboxamide;
N-(4-fluoro-3-methoxybenzyl)-6-(5-(4-hydroxycyclohexyl)-4,5-dihydroisoxazol-3-yl)-2-methylpyrimidine-4-carboxamide;
tert-butyl 4-(3-(6-(4-fluoro-3-methoxybenzylcarbamoyl)-2-methylpyrimidin-4-yl)-4,5-dihydroisoxazol-5-yl)piperidine-1-carboxylate;
N-(4-fluoro-3-methoxybenzyl)-2-methyl-6-(5-(pyridin-3-yl)-4,5-dihydroisoxazol-3-yl)pyrimidine-4-carboxamide;
N-(4-fluoro-3-methoxybenzyl)-6-(5-(4-(hydroxymethyl)phenyl)-4,5-dihydroisoxazol-3-yl)-2-methylpyrimidine-4-carboxamide;
N-(4-fluoro-3-methoxybenzyl)-6-(5-(4-(4-(hydroxymethyl)piperidin-1-yl)phenyl)-4,5-dihydroisoxazol-3-yl)-2-methylpyrimidin-4-carboxamide;
N-(4-fluoro-3-methoxybenzyl)-2-methyl-6-(5-(4-(morpholinomethyl)phenyl)-4,5-dihydroisoxazol-3-yl)pyrimidine-4-carboxamide;
6-(5-cyano-4,5-dihydroisoxazol-3-yl)-N-(4-methoxybenzyl)-2-methylpyrimidine-4-carboxamide;
N-(4-fluoro-3-methoxybenzyl)-2-methyl-6-(5-(4-(thiomorpholinomethyl)phenyl)-4,5-dihydroisoxazol-3-yl)pyrimidine-4-carboxamide;
6-(5-cyano-4,5-dihydroisoxazol-3-yl)-N-(4-fluoro-3-methoxybenzyl)-2-methylpyrimidine-4-carboxamide;
6-(5-(3-carbamoylphenyl)-4,5-dihydroisoxazol-3-yl)-N-(4-fluoro-3-methoxybenzyl)-2-methylpyrimidine-4-carboxamide;
N-(4-fluoro-3-methoxybenzyl)-2-methyl-6-(5-(3-(morpholinomethyl)phenyl)-4,5-dihydroisoxazol-3-yl)pyrimidine-4-carboxamide;
N-(4-fluoro-3-methoxybenzyl)-2-methyl-6-(5-(3-(methylcarbamoyl)phenyl)-4,5-dihydroisoxazol-3-yl)pyrimidine-4-carboxamide;
methyl 4-(3-(6-(4-fluoro-3-methoxybenzylcarbamoyl)-2-methylpyrimidin-4-yl)-4,5-dihydroisoxazol-5-yl)benzoate;

N-(4-fluoro-3-methoxybenzyl)-2-methyl-6-(5-(4-(methylcarbamoyl)phenyl)-4,5-dihydroisoxazol-3-yl)pyrimidine-4-carboxamide;
N-(4-fluoro-3-methoxybenzyl)-2-methyl-6-(5-(thiophen-3-yl)-4,5-dihydroisoxazol-3-yl)pyrimidine-4-carboxamide;
N-(4-fluoro-3-methoxybenzyl)-2-methyl-6-(5-(pyridin-4-yl)-4,5-dihydroisoxazol-3-yl)pyrimidine-4-carboxamide;
6-{5-[4-(1,1,1,-Dioxo-thiomorpholine-4-ylmethyl)phenyl]-4,5-dihydro-isoxazol-3-yl}-2-methylpyrimidine-4-carboxylate;
N-(4-fluoro-3-methoxybenzyl)-6-((R)-5-((2S,5S)-5-(hydroxymethyl)-1,4-dioxan-2-yl)-4,5-dihydroisoxazol-3-yl)-2-methylpyrimidine-4-carboxamide;
N-(4-fluoro-3-methoxybenzyl)-6-((S)-5-((2S,5S)-5-(hydroxymethyl)-1,4-dioxan-2-yl)-4,5-dihydroisoxazol-3-yl)-2-methylpyrimidin-4-carboxamide;
N-(4-Fluoro-3-methoxybenzyl)-6-((S)-5-((2S,5S)-5-(hydroxymethyl)-1,4-dioxan-2-yl)-4,5-dihydro-isoxazol-3-yl)-2-methylpyrimidine-4-carboxamide;
6-(5-((1r,4r)-4-(2-cyanoacetamido)cyclohexyl)-4,5-dihydroisoxazol-3-yl)-N-(4-fluoro-3-methoxybenzyl)-2-methylpyrimidine-4-carboxamide;
N-(4-fluoro-3-methoxybenzyl)-2-methyl-6-(5-((1r,4r)-4-(sulfamoylamino)cyclohexyl)-4,5-dihydroisoxazol-3-yl)pyrimidine-4-carboxamide
N-(4-fluoro-3-methoxybenzyl)-2-methyl-6-(5-(pyridin-3-yl)-4,5-dihydro-1H-pyrazol-3-yl)pyrimidine-4-carboxamide;
6-(3-(4-(2-hydroxyethoxy)phenyl)-4,5-dihydroisoxazol-5-yl)-N-(4-methoxybenzyl)-2-methylpyrimidine-4-carboxamide 2,2,2-trifluoroacetate;
N-(4-fluoro-3-methoxybenzyl)-2-methyl-6-(3-phenyl-4,5-dihydroisoxazol-5-yl)pyrimidine-4-carboxamide;
N-(4-fluoro-3-methoxybenzyl)-6-(3-(4-(2-hydroxyethoxy)phenyl)-4,5-dihydroisoxazol-5-yl)-2-methylpyrimidine-4-carboxamide;
N-(4-methoxybenzyl)-2-methyl-6-(3-phenyl-4,5-dihydroisoxazol-5-yl)pyrimidine-4-carboxamide;
N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide;
N-(4-fluoro-3-methoxybenzyl)-6-((R)-5-((2R,5R)-5-(hydroxymethyl)-1,4-dioxan-2-yl)-4,5-dihydroisoxazol-3-yl)-2-methylpyrimidine-4-carboxamide;
N-(4-fluoro-3-methoxybenzyl)-6-(5-(4-(2-hydroxyethylcarbamoyl)phenyl)-4,5-dihydroisoxazol-3-yl)-2-methylpyrimidine-4-carboxamide;
6-(5-((1-acetylpiperidin-4-yl)methyl)-4,5-dihydroisoxazol-3-yl)-N-(4-fluoro-3-methoxybenzyl)-2-methylpyrimidine-4-carboxamide;
N-(4-fluoro-3-methoxybenzyl)-2-methyl-6-(5-(pyrimidin-5-yl)-4,5-dihydroisoxazol-3-yl)pyrimidine-4-carboxamide;
N-(4-fluoro-3-methoxybenzyl)-6-(5-(4-(2-hydroxypropan-2-yl)phenyl)-4,5-dihydroisoxazol-3-yl)-2-methylpyrimidine-4-carboxamide;
N-(4-fluoro-3-methoxybenzyl)-6-(5-((1-(2-hydroxyacetyl)piperidin-4-yl)methyl)-4,5-dihydroisoxazol-3-yl)-2-methylpyrimidine-4-carboxamide;
N-(4-fluoro-3-methoxybenzyl)-2-methyl-6-(5-((1-(methylsulfonyl)piperidin-4-yl)methyl)-4,5-dihydroisoxazol-3-yl)pyrimidine-4-carboxamide;
6-(5-(2-carbamoylpyridin-4-yl)-4,5-dihydroisoxazol-3-yl)-N-(4-fluoro-3-methoxybenzyl)-2-methylpyrimidine-4-carboxamide;
6-(5-(1H-pyrazol-4-yl)-4,5-dihydroisoxazol-3-yl)-N-(4-fluoro-3-methoxybenzyl)-2-methylpyrimidine-4-carboxamide;
6-((R)-5-((1r,4R)-4-acetamidocyclohexyl)-4,5-dihydroisoxazol-3-yl)-N-(4-fluoro-3-methoxybenzyl)-2-methylpyrimidine-4-carboxamide;
N-(4-fluoro-3-methoxybenzyl)-2-methyl-6-((R)-5-((1r,4R)-4-(methylsulfonamido)cyclohexyl)-4,5-dihydroisoxazol-3-yl)pyrimidine-4-carboxamide;
N-(4-fluoro-3-methoxybenzyl)-6-((R)-5-((1r,4R)-4-(2-hydroxyacetamido)cyclohexyl)-4,5-dihydroisoxazol-3-yl)-2-methylpyrimidine-4-carboxamide;
N-(4-fluoro-3-methoxybenzyl)-2-methyl-6-(5-(pyrimidin-2-yl)-4,5-dihydroisoxazol-3-yl)pyrimidine-4-carboxamide;
N-(4-fluoro-3-methoxybenzyl)-2-methyl-6-(5-(tetrahydro-2H-pyran-4-yl)-4,5-dihydroisoxazol-3-yl)pyrimidine-4-carboxamide;
6-(5-((1r,4r)-4-acetamidocyclohexyl)-4,5-dihydroisoxazol-3-yl)-N-(4-fluoro-3-methoxybenzyl)-2-methylpyrimidine-4-carboxamide;
N-(4-Fluoro-3-methoxybenzyl)-2-methyl-6-(5-((1r,4r)-4-(methylsulfonamido)cyclohexyl)-4,5-dihydroisoxazol-3-yl)pyrimidine-4-carboxamide;
N-(4-Fluoro-3-methoxybenzyl)-6-(5-((1r,4r)-4-(2-hydroxyacetamido)cyclohexyl)-4,5-dihydroisoxazol-3-yl)-2-methylpyrimidine-4-carboxamide;
N-(4-fluoro-3-methylbenzyl)-2-methyl-6-(5-(pyridin-2-yl)-4,5-dihydroisoxazol-3-yl)pyrimidine-4-carboxamide;
6-(5-(1-acetylpiperidin-4-yl)-4,5-dihydroisoxazol-3-yl)-N-(4-fluoro-3-methylbenzyl)-2-methylpyrimidine-4-carboxamide;
N-(4-fluoro-3-methylbenzyl)-2-methyl-6-(5-(1-(methylsulfonyl)piperidin-4-yl)-4,5-dihydroisoxazol-3-yl)pyrimidine-4-carboxamide;
N-(4-fluoro-3-methylbenzyl)-6-(5-(1-(2-hydroxyacetyl)piperidin-4-yl)-4,5-dihydroisoxazol-3-yl)-2-methylpyrimidine-4-carboxamide;
N-(4-fluoro-3-methoxybenzyl)-2-methyl-6-(5-(pyrazin-2-yl)-4,5-dihydroisoxazol-3-yl)pyrimidine-4-carboxamide;
N-(4-fluoro-3-methoxybenzyl)-6-(5-(1-(2-hydroxy-2-methylpropanoyl)piperidin-4-yl)-4,5-dihydroisoxazol-3-yl)-2-methylpyrimidine-4-carboxamide;
6-(5-(1-(cyclopropylsulfonyl)piperidin-4-yl)-4,5-dihydroisoxazol-3-yl)-N-(4-fluoro-3-methoxybenzyl)-2-methylpyrimidine-4-carboxamide;
N-(3,4-difluorobenzyl)-2-methyl-6-(5-(pyridin-2-yl)-4,5-dihydroisoxazol-3-yl)pyrimidine-4-carboxamide;
6-(5-(1-acetylpiperidin-4-yl)-4,5-dihydroisoxazol-3-yl)-N-(3,4-difluorobenzyl)-2-methylpyrimidine-4-carboxamide;
N-(3,4-difluorobenzyl)-2-methyl-6-(5-(1-(methylsulfonyl)piperidin-4-yl)-4,5-dihydroisoxazol-3-yl)pyrimidine-4-carboxamide;
N-(3,4-difluorobenzyl)-6-(5-(1-(2-hydroxyacetyl)piperidin-4-yl)-4,5-dihydroisoxazol-3-yl)-2-methylpyrimidine-4-carboxamide;
6-(5-(1-(ethylsulfonyl)piperidin-4-yl)-4,5-dihydroisoxazol-3-yl)-N-(4-fluoro-3-methoxybenzyl)-2-methylpyrimidine-4-carboxamide;
N-(4-fluoro-3-methoxybenzyl)-6-(5-(1-isobutyrylpiperidin-4-yl)-4,5-dihydroisoxazol-3-yl)-2-methylpyrimidine-4-carboxamide;
N-(4-fluoro-3-methoxybenzyl)-2-methyl-6-(5-(1-(propylsulfonyl)piperidin-4-yl)-4,5-dihydroisoxazol-3-yl)pyrimidine-4-carboxamide;

N-(4-fluorobenzyl)-2-methyl-6-(5-(pyridin-2-yl)-4,5-dihydroisoxazol-3-yl)pyrimidine-4-carboxamide;

6-(5-(1-acetylpiperidin-4-yl)-4,5-dihydroisoxazol-3-yl)-N-(3-chloro-4-fluorobenzyl)-2-methylpyrimidine-4-carboxamide;

N-(3-chloro-4-fluorobenzyl)-6-(5-(1-(2-hydroxyacetyl)piperidin-4-yl)-4,5-dihydroisoxazol-3-yl)-2-methylpyrimidine-4-carboxamide;

N-(3-methoxybenzyl)-2-methyl-6-(5-(pyridin-2-yl)-4,5-dihydroisoxazol-3-yl)pyrimidine-4-carboxamide;

6-(5-(1-acetylpiperidin-4-yl)-4,5-dihydroisoxazol-3-yl)-N-(4-fluorobenzyl)-2-methylpyrimidine-4-carboxamide;

N-(4-fluorobenzyl)-2-methyl-6-(5-(1-(methylsulfonyl)piperidin-4-yl)-4,5-dihydroisoxazol-3-yl)pyrimidine-4-carboxamide;

N-(4-fluorobenzyl)-6-(5-(1-(2-hydroxyacetyl)piperidin-4-yl)-4,5-dihydroisoxazol-3-yl)-2-methylpyrimidine-4-carboxamide;

6-(5-(1-acetylpiperidin-4-yl)-4,5-dihydroisoxazol-3-yl)-N-(3-methoxybenzyl)-2-methylpyrimidine-4-carboxamide;

N-(3-methoxybenzyl)-2-methyl-6-(5-(1-(methylsulfonyl)piperidin-4-yl)-4,5-dihydroisoxazol-3-yl)pyrimidine-4-carboxamide;

6-(5-(1-(2-hydroxyacetyl)piperidin-4-yl)-4,5-dihydroisoxazol-3-yl)-N-(3-methoxybenzyl)-2-methylpyrimidine-4-carboxamide;

6-(5-(1-(cyclopropanecarbonyl)piperidin-4-yl)-4,5-dihydroisoxazol-3-yl)-N-(4-fluoro-3-methoxybenzyl)-2-methylpyrimidine-4-carboxamide;

6-(5-(1-(dimethylcarbamoyl)piperidin-4-yl)-4,5-dihydroisoxazol-3-yl)-N-(4-fluoro-3-methoxybenzyl)-2-methylpyrimidine-4-carboxamide;

6-(5-(1-(ethylcarbamoyl)piperidin-4-yl)-4,5-dihydroisoxazol-3-yl)-N-(4-fluoro-3-methoxybenzyl)-2-methylpyrimidine-4-carboxamide;

6-(5-(1-(2-(dimethylamino)acetyl)piperidin-4-yl)-4,5-dihydroisoxazol-3-yl)-N-(4-fluoro-3-methoxybenzyl)-2-methylpyrimidine-4-carboxamide;

6-(5-(1-(2-acetamidoacetyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-(1-(isopropylsulfonyl)piperidin-4-yl)-4,5-dihydroisoxazol-3-yl)-2-methylpyrimidine-4-carboxamide;

6-(5-(1-(2-cyanoacetyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-(1-(2-methoxyacetyl)piperidin-4-yl)-4,5-dihydroisoxazol-3-yl)-2-methylpyrimidine-4-carboxamide;

6-(5-(1-(cyclobutanecarbonyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-(2-(methylsulfonamido)acetyl)piperidin-4-yl)-4,5-dihydroisoxazol-3-yl)pyrimidine-4-carboxamide;

6-(5-(5-cyanopyridin-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-(5-(hydroxymethyl)pyridin-2-yl)-4,5-dihydroisoxazol-3-yl)-2-methylpyrimidine-4-carboxamide;

N-(4-fluoro-3-methoxybenzyl)-2-methyl-6-(5-(5-(methylcarbamoyl)pyridin-2-yl)-4,5-dihydroisoxazol-3-yl)pyrimidine-4-carboxamide;

N-(4-fluoro-3-methoxybenzyl)-6-(5-(1-(2-hydroxyethylcarbamoyl)piperidin-4-yl)-4,5-dihydroisoxazol-3-yl)-2-methylpyrimidine-4-carboxamide;

N-(4-fluoro-3-methoxybenzyl)-2-methyl-6-(5-(1-(2-(3-methylureido)acetyl)piperidin-4-yl)-4,5-dihydroisoxazol-3-yl)pyrimidine-4-carboxamide;

N-(4-fluoro-3-methoxybenzyl)-6-(5-(5-(1-hydroxyethyl)pyridin-2-yl)-4,5-dihydroisoxazol-3-yl)-2-methylpyrimidine-4-carboxamide;

N-(4-fluoro-3-methoxybenzyl)-6-(5-(1-((2-hydroxyethyl)(methyl)carbamoyl)piperidin-4-yl)-4,5-dihydroisoxazol-3-yl)-2-methylpyrimidine-4-carboxamide;

N-(4-fluoro-3-methoxybenzyl)-6-(5-(1-(isopropylcarbamoyl)piperidin-4-yl)-4,5-dihydroisoxazol-3-yl)-2-methylpyrimidine-4-carboxamide;

N-(4-fluoro-3-methoxybenzyl)-2-methyl-6-(5-(1-(1-methyl-1H-imidazol-2-ylsulfonyl)piperidin-4-yl)-4,5-dihydroisoxazol-3-yl)pyrimidine-4-carboxamide;

N-(4-fluoro-3-methoxybenzyl)-2-methyl-6-(5-(1-(1-methyl-1H-imidazol-4-ylsulfonyl)piperidin-4-yl)-4,5-dihydroisoxazol-3-yl)pyrimidine-4-carboxamide;

6-(5-(1-(1,2-dimethyl-1H-imidazol-4-ylsulfonyl)piperidin-4-yl)-4,5-dihydroisoxazol-3-yl)-N-(4-fluoro-3-methoxybenzyl)-2-methylpyrimidine-4-carboxamide;

6-(5-(1-(3,5-dimethylisoxazol-4-ylsulfonyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(5-(methylsulfonyl)pyridin-2-yl)-4,5-dihydroisoxazol-3-yl)pyrimidine-4-carboxamide;

N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide;

6-(5-(5-acetylpyridine-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(5-(3-methyl-1,2,4-oxadiazol-5-yl)pyridin-2-yl)-4,5-dihydroisoxazol-3-yl)pyrimidine-4-carboxamide 2,2,2-trifluoroacetate;

((2S,5R)-5-(3-(6-(3-chloro-4-fluorobenzylcarbamoyl)-2-methylpyrimidin-4-yl)-4,5-dihydroisoxazol-5-yl)-1,4-dioxan-2-yl)methyl 4-methylbenzenesulfonate;

N-(3-chloro-4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-chloro-4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(3-chloro-4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-chloro-4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-N-(4-methoxybenzyl)-2-methylpyrimidine-4-carboxamide;

6-((R)-5-((2R,5R)-5-(hydroxymethyl)-1,4-dioxan-2-yl)-4,5-dihydroisoxazol-3-yl)-N-(4-methoxybenzyl)-2-methylpyrimidine-4-carboxamide;

6-(5-((2R,5R)-5-(hydroxymethyl)-1,4-dioxan-2-yl)-4,5-dihydroisoxazol-3-yl)-N-(3-methoxybenzyl)-2-methylpyrimidine-4-carboxamide;

((2S,5R)-5-((S)-3-(6-(4-fluoro-3-methoxybenzylcarbamoyl)-2-methylpyrimidin-4-yl)-4,5-dihydroisoxazol-5-yl)-1,4-dioxan-2-yl)methyl 4-methylbenzenesulfonate;

methyl 4-(3-(2-(3-methoxybenzylcarbamoyl)pyridin-4-yl)-4,5-dihydroisoxazol-5-yl)benzoate;

N-(3-methoxybenzyl)-4-(5-(4-methoxyphenyl)-4,5-dihydroisoxazol-3-yl)picolinamide;

4-(5-(4-chlorophenyl)-5-methyl-4,5-dihydroisoxazol-3-yl)-N-(3-methoxybenzyl)picolinamide;

4-(3-(2-(3-methoxybenzylcarbamoyl)pyridin-4-yl)-4,5-dihydroisoxazol-5-yl)benzoic acid;

4-(5-(4-((dimethylamino)methyl)phenyl)-4,5-dihydroisoxazol-3-yl)-N-(4-methoxybenzyl)picolinamide;

4-(3-(2-(4-methoxybenzyl carbamoyl)pyridin-4-yl)-4,5-dihydroisoxazol-5-yl)benzoic acid;

4-(5-(4-chlorophenyl)-5-methyl-4,5-dihydroisoxazol-3-yl)-N-(4-methoxybenzyl)picolinamide;

N-(4-methoxybenzyl)-4-(5-(pyrazin-2-yl)-4,5-dihydroisoxazol-3-yl)picolinamide;

N-(4-methoxybenzyl)-4-(5-(4-methoxyphenyl)-4,5-dihydroisoxazol-3-yl)picolinamide;

6-((S)-5-((2R,5R)-5-(hydroxymethyl)-1,4-dioxan-2-yl)-4,5-dihydroisoxazol-3-yl)-N-(3-methoxybenzyl)-2-methylpyrimidine-4-carboxamide;

6-((R)-5-((2S,5S)-5-(hydroxymethyl)-1,4-dioxan-2-yl)-4,5-dihydroisoxazol-3-yl)-N-(3-methoxybenzyl)-2-methylpyrimidine-4-carboxamide;

6-((S)-5-((2S,5S)-5-(hydroxymethyl)-1,4-dioxan-2-yl)-4,5-dihydroisoxazol-3-yl)-N-(3-methoxybenzyl)-2-methylpyrimidine-4-carboxamide;

N-(4-fluorobenzyl)-6-((R)-5-((2S,5S)-5-(hydroxymethyl)-1,4-dioxan-2-yl)-4,5-dihydroisoxazol-3-yl)-2-methylpyrimidine-4-carboxamide;

N-(4-fluorobenzyl)-6-((S)-5-((2S,5S)-5-(hydroxymethyl)-1,4-dioxan-2-yl)-4,5-dihydroisoxazol-3-yl)-2-methylpyrimidine-4-carboxamide;

6-(R)-5-((2S,5S)-5-(hydroxymethyl)-1,4-dioxan-2-yl)-4,5-dihydroisoxazol-3-yl)-N-(4-methoxybenzyl)-2-methylpyrimidine-4-carboxamide;

6-((S)-5-((2S,5S)-5-(hydroxymethyl)-1,4-dioxan-2-yl)-4,5-dihydroisoxazol-3-yl)-N-(4-methoxybenzyl)-2-methylpyrimidine-4-carboxamide;

N-(3-chloro-4-fluorobenzyl)-6-((R)-5-((2S,5S)-5-(hydroxymethyl)-1,4-dioxan-2-yl)-4,5-dihydroisoxazol-3-yl)-2-methylpyrimidine-4-carboxamide;

N-(3-chloro-4-fluorobenzyl)-6-((S)-5-((2S,5S)-5-(hydroxymethyl)-1,4-dioxan-2-yl)-4,5-dihydroisoxazol-3-yl)-2-methylpyrimidine-4-carboxamide;

6-((S)-5-((2R,5R)-5-(acetamidomethyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-((S)-5-((2R,5R)-5-(methylsulfonamidoethyl)-1,4-dioxan-2-yl)-4,5-dihydroisoxazol-3-yl)pyrimidine-4-carboxamide;

N-(4-fluoro-3-methoxybenzyl)-2-methyl-6-((S)-5-((2R,5S)-5-(methylsulfonylmethyl)-1,4-dioxan-2-yl)-4,5-dihydroisoxazol-3-yl)pyrimidine-4-carboxamide;

N-(4-fluoro-3-methoxybenzyl)-2-methyl-6-(5-(1-(thiazol-2-ylcarbamoyl)piperidin-4-yl)-4,5-dihydroisoxazol-3-yl)pyrimidine-4-carboxamide;

6-(5-((1r,4r)-4-(Acetamidomethyl)cyclohexyl)-4,5-dihydroisoxazol-3-yl)-N-(4-fluoro-3-methoxybenzyl)-2-methylpyrimidine-4-carboxamide;

6-((R)-5-((1r,4R)-4-(acetamidomethyl)cyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(5-(oxazol-5-yl)pyridin-2-yl)-4,5-dihydroisoxazol-3-yl)pyrimidine-4-carboxamide;

N-(4-fluoro-3-methoxybenzyl)-2-methyl-6-(5-(6-(methylsulfonyl)pyridazin-3-yl)-4,5-dihydroisoxazol-3-yl)pyrimidine-4-carboxamide;

N-(4-fluoro-3-methoxybenzyl)-2-methyl-6-(5-(6-(3-methyl-1,2,4-oxadiazol-5-yl)pyridin-3-yl)-4,5-dihydroisoxazol-3-yl)pyrimidine-4-carboxamide;

6-(5-(6-acetylpyridine-3-yl)-4,5-dihydroisoxazol-3-yl)-N-(4-fluoro-3-methoxybenzyl)-2-methylpyrimidine-4-carboxamide;

6-(3-(6-(4-fluoro-3-methoxybenzylcarbamoyl)-2-methylpyrimidin-4-yl)-4,5-dihydroisoxazol-5-yl)pyridazine-3-carboxamide 2,2,2-trifluoroacetate;

6-(5-(6-cyanopyridazin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((R)-5-((1r,4R)-4-((2-hydroxyacetamido)methyl)cyclohexyl)-4,5-dihydroisoxazol-3-yl)-2-methylpyrimidine-4-carboxamide;

N-(4-fluoro-3-methoxybenzyl)-6-(5-((1r,4r)-4-((2-hydroxyacetamido)methyl)cyclohexyl)-4,5-dihydroisoxazol-3-yl)-2-methylpyrimidine-4-carboxamide;

N-(4-fluoro-3-methoxybenzyl)-2-methyl-6-(5-(1-methyl-3-(3-methyl-1,2,4-oxadiazol-5-yl)-1H-pyrazol-5-yl)-4,5-dihydroisoxazol-3-yl)pyrimidine-4-carboxamide;

6-(5-(3-carbamoyl-1-methyl-1H-pyrazol-5-yl)-4,5-dihydroisoxazol-3-yl)-N-(4-fluoro-3-methoxybenzyl)-2-methylpyrimidine-4-carboxamide;

6-(5-((1r,4r)-4-((2-cyanoacetamido)methyl)cyclohexyl)-4,5-dihydroisoxazol-3-yl)-N-(4-fluoro-3-methoxybenzyl)-2-methylpyrimidine-4-carboxamide;

6-(3-(6-((4-fluoro-3-methoxybenzyl)carbamoyl)-2-methylpyrimidin-4-yl)-4,5-dihydroisoxazol-5-yl)-N-methylpyridazine-3-carboxamide;

N-(4-fluoro-3-methoxybenzyl)-2-methyl-6-(5-(6-(3-methyl-1,2,4-oxadiazol-5-yl)pyridazin-3-yl)-4,5-dihydroisoxazol-3-yl)pyrimidine-4-carboxamide;

N-(4-fluoro-3-methoxybenzyl)-6-((S)-5-((2R,5R)-5-((2-hydroxyacetamido)methyl)-1,4-dioxan-2-yl)-4,5-dihydroisoxazol-3-yl)-2-methylpyrimidine-4-carboxamide;

N-(4-fluoro-3-methoxybenzyl)-2-methyl-6-(5-(6-(oxazol-5-yl)pyridin-3-yl)-4,5-dihydroisoxazol-3-yl)pyrimidine-4-carboxamide;

N-(4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-6-(5-(6-(hydroxymethyl)pyridin-3-yl)-4,5-dihydroisoxazol-3-yl)-2-methylpyrimidine-4-carboxamide;

N-(4-fluoro-3-methoxybenzyl)-6-(5-((1r,4r)-4-(3-(2-hydroxyethyl)ureido)cyclohexyl)-4,5-dihydroisoxazol-3-yl)-2-methylpyrimidine-4-carboxamide;

N-(4-fluoro-3-methoxybenzyl)-6-(5-((1r,4r)-4-(3-(2-hydroxyethyl)-3-methylureido)cyclohexyl)-4,5-dihydroisoxazol-3-yl)-2-methylpyrimidine-4-carboxamide;

N-(4-fluoro-3-methoxybenzyl)-2-methyl-6-(5-(5-(methylsulfonyl)pyrazin-2-yl)-4,5-dihydroisoxazol-3-yl)pyrimidine-4-carboxamide;

6-(5-(6-cyanopyridin-3-yl)-4,5-dihydroisoxazol-3-yl)-N-(4-fluoro-3-methoxybenzyl)-2-methylpyrimidine-4-carboxamide;

6-(5-(1-(3-(dimethylamino)propanoyl)piperidin-4-yl)-4,5-dihydroisoxazol-3-yl)-N-(4-fluoro-3-methoxybenzyl)-2-methylpyrimidine-4-carboxamide;

N-(4-fluoro-3-methylbenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methylbenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(3,4-difluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3,4-difluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

(2R,5S)-5-((S)-3-(6-((4-fluoro-3-methoxybenzyl)carbamoyl)-2-methylpyrimidin-4-yl)-4,5-dihydroisoxazol-5-yl)-1,4-dioxane-2-carboxylic acid;

N-(4-fluoro-3-methoxybenzyl)-2-methyl-6-(5-((1r,4r)-4-(3-methylureido)cyclohexyl)-4,5-dihydroisoxazol-3-yl)pyrimidine-4-carboxamide;

6-(5-((1r,4r)-4-(3,3-dimethylureido)cyclohexyl)-4,5-dihydroisoxazol-3-yl)-N-(4-fluoro-3-methoxybenzyl)-2-methylpyrimidine-4-carboxamide;

N-(3,4-dichlorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3,4-dichlorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-((2-cyanoacetamido)methyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((S)-5-((2R,5R)-5-((2-hydroxy-2-methylpropanamido)methyl)-1,4-dioxan-2-yl)-4,5-dihydroisoxazol-3-yl)-2-methylpyrimidine-4-carboxamide;

N-(4-fluoro-3-methoxybenzyl)-2-methyl-6-((S)-5-((2R,5R)-5-((3-methylureido)methyl)-1,4-dioxan-2-yl)-4,5-dihydroisoxazol-3-yl)pyrimidine-4-carboxamide;

6-((S)-5-((2R,5R)-5-((3,3-dimethylureido)methyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(pyrrolidine-1-carbonyl)-4,5-dihydroisoxazol-3-yl)pyrimidine-4-carboxamide;

6-(5-((1r,4r)-4-(2-(dimethylamino)acetamido)cyclohexyl)-4,5-dihydroisoxazol-3-yl)-N-(4-fluoro-3-methoxybenzyl)-2-methylpyrimidine-4-carboxamide;

6-(5-(1H-pyrazolo[3,4-b]pyridin-5-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-methyl-1H-pyrazolo[3,4-b]pyridin-5-yl)-4,5-dihydroisoxazol-3-yl)pyrimidine-4-carboxamide;

6-(5-(bromomethyl)-4,5-dihydroisoxazol-3-yl)-N-(4-fluoro-3-methoxybenzyl)-2-methylpyrimidine-4-carboxamide;

3-(6-((4-fluoro-3-methoxybenzyl)carbamoyl)-2-methylpyrimidin-4-yl)-N-(2-hydroxyethyl)-4,5-dihydroisoxazole-5-carboxamide;

3-(6-((4-fluoro-3-methoxybenzyl)carbamoyl)-2-methylpyrimidin-4-yl)-4,5-dihydroisoxazole-5-carboxamide;

methyl 3-(6-((4-fluoro-3-methoxybenzyl)carbamoyl)-2-methylpyrimidin-4-yl)-4,5-dihydroisoxazole-5-carboxylate;

N-(4-fluoro-3-methoxybenzyl)-6-((S)-5-((2R,5S)-5-(2-hydroxypropan-2-yl)-1,4-dioxan-2-yl)-4,5-dihydroisoxazol-3-yl)-2-methylpyrimidine-4-carboxamide;

N-(4-fluoro-3-methoxybenzyl)-2-methyl-6-((S)-5-((2R,5S)-5-(methylcarbamoyl)-1,4-dioxan-2-yl)-4,5-dihydroisoxazol-3-yl)pyrimidine-4-carboxamide;

N-(4-fluoro-3-methoxybenzyl)-2-methyl-6-(5-((1r,4r)-4-(methylcarbamoyl)cyclohexyl)-4,5-dihydroisoxazol-3-yl)pyrimidine-4-carboxamide 2,2,2-trifluoroacetate;

6-(5-((1r,4r)-4-carbamoylcyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-((1r,4r)-4-(2-hydroxy-2-methylpropanamido)cyclohexyl)-4,5-dihydroisoxazol-3-yl)-2-methylpyrimidine-4-carboxamide;

N-(4-fluoro-3-methoxybenzyl)-6-(5-((4-((S)-2-hydroxypropanamido)cyclohexyl)-4,5-dihydroisoxazol-3-yl)-2-methylpyrimidine-4-carboxamide;

N-(4-fluoro-3-methoxybenzyl)-6-(5-((3-(hydroxymethyl)pyrrolidin-1-yl)methyl)-4,5-dihydroisoxazol-3-yl)-2-methylpyrimidine-4-carboxamide 2,2,2-trifluoroacetate;

6-(5-((4-acetylpiperazin-1-yl)methyl)-4,5-dihydroisoxazol-3-yl)-N-(4-fluoro-3-methoxybenzyl)-2-methylpyrimidine-4-carboxamide 2,2,2-trifluoroacetate;

6-(5-(6-(dimethylamino)pyridazin-3-yl)-4,5-dihydroisoxazol-3-yl)-N-(4-fluoro-3-methoxybenzyl)-2-methylpyrimidine-4-carboxamide 2,2,2-trifluoroacetate;

N-(4-fluoro-3-methoxybenzyl)-2-methyl-6-(5-(6-(pyrrolidin-1-yl)pyridazin-3-yl)-4,5-dihydroisoxazol-3-yl)pyrimidine-4-carboxamide 2,2,2-trifluoroacetate;

6-(5-((1r,4r)-4-(3-(1,3-dihydroxypropan-2-yl)ureido)cyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-((1r,4r)-4-((2-hydroxyethyl)carbamoyl)cyclohexyl)-4,5-dihydroisoxazol-3-yl)-2-methylpyrimidine-4-carboxamide;

6-(5-((1r,4r)-4-(3-(2,3-dihydroxypropyl)-3-methylureido)cyclohexyl)-4,5-dihydroisoxazol-3-yl)-N-(4-fluoro-3-methoxybenzyl)-2-methylpyrimidine-4-carboxamide;

6-(5-((1r,4r)-4-Acetamidocyclohexyl)-4,5-dihydroisoxazol-3-yl)-N-(4-fluoro-3-methylbenzyl)-2-methylpyrimidine-4-carboxamide;

6-(5-(6-cyanopyridazin-3-yl)-4,5-dihydroisoxazol-3-yl)-N-(4-fluoro-3-methylbenzyl)-2-methylpyrimidine-4-carboxamide;

N-(4-fluoro-3-methoxybenzyl)-2-methyl-6-(5-((1r,4r)-4-(2-(methylamino)acetamido)cyclohexyl)-4,5-dihydroisoxazol-3-yl)pyrimidine-4-carboxamide;

N-(4-fluoro-3-methylbenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;

6-((S)-5-((2R,5R)-5-(acetamidomethyl)-1,4-dioxan-2-yl)-4,5-dihydroisoxazol-3-yl)-N-(4-fluoro-3-methylbenzyl)-2-methylpyrimidine-4-carboxamide;

6-((S)-5-((2R,5R)-5-(acetamidomethyl)-1,4-dioxan-2-yl)-4,5-dihydroisoxazol-3-yl)-N-(3-chloro-4-fluorobenzyl)-2-methylpyrimidine-4-carboxamide;

N-(3-chloro-4-fluorobenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;

N-(4-fluoro-3-methylbenzyl)-2-methyl-6-(5-(1-methyl-6-oxo-1,6-dihydropyridin-3-yl)-4,5-dihydroisoxazol-3-yl)pyrimidine-4-carboxamide 2,2,2-trifluoroacetate;

6-((S)-5-((2R,5R)-5-(hydroxymethyl)-1,4-dioxan-2-yl)-4,5-dihydroisoxazol-3-yl)-2-methyl-N-(3-methylbenzyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-(3-methylbenzyl)pyrimidine-4-carboxamide;

6-(5-(6-cyanopyridazin-3-yl)-4,5-dihydroisoxazol-3-yl)-N-(4-fluorobenzyl)-2-methylpyrimidine-4-carboxamide;

N-(4-fluorobenzyl)-2-methyl-6-(5-(1-methyl-6-oxo-1,6-dihydropyridin-3-yl)-4,5-dihydroisoxazol-3-yl)pyrimidine-4-carboxamide 2,2,2-trifluoroacetate;

N-(4-fluoro-3-methoxybenzyl)-6-(5-(1-(2-hydroxyethyl)-6-oxo-1,6-dihydropyridin-3-yl)-4,5-dihydroisoxazol-3-yl)-2-methylpyrimidine-4-carboxamide 2,2,2-trifluoroacetate;

N-(3-chloro-4-fluorobenzyl)-2-methyl-6-(5-(1-methyl-6-oxo-1,6-dihydropyridin-3-yl)-4,5-dihydroisoxazol-3-yl)pyrimidine-4-carboxamide;

N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

6-(5-(6-cyanopyridazin-3-yl)-4,5-dihydroisoxazol-3-yl)-N-(3,4-difluorobenzyl)-2-methylpyrimidine-4-carboxamide 2,2,2-trifluoroacetate;

N-(3-chloro-4-fluorobenzyl)-6-(5-(6-cyanopyridazin-3-yl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-N-(3-chloro-4-fluorobenzyl)-2-methylpyrimidine-4-carboxamide;

6-(5-((1r,4r)-4-acetamidocyclohexyl)-4,5-dihydroisoxazol-3-yl)-N-(4-fluorobenzyl)-2-methylpyrimidine-4-carboxamide;

6-(5-((1r,4r)-4-acetamidocyclohexyl)-4,5-dihydroisoxazol-3-yl)-N-(3,4-difluorobenzyl)-2-methylpyrimidine-4-carboxamide;

N-((2,3-dihydrobenzofuran-5-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-2-methyl-N-((2-methylbenzo[d]oxazol-5-yl)methyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-((2-methylbenzo[d]oxazol-5-yl)methyl)pyrimidine-4-carboxamide;

N-(4-fluoro-3-methoxybenzyl)-6-((S)-5-((2R,5R)-5-(methoxymethyl)-1,4-dioxan-2-yl)-4,5-dihydroisoxazol-3-yl)-2-methylpyrimidine-4-carboxamide;

N-(4-fluoro-3-methoxybenzyl)-6-((R)-5-((2R,5R)-5-(methoxymethyl)-1,4-dioxan-2-yl)-4,5-dihydroisoxazol-3-yl)-2-methylpyrimidine-4-carboxamide;

N-(4-fluoro-3-methoxybenzyl)-6-((S)-5-((2R,5R)-5-(((S)-2-hydroxypropanamido)methyl)-1,4-dioxan-2-yl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-N-(3,4-difluorobenzyl)-2-methylpyrimidine-4-carboxamide;

N-(3-chloro-4-fluorobenzyl)-6-(5-((1S,4r)-4-((S)-2-hydroxypropanamido)cyclohexyl)-4,5-dihydroisoxazol-3-yl)-2-methylpyrimidine-4-carboxamide;

N-((2,3-dihydrobenzo[b][1,4]dioxin-6-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-((2,3-dihydrobenzo[b][1,4]dioxin-6-yl)methyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methylbenzyl)-2-methyl-6-(5-(1-methyl-6-oxo-1,6-dihydropyridin-3-yl)-4,5-dihydroisoxazol-3-yl)pyrimidine-4-carboxamide;

6-((S)-5-((2R,5R)-5-(hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide 2,2,2-trifluoroacetate;

6-((R)-5-((2R,5R)-5-(hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide 2,2,2-trifluoroacetate;

N-(4-fluoro-3-methoxybenzyl)-2-methyl-6-(5-(1-methyl-2-oxo-1,2-dihydropyridin-4-yl)-4,5-dihydroisoxazol-3-yl)pyrimidine-4-carboxamide;

6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-methyl-6-oxo-1,6-dihydropyridazin-3-yl)-4,5-dihydroisoxazol-3-yl)pyrimidine-4-carboxamide;

tert-butyl ((1r,4r)-4-(3-(6-((4-fluoro-3-methoxybenzyl)carbamoyl)-2-methylpyrimidin-4-yl)-4,5-dihydroisoxazol-5-yl)cyclohexyl)carbamate;

N-(4-fluoro-3-methoxybenzyl)-2-methyl-6-(5-(1-(2-(methylamino)-2-oxoethyl)-6-oxo-1,6-dihydropyridin-3-yl)-4,5-dihydroisoxazol-3-yl)pyrimidine-4-carboxamide;

N-(4-fluoro-3-methoxybenzyl)-6-(5-(1-isopropyl-6-oxo-1,6-dihydropyridin-3-yl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-2-methyl-N-(pyridin-4-ylmethyl)pyrimidine-4-carboxamide;

6-((S)-5-((2R,5R)-5-(hydroxymethyl)-1,4-dioxan-2-yl)-4,5-dihydroisoxazol-3-yl)-2-methyl-N-(pyridin-4-ylmethyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-(pyridin-4-ylmethyl)pyrimidine-4-carboxamide;

6-(5-((1r,4r)-4-acetamidocyclohexyl)-4,5-dihydroisoxazol-3-yl)-2-methyl-N-((1-methyl-2-oxo-1,2-dihydropyridin-4-yl)methyl)pyrimidine-4-carboxamide;

6-(5-((1r,4r)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

N—((R)-1-(4-fluoro-3-methoxyphenyl)ethyl)-2-methyl-6-(5-phenyl-4,5-dihydroisoxazol-3-yl)pyrimidine-4-carboxamide;

N—((S)-1-(4-fluoro-3-methoxyphenyl)ethyl)-2-methyl-6-(5-phenyl-4,5-dihydroisoxazol-3-yl)pyrimidine-4-carboxamide;

6-((S)-5-((2R,5R)-5-(hydroxymethyl)-1,4-dioxan-2-yl)-4,5-dihydroisoxazol-3-yl)-2-methyl-N-((1-methyl-2-oxo-1,2-dihydropyridin-4-yl)methyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-((1-methyl-2-oxo-1,2-dihydropyridin-4-yl)methyl)pyrimidine-4-carboxamide;

6-(5-((1r,4r)-4-acetamidocyclohexyl)-4,5-dihydroisoxazol-3-yl)-2-methyl-N-(quinolin-4-ylmethyl)pyrimidine-4-carboxamide;

(S)—N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide N-(4-fluoro-3-methoxybenzyl)-2-methyl-6-(5-(1-methyl-2-oxo-1,2-dihydropyridin-4-yl)-4,5-dihydroisoxazol-3-yl)pyrimidine-4-carboxamide;

6-((S)-5-((1r,4S)-4-acetamidocyclohexyl)-4,5-dihydroisoxazol-3-yl)-N-(4-fluoro-3-methylbenzyl)-2-methylpyrimidine-4-carboxamide;

6-((S)-5-((2R,5R)-5-(hydroxymethyl)-1,4-dioxan-2-yl)-4,5-dihydroisoxazol-3-yl)-2-methyl-N-(quinolin-4-ylmethyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-(quinolin-4-ylmethyl)pyrimidine-4-carboxamide;

N-(4-fluoro-3-methoxybenzyl)-6-((S)-5-((2R,5R)-5-((2-hydroxy-2-methylpropanamido)methyl)-1,4-dioxan-2-yl)-4,5-dihydroisoxazol-3-yl)-2-methylpyrimidine-4-carboxamide;

6-((S)-5-((2R,5R)-5-(acetamidomethyl)-1,4-dioxan-2-yl)-4,5-dihydroisoxazol-3-yl)-N-(3-chloro-4-fluorobenzyl)-2-methylpyrimidine-4-carboxamide;

6-(5-(6-cyanopyridazin-3-yl)-4,5-dihydroisoxazol-3-yl)-N-(3,4-difluorobenzyl)-2-methylpyrimidine-4-carboxamide 2,2,2-trifluoroacetate;

6-((S)-5-((1r,4S)-4-acetamidocyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(4-fluoro-3-methoxybenzyl)-6-((R)-5-((1S,4R)-4-((S)-2-hydroxypropanamido)cyclohexyl)-4,5-dihydroisoxazol-3-yl)-2-methylpyrimidine-4-carboxamide;

N-(4-Fluorobenzyl)-6-(5-((1S,4r)-4-((S)-2-hydroxypropanamido)cyclohexyl)-4,5-dihydroisoxazol-3-yl)-2-methylpyrimidine-4-carboxamide;

N-(4-fluoro-3-methylbenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(4-fluoro-3-methylbenzyl)-6-((R)-5-((1S,4R)-4-((S)-2-hydroxypropanamido)cyclohexyl)-4,5-dihydroisoxazol-3-yl)-2-methylpyrimidine-4-carboxamide;

N-(3-chloro-4-fluorobenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(3-chloro-4-fluorobenzyl)-6-((R)-5-((1S,4R)-4-((S)-2-hydroxypropanamido)cyclohexyl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-N-((2-oxo-1,2,3,4,4a,8a-hexahydroquinolin-7-yl)methyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-((2-oxo-1,2,3,4-tetrahydroquinolin-7-yl)methyl)pyrimidine-4-carboxamide;

N-(4-fluoro-3-methoxybenzyl)-2-methyl-6-(5-(1-(2-(methylamino)-2-oxoethyl)-2-oxo-1,2-dihydropyridin-4-yl)-4,5-dihydroisoxazol-3-yl)pyrimidine-4-carboxamide;

N-(3,4-difluorobenzyl)-2-methyl-6-(5-(1-methyl-2-oxo-1,2-dihydropyridin-4-yl)-4,5-dihydroisoxazol-3-yl)pyrimidine-4-carboxamide;

(S)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

(R)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

N-(4-fluoro-3-methoxybenzyl)-6-(5-(6-methoxypyridazin-3-yl)-4,5-dihydroisoxazol-3-yl)-2-methylpyrimidine-4-carboxamide;

N-(4-fluoro-3-methoxybenzyl)-6-(5-(6-methoxypyridazin-3-yl)-4,5-dihydroisoxazol-3-yl)-2-methylpyrimidine-4-carboxamide;

(S)—N-(4-fluoro-3-methoxybenzyl)-2-methyl-6-(5-(1-(2-(methylamino)-2-oxoethyl)-6-oxo-1,6-dihydropyridazin-3-yl)-4,5-dihydroisoxazol-3-yl)pyrimidine-4-carboxamide;

(R)—N-(4-fluoro-3-methoxybenzyl)-2-methyl-6-(5-(1-(2-(methylamino)-2-oxoethyl)-6-oxo-1,6-dihydropyridazin-3-yl)-4,5-dihydroisoxazol-3-yl)pyrimidine-4-carboxamide;

2-methyl-6-(5-(1-methyl-6-oxo-1,6-dihydropyridin-3-yl)-4,5-dihydroisoxazol-3-yl)-N-((3-oxo-3,4-dihydro-2H-benzo[b][1,4]oxazin-6-yl)methyl)pyrimidine-4-carboxamide;

N-(4-fluoro-3-methoxybenzyl)-6-(5-(1-(2-(methoxy(methyl)amino)-2-oxoethyl)-6-oxo-1,6-dihydropyridin-3-yl)-4,5-dihydroisoxazol-3-yl)-2-methylpyrimidine-4-carboxamide;

6-(5-(5-chloro-1-(2-(methylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-(6-methoxy-5,6-dihydropyridin-2-yl)-4,5-dihydroisoxazol-3-yl)-2-methylpyrimidine-4-carboxamide;

6-(5-(1-cyclopropyl-6-oxo-1,6-dihydropyridazin-3-yl)-4,5-dihydroisoxazol-3-yl)-N-(4-fluoro-3-methoxybenzyl)-2-methylpyrimidine-4-carboxamide;

6-(5-(1-cyclopropyl-2-oxo-1,2-dihydropyridin-4-yl)-4,5-dihydroisoxazol-3-yl)-N-(4-fluoro-3-methoxybenzyl)-2-methylpyrimidine-4-carboxamide;

6-(5-(1-(2-(dimethylamino)-2-oxoethyl)-2-oxo-1,2-dihydropyridin-4-yl)-4,5-dihydroisoxazol-3-yl)-N-(4-fluoro-3-methoxybenzyl)-2-methylpyrimidine-4-carboxamide;

6-((S)-5-((1s,4R)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-((R)-5-((1r,4R)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

N-(4-fluoro-3-methoxybenzyl)-2-methyl-6-(5-(1-(2-(methylamino)-2-oxoethyl)-6-oxo-1,6-dihydropyridazin-3-yl)-4,5-dihydroisoxazol-3-yl)pyrimidine-4-carboxamide;

6-((S)-5-((2R,5R)-5-(hydroxymethyl)-1,4-dioxan-2-yl)-4,5-dihydroisoxazol-3-yl)-2-methyl-N-((1-methyl-6-oxo-1,6-dihydropyridin-3-yl)methyl)pyrimidine-4-carboxamide;

N-(4-fluoro-3-methoxybenzyl)-6-(5-(1-(2-(isopropylamino)-2-oxoethyl)-6-oxo-1,6-dihydropyridin-3-yl)-4,5-dihydroisoxazol-3-yl)-2-methylpyrimidine-4-carboxamide;

6-(5-((1S,4r)-4-((S)-2-hydroxypropanamido)cyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-(5-(3-chloro-5-cyclopropyl-4-oxocyclohexyl)-4,5-dihydroisoxazol-3-yl)-N-(4-fluoro-3-methoxybenzyl)-2-methylpyrimidine-4-carboxamide;

(S)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

(R)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

(R)-6-(5-(1-cyclopropyl-6-oxo-1,6-dihydropyridazin-3-yl)-4,5-dihydroisoxazol-3-yl)-N-(4-fluoro-3-methoxybenzyl)-2-methylpyrimidine-4-carboxamide;

6-(5-(1-cyclopropyl-6-oxo-1,6-dihydropyridin-3-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-(5-(1-(2-(cyclopropylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-1-methyl-6-oxo-5-(5-phenyl-4,5-dihydroisoxazol-3-yl)-1,6-dihydropyridazine-3-carboxamide;

N-(4-fluoro-3-methoxybenzyl)-6-(5-(1-(1-methoxyethyl)-2-oxo-1,2-dihydropyridin-4-yl)-4,5-dihydroisoxazol-3-yl)-2-methylpyrimidine-4-carboxamide; or N-(4-fluoro-3-methoxybenzyl)-6-(5-(1-(2-(isopropylamino)allyl)-2-oxo-1,2-dihydropyridin-4-yl)-4,5-dihydroisoxazol-3-yl)-2-methylpyrimidine-4-carboxamide.

24. The compound according to claim 23 wherein the compound is

N-(4-Fluoro-3-methoxybenzyl)-6-((S)-5-((2R,5R)-5-(hydroxymethyl)-1,4-dioxan-2-yl)-4,5-dihydro-isoxazol-3-yl)-2-methylpyrimidine-4-carboxamide;

N-(4-fluoro-3-methoxybenzyl)-6-((S)-5-((2S,5S)-5-(hydroxymethyl)-1,4-dioxan-2-yl)-4,5-dihydroisoxazol-3-yl)-2-methylpyrimidine-4-carboxamide;

6-((R)-5-((1r,4R)-4-acetamidocyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((R)-5-((1r,4R)-4-(2-hydroxyacetamido)cyclohexyl)-4,5-dihydroisoxazol-3-yl)-2-methylpyrimidine-4-carboxamide;

N-(3-chloro-4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide;

N-(4-fluoro-3-methoxybenzyl)-2-methyl-6-((S)-5-((2R,5S)-5-(methylsulfonylmethyl)-1,4-dioxan-2-yl)-4,5-dihydroisoxazol-3-yl)pyrimidine-4-carboxamide;

N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-(acetamidomethyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-((S)-5-((2R,5R)-5-(methylsulfonamidoethyl)-1,4-dioxan-2-yl)-4,5-dihydroisoxazol-3-yl)pyrimidine-4-carboxamide;

6-((R)-5-((1r,4R)-4-(acetamidomethyl)cyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(6-(methylsulfonyl)pyridazin-3-yl)-4,5-dihydroisoxazol-3-yl)pyrimidine-4-carboxamide;

(S)—N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide;

6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-methyl-6-oxo-1,6-dihydropyridazin-3-yl)-4,5-dihydroisoxazol-3-yl)pyrimidine-4-carboxamide;

6-(5-((1r,4r)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

N-(4-fluoro-3-methoxybenzyl)-2-methyl-6-(5-(1-(2-(methylamino)-2-oxoethyl)-6-oxo-1,6-dihydropyridin-3-yl)-4,5-dihydroisoxazol-3-yl)pyrimidine-4-carboxamide;

N-(4-fluoro-3-methylbenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(3,4-difluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3,4-difluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

(2R,5S)-5-((S)-3-(6-((4-fluoro-3-methoxybenzyl)carbamoyl)-2-methylpyrimidin-4-yl)-4,5-dihydroisoxazol-5-yl)-1,4-dioxane-2-carboxylic acid;

N-(4-fluoro-3-methoxybenzyl)-2-methyl-6-(5-((1r,4r)-4-(3-methylureido)cyclohexyl)-4,5-dihydroisoxazol-3-yl)pyrimidine-4-carboxamide;

6-(5-((1r,4r)-4-(3,3-dimethylureido)cyclohexyl)-4,5-dihydroisoxazol-3-yl)-N-(4-fluoro-3-methoxybenzyl)-2-methylpyrimidine-4-carboxamide;

N-(3,4-dichlorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-((2-cyanoacetamido)methyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-((S)-5-((2R,5R)-5-((3-methylureido)methyl)-1,4-dioxan-2-yl)-4,5-dihydroisoxazol-3-yl)pyrimidine-4-carboxamide;

(2S,5R)-5-((S)-3-(6-((4-fluoro-3-methoxybenzyl)carbamoyl)-2-methylpyrimidin-4-yl)-4,5-dihydroisoxazol-5-yl)-1,4-dioxane-2-carboxylic acid;

6-((S)-5-((2R,5R)-5-((3,3-dimethylureido)methyl)-1,4-dioxan-2-yl)-4,5-dihydroisoxazol-3-yl)-N-(4-fluoro-3-methoxybenzyl)-2-methylpyrimidine-4-carboxamide;

6-(5-((1r,4r)-4-(2-(dimethylamino)acetamido)cyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((S)-5-((2R,5S)-5-(2-hydroxypropan-2-yl)-1,4-dioxan-2-yl)-4,5-dihydroisoxazol-3-yl)-2-methylpyrimidine-4-carboxamide;

N-(4-fluoro-3-methoxybenzyl)-2-methyl-6-((S)-5-((2R,5S)-5-(methylcarbamoyl)-1,4-dioxan-2-yl)-4,5-dihydroisoxazol-3-yl)pyrimidine-4-carboxamide;

N-(4-fluoro-3-methoxybenzyl)-2-methyl-6-(5-((1r,4r)-4-(methylcarbamoyl)cyclohexyl)-4,5-dihydroisoxazol-3-yl)pyrimidine-4-carboxamide 2,2,2-trifluoroacetate;

6-(5-((1r,4r)-4-carbamoylcyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-((4-((S)-2-hydroxypropanamido)cyclohexyl)-4,5-dihydroisoxazol-3-yl)-2-methylpyrimidine-4-carboxamide;

N-(4-fluoro-3-methoxybenzyl)-6-(5-((1r,4r)-4-(2-hydroxy-2-methylpropanamido)cyclohexyl)-4,5-dihydroisoxazol-3-yl)-2-methylpyrimidine-4-carboxamide;

6-(5-((1r,4r)-4-(3-(1,3-dihydroxypropan-2-yl)ureido)cyclohexyl)-4,5-dihydroisoxazol-3-yl)-N-(4-fluoro-3-methoxybenzyl)-2-methylpyrimidine-4-carboxamide;

6-(5-((1r,4r)-4-(2-cyanoacetamido)cyclohexyl)-4,5-dihydroisoxazol-3-yl)-N-(4-fluoro-3-methoxybenzyl)-2-methylpyrimidine-4-carboxamide;

6-((S)-5-((2R,5S)-5-Carbamoyl-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(pyridin-3-yl)-4,5-dihydro-1H-pyrazol-3-yl)pyrimidine-4-carboxamide;

N-(4-fluoro-3-methoxybenzyl)-6-(5-((1r,4r)-4-((2-hydroxyethyl)carbamoyl)cyclohexyl)-4,5-dihydroisoxazol-3-yl)-2-methylpyrimidine-4-carboxamide;

6-(5-((1r,4r)-4-(3-(2,3-dihydroxypropyl)-3-methylureido)cyclohexyl)-4,5-dihydroisoxazol-3-yl)-N-(4-fluoro-3-methoxybenzyl)-2-methylpyrimidine-4-carboxamide;

6-(5-((1r,4r)-4-acetamidocyclohexyl)-4,5-dihydroisoxazol-3-yl)-N-(4-fluoro-3-methylbenzyl)-2-methylpyrimidine-4-carboxamide;

6-(5-(6-cyanopyridazin-3-yl)-4,5-dihydroisoxazol-3-yl)-N-(4-fluoro-3-methylbenzyl)-2-methylpyrimidine-4-carboxamide;

N-(4-fluoro-3-methoxybenzyl)-2-methyl-6-(5-((1r,4r)-4-(2-(methylamino)acetamido)cyclohexyl)-4,5-dihydroisoxazol-3-yl)pyrimidine-4-carboxamide;

N-(4-fluoro-3-methylbenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;

6-((S)-5-((2R,5R)-5-(acetamidomethyl)-1,4-dioxan-2-yl)-4,5-dihydroisoxazol-3-yl)-N-(4-fluoro-3-methylbenzyl)-2-methylpyrimidine-4-carboxamide;

N-(3-chloro-4-fluorobenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;

N-(4-fluoro-3-methylbenzyl)-2-methyl-6-(5-(1-methyl-6-oxo-1,6-dihydropyridin-3-yl)-4,5-dihydroisoxazol-3-yl)pyrimidine-4-carboxamide 2,2,2-trifluoroacetate;

6-((S)-5-((2R,5R)-5-(hydroxymethyl)-1,4-dioxan-2-yl)-4,5-dihydroisoxazol-3-yl)-2-methyl-N-(3-methylbenzyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-(3-methylbenzyl)pyrimidine-4-carboxamide;

6-(5-(6-cyanopyridazin-3-yl)-4,5-dihydroisoxazol-3-yl)-N-(4-fluorobenzyl)-2-methylpyrimidine-4-carboxamide;

N-(4-fluorobenzyl)-2-methyl-6-(5-(1-methyl-6-oxo-1,6-dihydropyridin-3-yl)-4,5-dihydroisoxazol-3-yl)pyrimidine-4-carboxamide 2,2,2-trifluoroacetate;

N-(4-fluoro-3-methoxybenzyl)-6-(5-(1-(2-hydroxyethyl)-6-oxo-1,6-dihydropyridin-3-yl)-4,5-dihydroisoxazol-3-yl)-2-methylpyrimidine-4-carboxamide 2,2,2-trifluoroacetate;

N-(3-chloro-4-fluorobenzyl)-2-methyl-6-(5-(1-methyl-6-oxo-1,6-dihydropyridin-3-yl)-4,5-dihydroisoxazol-3-yl)pyrimidine-4-carboxamide;

N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

N-(3-chloro-4-fluorobenzyl)-6-(5-(6-cyanopyridazin-3-yl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-N-(3-chloro-4-fluorobenzyl)-2-methylpyrimidine-4-carboxamide;

6-(5-((1r,4r)-4-acetamidocyclohexyl)-4,5-dihydroisoxazol-3-yl)-N-(4-fluorobenzyl)-2-methylpyrimidine-4-carboxamide;

6-(5-((1r,4r)-4-acetamidocyclohexyl)-4,5-dihydroisoxazol-3-yl)-N-(3,4-difluorobenzyl)-2-methylpyrimidine-4-carboxamide;

N-((2,3-dihydrobenzofuran-5-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-2-methyl-N-((2-methylbenzo[d]oxazol-5-yl)methyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-((2-methylbenzo[d]oxazol-5-yl)methyl)pyrimidine-4-carboxamide;

6-((S)-5-((1r,4S)-4-acetamidocyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((S)-5-((2R,5R)-5-(methoxymethyl)-1,4-dioxan-2-yl)-4,5-dihydroisoxazol-3-yl)-2-methylpyrimidine-4-carboxamide;

N-(4-fluoro-3-methoxybenzyl)-6-((R)-5-((2R,5R)-5-(methoxymethyl)-1,4-dioxan-2-yl)-4,5-dihydroisoxazol-3-yl)-2-methylpyrimidine-4-carboxamide;

N-(4-fluoro-3-methoxybenzyl)-6-((S)-5-((2R,5R)-5-(((S)-2-hydroxypropanamido)methyl)-1,4-dioxan-2-yl)-4,5-dihydroisoxazol-3-yl)-2-methylpyrimidine-4-carboxamide;

N-(4-fluoro-3-methoxybenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(4-fluoro-3-methoxybenzyl)-6-((R)-5-((1S,4R)-4-((S)-2-hydroxypropanamido)cyclohexyl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-N-(3,4-difluorobenzyl)-2-methylpyrimidine-4-carboxamide;

N-(3-chloro-4-fluorobenzyl)-6-(5-((1S,4r)-4-((S)-2-hydroxypropanamido)cyclohexyl)-4,5-dihydroisoxazol-3-yl)-2-methylpyrimidine-4-carboxamide;

N-((2,3-dihydrobenzo[b][1,4]dioxin-6-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-((2,3-dihydrobenzo[b][1,4]dioxin-6-yl)methyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(4-Fluorobenzyl)-6-(5-((1S,4r)-4-((S)-2-hydroxypropanamido)cyclohexyl)-4,5-dihydroisoxazol-3-yl)-2-methylpyrimidine-4-carboxamide;

N-(4-fluoro-3-methylbenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(4-fluoro-3-methylbenzyl)-6-((R)-5-((1S,4R)-4-((S)-2-hydroxypropanamido)cyclohexyl)-4,5-dihydroisoxazol-3-yl)-2-methylpyrimidine-4-carboxamide;

N-(3-chloro-4-fluorobenzyl)-6-((S)-5-((1S,4S)-4-((S)-2-hydroxypropan amido)cyclohexyl)-4,5-dihydroisoxazol-3-yl)-2-methylpyrimidine-4-carboxamide;

N-(3-chloro-4-fluorobenzyl)-6-((R)-5-((1S,4R)-4-((S)-2-hydroxypropanamido)cyclohexyl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide 2,2,2-trifluoroacetate;

6-((R)-5-((2R,5R)-5-(hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide 2,2,2-trifluoroacetate;

(S)—N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide N-(4-fluoro-3-methoxybenzyl)-2-methyl-6-(5-(1-methyl-2-oxo-1,2-dihydropyridin-4-yl)-4,5-dihydroisoxazol-3-yl)pyrimidine-4-carboxamide;

6-((S)-5-((1r,4S)-4-acetamidocyclohexyl)-4,5-dihydroisoxazol-3-yl)-N-(4-fluoro-3-methylbenzyl)-2-methylpyrimidine-4-carboxamide;

(S)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

(R)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

N-(4-fluoro-3-methoxybenzyl)-6-(5-(6-methoxypyridazin-3-yl)-4,5-dihydroisoxazol-3-yl)-2-methylpyrimidine-4-carboxamide;

(S)—N-(4-fluoro-3-methoxybenzyl)-2-methyl-6-(5-(1-(2-(methylamino)-2-oxoethyl)-6-oxo-1,6-dihydropyridazin-3-yl)-4,5-dihydroisoxazol-3-yl)pyrimidine-4-carboxamide;

2-methyl-6-(5-(1-methyl-6-oxo-1,6-dihydropyridin-3-yl)-4,5-dihydroisoxazol-3-yl)-N-((3-oxo-3,4-dihydro-2H-benzo[b][1,4]oxazin-6-yl)methyl)pyrimidine-4-carboxamide;

N-(4-fluoro-3-methoxybenzyl)-6-(5-(1-(2-(methoxy(methyl)amino)-2-oxoethyl)-6-oxo-1,6-dihydropyridin-3-yl)-4,5-dihydroisoxazol-3-yl)-2-methylpyrimidine-4-carboxamide;

6-(5-(5-chloro-1-(2-(methylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide;

6-((S)-5-((1s,4R)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-((R)-5-((1r,4R)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

N-(4-fluoro-3-methoxybenzyl)-6-(5-(1-(2-(isopropylamino)-2-oxoethyl)-6-oxo-1,6-dihydropyridin-3-yl)-4,5-dihydroisoxazol-3-yl)-2-methylpyrimidine-4-carboxamide;

6-(5-((1S,4r)-4-((S)-2-hydroxypropanamido)cyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-(5-(3-chloro-5-cyclopropyl-4-oxocyclohexyl)-4,5-dihydroisoxazol-3-yl)-N-(4-fluoro-3-methoxybenzyl)-2-methylpyrimidine-4-carboxamide;

(S)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

(R)-6-(5-(1-cyclopropyl-6-oxo-1,6-dihydropyridazin-3-yl)-4,5-dihydroisoxazol-3-yl)-N-(4-fluoro-3-methoxybenzyl)-2-methylpyrimidine-4-carboxamide;

6-(5-(1-cyclopropyl-6-oxo-1,6-dihydropyridin-3-yl)-4,5-dihydroisoxazol-3-yl)-2-methyl-N-((3-oxo-3,4-dihydro-2H-benzo[b][1,4]oxazin-6-yl)methyl)pyrimidine-4-ca)rboxamide;

6-(5-(1-(2-(cyclopropylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide; or N-(4-fluoro-3-methoxybenzyl)-1-methyl-6-oxo-5-(5-phenyl-4,5-dihydroisoxazol-3-yl)-1,6-dihydropyridazine-3-carboxamide.

In another embodiment the invention provides a pharmaceutical composition comprising a compound, biologically active metabolite, pro-drug, isomer, stereoisomer, solvate, hydrate or pharmaceutically acceptable salt according to any of the foregoing embodiments and a pharmaceutically acceptable carrier or excipient.

In another embodiment the invention provides a kit comprising a composition according to any of the foregoing embodiments, packaging and instructions for use.

In another embodiment the invention provides a method of treating a disease or condition comprising administering a therapeutically effective amount of a compound, biologically active metabolite, pro-drug, isomer, stereoisomer, solvate, hydrate or pharmaceutically acceptable salt according to any of the foregoing embodiments.

In another embodiment the invention provides a method according to the previous embodiment wherein the disease or condition is osteoarthritis, traumatic joint injurty (anterior cruciate igament tear/meniscal tear), rheumatoid arthritis, juvenile arthritis, psoriatic arthritis, gouty arthritis, degenerative joint disease, systemic lupus erythematosus, cardiovascular disorders, such as acute myocardial infarction, acute coronary syndrome, chronic heart failure, myocardial infarction, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease, the treatment of an ocular condition, a cancer, ankylosing spondylitis, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection, bone marrow transplant rejection, acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasulitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency related diseases, Hepatitis A, Hepatitis B, Hepatitis C, His bundle arrythmias, HIV infection/HIV neuropathy, common varied immunodeficiency, common variable hypogammaglobulinaemia, dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, SjSgren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute pain, chronic pain, Goodpasture's syndrome, pulmonary manifestation of polyarteritis nodosa, acute rheumatic fever, rheumatoid spondylitis, Still's disease, systemic sclerosis, Sjigren's syndrome, Takayasu's disease/arteritis, autoimmune thrombocytopaenia, toxicity, transplants, diabetic retinopathy, retinopathy of prematurity, choroidal neovascularization due to age-related macular degeneration, infantile hemangiomas, ascites, effusions, exudates, macular edema, cerebral edema, acute lung injury, adult respiratory distress syndrome, proliferative disorders, restenosis, fibrotic disorders, hepatic cirrhosis, atherosclerosis, mesangial cell proliferative disorders, diabetic nephropathy, malignant nephrosclerosis, thrombotic microangiopathy syndromes, glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma, diabetic retinopathy, retinopathy of prematurity, age-related macular degeneration, hyperproliferative disorder, thyroid hyperplasia, Grave's disease, cysts, hypervascularity of ovarian stroma characteristic of polycystic ovarian syndrome, Stein-Leventhal syndrome, or polycystic kidney.

In another embodiment the invention provides a method according to the previous embodiment wherein the disease or condition is osteoarthritis, rheumatoid arthritis, juvenile arthritis, psoriatic arthritis, degenerative joint disease or systemic lupus erythematosus.

DETAILED DESCRIPTION OF THE INVENTION

Many autoimmune diseases and disease associated with chronic inflammation, as well as acute responses, have been linked to excessive or unregulated production or activity of one or more cytokines.

The compounds of the invention are useful in the treatment of diseases mediated by MMP-13 enzyme such as Osteoarthritis as well as other related diseases such as Rheumatoid arthritis, Juvenile arthritis, Psoriatic arthritis, Gouty arthritis, Degenerative joint disease and Systemic lupus erythematosus.

The compounds of the invention are also useful in the treatment of cardiovascular disorders, such as acute myocardial infarction, acute coronary syndrome, chronic heart failure, myocardial infarction, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of an ocular condition, a cancer, rheumatoid arthritis, ankylosing spondilitis, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2 (REMICADE™), SIMPONI™ (golimumab), CIMZIA™, ACTEMRA™, CDP 571, and soluble p55 or p75 TNF receptors, derivatives, thereof, p75TNFRIgG (ENBREL™) or p55TNFRIgG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), crqmoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., NIK, IKK, p38 or MAP kinase inhibitors), IL-13 converting enzyme inhibitors, T-cell signalinginhibitors such as kinase inhibitors, ADAMTS-4/5 inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-IRI, sIL-IRII, sIL-6R), antiinflammatory cytokines (e.g. IL-4, IL-10, IL-II, IL-13 and TGFβ), celecoxib, folic acid, hydroxychloroquine sulfate, rofecoxib, etanercept, infliximab, naproxen, valdecoxib, taneazumab, fulranumab, REGN475, ABT-110, medi-578, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, SIP1 agonists (such as FTY720), anti-NGF (nerve growth factor) agents and Mesopram. Preferred combinations include methotrexate or leflunomide and in moderate or severe rheumatoid arthritis cases, cyclosporin and anti-TNF antibodies as noted above.

Non-limiting examples of therapeutic agents for inflammatory bowel disease with which a compound of Formula (I)

of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signaling by proinflammatory cytokines such as TNFα or IL-1 (e.g. NIK, IKK, or MAP kinase inhibitors); IL-1β converting enzyme inhibitors; TNFα converting enzyme inhibitors; T-cell signaling inhibitors such as kinase inhibitors; ADAMTS-4/5 inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g., NIK, IKK, p38 or MAP kinase inhibitors), IL-β converting enzyme inhibitors, TACE inhibitors, T-cell signaling inhibitors such as kinase inhibitors, ADAMTS-4/5 inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I) can be combined include the following: Interferon-alpha-2α, Interferon-alpha-2β, Interferon-alpha con1, Interferon-alpha-n1, pegylated interferon-alpha-2α, pegylated interferon-alpha-23, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) can be combined include the following: prednisone, azathioprine, albuterol, colchicine, albuterol sulfate, digoxin, gamma interferon, methylprednisolone sodium succinate, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hydrochloride/magnesium carbonate, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (U.S. Pat. No. 6,090,382, HUMIRA™), and efalizumab.

Non-limiting examples of therapeutic agents for restenosis with which a compound of Formula (I) can be combined include the following: sirolimus, paclitaxel, everolimus, tacrolimus, ABT-578, and acetaminophen.

Non-limiting examples of therapeutic agents for sciatica with which a compound of Formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene n-pap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts, TRIS salts, meglumine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I), and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) and mixtures thereof.

As used herein the term "pro-drug" refers to an agent which is converted into the parent drug in vivo by some physiological chemical process (e.g., a pro-drug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the pro-drug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1-C_4)$alkyl, $(C_1-C_{12})$alkanoyloxymethyl, (C₄-C₉)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C₁-C₂)alkylamino(C₂-C₃)alkyl (such as (3-dimethylaminoethyl), carbamoyl-(C₁-C₂)alkyl, N,N-di(C₁-C₂)-alkylcarbamoyl-(C₁-C₂)alkyl and piperidino-, pyrrolidino- or morpholino(C₂-C₃) alkyl.

Other exemplary pro-drugs release an alcohol of Formula (I) wherein the free hydrogen of the hydroxyl substituent is replaced by (C₁-C₆)alkanoyloxymethyl, 1-((C₁-C₆)alkanoyloxy)ethyl, 1-methyl-1-((C₁-C₆)alkanoyloxy)ethyl, (C₁-C₂) alkoxycarbonyloxymethyl, N—(C₁-C₆)alkoxycarbonylamino-methyl, succinoyl, (C₁-C₆)alkanoyl, α-amino(C₁-C₄)alkanoyl, arylacetyl and α-aminoacyl, or α-aminoacyl-α-aminoacyl wherein said α-aminoacyl moieties are independently any of the naturally occurring L-amino acids found in proteins, P(O)(OH)₂, —P(O)(O(C₁-C₆)alkyl)₂ or glycosyl (the radical resulting from detachment of the hydroxyl of the hemiacetal of a carbohydrate).

Other exemplary pro-drugs release an amine of Formula (I) wherein the free hydrogen of the amine group is replaced by —C(O)alkyl, —C(O)O-alkyl, N-phosphonoxyalkyl, alkyl, cycloalkyl, aryl, heteroaryl or heterocyclyl, wherein the alkyl, cycloalkyl, aryl, heteroaryl or heterocyclyl can be optionally substituted with, for example, halogen and hydroxyl.

The term "heterocyclic", "heterocyclyl" or "heterocyclylene", as used herein, include non-aromatic ring systems, including, but not limited to, monocyclic, bicyclic, and tricyclic rings, which can be completely saturated or which can contain one or more units of unsaturation. (for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, 1,4-dioxanyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "ring systems which are aromatic, partly aromatic or non-aromatic having one or more fused ring systems" refers to the ring systems demonstrated by non-limiting examples of moieties, include 4H-benzo[1,4]oxazin-3-one, pyridazinonyl, pyridonyl, pyrazinonyl and pyrimidinonyl.

The term "fused ring system" refers to connection via two adjacent atoms in a ring system "fused" to form a cyclic ring system.

In a particular embodiment, ring systems which are aromatic, partly aromatic or non-aromatic can be selected from

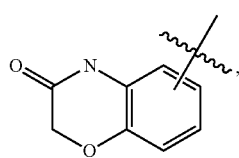

referred to as 4H-benzo[1,4]oxazin-3-one;

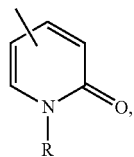

referred to as pyridonyl;

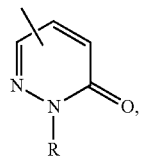

referred to as pyridazinonyl;

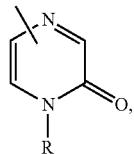

referred to as pyrazinonyl; and

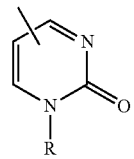

referred to as pyrimidinonyl. The meaning of the terms "nonaromatic", "partly aromatic" and "nonaromatic" are well understood by a person having ordinary skill in the art. For example when a ring system is termed aromatic, it should have its π electrons in the ring in accordance with the requirement to possess aromaticity. In the case where a ring system becomes partly aromatic, it means one of the cyclic rings is aromatic and the ring to which it is fused is non-aromatic. All non-aromatic ring systems do not comply with the definition of aromaticity known to person having ordinary skill in the art.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo[b]thienyl, benzimidazolyl, benzo[1,3]dioxolyl, benzofuranyl, benzoxazolyl, benzothiazolyl, benzothiadiazolyl, benzoxadiazolyl, benzo[1,3]benzo[1,4] oxazinyl, 2,3-dihydrobenzo[1,4]dioxinyl, 2,3-dihydrobenzofuranyl, 6,7-dihydro-5H-cyclopentapyrimidinyl, furanyl, imidazolyl, imidazopyridinyl, indolyl, indazolyl, isoxazolyl, isothiazolyl, octahydro-pyrrolopyrrolyl, oxadiazolyl, oxazolyl, phthalazinyl, pteridinyl, purinyl, pyranyl, 5,8-dihydro-6H-pyrano[3,4-d]pyridinyl, pyrazinyl, pyrazolyl, pyrazolo[3,4-b]pyridinyl, pyridazinyl, pyridinyl, pyrido[2,3-d] pyrimidinyl, pyrido[4,3-d]pyrimidinyl, pyrido[3,4-d]

pyrimidinyl, pyrimidinyl, pyrimido[4,5-d]pyrimidinyl, pyrrolyl, pyrrolo[2,3-d]pyrimidinyl, pyrazolo[3,4-d]pyrimidinyl, quinolinyl, quinazolinyl, 5,6,7,8-tetrahydroquinazolinyl, triazolyl, thiazolyl, thieno[2,3-d]pyrimidinyl, thieno[3,2-d]pyrimidinyl, thiophenyl, tetrazolyl, thiadiazolyl, thienyl, [1,3,5]triazinyl, 4H-5-oxa-2,3,9b-triazacyclopenta[a]naphthalenyl, 5,6,7,8-tetrahydro-imidazo[1,5-a]pyrazinyl, and 5,6,7,8-tetrahydro-triazolo[1,2,4]pyrazinyl.

As used herein, "alkyl" and "alkylene" include straight chained or branched hydrocarbons which are completely saturated. For purposes of exemplification, which should not be construed as limiting the scope of this invention, examples of alkyls are methyl, ethyl, propyl, isopropyl, butyl, pentyl, hexyl and isomers thereof.

As used herein, "alkenyl", "alkenylene", "alkynylene" and "alkynyl" mean hydrocarbon moieties containing two to eight carbons and include straight chained or branched hydrocarbons which contain one or more units of unsaturation, one or more double bonds for alkenyl and one or more triple bonds for alkynyl. For purposes of exemplification, which should not be construed as limiting the scope of this invention, examples of alkenyl are ethenyl, propenyl and butenyl, and examples of alkynyl are ethynyl, propynyl and butynyl.

As used herein, "aryl" or "arylene" groups include aromatic carbocyclic ring systems (e.g. phenyl) and fused polycyclic aromatic ring systems. For purposes of exemplification, which should not be construed as limiting the scope of this invention, aryl groups include phenyl, naphthyl, biphenyl and 1,2,3,4-tetrahydronaphthyl.

As used herein, "cycloalkyl" or "cycloalkylene" means $C_3$-$C_{12}$ monocyclic or multicyclic (e.g., bicyclic, tricyclic, etc.) hydrocarbons that are completely saturated or have one or more unsaturated bonds but do not amount to an aromatic group. For purposes of exemplification, which should not be construed as limiting the scope of this invention, examples of a cycloalkyl group are cyclopropyl, cyclobutyl, cyclopentyl, cyclopentenyl, cyclohexyl and cyclohexenyl.

As used herein, many moieties (i.e. alkyl, alkylene, cycloalkyl, cycloalkylene, aryl, arylene, heteroaryl, heteroarylene, heterocyclyl or heterocyclylene) or substituents are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent are present, then each substituent may be independently selected. Such means for substitution are well-known in the art and/or taught by the instant disclosure. For purposes of exemplification, which should not be construed as limiting the scope of this invention, some examples of groups that are substituents: deuterium, optionally substituted ($C_1$-$C_8$)alkyl groups, optionally substituted ($C_2$-$C_8$) alkenyl groups, ($C_2$-$C_8$) alkynyl groups, optionally substituted ($C_3$-$C_{10}$)cycloalkyl groups, optionally substituted ($C_1$-$C_8$) alkoxy groups, halogen (F, Cl, Br or I), halogenated ($C_1$-$C_8$) alkyl groups (for example but not limited to —$CF_3$), optionally substituted heterocyclyl groups, optionally substituted heteroaryl groups, —OH, —SH, —optionally substituted —($C_1$-$C_8$) alkoxy, —optionally substituted —($C_1$-$C_8$) thio alkoxy, —NH($C_1$-$C_8$)alkyl groups, —N(($C_1$-$C_8$)alkyl)$_2$ groups, —$NH_2$, —NH—($C_3$-$C_6$) cycloalkyl, —NH—($C_1$-$C_6$)alkyl-optionally substituted heterocycle, —NH-heterocycle, —C(O)-optionally substituted ($C_1$-$C_8$)alkyl groups, —C(O)$NH_2$, —C(O)NH($C_1$-$C_8$)-optionally substituted alkyl, —C(O)N(($C_1$-$C_8$)alkyl)$_2$, —C(O)NH—O—($C_1$-$C_8$) alkyl, —C(O)N($C_1$-$C_8$)alkyl-O—($C_1$-$C_8$)alkyl, —C(O)NH- optionally substituted heteroaryl, —C(O)H, —C(O)—($C_1$-$C_8$)alkyl groups, —C(O)-optionally substituted ($C_3$-$C_{10}$) cyclo alkyl groups, —C(O)OH, —C(O)O($C_1$-$C_8$)alkyl groups, —NHC(O)H, —NHC(O)($C_1$-$C_8$) optionally substituted alkyl groups, —NHC(O)($C_3$-$C_8$) optionally substituted cycloalkyl groups, —N(($C_1$-$C_8$)alkyl)C(O)H, —N(($C_1$-$C_8$) alkyl)C(O)($C_1$-$C_8$) optionally substituted alkyl groups, —NHC(O)$NH_2$, —NHC(O)NH-optionally substituted ($C_1$-$C_8$)alkyl groups, —N(($C_1$-$C_8$)alkyl)C(O)$NH_2$ groups, —NHC(O)N-optionally substituted (($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —NHS(O)$_2$—($C_1$-$C_8$) optionally substituted alkyl, —NHS(O)$_2$$NH_2$, —NHS(O)$_2$NH($C_1$-$C_6$)alkyl, —NHS(O)$_2$N($C_1$-$C_6$)alkyl)$_2$, —CN, —$NO_2$, —O—C(O)—($C_1$-$C_8$)alkyl, —O—S(O)$_2$-heteroaryl, —O—S(O)$_2$-aryl, —S($C_1$-$C_8$)alkyl groups, —S(O)($C_1$-$C_8$)alkyl groups, —S(O)$_2$($C_1$-$C_8$)alkyl groups, —S(O)$_2$($C_3$-$C_{10}$)cycloalkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$$NH_2$ groups, —S(O)$_2$-optionally substituted heteroaryl groups, —S(O)$_2$-optionally substituted heterocyclyl groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$) alkyl-O—($C_1$-$C_8$)alkyl groups, —NHOH, —NHO($C_1$-$C_8$) alkyl groups, —O-halogenated ($C_1$-$C_8$)alkyl groups (for example but not limited to —$OCF_3$), oxo, —S(O)$_2$-halogenated ($C_1$-$C_8$)alkyl groups (for example but not limited to —S(O)$_2$$CF_3$), —S-halogenated ($C_1$-$C_8$)alkyl groups (for example but not limited to —$SCF_3$), —($C_1$-$C_6$)alkyl-optionally substituted heterocycle (for example but not limited to azetidine, morpholine, piperidine, piperazine, pyrrolidine, tetrahydrofuran, thiomorpholine, or pyran), —($C_1$-$C_6$)alkyl-heteroaryl (for example but not limited to tetrazole, imidazole, furan, pyrazine or pyrazole), —optionally substituted phenyl, —NHC(O)O—($C_1$-$C_6$)alkyl groups, —N(($C_1$-$C_6$) alkyl)C(O)O—($C_1$-$C_6$)alkyl groups, —C(=NH)—($C_1$-$C_6$) alkyl groups, —C(=NOH)—($C_1$-$C_6$)alkyl groups, or —C(=N—O—($C_1$-$C_6$)alkyl)-($C_1$-$C_6$)alkyl groups.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few hours up to over several days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_5$ s with little or no toxicity. The dosage may vary within this range depending upon the dosage form employed and the route of administration utilized. The exact formulation, route of administration and dosage can be chosen by the individual physician in view of the patient's condition (see e.g. Fingl et al., 1975, in "The Pharmacological Basis of Therapeutics", Ch. 1 p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

The following examples are for illustrative purposes and are not to be construed as limiting the scope of the present invention.

General Synthetic Schemes

Compounds of the Invention May be Prepared Using the Synthetic Transformations Illustrated in Scheme I

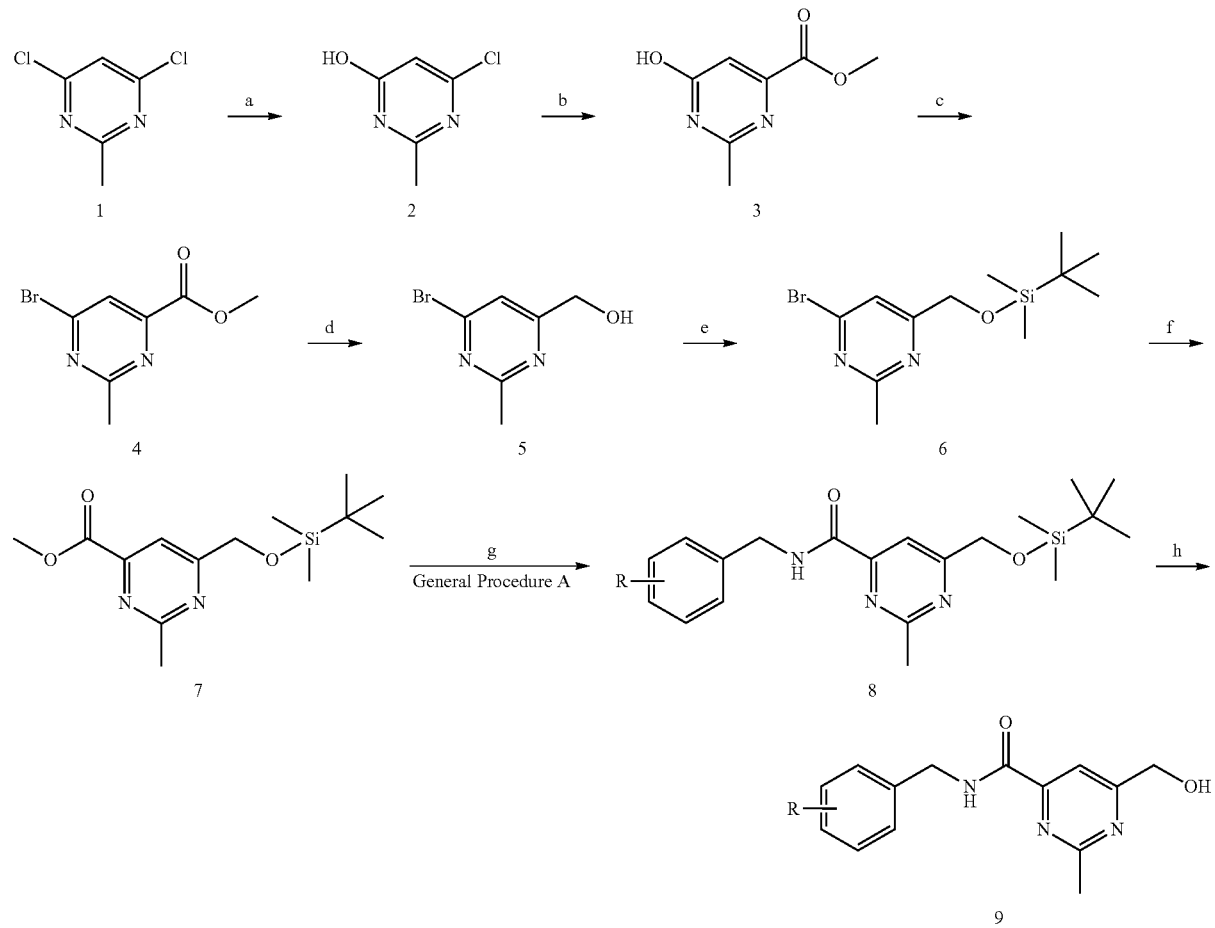

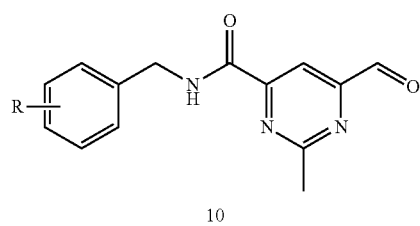 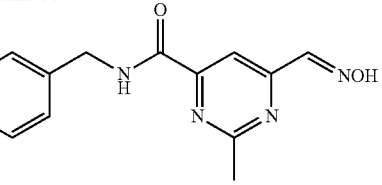

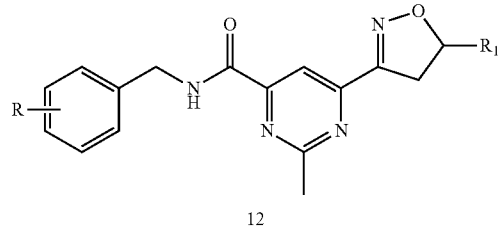

Compounds of the invention may be prepared using the synthetic transformations illustrated in Scheme I. Starting materials are commercially available, may be prepared by the procedures described herein, by literature procedures, or by procedures that would be well known to one skilled in the art of organic chemistry. In step a, commercially available 4,6-dichloro-2-methylpyrimidine is reacted with 13M $H_2SO_4$ using conditions such as those described in Preparation #1 to afford 6-chloro-2-methylpyrimidin-4-ol which is then subjected to carbonylation using CO gas in the presence of a palladium based catalyst (Preparation #2) or by methods known to one skilled in the art (for example, *Indian Journal of Chemistry* 2009, 48(B), 858-864) to afford methyl 6-hydroxy-2-methylpyrimidine-4-carboxylate. In step c, reaction of methyl 6-hydroxy-2-methylpyrimidine-4-carboxylate with a halogenating agent such as phosphorus oxybromide using conditions such as those described in Preparation #3 afford methyl 6-bromo-2-methylpyrimidine-4-carboxylate. In step d, methyl ester is reduced with metal hydride reagents such as sodium borohydride using the conditions described in Preparation #4 to afford (6-bromo-2-methylpyrimidin-4-yl) methanol. In step e, the primary alcohol is protected as its TBDMS ether to afford 4-bromo-6-((tert-butyldimethylsilyloxy)methyl)-2-methylpyrimidine by using the conditions described in Preparation #5 or by methods known to one skilled in the art (for example Larock, R. C "Comprehensive Organic Transformations: A guide to functional group preparations, Second Edition", 1999, Wiley-VCH or Green, T. W. and Wuts, P. G. M. "Protective Groups in Organic Synthesis, 3rd Edition", 1999, Wiley-Interscience). In step f, a carbomethoxy group is introduced with carbonylation by using conditions such as those described in Preparation #6 or by methods known to one skilled in the art (for, *Indian Journal of Chemistry* 2009, 48(B), 858.

In step g, nucleophilic displacement of ester with substituted benzyl amines using the conditions described in General Procedure A afford 8. Deprotection of the TBDMS group in compound 8 to yield 9 is performed using conditions described in Preparation #7 or by methods known to one skilled in the art (for example, the books from Larock, R. C. Greene, T. W. and Wuts, P. G. M. referenced above). The primary alcohol in compound 9 is oxidized to afford 10 using Dess-Martin periodinane or alternatively by methods known to one skilled in the art (for example, Alan H. Haines "Methods of the Oxidation of Organic Compounds, 1988, Academic Press). In step i, Compound 10 is treated with hydroxylamine hydrochloride in presence of an inorganic base such as sodium acetate in protic solvents such as EtOH to afford 11 (Preparation #9). An oxidative cycloaddition reaction between compound 11 and various olefins (such as heterocyclyl, cycloalkyl, heteroaryl, alkyl-heterocyclyl olefins) using General Procedure G yielded compounds of the present invention 12. Pure Enantiomers/diasteoremers of the present invention are separated using appropriate analytical preparative methods like Chiral preparative HPLC or reverse phase/normal phase preparative HPLC/chromatography.

Scheme II

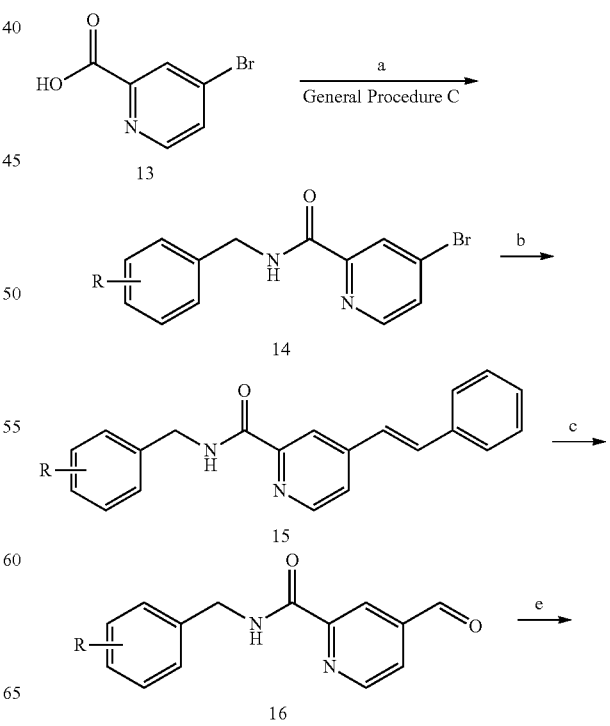

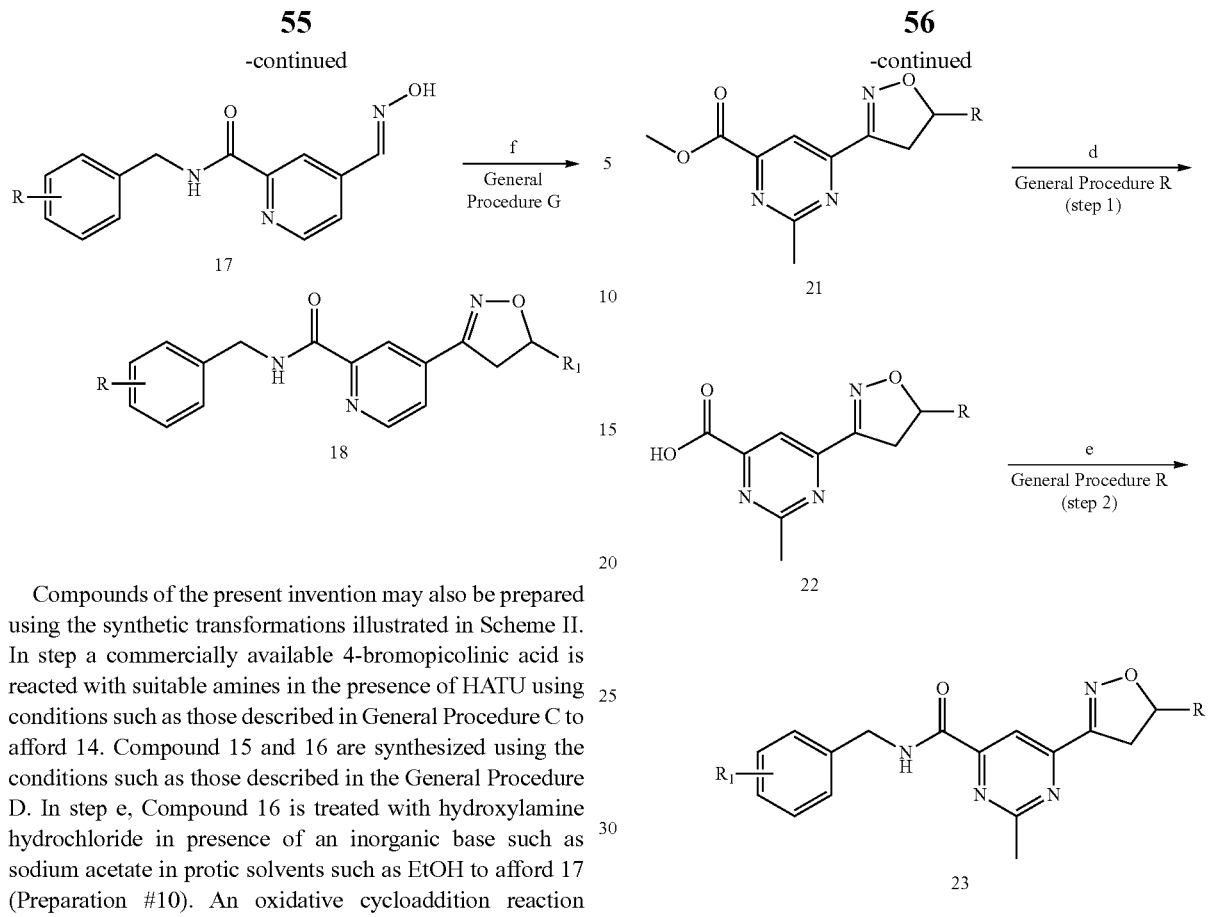

Compounds of the present invention may also be prepared using the synthetic transformations illustrated in Scheme II. In step a commercially available 4-bromopicolinic acid is reacted with suitable amines in the presence of HATU using conditions such as those described in General Procedure C to afford 14. Compound 15 and 16 are synthesized using the conditions such as those described in the General Procedure D. In step e, Compound 16 is treated with hydroxylamine hydrochloride in presence of an inorganic base such as sodium acetate in protic solvents such as EtOH to afford 17 (Preparation #10). An oxidative cycloaddition reaction between compound 17 and various olefins (such as heterocyclyl, cycloalkyl, heteroaryl, alkyl-heterocyclyl olefins) using General Procedure C yield compounds of the present invention 18.

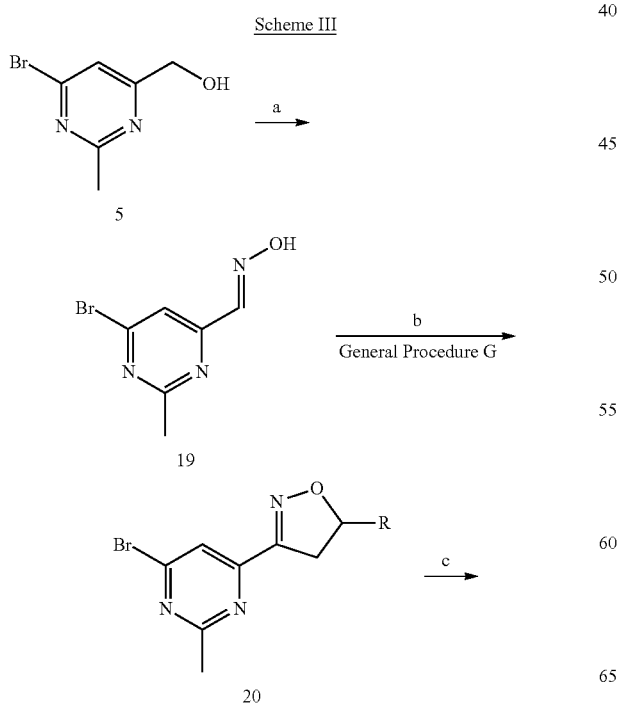

Compounds of the present invention may also be prepared using the synthetic transformations illustrated in Scheme III. In step a, compound 5 primary alcohol is oxidized using Dess-Martin Periodinate followed by oxime formation using general procedure B afford compound 19. Oxidative cycloaddition reaction between compound 19 and various olefins (such as aryl, heterocyclyl, cycloalkyl, heteroaryl, alkyl-heterocyclyl olefins) using General Procedure C yield compound 20 which is then subjected to carbonylation using CO gas in the presence of a palladium based catalyst (Preparation #21 or by methods known to one skilled in the art (for example, *Indian Journal of Chemistry* 2009, 48(B), 858-864) to afford compound 21. Ester hydrolysis using the conditions such as those described in general procedure R (step 1) afford 22. Amide reaction between compound 29 and various substituted aryl and heteroaryl benzyl amines using general procedure R (Step 2) yielded compounds of the present invention 23.

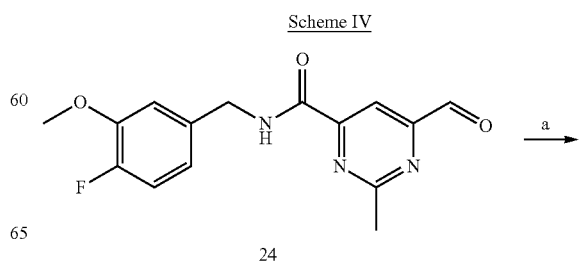

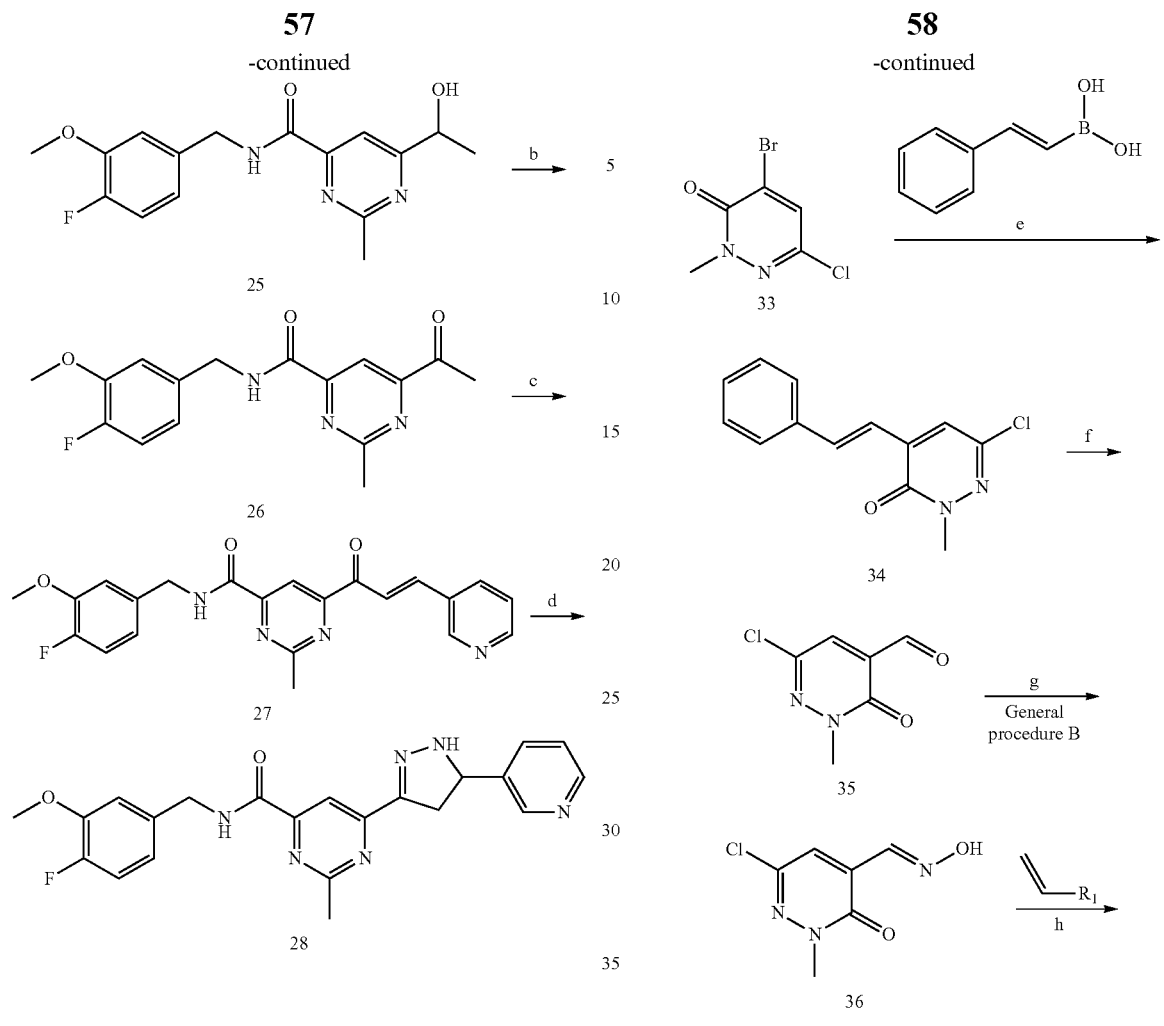

Compounds of the present invention may also be prepared using the synthetic transformations illustrated in Scheme IV. In step a, compound 24 is reacted with methyl magnesium bromide to afford 25 which is further oxidized using Dess-Martin Periodinate to afford compound 26. Aldol condensation using aryl aldehyde with compound 26 afford 27 which on cyclization with hydrazine hydrate gave the compounds of present invention 28

Scheme V:

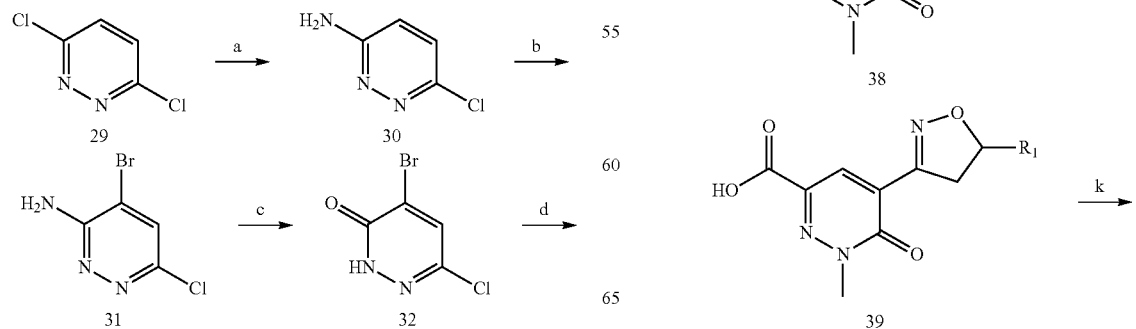

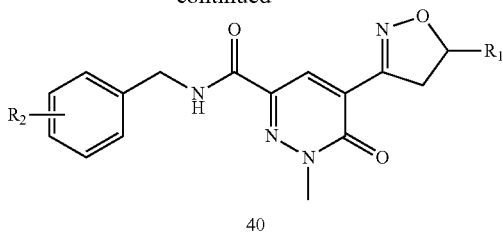

40

Compounds of the present invention may also be prepared using the synthetic transformations illustrated in Scheme V. In step a, commercially available 3,6-dichloropyradizine is subjected to amination using the conditions that are described in the preparation #25 to afford compound 30 which is further brominated using Bromine by following the conditions that are described in preparation #26 to afford 31. Further compound 31 is subjected to diazotization followed by hydrolysis by following the conditions that are described in preparation #27 yielded 32, which is further subjected to N-alkylation using methyl idodine by following the conditions that are described in preparation #28 yielded compound 33. Suzuki reaction between compound 33 and styrylboronic acid in presence of palladium catalyst using the conditions that are described in preparation #29 yielded compound 34, which subjected to oxidative cleavage using $OsO_4/NaIO_4$ by following the conditions that are described in preparation #30 yielded compound 35. In step g, Compound 35 is treated with hydroxylamine hydrochloride in presence of an inorganic base such as sodium acetate in protic solvents such as EtOH using the conditions that are described in general procedure B afforded 36 which is further subjected to oxidative cycloaddition reaction with various olefins (such as heterocyclyl, cycloalkyl, heteroaryl, alkyl-heterocyclyl olefins) using General Procedure G yielded 37. Compound 37 is subjected to carbonylation using CO gas in the presence of a palladium based catalyst (Preparation #33) or by methods known to one skilled in the art (for example, *Indian Journal of Chemistry* 2009, 48(B), 858-864) to afford compound 38 which is further subjected to base hydrolysis by following the conditions described in Preparation #34 yielded compound 39. Amidation reaction between compound 39 and various benzyl amines using the conditions that are described in general procedure R yielded the compounds of present invention.

LIST OF GENERAL PROCEDURES

General Procedure A: Preparation of amides by the nucleophilic displacement of ester with substituted benzyl amines
General procedure B: Formation of oximes
General Procedure C: Amide formation
General Procedure D: Aldehyde formation
General Procedure E: Wittig Olefination
General Procedure F: Synthesis of olefins from halogens
General Procedure G: Isoxazoline formation
General Procedure H: Deprotection of O-tosylate
General Procedure I: Formation of nitrile derivatives from O-tosylate derivatives:
General Procedure J: Nucleophlic displacement of O-tosylate with an amine
General Procedure K: Acidic cleavage of a Boc-protected amine
General Procedure L: Formation of acetyl amide from an amine
General Procedure M: Formation of a sulfonamide from an amine
General Procedure N: Formation of hydroxyacetyl amide from an amine
General Procedure O: Formation of sulphone from O—tosylate derivative
General Procedure P: Formation of an acid from alcohol
General Procedure Q: Formation of an ester from carboxylic acid
General Procedure R: Preparation of amide from methyl esters
General Procedure S: Preparation of tertiary-alcohols from methyl ester using methyl magnesium bromide
General Procedure T: Preparation of tetrazoles from nitrile derivatives
General Procedure U: Formation of a urea from an amine and a carbamoyl chloride
General Procedure V: Formation of a urea from an amine and isocyanate
General Procedure W: Formation of an amide from mixed carboxylic-carbonic anhydride and an amine
General Procedure X: Preparation of amides by the nucleophilic displacement of ester with amine
General Procedure Y: Formation of an amide from active ester
General Procedure Z: Formation of a urea from an amine with triphosgene
General Procedure AA: Formation of a urea from an amine with 4-nitrophenyl chloroformate
General Procedure AB: Formation of 1,2,4-oxadiazole from aryl esters
General Procedure AC: Formation of N-methyl urea
General Procedure AD: Cyclization of an aldehyde with a TOSMIC reagent to give an oxazole
General Procedure AE: Boc protection of amine with di-tert-butyl dicarbonate
General Procedure AF: Formation of ether linkage
General procedure AG: Formation of Boc protected amine from nitrile derivative The following examples are ordered according to the final general procedure used in their preparation. The synthetic routes to any novel intermediates are detailed by sequentially listing the general procedure (letter codes) in parentheses after their name with additional reactants or reagents as appropriate.

LIST OF ABBREVIATIONS

ACN Acetonitrile
BuLi n-Butyl lithium
CO Carbon monoxide
d doublet
DBU 1,8-Diazabicyclo[5.4.0]undec-7-ene
dd doublet of doublet
DCM Dichloromethane (methylene chloride)
DIEA N,N-diisopropylethylamine
DMF N,N-dimethylformamide
DMSO Dimethyl sulphoxide
DMAP Dimethylamino pyridine
DMA Dimethylacetamide
EDCI.HCl 1-(3-Dimethylaminopropyl)-3-ethylcarbodiimide hydrochloride
equiv. Equivalent(s)
EtOAc Ethyl acetate
EtOH Ethanol
g Gram(s)
h Hour(s)

HATU 2-(1H-7-Azabenzotriazol-1-yl)-1,1,3,3-tetramethyl uronium hexafluorophosphate Methanaminium
HOBT Hydroxybenzotriazole
IPA Isopropyl alcohol
KOAc Potassium Acetate
KOBt Potassium t-butoxide
m multiplet
MeOH Methyl alcohol
MeMgBr Methyl magnesium bromide
m-CPBA meta chloro perbenzoic acid
min Minute(s)
M Molarity
Mmol millimol
N Normality
NaH Sodium hydride
NaIO$_4$ Sodium periodate
OsO$_4$ Osmium tetraoxide
Pd(OAC)$_2$ Palladium (II)acetate
PyBOP Benzotriazole-1-yl-oxy-tris-pyrrolidino-phosphonium hexafluorophosphate
Rac Racemic
R$_t$ Retention time
RT Room temperature
s singlet
t triplet
TBAF Tetrabutyl ammonium fluoride
TBDMS-Cl Tert-butyl dimethyl silyl chloride
TEA Triethyl amine
TFA Trifluoroacetic acid
THF Tetrahydrofuran
TLC Thin layer chromatography
Temp Temperature
TFAA Trifluoroacetic anhydride Assays Time Resolved Fluorescence Resonance Energy Transfer (FRET) Enzyme Assays A recombinant human MMP13 catalytic domain (CD) construct encompassing residues 20-274 (SWISS-PROT P45452) was generated by synthetic gene methods and bacterial expression. MMP-13 activity assays were performed using the recombinant human MMP-13 CD at a 0.4 nM concentration and the fluorogenic substrate (QXL-520)-K-P-L-A~Nva-Dap(5-FAM)-A-R-NH$_2$ (Anaspec cat #60554-01, San Jose, Calif.) at a 0.25 µM concentration in assay buffer containing 50 µM Tris, pH 7.5, 10 mM CaCl$_2$, 150 mM NaCl, 0.05% Brij 35. The assay is based on the cleavage of this substrate by MMP-13, resulting in decrease of FRET between the donor-acceptor pair and subsequent fluorescence enhancement. The assays were carried out in 384-well plates (Greiner cat #781076, Germany) for 60 min at RT. After the incubation period, the reaction was quenched by the addition of 5 µL of 500 mM EDTA (100 mM final concentration) (Rankem, Cat #E0120, India) mixed well and the rate of substrate hydrolysis was determined by monitoring change in fluorescence at excitation and emission wavelengths of 485 nm and 535 nm respectively. Fluorescence was measured on a Victor V5 plate reader (Perkin Elmer, Turku, Finland). The test compounds used for assessing the potency of inhibition of MMP-13 activity were dissolved in DMSO (final DMSO concentration in the assay was 5%). Selected compounds were also screened against full length MMP13 (R&D Systems (Cat. No. 511-MM-010), Minneapolis, Minn.) at 2 nM concentration using the same fluorogenic substrate mentioned above. The enzyme was activated using 1 m Mp-aminophenylmercuric acetate—APMA (Cat #A-9563, Sigma, Germany).

Selectivity assays for all other MMPs and TACE were performed using the same MMP FRET substrate (0.25 M) and catalytic domain of human MMPs/TACE enzymes. Concentration and catalog number for the enzymes used in the assay were as follows: MMP-2 CD (12.5 nM) (Cat. No. BML-SE237-0010), MMP-3 CD (20 nM) (Cat. No. BML-SE109-0010), MMP-7 CD (12.5 nM) (Cat. No. BML-SE181-0010), MMP-8 CD (3.13 nM) (Cat. No. BML-SE255-0010), MMP-9 CD (1.56 nM) (Cat. No. BML-SE244-0010), MMP-12 CD (1.56 nM) (Cat. No. BML-SE138-0010), MMP-14 CD (10 nM) (Cat. No. BML-SE259-0010) and TACE (25 nM) (Cat. No. PF133). All MMP CD enzymes were purchased from Enzo Life Sciences, Plymouth Meeting, Pa. and TACE enzyme was obtained from EMD Chemical, Gibbstown, N.J.

Selectivity assays for ADAMTS-4 and ADAMTS-5 were performed using TAMRA-G-R-D-V-Q-E~F-R-G-V-T-A-V-T-R-K(QSY7)-R-G-R amide as substrate at concentrations of 0.5 µM for ADAMTS-4 and 1 µM for ADAMTS-5. The enzyme concentrations for ADAMTS-4 and ADAMTS-5 were 4 and 25 nM respectively and the rate of substrate hydrolysis was determined by monitoring change in fluorescence at excitation and emission wavelengths of 544 nm and 590 nm. Recombinant human ADAMTS-4 (residues 1-579, SWISS-PROT O75173) and ADAMTS-5 (residues 19-622, SWISS-PROT Q9UNA0) were generated by synthetic gene methods and bacterial expression for the assay.

Data analysis: The percent inhibition of the enzyme activity in presence of test compounds were calculated using the equation, percent (%) Inhibition=100−[(Fi/Fc)*100] where Fc is the fluorescence corresponding to initial enzyme activity and Fi is the fluorescence corresponding to the enzyme activity in presence of inhibitor. The IC$_{50}$ values were calculated by fitting the dose-response data to a sigmoidal curve fitting equation using Graph Pad prism software (Version 5, La Jolla, Calif.).

Acute Exogenous Full Length MMP-13 Induced Cartilage Degradation in Male Lewis Rats The test compound was prepared in 1% Tween 80 in 0.5% hydroxypropyl methyl cellulose at desirable concentration for dosing (1, 3, 10, 30, 100 mg/kg). One day before actual start of experiment the hairs around the left knee joint of male LEW/Han™Hsd rats (250-320 g; Harlan Laboratories) were clipped to which activated full length (FL) MMP-13 (prepared in-house; 5 or 10 µg in 100 µL/joint) or 100 µL PBS was injected. The animals were dosed with vehicle or test compounds at 1-10 mL/kg body weight at appropriate time before intra articular administration of FL-MMP-13 protein based on t-max of compounds. At time 0 hour, in vehicle control group, 100 µL filtered Dulbecco's phosphate buffered saline 1× (Invitrogen Ref no. 14190) was injected to left knee joint space using ½ cc insulin syringes (BD Biosciences Catalogue No. 328468) after anesthetizing with isoflourane (Forane® Abbott Laboratories, USA). For compound treated animal groups, 100 µL of activated FL-MMP-13 was injected. Two hours post challenge with PBS or FL-MMP13, animals were sacrificed using CO$_2$ exposure. Blood was collected from heart puncture into sodium heparin or lithium heparin (100 IU/mL of 0.9% NaCl) vials for plasma drug concentration analysis. Plasma was separated and stored at −20° C. until drug concentration analysis. After sacrifice of animals, 100 µL of filtered Dulbecco's phosphate buffered saline (1×) was injected in to the left knee joint space using a ½ cc insulin syringe. The synovial fluid was aspirated out and collected into a pre-labeled EDTA tube (BD Biosciences, Catalogue No. 365974) and kept on ice. Synovial fluid samples were spun down for 5 min at 16.1 relative centrifugal force and aliquoted into 96 well polypropylene round bottomed plates, sealed with aluminum seal. Samples were stored at −20° C. until analysis. Synovial fluid wais analyzed for cartilaps (CTX-II) (Immunodiagnostic Systems INC-Nordic bioscience, serum preclinical cartilaps ELISA, catalogue no AC-08F1) as per manufacturer's instructions. Drug concentration in synovial fluid and plasma was estimated by LCMS-MS using a validated method. Lower limit of detection is 1-5 ng/mL.

Cartilaps (CTX-II) levels in synovial fluid of FL-MMP13 injected male Lewis rats treated with vehicle or test compound was subtracted from PBS injected control group synovial fluid levels. The average PBS subtracted CTX-II levels in FL-MMP-13 injected group is considered as 100% response. Mean PBS subtracted CTX-II levels in treated groups were used for calculation of % inhibition. Logarithmically transformed data of % inhibition of CTX-II levels at various dose levels along with corresponding plasma and synovial fluid drug levels were used for estimation of $ED_{50}$ concentration using four parameter curve fit (GraphPad Prism 5 software).

Acute Rat Medial Meniscus Tear (MMT) Model of Osteoarthritis in Male Lewis Rats

The test compound was prepared in 1% Tween 80 in 0.5% hydroxypropyl methyl cellulose at desirable concentration for dosing (1, 3, 10, 30, 100 mg/kg). On the day of surgery (day 0), male LEW/Han™ Hsd rats were anesthetized in the anesthesia chamber using isoflurane (5%) with oxygen fixture. Anesthetized animals were placed on a temperature controlled surgery table. The skin over the medial aspect of the right femoro-tibial joint was clipped to remove the hair and surgically prepared with 70% alcohol wipe, followed by povidone-iodine and again by 70% alcohol wipe. The anaesthetized animals were placed on dorsal recumbence and transferred to a nose cone with 2-3% isoflurane and oxygen mixture to maintain anesthesia during surgery.

The animal's right leg was held in horizontal and flexion position supporting the knee joint depression with index fingernail. A horizontal incision of 1 cm length just near the knee joint depression was carried out. The fascia was cleaned by blunt dissection with straight scissor. The medial collateral ligament was located and cut with scalpel blade so that the two cut ends move in opposite direction (top and bottom). Through blunt dissection the medial meniscus, which is a shining body, was visualized and cut through the full thickness at its narrowest point to pull the cut meniscus back. The joint cavity was flushed with sterile saline and the skin incision was sutured with vicryl suture of size 3-0 (Ethilon, Catalogue no: NW2515). All procedures except medial meniscus tear were performed for sham surgery animals. Povidone iodine solution was applied on surgical site. Intactness of skin suture was checked daily, resutured where necessary. All animals were monitored daily for 6 days.

On day 6, the animals were dosed orally either twice (once in the morning and once in the evening) or once (in the evening) with vehicle or test compound at various dose levels. On day 7, one more dose of vehicle or test compound was administered. Three hours after last dosing, the animals were sacrificed with carbon dioxide exposure, synovial space of surgical knee joint was lavaged with 100 μL of filtered Dulbecco's phosphate buffered saline (1×) and synovial fluid was collected using a ½ cc insulin syringe. The synovial fluid was aspirated out and collected into pre-labeled EDTA tube (BD Biosciences, Catalogue No. 365974), and the samples were kept on ice. Blood was collected from heart puncture into sodium heparin or lithium heparin (100 IU/mL of 0.9% NaCl) vials for plasma drug concentration analysis. Plasma was separated and stored at −20° C. until analysis. Synovial fluid samples were spun down for 5 min at 16.1 relative centrifugal force. Synovial fluid was aliquoted into 96 well polypropylene round bottomed plates (Corning, catalogue no. 3799) and sealed with aluminum seal. Samples were stored at −20° C. Synovial fluid samples were analyzed for cartilaps (CTX-II) (Immunodiagnostic Systems INC-Nordic bioscience, serum preclinical cartilaps ELISA, Catalogue no AC-08F1) as per manufacturer's instructions. Drug concentration in synovial fluid and plasma was estimated by LCMS-MS using a validated method. Lower limit of detection is 1-5 ng/mL.

CTX-II levels in synovial fluid of MMT male Lewis rats treated with vehicle or test compound was subtracted from sham surgery control group synovial fluid levels. The average sham surgery group subtracted CTX-II levels in MMT vehicle treated group is considered as 100% response. Mean sham surgery group subtracted CTX-II levels in treated groups were used for calculation of % inhibition. Logarithmically transformed data of % inhibition of CTX-II levels at various dose levels along with corresponding plasma and synovial fluid drug levels were used for estimation of $ED_{50}$ concentration using four parameter curve fit (GraphPad Prism 5 software).

Analytical Methods

TABLE 1

LC/MS conditions
LC/MS data is referenced to the table of LC/MS conditions using the lower case method letter provided wherever applicable.

| Method | Conditions |
|---|---|
| a | Instrument: Agilent 1100 series with Single Quad Dual Mode mass spectrometer & API 2000, Triple Quad, ESI; Column: Mercury MS Synergi 2μ Max-RP 20 × 4.0 mm; Flow: 2.0 mL/min; Mobile Phase: A - 0.1% Formic acid in water B—ACN; Temp: 30° C.; Gradient: (T/% B): 0/30, 0.5/30, 1.5/95, 2.4/95, 2.5/30 and 3/30. |
| b | Instrument: API 2000, Triple Quad, ESI; Column: Mercury MS Synergi 2μ Max-RP 20 × 4.0 mm; Flow: 2.0 mL/min; Mobile Phase: A—0.1% Formic acid in water B - ACN; Temp: 30° C.; Gradient: (T/% B): 0/30, 0.5/30, 1.5/95, 2.4/95, 2.5/30 and 3/30. |
| c | Instrument: PE Sciex API 3000 Triple Quad systems, HPLC Agilent 1100 Series, Column: Synergi 2.5μ MAX-RP 100 A Mercury (20 × 4.0 mm); Mobile Phase: A: 0.1% Formic acid in water; B: ACN. Time Programme (T/% B): 0/30, 0.5/30, 1/85, 3.6/90 and 4/30, Pre run-1 min. Flow rate: 1.0 mL/min., Injection volume: 10 μL |
| d | Instrument: PE Sciex API 3000 Triple Quad systems, HPLC Agilent 1100 Series, Column: Synergi 2.5μ MAX-RP 100A Mercury (20 × 4.0 mm); Mobile Phase: A: 0.1% Formic acid in water; B: ACN. Time Programme (T/% B): 0/30, 0.5/30, 1.5/95, 2.4/95, 2.5/30 and 3.0/30, Pre run-1 min. Flow rate: 2.0 mL/min., Injection volume: 10 μL |

TABLE 1-continued

LC/MS conditions
LC/MS data is referenced to the table of LC/MS conditions using
the lower case method letter provided wherever applicable.

| Method | Conditions |
|---|---|
| e | Instrument: PE Sciex API 3000 Triple Quad systems, HPLC Agilent 1100 Series, Column: Synergi 2.5μ MAX-RP 100A Mercury (20 × 4.0 mm); Mobile Phase: A: 10 mM Ammonium acetate in water; B: ACN. Time Programme (T/% B): 0/20, 1.0/20, 2.5/95, 4.0/95, 4.5/20 and 5.0/20, Pre run-1 min. Flow rate: 1.0 mL/min., Injection volume: 10 μL |
| f | Instrument: Thermo MSQ-Plus mass spectrometer and Agilent 1200 HPLC system running Xcalibur 2.0.7, Open-Access 1.4, and custom login software. The mass spectrometer was operated under positive APCI ionization conditions. The HPLC system comprised an Agilent Binary pump, degasser, column compartment, autosampler and diode-array detector, with a Polymer Labs ELS-2100 evaporative light-scattering detector. The column used was a Phenomenex Luna Combi-HTS C8(2) 5 μm 100 Å (2.1 mm × 50 mm), at a temperature of 55° C. A gradient of 10-100% acetonitrile (A) and 0.1% trifluoroacetic acid in water (B) was used, at a flow rate of 2.0 mL/min (0-0.1 min 10% A, 0.1-2.6 min 10-100% A, 2.6-2.9 min 100% A, 2.9-3.0 min 100-10% A. 0.5 min post-run delay). |
| g | Instrument: PE Sciex API 3000 Triple Quad systems, HPLC Agilent 1100 Series, Column: Synergi 2.5μ MAX-RP 100A Mercury (20 × 4.0 mm); Mobile Phase: A: 0.1% Formic acid in water; B: ACN. Time Programme (T/% B): 0/20, 0.5/20, 2.5/20, 4.5/95, 5/20 flow 1.5 mL/min. |

TABLE 2

HPLC methods
HPLC data is referenced to the table of HPLC conditions using
the lower case method letter provided wherever applicable.

| Method | Conditions |
|---|---|
| a | HPLC: The column used for the chromatography was a 150 × 21.2 mm Zorbax XDB C18, (5 μm particles). The gradient was (T/% B): 0/35, 2/35, 10/50, 13/80, 16/80, 17/35, 18/35. Flow rate was 21.0 mL/min. Mobile phase conditions: A: Water; B: can Detection method is UVλ = 210 nm. |
| b | HPLC: The column used for the chromatography was a 250 × 10 mm Symmetry Shield RP-18 (7.5 μm particles). Flow rate was 5.0 mL/min. Mobile phase conditions: A: water; B: ACN, isocratic conditions: A:B = 60:40, Detection method is UVλ = 210 nm. |
| c | 1) Column: Lux 5μ Amylose-2 (250 × 60 mm), Mobile phase: 100% Ethanol, Flow; 1 mL/min, Temp −25° C.<br>2) Column: Chiral Pak AD (250 × 10 mm) 10 μM; Mobile Phase A: Hexane; B: IPA; C: EtOH, A:B:C = 60:20:20; Flow: 5.0 mL/min; Detection method: UVλ: 224 nm;<br>3) Column: Chiral Pak IC (250 mm × 10.0 mm) 5.0 μM Mobile Phase: A: -n-Hexane,:EtOH + MeOH (1:1) Isocratic: A:B (20:80) Flow Rate: 6.0 mL/min. Detection method: UV λ: 296 nm<br>4) Column Chiral Pak IC (250 mm × 10.0 mm) 5.0 μM; Mobile Phase: A: -n-Hexane, B: EtOH + MeOH (1:1), Isocratic: A:B (20:80), Flow Rate: 6.0 mL/min. Diluent: EtOH + MeOH. UVλ =: 296 nm<br>5) Column: Chiral Pak IC (250 mm × 10.0 mm) 5.0 μM; Mobile Phase: A: -n-Hexane, B: EtOH, Isocratic: A:B (10:90), Flow Rate: 6.0 mL/min. Diluent: EtOH, UVλ =: 296 nm.<br>6) Column: Chiral Pak IC (250 mm × 10.0 mm) 5.0 μM; Mobile Phase: A: -n-Hexane, B:EtOH + MeOH (1:1) Isocratic: A:B (25:75), Flow Rate: 6.0 mL/min. UVλ = 29 6 nm<br>7) Column: Chiral Pak IC (250 mm % 10.0 mm) 5 μM, Mobile Phase, A: EtOH, isocratic flow: A: 100%, flow rate: 6 mL/min, Temp: NA, diluent: DCM + MeOH, Wave length: 300 nm<br>UVλ =: 296 nm<br>8) Column: Chiral Pak IC (250 mm % 10.0 mm) 5μ, Mobile Phase, A: EtOH, isocratic flow: A: 100%, flow rate: 5 mL/min, Temp: NA, Wave length: 299 nm<br>9) Column: Chiral Pak IC (250 mm × 4.6 mm) 5μ, Mobile Phase, A: EtOH, isocratic flow: A: 100%, flow rate: 1.0 mL/min, Temp: NA, Wave length: 299 nm.<br>10) Column: Chiral Pak IC (250 mm × 4.6 mm) 5μ, Mobile Phase, D: MeOH, diluent MeOH + MP (sonicated), isocratic flow: D: 100%, flow rate: 1.5 mL/min, Temp: NA, Wave length: 299 nm, Concn__mg_pr_mL NA<br>11) Chiral Pak IC (250 mm × 10 mm) 5μ, mobile phase A: n-Hexane, D: EtOH, isocratic, A:D = 20:80, flow rate: 5.0 mL/min, wave length: 299 nm.<br>12) Column: Lux Amylose-2 axia Packed 250 × 21.2 mm × 5μ; Mobile Phase: 50:50::Heptane:Ethanol; Isocratic method; Flow: 20 mL/min: 25.0° c.;<br>13) Column: Chiral Pak IC (250 mm × 10.0 mm), 5.0 μm Mobile Phase: B: EtOH Isocratic: B(100%) Flow Rate: 1.0 mL/min. Diluent: MeOH + MP |

TABLE 2-continued

HPLC methods
HPLC data is referenced to the table of HPLC conditions using
the lower case method letter provided wherever applicable.

| Method | Conditions |
|---|---|
|  | 14) Column: Chiral Pak IC (250 mm × 4.6 mm), 5.0, Mobile Phase A: n-Hexane, D: EtOH; Isocratic: A:D (20:80); Flow Rate: 0.8 mL/min; Diluent: MeOH + MP |
| d | Column = Zorbax XDB C18 (150 × 21.2) mm, 5 μM Mobile Phase: A: H$^2$O; B: ACN (T/% B): 0/30, 2/30, 6/50, 16/80, 18/80, 19/30, 20/30, Flow 21.0 mL/min; UVλ = 210 nm |
| e | RP-HPLC: 30% to 80% ACN/0.01M Aq. KH2PO4 buffered to pH 6.5 over 18 min at 1.5 mL/min; UV λ = 210.0 nm; Symmetry Shield RP18 (150 mm × 4.6 mm), 5 μM column |
| f | Eclipse XDB C18 (150 × 21.2) mm, 5 μM; Mobile Phase A: H$_2$O; ACN A:B: 60:40 flow 21.0 mL/min; UVλ: 210 nm. |
| g | Chiral preparativepurification: Column: Lux Amylose-2 axia Packed 250 × 21.2 mm × 5 μM; Isocratic method:- 50:50::Heptane:Ethanol; Flow: 20 mL/min; Temperature:- RT |
| h | Samples were purified by preparative HPLC on a Phenomenex Luna C8(2) 5 μM 100 Å AXIA column (30 mm × 75 mm). A gradient of ACN (A) and 0.1% TFA in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). Samples were injected in 1.5 mL DMSO:MeOH (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 MeOH:10 mM NH$_4$OH (aq) at a flow rate of 0.8 mL/min. Loop-injection mass spectra were acquired using a Finnigan LCQ running LCQ Navigator 1.2 software and a Gilson 215 liquid handler for fraction injection controlled by an Abbott developed Visual Basic application. |
| i | Column: Chiral Pak AD-H (250 × 10) mm, 5 μM; Mobile Phase: A: Hexane: B: 0.1% TFA in EtOH, A:B is 25:7; Flow rate: 4 mL/min; UV λ-298 nm |
| j | Column: Chiral Pak AD-H (250 mm × 4.6 mm), 5 μM; Mobile Phase A: Hexane; B: 0.1% TFA in EtOH, Isocratic conditions: A:B (25:75); Flow: 0.8 mL/min; UV λ: 298 nm. |
| K | Column; phenomenex Luna C18C12, 250 × 21. mm; 5 μM Flow rate; 18.0 mL/min; WAVELENTH; 210 nm Mobile phase A; 10 mm Ammonium acetate in water B; ACN Elution; Gradient Time mints; 0.01/30, 2.00/40, 16.00/70, 18.00/100 |

PREPARATIONS AND EXAMPLES

The general synthetic methods used in each General Procedure follow and include an illustration of a compound that was synthesized using the designated General Procedure. None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® ChemDraw Ultra 11.0. Names of final products are given as generated by IUPAC conventions or CambridgeSoft® ChemDraw Ultra 11.0.

Preparation #1

6-Chloro-2-methylpyrimidin-4-ol

To stirred solution of 13M sulfuric acid (125 mL) at about 0° C., 4,6-dichloro-2-methylpyrimidine (20.0 g, 307 mmol) was added portion wise over about 30 min. The solution was then stirred at about 0° C. for about 1.5 h and the reaction was allowed to warm to ambient temperature over about 1.5 h. The reaction was allowed to stir at RT overnight. The acidic mixture was poured into stirred 6N sodium hydroxide (500 mL) in ice, maintaining the temperature <10° C. and stirred for about 10 min. The white solid was collected and washed with warm water to afford 6-chloro-2-methylpyrimidin-4-ol 40.2 g (91%) $^1$H NMR (400 MHz, DMSO) δ: 12.85 (brs, 1H), 6.34 (s, 1H), 2.30 (s, 3H). LC/MS (Table 1, Method d) R$_t$=0.74 min; MS m/z: 145.1 (M+H).

Preparation #2

Methyl 6-hydroxy-2-methylpyrimidine-4-carboxylate

A 2 L autoclave reactor was charged with 6-chloro-2-methylpyrimidin-4-ol (10.0 g, 69 mmol, Preparation #1,), [1,1,-bis(diphenyl phosphino)ferrocine]dichloro palladium (II) complex with DCM (2.83 g, 3.45 mmol), DIEA (18 mL, 103.5 mmol, Spectrochem) and MeOH (250 mL). The reaction mixture was heated to about 85° C. in the presence of carbon monoxide gas at 70 psi for about 12 h. The reaction mixture was cooled to RT, filtered through a Celite® pad and washed with MeOH (2×200 mL). The combined filtrates were concentrated, the solid obtained was washed with diethyl ether (100 mL) and dried under vacuum to afford methyl 6-hydroxy-2-methylpyrimidine-4-carboxylate 12.2 g (52.6%). ¹H NMR (400 MHz, DMSO) δ: 12.83 (brs, 1H), 6.72 (s, 1H), 3.82 (s, 3H), 2.33 (s, 3H). MS m/z 169.3 (M+H)⁺.

Preparation #3

Methyl 6-bromo-2-methylpyrimidine-4-carboxylate

POBr₃ (6.65 g, 23.2 mmol, Spectrochem) was added to a stirred solution of methyl 6-hydroxy-2-methylpyrimidine-4-carboxylate (5.0 g, 29.7 mmol, Preparation #2) in DMF (100 mL) at about 90° C. The reaction mixture was heated at the same temperature for about another 10 min and poured into ice water (500 mL). The solution was neutralized with 10% aqueous sodium carbonate solution (pH 7). This solution was extracted with EtOAc (3×200 mL). The combined organic layer was washed with water (2×100 mL) and brine solution (2×150 mL), and dried over sodium sulphate and concentrated in vacuum. The crude material was purified by silica gel chromatography using 15 to 25% of EtOAc in hexane as the eluent. Relevant fractions containing the required compound were combined and evaporated to dryness under reduced pressure to afford methyl 6-bromo-2-methylpyrimidine-4-carboxylate as an off white solid 5.2 g (75.7%). ¹H NMR (400 MHz, DMSO) δ: 8.02 (s, 1H), 4.03 (s, 3H), 2.83 (s, 3H); MS m/z: 231 (M+H)⁺.

Preparation #4

(6-Bromo-2-methylpyrimidin-4-yl)methanol

To a cold suspension of methyl 6-bromo-2-methylpyrimidine-4-carboxylate (5.4 g, 23.3 mmol, Preparation #3) in MeOH (100 mL) was added NaBH₄ (1.11 g, 29.13 mmol, Spectrochem) in small portions over a period of about 45 min at about −10° C. and stirred at the same temperature for about another 30 min. The reaction was quenched with saturated ammonium chloride solution (150 mL) and the product was extracted with EtOAc (2×200 mL). The combined organic extracts were dried over sodium sulphate and concentrated under reduced pressure to afford (6-bromo-2-methylpyrimidin-4-yl)methanol 4.10 g (87.2%). ¹H NMR (400 MHz, DMSO) δ: 7.56 (s, 1H), 5.72 (brs, 1H), 4.51 (d, J=3.6 Hz, 2H), 2.57 (s, 3H); MS m/z: 205(M+H)⁺.

Preparation #5

4-Bromo-6-((tert-butyldimethylsilyloxy)methyl)-2-methylpyrimidine

To an ice cold solution of (6-bromo-2-methylpyrimidin-4-yl)methanol (4.10 g, 20.2 mmol, Preparation #4) in DMF (40 mL) were added imidazole (5.50 g, 80.8 mmol, Spectrochem) and TBDMS-Cl (6.10 g, 40.4 mmol, Spectrochem). The resulting reaction mixture was warmed to RT and stirred about 5 h. The mixture was diluted with ice cold water (200 mL), the product was extracted with diethyl ether (3×200 mL) and washed with water (1×100 mL) and brine solution (1×150 mL). The organic layer was dried over sodium sulphate and concentrated in vacuum. The resulting crude material was purified by silica gel chromatography using 10 to 20% of EtOAc in hexane as the eluent. Relevant fractions containing the target compound were combined and evaporated to dryness under reduced pressure to afford 4-bromo-6-((tert-butyldimethylsilyloxy) methyl)-2-methylpyrimidine 5.9 g (93%). ¹H NMR (400 MHz, CDCl₃) δ: 7.54 (s, 1H), 4.72 (s, 2H), 2.67 (s, 3H), 0.96 (s, 9H), 0.13 (s, 6H); MS m/z: 319.2 (M+H)⁺.

Preparation #6

Methyl 6-((tert-butyldimethylsilyloxy)methyl)-2-methylpyrimidine-4-carboxylate

A 1L autoclave reactor was charged with 4-bromo-6-((tert-butyldimethylsilyloxy)methyl)-2-methylpyrimidine (4.6 g, 14.5 mmol, Preparation #5), [1 μl,-bis(diphenyl phosphino) ferrocine]dichloropalladium (II) complex with DCM (0.6 g, 0.73 mmol), DIEA (3.8 mL, 21.8 mmol, Spectrochem) and MeOH (100 mL). The reaction mixture was pressurized with 60 psi of carbon monoxide, and stirred at about 85° C. for about 12 h. The mixture was cooled to RT and concentrated under reduced pressure. The resulting crude material was purified by column chromatography using 15 to 20% of EtOAc in hexane as an eluent. Relevant fractions containing the target compound were combined and evaporated to dryness under reduced pressure to afford methyl 6-((tert-butyldimethylsilyloxy)methyl)-2-methylpyrimidine-4-carboxylate 3.1 g (72%). ¹H NMR (400 MHz, DMSO) δ: 7.71 (s, 1H), 4.68 (s, 2H), 3.79 (s, 3H), 2.54 (s, 3H), 0.81 (s, 9H), 0.008 (s, 6H); MS m/z: 297.2 (M+H)⁺.

General Procedure A

Preparation of Amides by the Nucleophilic Displacement of Ester with Substituted Benzyl Amines To a flask containing a benzyl amine (1-2 equiv, preferably 1.1 equiv) in an organic solvent (such as MeOH, EtOH, THF, or 1,4-dioxane, preferably MeOH) is added an organic base (such as TEA or DIEA, preferably DIEA) and an appropriate alkyl ester. The reaction mixture is heated to reflux for about 3 to 24 h (preferably about 15 h). The reaction mixture is cooled to RT and evaporated to dryness under reduced pressure. The residue obtained is re-dissolved in EtOAc, washed successively with 1N HCl solution, water and brine solution. The organic solvent is dried over sodium sulfate and concentrated under reduced pressure to obtain the target product.

Illustration of General Procedure A

Preparation #A.1

6-((Tert-butyldimethylsilyloxy)methyl)-N-(4-fluoro-3-methoxybenzyl)-2-methylpyrimidine-4-carboxamide

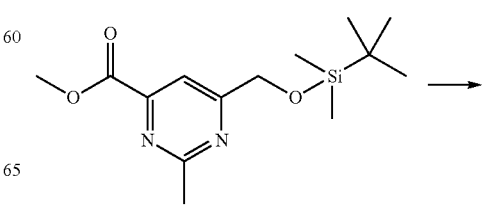

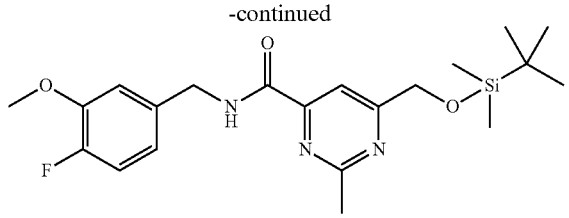

To a stirred solution of methyl 6-((tert-butyldimethylsilyloxy)methyl)-2-methylpyrimidine-4-carboxylate (4.70 g, 15.86 mmol, Preparation #6) in MeOH (50 mL) were added DIEA (8.3 mL, 47.59 mmol Spectrochem) and 4-fluoro-3-methoxybenzylamine (3.8 g, 24.58 mmol, WO 2008/083056). The reaction mixture was heated to about 70° C. for about 15 h. The solvents were removed in vacuo and the crude material partitioned between EtOAc (300 mL) and 1N HCl solution (300 mL). The layers were separated and the aqueous layer extracted with EtOAc (1×150 mL). The combined organic layers were washed successively with 1N HCl solution (1×200 mL), water (1×200 mL) and brine (1×250 mL), dried over sodium sulphate and evaporated to dryness. The residue obtained was purified by silica gel (60-120 mesh) chromatography eluting with 25 to 35% of EtOAc in hexane. Relevant fractions containing the target compound were combined and evaporated to dryness under reduced pressure to afford 6-((tert-butyldimethylsilyloxy)methyl)-N-(4-fluoro-3-methoxybenzyl)-2-methylpyrimidine-4-carboxamide 5.4 g (81%); $^1$H NMR (400 MHz, DMSO): δ 9.431-9.400 (t, J=6.0 Hz, 1H), 7.884 (s, 1H), 7.173-7.112 (m, 2H), 6.897-6.860 (m, 1H), 4.794 (s, 2H), 4.468-4.452 (d, J=6.4 Hz, 2H), 3.814 (s, 3H), 2.68 (s, 3H), 0.934 (s, 9H), 0.118 (s, 6H), MS m/z: 420 (M+H).

Other compounds synthesized using General procedure A are described in Tables A.1 and A.2

General Procedure B

Formation of Oximes

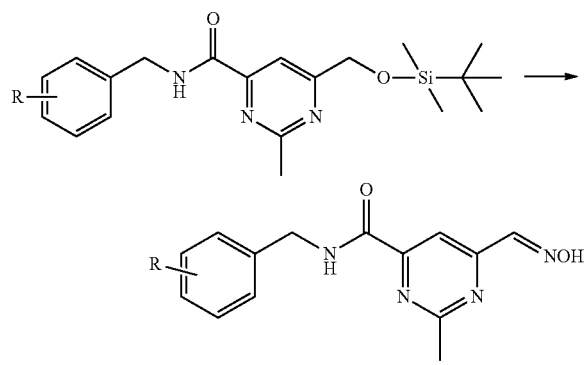

Step#1: To a cold solution of t-butyl dimethyl silyloxy derivative (1 equiv) in dry THF is added TBAF (1.3 equiv) drop wise at about 10° C. The resulting mixture is warmed to RT and stirred for about 45 min. The solution is diluted with EtOAc and washed successively with 1N HCL solution, water and brine. The organic layer is dried over sodium sulphate and evaporated to dryness under reduced pressure. The crude material obtained is triturated with hexane to afford the required alcohol.

Step#2: To a cold solution of alcohol (1 equiv) in an organic solvent (such as DCM or CHCl$_3$, preferably DCM) is added Dess-Martin periodinane (1 to 2 equiv, preferably 1.6 equiv) portion wise over about 45 min at about 0° C. The resulting suspension is allowed to warm to RT and stirred for about another 2 h. The reaction mixture is re-cooled to about 0° C., quenched with sodiumthiosulphate solution and stirred vigorously for about 30 min. The organic layer is separated, washed successively with saturated sodiumthiosulphate, water and brine. Further, the organic layer is dried over sodium sulphate and concentrated under reduced pressure to afford aldehyde derivative which is used for the next step.

Step#3: To a stirred solution of aldehyde (1 equv.) and NH$_2$OH.HCl (1-3 equiv preferably 1.6 equiv) in aqueous EtOH is added an inorganic base (such as sodium acetate, sodium bicarbonate, potassium bicarbonate, preferably sodium acetate 2 equiv). The reaction mixture is heated to reflux at about 90° C. for about 1 h. The mixture is concentrated under reduced pressure and diluted with EtOAc. The organic layer is washed successively with water and brine, dried over sodium sulphate and concentrated under reduced pressure to afford the required compound.

Illustration of General Procedure B

Formation of Oximes (Preparations #7, 8 &9)

Preparation #7

N-(4-fluoro-3-methoxybenzyl)-6-(hydroxymethyl)-2-methylpyrimidine-4-carboxamide

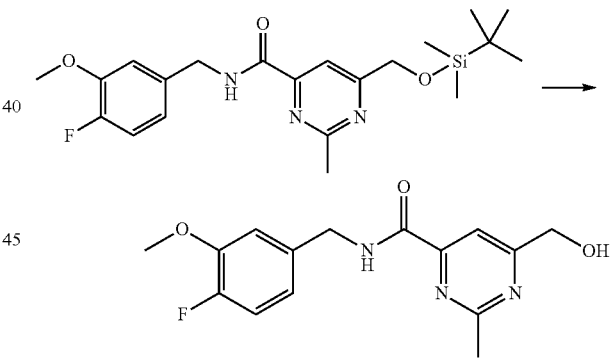

To a cold solution of 6-(((tert-butyldimethylsilyl)oxy)methyl)-N-(4-fluoro-3-methoxybenzyl)-2-methylpyrimidine-4-carboxamide (2.2 g, 5.25 mmol, Preparation#A.1) in dry THF (15 mL) was added TBAF (6.8 mL, 6.8 mmol, 1.0 M in THF) drop wise at about 10° C. The resulting mixture was warmed to RT and stirred for about 30 min. The solution was diluted with EtOAc (150 mL), and washed successively with 1N HCl solution (2×50 mL), water (100 mL) and brine (75 mL).

The organic layer was dried over sodium sulphate and evaporated to dryness under reduced pressure. The crude material obtained was triturated with hexane (3×15 mL) to afford N-(4-fluoro-3-methoxybenzyl)-6-(hydroxymethyl)-2-methypyrimidine-4-carboxamide 1.1 g (68.75%), $^1$H NMR (400 MHz, DMSO): δ 9.412-9.381 (t, J=6.4 Hz, 1H), 7.92 (s, 1H), 7.17-7.11 (m, 2H), 6.89-6.86 (m, 1H), 5.74-5.73 (brs, 1H), 4.600-4.585 (d, J=6.0 Hz, 2H), 4.481-4.465 (d, J=6.4 Hz, 2H), 3.81 (s, 3H), 2.68 (s, 3H), MS m/z: 306.2 (M+H)⁺.

Preparation #8

N-(4-fluoro-3-methoxybenzyl)-6-formyl-2-methylpyrimidine-4-carboxamide

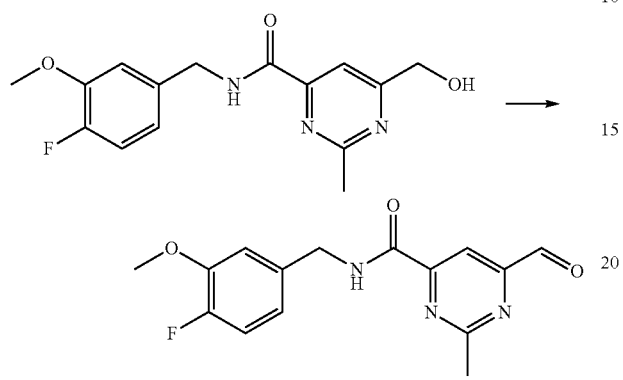

To a cold solution of N-(4-fluoro-3-methoxybenzyl)-6-(hydroxymethyl)-2-methylpyrimidine-4-carboxamide (7.23 g, 23.71 mmol, Preparation #7) in DCM (150 mL) was added Dess-Martin periodinane (16.10 g, 37.93 mmol, Spectrochem) portion wise over about 45 min at about 0° C. The resulting suspension was allowed to warm to RT and stirred for about another 2 h. The reaction mixture was re-cooled to about 0° C. and quenched with sodiumthiosulphate solution (150 mL) and stirred vigorously for about 30 min. The organic layer was separated, washed successively with saturated sodiumbicarbonate (1×100 mL), water (1×150 mL) and brine (1×150 mL), dried over sodium sulphate and concentrated under reduced pressure to afford N-(4-fluoro-3-methoxybenzyl)-6-formyl-2-methylpyrimidine-4-carboxamide 6.75 g (crude 94%), ¹H NMR (400 MHz, DMSO): δ 9.99 (s, 1H), 9.586-9.556 (t, J=6.4 Hz, 1H), 8.09 (s, 1H), 7.18-7.11 (m, 2H), 6.90-6.87 (m, 1H), 4.495-4.479 (d, J=6.4 Hz, 2H), 3.81 (s, 3H), 2.84 (s, 3H), MS m/z: 304.2 (M+H)⁺.

Preparation #9

N-(4-fluoro-3-methoxybenzyl)-6-((hydroxyimino)methyl)-2-methylpyrimidine-4-carboxamide

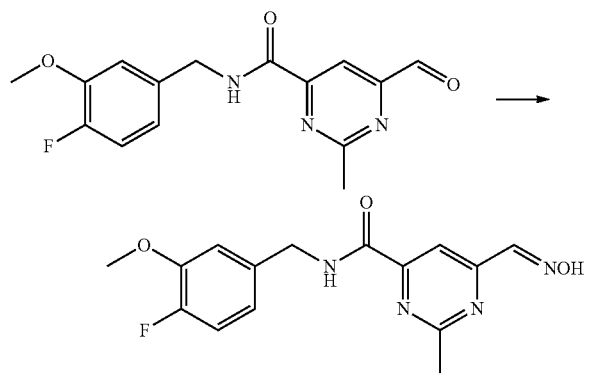

To a stirred solution of N-(4-fluoro-3-methoxybenzyl)-6-formyl-2-methylpyrimidine-4-carboxamide (6.75 g, 22.28 mmol, Preparation #8) and NH₂OH.HCl (3.09 g, 44.56 mmol, Sisco Research Labs) in aqueous EtOH (75%, 100 mL), was added sodium acetate (5.48 g, 66.84 mmol, Spectrochem). The reaction mixture was heated to reflux at about 100° C. for about 1 h. Then reaction mixture was cooled to RT and poured into ice cold water (140 mL). The resulting solids were filtered, washed with hexane (100 mL) and dried under vacuum to afford N-(4-fluoro-3-methoxybenzyl)-6-((hydroxyimino)methyl)-2-methylpyrimidine-4-carboxamide as a light yellow solid 5.60 g (80%), ¹H NMR (400 MHz, DMSO): δ 12.40 (s, 1H), 9.463-9.432 (t, J=8.1 Hz, 1H), 8.10 (s, 1H), 8.08 (s, 1H), 7.17-7.11 (m, 1H), 6.89-6.86 (m, 1H), 4.477-4.461 (d, J=6.4 Hz, 2H), 3.81 (s, 3H), 2.72 (s, 3H), MS m/z: 318.8 (M+H)⁺.

Other compounds synthesized using General procedure B are described in Table B.1

General Procedure C

Amide Formation

To a flask containing an acid derivative (1.0 equiv) in an organic solvent (such as DMF, DMA or CH₂Cl₂) is added HATU, (1.2 equiv) and organic base such as TEA, DIEA, or N-ethyl-N-isopropylpropan-2-amine, preferably N-ethyl-N-isopropylpropan-2-amine (1.2 equiv). After stirring for about 10 min at approximately 25° C., the appropriate amine (1.2 equiv) is added and the reaction is stirred for an additional 8-12 h, preferably 12 h. The reaction is basified with aqueous 1 N NaOH and washed three times with an organic solvent such as EtOAc, CH₂Cl₂ or ether. The organic solution is dried over Na₂SO₄ or MgSO₄, filtered, and concentrated under reduced pressure to give the target compound. Optionally, the target compound can be purified by crystallization or trituration from an appropriate solvent or solvents, or by preparative HPLC or flash chromatography.

Illustration of General Procedure C

Preparation:
4-Bromo-N-(4-methoxybenzyl)picolinamide

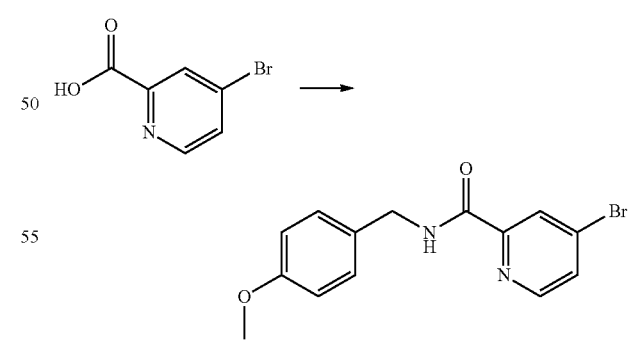

To a flask containing a 4-bromopicolinic acid (1.0 g) in DMF (10 mL) was added HATU (2.3 g) and N-ethyl-N-isopropylpropan-2-amine (1.0 mL) The mixture was stirred at about 25° C. for approximately 10 min followed by addition of (4-methoxyphenyl)methanamine (0.68 g). The reaction was then stirred at about 25° C. for about an additional 12 h. The reaction was basified to pH 10 with aqueous 1 N NaOH and washed three times with EtOAc. The organic solution was dried over $MgSO_4$, filtered, and concentrated under reduced pressure to afford 4-bromo-N-(4-methoxybenzyl)picolinamide as a clear oil (1.2 g, 75%). LC/MS (Table 1, method f). $R_t$=1.73 min; MS m/z 322 (M+H)$^+$.

General Procedure D

Aldehyde Formation

To a flask containing 4-bromo-N-(4-methoxybenzyl)picolinamide (1 equiv) in an organic solvent (such as DMF or 1,4-dioxane) is added (E)-4,4,5,5-tetramethyl-2-styryl-1,3,2-dioxaborolane (1.2 equiv), Pd(dppf)—chloroform adduct (0.05 equiv) and aqueous cesium carbonate (4.0 equiv). The mixture is stirred at about 95° C. for about 8-12 h. The reaction is diluted with water and washed three times with an organic appropriate solvent such as EtOAc, DCM, $CH_2Cl_2$ or ether. The organic solution is filtered over Celite®, and concentrated under reduced pressure to give the target compound. Alternatively, the product can be purified by crystallization or trituration from an appropriate solvent or solvents, or by preparative HPLC or flash chromatography. The above product is subsequently re-dissolved in an appropriate solvent (such as 1,4-dioxane, DMF, 1,4-dioxane/$H_2O$ or DMF/$H_2O$) and treated with sodium periodate (4.0 equiv). After stirring for approximately 30 min at RT, osmium tetroxide (0.04 equiv of a 0.1 M solution in t-butanol) is added to the reaction which is then stirred for about an additional 3-6 h at approximately 25° C.

The layers are separated and the organic solution is dried over $Na_2SO_4$ or $MgSO_4$, filtered, and concentrated under reduced pressure. The product can be purified by crystallization or trituration from an appropriate solvent or solvents, or by preparative HPLC or flash chromatography.

Illustration of General Procedure D

Preparation of
4-Formyl-N-(4-methoxybenzyl)picolinamide

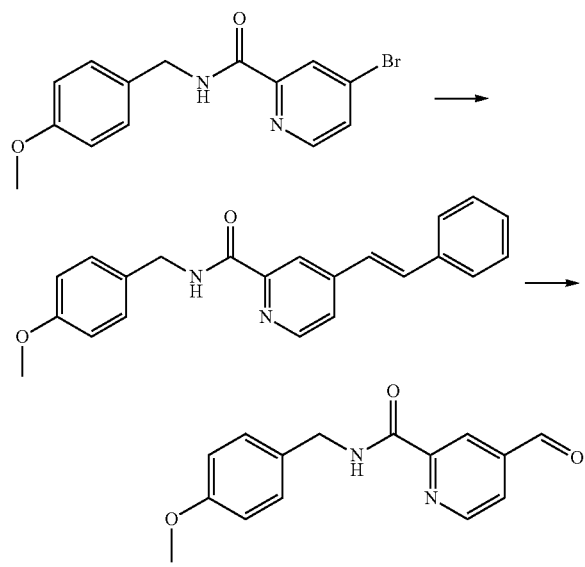

To a flask containing 4-bromo-N-(4-methoxybenzyl)picolinamide (0.3 g) in 1,4-dioxane (1.1 mL) was added (E)-4,4,5,5-tetramethyl-2-styryl-1,3,2-dioxaborolane (0.22 g), Pd(dppf)—chloroform adduct (0.04 g) and 2M aqueous cesium carbonate (1.9 mL). The mixture was stirred at about 95° C. for about 12 h. The reaction was diluted with water and washed three times with $CH_2Cl_2$. The organic solution was filtered over Celite®, and concentrated under reduced pressure yielding (E)-N-(4-methoxybenzyl)-4-styrylpicolinamide as a deep yellow oil (0.25 g, 80%). LC/MS (Table-1, Method f) $R_t$=2.03 min; MS m/z 345 (M+H)$^+$. This intermediate was then dissolved in 4.3 mL of 1,4-dioxane and treated with 0.87 mL of water and sodium periodate (0.75 g). After stirring for approximately 30 min at RT, osmium tetroxide (0.30 mL of a 0.1 M solution in t-butanol) was added to the reaction which was then stirred for about an additional 4 h at RT. The layers were separated and the organic solution was dried over $MgSO_4$, filtered, and concentrated under reduced pressure. The product was isolated by flash chromatography to give 4-formyl-N-(4-methoxybenzyl)picolinamide (0.25 g, 80%): LC/MS (Table 1, method-f) $R_t$=1.01 min; MS m/z 271 (M+H)$^+$.

Preparation #10

4-((Hydroxyimino)methyl)-N-(4-methoxybenzyl)picolinamide

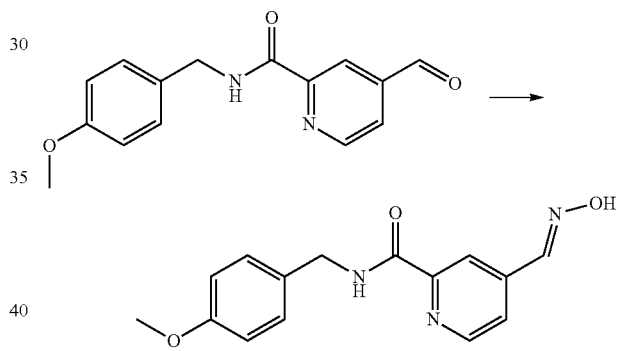

(E)-4-Formyl-N-(4-methoxybenzyl)picolinamide (0.10 g) was dissolved in EtOH (1.0 mL) and heated to reflux in the presence of hydroxylamine hydrochloride (0.024 g) for about 1 h. The reaction was cooled and (E)-4-((hydroxyimino)methyl)-N-(4-methoxybenzyl)picolinamide was isolated by vacuum filtration as a white solid and used without further purification.

General Procedure E

Wittig Olefination

A stirred suspension of methyltriphenyl phosphonium iodide or methyltriphenyl phosphonium bromide (2.0 equiv) in THF (about 20 mL) at about 0° C. under a nitrogen atmosphere is basified with a base (such as KOBt, BuLi, NaH, or DBU, preferably KOBt, about 2.0 to 2.5 equiv) and stirred at RT for about 1 h. To this reaction mixture, an appropriate aldehyde/ketone (about 1.0 equiv) in THF (15 mL) is added slowly. The resulting reaction mixture is stirred at RT for about another 3 h, quenched with water and the product extracted with diethyl ether. The combined organic extracts are washed with brine, dried over sodium sulphate and evaporated to dryness under reduced pressure. The residue obtained is purified by silica gel chromatography to afford the required olefin.

Illustration of General Procedure E

Preparation #E.1

Tert-butyldimethyl (2-(4-vinylphenoxy)ethoxy)silane

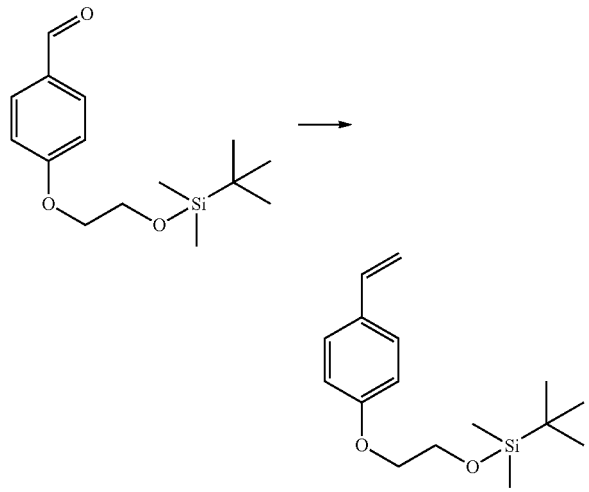

To a cold suspension of methyl triphenyl phosphonium iodide (2.88 g, 7.13 mmol) in THF (20 mL) was added KOBt (0.88 g, 7.84 mmol) slowly. The reaction mixture was warmed to RT and stirred for about 1 h. A solution of 4-(2-(tert-butyldimethylsilyloxy)ethoxy)benzaldehyde (1.0 g, 3.56 mmol) in THF (15 mL) was added slowly to the above reaction mixture and stirred for about another 3 h. The reaction was quenched with water and extracted with diethyl ether (3×75 mL). The combined organic extracts were washed with brine (1×75 mL), dried over sodium sulphate and concentrated under reduced pressure. The residue obtained was purified by silica gel chromatography using 10% EtOAc-hexane as the eluent. Relevant fractions containing the target compound were combined and evaporated to dryness under reduced pressure to afford tert-buyldimethyl (2-(4-vinylphenoxy)ethoxy)silane 0.65 g, (65%), $^1$H NMR (400 MHz, CDCl$_3$): δ 7.350-7.342 (d, J=3.2 Hz, 2H), 6.882-6.875 (d, J=2.8 Hz, 2H), 6.857-6.692 (m, 1H), 5.625-5.581 (d, J=17.6 Hz, 1H), 5.132-5.104 (d, J=11.2 Hz, 1H), 4.052-3.954 (m, 4H), 0.909 (s, 9H), 0.1 (s, 6H), MS m/z: 279.3 (M+H)$^+$.

Other compounds synthesized using General procedure E are described in Table E.1

General Procedure F

Synthesis of Olefins from Halogens

Method 1

To an appropriate aryl halide (1 equiv) dissolved in an organic solvent (such as THF, 1,4-dioxane, or toluene, preferably THF) are added tributylvinyl tin (2.2 equiv), palladium (II) acetate (0.14 equiv), and triphenylphosphine (0.3 equiv). The mixture is degassed with nitrogen then heated at about 80-100° C. (preferably at about 80° C.) for about 4 h to 12 h (preferably about 6 h). The reaction mixture is cooled to RT, filtered and washed with THF. The filtrate is evaporated to dryness under reduced pressure and the crude residue is purified by column chromatography on silica gel to afford the target olefin.

Illustration of General Procedure F

Method 1

Preparation #F.1

4-Vinyl-1H-pyrazole

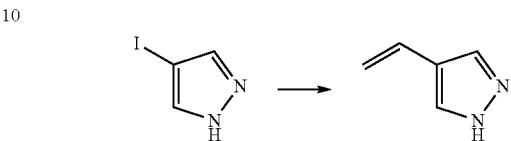

To a stirred solution of 4-iodo pyrazole (0.8 g, 4.14 mmol, Aldrich) in dry THF (20 mL) was added tributyl vinyl tin (2.2 mL, 9.12 mmol), palladium (II) acetate (0.14 g, 0.62 mmol) and triphenyl phosphine (0.33 g, 1.24 mol, Spectrochem). The mixture was degassed with nitrogen for about 15 min then heated to reflux for about 6 h. The reaction mixture was cooled to RT, filtered and washed with THF (10 mL). The filtrate was evaporated to dryness under reduced pressure and the crude material obtained was purified by column chromatography using 20 to 25% of EtOAc in hexane as an eluent. Relevant fractions containing the target compound were combined and evaporated to dryness under reduced pressure to afford 4-vinyl-1H-pyrazole as an off white solid 0.18 g (46%), $^1$H NMR (400 MHz, CDCl$_3$): δ 7.643 (s, 2H), 6.620-6.549 (m, 1H), 5.530-5.486 (d, J=17.6 Hz, 1H), 5.126-5.099 (d, J=10.8 Hz, 1H), MS m/z: 95.1 (M+H)$^+$.

Method II

A 100 mL sealed tube is charged with an appropriate aryl halide (1 equiv) solution in an organic solvent (such as THF, 1,4-dioxane, toluene, MeOH, isopropanol, or propanol, preferably isopropanol or propanol), potassium vinyltrifluoroborate (2 to 2.5 equiv preferably 2.2 equiv, Aldrich), [1,1,-bis (diphenyl phosphino)ferrocine]dichloro palladium(II) complex with DCM (0.1 to 0.5 equiv, preferably 0.1 equiv, Aldrich) and TEA (2 to 2.5 equiv, preferably 2.0 equiv). The mixture is degassed with nitrogen then heated at about 80-100° C. (preferably at about 80° C.) for about 4 h to 12 h (preferably about 12 h). The reaction mixture is evaporated to dryness under reduced pressure and the crude residue is purified by column chromatography on silica gel to afford the desired olefin.

Illustration of General Procedure F

Method II

Preparation #F.2

(6-Vinylpyridin-3-yl)methanol

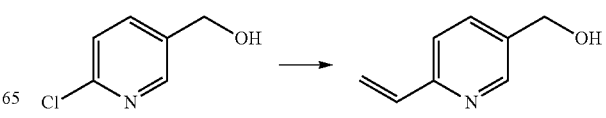

A 100 mL sealed tube was charged with a solution of (6-chloropyridin-3-yl)methanol (0.5 g, 3.4 mmol, *Org. Lett.* 2005, p 2965-2967) dissolved in isopropanol (10 mL), potassium vinyltrifluoroborate (1 g, 7.63 mmol, Aldrich), [1,1,-bis(diphenyl phosphino)ferrocine]dichloro palladium(II) complex with DCM (0.277 g, 0.34 mmol, Aldrich) and TEA (0.92 mL, 6.8 mmol). The mixture was degassed with nitrogen then heated at about 80° C. for about 12 h. The reaction mixture was cooled to RT, filtered and washed with isopropanol (10 mL). The filtrate was evaporated to dryness under reduced pressure and the crude material obtained was purified by silica gel column chromatography using 30 to 40% of EtOAc in hexane as an eluent. Relevant fractions containing the target compound were combined and evaporated to dryness under reduced pressure to afford (6-vinylpyridin-3-yl)methanol as a dark brown liquid 0.25 g (53%), $^1$H NMR (400 MHz, DMSO): δ 8.479 (s, 1H), 7.704-7.688 (d, J=6.4 Hz, 1H), 7.471-7.456 (d, J=6.0 Hz, 1H), 6.827-6.806 (m, 1H), 6.212-6.177 (d, J=14 Hz, 1H), 5.439-5.417 (d, J=8.8 Hz, 1H), 5.300 (m, 1H), 4.524 (d, J=4.4 Hz, 2H), MS m/z: 136 (M+H)$^+$.

Other compounds synthesized using General procedure F are described in Table F.1

Preparation #11

((2S,5S)-5-vinyl-1,4-dioxan-2-yl)methyl 4-methylbenzenesulfonate and ((2R,5R)-5-vinyl-1,4-dioxan-2-yl)methyl 4-methylbenzenesulfonate

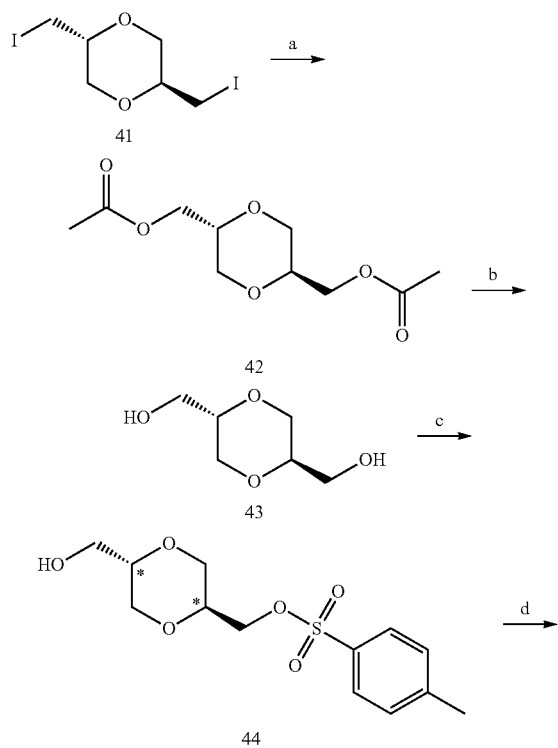

Scheme V

Trans-2,5-bis(iodo methyl)-1,4-dioxane (41) is synthesized by following methods described in WO2009016498A1 and is treated with potassium acetate in DMF at elevated temperature Step a which affords compound 42. Ester hydrolysis using the conditions such as those described in Step b or by methods known to one skilled in the art (for example, the books from Larock, R. C. Greene, T. W. and Wuts, P. G. M. referenced above in Scheme I) afford compound 43. In step c, mono tosylation using tosyl chloride to afford compound 44 by using the conditions such as those described in Step c. Swern oxidation of compound 44 using the conditions such as those described in Step d or by methods known to one skilled in the art (for example, Alan H. Haines "Methods of the Oxidation of Organic Compounds, 1988, Academic Press) yield compound 45. Wittig olefination of 45 using methyl triphenyl phosphonium iodide using the conditions that are described in Step e yielded compound 46 which is further is separated enantiomerically using chiral preparative HPLC to afford 47 and 48.

Step a: trans-2,5-bis(acetoxymethyl)-1,4-dioxane

A suspension of trans (2S,5R)-2,5-bis(iodomethyl)-1,4-dioxane (50 g, 135.8 mmol, WO2009016498A1) and potassium acetate (79.8 g, 814.8 mmol, Avra) in DMF (500 mL) was stirred at 80° C. for 16 hours. Then reaction mixture was cooled to RT and poured into ice cold water (1500 mL). The resulting solids were filtered and dried under vacuum to afford trans-2,5-bis-(acetoxymethyl)-1,4-dioxane 14.5 g(45%) as off white solid; $^1$H NMR (400 MHz, CDCl$_3$): δ 4.07 (d, J=5.2 Hz, 4H), 3.88-3.75 (m, 4H), 3.50-3.45 (m, 1H), 2.09 (s, 3H); MS m/z: 233.1 (m+H)$^+$.

Step b: trans-2,5-bis-(hydroxymethyll)-1,4-dioxane

To a stirred suspension of trans-2,5-bis-(acetoxymethyl)-1,4-dioxane (14.5 g, 220 mmol, Preparation #11: Step a) in MeOH (40 mL) was added 4N.dioxane.HCl (20 mL, 220 mmol) and heated to reflux for 1 h. Then reaction mixture was cooled to RT and the solvents were evaporated under reduced pressure. The resulting oily residue was triturated with 10% EtOAc in hexane (3×50 mL) to afford trans-2,5-bis-(hydroxymethyl)-1,4-dioxane 9.0 g (97%) as brown solid; $^1$H NMR (400 MHz, CDCl$_3$): δ 3.85-3.82 (m, 2H), 3.67-3.52 (m, 10H), 2.05 (bs, 1H); MS: m/z 149.1 (m+H)$^+$.

Step c: racemic ((2S*,5S*)-5-(hydroxymethyl)-1,4-dioxan-2-yl)methyl 4-methylbenzenesulfonate To a stirred solution of trans-2,5-bis-(hydroxymethyll)-1,4-dioxane (15 g, 101.3 mmol, Preparation #11: Step b) in DCM (60 mL) at 0° C., was added TEA (28.1 mL, 101.3 mmol, Spectrochem) followed by 4-methylbenzene-1-sulfonyl chloride (19.2 g, 101.3 mmol, Spectrochem). The reaction mixture allowed to stir at RT overnight. The mixture was quenched with 3N hydrochloric acid (150 mL), and the resulting solids were filtered. The organic phase of the filtrate was separated and aqueous layer extracted with DCM (50 mL). Combined organic layers were washed with 3N hydrochloric acid (2×100 mL), dried over sodium sulphate and concentrated under reduced pressure to afford racemic((2S*,5S*)-5-(hydroxymethyl)-1,4-dioxan-2-yl)methyl 4-methylbenzenesulfonate 14 g (45%); $^1$H NMR (400 MHz, CDCl$_3$): δ 7.79 (d, J=8.4 Hz, 2H), 7.36 (d, J=8.0 Hz, 2H), 4.01-3.93 (m, 2H), 3.84-3.70 (m, 3H), 3.62-3.39 (m, 5H), 2.45 (s, 3H), 2.17 (t, J=5.6 Hz, 1H); MS m/z: 303.2 (m+H)$^+$.

Step d: racemic ((2S*,5R*)-5-formyl-1,4-dioxan-2-yl)methyl 4-methylbenzenesulfonate A solution of oxalyl chloride (14.2 mL, 165.5 mmol, Spectrochem) in DCM (30 mL) was cooled to −78° C. and was added DMSO (21.1 mL, 298 mmol, Spectrochem) drop wise. The reaction mixture was stirred for 20 minutes at the same temperature and a solution of rac ((2S*,5S*)-5-(hydroxymethyl)-1,4-dioxan-2-yl)methyl 4-methylbenzenesulfonate (20 g, 66.2 mmol, Preparation #11: Step c) in DCM (60 mL) was added slowly. The reaction mixture was stirred at the same temperature for another 1 h and quenched with TEA (26.7 mL, 364.2 mmol). The reaction mixture was warmed to RT, diluted with DCM (50 mL) and washed successively with 1N HCl (2×150 mL), saturated sodium bicarbonate (2×100 mL) and brine (2×100 mL). The organic layer was dried over sodium sulphate and evaporated to dryness under reduced pressure to afford racemnic ((2S*,5R*)-5-formyl-1,4-dioxan-2-yl)methyl 4-methylbenzenesulfonate 20 g (crude, 100%); $^1$H NMR (400 MHz, CDCl$_3$): δ 9.55 (s, 1H), 7.80 (d, J=8.4 Hz, 2H), 7.37 (d, J=7.6 Hz, 2H), 4.01-3.92 (m, 5H), 3.76 (m, 1H), 3.53-3.42 (m, 2H), 2.45 (s, 3H); MS m/z: 301.3 (m+H)$^+$ Step e: racemic ((2S*,5S*)-5-vinyl-1,4-dioxan-2-yl) methyl 4-methylbenzenesulfonate To a suspension of methyl triphenyl phosphonium iodide (53.86 g, 133.3 mmol, Aldrich) in THF (100 mL) was added potassium tert-butoxide (18.68 g, 166 mmol, Aldrich) at 0° C. and stirred for min at the same temperature. A solution of racemic ((2S*,5R*)-5-formyl-1,4-dioxan-2-yl)methyl 4-methylbenzenesulfonate (25 g, 83 mmol, Preparation #11: Step d) in THF (50 mL) was added slowly to the above cold reaction mixture. After the addition was completed, the reaction mixture was warmed to RT, stirred for another 2 h and quenched with water (100 mL). The organic layer was separated, and the aqueous layer was extracted with EtOAc (2×150 mL). Combined organic extracts were washed with brine (100 mL), dried over sodium sulphate and concentrated under reduced pressure. The resulting crude material was purified by column chromatography on silica gel eluting with 15-20% EtOAc in hexane. Relevant fractions containing the required compound were combined and evaporated to dryness under reduced pressure to afford racemic((2S*,5S*)-5-vinyl-1,4-dioxan-2-yl)methyl 4-methylbenzenesulfonate 9 g (45%); $^1$H NMR (400 MHz, CDCl$_3$): δ 7.80 (d, J=8.0 Hz, 2H), 7.36 (d, J=8.0 Hz, 2H), 5.72-5.63 (m, 1H), 5.34-5.20 (m, 2H), 4.03-3.94 (m, 3H), 3.84-3.71 (m, 3H), 3.46-3.28 (m, 2H), 2.45 (s, 3H); MS m/z: 299.2 (m+H)$^+$. Racemic ((2S*,5S*)-5-vinyl-1,4-dioxan-2-yl)methyl 4-methylbenzenesulfonate was further separated enantiomerically using the chiral preparative HPLC (Table 2, method c-12) to afford ((2S,5S)-5-vinyl-1,4-dioxan-2-yl)methyl 4-methylbenzenesulfonate 4.2 g $^1$H NMR (400 MHz, CDCl$_3$): δ 7.80 (d, J=8.0 Hz, 2H), 7.36 (d, J=8.0 Hz, 2H), 5.72-5.63 (m, 1H), 5.34-5.20 (m, 2H), 4.03-3.94 (m, 3H), 3.84-3.71 (m, 3H), 3.46-3.28 (m, 2H), 2.45 (s, 3H); MS: m/z 299.2 (m+H) and ((2R,5R)-5-vinyl-1,4-dioxan-2-yl)methyl 4-methylbenzenesulfonate 4 g $^1$H NMR (400 MHz, CDCl$_3$): δ 7.80 (d, J=8.0 Hz, 2H), 7.36 (d, J=8.0 Hz, 2H), 5.72-5.63 (m, 1H), 5.34-5.20 (m, 2H), 4.03-3.94 (m, 3H), 3.84-3.71 (m, 3H), 3.46-3.28 (m, 2H), 2.45 (s, 3H); MS m/z: 299.2 (m+H)$^+$ General Procedure G Isoxazoline formation

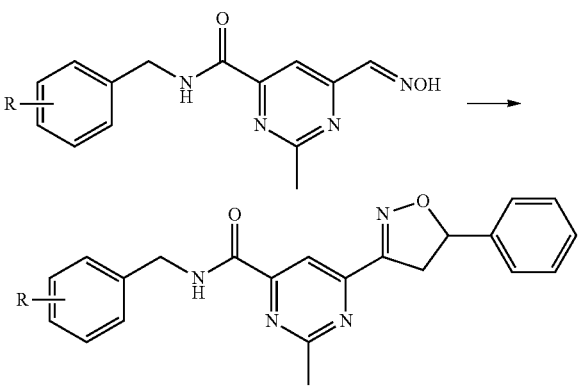

Method 1:

1-5 equiv. of aldoxime (preferably 1 equiv) and an alkene (1 equiv) are taken in an organic solvent (such as DCM, chloroform, THF, or 1,4-dioxane, preferably DCM) and treated with sodium hypochlorite solution. The reaction mixture is stirred at RT for about 1-2 h (preferably about 2 h) and quenched with water. The product is extracted with DCM. The organic layer is dried over sodium sulphate and concentrated under reduced pressure. The residue obtained is purified using silica gel column chromatography to obtain an isoxazoline derivative.

Method 2:

1-5 equiv. of aldoxime (preferably about 1 equiv) and an alkene (1.6 equiv) are taken in an organic solvent (such as DCM, chloroform, THF, or 1,4-dioxane, preferably chloroform) cooled in an ice bath and to it is added iodobenzene diacetate (1-5 equiv, preferably 1.6 equiv). The reaction mixture is stirred at RT for about 1-2 h (preferably about 1 h) and quenched with water. The product is extracted with DCM. The organic layer is dried over sodium sulphate and concentrated under reduced pressure. The residue obtained is purified using silica gel column chromatography to obtain an isoxazoline derivative.

Illustration of General Procedure G

Method 1 (G-1)

Example #G.1

N-(4-methoxybenzyl)-2-methyl-6-(5-phenyl-4,5-dihydroisoxazol-3-yl)pyrimidine-4-carboxamide

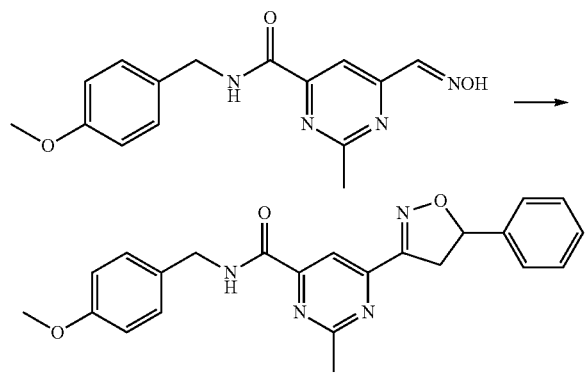

To a stirred suspension of 6-((hydroxyimino)methyl)-N-(4-methoxybenzyl)-2-methylpyrimidine-4-carboxamide (0.15 g, 0.50 mmol, Preparation #B.1.1) and styrene (0.057 g, 0.50 mmol) in DCM (10 mL) was added 4% sodium hypochlorite solution (1.5 mL, Sd Fine Chem.) drop wise for about 10 min at RT and stirred for about another 2 h. The reaction mixture was diluted with water (50 mL) and the product extracted with DCM (3×25 mL). The organic layer was dried over sodium sulphate and evaporated to dryness under reduced pressure. The resulting mixture was purified by silica gel (60-120 mesh) chromatography eluting with 20 to 30% of EtOAc in hexane. Relevant fractions containing the target compound were combined and evaporated to dryness under reduced pressure to afford N-(4-methoxybenzyl)-2-methyl-6-(5-phenyl-4,5-dihydroisoxazol-3-yl)pyrimidine-4-carboxamide as a white solid 0.07 g (34%). LC/MS (Table 1, method-b) $R_t$=1.93 min; MS m/z: 403 (M+H).

Illustration of General Procedure C

Method 2 (G-2)

Preparation #G.2

Tert-butyl 4-(3-(6-(4-methoxybenzylcarbamoyl)-2-methylpyrimidin-4-yl)-4,5-dihydroisoxazol-5-yl)piperidine-1-carboxylate

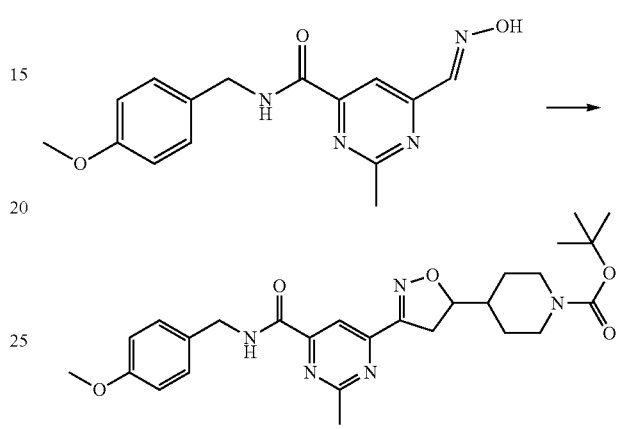

To a cold solution of (6-((hydroxyimino)methyl)-N-(4-methoxybenzyl)-2-methylpyrimidine-4-carboxamide (0.2 g, 0.66 mmol, Preparation #B.1.1) and tert-butyl 4-vinylpiperidine-1-carboxylate (0.168 g, 0.799 mmol, Preparation #E.1.2) in chloroform (20 mL) was added iodobenzene diacetate (0.343 g, 1.06 mmol) in one portion. The mixture was allowed to warm to RT and stirred for about another 1 h. The reaction mixture was quenched with water (20 mL) and the product was extracted with chloroform (2×20 mL). The organic layer was washed with water (2×15 mL), dried over sodium sulphate and evaporated to dryness. The residue obtained was purified by column chromatography using silica gel (60-120 mesh) eluting with 50% n-hexane and EtOAc. Relevant fractions containing the required compound were combined and evaporated to dryness under reduced pressure to afford tert-butyl 4-(3-(6-(4-methoxybenzylcarbamoyl)-2-methylpyrimidin-4-yl)-4,5-dihydroisoxazol-5-yl)piperidine-1-carboxylate 0.1 g (29%). MS m/z: 510 (M+H)$^+$.

Other compounds synthesized using General procedure G are described in Table G.1 and G.2

Example#G.3

N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide

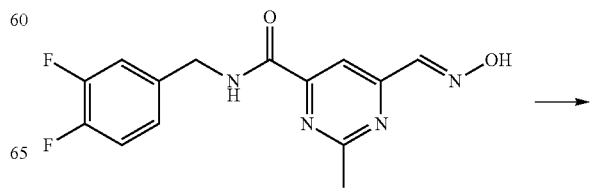

-continued

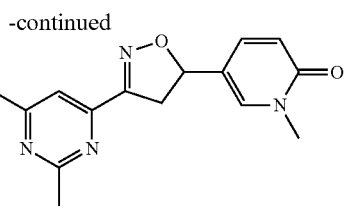

To a solution of N-(3,4-difluorobenzyl)-6-((hydroxyimino)methyl)-2-methylpyrimidine-4-carboxamide (13.60 g, 44.4 mmol, Preparation #A.1.2) and 1-methyl-5-vinylpyridin-2(1H)-one (6 g, 44.4 mmol, Preparation #F.1.13) in DCM (150 mL) was added 9% aqueous sodium hypochlorite solution (80 mL, 1296 mmol, Avra labs) drop wise at 10-15° C. for about 30 min. Reaction mixture was allowed to stir for another 15-30 min, diluted the reaction mixture with water (100 mL) and the product extracted with DCM (2×100 mL). The combined organic layers was dried over sodiumsulphate and evaporated to dryness. The resulting crude material was purified by silica gel column chromatography by eluting with 2% methanol in DCM. Relevant fractions containing product were combined and evaporated under reduced pressure to afford N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide 3 g (15.38%) as pale yellow solid; $^1$H NMR (400 MHz, DMSO): δ 9.606-9.574 (m, 1H), 8.179 (s, 1H), 7.872-7.866 (d, J=2.4 Hz, 1H), 7.527-7.497 (dd, J=9.6 Hz, 1H), 7.421-7.353 (m, 2H), 7.205-7.173 (m, 1H), 6.436-6.412 (d, J=9.6 Hz, 1H), 5.688-5.637 (m, 1H), 4.504-4.488 (d, J=6.4 Hz, 2H), 3.836-3.764 (m, 1H), 3.463-3.440 (m, 1H), 3.425 (s, 3H), 2.767 (s, 3H); MS m/z: 440.2 (M+H)$^+$.

Chiral separation of N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide to obtain (S)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide and (R)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide

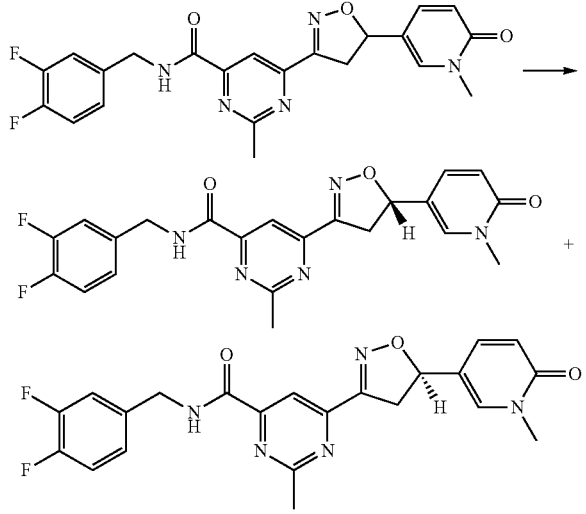

2.9 g of racemic N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide was separated enantiomercially using chiral preparative HPLC (Table 2, Method c-9) to obtain individual enentiomers: first eluting compound as (S)—N-(3,4-difluorobenzyl)-2-methyl-6-(5-(1-methyl-6-oxo-6-dihydropyridin-3-yl)-4,5-dihydroisoxazol-3-yl)pyrimidine-4-carboxamide 0.98 g (32.7%), $^1$H NMR (400 MHz, DMSO): δ 9.606-9.574 (m, 1H), 8.179 (s, 1H), 7.872-7.866 (d, J=2.4 Hz, 1H), 7.527-7.497 (dd, J=9.6 Hz, 1H), 7.414-7.353 (m, 2H), 7.205-7.173 (m, 1H), 6.436-6.413 (d, J=9.2 Hz, 1H), 5.758-5.638 (m, 1H), 4.504-4.488 (d, J=6.4 Hz, 2H), 3.836-3.764 (m, 1H), 3.475-3.440 (m, 1H), 3.425 (s, 3H), 2.767 (s, 3H); MS m/z: 440.3 (M+H)$^+$ and the second eluting compound as (R)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide 1 g (33.3%), $^1$H NMR (400 MHz, DMSO): δ 9.606-9.574 (m, 1H), 8.179 (s, 1H), 7.872-7.866 (d, J=2.4 Hz, 1H), 7.527-7.497 (dd, J=9.6 Hz, 1H), 7.414-7.353 (m, 2H), 7.205-7.173 (m, 1H), 6.436-6.413 (d, J=9.2 Hz, 1H), 5.758-5.638 (m, 1H), 4.504-4.488 (d, J=6.4 Hz, 2H), 3.836-3.764 (m, 1H), 3.475-3.440 (m, 1H), 3.425 (s, 3H), 2.767 (s, 3H); MS m/z: 440.2 (M+H)+;

Example#G.4

6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide and 6-(5-(5-chloro-1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide

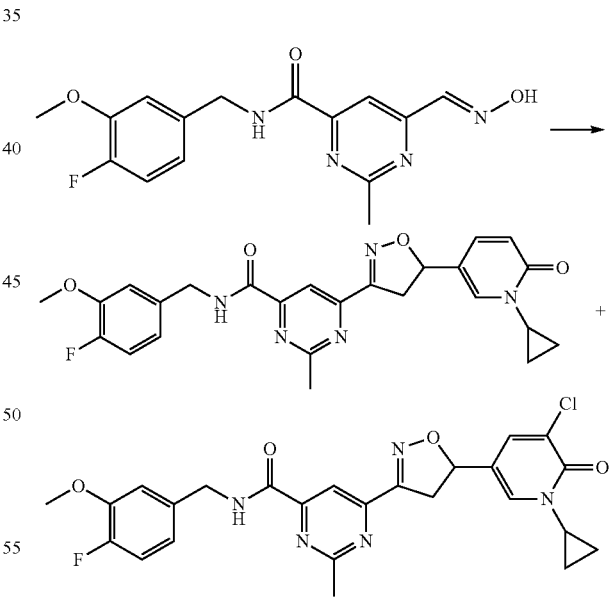

To a solution of N-(4-fluoro-3-methoxybenzyl)-6-((hydroxyimino)methyl)-2-methylpyrimidine-4-carboxamide (4.0 g, 12.57 mmol, Preparation #9) and 1-cyclopropyl-5-vinylpyridin-2(1H)-one (2.026, 12.57 mmol, Preparation #F.1.33) in DCM (60 mL) was added 9% aqueous sodium hypochlorite solution (60 mL, 12.57 mmol, Avra labs) drop wise at 10-15° C. for about 30 min. The reaction mixture was allowed to stir for another 15-30 min, reaction mixture was diluted with water (100 mL) and the product extracted with DCM (100 mL). The combined organic layers were dried over sodium sulphate and evaporated to dryness. The resulting crude material contained two products, and these were separated by silica gel column chromatography eluting with 2% methanol in DCM. Relevant fractions containing product were combined and evaporated under reduced pressure to obtain the first eluting compound as 6-(5-(5-chloro-1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide, $^1$H NMR (400 MHz, DMSO): δ 9.518-9.486 (m, 1H), 8.177 (s, 1H), 7.889-7.883 (d, J=2.4 Hz, 1H), 7.753-7.747 (d, J=2.4 Hz, 1H), 7.186-7.120 (m, 2H), 6.907-6.871 (m, 1H), 5.757-5.672 (m, 1H), 4.492-4.476 (d, J=6.4, Hz, 2H), 3.820 (s, 3H), 3.784-3.740 (m, 1H), 3.502-3.371 (m, 2H), 2.762 (s, 3H), 1.091-0.902 (m, 4H); MS m/z: 512.2 (M+H)+. and the second eluting compound as 6-(5-(5-chloro-1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide 0.28 g (4.67%) as a brown color solid. $^1$HNMR (400 MHz, DMSO): δ 9.515-9.485 (m, 1H), 8.179 (s, 1H), 7.680-7.675 (d, J=2 Hz, 1H), 7.489-7.459 (dd, J=9.6 Hz, 1H), 7.180-7.119 (m, 2H), 6.900-6.874 (m, 1H), 6.448-6.390 (dd, J=13.6 Hz, 1H), 5.757-5.661 (m, 1H), 4.489-4.474 (d, J=6 Hz, 2H), 3.817 (s, 3H), 3.805-3.732 (m, 1H), 3.472-3.342 (m, 2H), 2.759 (s, 3H), 1.073-0.863 (m, 4H); MS m/z: 478.2 (M+H)+.

Chiral Separation of 6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide to obtain (S)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide and (R)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide

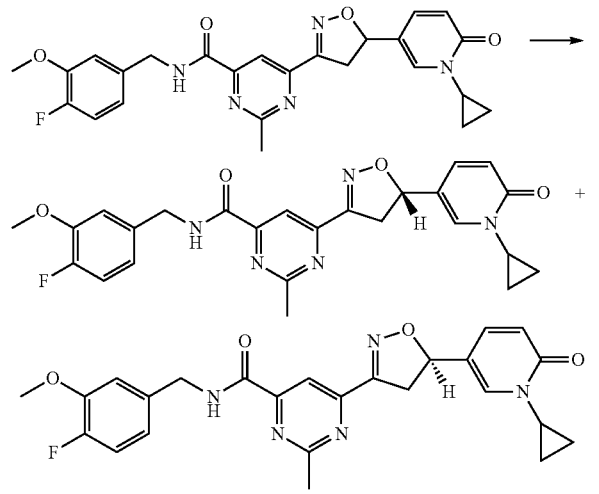

260 mg of 6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide was separated into single enantiomers using chiral preparative HPLC (Table 2, Method c-10): the first eluting compound was (S)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide 60 mg (21.4%) $^1$HNMR (400 MHz, DMSO) δ 9.514-9.482 (m, 1H), 8.179 (s, 1H), 7.680-7.674 (d, J=2.4 Hz, 1H), 7.488-7.459 (dd, J=9.2 Hz, 1H), 7.184-7.119 (m, 2H), 6.900-6.874 (m, 1H), 6.413-6.390 (d, J=9.2 Hz, 1H), 5.713-5.660 (m, 1H), 4.489-4.474 (d, J=6 Hz, 2H), 3.817 (s, 3H), 3.804-3.732 (m, 1H), 3.440-3.332 (m, 2H), 2.759 (s, 3H), 0.998-0.849 (m, 4H); MS m/z=478.2 (M+H)+; the second eluting compound was (R)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide 58 mg (20.7%). $^1$H NMR (400 MHz, DMSO): δ 9.515-9.484 (t, 1H), 8.180 (s, 1H), 7.681-7.675 (d, J=2.4 Hz, 1H), 7.491-7.460 (dd, J=10 Hz, 1H), 7.186-7.120 (m, 2H), 6.907-6.871 (m, 1H), 6.415-6.391 (d, J=9.6 Hz, 1H), 5.714-5.661 (m, 1H), 4.491-4.475 (d, J=6.4 Hz, 2H), 3.819 (s, 3H), 3.805-3.732 (m, 1H), 3.441-3.335 m, 2H), 2.759 (s, 3H), 0.991-0.816 (m, 4H); MS m/z: 478.2 (M+H)+;

Example#G.5

6-(5-(1H-Imidazol-4-yl)-4,5-dihydroisoxazol-3-yl)-N-(4-fluoro-3-methoxybenzyl)-2-methylpyrimidine-4-carboxamide

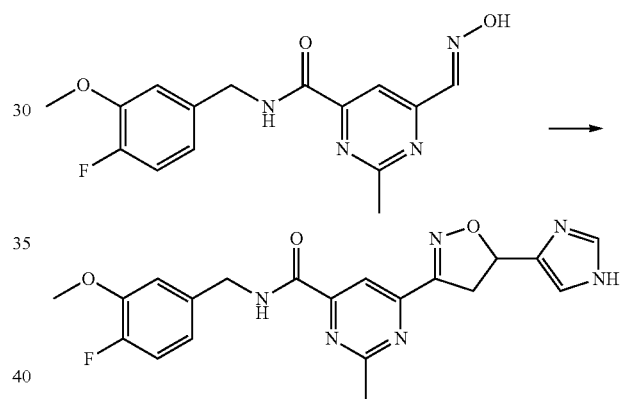

To a cold solution of N-(4-fluoro-3-methoxybenzyl)-6-((hydroxyimino)methyl)-2-methylpyrimidine-4-carboxamide (0.2 g, 0.628 mmol, Preparation #9,) and 1-trityl-4-vinyl-1H-imidazole (*Organic Letters* 2001, 3, 1319-1322) in DCM (20 mL) was added sodium hypochlorite solution (2.0 mL, Sd Fine Chem.) dropwise for about 10 min at RT and stirred for about another 1 h. The reaction mixture was diluted with DCM (30 mL) and washed with water (2×20 mL). The organic layer was dried over sodium sulphate and evaporated to dryness under reduced pressure. The resulting mixture was purified by silica gel chromatography eluting with 60 to 70% of EtOAc in hexane. Relevant fractions containing the target compound were combined and evaporated to dryness under reduced pressure to afford N-(4-fluoro-3-methoxybenzyl)-2-methyl-6-(5-(1-trityl-1H-imidazol-4-yl)-4,5-dihydroisoxazol-3-yl)pyrimidine-4-carboxamide as a light yellow solid 0.154 g, (37.5%). To a stirred solution of N-(4-fluoro-3-methoxybenzyl)-2-methyl-6-(5-(1-trityl-1H-imidazol-4-yl)-4,5-dihydroisoxazol-3-yl)pyrimidine-4-carboxamide(0.14 g, 0.24 mmol) in methanol (15 mL) was added concentrated HCl (1.2 mL). The reaction mixture was stirred at RT for about 4 h and excess solvent was evaporated under reduced pressure. The reaction mixture was quenched with 1N NaOH solution (5 mL), diluted with water (10 mL) and the product extracted with EtOAc (2×10 mL). The combined organic layers were washed successively with water (1×30 mL) and brine (1×20 mL). The organic layer was dried over sodium sulphate and evaporated to dryness under reduced pressure. The crude material was purified by preparative TLC (7% methanol in DCM) to afford 6-(5-(1H-imidazol-4-yl)-4,5-dihydroisoxazol-3-yl)-N-(4-fluoro-3-methoxybenzyl)-2-methylpyrimidine-4-carboxamide 0.039 g (41.4%); $^1$H NMR (400 MHz, DMSO): δ 8.178 (s, 1), 12.121 (s, 1H), 9.494 (m, 1H), 7.65 (s, 1H), 7.305 (s, 1H), 7.186-7.146 (m, 2H), 6.910-6.905 (m, 1H), 5.845-5.795 (m, 1H), 4.490-4.475 (d, 2H, J=6 Hz), 3.81 (s, 3H), 3.715-3.692 (m, 2H), 2.77 (s, 3H); MS m/z: 410.40 (M+H)$^+$.

Preparation #G.6

((2S,5R)-5-((S)-3-(6-(4-fluoro-3-methoxybenzylcarbamoyl)-2-methylpyrimidin-4-yl)-4,5-dihydroisoxazol-5-yl)-1,4-dioxan-2-yl)methyl 4-methylbenzenesulfonate and ((2S,5R)-5-((R)-3-(6-(4-fluoro-3-methoxybenzylcarbamoyl)-2-methylpyrimidin-4-yl)-4,5-dihydroisoxazol-5-yl)-1,4-dioxan-2-yl)methyl 4-methylbenzenesulfonate phy using silica gel (230-400 mesh) eluting with 40% EtOAc in n-hexane. First eluting compound fractions were combined and evaporated to dryness under reduced pressure, triturated with 40% EtOAc in hexane to afford ((2S,5R)-5-((S)-3-(6-(4-fluoro-3-methoxybenzylcarbamoyl)-2-methylpyrimidin-4-yl)-4,5-dihydroisoxazol-5-yl)-1,4-dioxan-2-yl)methyl 4-methylbenzenesulfonate 1.5 g (24%). $^1$H NMR (400 MHz, CDCl$_3$): δ 8.48 (s, 1H), 8.28 (t, J=6.4 Hz, 1H), 7.79 (d, J=8 Hz, 2H), 7.36 (d, J=8 Hz, 2H), 7.08-6.96 (m, 2H), 6.90-6.86 (m, 1H), 4.68-4.60 (m, 3H), 4.02-3.93 (m, 2H), 3.88 (s, 3H), 3.85-3.72 (m, 5H), 3.59-3.38 (m, 5H), 2.75 (s, 3H), 2.42 (s, 3H); MS m/z: 615 (m+H)$^+$.

Second eluting compound fractions were combined and evaporated to dryness under reduced pressure to afford ((2S,5R)-5-((R)-3-(6-((4-fluoro-3-methoxybenzyl)carbamoyl)-2-methylpyrimidin-4-yl)-4,5-dihydroisoxazol-5-yl)-1,4-dioxan-2-yl)methyl 4-methylbenzenesulfonate 1.2 g (19%). $^1$H NMR (400 MHz, CDCl$_3$): δ 8.48 (s, 1H), 8.28 (t, J=6.4 Hz, 1H), 7.79 (d, J=8 Hz, 2H), 7.36 (d, J=8 Hz, 2H), 7.07-6.96 (m, 2H), 6.89-6.86 (m, 1H), 4.79-4.73 (m, 1H), 4.62 (d, J=6.4 Hz, 2H), 4.02-3.94 (m, 2H), 3.88 (s, 3H), 3.85-3.60 (m, 7H), 3.47-3.40 (m, 3H), 2.74 (s, 3H), 2.45 (s, 3H); MS m/z: 615 (m+H)$^+$.

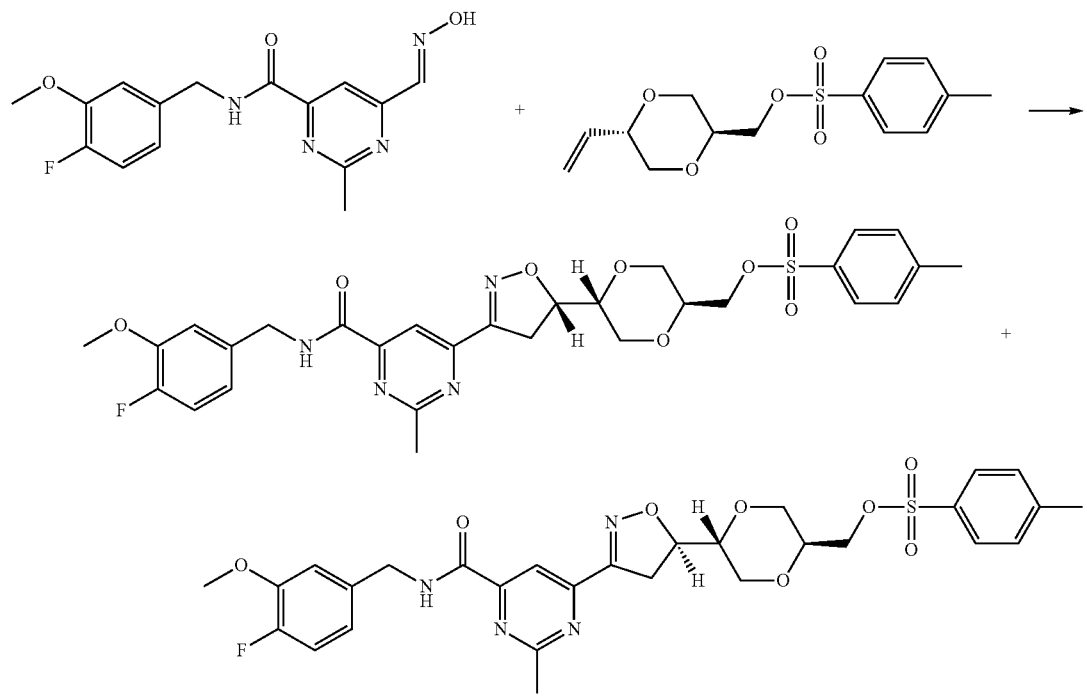

To a stirred solution of N-(4-fluoro-3-methoxybenzyl)-6-((hydroxyimino)methyl)-2-methyl pyrimidine-4-carboxamide (3.84 g, 12.08 mmol, Preparation #9) and ((2S,5S)-5-vinyl-1,4-dioxan-2-yl)methyl 4-methylbenzenesulfonate (3.0 g, 10.06 mmol, Preparation#11) in CHC$_3$ (30 mL), was added iodobenzene diacetate (6.48 g, 20.13 mmol, Aldrich) portion wise (divided in to 4 equal portions and added over a period of 4 hrs). After the addition is completed, the reaction mixture was stirred for another 5 h and quenched with water (100 mL). The product was extracted with DCM (2×100 mL). Combined organic layers were washed with brine solution (100 mL), dried over sodiumsulphate and evaporated to dryness. The residue obtained containing two diastereomers and other impurities was purified by flash column chromatogra- General Procedure H Deprotection of O-tosylate A solution of an appropriate O-tosylate derivative (1 equiv) and tetrabutylammonium acetate (1.5 to 2.5 equiv, preferably 2.2 equiv) in dimethylformamide is heated at about 60 to 100° C. (preferably about 70° C.) for about 3 to 15 h. The mixture is cooled to RT and the reaction vessel is charged sequentially with water (2 mL per Ig) and 1.0 N aqueous sodium hydroxide (6 mL per Sg). After stirring for about 20 min at RT, the mixture is diluted with EtOAc and washed with brine. The organic layer is dried over sodium sulphate and concentrated under reduced pressure. The residue obtained is purified by flash column chromatography to afford the target hydroxy derivative.

Illustrations of General Procedure H

Example #H.1

N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide

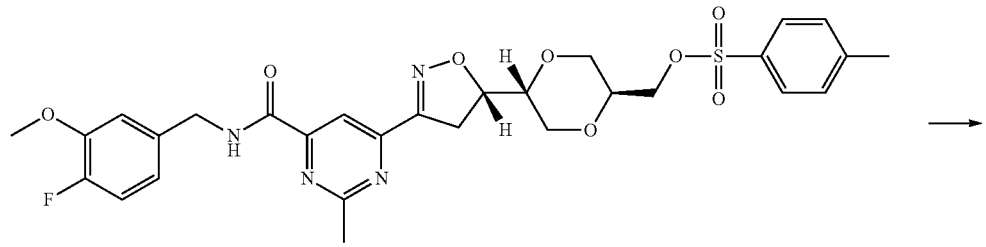

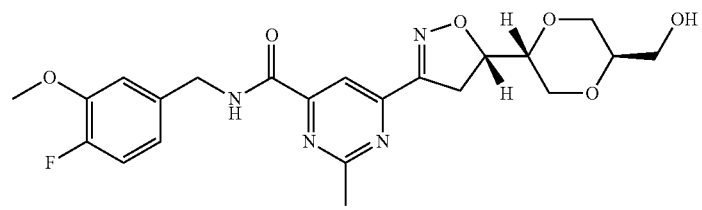

A solution of ((2S,5R)-5-((S)-3-(3-(4-fluoro-3-methoxybenzylcarbamoyl)-5-methylphenyl)-4,5-dihydroisoxazol-5-yl)-1,4-dioxan-2-yl)methyl 4-methylbenzenesulfonate (0.8 g, 1.30 mmol, Preparation #G.6) and tetra butyl ammonium acetate (0.86 g, 2.86 mmol, Aldrich) in DMF (5 mL) were stirred for 3 h. at 70° C. The reaction mixture was cooled to room temperature, the reaction vessel was charged sequentially with water (12 mL) and 1.0N aqueous sodium hydroxide (6 mL).

After stirring for 20 min at RT the mixture was diluted with EtOAc (200 mL) and washed with 50% aqueous sodiumchloride solution (2×150 mL). The organic layer was dried over sodiumsulphate and evaporated to dryness. The resulting crude material was purified by column chromatography on silica gel eluting with 60% EtOAc in hexane to afford N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide as an off-white solid 0.25 g (41%); $^1$H NMR (400 MHz, DMSO): δ 9.48 (t, J=6.4 Hz, 1H), 8.13 (s, 1H), 7.17-7.11 (m, 2H), 6.90-6.86 (m, 1H), 4.80-4.75 (m, 1H), 4.71 (t, J=5.6 Hz, 1H), 4.48 (d, J=6.4 Hz, 2H), 3.87-3.84 (m, 2H), 3.81 (s, 3H), 3.66-3.35 (m, 6H), 3.32-3.27 (m, 2H), 2.75 (s, 3H); LC/MS (Table 1, Method d) R$_t$=0.91 min; MS m/z: 461.3 (m+H)$^+$.

Example #H.2

N-(4-fluoro-3-methoxybenzyl)-6-((R)-5-((2R,5R)-5-(hydroxymethyl)-1,4-dioxan-2-yl)-4,5-dihydroisoxazol-3-yl)-2-methylpyrimidine-4-carboxamide

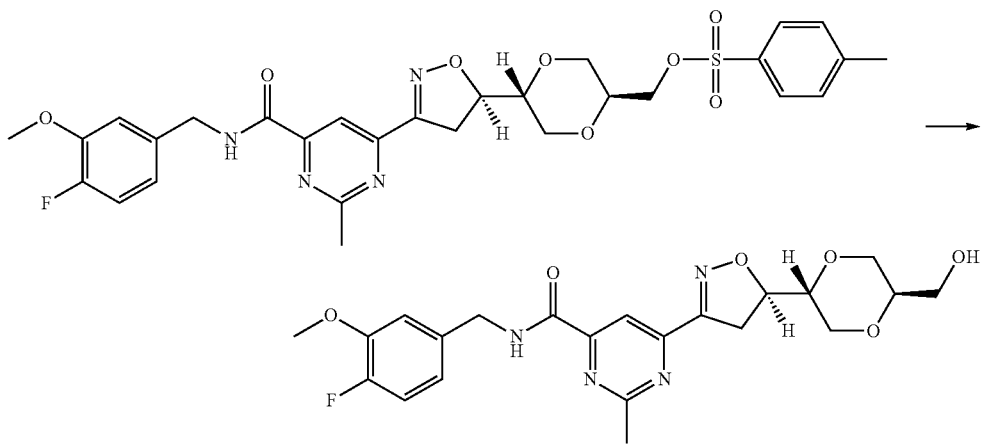

A solution of ((2S,5R)-5-((R)-3-(6-((4-fluoro-3-methoxybenzyl)carbamoyl)-2-methylpyrimidin-4-yl)-4,5-dihydroisoxazol-5-yl)-1,4-dioxan-2-yl)methyl 4-methylbenzenesulfonate (0.7 g, 1.13 mmol, Preparation #G.6) and tetra butyl ammonium acetate (0.72 g, 2.34 mmol, Aldrich) in DMF (5 mL) were stirred for 3 h at 70° C. The reaction mixture was cooled to RT, the reaction vessel was charged sequentially with water (10 mL) and 1.0N aqueous sodium hydroxide (5 mL). After string for 20 minu at RT it was diluted with EtOAc (200 mL) and washed with 50% aqueous sodiumchloride solution (2×150 mL). The organic layer was dried over sodiumsulphate and evaporated to dryness. The resulting crude material was purified by column chromatography on silica gel eluting with 60% EtOAc in hexane to afford N-(4-fluoro-3-methoxybenzyl)-6-((R)-5-((2R,5R)-5-(hydroxymethyl)-1,4-dioxan-2-yl)-4,5-dihydroisoxazol-3-yl)-2-methylpyrimidine-4-carboxamide 0.32 g (61%); $^1$H NMR (400 MHz, DMSO): δ 9.48 (t, J=6.4 Hz, 1H), 8.11 (s, 1H), 7.15-7.09 (m, 2H), 6.86-6.81 (m, 1H), 4.80-4.70 (m, 2H), 4.69 (t, J=5.2 Hz, 1H), 4.46 (d, J=6.4 Hz, 2H), 3.88-3.82 (m, 2H), 3.79 (s, 3H), 3.56-3.34 (m, 6H), 2.75 (s, 3H); LC/MS (Table 1, Method d) R$_t$=0.74 min; MS m/z: 461.1 (m+H)$^+$.

Examples #H.3 and #H.4

Preparation of N-(3-chloro-4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide and N-(3-chloro-4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide A solution of ((2S,5R)-5-((S*)-3-(6-(3-chloro-4-fluorobenzlcarbamoyl)-2-methylpyrimidin-4-yl)-4,5-dihydroisoxazol-5-yl)-1,4-dioxan-2-yl)methyl 4-methylbenzenesulfonate, 0.4 g, 0.647 mmol (preparation G.1.99) and tetrabutylammonium acetate (0.428 g, 1.42 mmol) in dimethylformamide (8 mL) were heated at about 70° C. for about 12 h. The reaction mixture was cooled to RT and the reaction vessel was charged sequentially with water (0.8 mL) and 1.0 N aqueous sodium hydroxide (2.4 mL). After stirring for about 20 min at RT, the mixture was diluted with EtOAc (150 mL) and washed with 50% aqueous sodium chloride (2×50 mL). The organic layer was dried over sodium sulphate, filtered and concentrated under reduced pressure to afford an orange oil. The diastereomeric residue obtained was purified preparative TLC 50% EtOAc and n-hexane as eluent to afford N-(3-chloro-4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide 0.028 g (9%) $^1$H NMR (400 MHz, DMSO): δ 9.60-9.57 (t, J=6.2 Hz, 1H), 8.12 (s, 1H), 7.55-7.53 (d, J=6.8 Hz, 1H), 7.39-7.35 (m, 2H), 4.81-4.70 (m, 2H), 4.49-4.47 (d, J=6.0 Hz, 2H), 3.86-3.81 (m, 2H), 3.65-3.62 (m, 1H), 3.45-3.35 (m, 6H), 3.29-3.26 (m, 1H), 2.76 (s, 3H), MS m/z 465.2 (M+H)$^+$and N-(3-chloro-4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide 0.025 g (8%) $^1$H NMR (400 MHz, DMSO): δ 9.60-9.58 (t, J=6.4 Hz, 1H), 8.12 (s, 1H), 7.55-7.53 (d, J=6.8 Hz, 1H), 7.39-7.35 (m, 2H), 4.84-4.79 (m, 1H), 4.71-4.69 (t, J=5.2 Hz, 1H), 3.86-3.80 (m, 2H), 3.60-3.35 (m, 7H), 3.31-3.29 (m, 1H), 2.75 (s, 3H), MS m/z: 465.2 (M+H)$^+$.

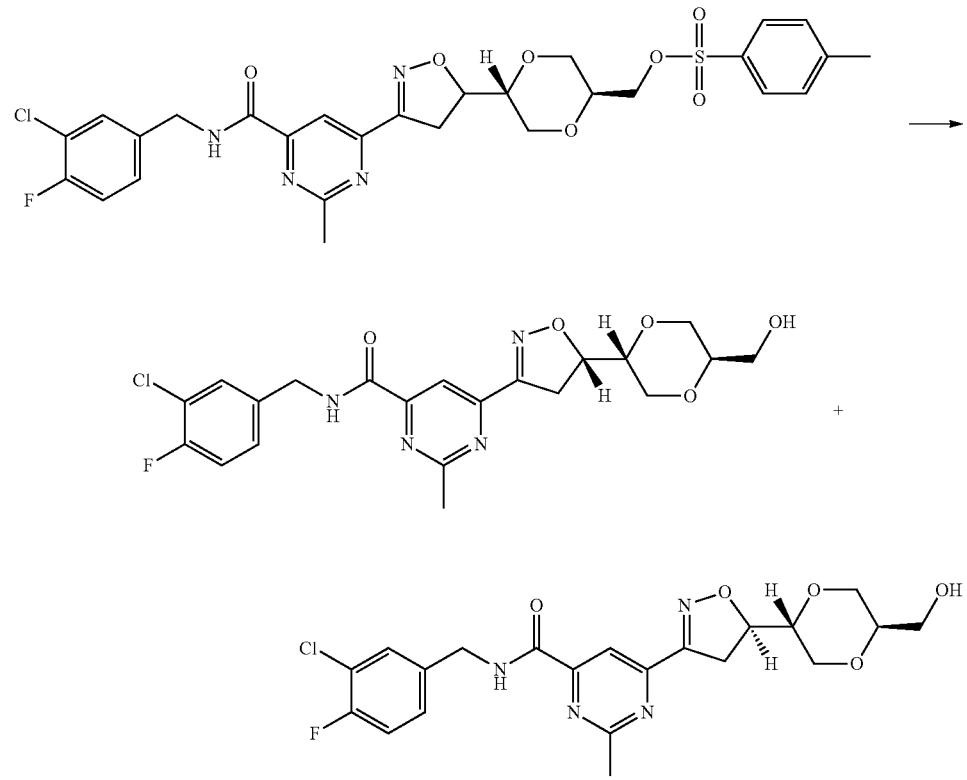 [SMILES: Cc1ccc(S(=O)(=O)OC[C@@H]2CO[C@@H](C3CC(c4cc(C(=O)NCc5ccc(F)c(Cl)c5)nc(C)n4)=NO3)CO2)cc1 ; Cc1nc(C(=O)NCc2ccc(F)c(Cl)c2)cc(C2=NO[C@H]([C@H]3CO[C@H](CO)CO3)C2)n1 ; Cc1nc(C(=O)NCc2ccc(F)c(Cl)c2)cc(C2=NO[C@@H]([C@H]3CO[C@H](CO)CO3)C2)n1]

Preparation #H.5

((2R,5S)-5-Vinyl-1,4-dioxan-2-yl)methanol

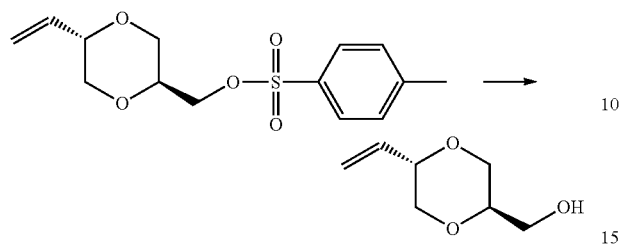

A solution of ((2S,5S)-5-vinyl-1,4-dioxan-2-yl)methyl 4-methylbenzenesulfonate (2.0 g, 6.70 mmol, Preparation #11) and tetrabutylammonium acetate (2.63 g, 8.71 mmol) in dimethylformamide (5 mL) were heated at about 70° C. for about 3 h. The reaction mixture was cooled to RT and the reaction vessel was charged sequentially with water (2 mL) and 1.0 N aqueous sodium hydroxide (4.0 mL). After stirring for about 20 min at RT, the mixture was diluted with EtOAc with (20 mL) and washed with brine solution (2×20 mL). The organic layer was dried over sodium sulphate and concentrated under reduced pressure. The crude material obtained was purified by column chromatography eluting with 30-40% EtOAc in hexane. The relevant fractions containing product were combined and concentrated to afford ((2R,5S)-5-vinyl-1,4-dioxan-2-yl)methanol. 0.7 g (72.4%). $^1$H NMR (400 MHz, CDCl$_3$): δ 5.77-5.68 (m, 1H), 5.38-5.22 (m, 2H), 4.04-3.99 (m, 1H), 3.86-3.81 (m, 2H), 3.68-3.52 (m, 4H), 3.44-3.38 (m, 1H); IR (Neat):3433 cm$^{-1}$ (OH str)

General Procedure I

Formation of Nitrile Derivatives from O-Tosylate Derivatives

To a stirred solution of an appropriate tosylate derivative (1 equiv) in an organic solvent such as DMSO, DMF, or 1,4-dioxane, preferably DMSO, is added sodium cyanide (3 equiv) and the mixture is heated to about 70° C. for about 3-10 h preferably 3 h. The mixture is allowed to cool to RT, diluted with water and the product extracted with EtOAc. The combined organic layers dried over sodium sulphate and concentrated under reduced pressure. The resulting product obtained was purified by preparative TLC or column chromatography to obtain the target compound

Illustration of General Procedure I

Example #1.1

6-((S)-5-((2R,5R)-5-(Cyanomethyl)-1,4-dioxan-2-yl)-4,5-dihydroisoxazol-3-yl)-N-(4-fluoro-3-methoxybenzyl)-2-methylpyrimidine-4-carboxamide

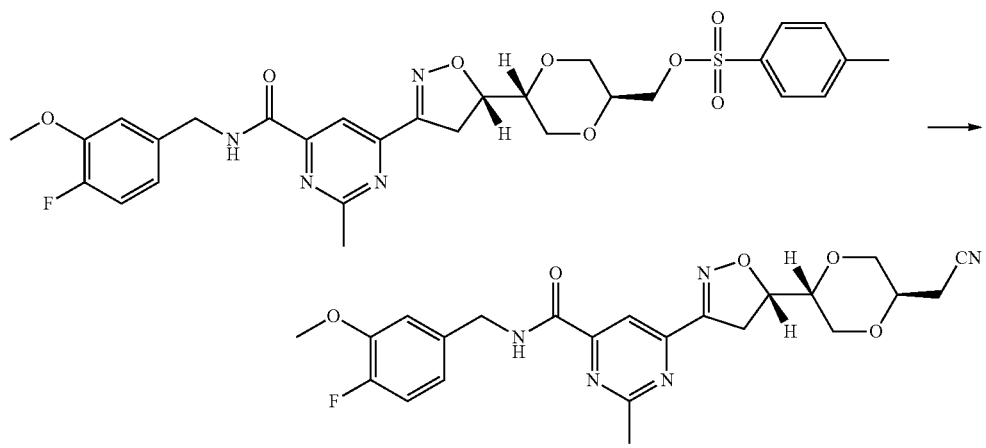

To a stirred solution of ((2S,5R)-5-((S)-3-(6-(4-fluoro-3-methoxybenzylcarbamoyl)-2-methylpyrimidin-4-yl)-4,5-dihydroisoxazol-5-yl)-1,4-dioxan-2-yl)methyl 4-methylbenzenesulfonate (0.2 g, 0.325 mmol, Example #G.6) in DMSO (3 mL) was added sodium cyanide (48 mg, 0.977 mmol) and the mixture was heated to about 70° C. for about 3 h.

The mixture was allowed to cool to RT, diluted with water (30 mL) and the product extracted with EtOAc (3×50 mL). The combined organic layers were dried over sodium sulphate and concentrated under reduced pressure. The resulting product obtained was purified by preparative TLC (eluting with 60% EtOAc in hexane) to afford 6-((S)-5-((2R,5R)-5-(cyanomethyl)-1,4-dioxan-2-yl)-4,5-dihydroisoxazol-3-yl)-N-(4-fluoro-3-methoxybenzyl)-2-methylpyrimidine-4-carboxamide. 70 mg (46%). $^1$H NMR (400 MHz, DMSO): δ 9.50-9.47 (t, J=6.4 Hz, 1H), 8.13 (s, 1H), 7.17-7.11 (m, 2H), 6.90-6.86 (m, 1H), 4.83-4.77 (m, 2H), 4.48-4.46 (d, J=6.4 Hz, 2H), 3.94-3.83 (m, 2H), 3.81 (s, 3H), 3.79-3.67 (m, 2H), 3.50-3.35 (m, 3H), 3.31-3.28 (m, 1H), 2.75 (s, 3H), 2.72-2.60 (m, 2H), MS m/z 470.2 (M+H)$^+$.

General Procedure J

Nucleophlic Displacement of O-Tosylate with an Amine

A 100 mL sealed tube is charged with a solution of an appropriate O-tosylate derivative (1 equiv) and ammonium hydroxide (10-20 equiv, preferably 18 equiv) in an organic solvent (such as DMSO or DMF, preferably DMSO). The reaction is heated to about 80-100° C. (preferably 80° C.) for about 1 to 12 h (preferably about 12 h). The reaction mixture is cooled to RT, diluted with water and the product is extracted with EtOAc. The organic layer is washed with brine and dried over sodium sulphate. The crude mass obtained upon concentration of the organic layer is purified using silica gel column chromatography to obtain the target material Illustration of General Procedure J Preparation #J.1

6-((S)-5-((2R,5R)-5-(Aminomethyl)-1,4-dioxan-2-yl)-4,5-dihydroisoxazol-3-yl)-N-(4-fluoro-3-methoxybenzyl)-2-methylpyrimidine-4-carboxamide dryness to afford 6-((S)-5-((2R,5R)-5-(aminomethyl)-1,4-dioxan-2-yl)-4,5-dihydroisoxazol-3-yl)-N-(4-fluoro-3-methoxybenzyl)-2-methylpyrimidine-4-arboxamide 0.8 g (71.3%); $^1$H NMR (400 MHz, DMSO): δ 9.48 (t, J=6 Hz, 1H), 8.13 (s, 1H), 7.17-7.11 (m, 2H), 6.90-6.86 (m, 1H), 4.81-4.76 (m, 1H), 4.48 (d, J=6.4 Hz, 2H), 3.89-3.82 (m, 2H), 3.81 (s, 3H), 3.66-3.62 (m, 2H), 3.47-3.31 (m, 7H), 2.75 (s, 3H), 2.57 (d, J=6 Hz, 1H), MS m/z 459.9 (m+H).

General Procedure K

Acidic Cleavage of a Boc-Protected Amine

To a flask containing an appropriate Boc-protected amine at RT is added a suitable acid (such as TFA or 4N 1,4-dioxane/HCl, preferably 4N 1,4-dioxane/HCl) and stirred at RT for about 1-6 h (preferably about 1 h). Excess solvent is removed under vacuum to afford the target compound.

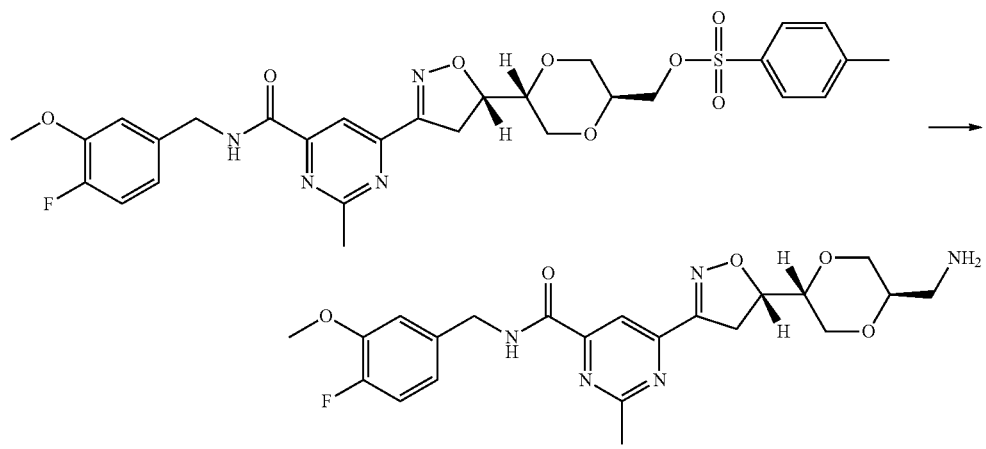

A 100 mL sealed tube was charged with ((2S,5R)-5-((S)-3-(6-(4-fluoro-3-methoxybenzylcarbamoyl)-2-methylpyrimidin-4-yl)-4,5-dihydroisoxazol-5-yl)-1,4-dioxan-2-yl)methyl 4-methylbenzenesulfonate (1.5 g, 2.440 mmol, Preparation #G.6), ammonium hydroxide (1.711 mL, 43.9 mmol, Rankem) and DMSO (10 mL). The reaction mixture was stirred at about 80° C. for about 12 h. The solution was cooled to RT, diluted with water (100 mL) and the product was extracted with EtOAc (2×50 mL). The combined organic layer was dried over sodium sulphate and concentrated under reduced pressure. The crude material obtained was purified by silicagel column chromatography eluting with saturated methanolicammonia in DCM (90:10). Relevant fractions containing the product were combined and concentrated to Illustration of General Procedure K Preparation #K.1

N-(4-fluoro-3-methoxybenzyl)-2-methyl-6-(5-(piperidin-4-yl)-4,5-dihydroisoxazol-3-yl)pyrimidine-4-carboxamide hydrochloride

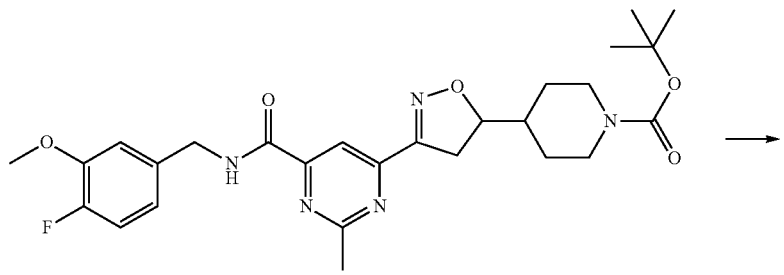

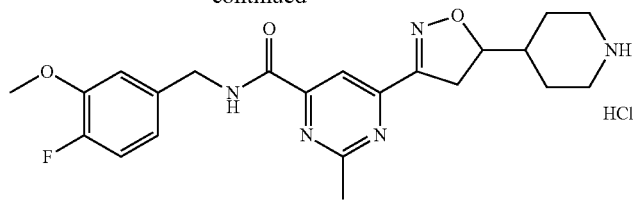

Tert-butyl-4-(3-(6-(4-fluoro-3-methoxybenzylcarbamoyl)-2-methylpyrimidin-4-yl)-4,5-dihydroisoxazol-5-yl)piperidine-1-carboxylate (0.3 g, 0.569 mmol, G.1.18) was dissolved in 4N 1,4-dioxane.HCl (5 mL) and stirred at RT for about 1 h. Excess solvent was removed in vacuo and the crude material was triturated with ether (2×10 mL) to afford N-(4-fluoro-3-methoxybenzyl)-2-methyl-6-(5-(piperidin-4-yl)-4,5-dihydroisoxazol-3-yl)pyrimidine-4-carboxamide hydrochloride as a white solid 0.2 g (82%). LC/MS (Table 1, method e) $R_t$=2.53 min; MS m/z 428.3 (M+H)$^+$.

Preparation #K.2

6-(5-((1r,4r)-4-Aminocyclohexyl)-4,5-dihydroisoxazol-3-yl)-N-(4-fluoro-3-methoxybenzyl)-2-methylpyrimidine-4-carboxamide hydrochloride

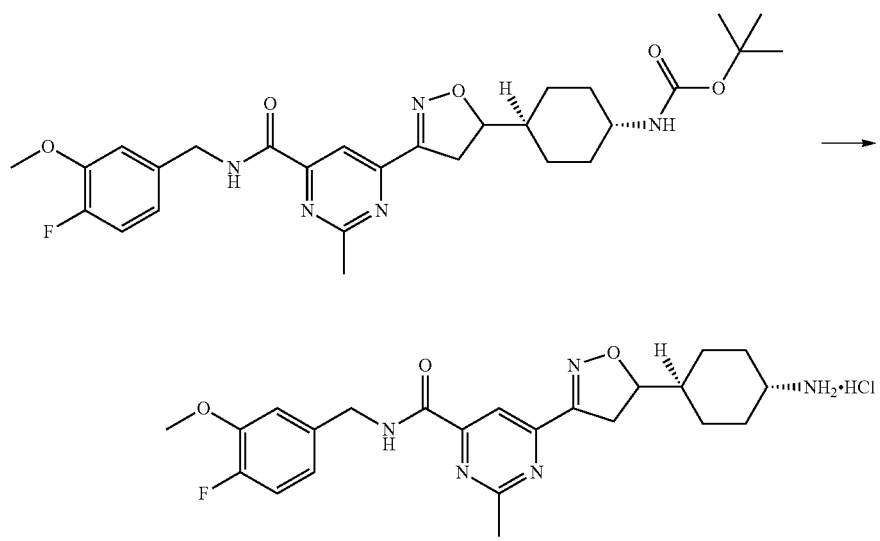

Tert-butyl ((1r,4r)-4-(3-(6-((4-fluoro-3-methoxybenzyl)carbamoyl)-2-methylpyrimidin-4-yl)-4,5-dihydroisoxazol-5-yl)cyclohexyl)carbamate (1.8 g, 3.32 mmol, Preparation #G.1.209) was dissolved in 4N1,4-dioxane/HCl (20 mL) and stirred at RT for about 3 h. Excess solvent was removed in vaccuo and the crude material was triturated with ether (2×100 mL) to afford 6-(5-((1r,4r)-4-aminocyclohexyl)-4,5-dihydroisoxazol-3-yl)-N-(4-fluoro-3-methoxybenzyl)-2-methylpyrimidine-4-carboxamide hydrochloride 1.4 g (88%) as yellow solid. LC/MS (Table 1, Method d) $R_t$=2.59 min; MS m/z 428.3 (M+H)$^+$.

General Procedure L

Formation of Acetyl Amide from an Amine

Acetyl chloride is added to a mixture of an appropriate amine hydrochloride salt and a suitable base (for example, TEA or DIEA, preferably TEA) in a suitable solvent (such as DCM or THF, preferably DCM) at about 0° C. The mixture is slowly warmed to RT and stirred for about 10 min-2 h (preferably about 10 min). The reaction mixture is diluted with water and extracted with DCM. The combined organic layers are washed with brine, dried over sodium sulphate and evaporated to dryness under reduced pressure. The residue obtained is purified by silica gel chromatography to afford the target compound.

Illustration of General Procedure L

Example #L.1

6-(5-(1-Acetylpiperidin-4-yl)-4,5-dihydroisoxazol-3-yl)-N-(4-fluoro-3-methoxybenzyl)-2-methylpyrimidine-4-carboxamide

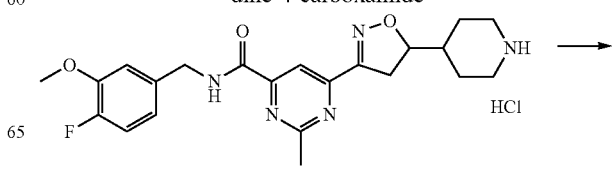

-continued

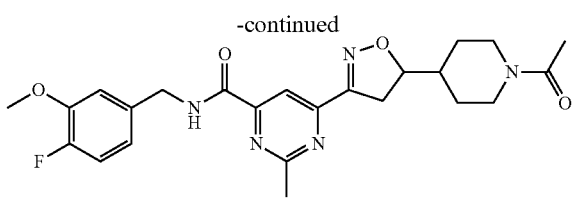

To a cold solution of N-(4-fluoro-3-methoxybenzyl)-2-methyl-6-(5-(piperidin-4-yl)-4,5-dihydroisoxazol-3-yl)pyrimidine-4-carboxamide hydrochloride (0.1 g, 0.215 mmol, Preparation #K. 1) and TEA (0.2 mL, 1.4 mmol, Sd Fine Chem) in DCM (10 mL) was added acetyl chloride (0.022 g, 0.28 mmol, Spectrochem). The reaction mixture was slowly warmed to RT and stirred for about 10 min. The reaction mixture was diluted with water (10 mL) and the product extracted with DCM (2×20 mL). The combined organic layers were washed with water (1×25 mL) followed by brine (1×50 mL). The organic layer was dried over sodium sulphate and concentrated under reduced pressure. The crude material obtained was purified using silica gel column chromatography eluted in 50% EtOAc-hexane. The relevant fractions containing the target compound were combined and evaporated to dryness under reduced pressure to afford 6-(5-(1-acetylpiperidin-4-yl)-4,5-dihydroisoxazol-3-yl)-N-(4-fluoro-3-methoxybenzyl)-2-methylpyrimidine-4-carboxamide as an off white solid 0.05 g (45%): $^1$H NMR (400 MHz, DMSO): δ 9.469 (t, J=5.6 Hz, 1H), 8.139 (s, 1H), 7.176-7.114 (m, 2H), 6.885 (brs, 1H), 4.679-4.660 (m, 1H), 4.483-4.467 (d, J=6.4 Hz, 2H), 4.436-4.406 (m, 1H), 3.815 (s, 3H), 3.496-3.424 (m, 2H), 3.295-3.239 (m, 2H), 3.194-2.978 (m, 1H), 2.753 (s, 3H), 1.983 (s, 3H), 1.909-1.621 (m, 3H), 1.243-1.189 (m, 2H). LC/MS (Table 1, method c) $R_t$=1.76 min; MS m/z: 470.1 (M+H)$^+$.

Example #K.2

6-((S)-5-((2R,5R)-5-(acetamidomethyl)-1,4-dioxan-2-yl)-4,5-dihydroisoxazol-3-yl)-N-(4-fluoro-3-methoxybenzyl)-2-methylpyrimidine-4-carboxamide To a stirred solution of 6-((S)-5-((2R,5R)-5-(aminomethyl)-1,4-dioxan-2-yl)-4,5-dihydroisoxazol-3-yl)-N-(4-fluoro-3-methoxybenzyl)-2-methylpyrimidine-4-carboxamide (0.08 g, 0.174 mmol, Preparation #J.1) in DCM (5 mL) at 0° C., was added TEA (0.073 mL, 0.522 mmol, Spectrochem) followed by acetyl chloride (0.015 mL, 0.209 mmol, Spectrochem). The reaction mixture was stirred for 30 min, was diluted with DCM (30 mL) and washed with water (2×20 mL). The organic layer dried over sodium sulphate and concentrated under reduced pressure. The resulting crude material was purified by preparative TLC eluting with 60% EtOAc in hexane to afford 6-((S)-5-((2R,5R)-5-(acetamidomethyl)-1,4-dioxan-2-yl)-4,5-dihydroisoxazol-3-yl)-N-(4-fluoro-3-methoxybenzyl)-2-methylpyrimidine-4-carboxamide 0.065 g (74%); $^1$H NMR (400 MHz, DMSO): δ 9.50 (t, J=5.6 Hz, 1H), 8.13 (s, 1H), 7.93 (t, J=5.6 Hz, 1H), 7.17-7.11 (m, 2H), 6.89-6.81 (m, 1H), 4.81-4.75 (m, 1H), 4.48 (d, J=6.4 Hz, 2H), 3.88-3.86 (m, 1H), 3.81 (s, 3H), 3.78-3.63 (m, 2H), 3.46-3.36 (m, 4H), 3.32-3.22 (m, 2H), 3.08-3.00 (m, 2H) 2.75 (s, 3H), 1.79 (s, 3H); LC/MS (Table 1, Method e) $R_t$=2.69 min; MS: m/z 502 (m+H)$^+$.

General Procedure M

Formation of a Sulfonamide from an Amine

An appropriate sulfonyl chloride is added to a mixture of an amine hydrochloride salt and a suitable base (for example, TEA or DIEA, preferably TEA) in a suitable solvent (such as DCM or THF, preferably DCM) at about 0-5° C., preferably about 0° C. The mixture is slowly warmed to RT and stirred for about 0.5-2 h (preferably about 0.5 h). The reaction mixture is diluted with water and extracted with DCM. The combined organic layers are washed with brine, dried over sodium sulphate and evaporated to dryness under reduced pressure. The residue obtained is purified by silica gel chromatography to afford the target compound.

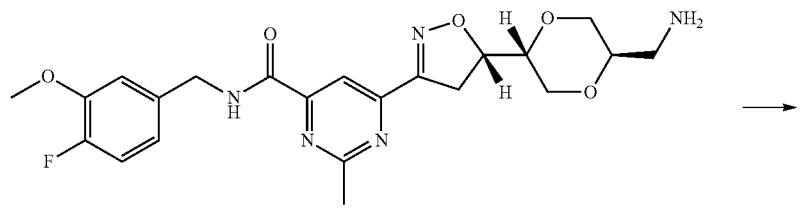

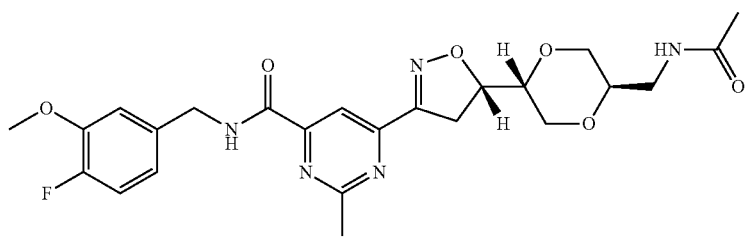

Illustration of General Procedure M

Example #M.1

N-(4-fluoro-3-methoxybenzyl)-2-methyl-6-(5-(1-(methylsulfonyl)piperidin-4-yl)-4,5-dihydroisoxazol-3-yl)pyrimidine-4-carboxamide

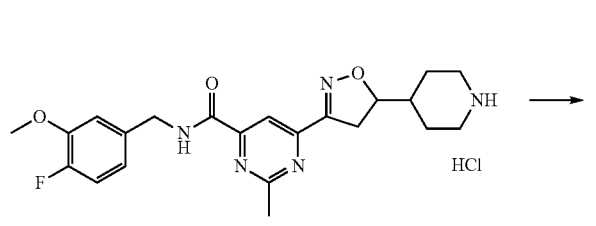

To a cold solution of N-(4-fluoro-3-methoxybenzyl)-2-methyl-6-(5-(piperidin-4-yl)-4,5-dihydroisoxazol-3-yl)pyrimidine-4-carboxamide hydrochloride (0.1 g, 0.215 mmol, Preparation #K.1) and TEA (0.141 g, 1.4 mmol, Sd Fine Chem) in DCM (10 mL) was added methane sulfonyl chloride (0.032 g, 0.28 mmol, Spectrochem). The reaction mixture was slowly warmed to RT and stirred for about 0.5 h. The reaction mixture was diluted with water (10 mL) and the product extracted with DCM (2×20 mL). The combined organic layers were washed with water (1×25 mL) followed by brine (1×50 mL). The organic layer was dried over sodium sulphate and concentrated under reduced pressure. The crude material obtained was purified using silica gel column chromatography eluted in 60% EtOAc-hexane. Relevant fractions containing the required compound were combined and evaporated to dryness under reduced pressure to afford N-(4-fluoro-3-methoxybenzyl)-2-methyl-6-(5-(1-(methylsulfonyl)piperidin-4-yl)-4,5-dihydroisoxazol-3-yl)pyrimidine-4-carboxamide as light pale yellow solid 0.065 g (55%): $^1$H NMR (400 MHz, DMSO): δ 9.501-9.469 (t, J=6.4 Hz, 1H), 8.144 (s, 1H), 7.179-7.135 (m, 2H), 6.901-6.890 (m, 1H), 4.730-4.692 (m, 1H), 4.483-4.467 (d, J=6.4 Hz, 2H), 3.815 (s, 3H), 3.617-3.587 (d, J=12 Hz, 2H), 3.517-3.489 (m, 2H), 2.848 (s, 3H) 2.755 (s, 3H), 2.699-2.639 (m, 2H), 1.896-1.864 (m, 1H), 1.740-1.711 (m, 2H), 1.323-1.236 (m, 2H). LC/MS (Table 1, Method c) $R_t$=4.71 min MS m/z: 506 (M+H)$^+$.

Preparation #M.2

N-(4-fluoro-3-methoxybenzyl)-2-methyl-6-((S)-5-((2R,5R)-5-(methylsulfonamidoethyl)-1,4-dioxan-2-yl)-4,5-dihydroisoxazol-3-yl)pyrimidine-4-carboxamide

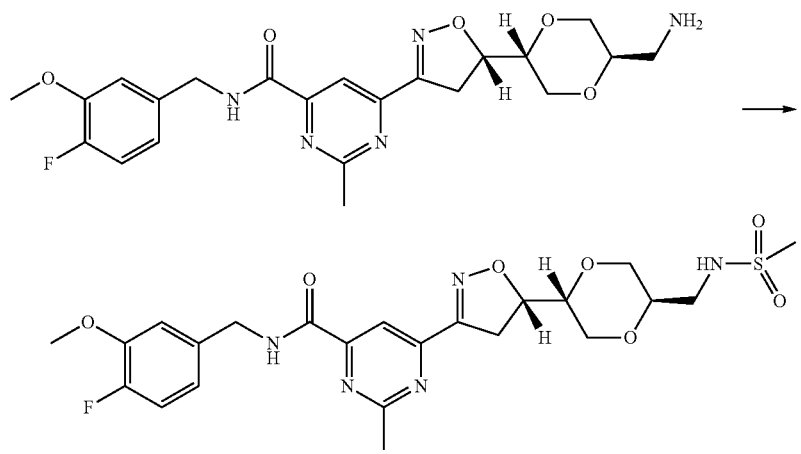

To a stirred solution of 6-((S)-5-((2R,5R)-5-(aminomethyl)-1,4-dioxan-2-yl)-4,5-dihydroisoxazol-3-yl)-N-(4-fluoro-3-methoxybenzyl)-2-methylpyrimidine-4-carboxamide (0.1 g, 0.217 mmol, Preparation #J.1) in DCM (5 mL) at 0° C., was added TEA (0.091 mL, 0.522 mmol, Spectrochem) followed by methanesulfonyl chloride (0.021 mL, 0.261 mmol, Spectrochem). The reaction mixture was stirred 30 min at the same temperature, diluted with DCM (30 mL) and washed with water (2×20 mL). The organic layer was dried over sodium sulphate and concentrated under reduced pressure. The resulting crude material was purified by preparative TLC eluting with 60% EtOAc in hexane to afford N-(4-fluoro-3-methoxybenzyl)-2-methyl-6-((S)-5-((2R,5R)-5-(methylsulfonamidoethyl)-1,4-dioxan-2-yl)-4,5-dihydroisoxazol-3-yl)pyrimidine-4-carboxamide 0.055 g (47%); $^1$H NMR (400 MHz, DMSO): δ 9.50 (t, J=6.0 Hz, 1H), 8.13 (s, 1H), 7.17-7.10 (m, 3H), 6.89-6.86 (m, 1H), 4.82-4.76 (m, 1H), 4.48 (d, J=6.4 Hz, 2H), 3.90-3.84 (m, 2H), 3.81 (s, 3H), 3.68-3.65 (m, 1H), 3.54-3.36 (m, 5H), 2.96 (t, J=5.6 Hz, 2H), 2.89 (s, 3H), 2.75 (s, 3H); LC/MS (Table 1, Method c) $R_t$=1.33 min; MS: m/z 538.1 (m+H).

General Procedure N

Formation of Hydroxyl Acetyl Amide from an Amine

A solution of an amine hydrochloride in a suitable solvent (such as DCM or THF, preferably DCM) is cooled to about 0°

C. and then a suitable base (such as TEA or DIEA, preferably TEA) is added followed by the addition of acetoxy acetyl chloride (1.0 to 1.2 equiv, preferably 1.1 equiv). The reaction mixture is stirred at RT for about 10 min to 0.5 h (preferably about 10 min). The reaction mixture is diluted with water and extracted with DCM. The combined organic layers are washed with brine, dried over sodium sulphate and evaporated to dryness under reduced pressure to afford an acetoxy acetamide derivative. This material is re-dissolved in ACN and treated with a suitable base (such as LiOH, KOH, or NaOH, preferably 2.5 N NaOH). The mixture is stirred at RT for about 2-6 h (preferably about 6 h). Excess solvent is removed under reduced pressure. The aqueous layer is acidified with 10% HCl solution and the product extracted with EtOAc. The combined organic layers are washed with brine, dried over sodium sulphate and evaporated to dryness under reduced pressure. The residue obtained is purified by silica gel chromatography to afford the target compound.

Illustration of General Procedure N

Example #N.1

N-(4-Fluoro-3-methoxybenzyl)-6-(5-(1-(2-hydroxyacetyl)piperidin-4-yl)-4,5-dihydroisoxazol-3-yl)-2-methylpyrimidine-4-carboxamide

Step 1

To a cold solution of N-(4-fluoro-3-methoxybenzyl)-2-methyl-6-(5-(piperidin-4-yl)-4,5-dihydroisoxazol-3-yl)pyrimidine-4-carboxamide hydrochloride (1.8 g, 3.87 mmol, Preparation #K.1) in dichloromethane (20 mL) were added TEA (3.3 mL, 23.2 mmol) and acetoxyacetyl chloride (0.5 mL, 4.65 mmol). The reaction mixture was slowly warmed to RT and stirred for about 10 min. The reaction mixture was diluted with water (10 mL) and the product was extracted with DCM (2×20 mL). The combined organic layers were washed with water (1×25 mL) followed by brine (1×50 mL). The organic layer was dried over sodium sulphate and concentrated under reduced pressure to afford 2-(4-(3-(6-(4-fluoro-3-methoxybenzylcarbamoyl)-2-methylpyrimidin-4-yl)-4,5-dihydroisoxazol-5-yl)piperidin-1-yl)-2-oxoethyl acetate as a brown solid 1.8 g (90%).

Step 2

2-(4-(3-(6-(4-Fluoro-3-methoxybenzylcarbamoyl)-2-methylpyrimidin-4-yl)-4,5-dihydroisoxazol-5-yl)piperidin-1-yl)-2-oxoethyl acetate (1.8 g, 3.5 mmol) was dissolved in ACN (20 mL) and 2.5 N sodium hydroxide (20 mL) was added. The mixture was stirred for about 6 h and then ACN was removed under reduced pressure. The aqueous layer was adjusted to pH 6 with 10% aqueous hydrogen chloride and then extracted with EtOAc (2×15 mL). The combined organic layers were dried over sodium sulphate and concentrated under reduced pressure. The crude material was purified by preparative HPLC (Table 2, Method a) to afford N-(4-fluoro-3-methoxybenzyl)-6-(5-(1-(2-hydroxyacetyl)piperidin-4-yl)-4,5-dihydroisoxazol-3-yl)-2-methylpyrimidine-4-carboxamide 0.65 g (39%): $^1$H NMR (400 MHz, DMSO): δ 9.499-9.467 (t, J=6.4 Hz, 1H), 8.139 (s, 1H), 7.143-7.114 (m, 2H), 6.900-6.884 (m, 1H), 4.684-4.657 (m, 1H), 4.482-4.38 (m, 4H), 4.095-4.049 (m, 3H), 3.815 (s, 3H), 3.495-3.451 (m, 1H), 3.217-3.196 (m, 2H), 2.911-2.800 (m, 1H), 2.752 (s, 3H), 1.855-1.684 (m, 3H), 1.234-1.105 (m, 2H). LC/MS $R_t$=1.22 (Table 1, method c) min; MS m/z: 486.3 (M+H)$^+$.

Example #N.2

N-(4-fluoro-3-methoxybenzyl)-6-((S)-5-((2R,5R)-5-(((S)-2-hydroxypropanamido)methyl)-1,4-dioxan-2-yl)-4,5-dihydroisoxazol-3-yl)-2-methylpyrimidine-4-carboxamide

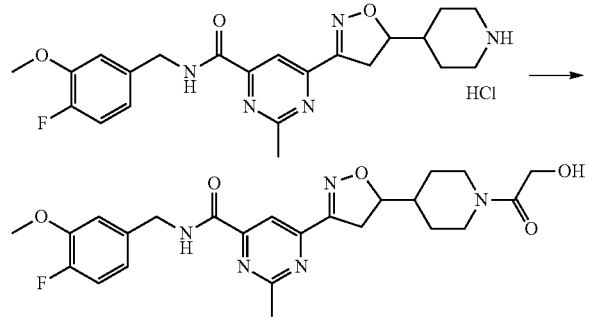

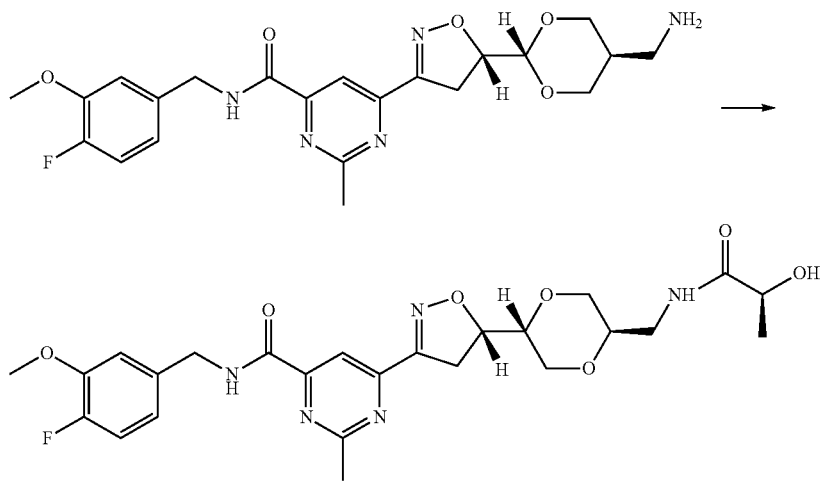

Step-1: (S)-1-((((2R,5R)-5-((S)-3-(6-((4-fluoro-3-methoxybenzyl)carbamoyl)-2-methylpyrimidin-4-yl)-4,5-dihydroisoxazol-5-yl)-1,4-dioxan-2-yl)methyl)amino)-1-oxopropan-2-yl acetate

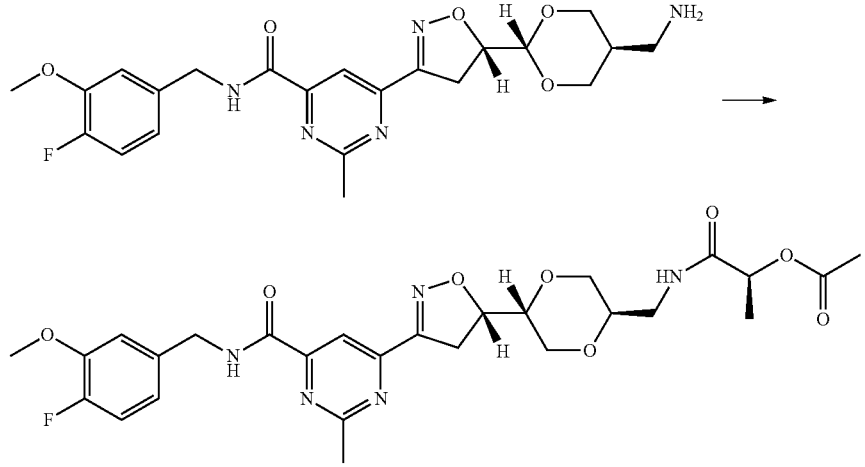

To a stirred solution of 6-((S)-5-((2R,5R)-5-(aminomethyl)-1,4-dioxan-2-yl)-4,5-dihydroisoxazol-3-yl)-N-(4-fluoro-3-methoxybenzyl)-2-methylpyrimidine-4-carboxamide (0.15 g, 0.326 mmol, Preparation #J.1) in DCM (3 mL) at 0° C., was added TEA (0.100 mL, 0.718 mmol) followed by (S)-(−)-2-acetoxypropionylchloride (0.045 mL, 0.359 mmol, Spectrochem). The reaction mixture was stirred for 30 min. at the same temperature and was quenched with water (10 mL). The product was extracted with DCM (2×10 mL). The combined organic layers were dried over sodium sulfate and concentrated under reduced pressure. The resulting crude was purified using silica gel column chromatography by eluting with 70% EtOAc in hexane. The relevant fractions containing compound were combined and concentrated to afford (S)-1-(((2R,5R)-5-((S)-3-(6-(4-fluoro-3-methoxybenzylcarbamoyl)-2-methylpyrimidin-4-yl)-4,5-dihydroisoxazol-5-yl)-1,4-dioxan-2-yl)methylamino)-1-oxopropan-2-yl acetate 0.11 g (58%); $^1$H NMR (400 MHz, DMSO): δ 9.48 (t, J=6.4 Hz, 1H), 8.13 (s, 1H), 7.17-7.11 (m, 2H), 6.89-6.86 (m, 1H), 4.87-4.85 (m, 1H), 4.79-4.78 (m, 1H), 4.48 (d, J=6.4 Hz, 2H), 3.88-3.85 (m, 1H), 3.81 (s, 3H), 3.74-3.63 (m, 2H), 3.49-3.37 (m, 4H), 3.26-3.21 (m, 2H), 3.09-3.07 (m, 2H), 2.75 (s, 3H), 2.04 (s, 3H), 1.30 (d, J=6.8 Hz, 3H); LC/MS (Table 1, method c) $R_t$=3.12 min; MS: m/z 574 (m+H)$^+$.

Step-2: N-(4-fluoro-3-methoxybenzyl)-6-((S)-5-((2R,5R)-5-(((S)-2-hydroxypropanamido)methyl)-1,4-dioxan-2-yl)-4,5-dihydroisoxazol-3-yl)-2-methylpyrimidine-4-carboxamide

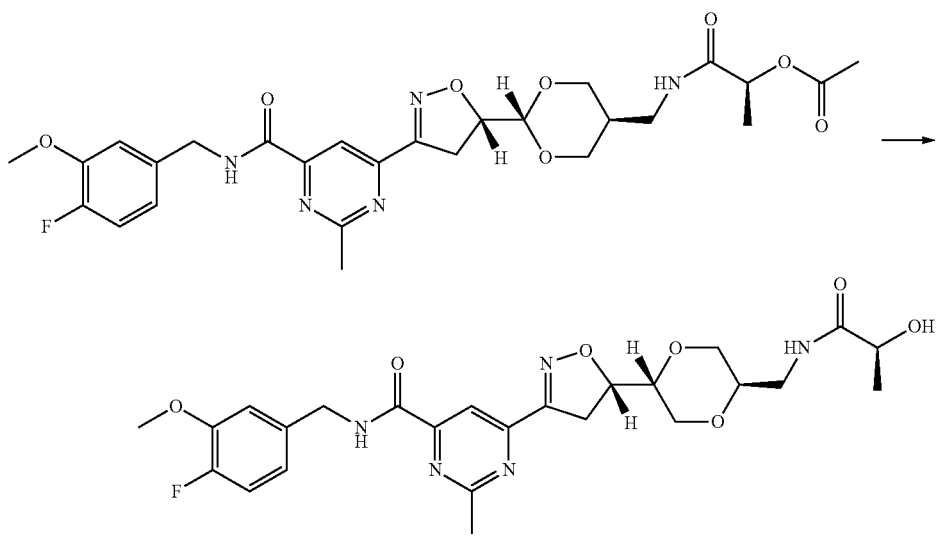

To a stirred solution of (S)-1-(((2R,5R)-5-((S)-3-(6-(4-fluoro-3-methoxybenzylcarbamoyl)-2-methylpyrimidin-4-yl)-4,5-dihydroisoxazol-5-yl)-1,4-dioxan-2-yl)methylamino)-1-oxopropan-2-yl acetate (0.11 g, 0.192 mmol) in ACN (3 mL) was added 2.5M lithium hydroxide (1.151 mL, 2.88 mmol) at RT. The reaction mixture was stirred for 3 h, diluted with EtOAc (25 mL) and washed with brine solution (2×15 mL). The organic layer was dried over sodium sulfate and concentrated under reduced pressure. The resulting crude material was purified by preparative TLC eluting with 100% EtOAc to afford N-(4-fluoro-3-methoxybenzyl)-6-((S)-5-((2R,5R)-5-(((S)-2-hydroxypropanamido) methyl)-1,4-dioxan-2-yl)-4,5-dihydroisoxazol-3-yl)-2-methylpyrimidine-4-carboxamide 0.055 g (52%); $^1$H NMR (400 MHz, DMSO): δ 9.48 (t, J=6.4 Hz, 1H), 8.13 (s, 3H), 7.68 (t, 1H), 7.17-7.13 (m, 2H), 6.88 (m, 1H), 5.5 (d, J=4.8 Hz, 1H), 4.81-4.75 (m, 1H), 4.48 (d, J=6.0 Hz, 2H), 3.96-3.86 (m, 2H), 3.81 (s, 3H), 3.76-3.73 (m, 1H), 3.66-3.63 (m, 1H), 3.52-3.3.36 (m, 4H), 3.29-3.11 (m, 1H), 3.09 (m, 2H), 2.75 (s, 3H), 1.19 (d, J=6.8 Hz, 3H); LC/MS (Table 1, method c) $R_t$=2.89 min; MS: m/z 532 (m+H)$^+$.

Example #N.3

(2S)-1-(((1r,4S)-4-(3-(6-((4-fluoro-3-methoxybenzyl)carbamoyl)-2-methylpyrimidin-4-yl)-4,5-dihydroisoxazol-5-yl)cyclohexyl)amino)-1-oxopropan-2-yl acetate

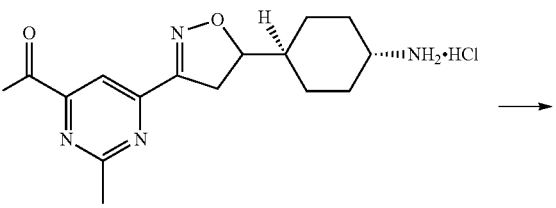

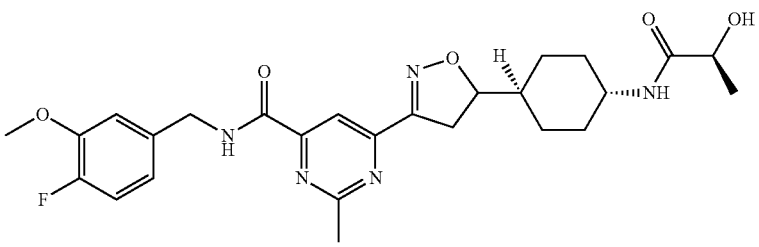

Step-1: To a solution of 6-(5-((1r,4r)-4-aminocyclohexyl)-4,5-dihydroisoxazol-3-yl)-N-(4-fluoro-3-methoxybenzyl)-2-methylpyrimidine-4-carboxamide hydrochloride (1.0 g, 2.092 mmol, Preparation#K.2) in DCM (20 mL) was added TEA (1.021 mL, 7.32 mmol, SD Finechem) followed by (S)-(−)-2-acetoxypropionyl chloride (0.265 mL, 2.092 mmol, Aldrich) drop wise over a period of 5 min at about 0° C. The resulting reaction mixture was stirred for 30 min at the same temperature. The reaction mixture was diluted with DCM (50 mL) and washed successively with 1N HCl solution (1×50 mL) and brine (1×50 mL). The organic solution was dried over sodium sulphate and concentrated under reduced pressure. The obtained residue was triturated with pentane (2×50 mL) to afford (2S)-1-((1r,4S)-4-(3-(6-(4-fluoro-3-ethoxybenzylcarbamoyl)-2-methylpyrimidin-4-yl)-4,5-dihydroisoxazol-5-yl)cyclohexyl amino)-1-oxopropan-2-yl acetate 1.05 g (90%). $^1$H NMR (400 MHz, DMSO) δ: 9.49 (t, J=6.0 Hz, 1H), 8.14 (s, 1H), 7.82 (d, J=7.6.0 Hz, 1H), 7.18-7.11 (m, 2H), 6.96 (s, 1H), 6.90-6.87 (m, 1H), 4.88-4.82 (m, 1H), 4.62-4.60 (q, J=2.4 Hz, 6.8 Hz, 1H), 4.48 (d, J=5.6 Hz, 2H), 3.82 (s, 3H), 3.57-3.35 (m, 2H), 3.24-3.17 (m, 1H), 2.75 (s, 3H), 2.04 (s, 3H), 1.87-1.49 (m, 5H), 1.29 (d, J=6.4 Hz, 3H), 1.26-1.07 (m, 3H).

Step-2

To an ice cold solution of (2S)-1-((1r,4S)-4-(3-(6-(4-fluoro-3-methoxybenzylcarbamoyl)-2-methylpyrimidin-4-yl)-4,5-dihydroisoxazol-5-yl)cyclohexylamino)-1-oxopropan-2-yl acetate (1.05 g, 1.890 mmol) in ACN (15 mL) was added 2.5M aqueous lithium hydroxide (10 mL, 37.8 mmol, Spectrochem) was added drop wise for 5 min. The mixture was stirred for about 3 h, diluted with EtOAc (200 mL). The organic layer was washed successively with 1M HCl solution (2×50 mL), water (1×50 mL) and brine (2×50 mL). The organic layer was dried over sodium sulphate and evaporated to dryness. The crude material obtained was purified using silica gel column chromatography by eluting with 20% acetone in DCM. Relevant fractions containing the required compound were combined and evaporated to dryness under reduced pressure to afford N-(4-fluoro-3-methoxybenzyl)-6-(5-((1S,4r)-4-((S)-2-hydroxypropanamido) cyclohexyl)-4,5-dihydroisoxazol-3-yl)-2-methylpyrimidine-4-carboxamide 0.5 g (52.5%) as light yellow solid, $^1$H NMR (400 MHz, DMSO) δ: 9.48 (t, J=6 Hz, 1H), 8.14 (s, 1H), 7.39 (d, J=8.0 Hz, 1H), 7.18-7.11 (m, 2H), 6.90-6.87 (m, 1H), 5.39 (d, J=5.2 Hz, 1H), 4.65-4.60 (m, 1H), 4.48 (d, J=6 Hz, 2H), 3.93-3.89 (m, 1H), 3.82 (s, 3H), 3.54-3.40 (m, 2H), 3.23-3.17 (m, 1H), 2.75 (s, 3H), 1.87-1.51 (m, 5H), 1.33-1.21 (m, 2H), 1.19 (d, J=6.8 Hz, 3H), 1.14-1.08 (m, 2H), MS m/z: 514.1 (M+H)$^+$.

Chiral separation of (2S)-1-(((1r,4S)-4-(3-(6-((4-fluoro-3-methoxybenzyl)carbamoyl)-2-methylpyrimidin-4-yl)-4,5-dihydroisoxazol-5-yl)cyclohexyl)amino)-1-oxopropan-2-yl acetate to obtain N-(4-fluoro-3-methoxybenzyl)-6-((S)-5-((1S,4S)-4-((S)-2-hydroxypropanamido)cyclohexyl)-4,5-dihydroisoxazol-3-yl)-2-methylpyrimidine-4-carboxamide and N-(4-fluoro-3-methoxybenzyl)-6-((R)-5-((1S,4S)-4-((S)-2-hydroxypropanamido)cyclohexyl)-4,5-dihydroisoxazol-3-yl)-2-methylpyrimidine-4-carboxamide

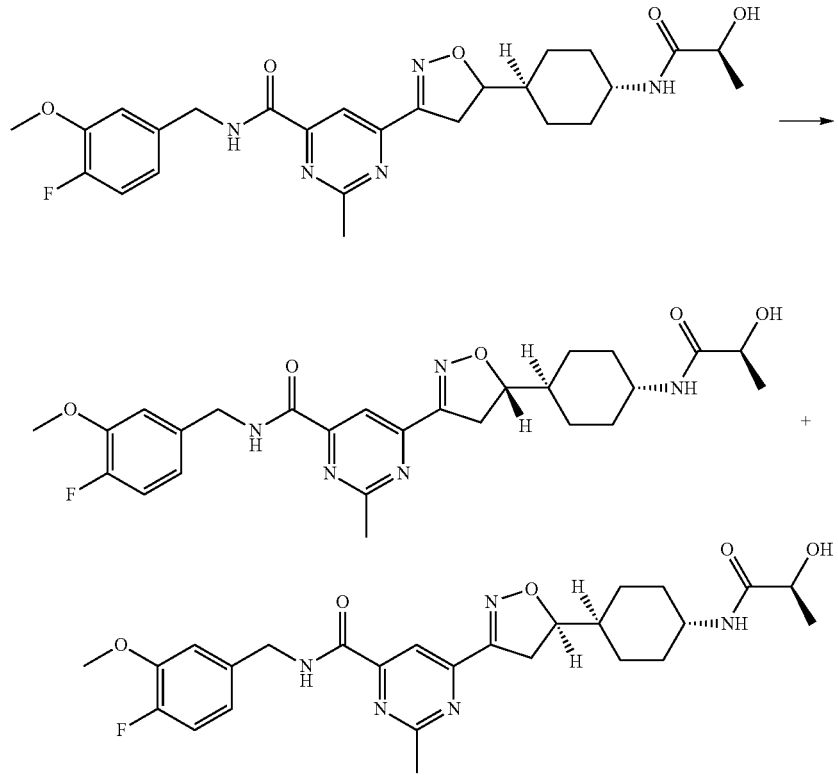

100 mg of racemic N-(4-fluoro-3-methoxybenzyl)-6-(5-((1S,4r)-4-((S)-2-hydroxypropanamido) cyclohexyl)-4,5-dihydroisoxazol-3-yl)-2-methylpyrimidine-4-carboxamide was separated enantiomerically using chiral preparative HPLC (Table 2, Method c-6) to obtain individual enantiomers: first eluting peak as N-(4-fluoro-3-methoxybenzyl)-6-((S)-5-((1S,4S)-4-((S)-2-hydroxypropanamido)cyclohexyl)-4,5-dihydroisoxazol-3 yl)-2-methylpyrimidine-4-carboxamide 33 mg (33%) $^1$H NMR (400 MHz, DMSO) δ: 9.49 (t, J=6.0 Hz, 1H), 8.13 (s, 1H), 7.39 (d, J=8.0 Hz, 1H), 7.17-7.11 (m, 2H), 6.89-6.86 (m, 1H), 5.38 (d, J=5.2 Hz, 1H), 4.65-4.60 (m, 1H), 4.48 (d, J=6 Hz, 2H), 3.92-3.87 (m, 1H), 3.81 (s, 3H), 3.52-3.40 (m, 2H), 3.23-3.16 (m, 1H), 2.75 (s, 3H), 1.86-1.51 (m, 5H), 1.33-1.21 (m, 2H), 1.19 (d, J=6.8 Hz, 3H), 1.14-1.08 (m, 2H); LC/MS (Table 1, method d) $R_t$: 3.03 min MS m/z: 514.4 (M+H)+ and the second eluting peak as N-(4-fluoro-3-methoxybenzyl)-6-((R)-5-((1S,4R)-4-((S)-2-hydroxypropanamido)cyclohexyl)-4,5-dihydroisoxazol-3-yl)-2-methylpyrimidine-4-carboxamide 27 mg (27%), $^1$H NMR (400 MHz, DMSO) δ: 9.49 (t, J=6.0 Hz, 1H), 8.13 (s, 1H), 7.38 (d, J=8.0 Hz, 1H), 7.17-7.11 (m, 2H), 6.88 (m, 1H), 5.39 (d, J=5.2 Hz, 1H), 4.64-4.58 (m, 1H), 4.48 (d, J=6 Hz, 2H), 3.92-3.89 (m, 1H), 3.81 (s, 3H), 3.52-3.40 (m, 2H), 3.23-3.16 (m, 1H), 2.75 (s, 3H), 1.86-1.51 (m, 5H), 1.27-1.23 (m, 2H), 1.18 (d, J=6.8 Hz, 3H), 1.14-1.08 (m, 2H); LC/MS (Table 1, Method d) $R_t$: 3.04 min, MS m/z: 514.3 (M+H)+

General Procedure O

Formation of Sulphone from O-Tosylate Derivative

Step 1

Sodium thiomethoxide (1-2 equiv preferably 2.0 equiv) is added to an appropriate O-tosylate derivative (1 equiv) in an organic solvent (such as DMSO or DMF, preferably DMSO). The reaction is heated to about 50-80° C. (preferably about 50° C.) for about 1 to 6 h (preferably about 1 h). The reaction mixture is diluted with water and the product is extracted with EtOAc. The combined organic layer is washed with brine and dried over sodium sulphate. The crude mass obtained upon concentration of the organic layer is purified using silica gel column chromatography to obtain the required material.

Step 2

To a cold solution of an appropriate thiomethyl derivative (1.0 equiv) in an organic solvent (such as DCM, CHCl$_3$, or THF, preferably DCM) is added 3-chloroperoxybenzoic acid (2-3 equiv preferably 3.0 equiv). The reaction mixture is stirred for about 2 h, diluted with DCM and washed with saturated aqueous sodium bicarbonate solution. The combined organic layer is dried over sodium sulfate and concentrated under reduced pressure. The crude material obtained upon concentration of the organic layer is purified using silica gel column chromatography to obtain the required material.

Illustration of General Procedure O

Example #O.1

N-(4-Fluoro-3-methoxybenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide

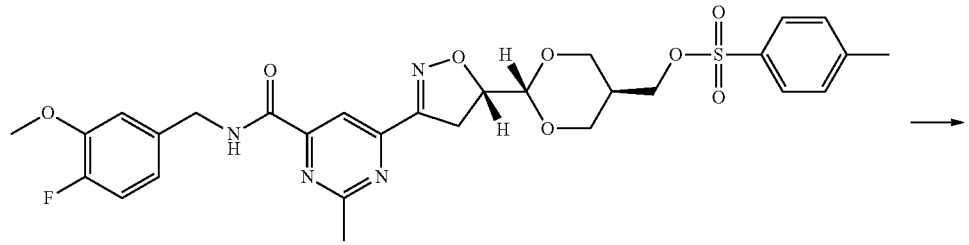

Step 1

Sodium thiomethoxide (0.16 g, 2.278 mmol) was added to a solution of ((2S,5R)-5-((S)-3-(6-(4-fluoro-3-methoxybenzylcarbamoyl)-2-methylpyrimidin-4-yl)-4,5-dihydroisoxazol-5-yl)-1,4-dioxan-2-yl)methyl 4-methylbenzenesulfonate (0.7 g, 1.139 mmol, Preparation#G.6) in DMSO (3 mL). The reaction mixture was heated at about 50° C. for about 1 h. The reaction mixture was diluted with water (20 mL) and the product was extracted with EtOAc (2×15 mL). The combined organic layers were dried over sodium sulphate and concentrated under reduced pressure. The crude material obtained was purified by silicagel column chromatography eluting with 40 to 50% EtOAc in hexane. Relevant fractions containing the required compound were combined and evaporated to dryness under reduced pressure to afford N-(4-fluoro-3-methoxybenzyl)-2-methyl-6-((S)-5-((2R,5S)-5-(smethylthiomethyl)-1,4-dioxan-2-yl)-4,5-dihydroisoxazol-3-yl)pyrimidine-4-carboxamide 0.4 g (71.6%); $^1$H NMR (400 MHz, DMSO): δ 9.48 (t, J=6.0 Hz, 1H), 8.13 (s, 1H), 7.17-7.11 (m, 2H), 6.90-6.87 (m, 1H), 4.80-4.79 (m, 1H), 4.48 (d, J=6.4 Hz, 2H), 3.88-3.84 (m, 3H), 3.81 (s, 3H), 3.67-3.64 (m, 1H), 3.49-3.33 (m, 4H), 3.29-3.17 (m, 1H), 2.76 (s, 3H), MS: m/z 491(M+H)$^+$.

Step 2

To a cold solution of N-(4-fluoro-3-methoxybenzyl)-2-methyl-6-((S)-5-((2R,5S)-5-((methylthio)methyl)-1,4-dioxan-2-yl)-4,5-dihydroisoxazol-3-yl)pyrimidine-4-carboxamide (0.4 g 0.815 mmol) in DCM (5 mL) was added m-CPBA (0.422 g, 2.446 mmol, Spectrochem). The reaction mixture was stirred for about 2 h. The reaction mixture was diluted with DCM (15 mL) and washed with saturated aqueous sodium bicarbonate solution (10 mL). The organic layer was dried over sodium sulfate and concentrated under reduced pressure. The crude material obtained was purified by silica gel column chromatography eluting with 60% EtOAc in hexane. Relevant fractions containing the target compound were combined and evaporated to dryness under reduced pressure to afford N-(4-fluoro-3-methoxybenzyl)-2-methyl-6-((S)-5-((2R,5S)-5-(methyl sulfonylmethyl)-1,4-dioxan-2-yl)-4,5-dihydroisoxazol-3-yl)pyrimidine-4-carboxamide 0.23 g, (52.1%), $^1$H NMR (400 MHz, DMSO): δ 9.48 (t, J=6.0 Hz, 1H), 8.13 (s, 1H), 7.17-7.11 (m, 2H), 6.90-6.87 (m, 1H), 4.81-4.80 (m, 1H), 4.48 (d, J=6.4 Hz, 2H), 3.95-3.84 (m, 3H), 3.81 (s, 3H), 3.69-3.64 (m, 1H), 3.49-3.33 (m, 4H), 3.29-3.17 (m, 1H), 3.00 (s, 3H), 2.76 (s, 3H), LC/MS (Table 1, method d) R$_t$=1.36 min; MS: m/z 523 (m+H)$^+$.

General Procedure P

Formation of an Acid from Alcohol

To a cold solution of an appropriate alcohol (1 equiv) in an organic solvent (such as DCM, THF, acetone, preferably acetone) is added Jones Reagent. The reaction mixture is warmed to RT and stirred for about 1-3 h (preferably 3 h). The reaction mixture is quenched with MeOH and stirred for about 10 min. The solids are removed by filtration and evaporated under reduced pressure.

The crude material is dissolved in water and the product is extracted with EtOAc. The combined organic layers dried over sodium sulphate and concentrated under reduced pressure to afford the target compound. Optionally, the target compound is purified by trituration from an appropriate solvent or solvents.

115
Illustration of General Procedure P.1

Example #P.1

(2S,5R)-5-((S)-3-(6-((4-Fluoro-3-methoxybenzyl)carbamoyl)-2-methylpyrimidin-4-yl)-4,5-dihydroisoxazol-5-yl)-1,4-dioxane-2-carboxylic acid

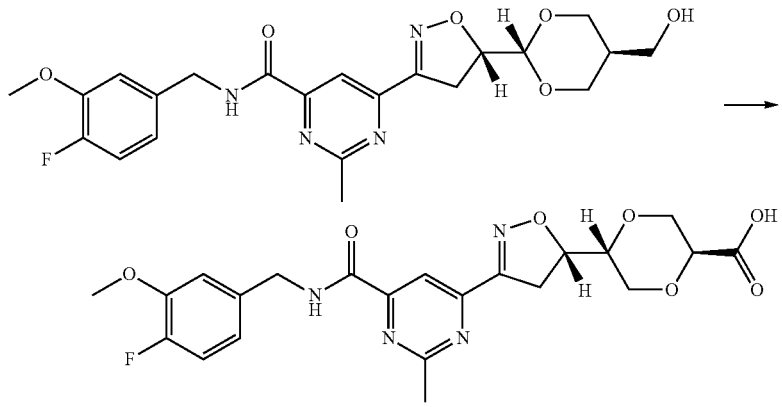

To a cold solution of N-(4-fluoro-3-methoxybenzyl)-6-((S)-5-((2R,5R)-5-(hydroxymethyl-1,4-dioxan-2-yl)-4,5-dihydroisoxazol-3-yl)-2-methylpyrimidine-4-carboxamide (0.5 g 1.086 mmol, Example H.1) in acetone (13 mL) was added Jones Reagent (8N, 1.8 mL, 1.086 mmol). The reaction mixture was slowly warmed to RT and stirred for about 3 h. The reaction mixture was quenched with methanol (4 mL) and stirred for about for 10 min. Solids were removed by filtration and evaporated under reduced pressure. The crude material was dissolved in water (15 mL) and the product extracted with EtOAc (2×25 mL). The organic layer was dried over sodium sulphate and evaporated to dryness under reduced pressure. The crude material obtained was triturated with 10% DCM in hexane to afford (2S,5R)-5-((S)-3-(6-(4-fluoro-3-methoxybenzylcarbainoyl)-2-methylpyrimidin-4-yl)-4,5-dihydroisoxazol-5-yl)-1,4-dioxane-2-carboxylic acid, 0.4 g (78%), MS m/z 475 (M+H)$^+$, LC/MS (Table 1 method d) R$_t$=1.87 min.

116
General Procedure Q

Formation of an Ester from Carboxylic Acid

To a flask containing an appropriate carboxylic acid (1.0 equiv) in) in an organic solvent (such as DMF, THF, preferably DMF) is added a suitable inorganic base (such as K$_2$CO$_3$ or Cs$_2$CO$_3$ preferably K$_2$CO$_3$) followed by a suitable alkyl halide (1.2 equiv). The reaction mixture is stirred at RT for about 2-5 h (preferably about 3 h). The reaction mixture is quenched with water. The separated solid is collected by filtration, washed with water and dried under vacuum to obtain the target compound.

Illustration of General Procedure Q

Preparation #Q.1

(2S,5R)-Methyl 5-((S)-3-(6-(4-fluoro-3-methoxybenzylcarbamoyl)-2-methylpyrimidin-4-yl)-4,5-dihydroisoxazol-5-yl)-1,4-dioxane-2-carboxylate

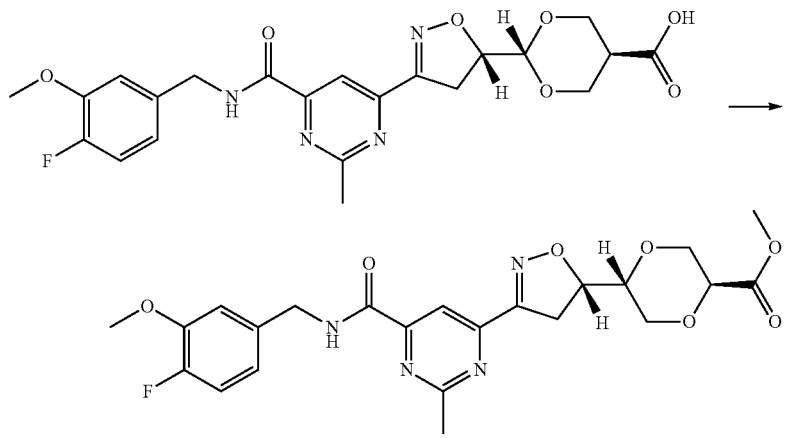

To a stirred solution of (2S,5R)-5-((S)-3-(6-(4-fluoro-3-methoxybenzylcarbamoyl)-2-methylpyrimidin-4-yl)-4,5-dihydroisoxazol-5-yl)-1,4-dioxane-2-carboxylic acid (0.3 g, 0.632 mmol, Example #P.1) in DMF (2 mL) was added potassium carbonate (0.131 g, 0.948 mmol) followed by iodomethane (0.108 g, 0.759 mmol). The reaction mixture was stirred at RT for about 3 h. The reaction mixture was quenched with water (15 mL), the product separated as solids and collected by filtration, washed with water (10 mL) and dried under vacuum to obtain (2S,5R)-methyl 5-((S)-3-(6-(4-fluoro-3-methoxybenzylcarbamoyl)-2-methylpyrimidin-4-yl)-4,5-dihydroisoxazol-5-yl)-1,4-dioxane-2-carboxylate 0.270 g, (87%), ES-MS: m/z 489 (m+H)$^+$, LC/MS (Table 1, method d) R$_t$=2.25 min.

Illustration of General Procedure R-1 (with HATU as Coupling Agent)

Example #R.1.1

6-(5-(4-Carbamoylphenyl)-4,5-dihydroisoxazol-3-yl)-N-(4-fluoro-3-methoxybenzyl)-2-methylpyrimidine-4-carboxamide

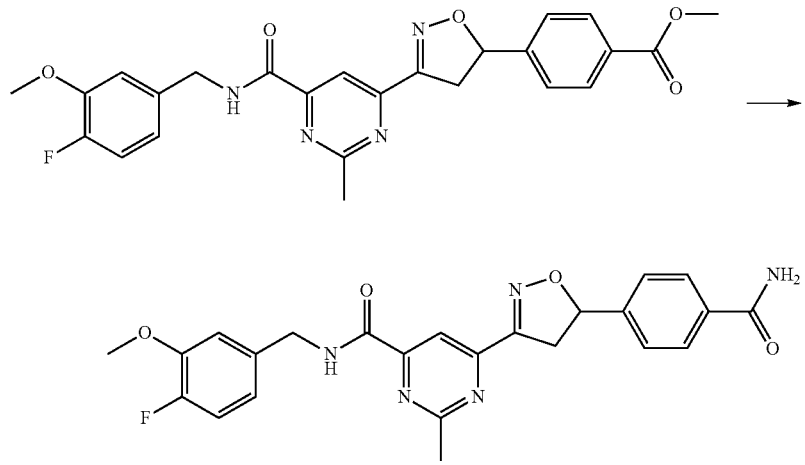

General Procedure R

Preparation of Amide from Alkyl Esters

Step 1

To a flask containing an appropriate alkyl ester in an aqueous organic solvent (such as THF or 1,4-dioxane, preferably in THF in 1:1 mixture) is added about 1.5 equiv. of lithium hydroxide and the mixture is stirred for about 4-8 h. (preferably about 4 h). Excess solvent is removed under vacuum and the solution is acidified with 10% HCl solution. The separated solid is collected by filtration and dried under vacuum to obtain the target carboxylic acid derivative.

Step 2

To a flask containing an appropriate carboxylic acid (1 equiv) in an organic solvent such as (DMF, DCM or THF, preferably DMF) is added a coupling agent (EDCI.HCl, HATU, HOBT, or PYBOP about 1-1.5 equiv, preferably HATU or HATU/EDCI.HCl, about 1.2 equiv) followed by addition of an organic base (such as TEA, DIEA, or N-methyl morpholine, preferably DIEA, about 1-2 equiv, preferably about 1.5 equiv). The mixture is stirred at RT for about 10 min-1 h (preferably about 10 min). To this reaction mixture is added an amine such as methyl amine 3M in methanol or 28% ammonium hydroxide solution. The reaction mixture is allowed to stir at RT for a period of about 1-4 h (preferably about 2 h). The mixture is quenched with ice cold water and product is extracted with EtOAc, then washed successively with 1N HCl solution, water and brine. The organic layer is dried over sodium sulphate and evaporated to dryness under reduced pressure. The residue obtained is purified using silica gel chromatography to afford the target amide derivative.

Step 1

To a cold stirred solution of methyl 4-(3-(6-(4-fluoro-3-methoxybenzylcarbamoyl)-2-methylpyrimidin-4-yl)-4,5-dihydroisoxazol-5-yl)benzoate (0.3 g, 0.62 mmol, G.1.29) in THF/water (1:1) was added lithium hydroxide (0.03 g, 1.2 mmol, Sd Fine Chem). The reaction mixture was stirred for about 3 h at RT and excess solvent was removed under reduced pressure. The aqueous layer was acidified with 10% HCl solution. The solid was collected by filtration, washed with water and dried under vacuum to afford 4-(3-(6-(4-fluoro-3-methoxybenzylcarbamoyl)-2-methylpyrimidin-4-yl)-4,5-dihydroisoxazol-5-yl)benzoic acid. (0.2 g), (69%).

Step 2

To a stirred solution of 4-(3-(6-(4-fluoro-3-methoxybenzylcarbamoyl)-2-methylpyrimidin-4-yl)-4,5-dihydroisoxazol-5-yl)benzoic acid (0.1 g, 0.215 mmol) in DMF (10 mL) was added HATU (0.123 g, 0.323 mmol) and DIEA (0.055 g, 0.43 mmol). The reaction mixture was stirred at RT for about 10 min. Ammonia solution (3 mL) was added and the reaction mixture stirred for about another 2 h. The reaction mixture was diluted with ice cold water (20 mL). The solid which was obtained was filtered, washed with water and dried under vacuum to afford 6-(5-(4-carbamoylphenyl)-4,5-dihydroisoxazol-3-yl)-N-(4-fluoro-3-methoxybenzyl)-2-methylpyrimidine-4-carboxamide (0.05 g), (50%) as an off white solid. LC/MS (Table 1, Method c) R$_1$=4.48 min. MS m/z: 464.2 (M+H)$^+$.

Illustration of General Procedure R-2 (with EDCI as Coupling Agent)

Example R-2.1

6-(5-(1-(2-(cyclopropylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide

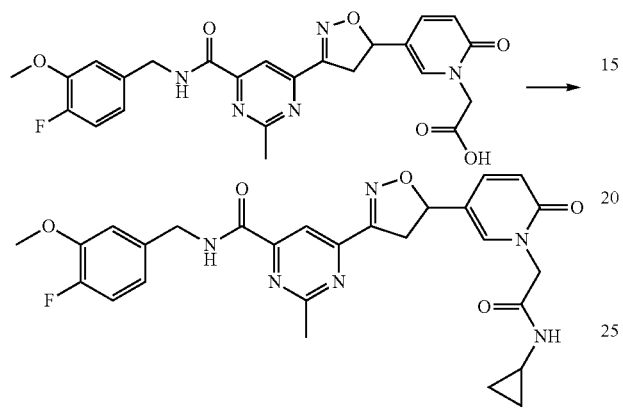

To a stirred solution 2-(5-(3-(6-(4-fluoro-3-methoxybenzylcarbamoyl)-2-methylpyrimidin-4-yl)-4,5-dihydroisoxazol-5-yl)-2-oxopyridin-1(2H)-yl)acetic acid (0.2 g, 0.404 mmol, G.1.225) in DMF (5 mL) was added cyclopropanamine (0.046 g, 0.807 mmol, Sd Fine Chem), EDCI.HCl (0.093 g, 0.484 mmol, spectrochem), HOBT (0.093 g, 0.605 mmol, spectrochem) and DIPEA (0.157 g, 1.211 mmol, spectrochem). The reaction mixture was stirred at RT for about 12 h. The reaction mixture was diluted with ice cold water (20 mL) and the product extracted with EtOAc (2×15 mL), The organic layer was dried over sodium sulphate and evaporated under reduced pressure to afford a thick mass. Crude compound was purified by preparative TLC, eluting with 2-4% methanol in DCM to afford 6-(5-(1-(2-(cyclopropylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide 21 mg (9.73%) as an off white solid. $^1$H NMR (400 MHz, DMSO): δ 9.519-9.487 (m, 1H), 8.282-8.273 (d, J=3.6 Hz, 1H), 8.190 (s, 1H), 7.768-7.762 (d, J=2.4 Hz, 1H), 7.558-7.529 (dd, J=9.2 Hz, 1H), 7.186-7.119 (m, 2H), 6.908-6.871 (m, 1H), 6.429-6.404 (d, J=10 Hz, 1H), 5.705-5.654 (m, 1H), 4.491-4.458 (m, 4H), 3.857-3.784 (m, 4H), 3.461-3.393 (m, 1H), 2.767 (s, 3H), 2.745-2.650 (m, 1H), 0.649-0.601 (m, 2H) 0.425-0.387 (m, 2H); MS m/z=533.3 (M−H)$^-$.

General Procedure S

Preparation of Tertiary-Alcohols from Methyl Ester Using Methyl Magnesium Bromide A flask containing an appropriate methyl ester derivative (1 equiv) in an organic solvent such as (DCM THF, or 1,4-dioxane, preferably THF) is cooled to about −78° C. and methyl magnesium bromide (3M in diethyl ether, 5 equiv) is added drop wise. Upon completion of addition, the reaction mixture is slowly warmed to RT and stirred for about 2-12 h (preferably 2 h). The reaction mixture is quenched with 1N HCl, diluted with water, and the product extracted with EtOAc. The organic layer is washed successively with water, brine and dried over sodium sulphate. The crude mass obtained upon concentration of the organic layer is purified to obtain the required material.

Illustration of General Procedure S

Example #S.1

N-(4-Fluoro-3-methoxybenzyl)-6-(5-(2-(2-hydroxypropan-2-yl)pyridin-4-yl)-4,5-dihydroisoxazol-3-yl)-2-methylpyrimidine-4-carboxamide

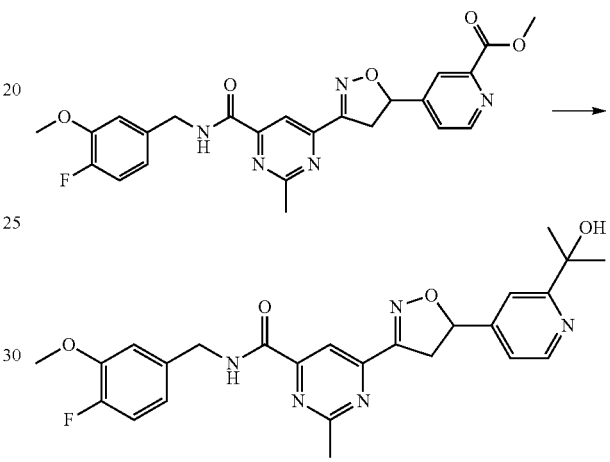

A solution of methyl 4-(3-(6-(4-fluoro-3-methoxybenzylcarbamoyl)-2-methylpyrimidin-4-yl)-4,5-dihydroisoxazol-5-yl)picolinate [0.2 g, 0.41 mmol Ex. #G.1.42 (step 1)] in THF (5 mL) was cooled to about −78° C. and methyl magnesium bromide was added drop wise (0.7 mL, 2.08 mmol, 3M in ether). Upon completion of addition, the reaction mixture was slowly warmed to RT and stirred for about 2 h. The reaction mixture was quenched with 1N HCl (5 mL), diluted with water (50 mL) and the product extracted with EtOAc (2×30 mL). The organic layer was washed successively with water (1×30 mL) and brine (1×20 mL), dried over sodium sulphate, evaporated to dryness under reduced pressure and the crude material was purified by preparative HPLC (Table 2, Method b) to afford N-(4-fluoro-3-methoxybenzyl)-6-(5-(2-(2-hydroxypropan-2-yl)pyridin-4-yl)-4,5-dihydroisoxazol-3-yl)-2-methylpyrimidine-4-carboxamide 0.15 g (7%); $^1$H NMR (DMSO): δ 9.51-9.48 (t, J=6.8 Hz, 1H), 8.503-8.489 (d, J=5.6 Hz, 1H), 8.201 (s, 1H), 7.689 (s, 1H), 7.257-7.242 (m, 3H), 6.902-6.891 (m, 1H), 5.993-5.944 (m, 1H), 5.253 (s, 1H), 4.487-4.470 (d, J=6.8 Hz, 2H), 4.058-3.984 (m, 1H), 3.813 (s, 3H), 3.445-3.381 (m, 1H), 2.746 (s, 3H), 1.427 (s, 6H): LC/MS (Table 1, Method c) R$_t$=1.07 min; MS m/z 480.2 (M+H)$^+$.

General Procedure T

Preparation of Tetrazoles from Nitrile Derivatives

A sealed tube is charged with an appropriate nitrile derivative (1 equiv), sodium azide (4 equiv), ammonium chloride (4 equiv) and DMF. The reaction mixture is heated at about 100° C. for about 8-12 h (preferably 12 h). The reaction mixture is cooled to RT and ice cold water is added. The product is extracted with EtOAc. The combined organic layer is washed with brine, dried over sodium sulphate and concentrated under reduced pressure. The crude material obtained is purified by preparative TLC to afford the target compound.

Example #T.1

Preparation of 6-(5-(2H-tetrazol-5-yl)-4,5-dihydroisoxazol-3-yl)-N-(4-fluoro-3-methoxybenzyl)-2-methylpyrimidine-4-carboxamide

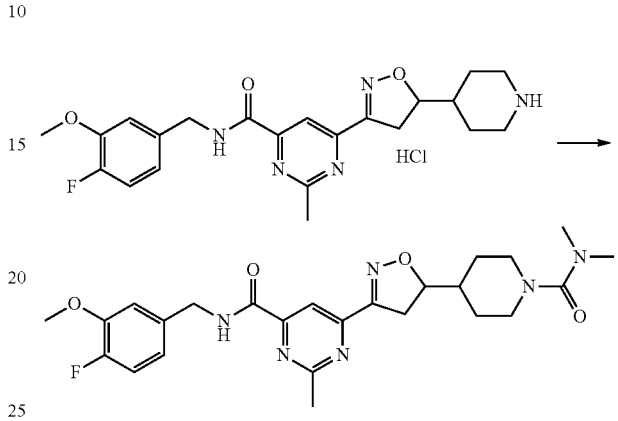

A 50 mL sealed tube is charged with 6-(5-cyano-4,5-dihydroisoxazol-3-yl)-N-(4-fluoro-3-methoxybenzyl)-2-methylpyrimidine-4-carboxamide (Ex.#G.1.25, 0.13 g, 0.35 mmol), sodium azide (0.091 g, 1.4 mmol, Sd Fine Chem), ammonium chloride (0.074 g, 1.4 mmol, Loba) and DMF (5 mL). The reaction mixture was heated at about 100° C. for about 12 h. The reaction mixture was cooled to RT and ice cold water (20 mL) was added. The product was extracted with EtOAc (3×15 mL). The combined organic layer was washed with brine (4×15 mL), dried over sodium sulphate and concentrated under reduced pressure. The crude material obtained was purified by preparative TLC (60% EtOAc in hexane) to afford 6-(5-(2H-tetrazol-5-yl)-4,5-dihydroisoxazol-3-yl)-N-(4-fluoro-3-methoxybenzyl)-2-methylpyrimidine-4-carboxamide 0.09 5 g (65%); LC/MS (Table 1, Method c) $R_t$=3.91 min; MS m/z 413 (M+H)$^+$.

General Procedure U

Formation of a Urea from an Amine and a Carbamoyl Chloride

A solution of an amine hydrochloride (1 equiv) in a suitable solvent such as DCM or THF (preferably DCM) is cooled to about 0° C. and then a suitable base such as TEA or DIEA (preferably TEA) (1 to 4.0 equiv, preferably 3.6 equiv) is added followed by the addition of carbamoyl chloride (1.0 to 1.3 equiv, preferably 1.24 equiv). The reaction mixture is stirred at RT for about 1-2 h (preferably 1 h). The reaction mixture is diluted with water and extracted with DCM. The combined organic layers are washed with brine, dried over sodium sulphate and evaporated to dryness under reduced pressure to give the target compound. The crude material is optionally purified by precipitation, crystallization or trituration from an appropriate solvent or solvents or by column chromatography to give the target compound.

Illustration of General Procedure U

Example #U.1

6-(5-(1-(Dimethylcarbamoyl)piperidin-4-yl)-4,5-dihydroisoxazol-3-yl)-N-(4-fluoro-3-methoxybenzyl)-2-methylpyrimidine-4-carboxamide

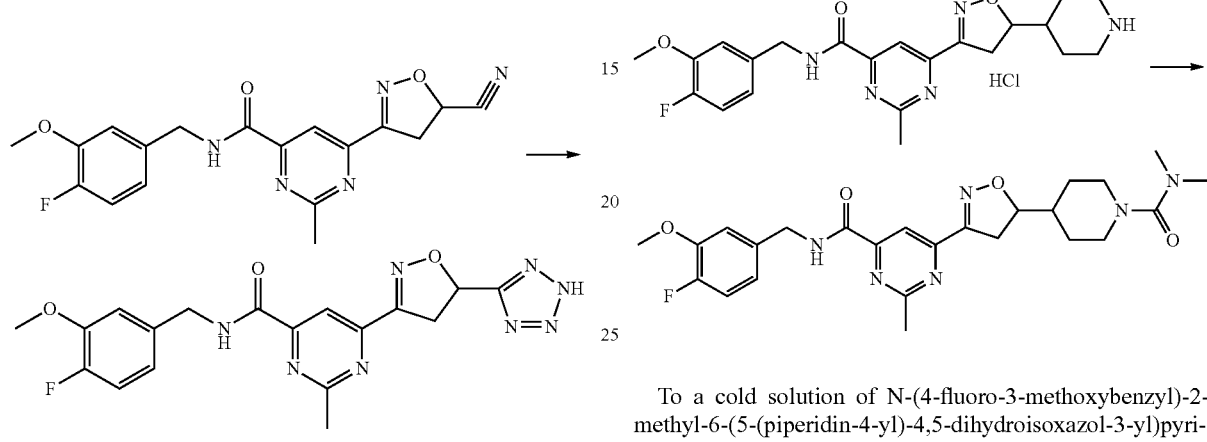

To a cold solution of N-(4-fluoro-3-methoxybenzyl)-2-methyl-6-(5-(piperidin-4-yl)-4,5-dihydroisoxazol-3-yl)pyrimidine-4-carboxamide hydrochloride (0.12 g, 0.25 mmol, Preparation #K.1) and TEA (0.091 g, 0.9 mmol, Sd Fine Chem) in DCM (15 mL) was added dimethyl carbamoyl chloride (0.033 g, 0.31 mmol, Aldrich). The reaction mixture was slowly warmed to RT and stirred for about 1 h. The reaction mixture was diluted with DCM (20 mL) and washed with water (2×15 mL). The combined organic layers were dried over sodium sulphate and concentrated under reduced pressure. The crude material obtained was purified using silica gel column chromatography eluted with 2-3% methanol in DCM. Relevant fractions containing the required compound were combined and evaporated to dryness under reduced pressure to afford 6-(5-(1-(dimethylcarbamoyl)piperidin-4-yl)-4,5-dihydroisoxazol-3-yl)-N-(4-fluoro-3-methoxybenzyl)-2-methylpyrimidine-4-carboxamide as an off white solid 0.064 g (50%): LC/MS (Table 1, Method c) $R_t$=1.83 min; MS m/z: 499.3 (M+H)$^+$.

General Procedure V

Formation of a Urea from an Amine and Isocyanate

To a solution of an amine hydrochloride (1 equiv) in a suitable solvent such as DCM or THF (preferably DCM) cooled to about 0° C. a suitable base such as TEA or DIEA (preferably TEA) (1-3.0 equiv, preferably 3.0 equiv) is added followed by the addition of ethyl isocyanate (1.0 to 1.2 equiv, preferably 1.19 equiv). The reaction mixture is warmed to RT and stirred for about 1 to 2 h (preferably 2 h). The reaction mixture is diluted with water and extracted with DCM. The combined organic layers are washed with brine, dried over sodium sulphate and evaporated to dryness under reduced pressure to give the target compound. The crude material is optionally purified by precipitation crystallization or trituration from an appropriate solvent or solvents or by column chromatography to give the target compound.

Illustration of General Procedure #V

Example #V.1

6-(5-(1-(Ethylcarbamoyl)piperidin-4-yl)-4,5-dihydroisoxazol-3-yl)-N-(4-fluoro-3-methoxybenzyl)-2-methylpyrimidine-4-carboxamide

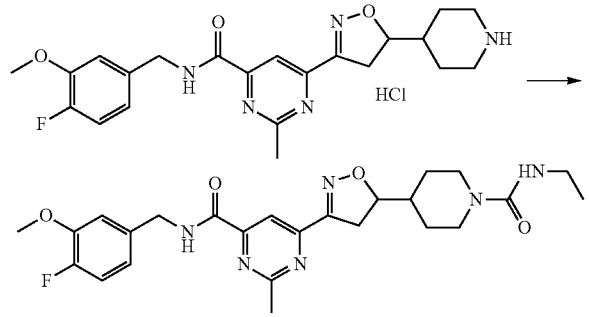

To a cold solution of N-(4-fluoro-3-methoxybenzyl)-2-methyl-6-(5-(piperidin-4-yl)-4,5-dihydroisoxazol-3-yl)pyrimidine-4-carboxamide hydrochloride (0.10 g, 0.21 mmol, Preparation #K.1) and TEA (0.065 g, 0.64 mmol, Sd Fine Chem) in DCM (10 mL) was added ethyl isocyanate (0.018 g, 0.25 mmol, Lancaster). The reaction mixture was slowly warmed to RT and stirred for about 2 h. The reaction mixture was diluted with water (20 mL) and the product extracted with DCM (2×20 mL). The combined organic layers were washed with water (1×25 mL) followed by brine (1×50 mL). The organic layer was dried over sodium sulphate and concentrated under reduced pressure. The crude material obtained was purified using silica gel column chromatography eluted in 1% methanol in DCM. Relevant fractions containing the required compound were combined and evaporated to dryness under reduced pressure to afford 6-(5-(1-(ethylcarbamoyl)piperidin-4-yl)-4,5-dihydroisoxazol-3-yl)-N-(4-fluoro-3-methoxybenzyl)-2-methylpyrimidine-4-carboxamide as an off white solid 60 mg (56%): LC/MS (Table 1, Method c) $R_t$=1.83 min; MS m/z: 499.2 $(M+H)^+$.

General Procedure W

Formation of an Amide from Mixed Carboxylic-Carbonic Anhydride and an Amine

A solution of carboxylic acid (1 equiv) in a suitable solvent such as DCM, THF, or 1,4-dioxane (preferably THF) is cooled to about −78° C. and then a suitable base such as TEA, DIEA or N-methyl morpholine (preferably N-methyl morpholine) 5-15 equiv (preferably 5 equiv) is added followed by the addition of isobutyl chloroformate 5-10 equiv (preferably 6.73 equiv). The mixture is warmed to RT and stirred for about 0.5-1 h (preferably about 0.5 h). To this reaction mixture is added a solution of amine hydrocholide (1 equiv) in THF and stirred for a period of about 1-4 h (preferably about 1 h). The mixture is quenched with ice cold water and product is extracted with EtOAc. The combined organic layers are washed successively with water and brine. The organic layer is dried over sodium sulphate and evaporated to dryness under reduced pressure. The residue obtained is purified using silica gel chromatography to afford the desired amide derivative.

Illustration of General Procedure W

Example #W.1

6-(5-(1-(2-Acetamidoacetyl)piperidin-4-yl)-4,5-dihydroisoxazol-3-yl)-N-(4-fluoro-3-methoxybenzyl)-2-methylpyrimidine-4-carboxamide

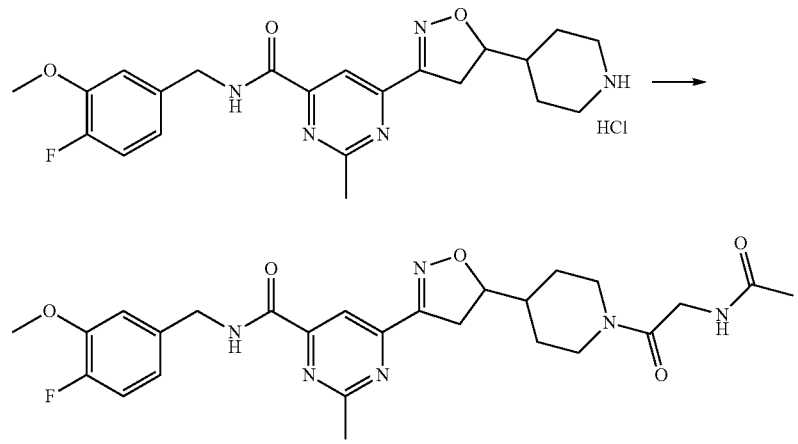

A solution of N-acetyl glycine (0.045 g, 0.38 mmol) and N-methyl morpholine (0.5 mL, 5.12 mmol, Spectrochem) in THF (5 mL) was cooled to about −78° C. and isobutyl chloroformate (0.3 mL, 2.56 mmol, Spectrochem) was added drop wise. The reaction mixture was stirred for about 0.5 h and N-(4-fluoro-3-methoxybenzyl)-2-methyl-6-(5-(piperidin-4-yl)-4,5-dihydroisoxazl-3-yl)pyrimidine-4-carboxamide hydrochloride (0.15 g, 0.323 mmol, Preparation #K.1) in THF (10 mL) was added. The reaction mixture was slowly warmed to RT and stirred for about 1 h. The reaction mixture was diluted with water (10 mL) and the product extracted with EtOAc (2×20 mL). The combined organic layers were washed with water (1×25 mL) followed by brine (1×50 mL). The organic layer was dried over sodium sulphate and concentrated under reduced pressure.

The crude material obtained was purified using silica gel column chromatography eluted in 1% MeOH in DCM. Relevant fractions containing the required compound were combined and evaporated to dryness under reduced pressure to 6-(5-(1-(2-acetamidoacetyl)piperidin-4-yl)-4,5-dihydroisoxazol-3-yl)-N-(4-fluoro-3-nethoxybenzyl)-2-methylpyrimidine-4-carboxamide as off white solid 0.029 g (17%). LC/MS (Table 1, Method c) $R_t$=2.71 min; MS m/z: 527.4 (M+H)$^+$.

General Procedure X

Preparation of Amides by the Nucleophilic Displacement of Ester with Amine

A sealed tube is charged with appropriate amine derivative (1 equiv), TEA (5 equiv) and an ester derivative (10-20 equiv, preferably 15 equiv). The reaction mixture is heated at about 150° C. for about 1-12 h (preferably about 12 h). The reaction mixture is cooled to RT, diluted with water and extracted with EtOAc. Combined organic extracts are dried over sodium sulphate and concentrated under reduced pressure. The crude material obtained is purified by preparative TLC to afford the target compound.

Illustration of General Procedure X

Example #X.1

6-(5-(1-(2-Cyanoacetyl)piperidin-4-yl)-4,5-dihydroisoxazol-3-yl)-N-(4-fluoro-3-methoxybenzyl)-2-methylpyrimidine-4-carboxamide

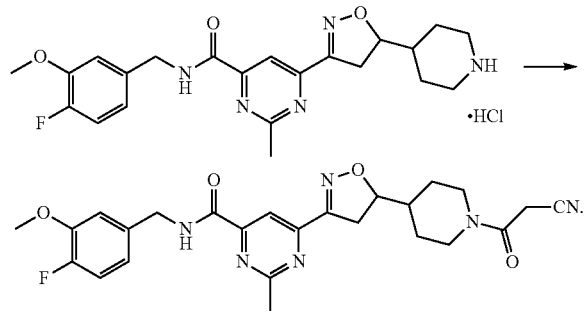

A 100 mL sealed tube was charged with N-(4-fluoro-3-methoxybenzyl)-2-methyl-6-(5-(piperidin-4-yl)-4,5-dihydroisoxazol-3-yl)pyrimidine-4-carboxamide hydrochloride (0.15 g, 0.32 mmol, Preparation #K.1), triethyl amine (0.163 g, 1.6 mmol, Sd Fine Chem), and ethyl cyanoacetate (0.54 mL, 4.8 mmol). The reaction mixture was heated at about 150° C. for about 12 h, cooled to RT and water (15 mL) was added. The product was extracted with EtOAc (2×15 mL). The combined organic layer was dried over sodium sulphate and concentrated under reduced pressure. The crude material obtained was purified by preparative HPLC (Table 2, Method d) to afford 6-(5-(1-(2-cyanoacetyl)piperidin-4-yl)-4,5-dihydroisoxazol-3-yl)-N-(4-fluoro-3-methoxybenzyl)-2-methylpyrimidine-4-carboxamide as an off white solid 0.065 g (40.8%). LC/MS (Table 1, Method c) $R_t$=1.38 min; MS m/z: 495.3 (M+H)$^+$.

General Procedure Y

Formation of an amide from active ester

To a solution of an amine hydrochloride (1 equiv) in a suitable solvent such as DCM or THF (preferably DCM) is added a suitable base such as TEA or DIEA (preferably TEA) (1 to 4.0 equiv preferably 3.0 equiv) and perfluoro phenyl-2-(methyl sulfonyl)acetate (1.0 to 1.5 equiv preferably 1.5 equiv, See Ref: US 20090312338). The reaction mixture is stirred at RT for about 1-24 h (preferably about 16 h). Solvent is removed under reduced pressure and purified by preparative HPLC to afford the target amide compound.

Illustration of General Procedure Y

Example #Y.1: Preparation of N-(4-fluoro-3-methoxybenzyl)-2-methyl-6-(5-(1-(2-(methylsulfonyl)acetyl)piperidin-4-yl)-4,5-dihydroisoxazol-3-yl)pyrimidine-4-carboxamide

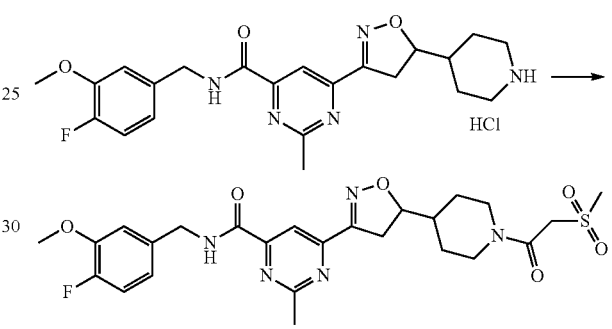

To a stirred solution of N-(4-fluoro-3-methoxybenzyl)-2-methyl-6-(5-(piperidin-4-yl)-4,5-dihydroisoxazol-3-yl)pyrimidine-4-carboxamide hydrochloride (0.20 g, 0.43 mmol Preparation #K. 1) in DCM (10 mL) was added TEA (0.13 g, 1.29 mmol, Spectrochem) and perfluorophenyl-2-(methylsulfonyl)acetate (0.196 g, 0.645 mmol, See Ref: US 20090312338). The resulting solution was stirred at RT for about 16 h. The crude reaction mixture was purified by preparative HPLC (Table 2, Method f) to afford N-(4-fluoro-3-methoxybenzyl)-2-methyl-6-(5-(1-(2-(methylsulfonyl)acetyl)piperidin-4-yl)-4,5-dihydroisoxazol-3-yl)pyrimidine-4-carboxamide 0.072 g (31.3%); LC/MS (Table 1, Method d) $R_t$=0.55 min; MS m/z: 548.3 (M+H)$^+$.

General Procedure Z

Formation of a Urea from an Amine with Triphosgene

To a solution of an amine hydrochloride (1 equiv) in a suitable solvent such as DCM or THF (preferably DCM) is added a suitable base such as TEA or DIEA (preferably TEA) (1 to 3.0 equiv, preferably 3.0 equiv) followed bytriphosgene (0.3 to 0.7 equiv, preferably 0.6 equiv). The reaction mixture is stirred at RT for about 15 to 30 min (preferably about 30 min). Then a suitable amine (1 to 1.5 equiv preferably 1.5 equiv), is added to the reaction mixture and the mixture is stirred for about 12 h. The reaction mixture is diluted with DCM and washed with water. The combined organic layers are dried over sodium sulphate and evaporated to dryness under reduced pressure to give the target compound. The crude material is optionally purified by precipitation crystallization or trituration from an appropriate solvent or solvents or by column chromatography to give the target compound.

Illustration of General Procedure Z

Example #Z.1

Preparation of N-(4-fluoro-3-methoxybenzyl)-6-(5-(1-(2-hydroxy ethyl carbamoyl)piperidin-4-yl)-4,5-dihydroisoxazol-3-yl)-2-methylpyrimidine-4-carboxamide

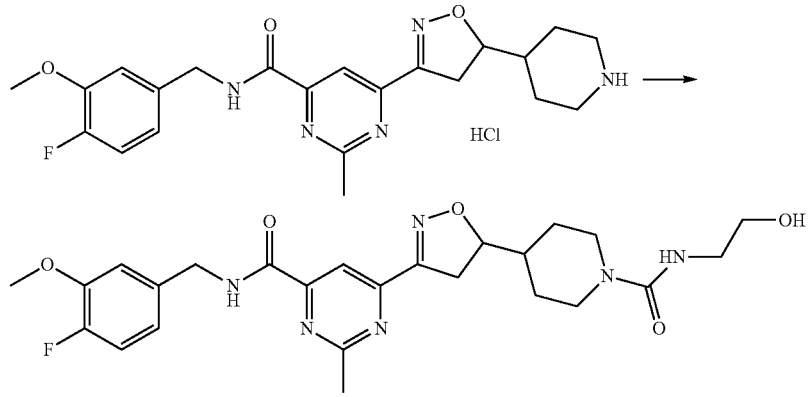

To a cold of solution of N-(4-fluoro-3-methoxybenzyl)-2-methyl-6-(5-(piperidin-4-yl)-4,5-dihydroisoxazol-3-yl)pyrimidine-4-carboxamide hydrochloride (0.12 g, 0.25 mmol, Preparation #K.1) in DCM (10 mL) was added TEA (0.077 g, 0.76 mmol, Sd Fine Chem) followed by triphosgene (0.045 g, 0.154 mmol, Spectrochem). The reaction mixture was slowly warmed to RT and stirred for about 0.5 h. Ethanolamine (0.023 g, 0.38 mmol, Spectrochem) was added and the reaction mixture was stirred at RT for about 12 h. The reaction mixture was diluted with DCM (20 mL) and washed with water (2×15 mL). The combined organic layers were dried over sodium sulphate and concentrated under reduced pressure. The crude material obtained was purified by preparative TLC (2% MeOH/DCM) to afford N-(4-fluoro-3-methoxybenzyl)-6-(1-(5-(1-(2-hydroxyethylcarbamoyl)piperidin-4-yl)-4,5-dihydroisoxazol-3-yl)-2-methylpyrimidine-4-carboxamide as a light yellow solid, 0.051 g (39%), LC/MS (Table 1, Method d) $R_f$=0.36 min; MS m/z: 515.1 (M+H)$^+$.

General Procedure AA

Formation of a Urea from an Amine with 4-Nitrophenyl Chloroformate

To a solution of an amine hydrochloride (1 equiv) in a suitable solvent such as DCM, THF, or DMF (preferably DMF) is added a suitable base such as TEA or DIEA (preferably TEA) (1 to 5.0 equiv, preferably 5.0 equiv) followed by 4-nitrophenyl arylcarbamate (1.0 to 1.5 equiv, preferably 1.48 equiv, see WO 2005070891) The reaction mixture is heated to about 80° C. for about 12 to 15 h (preferably 12 h). The reaction mixture is cooled to RT, poured into ice water and the product is extracted with ethyl acetate. The combined organic layers are washed with brine, dried over sodium sulphate and evaporated to dryness. The crude material is optionally purified by precipitation, crystallization or trituration from an appropriate solvent or solvents or by column chromatography to get the target compound.

Illustration of General Procedure AA

Example #AA.1

Preparation of N-(4-fluoro-3-methoxybenzyl)-6-(5-(1-(isoxazol-3-ylcarbamoyl)piperidin-4-yl)-4,5-dihydroisoxazol-3-yl)-2-methylpyrimidine-4-carboxamide

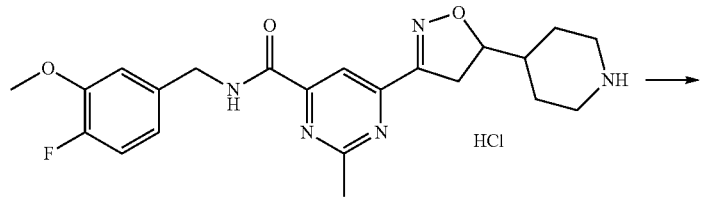

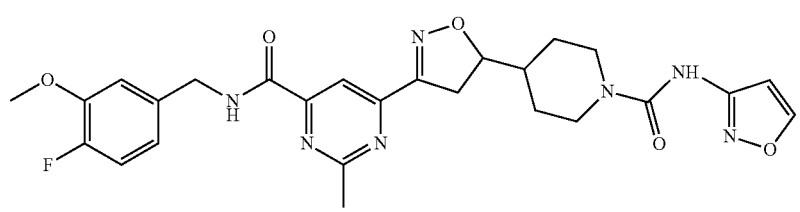

To a stirred solution of N-(4-fluoro-3-methoxybenzyl)-2-methyl-6-(5-(piperidin-4-yl)-4,5-dihydroisoxazol-3-yl)pyrimidine-4-carboxamide hydrochloride (0.2 g, 0.431 mmol, Preparation #K.1) and TEA (0.21 g, 21.5 mmol, Spectrochem) in DMF (10 mL) was added 4-nitrophenyl isoxazol-3-ylcarbamate (0.19 g, 0.64 mmol). The reaction mixture was heated to about 80° C. for about 12 h. The reaction mixture was cooled to RT and diluted with ice water (50 mL) and the product extracted with EtOAc (3×50 mL). The combined organic layers were washed with brine (1×50 mL), dried over sodium sulphate and evaporated to dryness. The crude material was purified by silica gel column chromatography eluted with 2-3% methanol in DCM. Relevant fractions containing the required compound were combined and evaporated to dryness under reduced pressure to afford the crude derivative which was further purified by preparative TLC using 2% MeOH in DCM to afford N-(4-fluoro-3-methoxybenzyl)-6-(5-(1-(isoxazol-3-ylcarbamoyl)piperidin-4-yl)-4,5-dihydroisoxazol-3-yl)-2-methylpyrimidine-4-carboxamide as an off white solid 0.071 g (30.8%): LC/MS (Table 1, Method d) $R_t$=1.38 min; MS m/z: 538.3 (M+H)$^+$.

General Procedure AB

Formation of 1,2,4-Oxadiazole from Aryl Esters

To a solution of an appropriate aryl ester (1 equiv) in toluene is added N-hydroxy acetimidine (1.0 to 1.2 equiv, preferably 1 equiv) followed by potassium carbonate (1.0 to 1.2 equiv, preferably 1 equiv). The reaction mixture is refluxed for about 1 to 12 h (preferably about 12 h). The reaction mixture is cooled to RT, diluted with water and the product extracted with EtOAc. The combined organic extracts are washed successively with 1N HCl, water and brine then dried over sodium sulphate and evaporated to dryness. The crude material is optionally purified by precipitation, crystallization or trituration from an appropriate solvent or solvents or by column chromatography to give the target compound.

Illustration of General Procedure AB

Preparation #AB.1

3-Methyl-5-(6-vinylpyridin-3-yl)-1,2,4-oxadiazole

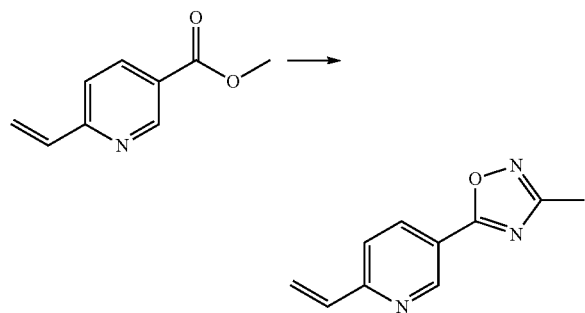

To a solution of methyl 6-vinylnicotinate (0.4 g, 2.45 mmol, Preparation #F.1.14) in toluene (15 mL) was added N-hydroxy acetimidine (0.2 g, 2.69 mmol) followed by potassium carbonate (0.379 g, 2.69 mmol). The reaction mixture was refluxed for about 12 h. The reaction mixture was cooled to RT, diluted with water (100 mL) and the product extracted with EtOAc (2×150 mL). The combined organic extracts were washed successively with 1N HCl (1×100 mL), water (1×100 mL) and brine (1×100 mL) then dried over sodium sulphate and evaporated to dryness.

The residue obtained was purified by silica gel (60-120 mesh) chromatography eluting with 10% of EtOAc in hexane. Relevant fractions containing the target compound were combined and evaporated to dryness under reduced pressure to afford 3-methyl-5-(6-vinylpyridin-3-yl)-1,2,4-oxadiazole as a pale yellow solid 0.068 g (14.8%); MS m/z: 188 (M+H)$^+$. $^1$H NMR (400 MHz, DMSO): δ 9.2 (s, 1H), 8.42 (d, J=8.4 Hz, 1H), 7.7 (d, J=8.4 Hz, 1H), 6.9 (m, 1H), 6.4 (d, J=9.6 Hz, 1H), 5.6 (d, J=10.8 Hz, 1H), 2.5 (s, 3H), MS m/z: 188 (M+H)$^+$.

General Procedure AC

Formation of N-methyl urea

To a solution of amine hydrochloride salt (1 equiv) and DIEA (2-4 equiv, preferably 2 equiv) in an organic solvent (such as DCM, THF, or 1,4-dioxane, preferably DCM) is added N-succinimidyl N-methylcarbamate (2 to 4 equiv, preferably 2 equiv). The reaction mixture is stirred for about 24-48 h (preferably about 24 h) at RT. The reaction mixture is diluted with water and the product extracted with DCM. The combined organic layers are washed successively with 0.1M aqueous NaOH and brine. The organic layer is dried over sodium sulphate and evaporated to dryness under reduced pressure. The crude material obtained is triturated with diethyl ether to afford the target urea.

Illustration of General Procedure AC

Example #AC.1

N-(4-Fluoro-3-methoxybenzyl)-2-methyl-6-(5-(1-(methylcarbamoyl)piperidin-4-yl)-4,5-dihydroisoxazol-3-yl)pyrimidine-4-carboxamide

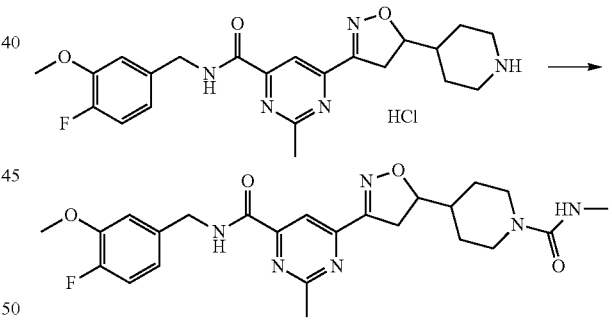

To a solution of N-(4-fluoro-3-methoxybenzyl)-2-methyl-6-(5-(piperidin-4-yl)-4,5-dihydroisoxazol-3-yl)pyrimidine-4-carboxamide hydrochloride (0.15 g, 0.323 mmol, Preparation #K.1) and DIEA (0.0835 g, 0.647 mmol, Sd Fine Chem) in DCM (15 mL) was added N-succinimidyl N-methylcarbamate (0.11 g, 0.647 mmol, Aldrich). The reaction mixture was stirred for about 24 h at RT. The reaction mixture was diluted with water (15 mL) and the product extracted with DCM (3×20 mL). The combined organic layers were washed successively with 0.1M aqueous NaOH (3×15 mL) and brine (1×50 mL). The organic layer was dried over sodium sulphate and evaporated to dryness under reduced pressure. The crude material obtained was triturated with diethyl ether to afford N-(4-fluoro-3-methoxybenzyl)-2-methyl-6-(S-(1-(methylcarbamoyl)piperidin-4-yl)-4,5-dihydroisoxazol-3-yl)pyrimidine-4-carboxamide 0.06 mg (38.4%) as a pale yellow solid. LC/MS (Table 1, Method e) R$_t$=3.13 min; MS m/z: 485.3 (M+H)$^+$.

General Procedure AD

Cyclization of an Aldehyde with a TOSMIC Reagent to Give an Oxazole

Toluenesulphonylmethyl isocyanide (1.0-1.5 equiv preferably 1.0 equiv) is added to a stirred suspension of an appropriate aldehyde (1 equiv) and a suitable inorganic base (such as potassium carbonate, sodium carbonate, sodium bicarbonate, preferably potassium carbonate, 1.0-1.5 equiv preferably 1.0 equiv) in a suitable solvent (such as 1,4-dioxane, THF, MeOH, preferably MeOH). The reaction mixture is heated to reflux for about 1-5 h (preferably 4 h), diluted with water and the product is extracted with EtOAc. The organic layer is washed successively with water, brine and dried over sodium sulphate. The crude mass obtained upon concentration of the organic layer is purified by column chromatography to obtain the required material.

Illustration of General Procedure AD

Preparation #AD.1

5-(6-Chloropyridin-3-yl)oxazole

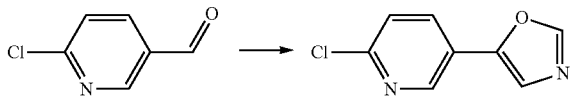 [SMILES: O=Cc1ccc(Cl)nc1 ; Clc1ccc(-c2cnco2)cn1]

To a stirred suspension of 6-chloronicotinaldehyde (1.5 g, 10.59 mmol, Organic Letters 2005, 7(14) 2965-2967) and potassium carbonate (1.46 g, 10.5 mmol) in MeOH (50 mL) was added toluenesulphonylmethyl isocyanide (2.06 g, 10.59 mmol, Aldrich). The reaction mixture was heated to reflux for about 4 h. The reaction mixture diluted with water (50 mL) and the product was extracted with EtOAc (2×150 mL). The combined organic layers were washed successively with water (2×50 mL) and brine (1×50 mL), dried over sodium sulphate and evaporated to dryness. The crude material was purified by silica gel column chromatography eluted with 15% EtOAC in hexane. Relevant fractions containing the required compound were combined and evaporated to dryness under reduced pressure to afford 5-(6-chloropyridin-3-yl)oxazole as an off white solid 1.2 g (42.8. %), $^1$H NMR (400 MHz, CDCl$_3$): δ 8.7 (d, J=2.0 Hz, 1H), 7.98 (s, 1H), 7.91 (d, J=2.4 Hz, 1H), 7.45 (s, 1H), 7.42 (d, J=8.4 Hz, 1H), MS m/z: 181 (M+H)$^+$.

Preparation #AD.2

5-(5-Bromopyridin-2-yl)oxazole

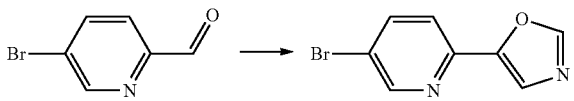 [SMILES: O=Cc1ccc(Br)cn1 ; Brc1ccc(-c2cnco2)nc1]

To a stirred suspension of 5-bromopicolinaldehyde (0.412 g, 2.215 mmol, Tetrahedron Letters 2008, 64, 3794-3801) and potassium carbonate (0.3358 g, 2.43 mmol, Rankem) in MeOH (20 mL) was added toluenesulphonylmethyl isocyanide (0.4757 g, 2.43 mmol). The reaction mixture was heated to reflux for about 4 h. The reaction mixture diluted with water (100 mL) and the product was extracted with EtOAc (2×75 mL). The combined organic layers were washed successively with water (2×50 mL) and brine (1×50 mL), dried over sodium sulphate and evaporated to dryness. The crude material obtained was purified by silica gel column chromatography eluted with 10% EtOAC in hexane. Relevant fractions containing the target compound were combined and evaporated to dryness under reduced pressure to afford 5-(5-bromopyridin-2-yl)oxazole as an off white solid 0.35 g (70.2%), $^1$H NMR (400 MHz, DMSO): δ 8.7 (d, J=2.4 Hz, 1H), 8.57 (s, 1H), 8.2 (dd, J=8.4 Hz, 1H), 7.8 (s, 1H), 7.7 (d, J=8.8 Hz, 1H), MS m/z: 226 (M+H)$^+$.

General Procedure AE

BocProtection of Amine with Di-Tert-Butyl Dicarbonate

Ditert.butylpyrocarbonate is added to a solution of an appropriate amine derivative (1.05 equiv) and a suitable base (such as TEA or DIEA preferably TEA 1.0 equiv) in a suitable solvent (such as 1,4-dioxane, DMF, THF preferably THF) containing a catalytic amount of DMAP. The reaction mixture is stirred at RT for about 2-6 h (preferably 4 h). The reaction mixture is diluted with EtOAc and washed successively with saturated sodium bicarbonate solution and brine. The organic layer is dried over sodium sulphate and evaporated to dryness under reduced pressure.

The residue obtained is purified by silica gel chromatography to afford the required compound.

Illustration of General Procedure AE

Preparation #AE.1

Tert-butyl 5-bromo-1H-pyrazolo[3,4-b]pyridine-1-carboxylate

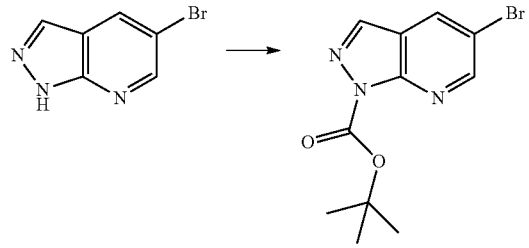 [SMILES: Brc1cnc2[nH]ncc2c1 ; CC(C)(C)OC(=O)n1ncc2cc(Br)cnc21]

To a stirred solution of the 5-bromo-1H-pyrazolo[3,4-b]pyridine (0.5 g, 2.52 mmol, reference US 2009035381) and TEA (0.352 mL, 2.52 mmol, Rankem) in THF (20 mL) was added di-tert. butyl dicarbonate (0.616 mL, 2.65 mmol Spectrochem) and a catalytic amount of DMAP (0.077 g, 0.631 mmol, Spectrochem). The reaction mixture was stirred at RT for about 4 h. The reaction mixture was diluted with EtOAc (100 mL) and washed successively with saturated sodium bicarbonate solution (25 mL) and brine (1×20 mL). The organic layer was dried over sodium sulphate and concentrated under reduced pressure. The crude material obtained was purified using silica gel column chromatography eluted in 20% EtOAc-hexane. Relevant fractions containing the required compound were combined and evaporated to dryness under reduced pressure afforded tert-butyl 5-bromo-1H-pyrazolo[3,4-b]pyridine-1-carboxylate as a pale yellow solid. 0.510 g, (67.7%), $^1$H NMR: (400 MHz, DMSO) δ: 8.798-8.792 (d, J=2.4 Hz, 1H) 8.648-8.643 (d, J=2.1 Hz, 1H) 8.417 (s, 1H) 1.69 (s, 9H), MS m/z: 198.2 (M+H)$^+$.

General Procedure AF

Formation of Ether Linkage

To a flask containing an appropriate alcohol (1.0 equiv) in an organic solvent (such as THF or DMF, preferably THF) is added 60% sodium hydride in mineral oil (1.0 equiv) at about 0° C. The reaction mixture is slowly warmed to RT and stirred for about 10 min-1.0 h (preferably 25 min). The reaction mixture was cooled to about 0° C. and iodomethane (1.0 equiv) was added. Upon completion of addition, the reaction mixture is slowly warmed to RT and stirred for about 2-5 h (preferably 2 h). The reaction mixture is diluted with water (20 mL) and the product extracted with EtOAc. The organic layer is dried over sodium sulphate and evaporated to dryness under reduced pressure. The residue obtained is purified using silica gel chromatography to afford the target compound.

Illustration of General Procedure AF

Preparation #AF.1

(2R,5S)-2-(Methoxymethyl)-5-vinyl-1,4-dioxane

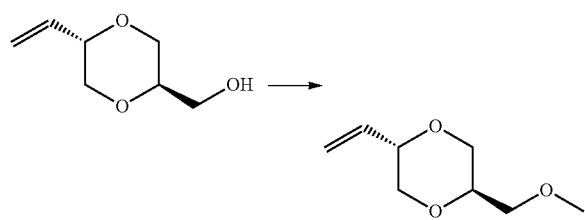

To a solution of ((2R,5S)-5-vinyl-1,4-dioxan-2-yl)methanol (Preparation #17, 0.25 g, 1.734 mmol) in THF (3 mL) was added NaH (41.6 mg, 1.734 mmol) at 0° C. The reaction mixture was slowly warmed to RT and stirred for 25 min. The reaction mixture was cooled to about 0° C. and iodomethane (0.108 mL, 1.734 mmol) was added. Upon completion of addition, the reaction mixture was slowly warmed to RT and stirred for about 2.5 h. The reaction mixture was diluted with water (20 mL) and the product extracted with EtOAc (2×10 mL). The organic layer dried over sodium sulfate and concentrated under reduced pressure. The crude material obtained was purified by column chromatography eluting with 10% EtOAc in hexane to afford (2R,5S)-2-(methoxymethyl)-5-vinyl-1,4-dioxane 0.1 g (36.5%), $^1$H NMR (400 MHz, CDCl$_3$): δ 5.75-5.67 (m, 1H), 5.36-5.32 (m, 1H), 5.23-5.20 (m, 1H), 4.05-4.00 (m, 1H), 3.87-3.70 (m, 3H), 3.55-3.49 (m, 1H), 3.42-3.35 (m, 6H), ES-MS: m/z 158 (m+H).

Example #1

6-(5-((1r,4r)-4-(2-Cyanoacetamido)cyclohexyl)-4,5-dihydroisoxazol-3-yl)-N-(4-fluoro-3-methoxybenzyl)-2-methylpyrimidine-4-carboxamide

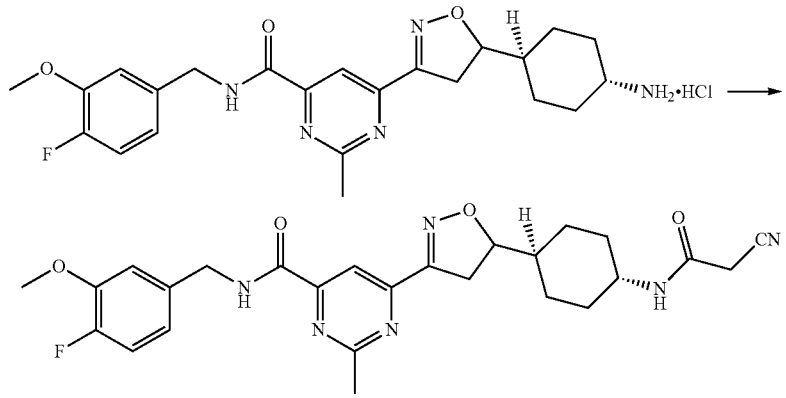

To a cold solution of 6-(5-((1r,4r)-4-aminocyclohexyl)-4,5-dihydroisoxazol-3-yl)-N-(4-fluoro-3-methoxybenzyl)-2-methylpyrimidine-4-carboxamide hydrochloride (0.30 g, 0.63 mmol, Preparation #K.2) in DCM (20 mL) was added TEA (0.35 mL, 2.51 mmol) and perfluorophenyl-2-cyanoacetate (0.316 g, 1.26 mmol, US 20090312338). The reaction mixture was slowly warmed to RT and stirred for about 12 h. The reaction mixture was diluted with DCM (150 mL) and washed with 1N HCl (70 mL) and brine (100 mL). The organic layer was dried over sodium sulphate and evaporated to dryness under reduced pressure. The crude material obtained was purified by preparative TLC (using 70% EtOAc in hexane as an eluent) to afford 6-(5-((1r,4r)-4-(2-cyanoacetamido)cyclohexyl)-4,5-dihydroisoxazol-3-yl)-N-(4-fluoro-3-methoxybenzyl)-2-methylpyrimidine-4-carboxamide as a white solid. 38 mg (11.9%), LC/MS (Table 1, Method d) R$_t$=2.09 min; MS m/z: 509.2 (M+H)$^+$.

Example #2

N-(4-Fluoro-3-methoxybenzyl)-2-methyl-6-(5-((1r,4r)-4-(sulfamoylamino)cyclohexyl)-4,5-dihydroisoxazol-3-yl)pyrimidine-4-carboxamide

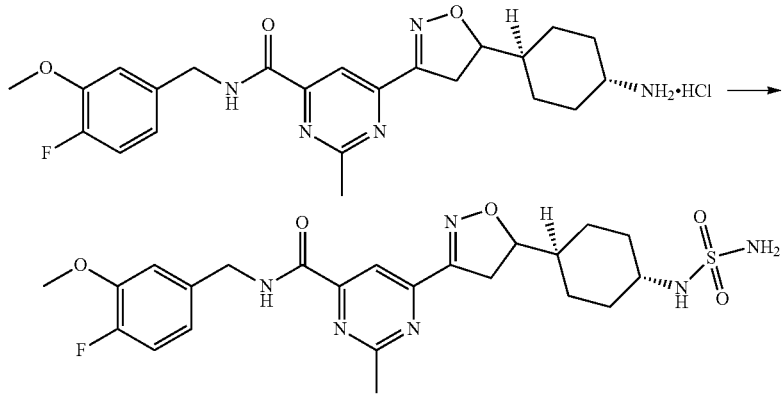

To a cold solution of chlorosulfonylisocyanate (1 equiv) in DCM (10 mL) was added t-butanol (0.030 mL, 0.314 mmol, Spectrochem). The reaction mixture was slowly warmed to RT, stirred for about 90 min. TEA (0.2 mL 1.43 mmol, Loba) was added. The resulting solution was added drop wise to a stirred solution of 6-(5-((1r,4r)-4-aminocyclohexyl)-4,5-dihydroisoxazol-3-yl)-N-(4-fluoro-3-methoxybenzyl)-2-methylpyrimidine-4-carboxamide hydrochloride (0.1 g, 0.209 mmol, Preparation #K.2) and TEA (0.204 mL, 1.465 mmol, Loba) in DCM (10 mL) at about 0° C. The reaction mixture was warmed to RT and stirred for about another 3 h. The reaction mixture was diluted with water (20 mL) and the product extracted with DCM (2×50 mL). The combined organic extracts were washed successively with 0.5 N HCl (2×50 mL), water (1×20 mL) and brine (1×50 mL). The organic layer was dried over sodium sulphate and evaporated to dryness under reduced pressure. The crude material obtained was triturated with hexane (50 mL) to afford tert-butyl N-((1r,4r)-4-(3-(6-((4-fluoro-3-methoxybenzyl)carbamoyl)-2-methylpyrimidin-4-yl)-4,5-dihydroisoxazol-5-yl)cyclohexyl)sulfamoylcarbamate 0.105 g (81%) MS m/z: 621.4 (M+H)$^+$. To a cold solution of tert-butyl N-((1r,4r)-4-(3-(6-((4-fluoro-3-methoxybenzyl)carbamoyl)-2-methylpyrimidin-4-yl)-4,5-dihydroisoxazol-5-yl)cyclohexyl)sulfamoylcarbamate (0.105 g, 0.169 mmol) in DCM (10 mL) was added TFA (0.261 mL, 3.38 mmol). The reaction mixture was warmed to RT and stirred for about 3 h. The solvents were removed in vaccuo. The reaction mixture diluted with EtOAc (100 mL), washed successively with saturated sodium bicarbonate solution (50 mL) and brine (50 mL). The organic layer was dried over sodium sulphate and evaporated to dryness. The crude material obtained was purified by preparative TLC (20% acetone in DCM) to afford N-(4-fluoro-3-methoxybenzyl)-2-methyl-6-(5-((1r, 4r)-4-(sulfamoylamino)cyclohexyl)-4,5-dihydroisoxazol-3-yl)pyrimidine-4-carboxamide 0.045 g (48.7%) as a light yellow solid. LC/MS (Table 1, Method d) R$_t$=8.03 min, MS m/z: 521.4 (M+H)$^+$.

Preparation #12

1-Methyl-5-vinyl-1H-pyrazolo[3,4-b]pyridine

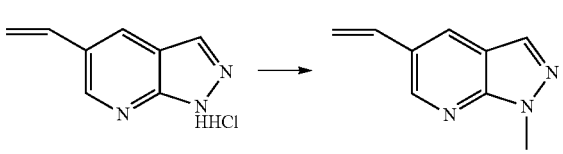

To a cold solution of 5-vinyl-1H-pyrazolo[3,4-b]pyridine hydrochloride (F.1.28, 0.1 g, 0.551 mmol) in DMF (10 mL) was added potassium carbonate (0.152 g, 1.101 mmol) and iodomethane (0.038 mL, 0.606 mmol). The reaction mixture was slowly warmed to RT and stirred for about 3 h. The reaction mixture was diluted with water (50 mL) and the product extracted with EtOAc (2×75 mL). The combined organic layers were washed with brine (1×20 mL), dried over sodium sulphate and evaporated to dryness under reduced pressure to afford 1-methyl-5-vinyl-1H-pyrazolo[3,4-b]pyridine 0.08 g (91%), $^1$H NMR (400 MHz, DMSO) δ: 8.732-8.726 (d, J=2.4 Hz, 1H), 8.327-8.322 (d, J=2 Hz, 1H), 8.14 (s, 1H), 6.9 (m, 1H), 5.986-5.940 (d, J=18.4 Hz, 1H), 5.343-5.314 (d, J=11.6 Hz, 1H), 4.05 (s, 3H), MS m/z: 160(M+H)$^+$.

Preparation #13

2,3-Dihydrobenzofuran-5-yl)methanamine

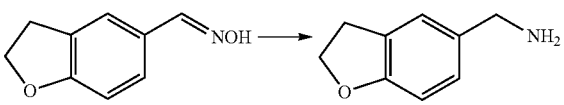

To a stirred solution of 2,3-dihydrobenzofuran-5-carbaldehyde oxime (2.7 g, 16.55 mmol, WO2008/106139) in methanol (150 mL) was added Raney® nickel (2.8 g). The reaction mixture was hydrogenated at 60 psi for about 4 h. The reaction mixture was filtered through a Celite® pad and washed with MeOH (50 mL). The filtrate was concentrated under reduced pressure. The crude material was redissolved in EtOAc (100 mL), washed with water (2×50 mL), dried over sodium sulphate and evaporated to dryness under reduced pressure to afford 2,3-dihydrobenzofuran-5-yl)methanamine (1.6 g), (64.8%), $^1$H NMR (400 MHz, DMSO): δ 7.17 (s, 1H), 7.013-6.992 (d, J=8.4 Hz, 1H), 6.672-6.641 (d, J=12.4 Hz, 1H), 4.50-4.45 (m, 2H), 3.57 (s, 2H), 3.15-3.10 (m, 2H), MS m/z=133.8 (—NH$_2$)

Preparation #14

1-(4-Fluoro-3-methoxyphenyl)ethanone

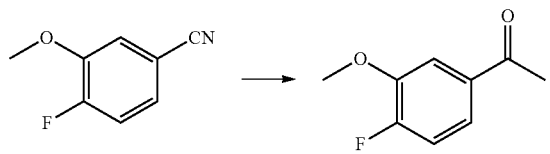

To an ice cold solution of 4-fluoro-3-methoxybenzonitrile (25 g, 165 mmol, Combi Blocks) in THF (250 mL), methyl magnesium bromide was added drop wise (110 mL, 331 mmol, 3M in ether). Upon completion of the addition, reaction mixture was slowly warmed to RT and stirred for about 1 h. The reaction mixture was quenched with saturated ammonium chloride solution (100 mL) and the product was extracted with EtOAc (2×150 mL). The organic layer was washed with brine (2×150 mL) and dried over sodium sulphate. The organic layer was evaporated to dryness under reduced pressure and the crude material obtained was purified by silica gel chromatography eluting with 10% EtOAc in hexane. Relevant fractions containing the target compound were combined and evaporated to dryness under reduced pressure to afford 1-(4-fluoro-3-methoxyphenyl)ethanone as colourless oil 4.2 g (15.10%). $^1$H NMR (400 MHz, DMSO) δ: 7.64 (m, 2H), 7.39 (m, 1H), 3.91 (s, 3H), 2.58 (s, 3H). MS m/z 169.2 (m+H)$^+$.

Preparation #15

(Z)-1-(4-Fluoro-3-methoxyphenyl)ethanoneoxime

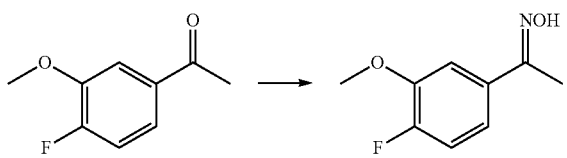

To a stirred solution of 1-(4-fluoro-3-methoxyphenyl)ethanone (2 g, 11.89 mmol, Preparation #14), NH$_2$OH.HCl (1.653 g, 23.79 mmol, Sisco Research Labs) in ethanol (15 mL) and water (5 mL), was added sodium acetate (2.93 g, 35.7 mmol). The reaction mixture was heated to reflux at about 90° C. for about 1 h. The mixture was concentrated under reduced pressure and diluted with EtOAc (100 mL). The organic layer was washed successively with water (1×50 mL) and brine (1×50 mL). The organic layer was dried over sodium sulphate and concentrated under reduced pressure to afford 1-(4-fluoro-3-methoxyphenyl)ethanoneoxime 2 g (92%); $^1$H NMR (400 MHz, DMSO) δ:11.21 (s, 1H), 7.41 (q, J=2 Hz, 1H), 7.24 (m, 2H), 3.86 (s, 3H), MS m/z: 184.1 (m+H)$^+$.

Preparation #16

1-(4-Fluoro-3-methoxyphenyl)ethanamine

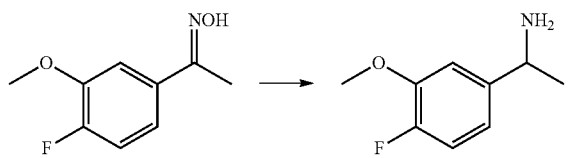

To a stirred solution of 1-(4-fluoro-3-methoxyphenyl)ethanoneoxime (1.4 g, 7.64 mmol, Preparation #15) in methanol (30 mL) was added Raney® nickel (0.35 g, 7.64 mmol). The reaction mixture was hydrogenated under balloon pressure for about 12 h. The reaction mixture was filtered through a Celite® pad and washed with MeOH (75 mL). The filtrate was concentrated under reduced pressure. The resulting crude material was purified by silica gel chromatography eluting with 10% methanol in DCM. Relevant fractions containing the target compound were combined and evaporated to dryness under reduced pressure to afford 1-(4-fluoro-3-methoxyphenyl)ethanamine 0.3 g (23.20%), $^1$H NMR (400 MHz, DMSO) δ:8.16 (bs, 2H), 7.47 (d, J=2.4 Hz, 1H), 7.25 (m, 1H), 7.06 (m, 1H), 4.34 (q, J=6.4 Hz, 1H), 3.86 (s, 3H), 1.49 (d, J=6.8 Hz, 3H), MS m/z: 170.2 (m+H)$^+$, HPLC (Table 2, Method k)

Preparation #17

6-Bromo-2-methylpyrimidine-4-carbaldehyde oxime

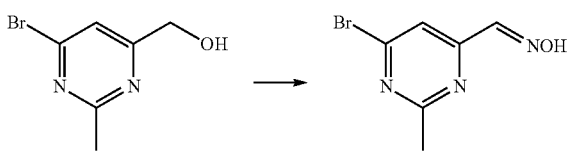

Step 1:

To a cold solution of (6-bromo-2-methylpyrimidin-4-yl) methanol (15 g, 73.9 mmol, Preparation #4) in DCM (300 mL) was added Dess-Martin periodinane (47.0 g, 111 mmol). The resulting suspension was allowed to warm to RT and stirred for about 2 h. The reaction mixture was re-cooled to about 0° C., quenched with sodiumthiosulphate solution (200 mL) and stirred vigorously for about 30 min. The organic layer was separated and washed successively with saturated sodium bicarbonate (2×200 mL), water (1×200 mL) and brine (1×200 mL). The organic layer was dried over sodium sulphate and concentrated under reduced pressure to afford 6-bromo-2-methylpyrimidine-4-carbaldehyde 11 g (74.1%), $^1$H NMR (400 MHz, DMSO) δ: 9.88 (s, 1H), 7.96 (s, 1H), 2.73 (s, 3H), IR Neat 1720 (C=O) cm$^{-1}$ Step 2

To a stirred solution of 6-bromo-2-methylpyrimidine-4-carbaldehyde (11 g, 54.7 mmol, Preparation #17 step 1) and NH$_2$OH.HCl (7.61 g, 109 mmol, Sisco Research Labs) in ethanol (75 mL) and water (25 mL) was added sodium acetate acetate (13.47 g, 164 mmol). The reaction mixture was heated to reflux at about 90° C. for about 1 h. The mixture was cooled to RT and diluted with water (200 mL). The separated product (solid) was collected by filtration, washed with water and dried under vacuum to afford 6-bromo-2-methylpyrimidine-4-carbaldehyde oxime 4.0 g (33.8%), $^1$H NMR (400 MHz, DMSO) δ: 12.43 (s, 1H), 8.01 (s, 1H), 7.78 (s, 1H), 2.61 (s, 3H), MS m/z: 216 (negative mode).

Preparation #18

3-(6-Bromo-2-methylpyrimidin-4-yl)-5-phenyl-4,5-dihydroisoxazole

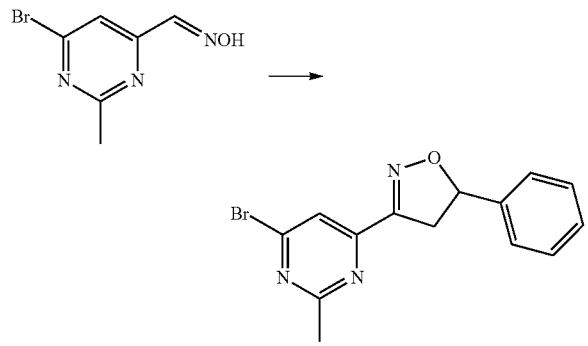

To a cold solution of 6-bromo-2-methylpyrimidine-4-carbaldehyde oxime (0.4 g, 1.852 mmol Preparation #17) and styrene (0.257 mL, 2.222 mmol) in DCM (10 mL) was added sodium hypochlorite solution (0.229 mL, 3.70 mmol). The reaction mixture was stirred for about 2 h and diluted with DCM (50 mL), successively washed with water (2×30 mL) and brine (1×30 mL). The organic layer was dried over sodium sulphate and evaporated to dryness under reduced pressure. The resulting mixture was purified by silica gel-chromatography eluting with 40% EtOAc in hexane. Relevant fractions containing the required compound were combined and evaporated to dryness under reduced pressure to afford 3-(6-bromo-2-methylpyrimidin-4-yl)-5-phenyl-4,5-dihydroisoxazol 0.25 g (42.4%), $^1$H NMR (400 MHz, DMSO): δ 8.00 (s, 1H), 7.40 (m, 5H), 5.90 (m, 1H), 3.93 (m, 1H), 3.41 (m, 1H), 2.64 (s, 3H), MS m/z: 320 (M+H)$^+$.

Preparation #19

2-Methyl-6-(5-phenyl-4,5-dihydroisoxazol-3-yl)pyrimidine-4-carboxylate

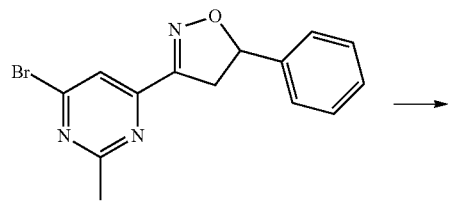

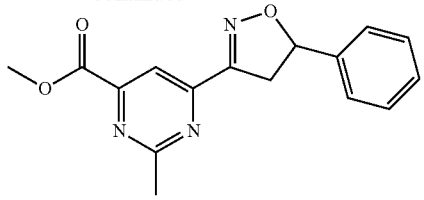

A 50 mL autoclave reactor was charged with 3-(6-bromo-2-methylpyrimidin-4-yl)-5-phenyl-4,5-dihydroisoxazole (0.25 g, 0.786 mmol, Preparation #18), [1,1,-bis(diphenylphosphino)ferrocine]dichloro palladium(II) complex with DCM (0.064 g, 0.079 mmol), DIEA (0.206 mL, 1.179 mmol, Spectrochem) and MeOH (20 mL). The reaction mixture was heated to about 70° C. in the presence of carbon monoxide gas at 70 psi for about 12 h. The reaction mixture was cooled to RT, filtered through a Celite® pad and washed with MeOH (20 mL). The combined filtrates were concentrated; the solid obtained was washed with diethyl ether (100 mL) and dried under vacuum. Crude material obtained was purified by column chromatography eluted with 40% EtOAc in hexane. Relevant fractions containing the target compound were combined and evaporated to dryness under reduced pressure to afford 2-methyl-6-(5-phenyl-4,5-dihydroisoxazol-3-yl)pyrimidine-4-carboxylate 0.15 g, (64.2%), $^1$H NMR (400 MHz, DMSO) 8:8.18 (s, 1H), 7.43 (m, 5H), 5.93 (m, 1H), 3.98 (m, 1H), 3.94 (s, 3H), 3.45 (m, 1H), 2.73 (s, 3H). MS m/z: 320 (m+Na).

Preparation #20

2-Methyl-6-(5-phenyl-4,5-dihydroisoxazol-3-yl)pyrimidine-4-carboxylic acid

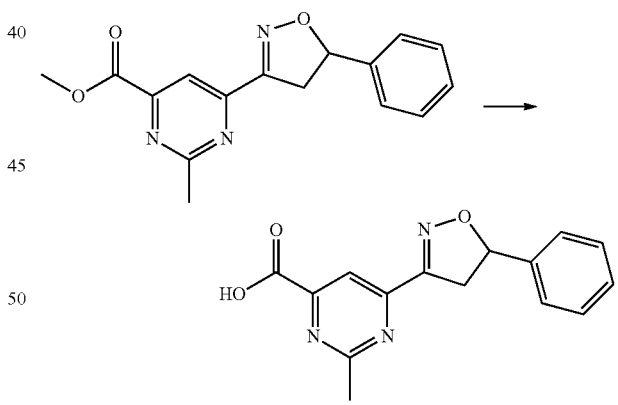

To a stirred solution of methyl 2-methyl-6-(5-phenyl-4,5-dihydroisoxazol-3-yl)pyrimidine-4-carboxylate (0.15 g, 0.505 mmol, Preparation #19) in methanol (1.5 mL) and water (0.5 mL) mixture was added lithium hydroxide (0.036 g, 1.514 mmol, Sd Fine Chem). The reaction mixture was stirred for about 10 min at RT and the organic solvent was removed under reduced pressure. The aqueous layer was acidified with 10% citric acid solution. The solid was collected by filtration, washed with water and dried under vacuum to afford 2-methyl-6-(5-phenyl-4,5-dihydroisoxazol-3-yl)pyrimidine-4-carboxylic acid 0.1 g, (70.0%) as a yellow solid. $^1$H NMR (400 MHz, DMSO) δ 14.0 (bs, 1H), 8.16 (s, 1H), 7.42 (m, 5H), 5.92 (m, 1H), 3:98 (m, 1H), 3.45 (m, 1H), 2.72 (s, 3H), MS m/z: 284.2 (m+H)+.

Preparation #21

1-Methyl-2-oxo-1,2-dihydropyridine-4-carbonitrile

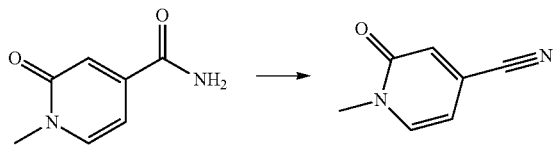

To a cold solution of 1-methyl-2-oxo-1,2-dihydropyridine-4-carboxamide (7.2 g, 47.3 mmol, *Journal of Organic Chemistry*, 1959, 24, 196) in DCM (70 mL) was added TEA (13.19 mL, 95 mmol) and TFAA (8.02 mL, 56.8 mmol) at about 0° C. The reaction mixture was stirred for about 2 h at about 0° C. The reaction mixture was filtered and the filtrate was diluted with DCM (100 mL). The organic layer was washed successively with water (2×70 mL) and brine (1×70 mL). The organic layer was dried over sodium sulphate and concentrated under reduced pressure to afford 1-methyl-2-oxo-1,2-dihydropyridine-4-carbonitrile as a white solid 3.3 g, (52.0%), $^1$H NMR (400 MHz, DMSO) δ: 7.94-7.92 (d, J=7.2 Hz, 1H), 7.00 (s, 1H), 6.53-6.50 (dd, J=2 Hz, 1 Hz), 3.45 (s, 3H), LC/MS (Table 1, Method d) $R_t$=0.77 min.

General Procedure AG: Formation of Boc Protected Amine from Nitrile Derivative:

To a mixture of appropriate nitrile derivative (1 equiv), nickel chloride hexahydate (0.1 to 0.5 equiv, preferably 0.1 equiv) and di-tert-butyldicarbonate (2-5 equiv, preferably 2 equiv) in a protic solvent such as MeOH, EtOH, (preferably MeOH) is added sodium borohydride (3-5 equiv, preferably 4 equiv) at 0° C. The reaction mixture is slowly warmed to RT and stirred for about 2-12 h (preferably 2 h). The reaction mixture is quenched with water filtered through a Celite® pad and washed with EtOAc. The organic layer is successively washed with water, brine and dried over sodium sulphate. The crude mass obtained upon concentration of the organic layer is purified to obtain the required material.

Preparation #AG.1

Tert-butyl ((1-methyl-2-oxo-1,2-dihydropyridin-4-yl)methyl)carbamate

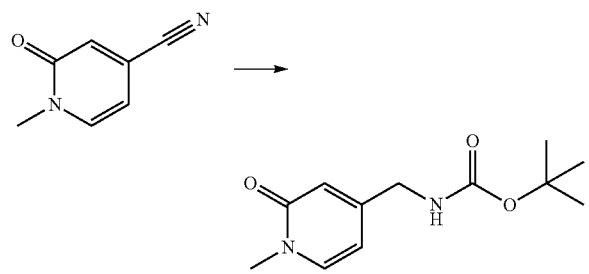

To a cold solution of 1-methyl-2-oxo-1,2-dihydropyridine-4-carbonitrile (4.6 g, 34.3 mmol, Preparation #21), di-tert-butyldicarbonate (4.6 g, 34.3 mmol), nickel chloride hexa hydrate (0.815 g, 3.43 mmol) in MeOH (50 mL) was added sodium borohydride (5.19 g, 137 mmol) portion wise at about 0° C. for about 1 h. The reaction mixture was slowly warmed to RT and stirred for about 3 h. The reaction mixture was quenched with water, filtered through a Celite® pad and washed with EtOAc (150 mL). The organic layer was washed successively with water (1×100 mL) and brine (1×100 mL). The organic layer was dried over sodium sulphate and concentrated under vacuum. The resulting crude material was purified by silica gel chromatography using 10% MeOH in DCM as the eluent. Relevant fractions containing the target compound were combined and evaporated to dryness under reduced pressure to afford tert-butyl (1-methyl-2-oxo-1,2-dihydropyridin-4-yl)methyl carbamate, 4.2 g (51.4%) as a yellow solid. $^1$H NMR (400 MHz, DMSO) δ: 7.60-7.59 (d, J=7.2 Hz, 1H), 7.40-7.37 (t, J=6 Hz, 1H), 6.14 (s, 1H), 6.07-6.05 (dd, J=2 Hz, 1H), 3.93-3.92 (d, J=6 Hz, 1H), 3.36 (s, 3H), LC/MS (Table 1, Method d) $R_t$=2.31 min.

Preparation #AG.2

Tert-butyl ((1-methyl-6-oxo-1,6-dihydropyridin-3-yl)methyl)carbamate

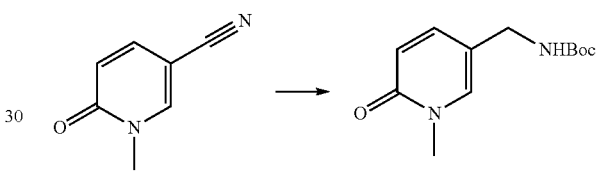

To a cold solution of 1-methyl-6-oxo-1,6-dihydropyridine-3-carbonitrile (4 g, 29.8 mmol, *Journal of Heterocyclic Chem*, 23, 1986, 1015), di-tert-butyldicarbonate (13.85 mL, 59.64 mmol, Spectrochem), nickel chloride hexahydate (0.709 g, 2.98 mmol, Loba) in methanol (100 mL), was added sodium borohydride (4.51 g, 119 mmol, Spectrochem) portion wise at about 0° C. for 15 min. The reaction mixture was slowly warmed to RT and stirred for about 2 h. The reaction mixture was quenched with water, filtered through a Celite® pad and washed with EtOAc (150 mL). The organic layer was washed successively with water (50 mL) and brine (50 mL). The organic layer was dried over sodium sulphate and concentrated under reduced pressure to afford tert-butyl (1-methyl-6-oxo-, 6-dihydropyridin-3-yl)methylcarbamate 2 g (28.1%), $^1$H-NMR (400 MHz, DMSO): δ 7.513 (s, 1H), 7.34 (d, J=2.4 Hz, 1H), 7.32 (t, J=2.4 Hz, 1H), 6.37 (d, J=8.8 Hz, 1H), 3.84 (d, J=6 Hz, 2H), 3.385 (s, 3H), 1.378 (s, 9H), LC/MS (Table 1, Method-d) $R_t$=1.001 min Preparation of #22

N-(4-fluoro-3-methoxybenzyl)-6-(1-hydroxyethyl)-2-methylpyrimidine-4-carboxamide

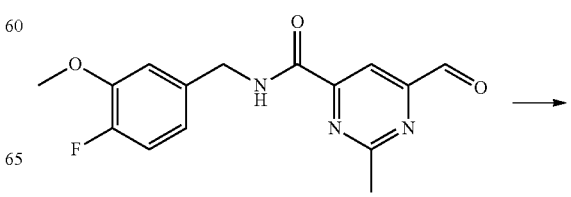

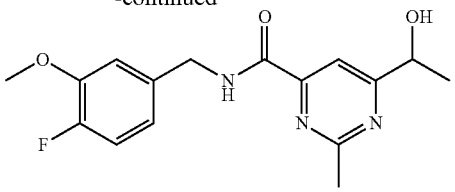

A solution of N-(4-fluoro-3-methoxybenzyl)-6-formyl-2-methylpyrimidine-4-carboxamide (2 g, 6.59 mmol, Preparation #8) in THF (200 mL) was cooled to about −78° C. and methyl magnesium bromide was added drop wise (8.79 mL, 26.4 mmol, 3M in ether). Upon completion of addition, the reaction mixture stirred for about 4 h at −78° C. The reaction mixture was quenched with aqueous ammoniumchloride (20 mL) and the product extracted with EtOAc (2×100 mL). The organic layer was washed successively with water (1×50 mL), brine (1×50 mL), dried over sodium sulphate and concentrated under reduced pressure to afford N-(4-fluoro-3-methoxybenzyl)-6-(1-hydroxyethyl)-2-methylpyrimidine-4-carboxamide (1 g, 47.6% yield) as a light yellow solid. $^1$H NMR (400 MHz, DMSO): δ 9.40 (bs, 1H) 7.95 (s, 1H) 7.17-7.11 (m, 2H) 6.89-6.88 (m, 1H) 5.75-5.71 (m, 1H) 4.49-4.47 (m, 2H) 3.81 (s, 3H) 2.68 (s, 3H) MS m/z=320 (m+H)$^+$.

Preparation of #23

N-(4-fluoro-3-methoxybenzyl)-6-(1-hydroxyethyl)-2-methylpyrimidine-4-carboxamide

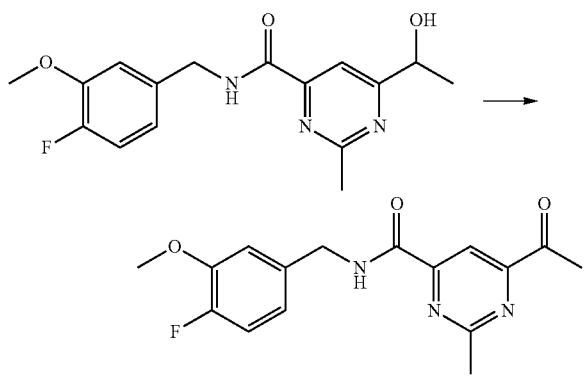

To a cold solution of N-(4-fluoro-3-methoxybenzyl)-6-(1-hydroxyethyl)-2-methylpyrimidine-4-carboxamide (1 g, 3.13 mmol, Preparation #22) in DCM (200 mL) was added Dess-Martin periodinane (3.98 g, 9.39 mmol, Spectrochem) portion wise over about 45 min at about 0° C. The resulting suspension was allowed to warm to RT and stirred for about another 2 h. The reaction mixture was re-cooled to about 0° C. and quenched with sodiumthiosulphate solution (50 mL) and stirred vigorously for about 30 min. The organic layer was separated, washed successively with saturated sodiumthiosulphate (1×100 mL), water (1×100 mL) and brine (1×100 mL). Finally the organic layer was dried over sodium sulphate and concentrated under reduced pressure to get crude which was purified by column chromatography eluting with 20% EtOAc in hexane. Relevant fractions containing the required compound were combined and evaporated to dryness under reduced pressure to afford N-(4-fluoro-3-methoxybenzyl)-6-(1-hydroxyethyl)-2-methylpyrimidine-4-carboxamide 0.6 g (66.6%) as a white solid $^1$H NMR (400 MHz, CDCl$_3$): δ 8.47 (s, 1H) 8.25 (bs, 1H) 7.07-6.88 (m, 3H) 4.62 (m, 2H) 3.88 (s, 3H) 2.83 (s, 3H) 2.72 (s, 3H), MS m/z: 318 (m+H)

Preparation #24

(E)-N-(4-fluoro-3-methoxybenzyl)-2-methyl-6-(3-(pyridin-3-yl)acryloyl)pyrimidine-4-carboxamide

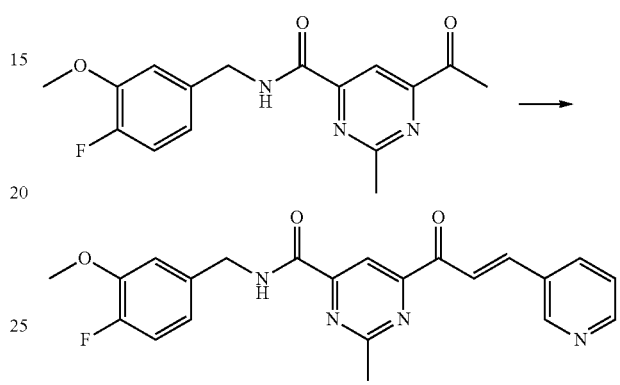

To a cold solution of 6-acetyl-N-(4-fluoro-3-methoxybenzyl)-2-methylpyrimidine-4-carboxamide (0.050 g, 0.158 mmol, Preparation #23) and nicotinaldehyde (0.0168 mg, 0.158 mmol) in DCM (2 mL) was added aluminium chloride (0.02311 g, 0.173 mmol). The reaction mixture was allowed to stir for 15 minutes and added TEA (0.033 mL, 0.236 mmol). The reaction mixture was slowly warmed to RT and stirred for 3 h. The reaction mixture was heated to about 50° C. for 0.5 h then cooled to RT and poured into cold water (20 mL) and the product was extracted with diethyl ether (2×20 mL). The organic layer was washed successively with water (1×20 mL), brine (1×20 mL), dried over sodium sulphate and evaporated to dryness. The residue obtained was purified by preparative TLC eluting with 50% EtOAC/hexane to afford N-(4-fluoro-3-methoxybenzyl)-2-methyl-6-(3-(pyridin-3-yl)acryloyl)pyrimidine-4-carboxamide 0.015 g, (23.42%), $^1$H NMR (400 MHz, DMSO): δ 9.59 (bs, 1H) 9.00 (s, 1H) 8.67 (s, 1H) 8.33-8.17 (m, 3H) 8.00-7.96 (m, 1H) 7.52-7.51 (m, 1H) 7.19-7.17 (m, 2H) 6.92-6.91 (m, 1H) 4.51-4.49 (m, 2H) 3.82 (s, 3H) 2.89 (s, 3H), MS m/z: 407 (M+H)+.

Example #3

N-(4-fluoro-3-methoxybenzyl)-2-methyl-6-(5-(pyridin-3-yl)-4,5-dihydro-1H-pyrazol-3-yl)pyrimidine-4-carboxamide

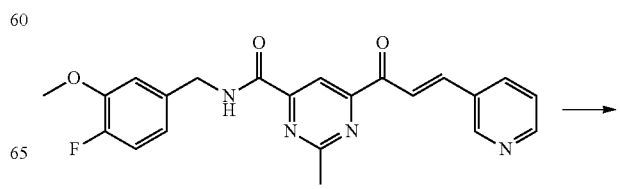

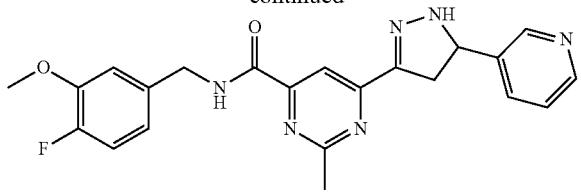

To a stirred solution of N-(4-fluoro-3-methoxybenzyl)-2-methyl-6-(3-(pyridin-3-yl)acryloyl)pyrimidine-4-carboxamide (0.015 g, 0.037 mmol Preparation #24) in ethanol (20 mL) was added hydrazine hydrate (5.43 μL 0.111 mmol). The reaction mixture was heated to about 100° C. for 8 h. Solvent was removed under reduced pressure and diluted with EtOAc (30 mL). The organic layer was washed successively with water (1×20 mL), brine (1×20 mL) and dried over sodium sulphate. Finally the organic layer was evaporated to dryness tinder reduced pressure and the crude material obtained was purified by preparative HPLC (Table 2, Method 1) to afford N-(4-fluoro-3-methoxybenzyl)-2-methyl-6-(5-(pyridin-3-yl)-4,5-dihydro-H-pyrazol-3-yl)pyrimidine-4-carboxamide 0.015 g, (97%), $^1$H NMR (d-DMSO): δ 9.39-9.37 (m, 1H) 8.82 (s, 1H) 8.50-8.50 (m, 2H) 8.14 (s, 1H) 7.75 (d, J=8 Hz, 1H) 7.40-7.39 (m, 1H) 7.37-7.15 (m, 2H) 6.88 (bs, 1H) 5.20-5.00 (m, 1H) 4.47-4.46 (m, 2H) 3.81 (s, 3H) 3.61-3.58 (m, 1H) 3.00-2.97 (m, 1H) 2.70 (s, 3H), LC/MS (Table 1, Method d) $R_t$=4.16 min.

Preparation #25

6-Chloropyridazin-3-amine

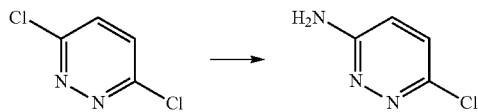 [SMILES: Clc1ccc(Cl)nn1 ; Nc1ccc(Cl)nn1]

3,6-Dichloro pyridazine (25 g, 0.167 mol, Aldrich) was heated at about 130° C. with aqueous ammonia (200 mL) in a sealed tube for 16 h. The reaction mixture was cooled to RT, Solids obtained were collected by filtration, washed with water and dried under vacuum to afford 6-chloropyridazin-3-amine 16 g (75%) as off white solid. $^1$H NMR (400 MHz, DMSO) δ 7.372-7.349 (d, J=9.2 Hz, 1H), 6.852-6.828 (d, J=9.3 Hz, 1H) 6.613 (br s, 2H); MS m/z: 130.1 (M+H)+;

Preparation #26

4-Bromo-6-chloropyridazin-3-amine

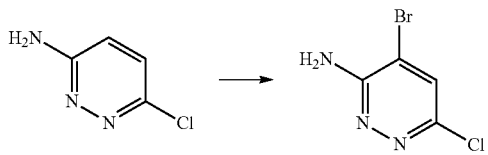 [SMILES: Nc1ccc(Cl)nn1 ; Nc1nnc(Cl)cc1Br]

To a solution of 6-chloropyridazin-3-amine (16 g, 0.124 mol, Preparation #25) in methanol (200 mL) was added NaHCO$_3$ (20.84 g, 0.24 mols). The reaction mixture was stirred for 30 min at RT and bromine (19.6 g, 0.124 mol, Spectrochem) added drop wise. Then reaction mixture was stirred for another 16 h and concentrated under vacuum. Crude material obtained was purified using silica gel column chromatography by eluting with 50% EtOAc in hexane to afford 4-bromo-6-chloropyridazin-3-amine 12 g (46%) as brown solid. $^1$H NMR (400 MHz, DMSO) δ 7.548 (s, 1H), 5.341 (br s, 2H); MS m/z=208.0 M+H+;

Preparation #27

4-Bromo-6-chloropyridazin-3(21)-one

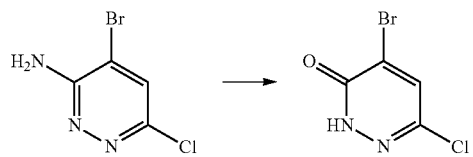 [SMILES: Nc1nnc(Cl)cc1Br ; O=c1[nH]nc(Cl)cc1Br]

To a cooled solution (0-5° C.) of sodium nitrite (5.96 g, 86 mmol, Lobachem) in sulfuric acid (90 mL, 57.6 mmol) was added 4-bromo-6-chloropyridazin-3-amine (12 g, 57.6 mmol, Preparation #26) in acetic acid (300 mL). The mixture was stirred for 1 hr at about 20° C. and water was added (450 mL). The reaction mixture stirred for another 5 h at RT. The reaction mixture was extracted with EtOAc (3×200 mL), dried over sodium sulphate and evaporated on rotovapor. The residue obtained was purified by silica gel column chromatography by eluting with 50% EtOAc in hexane to afford 4-bromo-6-chloropyridazin-3(2H)-one 10 g, (83%) as pale yellow solids; $^1$H NMR (400 MHz, DMSO) δ 13.527 (s, 1H), 8.203 (s, 1H). MS m/z: 208.8 (M−H)$^-$, Preparation #28

4-Bromo-6-chloro-2-methylpyridazin-3(2H)-one

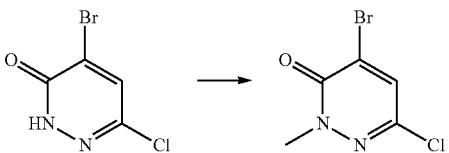

To a solution of 4-bromo-6-chloropyridazin-3(2H)-one (10 g, 47.7 mmol, Preparation #27) in DMF (100 mL) was added cesium carbonate (23.34 g, 71.6 mmol, Aldrich) followed by iodomethane (10.17 g, 71.6 mmol) and stirred at RT for about 4 h. The reaction mixture was poured into ice cold water (200 mL) and the product extracted with EtOAc (3×100 mL). The combined organic layers were dried over sodium sulphate and evaporated under reduced pressure to afford 4-bromo-6-chloro-2-methylpyridazin-3(2H)-one 8 g (75%) as brown solid; $^1$H NMR (400 MHz, CDCl$_3$) δ 7.624 (s, 1H), 3.809 (s, 3H); MS m/z: 222.8 (M+H)+,

Preparation #29

6-Chloro-2-methyl-4-styrylpyridazin-3(2H)-one

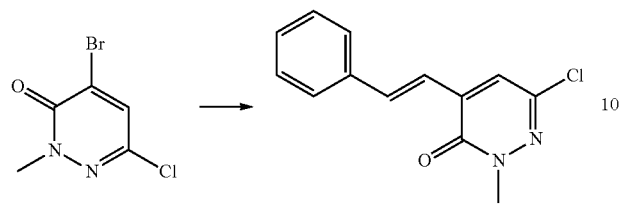

A mixture of 4-bromo-6-chloro-2-methylpyridazin-3(2H)-one (8 g, 35.8 mmol, Preparation #28), styrylboronic acid (6.62 g, 44.8 mmol, Combiblocks), bis(triphenylphosphine)palladium(II) chloride (2.51 g, 3.58 mmol, Hindustan Platiniums) and potassium phosphate (11.40 g, 53.7 mmol, Aldrich) in aqueous dioxane (75%: 100 mL) was heated to about 85° C. for 6 h. The reaction mixture was cooled to RT and then concentrated on the rotovapor to 25 mL. The oily residue obtained was partitioned between EtOAc (100 mL) and water (50 mL). The layers were separated and then the aqueous layer was extracted with EtOAc (2×100 mL). The combined organic layers were dried over sodium sulphate and evaporated under reduced pressure. The residue obtained was purified by silica gel column chromatography by eluting with 10-20% ETOAc in hexane. The relevant fractions containing the product were combined and evaporated under reduced pressure to afford 6-chloro-2-methyl-4-styrylpyridazin-3(2H)-one 6 g (67.9%) as yellow solid. $^1$H NMR (400 MHz, CDCl$_3$) δ 7.878-7.838 (d, J=17 Hz, 1H) 7.620-7.560 (m, 2H) 7.412-7.344 (m, 3H) 7.279 (s, 1H) 7.177-7.136 (d, J=16 Hz, 1H) 3.809 (s, 3H); MS m/z: 247.1 (M+H)+

Preparation #30

6-Chloro-2-methyl-3-oxo-2,3-dihydropyridazine-4-carbaldehyde

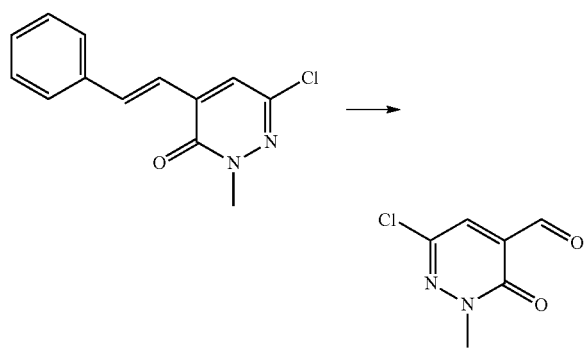

A mixture of 6-chloro-2-methyl-4-styrylpyridazin-3(2H)-one (6 g, 24.32 mmol, Preparation #29), 4% aqueous osmium (VIII) oxide (0.1 mL, 1.216 mmol, Alfa-Aeser), 2,6-dimethylpyridine (5.21 g, 48.6 mmol, Aldrich) and sodium periodate (20.81 g, 97 mmol, Spectrochem) in aqueous dioxane (75%, 80 mL) was stirred at RT for about 3 h. The reaction mixture was diluted with water and the product extracted with EtOAc (5×60 mL). The combined organic layers were dried over sodium sulphate and evaporated under reduced pressure. The residue obtained was purified by silica gel (60-120) column chromatography by eluting with 30-50% EtOAc in hexane to afford 6-chloro-2-methyl-3-oxo-2,3-dihydropyridazine-4-carbaldehyde 2 g (47.7%) as pale yellow solid; $^1$H NMR (400 MHz, CDCl$_3$) δ 10.359 (s, 1H), 7.658 (s, 1H), 3.846 (s, 3H); MS m/z: 170.9 (M−H)−

Preparation #31

6-Chloro-2-methyl-3-oxo-2,3-dihydropyridazine-4-carbaldehyde oxime

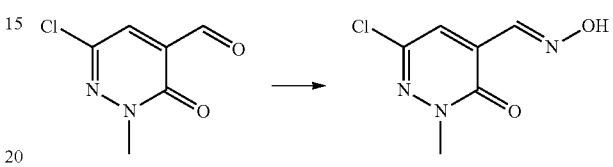

To a solution of 6-chloro-2-methyl-3-oxo-2,3-dihydropyridazine-4-carbaldehyde (2 g, 11.59 mmol, Preparation #30) in MeOH (30 mL) was added a solution of hydroxylamine hydrochloride (0.966 g, 13.91 mmol) in water (5 mL) and heated to about 70° C. for 1 h. The mixture was cooled to RT and solids obtained were collected by filtration to afford the 6-chloro-2-methyl-3-oxo-2,3-dihydropyridazine-4-carbaldehyde oxime 1.6 g, (73.6%) as an off white solid. $^1$H NMR (400 MHz, DMSO) δ 12.316 (s, 1H), 8.092 (s, 1H), 7.675 (s, 1H), 3.651 (s, 3H); MS m/z: 185.7 (M−H)−

Preparation #32

6-Chloro-2-methyl-4-(5-phenyl-4,5-dihydroisoxazol-3-yl)pyridazin-3(2H)-one

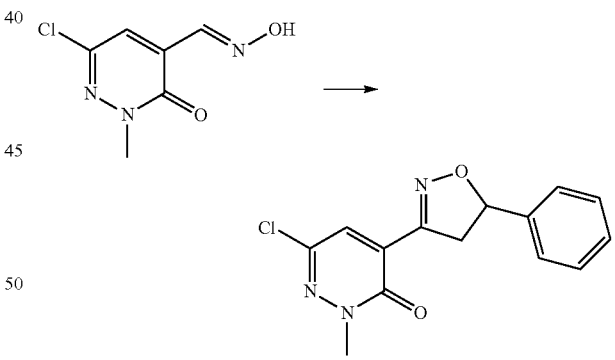

To an ice cold mixture of 6-chloro-2-methyl-3-oxo-2,3-dihydropyridazine-4-carbaldehyde oxime (300 mg, 1.599 mmol, Preparation #31) and styrene (250 mg, 2.399 mmol, Aldrich) in DCM (15 mL) was added 5% aqueous sodium hypochlorite solution (5 mL, 1.599 mmol). The reaction mixture was warmed to RT over 1 h. The reaction mixture was diluted with dichloromethane (15 mL) and washed with water (10 mL). The organic layer was dried over sodium sulphate and evaporated under reduced pressure. The residue obtained was purified by solvent washings with hexane to afford 6-chloro-2-methyl-4-(5-phenyl-4,5-dihydroisoxazol-3-yl)pyridazin-3(2H)-one 0.250 g (54%) as a pale yellow solid. $^1$H NMR (400 MHz, CDCl$_3$) δ 7.816 (s, 1H), 7.400-7.327 (m, 5H), 5.807-5.758 (m, 1H) 4.001-3.927 (m, 1H) 3.773 (s, 3H) 3.627-3.558 (m, 1H); MS m/z: 312.2 (M+H)+;

Preparation #33

Methyl 1-methyl-6-oxo-5-(5-phenyl-4,5-dihydroisoxazol-3-yl)-1,6-dihydropyridazine-3-carboxylate

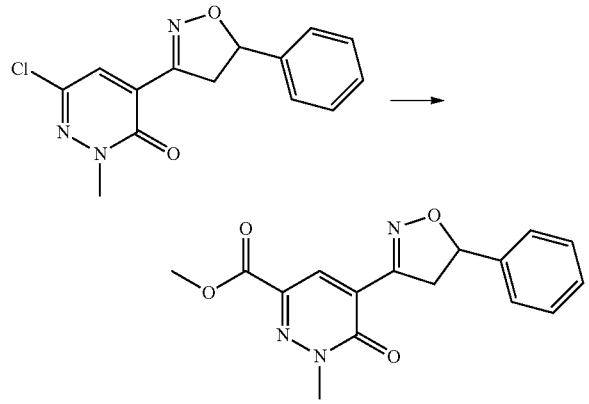

A 100 mL pressure vessel was charged with 6-chloro-2-methyl-4-(5-phenyl-4,5-dihydroisoxazol-3-yl)pyridazin-3 (2H)-one (200 mg, 0.690 mmol, Preparation #32), PdCl₂ (dppf)-CH₂Cl₂ adduct (56.4 mg, 0.069 mmol), N-ethyl-N-isopropylpropan-2-amine (178 mg, 1.381 mmol) and methanol (30 mL). The vessel was tightly closed, filled with CO (80 psi) and heated to about 80° C. for 6 h. The reaction mixture was cooled to RT and excess of CO was released carefully in a ventilated hood. The reaction mixture was concentrated under vacuum. The residue obtain was purified using silicagel column chromatography by eluting with 50% EtOAc in hexane. The relevant fractions containing the product were combined and evaporated under reduced pressure to afford methyl 1-methyl-6-oxo-5-(5-phenyl-4,5-dihydroisoxazol-3-yl)-1,6-dihydropyridazine-3-carboxylate 0.150 g (69.4%) as pale yellow solids. ¹H NMR (400 Hz, CDCl₃) δ 8.434 (s, 1H), 7.383-7.326 (m, 5H), 5.815-5.765 (m, 1H), 4.003-3.930 (m, 4H), 3.920 (s, 3H), 3.615-3.547 (m, 1H). MS m/z: 314.2 (M+H)+;

Preparation #34

1-Methyl-6-oxo-5-(5-phenyl-4,5-dihydroisoxazol-3-yl)-1,6-dihydropyridazine-3-carboxylic acid

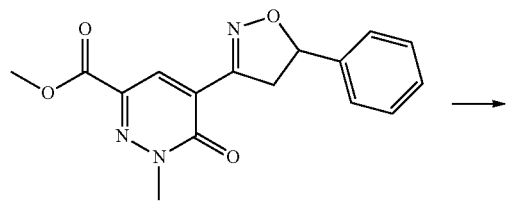

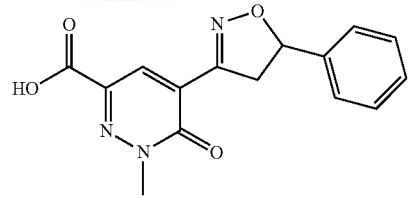

To a solution of methyl 1-methyl-6-oxo-5-(5-phenyl-4,5-dihydroisoxazol-3-yl)-1,6-dihydropyridazine-3-carboxylate (200 mg, 0.638 mmol, Preparation #33) in a mixture of methanol (2 mL) and THF (4 mL) was added lithium hydroxide (30.6 mg, 1.277 mmol, Spectrochem) dissolved in water (2 mL). The reaction mixture was stirred at RT for about 3 h. The reaction mixture was concentrated under vacuum and dissolved in water (10 mL). Further it was acidified to pH 2 with 2N HCl and the solids obtained were collected by filtration to afford 1-methyl-6-oxo-5-(5-phenyl-4,5-dihydroisoxazol-3-yl)-1,6-dihydropyridazine-3-carboxylic acid 0.150 g (79%) as light brown solids. ¹H NMR (400 MHz, DMSO) δ 13.8 (br s, 1H), 8.122 (s, 1H), 7.405-7.331 (m, 5H), 5.806-5.757 (m, 1H), 3.958-3.886 (m, 1H) 3.762 (s, 3H), 3.506-3.441 (m, 1H). MS m/z: 298.0 (M–H)–

Example #4

N-(4-fluoro-3-methoxybenzyl)-1-methyl-5-(5-phenyl-4,5-dihydroisoxazol-3-yl)-1,6-dihydropyridazine-3-carboxamide

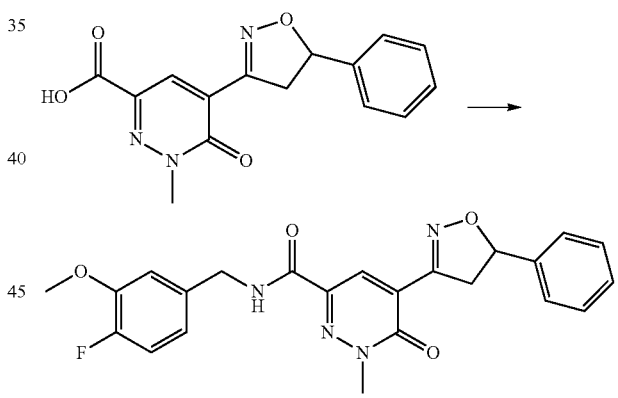

To a solution of 1-methyl-6-oxo-5-(5-phenyl-4,5-dihydroisoxazol-3-yl)-1,6-dihydropyridazine-3-carboxylic acid (150 mg, 0.501 mmol, Preparation #34) in DMF (4 mL) was added (4-fluoro-3-methoxyphenyl)methanamine (93 mg, 0.601 mmol, WO 2008/083056), N-ethyl-N-isopropylpropan-2-amine (194 mg, 1.504 mmol, Spectrochem) and followed by HATU (286 mg, 0.752 mmol, Molekule). The reaction mixture was stirred at RT for 16 h. and was quenched with ice cold water (10 mL). The product was extracted with EtOAc (3×20 mL). The combined organic layers were dried over sodium sulphate and evaporated to dryness under vacuum. The residue obtained was purified by silica gel column chromatography by eluenting with 40-60% EtOAc in hexane. The relevant fractions containing the product were combined and evaporated under reduced pressure to afford N-(4-fluoro-3-methoxybenzyl)-1-methyl-6-oxo-5-(5-phenyl-4,5-dihydroisoxazol-3-yl)-1,6-dihydropyridazine-3-carboxamide 90 mg, (41.1%) as pale yellow solids. $^1$H NMR (400 MHz, DMSO) δ 9.159-9.127 (m, 1H), 8.143 (s, 1H), 7.422-7.331 (m, 5H), 7.167-7.117 (m, 2H), 6.886-6.849 (m, 1H), 5.812-5.763 (m, 1H), 4.436-4.420 (d, J=6.4 Hz, 2H), 3.964-3.892 (m, 1H) 3.819 (s, 3H), 3.781 (s, 3H), 3.508-3.443 (m, 1H). MS m/z 437.3 (M+H)+;

Preparation #35

2-(5-bromo-2-oxopyridin-1(2H)-yl)-N-methylacetamide

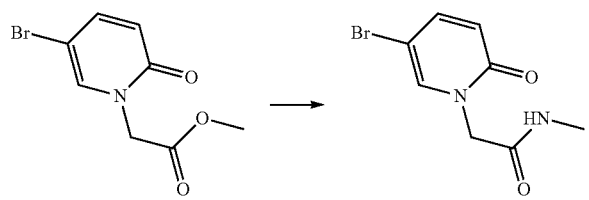

A solution of methyl 2-(5-bromo-2-oxopyridin-1(2H)-yl) acetate (0.5 g, 1.92 mmol, WO 2009134400) in 2M solution of Methyl amine in THF (5 mL) was stirred at RT for 16 h. The separated solid is collected by filtration and dried under vacuum to afford 2-(5-bromo-2-oxopyridin-1(2H)-yl)-N-methylacetamide as off-white solid, 0.35 g (74%), $^1$H NMR (400 MHz, DMSO): 8.09 (1H, d, J=4.4 Hz), 7.93 (1H, d, J=2.4 Hz), 7.54 (1H, dd, J=3.0, 9.8 Hz), 6.36 (1H, d, J=9.8 Hz), 4.47 (2H, s), 2.61 (3H, d, J=4.9 Hz). ES-MS: 247.1 (M+2H).

Preparation #36

Ethyl 2-(3-chloro-6-oxopyridazin-1(6H)-yl)acetate

To a solution of 6-chloropyridazin-3-ol (0.5 g, 3.83 mmol, WO2011015629) in DMF (5 mL) was added potassium carbonate (1.059 g, 7.66 mmol, Rankem) followed by ethyl 2-bromoacetate (0.960 g, 5.75 mmol, Spectrochem). The reaction mixture was stirred at RT for 5 h. The reaction mixture was quenched with water (2 mL) and the product was extracted with EtOAc (3×20 mL). Combined organic layers were washed successively with water (20 mL) and brine (20 mL). The organic layer was dried over sodium sulphate and evaporated under vacuum to afford ethyl 2-(3-chloro-6-oxopyridazin-1(6H)-yl)acetate 0.5 g (60.3%) as pale yellow solids. $^1$H NMR (400 MHz, CDCl$_3$): δ 7.266-7.236 (d, J=12 Hz, 1H), 6.965-6.945 (d, J=7.6 Hz, 1H) 4.819 (s, 2H) 4.273-4.230 (m, 2H) 1.309-1.279 (m, 3H); MS m/z=217.2 (M+H)+.

TABLE A.1

Compounds Prepared Using General Procedure A

| Preparation # | Benzyl amine | Product | | MS m/z: (M + H)+ |
|---|---|---|---|---|
| A.1.1 | 3-methyl-4-fluorobenzylamine (Matrix scientific) | pyrimidine carboxamide product | $^1$H NMR (400 MHz, DMSO): δ 9.419-9.387 (t, J = 6.8 Hz, 1H), 7.88 (s, 1H), 7.240-7.045 (m, 3H), 4.79 (s, 2H), 4.441-4.425 (d, J = 6.4 Hz, 2H), 2.68 (s, 3H), 2.20 (s, 3H), 0.936 (s, 9H), 0.119 (s, 6H). | 404.3 |
| A.1.2 | 3,4-difluorobenzylamine (Matrix scientific) | pyrimidine carboxamide product | $^1$H NMR (400 MHz, DMSO): δ 9.523-9.493 (t, J = 6.0 Hz, 1H), 7.88 (s, 1H), 7.39-7.36 (m, 2H), 7.18 (s, 1H), 4.79 (s, 2H), 4.478-4.463 (d, J = 6.0 Hz, 2H), 2.69 (s, 3H), 0.938 (s, 9H), 0.111 (s, 6H) | 408 |

TABLE A.1-continued

Compounds Prepared Using General Procedure A

| Preparation # | Benzyl amine | Product | | MS m/z: (M + H)+. |
|---|---|---|---|---|
| A.1.3 | 3-Cl, 4-F benzylamine (Matrix scientific) | corresponding pyrimidine-4-carboxamide with OTBDMS-methyl | $^1$H NMR (400 MHz, DMSO): δ 9.539-9.507 (t, J = 6.4 Hz, 1H), 7.877 (s, 1H), 7.530-7.531 (m, 1H), 7.370-7.343 (m, 2H), 4.79 (s, 2H), 4.474-4.458 (d, J = 6.4 Hz, 2H), 2.69 (s, 3H), 0.934 (s, 9H), 0.117 (s, 6H). | 424 |
| A.1.4 | 4-F benzylamine (Aldrich) | corresponding pyrimidine-4-carboxamide | $^1$H NMR (400 MHz, CDCl$_3$): δ 8.15 (t, 1H), 7.35-7.32 (m, 2H), 7.06-7.01 (m, 2H), 4.80 (d, 2H), 4.64-4.62 (s, 2H), 2.70 (s, 3H), 0.96 (s, 9H), 0.13 (s, 6H). | 390 |
| A.1.5 | 3-methoxy benzylamine (Aldrich) | corresponding pyrimidine-4-carboxamide | $^1$H NMR (400 MHz, CDCl$_3$): δ 8.35 (t, 1H), 8.16 (s, 1H), 7.30 (t, J = 8.4 Hz, 1H), 6.96-6.83 (m, 3H), 4.81 (s, 2H), 4.65 (d, J = 6.4 Hz, 2H), 3.80 (s, 3H), 2.70 (s, 3H), 0.97 (s, 9H), 0.13 (s, 6H) | 402 |
| A.1.6 | 4-methoxy benzylamine (Aldrich) | corresponding pyrimidine-4-carboxamide | $^1$H NMR (400 MHz, DMSO): δ 9.33 (t, 1H), 7.88 (s, 1H), 7.26 (d, 2H, J = 8.8 Hz), 6.87 (d, 2H, J = 4.8 Hz), 4.79 (s, 2H), 4.42 (d, J = 6.0 Hz, 2H), 3.72 (s, 3H), 2.67 (s, 3H), 0.94 (s, 9H), 0.12 (s, 6H). | 402 |
| A.1.7 | 3-F benzylamine (Aldrich) | corresponding pyrimidine-4-carboxamide with OTBDMS | $^1$H NMR (400 MHz CDCl$_3$): δ 8.40 (bs, 1H) 8.20 (s, 1H) 7.25 (s, 1H) 7.20-6.95 (m, 3H) 4.80 (s, 2H) 4.65 (s, 2H) 2.65 (s, 3H) 1.00 (s, 9H) 0.14 (s, 6H) | 390 |

TABLE A.1-continued

Compounds Prepared Using General Procedure A

| Preparation # | Benzyl amine | Product | | MS m/z: (M + H)+ |
|---|---|---|---|---|
| A.1.8 | 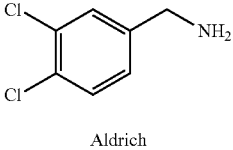<br>Aldrich | 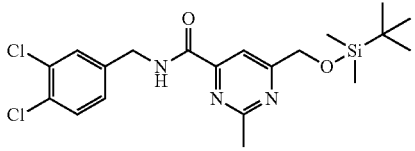 [SMILES: Cc1nc(CO[Si](C)(C)C(C)(C)C)cc(C(=O)NCc2ccc(Cl)c(Cl)c2)n1] | ¹HNMR (400 MHz, DMSO): δ 9.54 (t, J = 6.2 Hz, 1H), 7.87 (s, 1H), 7.58-7.57 (m, 2H), 7.33-730 (m, 1H), 4.78 (s, 2H), 4.48-4.46 (d, J = 6.4 Hz, 2H), 2.68 (s, 3H), 0.92 (s, 9H), 0.11 (s, 6H), | 440 |
| A.1.9 | 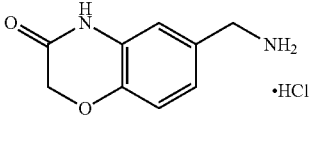 [SMILES: NCc1ccc2c(c1)NC(=O)CO2 ; Cl]<br>WO2008/63671 | 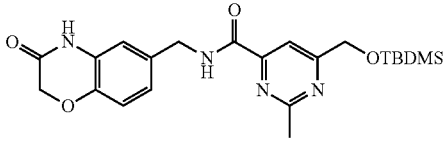 [SMILES: Cc1nc(CO[Si](C)(C)C(C)(C)C)cc(C(=O)NCc2ccc3c(c2)NC(=O)CO3)n1] | ¹H NMR (400 MHz, DMSO): δ 10.64 (s, 1H), 9.40 (t, 1H), 7.88 (s, 1H), 6.88 (m, 3H), 4.79 (s, 2H), 4.51 (s, 2H), 4.39 (d, J = 6.4 Hz, 2H), 2.68 (s, 3H), 0.93 (s, 9H), 0.12 (s, 6H). | LC/MS: (Table 1, Method d) $R_t$ = 3.5 min. |
| A.1.10 | 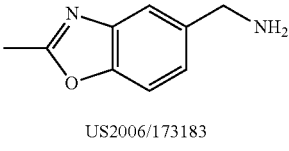<br>US2006/173183 | 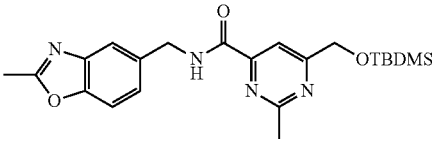 [SMILES: Cc1nc(CO[Si](C)(C)C(C)(C)C)cc(C(=O)NCc2ccc3oc(C)nc3c2)n1] | ¹H NMR (400 MHz, DMSO): δ 9.49 (t, 1H), 7.88 (s, 1H), 7.59 (m, 2H), 7.34 (d, J = 8.8 Hz, 1H), 4.79 (s, 2H), 4.59 (d, J = 6.4, 2H), 2.68 (s, 3H), 2.59 (s, 3H), 0.93 (s, 9H), 0.11 (s, 6H). | LC/MS: (Table 1, Method d) $R_t$ = 4.11 min |
| A.1.11 | 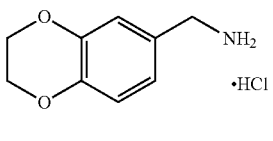 [SMILES: NCc1ccc2c(c1)OCCO2 ; Cl]<br>US2010/29835 | 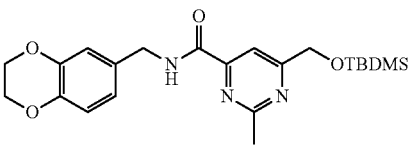 [SMILES: Cc1nc(CO[Si](C)(C)C(C)(C)C)cc(C(=O)NCc2ccc3c(c2)OCCO3)n1] | ¹H NMR (400 MHz, DMSO): δ: 9.327 (t, 1H), 7.874 (s, 1H), 6.831-6.784 (s, 3H), 4.81-4.790 (d, J = 8 Hz, 2H), 4.367-4.351 (d, J = 6.4 Hz, 2H), 4.20 (s, 4H), 2.499 (s, 3H), 0.936 (s, 9H), 0.117 (s, 6H). | 430.2 |

TABLE A.1-continued

Compounds Prepared Using General Procedure A

| Preparation # | Benzyl amine | Product | | MS m/z: (M + H)+. |
|---|---|---|---|---|
| A.1.12 | 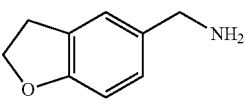 [SMILES: NCc1ccc2c(c1)CCO2] Preparation #26 | 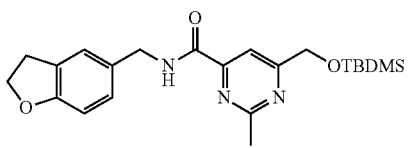 [SMILES: Cc1nc(CO[Si](C)(C)C(C)(C)C)cc(C(=O)NCc2ccc3c(c2)CCO3)n1] | ¹H NMR (400 MHz, CDCl₃): δ 8.15 (bs, 1H), 8.05 (s, 1H), 7.22 (s, 1H), 7.120-7.100 (d, J = 8 Hz, 1H), 6.771-6.750 (d, J = 8.4 Hz, 1H), 4.80 (s, 2H), 4.59-4.570 (m, 4H), 3.231-3.189 (t, J = 8 Hz, 2H), 2.69 (s, 3H), 0.97 (s, 9H), 0.137 (s, 6H) | 414.1 |

Examples prepared with Methyl 2-methyl-6-(3-phenyl-4,5-dihydroisoxazol-5-yl)pyrimidine-4-carboxylate derivatives (described in Table A.2) using General Procedure A

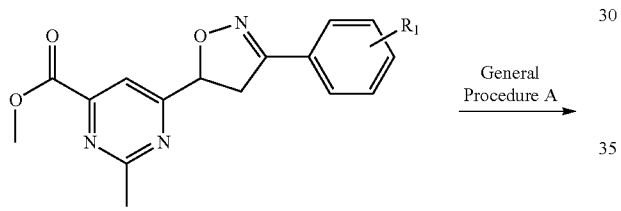

General Procedure A →

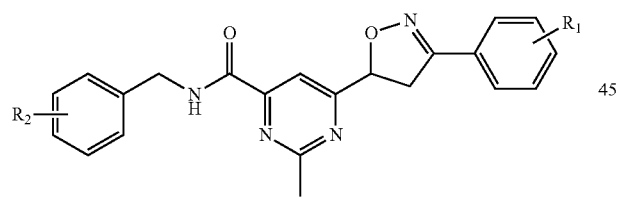

TABLE A.2

| Example # | Benzyl amines | Product | LC/MS R_t Time in min (method) | m/z ESMS (M + H)+ |
|---|---|---|---|---|
| A.2.8 | 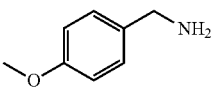 | 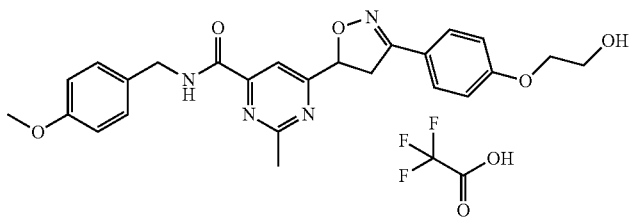 | 1.31 (b) | 463 |

TABLE A.2-continued

| Example # | Benzyl amines | Product | LC/MS R$_t$ Time in min (method) | m/z ESMS (M + H)$^+$ |
|---|---|---|---|---|
| A.2.9 | 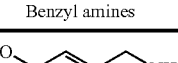 | 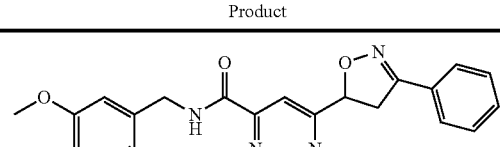 | 1.86 (b) | 420.8 |
| A.2.10 | 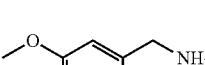 | 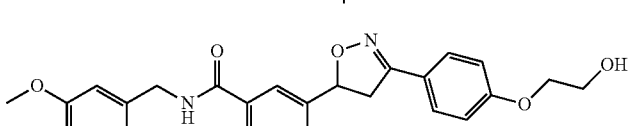 | 0.71 (c) | 481.3 |
| A.2.11 | 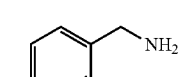 | 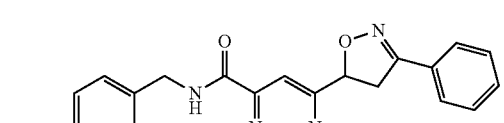 | 1.86 (b) | 403.3 |

TABLE B.1

Compounds Prepared Using General Procedure B

| Preparation # | Product | Analytical data |
|---|---|---|
| B.1.1 | | $^1$H NMR (400 MHz; DMSO): δ 12.39 (s, 1H), 9.36 (t, 1H), 8.105 (s, 1H), 8.074 (s, 1H), 7.275-7.254 (d, J = 8.4 Hz, 2H), 6.890-6.868 (d, J = 7.2 Hz, 2H), 4.435-4.419 (d, J = 6.4 Hz, 2H), 3.721 (s, 3H), 2.71 (s, 3H), MS m/z: 301.4 (M + H)$^+$ |
| B.1.2 | | $^1$H NMR (400 MHz DMSO): δ 12.40 (s, 1H), 9.53 (t, J = 6.4 Hz, 1H), 8.11 (s, 2H), 8.07 (s, 1H), 7.41-7.34 (m, 2H), 4.48 (d, J = 6.4 Hz, 2H), 2.72 (s, 3H), MS: m/z 307 (M + H) |
| B.1.3 | | $^1$H NMR (400 MHz, DMSO): δ 12.413 (S, 1H), 9.556 (t, 1H), 8.111-8.078 (d, J = 13.2 Hz, 2H), 7.554-7.538 (d, J = 6.4 Hz, 1H), 7.394-7.366 (d, J = 11.2 Hz, 2H), 4.491-4.475 (d, J = 6.4 Hz, 2H), 2.731 (s, 3H), MS: m/z: 321.1 (M − H) |
| B.1.4 | | $^1$H NMR (400 MHz, DMSO): δ 12.40 (s, 1H), 9.57 (t, J = 6.4 Hz, 1H), 8.11 (s, 1H), 8.07 (s, 1H), 7.58 (d, J = 3.2 Hz, 2H), 7.34-7.30 (m, 2H), 4.49 (d, J = 6.4 Hz, 2H), 2.73 (s, 3H), MS: m/z 339.1 (M + H)$^+$ |

TABLE B.1-continued

Compounds Prepared Using General Procedure B

| Preparation # | Product | Analytical data |
|---|---|---|
| B.1.5 | 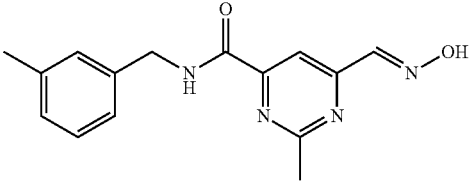 [SMILES: Cc1cccc(CNC(=O)c2cc(/C=N/O)nc(C)n2)c1] | $^1$H NMR (400 MHz, DMSO): δ 12.40 (s, 1H), 9.43 (t, J = 6.4 Hz, 1H), 8.10 (d, J = 11.2 Hz, 1H), 7.22 (m, 4H), 4.47 (d, J = 6 Hz, 2H), 2.72 (s, 3H), 2.27 (s, 3H), MS m/z 283.0 (M − H). |
| B.1.6 | 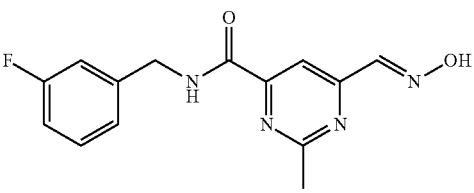 [SMILES: Cc1nc(/C=N/O)cc(C(=O)NCc2cccc(F)c2)n1] | $^1$H NMR: (400 MHz, CDCl$_3$): δ 9.80 (bs, 1H) 8.47 (s, 1H) 8.19 (s, 1H) 7.36-7.26 (m, 1H) 7.26-6.98 (m, 3H) 4.68 (s, 2H) 2.77 (s, 3H), MS m/z = 289 (M + H)$^+$ |
| B.1.7 | 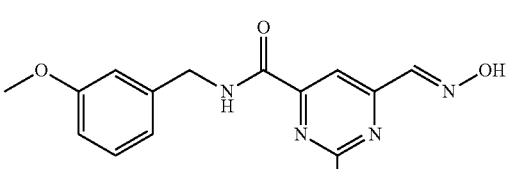 | $^1$H NMR: (400 MHz, DMSO): δ 12.40 (s, 1H), 9.44 (t, J = 6.4 Hz, 1H), 8.10 (s, 1H), 8.08 (s, 1H), 7.25-7.21 (m, 1H), 6.91-6.80 (m, 3H), 4.48 (d, J = 6.0 Hz, 2H), 3.73 (s, 3H), 2.72 (s, 3H), MS m/z 301.2 (M + H)$^+$ |
| B.1.8 | 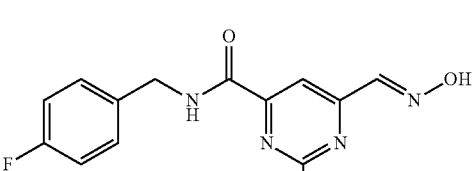 | $^1$H NMR (400 MHz, DMSO) δ 12.40 (s, 1H), 9.50 (t, J = 6.4 Hz, 1H) 8.10 (s, 1H), 8.07 (s, 1H), 7.38-7.35 (m, 2H), 7.16-7.12 (m, 2H), 4.48 (d, J = 6.0 Hz, 2H), 2.72 (s, 3H). MS m/z = 289 (M + H)$^+$ |
| B.1.9 | 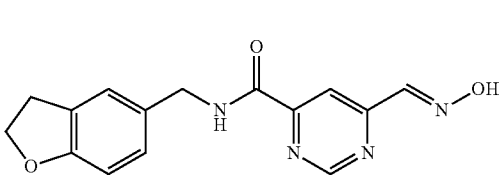 | $^1$H NMR (400 MHz, DMSO): δ 12.39 (s, 1H), 9.336-9.320 (m, 1H), 8.104 (s, 1H), 8.075 (m, 1H), 7.205 (s, 1H), 7.068-7.048 (d, J = 8 Hz, 1H), 6.698-6.677 (d, J = 8.4 Hz, 1H), 4.507-4.463 (t, J = 8.8 Hz, 2H), 4.411-4.395 (d, J = 6.4 Hz, 2H), 3.156-3.112 (t, J = 8.8 Hz, 2H), 2.71 (s, 3H), MS m/z = 312.2 (M + H)$^+$ |
| B.2.0 | 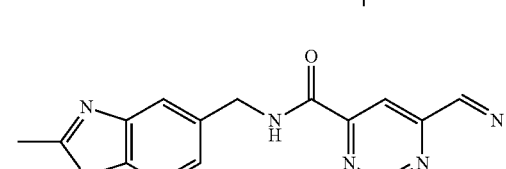 | $^1$H NMR (400 MHz, DMSO) δ 12.40 (s, 1H), 9.43 (t, J = 6.4 Hz, 1H), 8.10 (d, J = 11.2 Hz, 1H), 7.22 (m, 4H), 4.47 (d, J = 6 Hz, 2H), 2.72 (s, 3H), 2.27 (s, 3H), MS m/z: 283.0 (M − H) |
| B.2.1 | 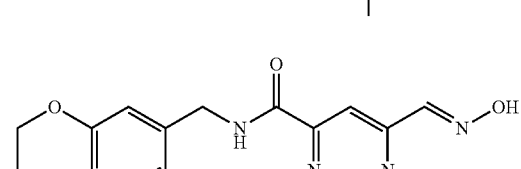 | $^1$H NMR (400 MHz, DMSO): δ 9.360 (t, 1H), 8.104-8.070 (d, J = 13.6 Hz, 2H), 6.834-6.787 (d, J = 18.8 Hz, 3H), 4.378-4.362 (d, J = 6.4 Hz, 2H), 4.200 (s, 4H), 2.715 (s, 3H), MS: m/z: 329.3 (M + H)$^+$ |

TABLE B.1-continued

Compounds Prepared Using General Procedure B

| Preparation # | Product | Analytical data |
|---|---|---|
| B.2.2 | 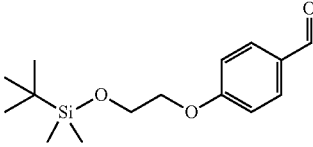 [SMILES: CC(C)(C)[Si](C)(C)OCCOc1ccc(C=O)cc1] | $^1$H NMR (400 MHz, DMSO): δ 12.4 (s, 1H), 10.64 (s, 1H), 9.43 (t, 1H), 8.11 (s, 1H), 8.07 (s, 1H), 6.88 (m, 3H), 4.51 (s, 2H) 4.40 (d, J = 6.4 Hz, 2H), 2.72 (s, 3H), LC/MS (Table 1, method d) R$_t$ = 2.64 min. |

TABLE E.1

Olefins synthesized using General Procedure E

| Prep. #. | Carbonyl compound | Product | Analytical data | Reference/source for carbonyl compound |
|---|---|---|---|---|
| E.1.1 | 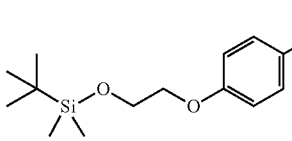 | 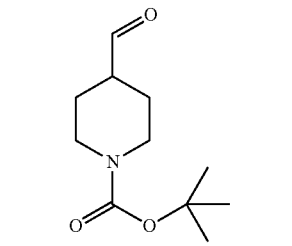 | $^1$H NMR (400 MHz, CDCl$_3$): δ 7.350-7.342 (d, J = 3.2 Hz, 2H), 6.882-6.875 (d, J = 2.8 Hz, 2H), 6.857-6.692 (m, 1H), 5.625-5.581 (d, J = 17.6 Hz, 1H), 5.132-5.104 (d, J = 11.2 Hz, 1H), 4.052-3.954 (m, 4H), 0.909 (s, 9H), 0.1 (s, 6H), MS m/z: 279.3 (M + H)$^+$. | European Journal of Medicinal Chemistry, 44, 4235-4243, 2009. |
| E.1.2 | 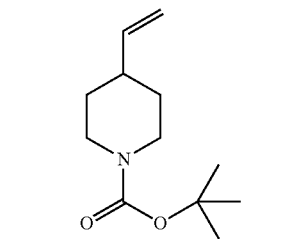 | 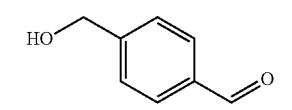 | $^1$H NMR (400 MHz, DMSO): δ 5.827-5.785 (m, 1H), 5.033-4.927 (m, 2H), 3.935-3.905 (m, 2H), 2.73-2.666 (m, 2H), 2.128-2.113 (m, 1H), 1.616-1.612 (m, 2H), 1.387 (s, 9H), 1.179-1.087 (m, 2H). MS m/z: 212 (M + H)$^+$. | Bioorganic & Medicinal Chemistry Letters, 11, 491-494, 2001 |
| E.1.3 | 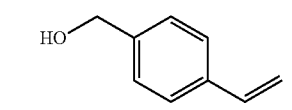 | 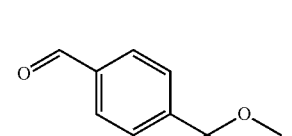 | $^1$H NMR (400 MHz, DMSO): δ 7.435-7.414 (d, J = 8.4 Hz, 2H), 7.297-7.277 (d, J = 8.0 Hz, 2H), 6.751-6.680 (m, 1H), 5.820-5.776 (d, J = 1.6 Hz, 1H), 5.232-5.203 (d, J = 11.6 Hz, 1H), 5.1872-5.173 (brs, 1H), 4.490-4.476 (m, 2H). | WO 2008154642 |
| E.1.4 | 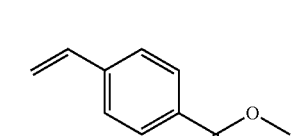 | | $^1$H NMR (400 MHz, DMSO): δ 7.945-7.924 (d, J = 8.4 Hz, 2H), 7.635-7.613 (d, J = 8.8 Hz, 2H), 6.860-6.787 (m, 1H), 6.027-5.982 (d, J = 18 Hz, 1H), 5.449-5.421 (d, J = 11.2 Hz, 1H), 3.850 (s, 3H) | Aldrich |

TABLE E.1-continued

Olefins synthesized using General Procedure E

| Prep. #. | Carbonyl compound | Product | Analytical data | Reference/ source for carbonyl compound |
|---|---|---|---|---|
| E.1.5 | | | ¹H NMR (400 MHz, CDCl₃): δ 7.356-7.253 (m, 2H), 6.870-6.696 (m, 2H), 6.670-6.626 (m, 1H), 5.628-5.584 (d, J = 17.6 Hz, 1H), 5.134-5.107 (d, J = 10.8 Hz, 1H), 3.82 (s, 3H). MS m/z: 135.2 (M + H)⁺. | Aldrich |
| E.1.6 | | | ¹H NMR (400 MHz, CDCl₃): δ 7.308-7.297 (d, J = 4.4 Hz, 2H), 6.686-6.673 (d, J = 5.2 Hz, 2H), 6.638-6.594 (m, 1H), 5.557-5.511 (d, J = 18.4 Hz, 1H), 5.027-4.998 (d, J = 11.6 Hz, 1H), 2.952 (s, 6H). MS m/z: 148.1 (M + H)⁺. | Commercial (Loba) |
| E.1.7 | | | ¹H NMR (400 MHz, CDCl₃): δ 8.623 (s, 1H), 8.496-8.483 (t, J = 3.6 Hz 1H), 7.740-7.720 (d, J = 8 Hz, 1H), 7.272-7.242 (m, 1H), 6.745-6.673 (m, 1H), 5.853-5.809 (d, J = 17.6 Hz, 1H), 5.398-5.371 (d, J = 10.8 Hz, 1H). MS m/z: 106.1 (M + H)⁺. | Aldrich |
| E.1.8 | | | ¹H NMR (400 MHz, DMSO): δ 7.526-7.360 (m, 3H), 6.760-6.690 (m, 1H), 5.674-5.627 (d, J = 18.8 Hz, 1H), 5.194-5.164 (d, J = 12 Hz, 1H). | Aldrich |
| E.1.9 | | | ¹H NMR (400 MHz, CDCl₃): δ 5.76-5.68 (m, 1H), 5.36-5.32 (d, J = 17.6 Hz, 1H), 5.23-5.20 (d, J = 10.8, 1H), 4.00-3.34 (m, 8H), 0.88 (s, 9H), 0.05 (s, 6H). | Preparation #11 |
| E.1.10 | | | ¹H NMR (400 MHz, CDCl₃): δ 5.76-5.68 (m, 1H), 5.36-5.32 (d, J = 17.6 Hz, 1H), 5.23-5.20 (d, J = 10.8, 1H), (4.00-3.34 (m, 8H), 0.88 (s, 9H), 0.05 (s, 6H). | Preparation #11 |
| E.1.11 | | | ¹H NMR (400 MHz, DMSO): δ 5.82-5.74 (m, 1H), 5.029-4.98 (m, 2H), 3.92-3.89 (d, J = 12.4 Hz, 2H), 2.669-2.50 (m, 2H), 1.979-1.94 (m, 2H), 1.61-1.58 (m, 2H), 1.48-1.45 (m, 1H), 1.38 (s, 9H), 1.012-0.83 (m, 2H) | *Journal of Medicinal Chemistry*, 48 (6), 2100-2107, 2005. |

TABLE E.1-continued

Olefins synthesized using General Procedure E

| Prep. #. | Carbonyl compound | Product | Analytical data | Reference/ source for carbonyl compound |
|---|---|---|---|---|
| E.1.12 | | | $^1$H NMR (400 MHz, DMSO): δ 6.702-6.684 (d, J = 7.2 Hz, 1H), 5.791-5.764 (m, 1H), 4.988-4.948 (d, J = 16 Hz, 1H), 4.896-4.871 (d, J = 10 Hz, 1H), 3.149-3.131 (m, 1H), 1.789-1.672 (m, 5H), 1.369 (s, 9H), 1.181-1.065 (m, 4H). MS m/z: 224 (M − H). | EP 1961744 A1 |
| E.1.13 | | | $^1$H NMR (400 MHz, DMSO): δ 5.835-5.750 (m, 1H), 4.983-4.958 (d, J = 10 Hz, 1H), 4.954-4.927 (d, J = 10.8 Hz 1H), 3.858-3.823 (dd, J = 2.4 Hz, 2H), 3.348-3.285 (m, 2H), 2.196-2.184 (m, 1H), 1.326-1.283 (m, 4H). | WO 2006074003 |
| E.1.14 | | | $^1$H NMR (400 MHz, CDCl$_3$): δ 7.25-6.80 (m, 4H), 5.35 (s, 1H), 5.07 (s, 1H), 4.052-4.040 (d, J = 4.8 Hz, 2H), 3.986-3.973 (d, J = 5.2 Hz, 2H), 2.13 (s, 3H), 0.913 (s, 9H), 0.104 (s, 6H), MS m/z: 293.3 (M + H)$^+$. | Journal of Medicinal Chemistry 526394-6401, 2009 |
| E.1.15 | | | $^1$H NMR (400 MHz, CDCl$_3$): δ 7.258 (s, 1H), 7.035-6.813 (m, 3H), 6.718-6.647 (m, 1H) 5.761-5.717 (d, J = 17.6 Hz, 1H), 5.269-5.242 (d, J = 10.8 Hz, 1H), 4.103-4.091 (d, J = 4.8 Hz, 4H), MS m/z: 165.4 (M + H)$^+$. | Chemistry A European Journal, 12223-12233, 2009 |
| E.1.16 | | | $^1$H NMR (400 MHz, DMSO): δ 7.484-7.464 (d, J = 8.0 Hz, 2H,), 7.290-7.270 (d, J = 8.0 Hz, 2H,), 5.41 (s, 1H), 5.075 (s, 1H), 4.70 (s, 2H), 2.098 (s, 3H), 0.904 (s, 9H), 0.078 (s, 6H), MS m/z: 263.2 (M + H)$^+$. | Tetrahedron Letters, 46, 1971-1973, 2005. |
| E.1.18 | | | $^1$H NMR (400 MHz, DMSO): δ 7.294-7.272 (d, J = 8.8 Hz, 2H), 6.891-6.896 (d, J = 8.8 Hz 2H), 6.630-6.559 (m, 1H), 5.598-5.555 (d, J = 17.2 Hz, 1H), 5.030-5.001 (d, J = 11.6 Hz, 1H), 3.749-3.717 (d, J = 12.8 Hz, 2H), 3.465-3.450 (d, J = 6.0 Hz, 2H), 2.680-2.645 (m, 2H), 1.730-1.700 (d, J = 12.0 Hz, 2H), 2.590-2.497 (m, 1H), 1.286-1.217 (m, 2H), 0.870 (s, 9H), 0.035 (s, 6H). MS m/z: 332.3 (M + H)$^+$. | Tetrahedron, 57, 4781-85, 2001 |

TABLE E.1-continued

Olefins synthesized using General Procedure E

| Prep. #. | Carbonyl compound | Product | Analytical data | Reference/source for carbonyl compound |
|---|---|---|---|---|
| E.1.19 | | | ¹H NMR (400 MHz, DMSO): δ 7.431-7.411 (d, J = 8.0 Hz, 2H), 7.286-7.265 (d, J = 8.4 Hz, 2H), 6.751-6.680 (m, 1H), 5.822-5.778 (d, J = 17.6 Hz, 1H), 5.243-5.216 (d, J = 10.8 Hz, 1H), 3.574-3.439 (m, 6H), 2.333-2.270 (m, 4H). MS m/z: 204 (M + H)⁺. | Journal of Organic Chemistry, 70, 5571-5578, 2005 |
| E.1.20 | | | ¹H NMR (400 MHz, DMSO): δ 6.786 (s, 1H), 5.789-5.713 (m, 1H), 5.729-5.713 (d, J = 6.4 Hz, 1H), 5.009-5.005 (d, J = 1.6 Hz, 1), 2.758-2.743 (d, J = 6 Hz, 2H), 1.86-1.85 (m, 1H), 1.705-1.680 (d, J = 10 Hz, 2H), 1.439-1.431 (m, 1H), 1.36 (s, 9H), 1.317-1.289 (d, J = 11.2 Hz, 2H), 1.27-1.23 (m, 2H), 1.02-0.963 (m, 2H), MS m/z = 240.1 (M + H) | WO 2007002126 |
| E.1.21 | | | ¹H NMR (400 MHz, (DMSO) δ: 5.80 (m, 1H), 5.00 (m, 2H), 3.58 (s, 3H), 2.28 (m, 1H), 1.95 (m, 2H), 1.76 (m, 2H), 1.59 (m, 1H), 1.38 (m, 2H), 1.15 (m, 2H). IR: (Ester C═O str) (1734) cm⁻¹ | EP 1772454 A1 |

TABLE F.1

Olefins prepared by General Procedure F.

| Preparation # | Halo compound | Product (Olefin) | References/source for Halo compound | Analytical data | Method |
|---|---|---|---|---|---|
| F.1.1 | | | WO 2009151598 | ¹H NMR (400 MHz, DMSO): δ 7.542-7.521 (m, 2H), 7.449-7.429 (m, 2H), 6.759-6.715 (m, 1H), 5.834-5.790 (d, J = 17.6 Hz, 1H), 5.255-5.227 (d, J = 11.2 Hz, 1H), 3.643 (s, 2H), 3.099-3.086 (m, 4H), 2.869-2.844 (m, 4H) MS m/z: 252 (M + H)⁺. | I |

TABLE F.1-continued

Olefins prepared by General Procedure F.

| Preparation # | Halo compound | Product (Olefin) | References/ source for Halo compound | Analytical data | Method |
|---|---|---|---|---|---|
| F.1.2 | | | *Bioorganic Medicinal Chemistry Letters*, 12, 2989-2992, 2002. | $^1$H NMR (400 MHz, DMSO): δ 7.375-7.207 (m, 4H), 6.767-6.696 (m, 1H), 5.840-5.794 (d, J = 18.5 Hz, 1H,), 5.266-5.239 (d, J = 10.8 Hz, 1H), 3.578-3.555 (m, 4H), 3.451 (s, 2H), 2.498-2.333 (m, 4H). MS m/z: 204.1 (M + H)$^+$. | I |
| F.1.3 | | | Aldrich | $^1$H NMR (400 MHz, CDCl$_3$): δ 9.103 (s, 1H), 8.766 (s, 2H), 6.698-6.627 (m, 1H), 5.956-5.911 (d, J = 18 Hz, 1H), 5.533-5.505 (d, J = 11.2 Hz, 1H), MS m/z: 107.2 (M + H)$^+$. | I |
| F.1.4 | | | Aldrich | $^1$H NMR (400 MHz, CDCl$_3$): δ 7.643 (s, 2H), 6.620-6.549 (m, 1H), 5.530-5.486 (d, J = 17.6 Hz, 1H), 5.126-5.099 (d, J = 10.8 Hz, 1H), MS m/z: 95.1 (M + H)$^+$. | I |
| F.1.5 | | | Aldrich | $^1$H NMR (400 MHz, DMSO): δ 8.772-8.760 (d, J = 4.8 Hz), 2H), 7.361-7.337 (m, 1H), 6.828-6.759 (m, 1H), 6.542-6.499 (d, J = 17.2 Hz, 1H), 5.736-5.710 (d, J = 10.4 Hz, 1H). | I |
| F.1.6 | | | *Journal of Medicinal Chemistry*, 38, 3368-3383, 1995 | $^1$H NMR (400 MHz, DMSO): δ 7.441-7.376 (m, 4H), 6.741-6.669 (m, 1H), 5.800-5.755 (d, J = 18 Hz, 1H), 5.216-5.190 (d, J = 10.4 Hz, 1H), 5.00 (s, 1H), 1.40 (s, 6H). | I |
| F1.7 | | | WO 2009151598 | $^1$H NMR (400 MHz, DMSO): δ 7.425-7.405 (d, J = 8.0 Hz 2H,), 7.69-7.249 (d, J = 8.0 Hz 2H,), 6.749-6.678 (m, 1H), 5.818-5.772 (d, J = 18.4 Hz, 1H), 5.241-5.213 (d, J = 11.2 Hz, 1H), 3.473 (s, 2H), 2.599 (s, 8H), MS m/z: 219.9 (M + H)$^+$. | I |
| F1.8 | | | Aldrich | $^1$H NMR (400 MHz, DMSO): δ 8.011 (s, 1H), 7.878-7.776 (m, 2H), 7.551-7.511 (m, 1H), 6.870-6.799 (m, 1H), 5.950-5.906 (d, J = 17.6 Hz, 1H), 5.373-5.346 (d, J = 10.8 Hz, 1H), 3.86 (s, 3H). | I |

TABLE F.1-continued

Olefins prepared by General Procedure F.

| Preparation # | Halo compound | Product (Olefin) | References/source for Halo compound | Analytical data | Method |
|---|---|---|---|---|---|
| F.1.9 | | | Apollo Scientific | $^1$H NMR (400 MHz, CDCl$_3$): δ 8.696-8.683 (d, J = 5.2 Hz, 1H), 8.147 (s, 1H), 7.445-7.436 (d, J = 3.6 Hz, 1H), 6.767-6.696 (m, 1H), 6.100-6.056 (d, J = 17.6 Hz, 1H), 5.601-5.575 (d, J = 10.4 Hz, 1H), 4.024 (s, 3H), MS m/z: 164.3 (M + H)$^+$. | I |
| E.1.10 | | | Org Lett., 7(14), 2965-2967, 2005 | $^1$H NMR (400 MHz, DMSO): δ 8.479 (s, 1H), 7.704-7.688 (d, J = 6.4 Hz 1H), 7.471-7.456 (d, J = 6.0 Hz 1H), 6.827-6.806 (m, 1H), 6.212-6.177 (d, J = 14 Hz, 1H), 5.439-5.417 (d, J = 8.8 Hz, 1H), 5.300 (m, 1H), 4.524 (d, J = 4.4 Hz, 2H), MS m/z: 136 (M + H)$^+$. | II |
| F.1.11 | | | 6-chloronicotinaldehyde Org Lett., 7(14), 2965-2967, 2005 was reduced using General Procedure K | $^1$H NMR (400 MHz, CDCl$_3$): δ 8.55 (s, 1H), 7.912-7.810 (m, 2H), 6.858-6.787 (m, 1H), 6.205-6.159 (d, J = 18.4 Hz, 1H), 5.491-5.464 (d, J = 10.8 Hz, 1H), 4.969-4.954 (m, 1H), 4.396 (brs, 1H), 1.537-1.520 (d, J = 6.8 Hz, 3H), MS m/z: 150 (M + H)$^+$. | II |
| F.1.12 | | | US, 2007/0027184A1 | $^1$H NMR (400 MHz, CDCl$_3$): δ 9.12 (s, 1H), 8.214-8.188 (d, J = 8.4 Hz 1H), 7.447-7.426 (d, J = 8.4 Hz, 1H), 6.912-6.841 (m, 1H), 6.385-6.341 (d, J = 17.6 Hz, 1H), 5.658-5.631 (d, J = 10.8 Hz, 1H), 2.635 (s, 3H), MS m/z: 148.1 (M + H)$^+$. | II |
| F.1.13 | | | WO 2009134400 | $^1$H NMR (400 MHz, CDCl$_3$): δ 7.591-7.585 (d, J = 6.8 Hz, 1H), 7.237-7.231 (s, 1H), 6.601-6.577 (d, J = 9.6 Hz, 1H), 6.441-6.370 (m, 1H), 5.481-5.437 (d, J = 17.6 Hz, 1H), 5.144-5.117 (d, J = 10.8 Hz, 1H), 3.548 (s, 3H), MS m/z: 136 (M + H)$^+$. | II |

TABLE F.1-continued

Olefins prepared by General Procedure F.

| Preparation # | Halo compound | Product (Olefin) | References/ source for Halo compound | Analytical data | Method |
|---|---|---|---|---|---|
| F.1.14 | | | Aldrich | $^1$H NMR (400 MHz, CDCl$_3$): δ 9.168 (s, 1H), 8.261-8.256 (d, J = 2.0 Hz, 1H), 7.416-7.396 (d, J = 8.0 Hz, 1H), 6.903-6.834 (m, 1H), 6.367-6.325 (d, J = 16.8 Hz, 1H), 5.640-5.613 (d, J = 10.8 Hz, 1H), 3.951 (s, 3H), MS m/z: 164.1 (M + H)$^+$. | II |
| F.1.15 | | | WO2009016498 | $^1$H NMR (400 MHz, CDCl$_3$): δ 7.82 (s, 1H), 6.837-6.767 (m, 1H), 6.562-6.518 (d, J = 17.6 Hz, 1H), 5.799-5.772 (d, J = 10.8 Hz, 1H), 4.031 (s, 3H), 2.834 (s, 3H), MS m/z: 179 (M + H)$^+$ | I |
| F.1.16 | | | *Bioorganic Medicinal Chemistry*, 13, 1805-1809, 2005. | $^1$H NMR (400 MHz, CDCl$_3$): δ 9.089 (s, 1H), 8.184-8.157 (d, J = 5.6 Hz, 1H), 7.512-7.491 (d, J = 8.4 Hz, 1H), 6.925-6.858 (m, 1H), 6.449-6.405 (d, J = 16.4 Hz 1H), 5.728-5.701 (d, J = 10.8 Hz, 1H), 3.110 (s, 3H). MS m/z: 184.0 (M + H)$^+$. | II |
| F.1.17 | | | Preparation #21 | $^1$H NMR: (400 MHz, CDCl$_3$) δ: 8.8 (d, J = 2 Hz, 1H), 7.97 (s, 1H), 7.91 (dd, J = 8.4 Hz, 1H), 7.46 (m, 2H), 6.8 (m, 1H), 6.28 (d, J = 17.2 Hz, 1H), 5.56 (d, J = 10.8 Hz, 1H), m/z: 173 MS (M + H)+ | II |
| F.1.18 | | | US 20110021531 | $^1$H NMR: (400 MHz, CDCl$_3$) δ: 8.1 (d, J = 8.8 Hz, 1H), 7.8 (d, J = 8.8 Hz, 1H), 7.15 (m, 1H), 6.5 (d, J = 17.6 Hz, 1H), 5.91 (d, J = 11.2 Hz, 1H), 3.4 (s, 3H), MS m/z: 185.1 (M + H)+ | II |
| F.1.19 | | | Tetrahedron, 2008, 64, 3794-3801 | $^1$H NMR (400 MHz, CDCl$_3$): δ 8.7 (d, J = 2 Hz, 1H), 7.9 (m, 2H), 2.69 (s, 3H), MS m/z: 148.1 (M + H)+ | II |
| F.1.20 | | | WO 2007/143823 | $^1$H NMR: (400 MHz, DMSO): δ 8.21-8.189 (d, J = 8.8 Hz, 1H), 8.143-8.121 (d, J = 8.8 Hz, 1H), 7.127-7.155 (m, 1H), 6.508-6.552 (m, 1H), 5.850-5.877 (m, 1H), 3.96 (s, 3H), MS m/z: 165.1 (M + H)+ | II |

TABLE F.1-continued

Olefins prepared by General Procedure F.

| Preparation # | Halo compound | Product (Olefin) | References/source for Halo compound | Analytical data | Method |
|---|---|---|---|---|---|
| F.1.21 | 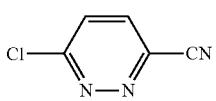 | 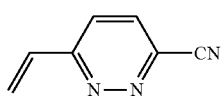 | J. Med. Chem. 2007, 50, 3086-3100 | $^1$H NMR (400 MHz, CDCl$_3$): δ 7.784-7.767 (d, J = 6.8 Hz, 1H), 7.701-7.679 (d, J = 8.8 Hz, 1H), 7.133-7.016 (m, 1H), 6.514-6.469 (d, J = 18 Hz, 1H), 5.924-5.897 (d, J = 10.8 Hz, 1H), MS m/z: 132 (M + H)$_+$ | II |
| F.1.22 | 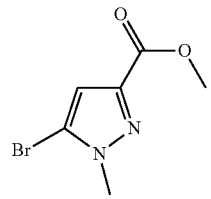 | 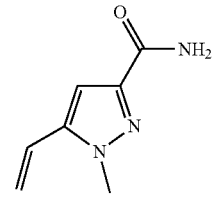 | WO 2010/045188 | $^1$H NMR (400 MHz, CDCl$_3$): δ: 6.92 (s, 1H), 6.59 (t, 1H), 5.78 (d, J = 16, 1H), 5.46 (d, J = 11.6 Hz, 1H). 4.39 (q, 2H), 3.94 (s, 3H), 1.39 (t, 3H), MS m/z: 181 (m + H)$^+$. | L (Method-2) & II |
| F.1.23 | 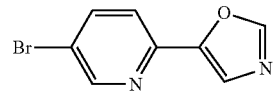 | 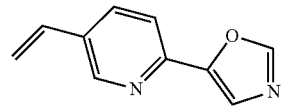 | Preparation #AD.2 | $^1$H NMR: (400 MHz, DMSO) δ: 8.719 (d, J = 2 Hz 1H), 8.5 (s, 1H), 8.08 (dd, J = 8 Hz, 1H), 7.806 (s, 1H), 7.7 (d, J = 7.6 Hz, 1H), 6.8 (m, 1H), 6.07 (d, J = 17.6 Hz, 1H), 5.48 (d, J = 10.8 Hz, 1H), MS m/z = 173.1 (M + H)$^+$ | II |
| F.1.24 | 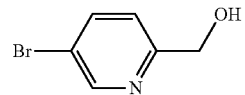 | 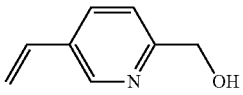 | *Bioorganic Medicinal Chemistry Letters*, 2010, 20(19), 5781-5786. | $^1$H NMR: (400 MHz, DMSO) δ 8.5 (d, J = 1.6 Hz, 1H), 7.9 (dd, J = 8 Hz, 1H), 7.4 (d, J = 8.4 Hz, 1H), 6.79 (m, 1H), 5.95 (d, J = 17.6 Hz, 1H), 5.4 (m, 1H), 5.36 (d, J = 11.2 Hz, 1H), 4.5 (d, J = 5.6 Hz, 2H), MS m/z: 136.1 (M + H)$^+$ | II |
| F.1.25 | 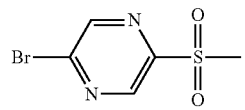 | 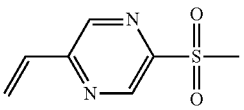 | PCT 2009099080 | $^1$H NMR: (400 MHz, CDCl$_3$) δ: 9.2 (s, 1H), 8.6 (s, 1H), 6.95-6.93 (m, 1H), 6.593-6.551 (d, J = 16.8 Hz, 1H), 5.868-5.841 (d, J = 10.8 Hz, 1H), 3.2 (s, 3H), MS m/z = 185 (M + H)$^+$. | II |
| F.1.26 | 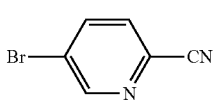 | 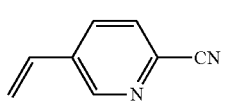 | BMCL 2006, 16, 1277-1281 | $^1$H NMR: (400 MHz, CDCl$_3$): δ 8.7 (s, 1H), 7.84 (dd, J = 8 Hz 1H), 7.67 (d, J = 8.4 Hz, 1H), 6.78 (m, 1H), 6.00 (d, J = 17.6 Hz, 1H), 5.61 (d, J = 10.4 Hz, 1H), MS m/z = 131.1 (M + H)$^+$. | II |

TABLE F.1-continued

Olefins prepared by General Procedure F.

| Preparation # | Halo compound | Product (Olefin) | References/ source for Halo compound | Analytical data | Method |
|---|---|---|---|---|---|
| F.1.27 | (structure: 4-iodo-1-(2-hydroxyethyl)pyrazole) | (structure: 4-vinyl-1-(2-hydroxyethyl)pyrazole) | WO 2008088881 | ¹H NMR (400 MHz, DMSO) δ 7.78 (s, 1H), 7.58 (s, 1H), 6.55-6.48 (m, 1H), 5.47-5.42 (d, J = 19.2 Hz, 1H), 5.00-4.97 (d, J = 12.8 Hz, 1H), 4.87 (t, J = 5.2 Hz, 1H), 4.09 (t, J = 5.6 Hz, 2H), 3.72-3.70 (q, 2H), MS m/z: 139.1 (M + H)⁺. | II |
| F.1.28 | (structure: 5-bromo-1-Boc-pyrazolo[3,4-b]pyridine) | (structure: 5-vinyl-pyrazolo[3,4-b]pyridine·HCl) | Preparation #23 & General procedure G | ¹H NMR: (400 MHz, DMSO) δ: 13.66 (s, 1H) 8.698-8.693 (d, J = 2 Hz, 1H) 8.316-8.311 (d, J = 2 Hz, 1H) 8.144-8.140 (d, J = 1.6 Hz, 1H) 6.8 (m, 1H) 5.976-5.932 (d, J = 17.6 Hz, 1H) 5.330-5.300 (d, J = 12 Hz, 1H), MS m/z: 146.2 (M + H)⁺. | I |
| F.1.29 | (structure: 3-chloro-6-(dimethylamino)pyridazine) | (structure: 3-vinyl-6-(dimethylamino)pyridazine) | *Journal of Heterocyclic Chemistry*, 2000, 37, 1591-1596. | ¹H NMR: (400 MHz, DMSO) δ: 7.664-7.640 (d, J = 9.6, 1H), 7.079-7.055 (d, J = 9.6, 1H), 6.879-6.807 (m, 1H), 5.996-5.951 (d, J = 18, 1H), 5.393-5.365 (d, J = 11.2, 1H), 3.083 (s, 1H), MS m/z: : 150 (M + H)⁺. | II |
| F.1.30 | (structure: 3-chloro-6-(pyrrolidin-1-yl)pyridazine) | (structure: 3-vinyl-6-(pyrrolidin-1-yl)pyridazine) | U.S. Pat. No. 4,104,385 | ¹H NMR (400 MHz, DMSO): δ 7.65 (d, J = 9.6 Hz, 1H), 6.8 (m, 2H), 5.97 (d, J = 1.2 Hz, 1H), 5.36 (d, J = 11.6 Hz, 1H), 3.48 (t, J = 6.4 Hz, 4H), 1.98 (m, 4H). MS m/z: 176.1 (M + H)⁺. | II |
| F.1.31 | (structure: 5-bromo-1-(2-hydroxyethyl)pyridin-2(1H)-one) | (structure: 5-vinyl-1-(2-hydroxyethyl)pyridin-2(1H)-one) | WO 2009134400 | LC/MS (See Table 1 Method d) R$_f$ = 0.20, m/z: 166.2 (M + H)⁺. | II |
| F.1.32 | (structure: 4-bromo-1-methylpyridin-2(1H)-one) | (structure: 4-vinyl-1-methylpyridin-2(1H)-one) | Combi blocks | ¹H NMR (400 MHz, DMSO) δ 7.233-7.216 (d, J = 2.8 Hz, 1H), 6.577-6.479 (m, 2H), 6.302-6.280 (dd, J = 7 Hz. 6, 1H), 5.85-5.806 (d, J = 17.6 Hz, 1H), 5.481-5.454 (d, J = 10.8 Hz, 1H), 3.52 (s, 3H), LC/MS: (Table 1, Method-e) R$_t$: 2.336 min. | II |

TABLE F.1-continued

Olefins prepared by General Procedure F.

| Preparation # | Halo compound | Product (Olefin) | References/source for Halo compound | Analytical data | Method |
|---|---|---|---|---|---|
| F.1.33 | 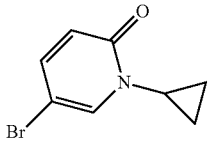 [SMILES: O=c1ccc(Br)cn1C1CC1] | 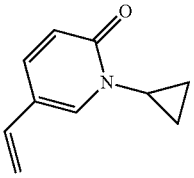 | WO 2009134400 | ¹H NMR (400 MHz, CDCl₃) δ: 7.560-7.530 (dd, J = 9.6 Hz, 1H), 7.224-7.218 (d, J = 4.4 Hz, 1H), 6.606-6.552 (dd, J = 12.4 Hz, 1H), 6.440 (m, 1H), 5.465-5.421(d, J = 17.6 Hz, 1H), 5.135-5.107 (d, J = 11.2 Hz, 1H), 3.346 (m, 1H) 1.16 (m, 2H), 0.897 (m, 2H); LC/MS (Table 1, Method d) R$_t$: 2.42 min | II |
| F.1.34 | 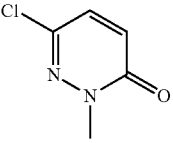 | 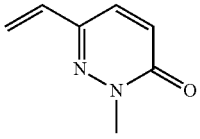 | WO 2011015629 | ¹H NMR: (400 MHz, CDCl₃) δ: 7.489-7.465 (d, J = 9.6, 1H), 6.936-6.911 (d, J = 10 Hz, 1H), 6.72-6.52 (m, 1H), 5.808-5.763 (d, J = 18 Hz, 1H), 5.521-5.493 (d, J = 11.2 Hz, 1H), 3.78 (s, 3H), MS m/z = 137.1 (M + H)⁺ | II |
| F.1.35 | 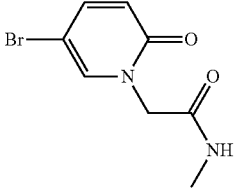 | 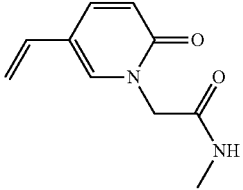 | Preparation #35 | ¹H NMR (400 MHz, DMSO): δ 8.087 (bs, 1H), 7.774-7.768 (d, J = 2.4 Hz, 1H), 7.751-7.745 (d, J = 2.4 Hz, 1H), 6.502-6.390 (m, 2H), 5.575-5.531 (d, J = 17.6 Hz, 1H), 5.097-5.070 (d, J = 10.8 Hz, 1H), 4.47 (s, 2H), 2.61 (s, 3H), MS m/z = 192.8 (M + H)⁺. | II |
| F.1.36 | 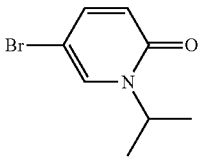 | 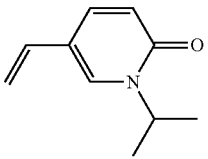 | WO 2009134400 | ¹H NMR (400 MHz, CDCl₃): δ 7.551-7.544 (d, J = 2.8 Hz, 1H), 7.234-7.228 (d, J = 2.4 Hz, 1H), 6.596-6.573 (d, J = 9.2 Hz, 1H), 6.457-6.13 (m, 1H), 5.476-5.432 (d, J = 17.6 Hz, 1H), 5.28-5.23 (m, 1H), 5.141-5.113 (d, J = 11.2 Hz, 1H), 1.371-1.354 (m, 6H), LC/MS (Table 1 Method e) R$_t$: 2.53 min | II |
| F.1.37 | 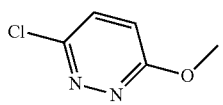 | 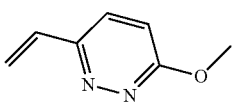 | WO 2006004589 | ¹H NMR (400 MHz, CDCl3): δ 7.553-7.530 (d, J = 9.2 Hz, 1H), 7.028-6.941 (m, 2H), 6.063-6.019 (d, J = 17.6 Hz, 1H), 5.577-5.549 (d, J = 11.2 Hz, 1H), 4.142 (s, 3H); MS m/z: 137.1 (M + H)+. | II |

TABLE F.1-continued

Olefins prepared by General Procedure F.

| Preparation # | Halo compound | Product (Olefin) | References/ source for Halo compound | Analytical data | Method |
|---|---|---|---|---|---|
| F.1.38 | | | WO 2009134400 | $^1$H NMR (400 MHz, DMSO): δ 7.818-7.789 (dd, J = 2.4 Hz, 9.3 Hz, 1H), 7.747-7.741 (m, 1H), 6.495-6.424 (m, 2H), 5.600-5.556 (d, J = 17.6 Hz, 1H), 5.125-5.097 (d, J = 11.2 Hz, 1H), 4.668 (s, 2H), 4.169-4.116 (m, 2H), 1.222-1.174 (m, 3H); MS m/z: 208.2 (M + H)+. | I |
| F.1.39 | | | WO 2010010017 | $^1$H NMR (400 MHz, DMSO): δ 7.687-7.648, (dd, J = 7.3 Hz, 8.3 Hz, 1H), 7.014-6.996 (d, J = 7.3 Hz, 1H), 6.773-6.695 (m, 2H), 6.266-6.219 (dd, J = 1.9 Hz, 17.1 Hz, 1H) 5.440-5.408 (dd, J = 1.9 Hz, 10.7 Hz, 1H), 3.875 (s, 3H). LC/MS (Table 1 Method e) R$_t$: 3.107 min | I |
| F.1.40 | | | WO 2009134387 | $^1$H NMR (400 MHz, CDCl$_3$): δ 7.442-7.417 (d, J = 10 Hz, 1H), 6.922-6.899 (m, 1H), 6.627-6.555 (m, 1H), 5.781-5.737 (d, J = 17.6 Hz, 1H), 5.494-5.466 (d, J = 11.2 Hz, 1H), 4.179-4.120 (m, 1H), 1.171-1.121 (m, 2H), 1.035-0.991 (m, 2H). MS m/z: 163.0 (M + H)+. | II |
| F.1.41 | | | Preparation #36 | $^1$H NMR (400 MHz, CDCl$_3$): δ 7.529-7.504 (d, J = 10 Hz, 1H), 6.969-6.944 (d, J = 10 Hz, 1H), 6.645-6.573 (m, 1H), 5.823-5.777 (d, J = 18.4 Hz, 1H), 5.549-5.521 (d, J = 11.2 Hz, 1H), 4.865 (s, 1H), 4.272-4.219 (m, 2H), 1.308-1.259 (m, 3H). MS m/z: 209.0 (M + H)+. | II |

TABLE F.1-continued

Olefins prepared by General Procedure F.

| Preparation # | Halo compound | Product (Olefin) | References/ source for Halo compound | Analytical data | Method |
|---|---|---|---|---|---|
| F.1.42 | (4-bromo-3-methyl-2-oxopyridin-1(2H)-yl acetic acid ethyl ester) | (4-vinyl-3-methyl-2-oxopyridin-1(2H)-yl acetic acid ethyl ester) | | ¹H-NMR (400 MHz, DMSO): δ 8.044-8.033 (d, J = 4.4 Hz, 1H), 7.544-7.527 (d, J = 6.8 Hz, 1H), 6.621-6.550 (m, 1H), 6.467-6.443 (dd, J = 9.6 Hz, 1H), 6.337-6.332 (d, J = 2 Hz, 1H), 6.021-5.977 (d, J = 17.6 Hz, 1H), 5.522-5.494 (d, J = 11.2 Hz, 1H), 4.463 (s, 2H), 2.510-2.505 d, J = 2 Hz, 3H). MS m/z: 193.2 (M + H)+. | I |
| F.1.43 | (4-bromo-1-cyclopropylpyridin-2(1H)-one) | (3-bromo-1-cyclopropylpyridin-2(1H)-one) | | ¹H NMR (400 MHz, CDCl₃): δ 7.4722-7.454 (d, J = 7.2 Hz, 1H), 6.603-6.531 (m, 1H), 6.402-6.379 (m, 1H), 6.324 (s, 1H), 5.995-5.951 (d, J = 17.6 Hz, 1H), 5.501-5.474 (d, J = 10.8 Hz, 1H), 3.305-3.287 (m, 1H), 1.070-0.990 (m, 4H); MS m/z: 162.2 (M + H)+. | I |

TABLE G.1

Examples of isoxazolines prepared by General Procedures G

| Ex. # | Olefin | Product (Isoxazoline) IUPAC name |
|---|---|---|
| G.1.1 | (Preparation #E.1.14) | 6-(5-(4-(2-Hydroxyethoxy)-phenyl)-5-methyl-4,5-dihydroisoxazol-3-yl)-N-(4-methoxybenzyl)-2-methylpyrimidine-4-carboxamide 2,2,2-trifluoroacetate |
| G.1.2 | (Preparation #E.1.1) | 6-(5-(4-(2-Hydroxyethoxy)-phenyl)-4,5-dihydroisoxazol-3-yl)-N-(4-methoxybenzyl)-2-methylpyrimidine-4-carboxamide |
| G.1.3 | Aldrich | N-(4-Methoxybenzyl)-2-methyl-6-(5-phenyl-4,5-dihydroisoxazol-3-yl)pyrimidine-4-carboxamide |

TABLE G.1-continued

Examples of isoxazolines prepared by General Procedures G

| | | |
|---|---|---|
| G.1.4 | (Preparation #E.1.16) | 6-(5-(4-(Hydroxymethyl)-phenyl)-5-methyl-4,5-dihydroisoxazol-3-yl)-N-(4-methoxybenzyl)-2-methylpyrimidine-4-carboxamide |
| G.1.5 | (Preparation #E.1.5) | N-(4-Methoxybenzyl)-6-(5-(4-methoxyphenyl)-4,5-dihydroisoxazol-3-yl)-2-methylpyrimidine-4-carboxamide |
| G.1.6 | | N-(4-Methoxybenzyl)-2-methyl-6-(5-(4-morpholinophenyl)-4,5-dihydroisoxazol-3-yl)pyrimidine-4-carboxamide |
| G.1.7 | | N-(4-Methoxybenzyl)-2-methyl-6-(5-(4-(piperidin-1-yl)phenyl)-4,5-dihydroisoxazol-3-yl)pyrimidine-4-carboxamide |
| G.1.8 | (Preparation #E.1.6) | 6-(5-(4-(Dimethylamino)-phenyl)-4,5-dihydroisoxazol-3-yl)-N-(4-methoxybenzyl)-2-methylpyrimidine-4-carboxamide |
| G.1.9 | (Preparation #E.1.15) | 6-(5-(3-(2-Hydroxyethoxy)phenyl)-4,5-dihydroisoxazol-3-yl)-N-(4-methoxybenzyl)-2-methylpyrimidine-4-carboxamide |
| G.1.10 | Aldrich | N-(4-Methoxybenzyl)-2-methyl-6-(5-(pyridin-2-yl)-4,5-dihydroisoxazol-3-yl)pyrimidine-4-carboxamide |
| G.1.11 | Aldrich | 6-(5-Cyclohexyl-4,5-dihydroisoxazol-3-yl)-N-(4-methoxybenzyl)-2-methylpyrimidine-4-carboxamide |
| G.1.12 | (Preparation #E.1.3) | 6-(5-(4-(Hydroxymethyl)-phenyl)-4,5-dihydroisoxazol-3-yl)-N-(4-methoxybenzyl)-2-methylpyrimidine-4-carboxamide |

TABLE G.1-continued

Examples of isoxazolines prepared by General Procedures G

| | | |
|---|---|---|
| G.1.13 | 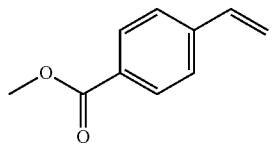<br>(Preparation #E.1.4) | 6-(5-(4-Carbamoyl phenyl)-4,5-dihydroisoxazol-3-yl)-N-(4-methoxybenzyl)-2-methylpyrimidine-4-carboxamide |
| G.1.14 | 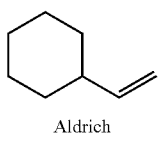<br>Aldrich | 6-(5-Cyclohexyl-4,5-dihydroisoxazol-3-yl)-N-(4-fluoro-3-methoxybenzyl)-2-methylpyrimidine-4-carboxamide |
| G.1.15 | 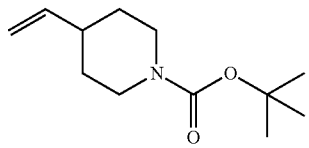<br>(Preparation #E.1.2) | 6-(5-(1-Acetylpiperidin-4-yl)-4,5-dihydroisoxazol-3-yl)-N-(4-methoxybenzyl)-2-methylpyrimidine-4-carboxamide |
| G.1.16 | 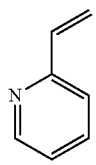<br>Aldrich | N-(4-Fluoro-3-methoxybenzyl)-2-methyl-6-(5-(pyridin-2-yl)-4,5-dihydroisoxazol-3-yl)pyrimidine-4-carboxamide |
| G.1.17 | 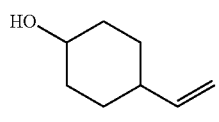<br>(EP 897928A1) | N-(4-Fluoro-3-methoxybenzyl)-6-(5-(4-hydroxycyclohexyl)-4,5-dihydroisoxazol-3-yl)-2-methylpyrimidine-4-carboxamide |
| G.1.18 | 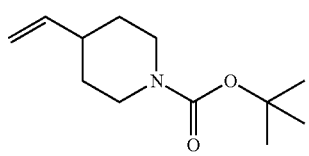<br>(Preparation #E.1.2) | Tert-butyl 4-(3-(6-(4-fluoro-3-methoxybenzyl-carbamoyl)-2-methylpyrimidin-4-yl)-4,5-dihydroisoxazol-5-yl)piperidine-1-carboxylate |
| G.1.19 | 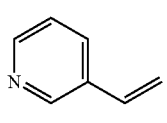<br>(Preparation #E.1.7) | N-(4-Fluoro-3-methoxybenzyl)-2-methyl-6-(5-(pyridin-3-yl)-4,5-dihydroisoxazol-3-yl)pyrimidine-4-carboxamide |
| G.1.20 | 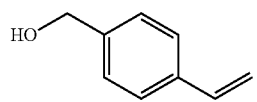<br>(Preparation #E.1.3) | N-(4-Fluoro-3-methoxybenzyl)-6-(5-(4-(hydroxymethyl)-phenyl)-4,5-dihydroisoxazol-3-yl)-2-methylpyrimidine-4-carboxamide |

TABLE G.1-continued

Examples of isoxazolines prepared by General Procedures G

| | | |
|---|---|---|
| G.1.21 | 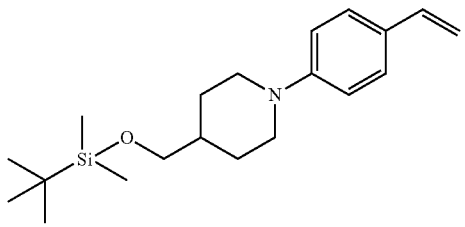<br>(Preparation #E.1.18) | N-(4-Fluoro-3-methoxybenzyl)-6-(5-(4-(4-(hydroxymethyl)-piperidin-1-yl)phenyl)-4,5-dihydroisoxazol-3-yl)-2-methylpyrimidin-4-carboxamide |
| G.1.22 | 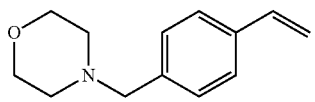<br>(Preparation #E.1.19) | N-(4-Fluoro-3-methoxybenzyl)-2-methyl-6-(5-(4-(morpholinomethyl)-phenyl)-4,5-dihydroisoxazol-3-yl)pyrimidine-4-carboxamide |
| G.1.23 | 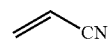<br>(Spectrochem) | 6-(5-Cyano-4,5-dihydroisoxazol-3-yl)-N-(4-methoxybenzyl)-2-methylpyrimidine-4-carboxamide |
| G.1.24 | 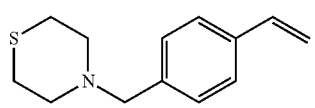<br>(Preparation #F.1.7) | N-(4-Fluoro-3-methoxybenzyl)-2-methyl-6-(5-(4-(thiomorpholino-methyl)phenyl)-4,5-dihydroisoxazol-3-yl)pyrimidine-4-carboxamide |
| G.1.25 | 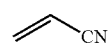<br>(Spectrochem) | 6-(5-Cyano-4,5-dihydroisoxazol-3-yl)-N-(4-fluoro-3-methoxybenzyl)-2-methylpyrimidine-4-carboxamide |
| G.1.26 | 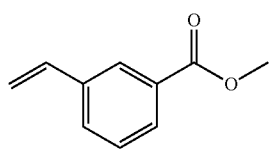<br>(Preparation #F.1.8) | 6-(5-(3-Carbamoyl phenyl)-4,5-dihydroisoxazol-3-yl)-N-(4-fluoro-3-methoxybenzyl)-2-methylpyrimidine-4-carboxamide |
| G.1.27 | 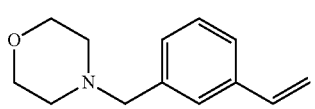<br>(Preparation #F.1.2) | N-(4-Fluoro-3-methoxybenzyl)-2-methyl-6-(5-(3-(morpholinomethyl)-phenyl)-4,5-dihydroisoxazol-3-yl)pyrimidine-4-carboxamide |
| G.1.28 | 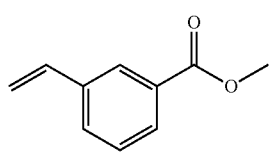<br>(Preparation #F.1.8) | N-(4-Fluoro-3-methoxybenzyl)-2-methyl-6-(5-(3-(methylcarbamoyl)-phenyl)-4,5-dihydroisoxazol-3-yl)pyrimidine-4-carboxamide |

TABLE G.1-continued

Examples of isoxazolines prepared by General Procedures G

| | | |
|---|---|---|
| G.1.29 | 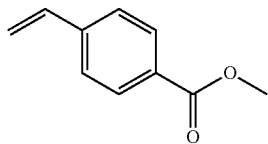<br>(Preparation #E.1.4) | Methyl 4-(3-(6-(4-fluoro-3-methoxybenzyl-carbamoyl)-2-methylpyrimidin-4-yl)-4,5-dihydroisoxazol-5-yl)benzoate |
| G.1.30 | 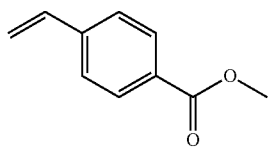<br>(Preparation #E.1.4) | N-(4-Fluoro-3-methoxybenzyl)-2-methyl-6-(5-(4-(methylcarbamoyl)-phenyl)-4,5-dihydroisoxazol-3-yl)pyrimidine-4-carboxamide |
| G.1.31 | 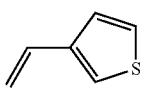<br>(Preparation #E.1.8) | N-(4-Fluoro-3-methoxybenzyl)-2-methyl-6-(5-(thiophen-3-yl)-4,5-dihydroisoxazol-3-yl)pyrimidine-4-carboxamide |
| G.1.32 | 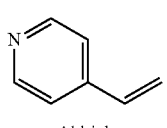<br>Aldrich | N-(4-Fluoro-3-methoxybenzyl)-2-methyl-6-(5-(pyridin-4-yl)-4,5-dihydroisoxazol-3-yl)pyrimidine-4-carboxamide |
| G.1.33 | 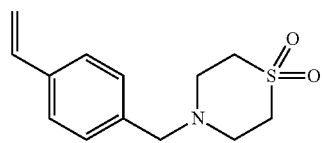<br>(Preparation #F.1.1) | 6-{5-[4-(1,1,1,-Dioxo-thiomorpholine-4-yl methyl)phenyl]-4,5-dihydro-isoxazol-3-yl}-2-methyl pyrimidine-4-carboxylate |
| G.1.34 | 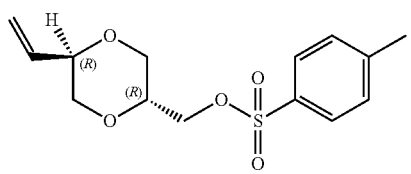<br>(Preparation #11) | N-(4-Fluoro-3-methoxybenzyl)-6-((R)-5-((2S,5S)-5-(hydroxymethyl)-1,4-dioxan-2-yl)-4,5-dihydroisoxazol-3-yl)-2-methylpyrimidine-4-carboxamide |
| G.1.35 |  | N-(4-Fluoro-3-methoxybenzyl)-6-((S)-5-((2S,5S)-5-(hydroxymethyl)-1,4-dioxan-2-yl)-4,5-dihydroisoxazol-3-yl)-2-methylpyrimidine-4-carboxamide |
| G.1.36 | 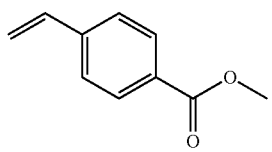<br>(Preparation #E.1.4) | N-(4-Fluoro-3-methoxybenzyl)-6-(5-(4-(2-hydroxyethyl-carbamoyl)phenyl)-4,5-dihydroisoxazol-3-yl)-2-methylpyrimidine-4-carboxamide |

TABLE G.1-continued

Examples of isoxazolines prepared by General Procedures G

| G.1.37 | 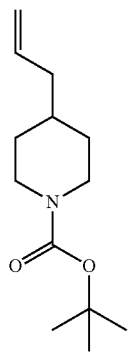 (Preparation #E.1.11) | 6-(5-((1-Acetylpiperidin-4-yl)methyl)-4,5-dihydroisoxazol-3-yl)-N-(4-fluoro-3-methoxybenzyl)-2-methylpyrimidine-4-carboxamide |
| --- | --- | --- |
| G.1.38 | 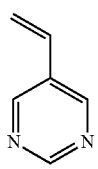 (Preparation #F.1.3) | N-(4-Fluoro-3-methoxybenzyl)-2-methyl-6-(5-(pyrimidin-5-yl)-4,5-dihydroisoxazol-3-yl)pyrimidine-4-carboxamide |
| G.1.39 | 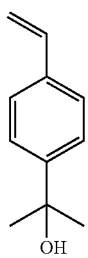 (Preparation #F.1.6) | N-(4-Fluoro-3-methoxybenzyl)-6-(5-(4-(2-hydroxypropan-2-yl)phenyl)-4,5-dihydroisoxazol-3-yl)-2-methylpyrimidine-4-carboxamide |
| G.1.40 | 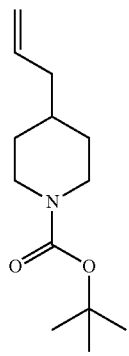 (Preparation #D.1.11) | N-(4-Fluoro-3-methoxybenzyl)-6-(5-((1-(2-hydroxyacetyl)-piperidin-4-yl)-methyl)-4,5-dihydroisoxazol-3-yl)-2-methyl-pyrimidine-4-carboxamide |

TABLE G.1-continued

Examples of isoxazolines prepared by General Procedures G

| | | | |
|---|---|---|---|
| G.1.41 | 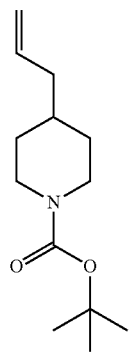<br>(Preparation #E.1.11) | | N-(4-Fluoro-3-methoxybenzyl)-2-methyl-6-(5-((1-(methylsulfonyl)-piperidin-4-yl)methyl)-4,5-dihydroisoxazol-3-yl)pyrimidine-4-carboxamide |
| G.1.42 | 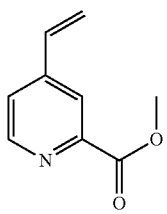<br>(Preparation #F.1.9) | | 6-(5-(2-Carbamoyl pyridin-4-yl)-4,5-dihydroisoxazol-3-yl)-N-(4-fluoro-3-methoxybenzyl)-2-methylpyrimidine-4-carboxamide |
| G1.43 | 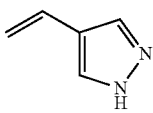<br>(Preparation #F.1.4) | | 6-(5-(1H-Pyrazol-4-yl)-4,5-dihydroisoxazol-3-yl)-N-(4-fluoro-3-methoxybenzyl)-2-methylpyrimidine-4-carboxamide |
| G.1.44 | 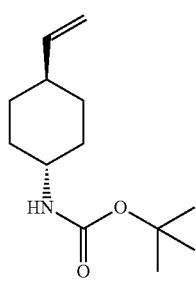<br>(Preparation #E.1.12) | | 6-(5-((1r,4r)-4-Acetamidocyclohexyl)-4,5-dihydroisoxazol-3-yl)-N-(4-fluoro-3-methoxybenzyl)-2-methylpyrimidine-4-carboxamide |
| G.1.45 | 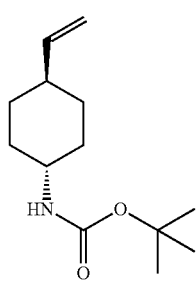<br>(Preparation #E.1.12) | | N-(4-Fluoro-3-methoxybenzyl)-2-methyl-6-(5-((1r,4r)-4-(methylsulfonamido)-cyclohexyl)-4,5-dihydroisoxazol-3-yl)pyrimidine-4-carboxamide |

TABLE G.1-continued

Examples of isoxazolines prepared by General Procedures G

| | | |
|---|---|---|
| G.1.46 | 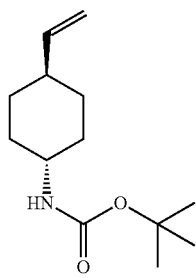<br>(Preparation #E.1.12) | N-(4-Fluoro-3-methoxybenzyl)-6-(5-((1r,4r)-4-(2-hydroxyacetamido)-cyclohexyl)-4,5-dihydroisoxazol-3-yl)-2-methyl-pyrimidine-4-carboxamide |
| G.1.47 | 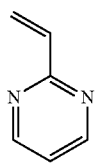<br>(Preparation #F.1.5) | N-(4-Fluoro-3-methoxybenzyl)-2-methyl-6-(5-(pyrimidin-2-yl)-4,5-dihydroisoxazol-3-yl)pyrimidine-4-carboxamide |
| G.1.48 | 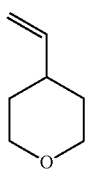<br>(Preparation #E.1.13) | N-(4-Fluoro-3-methoxybenzyl)-2-methyl-6-(5-(tetrahydro-2H-pyran-4-yl)-4,5-dihydroisoxazol-3-yl)pyrimidine-4-carboxamide |
| G.1.49 | 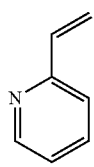<br>Aldrich | N-(4-Fluoro-3-methylbenzyl)-2-methyl-6-(5-(pyridin-2-yl)-4,5-dihydroisoxazol-3-yl)pyrimidine-4-carboxamide |
| G.1.50 | 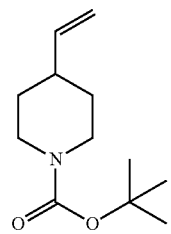<br>(Preparation #E.1.2) | 6-(5-(1-Acetylpiperidin-4-yl)-4,5-dihydroisoxazol-3-yl)-N-(4-fluoro-3-methylbenzyl)-2-methylpyrimidine-4-carboxamide |
| G.1.51 | 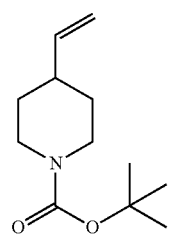<br>(Preparation #E.1.2) | N-(4-Fluoro-3-methylbenzyl)-2-methyl-6-(5-(1-(methyl-sulfonyl)piperidin-4-yl)-4,5-dihydroisoxazol-3-yl)pyrimidine-4-carboxamide |

TABLE G.1-continued

Examples of isoxazolines prepared by General Procedures G

| G.1.52 | 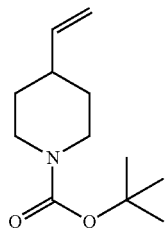 (Preparation #E.1.2) | N-(4-Fluoro-3-methylbenzyl)-6-(5-(1-(2-hydroxyacetyl)-piperidin-4-yl)-4,5-dihydroisoxazol-3-yl)-2-methylpyrimidine-4-carboxamide |
| --- | --- | --- |
| G.1.53 | 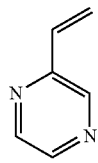 Aldrich | N-(4-Fluoro-3-methoxybenzyl)-2-methyl-6-(5-(pyrazin-2-yl)-4,5-dihydroisoxazol-3-yl)pyrimidine-4-carboxamide |
| G.1.54 | 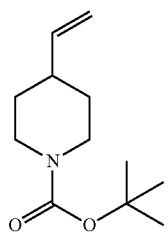 (Preparation #E.1.2) | N-(4-Fluoro-3-methoxybenzyl)-6-(5-(1-(2-hydroxy-2-methylpropanoyl)-piperidin-4-yl)-4,5-dihydroisoxazol-3-yl)-2-methylpyrimidine-4-carboxamide |
| G.1.55 | 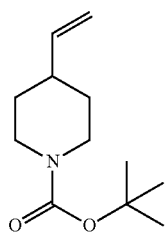 (Preparation #E.1.2) | 6-(5-(1-(Cyclopropyl-sulfonyl) piperidin-4-yl)-4,5-dihydro-isoxazol-3-yl)-N-(4-fluoro-3-methoxybenzyl)-2-methylpyrimidine-4-carboxamide |
| G.1.56 | 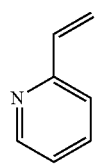 Aldrich | N-(3,4-Difluorobenzyl)-2-methyl-6-(5-(pyridin-2-yl)-4,5-dihydro-isoxazol-3-yl)pyrimidine-4-carboxamide |
| G.1.57 | 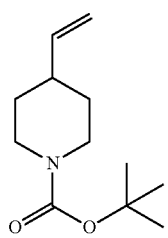 (Preparation #E.1.2) | 6-(5-(1-Acetyl-piperidin-4-yl)-4,5-dihydroisoxazol-3-yl)-N-(3,4-difluoro-benzyl)-2-methyl-pyrimidine-4-carboxamide |

TABLE G.1-continued

Examples of isoxazolines prepared by General Procedures G

| | | |
|---|---|---|
| G.1.58 | 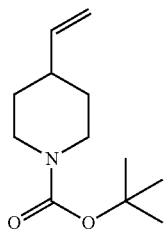<br>(Preparation #E.1.2) | N-(3,4-Difluorobenzyl)-2-methyl-6-(5-(1-(methylsulfonyl)piperidin-4-yl)-4,5-dihydroisoxazol-3-yl)pyrimidine-4-carboxamide |
| G.1.59 | 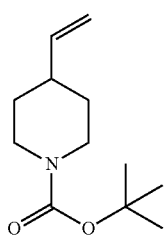<br>(Preparation #E.1.2) | N-(3,4-Difluorobenzyl)-6-(5-(1-(2-hydroxyacetyl)piperidin-4-yl)-4,5-dihydroisoxazol-3-yl)-2-methylpyrimidine-4-carboxamide |
| G.1.60 | 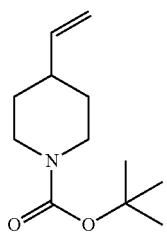<br>(Preparation #E.1.2) | 6-(5-(1-(Ethylsulfonyl)piperidin-4-yl)-4,5-dihydroisoxazol-3-yl)-N-(4-fluoro-3-methoxybenzyl)-2-methylpyrimidine-4-carboxamide |
| G.1.61 | 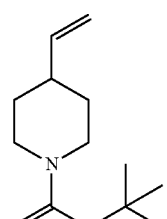<br>(Preparation #E.1.2) | N-(4-Fluoro-3-methoxybenzyl)-6-(5-(1-isobutyrylpiperidin-4-yl)-4,5-dihydroisoxazol-3-yl)-2-methylpyrimidine-4-carboxamide |
| G.1.62 | 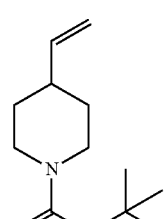<br>(Preparation #E.1.2) | N-(4-Fluoro-3-methoxybenzyl)-2-methyl-6-(5-(1-(propylsulfonyl)piperidin-4-yl)-4,5-dihydroisoxazol-3-yl)pyrimidine-4-carboxamide |
| G.1.63 | 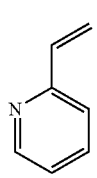<br>Aldrich | N-(4-Fluorobenzyl)-2-methyl-6-(5-(pyridin-2-yl)-4,5-dihydroisoxazol-3-yl)pyrimidine-4-carboxamide |

TABLE G.1-continued

Examples of isoxazolines prepared by General Procedures G

| | | |
|---|---|---|
| G.1.64 | 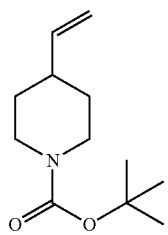<br>(Preparation #E.1.2) | 6-(5-(1-Acetylpiperidin-4-yl)-4,5-dihydroisoxazol-3-yl)-N-(3-chloro-4-fluorobenzyl)-2-methylpyrimidine-4-carboxamide |
| G.1.65 | 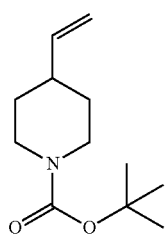<br>(Preparation #E.1.2) | N-(3-Chloro-4-fluorobenzyl)-6-(5-(1-(2-hydroxyacetyl)-piperidin-4-yl)-4,5-dihydroisoxazol-3-yl)-2-methylpyrimidine-4-carboxamide |
| G.1.66 | 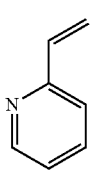<br>Aldrich | N-(3-Methoxybenzyl)-2-methyl-6-(5-(pyridin-2-yl)-4,5-dihydroisoxazol-3-yl)pyrimidine-4-carboxamide |
| G.1.67 | 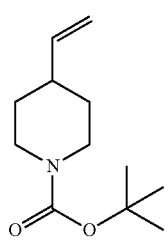<br>(Preparation #E.1.2) | 6-(5-(1-Acetylpiperidin-4-yl)-4,5-dihydroisoxazol-3-yl)-N-(4-fluorobenzyl)-2-methylpyrimidine-4-carboxamide |
| G.1.68 | 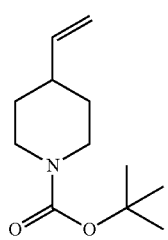<br>(Preparation #E.1.2) | N-(4-Fluorobenzyl)-2-methyl-6-(5-(1-(methylsulfonyl)piperidin-4-yl)-4,5-dihydroisoxazol-3-yl)pyrimidine-4-carboxamide |
| G.1.69 | 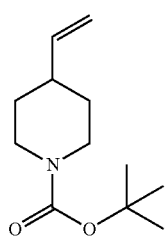<br>(Preparation #E.1.2) | N-(4-Fluorobenzyl)-6-(5-(1-(2-hydroxyacetyl)piperidin-4-yl)-4,5-dihydroisoxazol-3-yl)-2-methylpyrimidine-4-carboxamide |

TABLE G.1-continued

Examples of isoxazolines prepared by General Procedures G

G.1.70 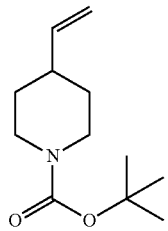
(Preparation #E.1.2)

6-(5-(1-Acetylpiperidin-4-yl)-4,5-dihydroisoxazol-3-yl)-N-(3-methoxybenzyl)-2-methylpyrimidine-4-carboxamide G.1.71 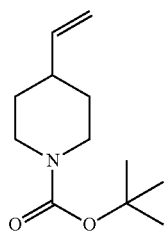
(Preparation #E.1.2)

N-(3-Methoxybenzyl)-2-methyl-6-(5-(1-(methylsulfonyl)piperidin-4-yl)-4,5-dihydroisoxazol-3-yl)pyrimidine-4-carboxamide G.1.72 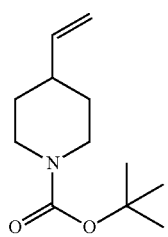
(Preparation #E.1.2)

6-(5-(1-(2-Hydroxyacetyl)-piperidin-4-yl)-4,5-dihydroisoxazol-3-yl)-N-(3-methoxybenzyl)-2-methylpyrimidine-4-carboxamide G.1.73 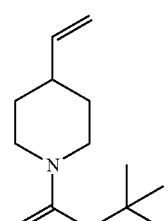
(Preparation #E.1.2)

6-(5-(1-(Cyclopropane-carbonyl)piperidin-4-yl)-4,5-dihydroisoxazol-3-yl)-N-(4-fluoro-3-methoxybenzyl)-2-methylpyrimidine-4-carboxamide G.1.74 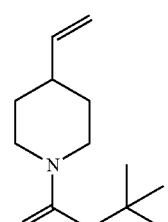
(Preparation #E.1.2)

6-(5-(1-(d\Dimethyl-carbamoyl)piperidin-4-yl)-4,5-dihydroisoxazol-3-yl)-N-(4-fluoro-3-methoxybenzyl)-2-methylpyrimidine-4-carboxamide TABLE G.1-continued Examples of isoxazolines prepared by General Procedures G

| G.1.75 | 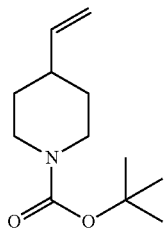<br>(Preparation #E.1.2) | 6-(5-(1-(Ethylcarbamoyl)-piperidin-4-yl)-4,5-dihydroisoxazol-3-yl)-N-(4-fluoro-3-methoxybenzyl)-2-methylpyrimidine-4-carboxamide |
| --- | --- | --- |
| G.1.76 | 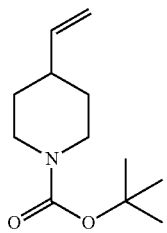<br>(Preparation #E.1.2) | 6-(5-(1-(2-(Dimethylamino)-acetyl)piperidin-4-yl)-4,5-dihydroisoxazol-3-yl)-N-(4-fluoro-3-methoxybenzyl)-2-methylpyrimidine-4-carboxamide. Trifluoroacetic acid salt |
| G.1.77 | 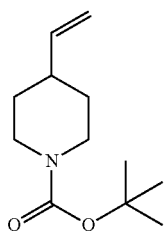<br>(Preparation #E.1.2) | 6-(5-(1-(2-Acetamidoacetyl)-piperidin-4-yl)-4,5-dihydroisoxazol-3-yl)-N-(4-fluoro-3-methoxybenzyl)-2-methylpyrimidine-4-carboxamide |
| G.1.78 | 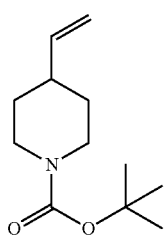<br>(Preparation #E.1.2) | N-(4-Fluoro-3-methoxybenzyl)-6-(5-(1-(isopropylsulfonyl)-piperidin-4-yl)-4,5-dihydroisoxazol-3-yl)-2-methylpyrimidine-4-carboxamide |
| G.1.79 | 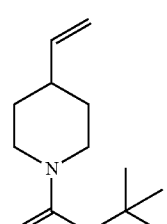<br>(Preparation #E.1.2) | 6-(5-(1-(2-Cyanoacetyl)piperidin-4-yl)-4,5-dihydroisoxazol-3-yl)-N-(4-fluoro-3-methoxybenzyl)-2-methylpyrimidine-4-carboxamide |

TABLE G.1-continued

Examples of isoxazolines prepared by General Procedures G

G.1.80 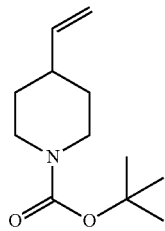
(Preparation #E.1.2)
N-(4-Fluoro-3-methoxybenzyl)-6-(5-(1-(2-methoxyacetyl)piperidin-4-yl)-4,5-dihydroisoxazol-3-yl)-2-methylpyrimidine-4-carboxamide G.1.81 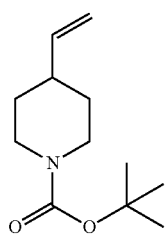
(Preparation #E.1.2)
6-(5-(1-(Cyclobutanecarbonyl)-piperidin-4-yl)-4,5-dihydroisoxazol-3-yl)-N-(4-fluoro-3-methoxybenzyl)-2-methylpyrimidine-4-carboxamide G.1.82 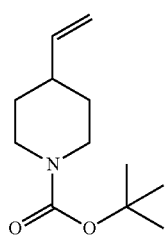
(Preparation #E.1.2)
N-(4-Fluoro-3-methoxybenzyl)-2-methyl-6-(5-(1-(2-(methylsulfonamido)-acetyl)piperidin-4-yl)-4,5-dihydroisoxazol-3-yl)pyrimidine-4-carboxamide G-1.83 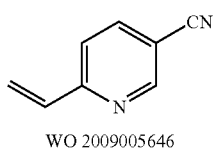
WO 2009005646
6-(5-(5-Cyanopyridin-2-yl)-4,5-dihydroisoxazol-3-yl)-N-(4-fluoro-3-methoxybenzyl)-2-methylpyrimidine-4-carboxamide G.1.84 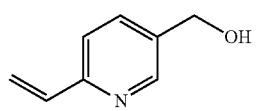
(Preparation #F.1.10)
N-(4-Fluoro-3-methoxybenzyl)-6-(5-(5-(hydroxymethyl)-pyridin-2-yl)-4,5-dihydroisoxazol-3-yl)-2-methylpyrimidine-4-carboxamide G.1.85 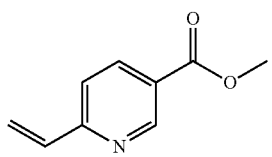
(Preparation #F.1.14)
N-(4-Fluoro-3-methoxybenzyl)-2-methyl-6-(5-(5-(methylcarbamoyl)pyridin-2-yl)-4,5-dihydroisoxazol-3-yl)pyrimidine-4-carboxamide TABLE G.1-continued Examples of isoxazolines prepared by General Procedures G

| | | |
|---|---|---|
| G.1.86 | 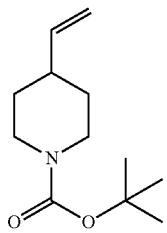<br>(Preparation #E.1.2) | N-(4-Fluoro-3-methoxybenzyl)-6-(5-(1-(2-hydroxyethyl-carbamoyl)piperidin-4-yl)-4,5-dihydroisoxazol-3-yl)-2-methylpyrimidine-4-carboxamide |
| G.1.87 | 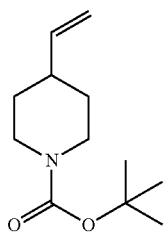<br>(Preparation #E.1.2) | N-(4-Fluoro-3-methoxybenzyl)-2-methyl-6-(5-(1-(2-(3-methylureido)acetyl)-piperidin-4-yl)-4,5-dihydroisoxazol-3-yl)pyrimidine-4-carboxamide |
| G.1.88 | 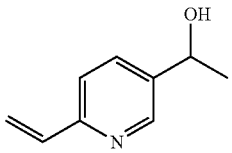<br>(Preparation #F.1.11) | N-(4-Fluoro-3-methoxybenzyl)-6-(5-(5-(1-hydroxyethyl)-pyridin-2-yl)-4,5-dihydroisoxazol-3-yl)-2-methylpyrimidine-4-carboxamide |
| G.1.89 | 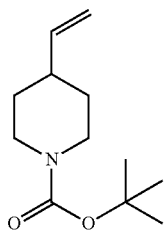<br>(Preparation #E.1.2) | N-(4-Fluoro-3-methoxybenzyl)-6-(5-(1-((2-hydroxyethyl)-(methyl)carbamoyl)-piperidin-4-yl)-4,5-dihydroisoxazol-3-yl)-2-methyl-pyrimidine-4-carboxamide |
| G.1.90 | 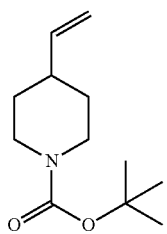<br>(Preparation #E.1.2) | N-(4-Fluoro-3-methoxybenzyl)-6-(5-(1-(isopropylcarbamoyl)-piperidin-4-yl)-4,5-dihydroisoxazol-3-yl)-2-methylpyrimidine-4-carboxamide |
| G.1.91 | 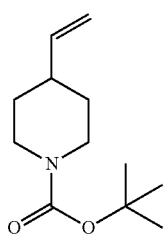<br>(Preparation #E.1.2) | N-(4-Fluoro-3-methoxybenzyl)-2-methyl-6-(5-(1-(1-methyl-1H-imidazol-2-ylsulfonyl)piperidin-4-yl)-4,5-dihydroisoxazol-3-yl)pyrimidine-4-carboxamide |

TABLE G.1-continued

Examples of isoxazolines prepared by General Procedures G

| G.1.92 | 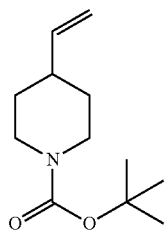 (Preparation #E.1.2) | N-(4-Fluoro-3-methoxybenzyl)-2-methyl-6-(5-(1-(1-methyl-1H-imidazol-4-ylsulfonyl)piperidin-4-yl)-4,5-dihydroisoxazol-3-yl)pyrimidine-4-carboxamide |
| --- | --- | --- |
| G.1.93 | 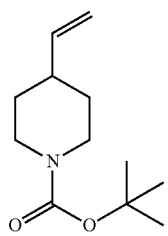 (Preparation #E.1.2) | 6-(5-(1-(1,2-Dimethyl-1H-imidazol-4-ylsulfonyl)piperidin-4-yl)-4,5-dihydroisoxazol-3-yl)-N-(4-fluoro-3-methoxybenzyl)-2-methylpyrimidine-4-carboxamide |
| G.1.94 | 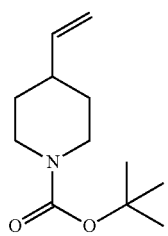 (Preparation #E.1.2) | 6-(5-(1-(3,5-Dimethylisoxazol-4-ylsulfonyl)piperidin-4-yl)-4,5-dihydroisoxazol-3-yl)-N-(4-fluoro-3-methoxybenzyl)-2-methylpyrimidine-4-carboxamide |
| G.1.95 | 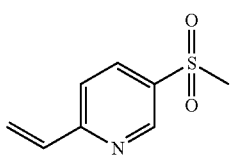 (Preparation #F.1.16) | N-(4-Fluoro-3-methoxybenzyl)-2-methyl-6-(5-(5-(methylsulfonyl)-pyridin-2-yl)-4,5-dihydroisoxazol-3-yl)pyrimidine-4-carboxamide |
| G.1.96 | 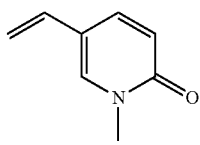 (Preparation #F.1.13) | N-(4-Fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide |
| G.1.97 | 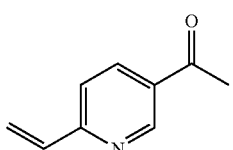 (Preparation #F.1.12) | 6-(5-(5-Acetyl-pyridin-2-yl)-4,5-dihydroisoxazol-3-yl)-N-(4-fluoro-3-methoxybenzyl)-2-methylpyrimidine-4-carboxamide |

TABLE G.1-continued

Examples of isoxazolines prepared by General Procedures G

| | | |
|---|---|---|
| G.1.98 | 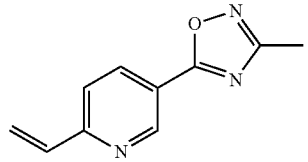<br>(Preparation #AB.1) | N-(4-Fluoro-3-methoxybenzyl)-2-methyl-6-(5-(5-(3-methyl-1,2,4-oxadiazol-5-yl)pyridin-2-yl)-4,5-dihydroisoxazol-3-yl)pyrimidine-4-carboxamide 2,2,2-trifluoroacetate |
| G.1.99 | 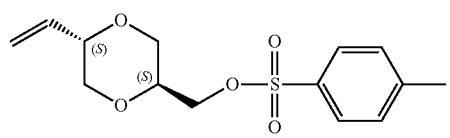<br>(Preparation #11) | ((2S,5R)-5-(3-(6-(3-Chloro-4-fluorobenzyl-carbamoyl)-2-methyl-pyrimidin-4-yl)-4,5-dihydroisoxazol-5-yl)-1,4-dioxan-2-yl)methyl 4-methyl-benzenesulfonate |
| G.1.100 | 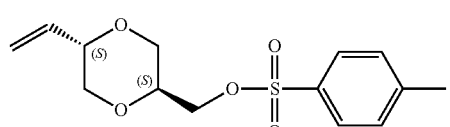<br>(Preparation #11) | N-(3-Chloro-4-fluorobenzyl)-6-((S)-5-((2R,5R)-5-(hydroxy-methyl)-1,4-dioxan-2-yl)-4,5-dihydroisoxazol-3-yl)-2-methylpyrimidine-4-carboxamide |
| G.1.101 | 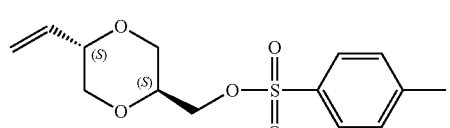<br>(Preparation #11) | N-(3-Chloro-4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide |
| G.1.102 | 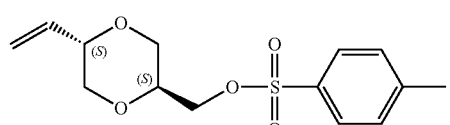<br>(Preparation #11) | N-(4-Fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide |
| G.1.103 | 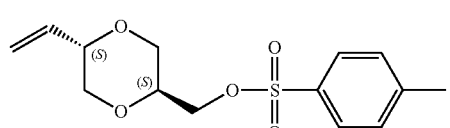<br>(Preparation #11) | N-(4-Fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide |
| G.1.104 | 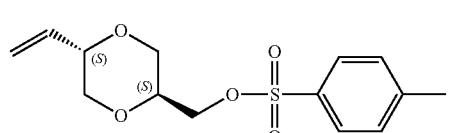<br>(Preparation #11) | 6-((S)-5-((2R,5R)-5-(Hydroxymethyl)-1,4-dioxan-2-yl)-4,5-dihydroisoxazol-3-yl)-N-(4-methoxybenzyl)-2-methylpyrimidine-4-carboxamide |
| G.1.105 | 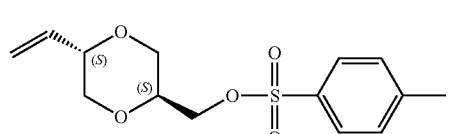<br>(Preparation #11) | 6-((R)-5-((2R,5R)-5-(Hydroxymethyl)-1,4-dioxan-2-yl)-4,5-dihydroisoxazol-3-yl)-N-(4-methoxybenzyl)-2-methylpyrimidine-4-carboxamide |

TABLE G.1-continued

Examples of isoxazolines prepared by General Procedures G

| | | |
|---|---|---|
| G.1.106 | (Preparation #11) | 6-(5-((2R,5R)-5-(Hydroxymethyl)-1,4-dioxan-2-yl)-4,5-dihydroisoxazol-3-yl)-N-(3-methoxybenzyl)-2-methylpyrimidine-4-carboxamide |
| G.1.107 | (Preparation E.1.4) | Methyl 4-(3-(2-(3-methoxybenzylcarbamoyl)-pyridin-4-yl)-4,5-dihydroisoxazol-5-yl)benzoate |
| G.1.108 | (Preparation E.1.5) | N-(3-Methoxybenzyl)-4-(5-(4-methoxyphenyl)-4,5-dihydroisoxazol-3-yl)picolinamide |
| G.1.109 | | 4-(5-(4-Chlorophenyl)-5-methyl-4,5-dihydroisoxazol-3-yl)-N-(3-methoxybenzyl)-picolinamide |
| G.1.110 | (Preparation E.1.4) | 4-(3-(2-(3-Methoxy-benzylcarbamoyl)-pyridin-4-yl)-4,5-dihydroisoxazol-5-yl)benzoic acid |
| G.1.111 | | 4-(5-(4-((Dimethyl-amino)methyl)phenyl)-4,5-dihydroisoxazol-3-yl)-N-(4-methoxybenzyl)picolinamide |
| G.1.112 | (Preparation E.1.4) | 4-(3-(2-(4-Methoxy-benzylcarbamoyl)-pyridin-4-yl)-4,5-dihydroisoxazol-5-yl)benzoic acid |
| G.1.113 | | 4-(5-(4-Chlorophenyl)-5-methyl-4,5-dihydroisoxazol-3-yl)-N-(4-methoxybenzyl)picolinamide |
| G.1.114 | Aldrich | N-(4-Methoxybenzyl)-4-(5-methyl-5-phenyl-4,5-dihydroisoxazol-3-yl)picolinamide |
| G.1.115 | Aldrich | N-(4-Methoxybenzyl)-4-(5-(pyrazin-2-yl)-4,5-dihydroisoxazol-3-yl)picolinamide |
| G.1.116 | (Preparation E.1.5) | N-(4-Methoxybenzyl)-4-(5-methoxyphenyl)-4,5-dihydroisoxazol-3-yl)picolinamide |

| | | |
|---|---|---|
| G.1.117 | 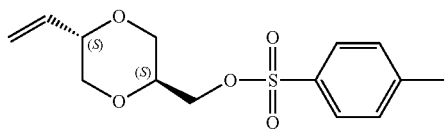<br>(Preparation #11) | 6-((S)-5-((2R,5R)-5-(Hydroxymethyl)-1,4-dioxan-2-yl)-4,5-dihydroisoxazol-3-yl)-N-(3-methoxybenzyl)-2-methylpyrimidine-4-carboxamide |
| G.1.118 | | 6-((R)-5-((2S,5S)-5-(Hydroxymethyl)-1,4-dioxan-2-yl)-4,5-dihydroisoxazol-3-yl)-N-(3-methoxybenzyl)-2-methylpyrimidine-4-carboxamide |
| G.1.119 | 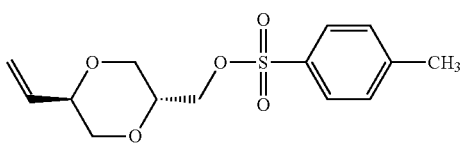<br>(Preparation #11) | 6-((S)-5-((2S,5S)-5-(Hydroxymethyl)-1,4-dioxan-2-yl)-4,5-dihydroisoxazol-3-yl)-N-(3-methoxybenzyl)-2-methylpyrimidine-4-carboxamide |
| G.1.120 | 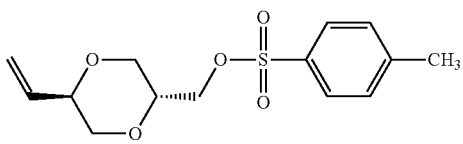<br>(Preparation #11) | N-(4-Fluorobenzyl)-6-((R)-5-((2S,5S)-5-(hydroxymethyl)-1,4-dioxan-2-yl)-4,5-dihydroisoxazol-3-yl)-2-methylpyrimidine-4-carboxamide |
| G.1.121 | | N-(4-Fluorobenzyl)-6-((S)-5-((2S,5S)-5-(hydroxymethyl)-1,4-dioxan-2-yl)-4,5-dihydroisoxazol-3-yl)-2-methylpyrimidine-4-carboxamide |
| G.1.122 | 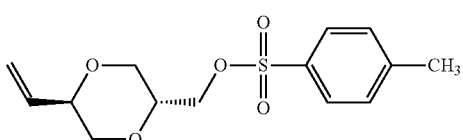<br>(Preparation #11) | 6-((R)-5-((2S,5S)-5-(Hydroxymethyl)-1,4-dioxan-2-yl)-4,5-dihydroisoxazol-3-yl)-N-(4-Methoxybenzyl)-2-methylpyrimidine-4-carboxamide |
| G.1.123 | | 6-((S)-5-((2S,5S)-5-(Hydroxymethyl)-1,4-dioxan-2-yl)-4,5-dihydroisoxazol-3-yl)-N-(4-methoxybenzyl)-2-methylpyrimidine-4-carboxamide |
| G.1.124 | 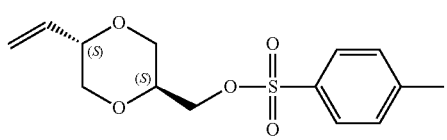<br>(Preparation #11) | N-(4-Fluoro-3-methoxybenzyl)-2-methyl-6-((S)-5-((2R,5R)-5-(methylsulfon-amidomethyl)-1,4-dioxan-2-yl)-4,5-dihydroisoxazol-3-yl)pyrimidine-4-carboxamide |

TABLE G.1-continued

Examples of isoxazolines prepared by General Procedures G

| | | |
|---|---|---|
| G.1.125 | 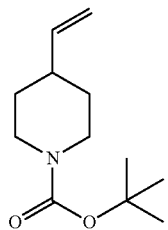<br>(Preparation #E.1.2) | N-(4-Fluoro-3-methoxybenzyl)-2-methyl-6-(5-(1-(thiazol-2-ylcarbamoyl)piperidin-4-yl)-4,5-dihydroisoxazol-3-yl)pyrimidine-4-carboxamide |
| G.1.126 | 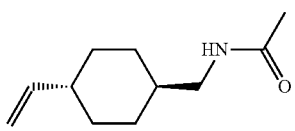<br>(Preparation E.1.20) | 6-(5-((1r,4r)-4-(Acetamidomethyl)cyclohexyl)-4,5-dihydroisoxazol-3-yl)-N-(4-fluoro-3-methoxybenzyl)-2-methylpyrimidine-4-carboxamide |
| G.1.127 | 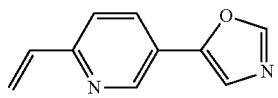<br>(Preparation F.1.17) | N-(4-Fluoro-3-methoxybenzyl)-2-methyl-6-(5-(5-(oxazol-5-yl)pyridin-2-yl)-4,5-dihydroisoxazol-3-yl)pyrimidine-4-carboxamide |
| G.1.128 | 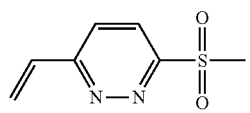<br>(Preparation F.1.18) | N-(4-Fluoro-3-methoxybenzyl)-2-methyl-6-(5-(6-(methylsulfonyl)pyridazin-3-yl)-4,5-dihydroisoxazol-3-yl)pyrimidine-4-carboxamide |
| G.1.129 | 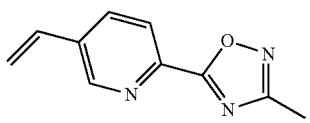<br>(Preparation #X.1.1) | N-(4-Fluoro-3-methoxybenzyl)-2-methyl-6-(5-(6-(3-methyl-1,2,4-oxadiazol-5-yl)pyridin-3-yl)-4,5-dihydroisoxazol-3-yl)pyrimidine-4-carboxamide |
| G.1.130 | 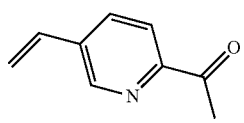<br>(Preparation F.1.19) | 6-(5-(6-Acetylpyridin-3-yl)-4,5-dihydroisoxazol-3-yl)-N-(4-fluoro-3-methoxybenzyl)-2-methylpyrimidine-4-carboxamide |
| G.1.131 | 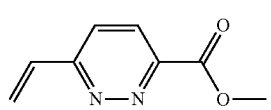<br>(Preparation F.1.20) | 6-(3-(6-((4-Fluoro-3-methoxybenzyl)carbamoyl)-2-methylpyrimidin-4-yl)-4,5-dihydroisoxazol-5-yl)pyridazine-3-carboxamide 2,2,2-trifluoroacetate |
| G.1.132 | 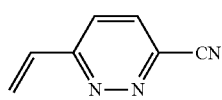<br>(Preparation F.1.21) | 6-(5-(6-Cyanopyridazin-3-yl)-4,5-dihydroisoxazol-3-yl)-N-(4-fluoro-3-methoxybenzyl)-2-methylpyrimidine-4-carboxamide |

TABLE G.1-continued

Examples of isoxazolines prepared by General Procedures G

| | | |
|---|---|---|
| G.1.133 | 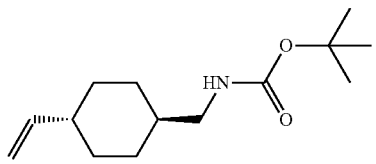<br>(Preparation #E.1.20) | N-(4-Fluoro-3-methoxybenzyl)-6-(5-((1r,4r)-4-((2-hydroxyacetamido)methyl)cyclohexyl)-4,5-dihydroisoxazol-3-yl)-2-methylpyrimidine-4-carboxamide |
| G.1.134 | 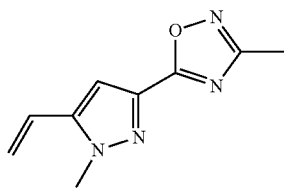<br>(Preparation #X.1.2) | N-(4-Fluoro-3-methoxybenzyl)-2-methyl-6-(5-(1-methyl-3-(3-methyl-1,2,4-oxadiazol-5-yl)-1H-pyrazol-5-yl)-4,5-dihydroisoxazol-3-yl)pyrimidine-4-carboxamide |
| G.1.135 | 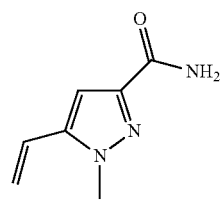<br>(Preparation F.1.22) | 6-(5-(3-Carbamoyl-1-methyl-1H-pyrazol-5-yl)-4,5-dihydroisoxazol-3-yl)-N-(4-fluoro-3-methoxybenzyl)-2-methylpyrimidine-4-carboxamide |
| G.1.136 | 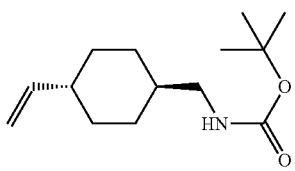<br>(Preparation #E.1.20) | 6-(5-((1r,4r)-4-((2-Cyanoacetamido)methyl)cyclohexyl)-4,5-dihydroisoxazol-3-yl)-N-(4-fluoro-3-methoxybenzyl)-2-methylpyrimidine-4-carboxamide |
| G1.137 | 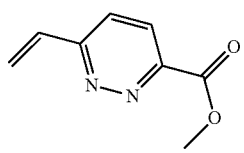<br>(Preparation F.1.20) | 6-(3-(6-((4-Fluoro-3-methoxybenzyl)carbamoyl)-2-methylpyrimidin-4-yl)-4,5-dihydroisoxazol-5-yl)-N-methylpyridazine-3-carboxamide |
| G.1.138 | 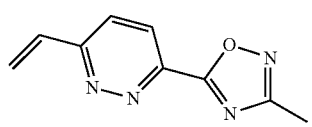<br>(Preparation #X.1.3) | N-(4-Fluoro-3-methoxybenzyl)-2-methyl-6-(5-(6-(3-methyl-1,2,4-oxadiazol-5-yl)pyridazin-3-yl)-4,5-dihydroisoxazol-3-yl)pyrimidine-4-carboxamide |
| G.1.139 | 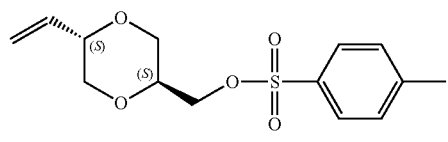<br>(Preparation E.1.17a) | N-(4-Fluoro-3-methoxybenzyl)-6-((S)-5-((2R,5R)-5-((2-hydroxyacetamido)methyl)-1,4-dioxan-2-yl)-4,5-dihydroisoxazol-3-yl)-2-methylpyrimidine-4-carboxamide |

TABLE G.1-continued

Examples of isoxazolines prepared by General Procedures G

| | | |
|---|---|---|
| G.1.140 | (Preparation F.1.23) | N-(4-Fluoro-3-methoxybenzyl)-2-methyl-6-(5-(6-(oxazol-5-yl)pyridin-3-yl)-4,5-dihydroisoxazol-3-yl)pyrimidine-4-carboxamide |
| G.1.141 | (preparation F.1.24) | N-(4-Fluoro-3-methoxybenzyl)-6-(5-(6-(hydroxymethyl)pyridin-3-yl)-4,5-dihydroisoxazol-3-yl)-2-methylpyrimidine-4-carboxamide |
| G.1.142 | (Preparation #E.1.12) | N-(4-Fluoro-3-methoxybenzyl)-6-(5-((1r,4r)-4-(3-(2-hydroxyethyl)-ureido)cyclohexyl)-4,5-dihydroisoxazol-3-yl)-2-methylpyrimidine-4-carboxamide |
| G.1.143 | (Preparation #E.1.12) | N-(4-Fluoro-3-methoxybenzyl)-6-(5-((1r,4r)-4-(3-(2-hydroxyethyl)-3-methylureido)-cyclohexyl)-4,5-dihydroisoxazol-3-yl)-2-methylpyrimidine-4-carboxamide |
| G.1.144 | (Preparation #F.1.25) | N-(4-Fluoro-3-methoxybenzyl)-2-methyl-6-(5-(5-(methylsulfonyl)pyrazin-2-yl)-4,5-dihydroisoxazol-3-yl)pyrimidine-4-carboxamide |
| G.1.145 | (Preparation #F.1.26) | 6-(5-(6-Cyanopyridin-3-yl)-4,5-dihydroisoxazol-3-yl)-N-(4-fluoro-3-methoxybenzyl)-2-methylpyrimidine-4-carboxamide |
| G.1.146 | (Preparation #E.1.2) | 6-(5-(1-(3-(Dimethylamino)propanoyl)piperidin-4-yl)-4,5-dihydroisoxazol-3-yl)-N-(4-fluoro-3-methoxybenzyl)-2-methylpyrimidine-4-carboxamide |
| G.1.147 | (Preparation #11) | N-(4-Fluoro-3-methylbenzyl)-6-((S)-5-((2R,5R)-5-(hydroxymethyl)-1,4-dioxan-2-yl)-4,5-dihydroisoxazol-3-yl)-2-methylpyrimidine-4-carboxamide |
| G.1.148 | | N-(4-Fluoro-3-methylbenzyl)-6-((R)-5-((2R,5R)-5-(hydroxymethyl)-1,4-dioxan-2-yl)-4,5-dihydroisoxazol-3-yl)-2-methylpyrimidine-4-carboxamide |

TABLE G.1-continued

Examples of isoxazolines prepared by General Procedures G

| | | |
|---|---|---|
| G.1.149 | 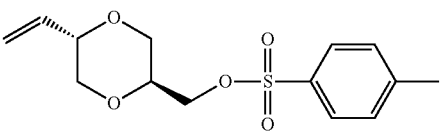<br>(Preparation #11) | N-(3,4-Difluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide |
| G.1.150 | | N-(3,4-Difluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide |
| G.1.151 | 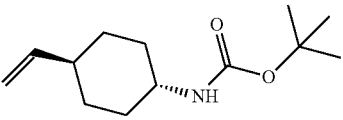<br>(Preparation #E.1.12) | N-(4-Fluoro-3-methoxybenzyl)-2-methyl-6-(5-((1r,4r)-4-(3-methylureido)-cyclohexyl)-4,5-dihydroisoxazol-3-yl)pyrimidine-4-carboxamide |
| G.1.152 | 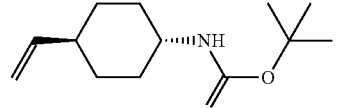<br>(Preparation #E.1.12) | 6-(5-((1r,4r)-4-(3,3-Dimethylureido)-cyclohexyl)-4,5-dihydroisoxazol-3-yl)-N-(4-fluoro-3-methoxybenzyl)-2-methylpyrimidine-4-carboxamide |
| G.1.153 | 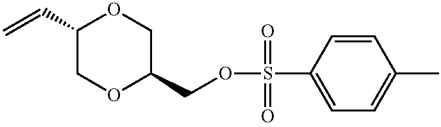<br>(Preparation #11) | N-(3,4-Dichlorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide |
| G.1.154 | 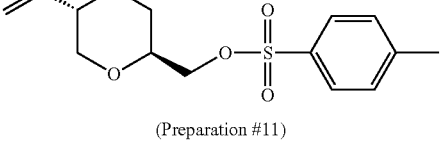<br>(Preparation #11) | N-(3,4-Dichlorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide |
| G.1.155 | 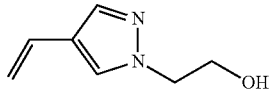<br>(Preparation #F.1.27) | N-(4-Fluoro-3-methoxybenzyl)-6-(5-(1-(2-hydroxyethyl)-1H-pyrazol-4-yl)-4,5-dihydroisoxazol-3-yl)-2-methylpyrimidine-4-carboxamide |
| G.1.156 | 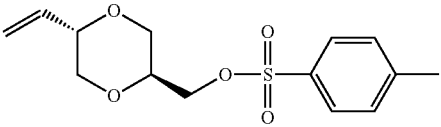<br>(Preparation #11) | 6-((S)-5-((2R,5R)-5-((2-Cyanoacetamido)methyl)-1,4-dioxan-2-yl)-4,5-dihydroisoxazol-3-yl)-N-(4-fluoro-3-methoxybenzyl)-2-methylpyrimidine-4-carboxamide |
| G.1.157 | 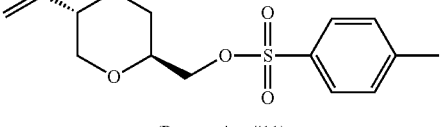<br>(Preparation #11) | N-(4-Fluoro-3-methoxybenzyl)-6-((S)-5-((2R,5R)-5-((2-hydroxy-2-methylpropanamido)methyl)-1,4-dioxan-2-yl)-4,5-dihydroisoxazol-3-yl)-2-methylpyrimidine-4-carboxamide |

TABLE G.1-continued

Examples of isoxazolines prepared by General Procedures G

| | | |
|---|---|---|
| G.1.158 | (Preparation #11) | N-(4-Fluoro-3-methoxybenzyl)-2-methyl-6-((S)-5-((2R,5R)-5-((3-methylureido)methyl)-1,4-dioxan-2-yl)-4,5-dihydroisoxazol-3-yl)pyrimidine-4-carboxamide |
| G.1.159 | (Preparation #11) | 6-((S)-5-((2R,5R)-5-((3,3-Dimethylureido)methyl)-1,4-dioxan-2-yl)-4,5-dihydroisoxazol-3-yl)-N-(4-fluoro-3-methoxybenzyl)-2-methylpyrimidine-4-carboxamide |
| G.1.160 | (Preparation #E.1.12) | 6-(5-((1r,4r)-4-(2-(Dimethylamino)acetamido)cyclohexyl)-4,5-dihydroisoxazol-3-yl)-N-(4-fluoro-3-methoxybenzyl)-2-methylpyrimidine-4-carboxamide |
| G.1.161 | (Preparation #F.1.28) | 6-(5-(1H-Pyrazolo[3,4-b]pyridin-5-yl)-4,5-dihydroisoxazol-3-yl)-N-(4-fluoro-3-methoxybenzyl)-2-methylpyrimidine-4-carboxamide |
| G.1.162 | (Preparation #26) | N-(4-Fluoro-3-methoxybenzyl)-2-methyl-6-(5-(1-methyl-1H-pyrazolo[3,4-b]pyridin-5-yl)-4,5-dihydroisoxazol-3-yl)pyrimidine-4-carboxamide |
| G.1.163 | (Preparation #11) | N-(4-Fluoro-3-methoxybenzyl)-6-((S)-5-((2R,5S)-5-(2-hydroxypropan-2-yl)-1,4-dioxan-2-yl)-4,5-dihydroisoxazol-3-yl)-2-methylpyrimidine-4-carboxamide |
| G.1.164 | (Preparation #11) | N-(4-Fluoro-3-methoxybenzyl)-2-methyl-6-((S)-5-((2R,5S)-5-(methylcarbamoyl)-1,4-dioxan-2-yl)-4,5-dihydroisoxazol-3-yl)pyrimidine-4-carboxamide |
| G.1.165 | (Preparation #E.1.21) | N-(4-Fluoro-3-methoxybenzyl)-2-methyl-6-(5-((1r,4r)-4-(methylcarbamoyl)cyclohexyl)-4,5-dihydroisoxazol-3-yl)pyrimidine-4-carboxamide 2,2,2-trifluoroacetate |
| G.1.166 | (Preparation #E.1.21) | 6-(5-((1r,4r)-4-Carbamoylcyclohexyl)-4,5-dihydroisoxazol-3-yl)-N-(4-fluoro-3-methoxybenzyl)-2-methylpyrimidine-4-carboxamide |

TABLE G.1-continued

Examples of isoxazolines prepared by General Procedures G

| G.1.167 | 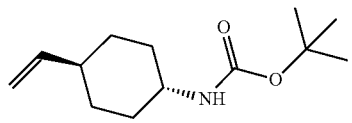<br>(Preparation #E.1.12) | N-(4-Fluoro-3-methoxybenzyl)-6-(5-((1r,4r)-4-(2-hydroxy-2-methylpropanamido)cyclohexyl)-4,5-dihydroisoxazol-3-yl)-2-methylpyrimidine-4-carboxamide |
| --- | --- | --- |
| G.1.168 | 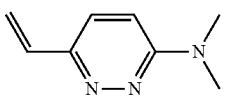<br>(Preparation #F.1.30) | 6-(5-(6-(Dimethylamino)pyridazin-3-yl)-4,5-dihydroisoxazol-3-yl)-N-(4-fluoro-3-methoxybenzyl)-2-methylpyrimidine-4-carboxamide 2,2,2-trifluoroacetate |
| G.1.169 | 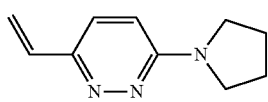<br>(Preparation #F.1.31) | N-(4-Fluoro-3-methoxybenzyl)-2-methyl-6-(5-(6-(pyrrolidin-1-yl)pyridazin-3-yl)-4,5-dihydroisoxazol-3-yl)pyrimidine-4-carboxamide 2,2,2-trifluoroacetate |
| G.1.170 | 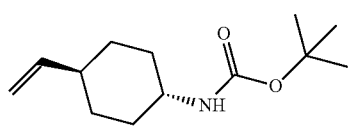<br>(Preparation #E.1.12) | 6-(5-((1r,4r)-4-(3-(1,3-Dihydroxypropan-2-yl)ureido)cyclohexyl)-4,5-dihydroisoxazol-3-yl)-N-(4-fluoro-3-methoxybenzyl)-2-methylpyrimidine-4-carboxamide |
| G.1.171 | 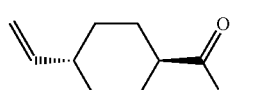<br>(Preparation #E.1.21) | N-(4-Fluoro-3-methoxybenzyl)-6-(5-((1r,4r)-4-((2-hydroxyethyl)carbamoyl)cyclohexyl)-4,5-dihydroisoxazol-3-yl)-2-methylpyrimidine-4-carboxamide |
| G.1.172 | 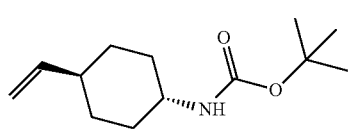<br>(Preparation #E.1.12) | 6-(5-((1r,4r)-4-(3-(2,3-Dihydroxypropyl)-3-methylureido)cyclohexyl)-4,5-dihydroisoxazol-3-yl)-N-(4-fluoro-3-methoxybenzyl)-2-methylpyrimidine-4-carboxamide |
| G.1.173 | 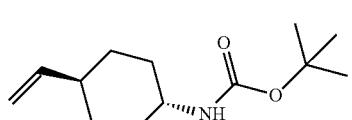<br>(Preparation #E.1.12) | 6-(5-((1r,4r)-4-Acetamidocyclohexyl)-4,5-dihydroisoxazol-3-yl)-N-(4-fluoro-3-methylbenzyl)-2-methylpyrimidine-4-carboxamide |
| G.1.174 | 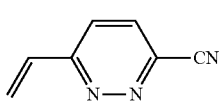<br>(Preparation #F.1.21) | 6-(5-(6-Cyanopyridazin-3-yl)-4,5-dihydroisoxazol-3-yl)-N-(4-fluoro-3-methylbenzyl)-2-methylpyrimidine-4-carboxamide |
| G.1.175 | 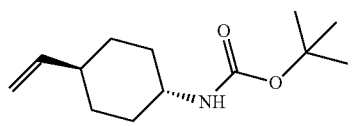<br>(Preparation #E.1.12) | N-(4-Fluoro-3-methoxybenzyl)-2-methyl-6-(5-((1r,4r)-4-(2-(methylamino)acetamido)cyclohexyl)-4,5-dihydroisoxazol-3-yl)pyrimidine-4-carboxamide |

TABLE G.1-continued

Examples of isoxazolines prepared by General Procedures G

G.1.176 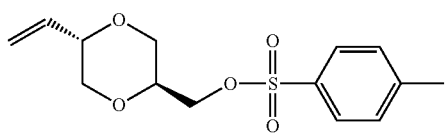

(Preparation #11)

N-(4-Fluoro-3-methylbenzyl)-
2-methyl-6-((S)-5-((2R,5S)-
5-((methylsulfonyl)methyl)-
1,4-dioxan-2-yl)-4,5-
dihydroisoxazol-3-yl)
pyrimidine-4-carboxamide G.1.177 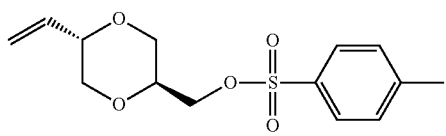

(Preparation #11)

6-((S)-5-((2R,5R)-5-
(Acetamidomethyl)-1,4-
dioxan-2-yl)-4,5-
dihydroisoxazol-3-yl)-
N-(4-fluoro-3-methylbenzyl)-
2-methylpyrimidine-4-
carboxamide G.1.178 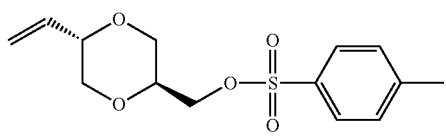

(Preparation #11)

6-((S)-5-((2R,5R)-5-
(Acetamidomethyl)-1,4-
dioxan-2-yl)-4,5-
dihydroisoxazol-3-yl)-N-
(3-chloro-4-fluorobenzyl)-
2-methylpyrimidine-4-
carboxamide G.1.179 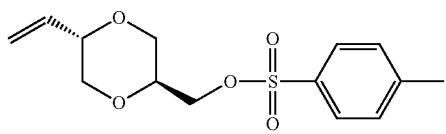

(Preparation #11)

N-(3-Chloro-4-
fluorobenzyl)-2-methyl-
6-((S)-5-((2R,5S)-5-
((methylsulfonyl)methyl)-
1,4-dioxan-2-yl)-4,5-
dihydroisoxazol-3-
yl)pyrimidine-4-
carboxamide G.1.180 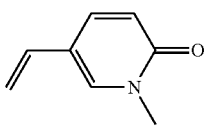

(Preparation #F.1.13)

N-(4-Fluoro-3-
methylbenzyl)-2-
methyl-6-(5-(1-methyl-6-
oxo-1,6-dihydropyridin-3-
yl)-4,5-dihydroisoxazol-3-
yl)pyrimidine-4-carboxamide
2,2,2-trifluoroacetate G.1.181 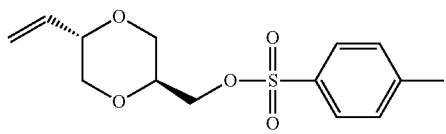

(Preparation #11)

6-((S)-5-((2R,5R)-5-
(Hydroxymethyl)-1,4-
dioxan-2-yl)-4,5-dihydro-
isoxazol-3-yl)-2-methyl-N-
(3-methylbenzyl)
pyrimidine-4-carboxamide

G.1.182

6-((R)-5-((2R,5R)-5-
(Hydroxymethyl)-1,4-
dioxan-2-yl)-4,5-
dihydroisoxazol-3-yl)-2-
methyl-N-(3-methylbenzyl)-
pyrimidine-4-carboxamide G.1.183 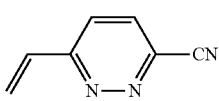

(Preparation #F.1.21)

6-(5-(6-Cyanopyridazin-
3-yl)-4,5-dihydroisoxazol-3-
yl)-N-(4-fluorobenzyl)-2-
methylpyrimidine-4-
carboxamide G.1.184 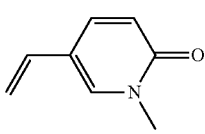

(Preparation #F.1.13)

N-(4-Fluorobenzyl)-2-
methyl-6-(5-(1-methyl-6-
oxo-1,6-dihydropyridin-
3-yl)-4,5-dihydroisoxazol-
3-yl)pyrimidine-4-
carboxamide 2,2,2-
trifluoroacetate TABLE G.1-continued Examples of isoxazolines prepared by General Procedures G

| | | |
|---|---|---|
| G.1.185 | 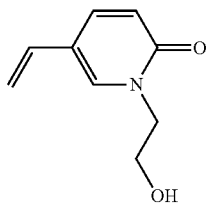<br>(Preparation #F.1.32) | N-(4-Fluoro-3-methoxybenzyl)-6-(5-(1-(2-hydroxyethyl)-6-oxo-1,6-dihydropyridin-3-yl)-4,5-dihydroisoxazol-3-yl)-2-methylpyrimidine-4-carboxamide 2,2,2-trifluoroacetate |
| G.1.186 | 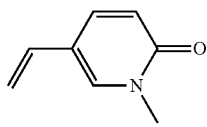<br>(Preparation #F.1.13) | N-(3-Chloro-4-fluorobenzyl)-2-methyl-6-(5-(1-methyl-6-oxo-1,6-dihydropyridin-3-yl)-4,5-dihydroisoxazol-3-yl)pyrimidine-4-carboxamide |
| G.1.187 | 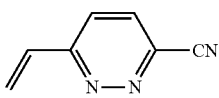<br>(Preparation #F.1.21) | 6-(5-(6-Cyanopyridazin-3-yl)-4,5-dihydroisoxazol-3-yl)-N-(3,4-difluorobenzyl)-2-methylpyrimidine-4-carboxamide 2,2,2-trifluoroacetate |
| G.1.188 | 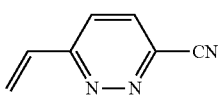<br>(Preparation #F.1.21) | N-(3-Chloro-4-fluorobenzyl)-6-(5-(6-cyanopyridazin-3-yl)-4,5-dihydroisoxazol-3-yl)-2-methylpyrimidine-4-carboxamide |
| G.1.189 | 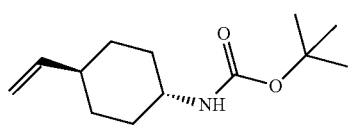<br>(Preparation #E.1.12) | 6-(5-((1r,4r)-4-Acetamidocyclohexyl)-4,5-dihydroisoxazol-3-yl)-N-(3-chloro-4-fluorobenzyl)-2-methylpyrimidine-4-carboxamide |
| G.1.190 | 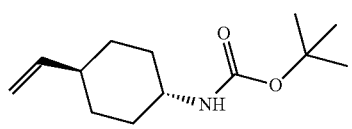<br>(Preparation #E.1.12) | 6-(5-((1r,4r)-4-Acetamidocyclohexyl)-4,5-dihydroisoxazol-3-yl)-N-(4-fluorobenzyl)-2-methylpyrimidine-4-carboxamide |
| G.1.191 | 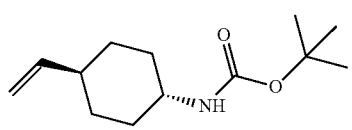<br>(Preparation #E.1.12) | 6-(5-((1r,4r)-4-Acetamidocyclohexyl)-4,5-dihydroisoxazol-3-yl)-N-(3,4-difluorobenzyl)-2-methylpyrimidine-4-carboxamide |
| G.1.192 | 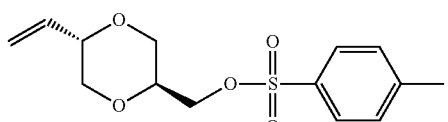<br>(Preparation #11) | N-((2,3-Dihydrobenzofuran-5-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide |
| G.1.193 | 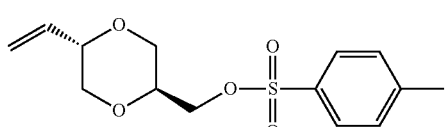<br>(Preparation #11) | N-(3-Fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide |

TABLE G.1-continued

Examples of isoxazolines prepared by General Procedures G

| | | |
|---|---|---|
| G.1.194 | | N-(3-Fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide |
| G.1.195 | 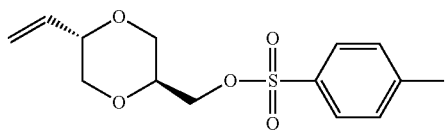<br>(Preparation #11) | 6-((S)-5-((2R,5R)-5-(Hydroxymethyl)-1,4-dioxan-2-yl)-4,5-dihydroisoxazol-3-yl)-2-methyl-N-((2-methyl-benzo[d]oxazol-5-yl)methyl)pyrimidine-4-carboxamide |
| G.1.196 | | 6-((R)-5-((2R,5R)-5-(Hydroxymethyl)-1,4-dioxan-2-yl)-4,5-dihydroisoxazol-3-yl)-2-methyl-N-((2-methyl-benzo[d]oxazol-5-yl)methyl)pyrimidine-4-carboxamide |
| G.1.197 | 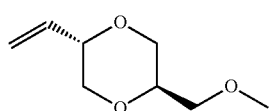<br>(Preparation #AF.1) | N-(4-Fluoro-3-methoxybenzyl)-6-((S)-5-((2R,5R)-5-(methoxy-methyl)-1,4-dioxan-2-yl)-4,5-dihydroisoxazol-3-yl)-2-methylpyrimidine-4-carboxamide |
| G.1.198 | | N-(4-Fluoro-3-methoxybenzyl)-6-((R)-5-((2R,5R)-5-(methoxymethyl)-1,4-dioxan-2-yl)-4,5-dihydroisoxazol-3-yl)-2-methylpyrimidine-4-carboxamide |
| G.1.199 | 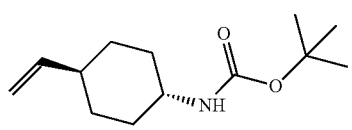<br>(Preparation #E.1.12) | 6-(5-((1r,4r)-4-Acetamidocyclohexyl)-4,5-dihydroisoxazol-3-yl)-N-(3,4-difluoro-benzyl)-2-methyl-pyrimidine-4-carboxamide |
| G.1.200 | 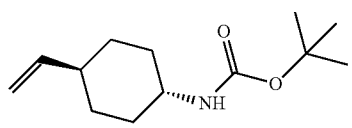<br>(Preparation #E.1.12) | N-(3-Chloro-4-fluorobenzyl)-6-(5-((1S,4r)-4-((S)-2-hydroxypropanamido)-cyclohexyl)-4,5-dihydroisoxazol-3-yl)-2-methylpyrimidine-4-carboxamide |
| G.1.201 | 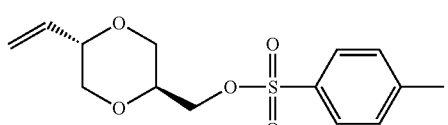<br>(Preparation #11) | N-((2,3-Dihydro-benzo[b][1,4]dioxin-6-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide |
| G.1.202 | | N-((2,3-Dihydro-benzo[b][1,4]dioxin-6-yl)methyl)-6-((R)-5-((2R,5R)-5-(hydroxymethyl)-1,4-dioxan-2-yl)-4,5-dihydroisoxazol-3-yl)-2-methylpyrimidine-4-carboxamide |

TABLE G.1-continued

Examples of isoxazolines prepared by General Procedures G

G.1.203 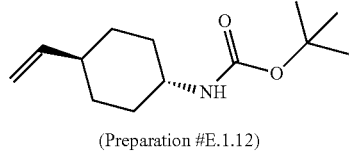
(Preparation #E.1.12)

N-(4-Fluorobenzyl)-6-(5-((1S,4r)-4-((S)-2-hydroxypropanamido)-cyclohexyl)-4,5-dihydroisoxzol-3-yl)-2-methylpyrimidine-4-carboxamide G.1.204 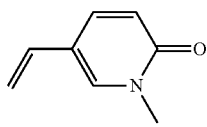
(Preparation #F.1.13)

N-(4-Fluoro-3-methylbenzyl)-2-methyl-6-(5-(1-methyl-6-oxo-1,6-dihydropyridin-3-yl)-4,5-dihydroisoxazol-3-yl)pyrimidine-4-carboxamide G.1.205 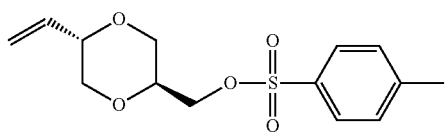
(Preparation #11)

6-((S)-5-((2R,5R)-5-(Hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)-methyl)pyrimidine-4-carboxamide 2,2,2-trifluoroacetate

G.1.206

6-((R)-5-((2R,5R)-5-(Hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)methyl)-pyrimidine-4-carboxamide 2,2,2-trifluoroacetate G.1.207 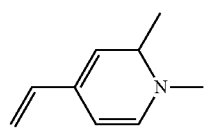
(Preparation #F.1.32)

N-(4-Fluoro-3-methoxybenzyl)-2-methyl-6-(5-(1-methyl-2-oxo-1,2-dihydropyridin-4-yl)-4,5-dihydroisoxazol-3-yl)pyrimidine-4-carboxamide G.1.208 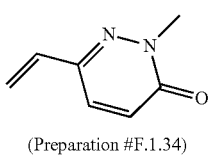
(Preparation #F.1.34)

N-(4-Fluoro-3-methoxybenzyl)-2-methyl-6-(5-(1-methyl-6-oxo-1,6-dihydropyridazin-3-yl)-4,5-dihydroisoxazol-3-yl)pyrimidine-4-carboxamide G.1.209 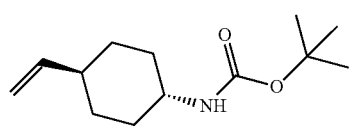
(Preparation #E.1.12 tert-Butyl ((1r,4r)-4-(3-(6-((4-fluoro-3-methoxybenzyl)carbamoyl)-2-methylpyrimidin-4-yl)-4,5-dihydroisoxazol-5-yl)cyclohexyl)carbamate G.1.210 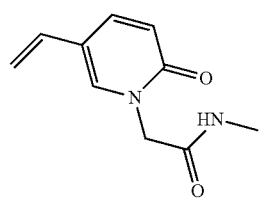
(Preparation #F.1.35)

N-(4-fluoro-3-methoxybenzyl)-2-methyl-6-(5-(1-(2-(methylamino)-2-oxoethyl)-6-oxo-1,6-dihydropyridin-3-yl)-4,5-dihydroisoxazol-3-yl)pyrimidine-4-carboxamide TABLE G.1-continued Examples of isoxazolines prepared by General Procedures G

| | | |
|---|---|---|
| G.1.211 | 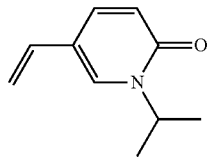<br>(Preparation #F.1.36) | N-(4-fluoro-3-methoxybenzyl)-6-(5-(1-isopropyl-6-oxo-1,6-dihydro-pyridin-3-yl)-4,5-dihydroisoxazol-3-yl)-2-methylpyrimidine-4-carboxamide |
| G.1.212 | 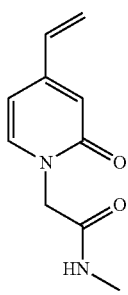<br>(Preparation #F.1.35) | N-(4-fluoro-3-methoxybenzyl)-2-methyl-6-(5-(1-(2-(methylamino)-2-oxoethyl)-2-oxo-1,2-dihydropyridin-4-yl)-4,5-dihydroisoxazol-3-yl)pyrimidine-4-carboxamide |
| G.1.213 | 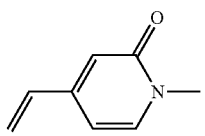<br>(Preparation #F.1.32) | N-(3,4-difluorobenzyl)-2-methyl-6-(5-(1-methyl-2-oxo-1,2-dihydropyridin-4-yl)-4,5-dihydroisoxazol-3-yl)pyrimidine-4-carboxamide |
| G.1.214 | 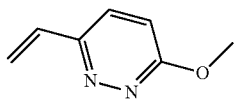<br>(Preparation #F.1.37) | N-(4-fluoro-3-methoxybenzyl)-6-(5-(6-methoxypyridazin-3-yl)-4,5-dihydroisoxazol-3-yl)-2-methylpyrimidine-4-carboxamide |
| G.1.215 | 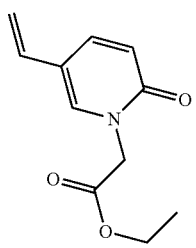<br>(Preparation #F.1.38) | 6-(5-(1-(2-(dimethylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide |
| G.1.216 | 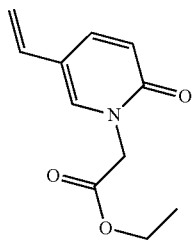<br>(Preparation #F.1.38) | N-(4-fluoro-3-methoxybenzyl)-6-(5-(1-(2-(methoxy(methyl)amino)-2-oxoethyl)-6-oxo-1,6-dihydropyridin-3-yl)-4,5-dihydroisoxazol-3-yl)-2-methylpyrimidine-4-carboxamide |

TABLE G.1-continued

Examples of isoxazolines prepared by General Procedures G

| G.1.217 | 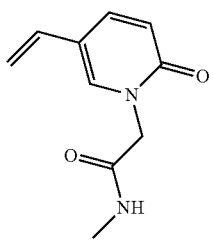<br>(Preparation #F.1.35) | 6-(5-(5-chloro-1-(2-(methylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide |
| --- | --- | --- |
| G.1.218 | 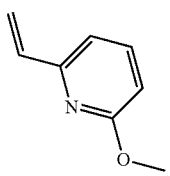<br>(Preparation #F.1.39) | N-(4-fluoro-3-methoxybenzyl)-6-(5-(6-methoxypyridin-2-yl)-4,5-dihydroisoxazol-3-yl)-2-methylpyrimidine-4-carboxamide |
| G.1.219 | 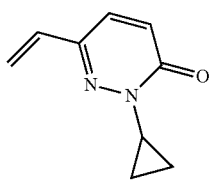<br>(Preparation #F.1.40) | 6-(5-(1-cyclopropyl-6-oxo-1,6-dihydro-pyridazin-3-yl)-4,5-dihydroisoxazol-3-yl)-N-(4-fluoro-3-methoxybenzyl)-2-methylpyrimidine-4-carboxamide |
| G.1.220 | 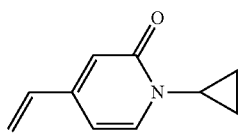<br>(Preparation #F.1.43) | 6-(5-(1-cyclopropyl-2-oxo-1,2-dihydropyridin-4-yl)-4,5-dihydroisoxazol-3-yl)-N-(4-fluoro-3-methoxybenzyl)-2-methylpyrimidine-4-carboxamide |
| G.1.221 | 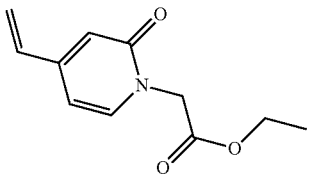<br>(Preparation #F.1.42) | 6-(5-(1-(2-(dimethylamino)-2-oxoethyl)-2-oxo-1,2-dihydropyridin-4-yl)-4,5-dihydroisoxazol-3-yl)-N-(4-fluoro-3-methoxybenzyl)-2-methylpyrimidine-4-carboxamide |
| G.1.222 | 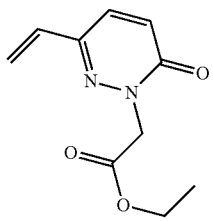<br>(Preparation #F.1.41) | N-(4-fluoro-3-methoxybenzyl)-2-methyl-6-(5-(1-(2-(methylamino)-2-oxoethyl)-6-oxo-1,6-dihydropyridazin-3-yl)-4,5-dihydroisoxazol-3-yl)pyrimidine-4-carboxamide |
| G.1.223 | 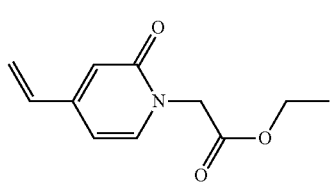<br>(Preparation #F.1.42) | N-(4-fluoro-3-methoxybenzyl)-6-(5-(1-(2-(isopropylamino)-2-oxoethyl)-6-oxo-1,6-dihydropyridin-3-yl)-4,5-dihydroisoxazol-3-yl)-2-methylpyrimidine-4-carboxamide |

TABLE G.1-continued

Examples of isoxazolines prepared by General Procedures G

| G.1.224 | 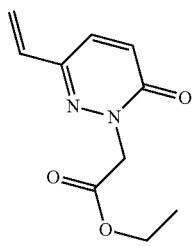<br>(Preparation #F.1.41) | 6-(5-(1-(2-(dimethylamino)-2-oxoethyl)-6-oxo-1,6-dihydropyridazin-3-yl)-4,5-dihydroisoxazol-3-yl)-N-(4-fluoro-3-methoxybenzyl)-2-methylpyrimidine-4-carboxamide |
|---|---|---|
| G.1.225 | 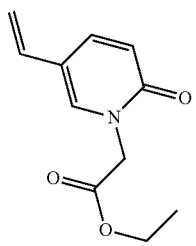<br>(Preparation #F.1.38) | 6-(5-(1-(2-(cyclopropylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide |
| G.1.226 | 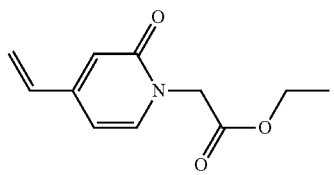<br>(Preparation #F.1.42) | N-(4-fluoro-3-methoxybenzyl)-6-(5-(1-(2-(methoxy(methyl)amino)-2-oxoethyl)-2-oxo-1,2-dihydropyridin-4-yl)-4,5-dihydroisoxazol-3-yl)-2-methylpyrimidine-4-carboxamide |
| G.1.227 | 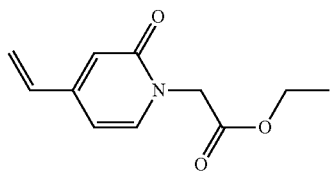<br>(Preparation #F.1.42) | N-(4-fluoro-3-methoxybenzyl)-6-(5-(1-(2-(isopropylamino)-2-oxoethyl)-2-oxo-1,2-dihydropyridin-4-yl)-4,5-dihydroisoxazol-3-yl)-2-methyl-pyrimidine-4-carboxamide |

| Ex. # | Product (Isoxazoline) Structure | General Procedure | LC/MS* $R_t$ Time in min (method) | m/z ESMS $(M + H)^+$ |
|---|---|---|---|---|
| G.1.1 | ![structure] | G-1 & B (step #1) | 1.78 (b) | 477.5 |
| G.1.2 | ![structure] | G-1 & B (step #1) | 1.45 (b) | 463.3 |

TABLE G.1-continued

Examples of isoxazolines prepared by General Procedures G

| | | | | |
|---|---|---|---|---|
| G.1.3 | | G-1 | 1.93 (b) | 403.4 |
| G.1.4 | | G-1 & B (step #1) | 1.73 (b) | 447.4 |
| G.1.5 | | G-1 | 1.90 (b) | 433.3 |
| G.1.6 | | G-1 | 2.21 (a) | 488.4 |
| G.1.7 | | G-1 | 1.65 (b) | 486.3 |
| G.1.8 | | G-1 | 1.87 (b) | 446.3 |
| G.1.9 | | G-1 | 1.71 (b) | 463.3 |
| G.1.10 | | G-1 | 1.67 (b) | 404.3 |
| G.1.11 | | G-2 | 1.69 (b) | 409.4 |

TABLE G.1-continued

Examples of isoxazolines prepared by General Procedures G

| | | | | |
|---|---|---|---|---|
| G.1.12 | | G-1 | 1.67 (b) | 433.2 |
| G.1.13 | | G-1 & R | 1.55 (b) | 446.4 |
| G.1.14 | | G-2 | 2.09 (b) | 427.2 |
| G.1.15 | | G-2, K & L | 1.57 (b) | 452.2 |
| G.1.16 | | G-1 | 3.14 (b) | 422.2 |
| G.1.17 | | G-1 | 2.42 (c) | 443.3 |
| G.1.18 | | G-2 | | 528.2 |
| G.1.19 | | G-1 | 1.72 (c) | 422.2 |
| G.1.20 | | G-1 | 0.79 (c) | 451.2 |

TABLE G.1-continued

Examples of isoxazolines prepared by General Procedures G

| | | | | |
|---|---|---|---|---|
| G.1.21 | | G-1 & B (step #1) | 1.60 (c) | 534.3 |
| G.1.22 | | G-1 | 1.44 (c) | 520.3 |
| G.1.23 | | G-1 & T | 1.42 (c) | 395.2 |
| G.1.24 | | G-1 | 4.54 (c) | 536.2 |
| G.1.25 | | G-1 | | |
| G.1.26 | | G-1 & R | 4.50 (c) | 464.3 |
| G.1.27 | | G-1 | 4.20 (c) | 520.2 |
| G.1.28 | | G-1 & R | 4.62 (c) | 478.3 |

TABLE G.1-continued

Examples of isoxazolines prepared by General Procedures G

| | | | | |
|---|---|---|---|---|
| G.1.29 | | G-1 | | |
| G.1.30 | | G-1 & R | 4.57 (c) | 478.3 |
| G.1.31 | | G-1 | 2.02 (c) | 427.2 |
| G.1.32 | | G-1 | 1.30 (c) | 422.2 |
| G.1.33 | | G-1 | 0.70 (c) | 568.3 |
| G.1.34 | | G-2 & H | 2.68 (e) | 461.2 |
| G.1.35 | | G-2 & H | 0.37 (d) | 461.2 |
| G.1.36 | | G-1, R [using 2-((tert-butyldimethyl-silyl oxy)-ethanamine], & B (step #1) | 0.53 (c) | 508.3 |

TABLE G.1-continued

Examples of isoxazolines prepared by General Procedures G

| | | | | |
|---|---|---|---|---|
| G.1.37 | | G-1, K & L | 0.93 (c) | 484.1 |
| G.1.38 | | G-1 | 0.51 (c) | 423.2 |
| G.1.39 | | G-1 | 1.48 (c) | 479.2 |
| G.1.40 | | G-1, K & N | 0.69 (c) | 500.2 |
| G.1.41 | | G-1, K & M | 1.14 (c) | 520.3 |
| G.1.42 | | G-1 & R | 0.46 (c) | 465.3 |
| G.1.43 | | G-1 | 0.78 (c) | 411.2 |
| G.1.44 | | G-2, K & L | 2.09 (c) | 484.3 |

TABLE G.1-continued
Examples of isoxazolines prepared by General Procedures G
| G.1.45 | 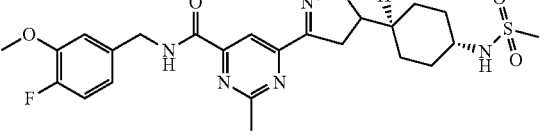 | G-2, K & M | 1.72 (c) | 520.3 |
| G.1.46 | 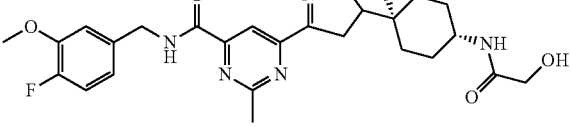 | G-2, K & N | 1.04 (c) | 500.2 |
| G.1.47 | 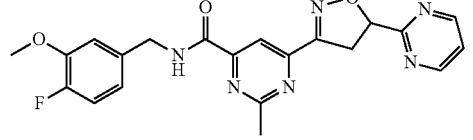 | G-1 | 1.62 (c) | 423.2 |
| G.1.48 | 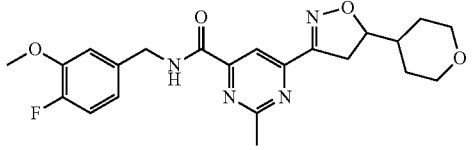 [SMILES: COc1cc(CNC(=O)c2cc(C3=NOC(C4CCOCC4)C3)nc(C)n2)ccc1F] | G-1 | 1.95 (c) | 429.3 |
| G.1.49 | 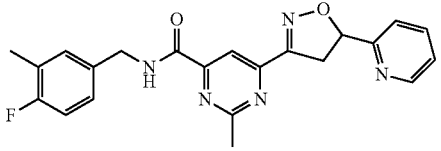 [SMILES: Cc1nc(C(=O)NCc2ccc(F)c(C)c2)cc(C2=NOC(c3ccccn3)C2)n1] | G-1 | 1.91 (c) | 406 |
| G.1.50 | 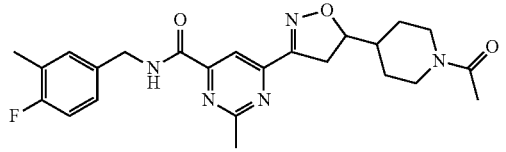 [SMILES: CC(=O)N1CCC(C2CC(c3cc(C(=O)NCc4ccc(F)c(C)c4)nc(C)n3)=NO2)CC1] | G-2, K & L | 1.74 (c) | 454.3 |
| G.1.51 | 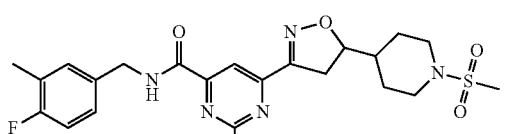 | G-2, K & M | 2.02 (c) | 490.2 |
| G.1.52 | 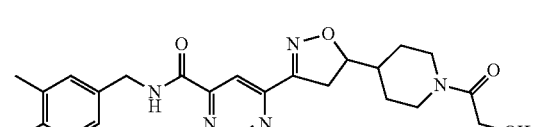 | G-2, K & N | 1.68 (c) | 470.4 |
| G.1.53 | 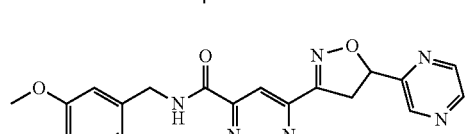 | G-1 | 1.66 (c) | 423.1 |

TABLE G.1-continued

Examples of isoxazolines prepared by General Procedures G

| | | | | |
|---|---|---|---|---|
| G.1.54 | | G-2, K & N | 1.67 (c) | 514.1 |
| G.1.55 | | G-2, K & M | 2.18 (c) | 532.4 |
| G.1.56 | | G-1 | 1.81 (c) | 410.4 |
| G.1.57 | | G-2, K & L | 1.80 (c) | 458.3 |
| G.1.58 | | G-2, K & M | 1.97 (c) | 494.4 |
| G.1.59 | | G-2, K & N | 1.73 (c) | 474.3 |
| G.1.60 | | G-2, K & M | 1.98 (c) | 520.4 |
| G.1.61 | | G-2, K & L | 1.90 (c) | 498.3 |
| G.1.62 | | G-2, K & M | 2.04 (c) | 534.3 |

TABLE G.1-continued

Examples of isoxazolines prepared by General Procedures G

| | | | | |
|---|---|---|---|---|
| G.1.63 | | G-1 | 1.91 (c) | 392.2 |
| G.1.64 | | G-2, K & L | 1.87 (c) | 474.3 |
| G.1.65 | | G-2, K & N | 4.91 (c) | 490.3 |
| G.1.66 | | G-1 | 1.82 (c) | 404.2 |
| G.1.67 | | G-2, K & L | 0.81 (d) | 440.2 |
| G.1.67 | | G-2, K & M | 1.38 (d) | 476.2 |
| G.1.68 | | G-2, K & M | 1.38 (d) | 476.2 |
| G.1.69 | | G-2, K & N | 1.62 (c) | 456.3 |
| G.1.70 | | G-2, K & L | 1.74 (c) | 452.4 |

TABLE G.1-continued

Examples of isoxazolines prepared by General Procedures G

| | | | | |
|---|---|---|---|---|
| G.1.71 | | G-2, K & M | 1.87 (c) | 488.4 |
| G.1.72 | | G-2, K & N | 0.78 (d) | 468.1 |
| G.1.73 | | G-2, K & L | 1.93 (c) | 496.3 |
| G.1.74 | | G-2, K & U | 1.83 (c) | 499.3 |
| G.1.75 | | G-2, K & V | 1.83 (d) | 499.2 |
| G.1.76 | | G-2, K & W | 3.05 (e) | 513.4 |
| G.1.77 | | G-2, K & W | 2.71 (e) | 527.4 |
| G.1.78 | | G-2, K & M | 1.60 (d) | 534.4 |
| G.1.79 | | G-2, K & X | 1.38 (c) | 495.3 |

TABLE G.1-continued

Examples of isoxazolines prepared by General Procedures G

| | | | | |
|---|---|---|---|---|
| G.1.80 | | G-2, K & L | 0.77 (d) | 500.4 |
| G.1.81 | | G-2, K & L | 1.51 (d) | 510.3 |
| G.1.82 | | G-2, K, Y (using N-Boc glycine active ester), K & M | 0.67 (d) | 563.3 |
| G.1.83 | | G-1 | 1.26 (d) | 447.2 |
| G.1.84 | | G-1 | 0.34 (d) | 452.2 |
| G.1.85 | | G-1 & R. | 0.44 (d) | 479.3 |
| G.1.86 | | G-2 & Z | 0.36 (d) | 515.1 |
| G.1.87 | | G-2, [using peYrfluorophenyl 2-(tert-butoxy-carbonylamino)-acetate active ester], K & AC | 0.35 (d) | 542.2 |
| G.1.88 | | G-1 | 0.44 (d) | 466.0 |

TABLE G.1-continued

Examples of isoxazolines prepared by General Procedures G

| | | | | |
|---|---|---|---|---|
| G.1.89 | | G-2 & Z | 0.49 (d) | 529.0 |
| G.1.90 | | G-2 & Z | 1.38 (d) | 513.2 |
| G.1.91 | | G-2, K & M | 1.01 (d) | 572.3 |
| G.1.92 | | G-2, K & M | 1.22 (d) | 572.2 |
| G.1.93 | | G-2, K & M | 1.30 (d) | 586.3 |
| G.1.94 | | G-2, K & M | 1.61 (d) | 585.1 (Negative mode) |
| G.1.95 | | G-1 | 1.33 (d) | 500.2 |
| G.1.96 | | G-1 | 2.66 (e) | 452.1 |
| G.1.97 | | G-1 | 1.42 (d) | 464.2 |

TABLE G.1-continued

Examples of isoxazolines prepared by General Procedures G

| | | | | |
|---|---|---|---|---|
| G.1.98 | | G-1 | 1.53 (d) | 504.2 |
| G.1.99 | | G-2 | | 619.1 |
| G.1.100 | | G-2 & H | 1.23 (d) | 465.2 |
| G.1.101 | | G-2 & H | 2.75 (e) | 465.1 |
| G.1.102 | | G-2 & H | 2.64 (e) | 431.1 |
| G.1.103 | | G-2 & H | 2.63 (e) | 431.1 |
| G.1.104 | | G-2 & H | 2.57 (e) | 443.2 |
| G.1.105 | | G-2 & H | 0.44 (d) | 443.2 |
| G.1.106 | | G-2 & H | 0.53 (d) | 443.2 |

TABLE G.1-continued

Examples of isoxazolines prepared by General Procedures G

| | | | | |
|---|---|---|---|---|
| G.1.107 | | G-1 | 1.52 (f) | 432.2 |
| G.1.108 | | G-1 | 1.91 (f) | 418.3 |
| G.1.109 | | G-1 | 2.13 (f) | 436.3 |
| G.1.110 | | G-1 | 1.64 (f) | 445.2 |
| G.1.111 | | G-1 | 1.75 (f) | 445.4 |
| G.1.112 | | G-1 | 1.79 (f) | 431.9 |
| G.1.113 | | G-1 | 2.36 (f) | 435.9 |
| G.1.114 | | G-1 | 2.15 (f) | 402.4 |
| G.1.115 | | G-1 | 1.76 (f) | 390.0 |
| G.1.116 | | G-1 | 1.91 (f) | 418.3 |
| G.1.117 | | G-2 & H | 0.77 (d) | 443.3 |

TABLE G.1-continued
Examples of isoxazolines prepared by General Procedures G
| | | | | |
|---|---|---|---|---|
| G.1.118 | 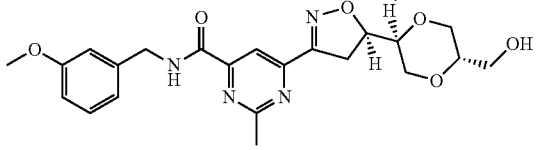 | | 2.55 (e) | 443.0 |
| G.1.119 | 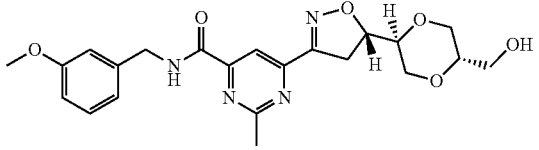 [SMILES: COc1cccc(CNC(=O)c2cc(C3=NO[C@H]([C@@H]4CO[C@@H](CO)CO4)C3)nc(C)n2)c1] | G-2 & H | 2.59 (e) | 443.1 |
| G.1.120 | 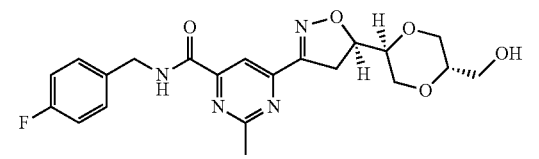 [SMILES: Cc1nc(C(=O)NCc2ccc(F)cc2)cc(C2=NO[C@@H]([C@@H]3CO[C@@H](CO)CO3)C2)n1] | G-2 & H | 2.54 (e) | 431.1 |
| G.1.121 | 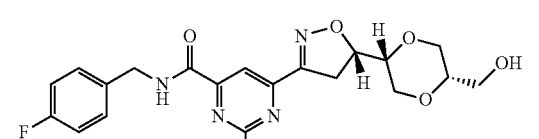 | | 2.57 (e) | 431.2 |
| G.1.122 | 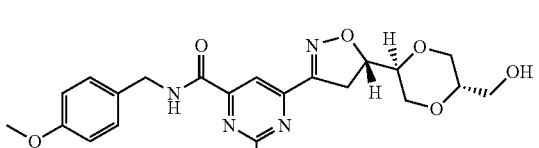 | G-2 & H | 2.69 (e) | 443.1 |
| G.1.123 | 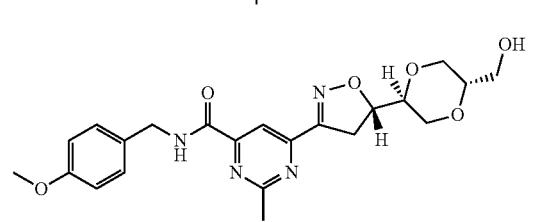 | | 2.63 (e) | 443.1 |
| G.1.124 | 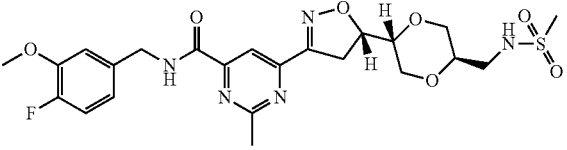 [SMILES: COc1cc(CNC(=O)c2cc(C3=NO[C@H]([C@H]4CO[C@H](CNS(C)(=O)=O)CO4)C3)nc(C)n2)ccc1F] | G-2, J & M | 1.33 (d) | 583.1 |
| G.1.125 | 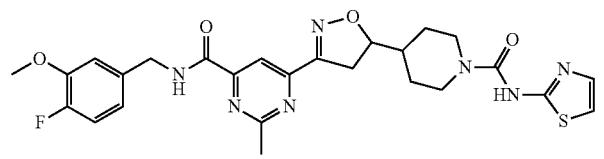 [SMILES: COc1cc(CNC(=O)c2cc(C3=NOC(C4CCN(C(=O)Nc5nccs5)CC4)C3)nc(C)n2)ccc1F] | G-2, K & AA | 1.39 (d) | 554.0 |
| G.1.126 | 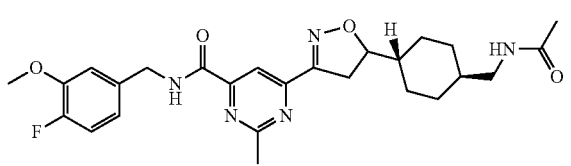 [SMILES: COc1cc(CNC(=O)c2cc(C3=NOC([C@H]4CC[C@H](CNC(C)=O)CC4)C3)nc(C)n2)ccc1F] | G-2, K & L | 1.39 (d) | 498.1 |

TABLE G.1-continued

Examples of isoxazolines prepared by General Procedures G

| | | | | |
|---|---|---|---|---|
| G.1.127 | | G-1 | 1.32 (d) | 489.1 |
| G.1.128 | | G-1 | 1.33 (d) | 501.2 |
| G.1.129 | | G-1 | 1.46 (d) | 504 |
| G.1.130 | | G-1 | 1.50 (d) | 464.2 |
| G.1.131 | | G-1, W | 2.72 (e) | 466.1 |
| G.1.132 | | G-1 | 4.76 (e) | 448.0 |
| G.1.133 | | G-2, K & N | 1.24 (d) | 514.0 |
| G.1.134 | | G-1 | 1.53 (d) | 507.1 |
| G.1.135 | | G-1 | 1.86 (g) | 468.2 |

TABLE G.1-continued

Examples of isoxazolines prepared by General Procedures G

| | | | | |
|---|---|---|---|---|
| G.1.136 | | G-2, K & L | 2.20 (g) | 523.4 |
| G.1.137 | | G-1 & R | 1.95 (g) | 480.0 |
| G.1.138 | | G-1 | 2.16 (g) | 505.1 |
| G.1.139 | | G-2, J & N | 1.83 (g) | 518.2 |
| G.1.140 | | G-1 | 2.16 (g) | 489.3 |
| G.1.141 | | G-1 | 1.40 (g) | 452.3 |
| G.1.142 | | G-2, K & Z | 1.89 (g) | 529.4 |
| G.1.143 | | G-2, K & Z | 1.92 (g) | 543.3 |
| G.1.144 | | G-1 | 2.14 (g) | 501.1 |

TABLE G.1-continued
Examples of isoxazolines prepared by General Procedures G
| | | | | |
|---|---|---|---|---|
| G.1.145 |  | G-1 | 2.26 (g) | 447.2 |
| G.1.146 | 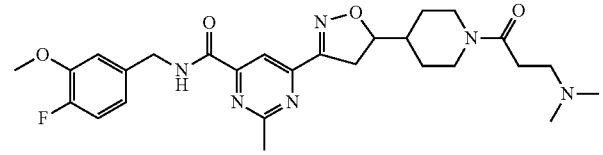 | G-2, K & L | 2.93 (e) | 527.3 |
| G.1.147 | 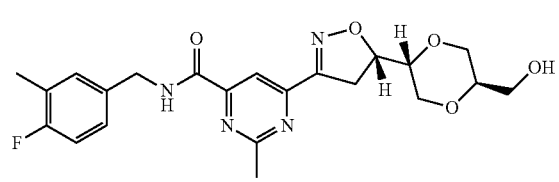 [SMILES: Cc1nc(C(=O)NCc2ccc(F)c(C)c2)cc(C2=NO[C@H]([C@H]3CO[C@H](CO)CO3)C2)n1] | G-2 & H | 2.06 (d) | 445.3 |
| G.1.148 | 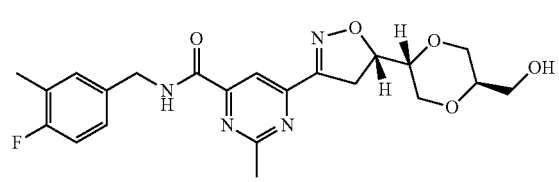 [SMILES: Cc1nc(C(=O)NCc2ccc(F)c(C)c2)cc(C2=NO[C@H]([C@H]3CO[C@H](CO)CO3)C2)n1] | | 2.03 (d) | 445.3 |
| G.1.149 | 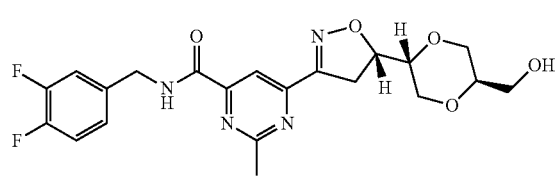 [SMILES: Cc1nc(C(=O)NCc2ccc(F)c(F)c2)cc(C2=NO[C@H]([C@H]3CO[C@H](CO)CO3)C2)n1] | G-2 & H | 1.92 (d) | 449.4 |
| G.1.150 | 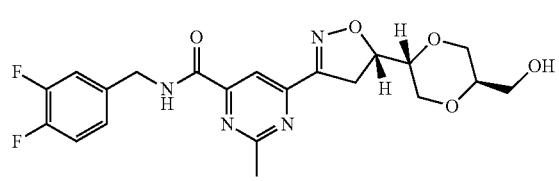 | | 1.86 (d) | 449.3 |
| G.1.151 | 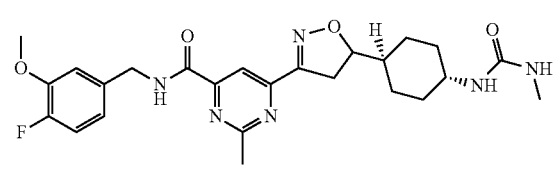 [SMILES: CNC(=O)N[C@H]1CC[C@H](C2CC(c3cc(C(=O)NCc4ccc(F)c(OC)c4)nc(C)n3)=NO2)CC1] | G-2, K & AC | 2.02 (d) | 499.4 |
| G.1.152 | 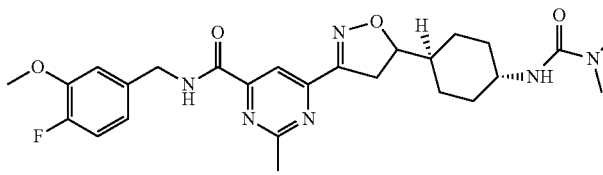 | G-2, K & U | 2.13 (d) | 513.5 |
| G.1.153 | 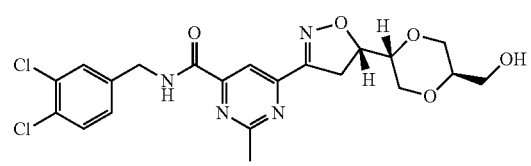 [SMILES: Cc1nc(C(=O)NCc2ccc(Cl)c(Cl)c2)cc(C2=NO[C@H]([C@H]3CO[C@H](CO)CO3)C2)n1] | G-2 & H | 2.20 (d) | 481.2 |

TABLE G.1-continued

Examples of isoxazolines prepared by General Procedures G

| | | | | |
|---|---|---|---|---|
| G.1.154 | | G-2 & H | 2.17 (d) | 481.2 |
| G.1.155 | | G-1 | 1.91 (d) | 455.0 |
| G.1.156 | | G-2, J, R (step 2) | 1.94 (d) | 527.2 |
| G.1.157 | | G-2, J & N | 1.88 (d) | 546.3 |
| G.1.158 | | G-2, J & AC | 1.80 (d) | 517.3 |
| G.1.159 | | G-2, J & U | 1.98 (d) | 531.2 |
| G.1.160 | | G-2, K & L | 1.73 (d) | 527.2 |
| G.1.161 | | G-1 | 1.92 (d) | 462.4 |
| G.1.162 | | G-1 | 2.21 (d) | 476.0 |

TABLE G.1-continued

Examples of isoxazolines prepared by General Procedures G

| G.1.163 | G-2, H, Q, & S | 2.13 (d) | 489.2 |
| G.1.164 | G-2, H, Q & R | 1.94 (d) | 488.3 |
| G.1.165 | G-2 & R | 2.08 (d) | 484.3 |
| G.1.166 | G-2 & R | 2.04 (d) | 470.3 |
| G.1.167 | G-2, K & N | 2.04 (d) | 528.3 |
| G.1.168 | G-1 | 2.82 (e) | 466.2 |
| G.1.169 | G-1 | 3.09 (e) | 492.1 |
| G.1.170 | G-2, K & Z | 1.83 (d) | 559.2 |

TABLE G.1-continued

Examples of isoxazolines prepared by General Procedures G

| | | | | |
|---|---|---|---|---|
| G.1.171 | | G-2 & R-2 (Step 2) | 1.85 (d) | 514.3 |
| G.1.172 | | G-2, K & Z | 1.80 (d) | 573.4 |
| G.1.173 | | G-2, K & L | 2.18 (d) | 468.3 |
| G.1.174 | | G-1 | 2.31 (d) | 432.0 |
| G.1.175 | | G-2, K, R (Step 2) & K | 2.12 (e) | 513.0 |
| G.1.176 | | G-2 & AO | 2.25 (d) | 507.2 |
| G.1.177 | | G-2, J & L | 2.07 (d) | 486.3 |
| G.1.178 | | G-2, J & L | 1.99 (d) | 506.1 |
| G.1.179 | | G-2 & O | 2.17 (d) | 527.2 |

TABLE G.1-continued

Examples of isoxazolines prepared by General Procedures G

| | | | | |
|---|---|---|---|---|
| G.1.180 | | G-1 | 5.62 (d) | 436.1 |
| G.1.181 | | G-2 & H | 2.06 (d) | 427.1 |
| G.1.182 | | | 1.97 (d) | 426.9 |
| G.1.183 | | G-1 | 2.28 (d) | 418.1 |
| G.1.184 | | G-1 | 1.90 (d) | 422.3 |
| G.1.185 | | G-1 | 1.83 (d) | 482.0 |
| G.1.186 | | G-1 | 2.04 (d) | 456.1 |
| G.1.187 | | G-1 | 2.23 (d) | 436.1 |

TABLE G.1-continued

Examples of isoxazolines prepared by General Procedures G

| | | | | |
|---|---|---|---|---|
| G.1.188 | | G-1 | 2.34 (d) | 451.9 |
| G.1.189 | | G-2 K & L | 2.23 (d) | 488.2 |
| G.1.190 | | G-2 K & L | 2.00 (d) | 454.1 |
| G.1.191 | | G-2 K & L | 2.08 (d) | 472.1 |
| G.1.192 | | G-2 & H | 2.905 (d) | 455.3 |
| G.1.193 | | G-2 & H | 1.96 (d) | 431.1 |
| G.1.194 | | | 1.85 (d) | 431.0 |
| G.1.195 | | G-2 & H | 2.70 (d) | 468.3 |
| G.1.196 | | | 2.67 (d) | 468.1 |

TABLE G.1-continued

Examples of isoxazolines prepared by General Procedures G

| | | | | |
|---|---|---|---|---|
| G.1.197 | | G-2 | 3.27 (d) | 473.3 (Negative mode) |
| G.1.198 | | | 3.22 (d) | 475.2 |
| G.1.199 | | G-2, K & N | 3.20 (d) | 498.3 |
| G.1.200 | | G-2, K & N | 3.21 (d) | 518.2 |
| G.1.201 | | G-2 & H | 2.62 (e) | 471.1 |
| G.1.202 | | | 2.86 (d) | 471.2 |
| G.1.203 | | G-2, K & N | 3.00 (d) | 484.3 |
| G.1.204 | | G-1 | 3.13 (e) | 436.3 |
| G.1.205 | | G-2 & H | 2.65 (e) | 484.1 |

TABLE G.1-continued

Examples of isoxazolines prepared by General Procedures G

| | | | | |
|---|---|---|---|---|
| G.1.206 | | | 2.63 (e) | 484.2 |
| G.1.207 | | G-1 | 2.75 (d) | 452.3 |
| G.1.208 | | G-1 | 2.10 (d) | 453.2 |
| G.1.209 | | G-2 | 3.77 (d) | 542.3 |
| G.1.210 | | G-1 | 1.84 (e) | 509.4 |
| G.1.211 | | G-1 | 2.86 (e) | 480.4 |
| G.1.212 | | G-1 | 1.79 (d) | 509.3 |
| G.1.213 | | G-1 | 2.71 (e) | 440.3 |

TABLE G.1-continued

Examples of isoxazolines prepared by General Procedures G

| | | | | |
|---|---|---|---|---|
| G.1.214 | | G-1 | 2.40 (d) | 453.3 |
| G.1.215 | | G-1, X | 2.10 (d) | 523.4 |
| G.1.216 | | G-1, R | 2.23 (d) | 540.1 |
| G.1.217 | | G-1, | 2.21 (d) | 543.4 |
| G.1.218 | | G-1 | 2.85 (d) | 452.1 |
| G.1.219 | | G-1 | 2.38 (d) | 479.2 |
| G.1.220 | | G-1 | 2.24 (d) | 476.3 |
| G.1.221 | | G-1, X | 2.05 (d) | 523.3 |

TABLE G.1-continued
Examples of isoxazolines prepared by General Procedures G
| | | | | |
|---|---|---|---|---|
| G.1.222 | 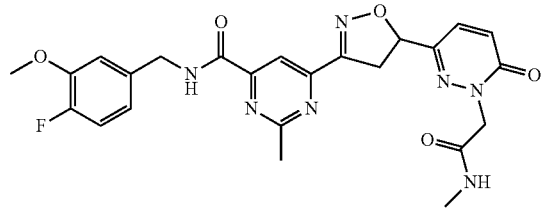 [SMILES: CNC(=O)Cn1nc(C2CC(c3cc(C(=O)NCc4ccc(F)c(OC)c4)nc(C)n3)=NO2)ccc1=O] | G-1, X | 2.02 (d) | 510.3 |
| G.1.223 | 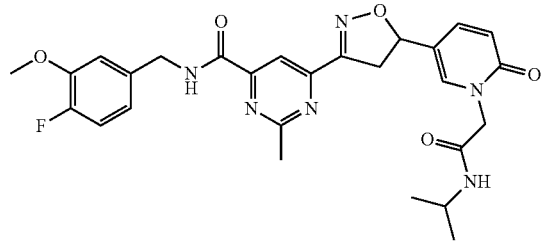 [SMILES: COc1cc(CNC(=O)c2cc(C3=NOC(c4ccc(=O)n(CC(=O)NC(C)C)c4)C3)nc(C)n2)ccc1F] | G-1, X | 2.25 (d) | 537.3 |
| G.1.224 | 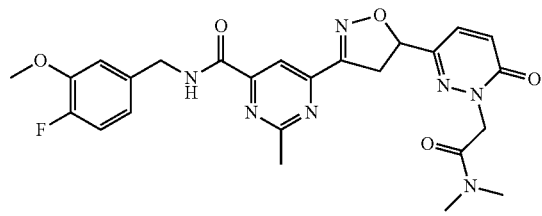 [SMILES: COc1cc(CNC(=O)c2cc(C3=NOC(c4ccc(=O)n(CC(=O)N(C)C)n4)C3)nc(C)n2)ccc1F] | G-1, R | 2.13 (d) | 524.4 |
| G.1.225 | 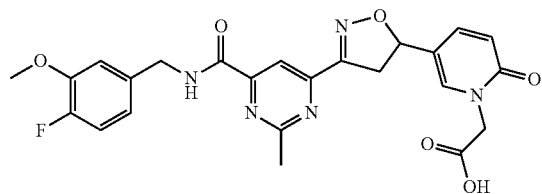 [SMILES: COc1cc(CNC(=O)c2cc(C3=NOC(c4ccc(=O)n(CC(=O)O)c4)C3)nc(C)n2)ccc1F] | G-1, R (step 1) | 2.08 (d) | 494.4 (M − H) |
| G.1.226 | 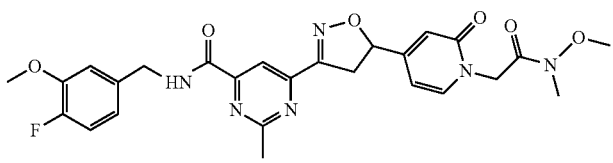 | G-1, R | 2.20 (d) | 537.3 |
| G.1.227 | 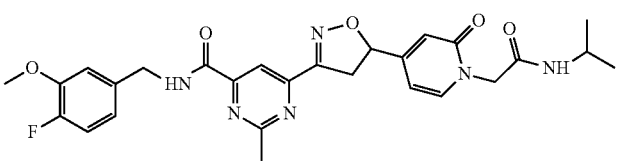 [SMILES: COc1cc(CNC(=O)c2cc(C3=NOC(c4ccn(CC(=O)NC(C)C)c(=O)c4)C3)nc(C)n2)ccc1F] | G-1, R | 2.18 (d) | 537.3 |

TABLE G.2

Isoxazolines prepared with methyl 2-methyl-6-vinylpyrimidine-4-carboxylate using General Procedure G method 1

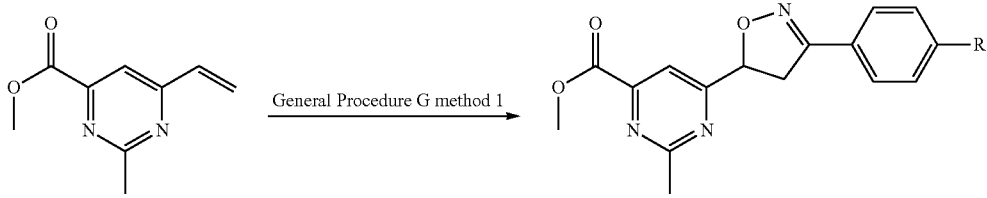

F.1.15

| Preparation # | Product | m/z ESMS (M + H)+ | Oxime |
|---|---|---|---|
| G.2.1 | | 358 | (JOC 2010, 75, 627-636) |
| G.2.2 | | 298 | (WO 2010075290) |

TABLE R.1

Examples of isoxazolines prepared by General Procedure R

| Ex. # | Benzyl amine | Product (Isoxazoline) | |
|---|---|---|---|
| | | IUPAC name | Structure |
| R.1.1 | Aldrich | 6-(5-((1r,4r)-4-Acetamido-cyclohexyl)-4,5-dihydro-isoxazol-3-yl)-2-methyl-N-(pyridin-4-ylmethyl) pyrimidine-4-carboxamide | |
| R.1.2 | Aldrich | 6-((S)-5-((2R,5R)-5-(Hydroxy-methyl)-1,4-dioxan-2-yl)-4,5-dihydro-isoxazol-3-yl)-2-methyl-N-(pyridin-4-ylmethyl) pyrimidine-4-carboxamide | |

TABLE R.1-continued

| | | | |
|---|---|---|---|
| R.1.3 | 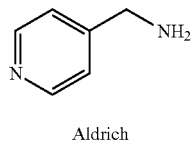

Aldrich | 6-((R)-5-((2R,5R)-5-(ydroxy-methyl)-1,4-dioxan-2-yl)-4,5-dihydro-isoxazol-3-yl)-2-methyl-N-(pyridin-4-ylmethyl) pyrimidine-4-carboxamide | 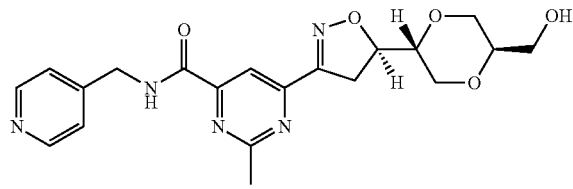 [SMILES: Cc1nc(C(=O)NCc2ccncc2)cc(C2=NO[C@@H]([C@H]3CO[C@H](CO)CO3)C2)n1] |
| R.1.4 | 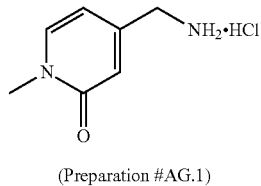

(Preparation #AG.1) | 6 6-(5-((1r,4r)-4-Acetamido-cyclohexyl)-4,5-dihydro-isoxazol-3-yl)-2-methyl-N-((1-methyl-2-oxo-1,2-dihydro-pyridin-4-yl)methyl) pyrimidine-4-carboxamide | 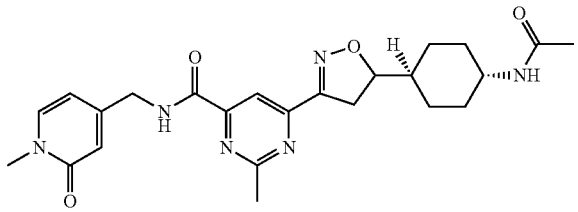 [SMILES: CC(=O)N[C@H]1CC[C@H](C2CC(c3cc(C(=O)NCc4ccn(C)c(=O)c4)nc(C)n3)=NO2)CC1] |
| R.1.5 | 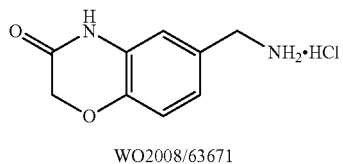

WO2008/63671 | 6-(5-((1r,4r)-4-Acetamido-cyclohexyl)-4,5-dihydro-isoxazol-3-yl)-2-methyl-N-((3-oxo-3,4-dihydro-2H-benzo[b][1,4]oxazin-6-yl)methyl) pyrimidine-4-carboxamide | 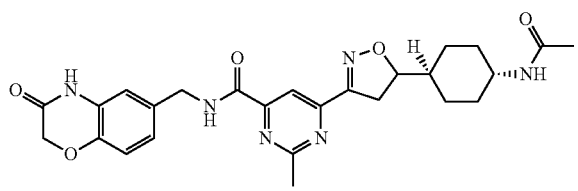 [SMILES: CC(=O)N[C@H]1CC[C@H](C2CC(c3cc(C(=O)NCc4ccc5c(c4)NC(=O)CO5)nc(C)n3)=NO2)CC1] |
| R.1.6 | 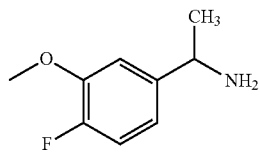

Preparation #16 | N-((R)-1-(4-Fluoro-3-methoxy-phenyl) ethyl)-2-methyl-6-(5-phenyl-4,5-dihydro-isoxazol-3-yl)pyrimidine-4-carboxamide | 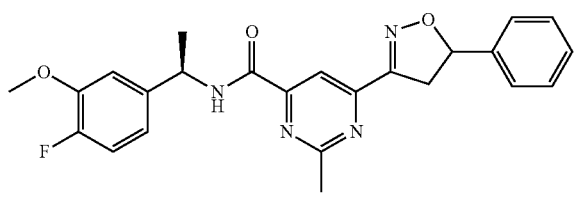 [SMILES: COc1cc([C@@H](C)NC(=O)c2cc(C3=NOC(c4ccccc4)C3)nc(C)n2)ccc1F] |
| | | N-((S)-1-(4-Fluoro-3-methoxy-phenyl)ethyl)-2-methyl-6-(5-phenyl-4,5-dihydro-isoxazol-3-yl)pyrimidine-4-carboxamide | 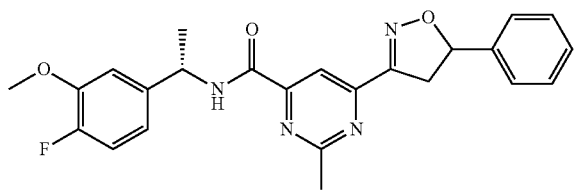 [SMILES: COc1cc([C@H](C)NC(=O)c2cc(C3=NOC(c4ccccc4)C3)nc(C)n2)ccc1F] |
| R.1.7 | 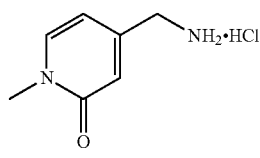

(preparation #AG.1) | 6-((S)-5-((2R,5R)-5-(hydroxy-methyl)-1,4-dioxan-2-yl)-4,5-dihydro-isoxazol-3-yl)-2-methyl-N-((1-methyl-2-oxo-1,2-dihydro-pyridin-4-yl)methyl) pyrimidine-4-carboxamide | 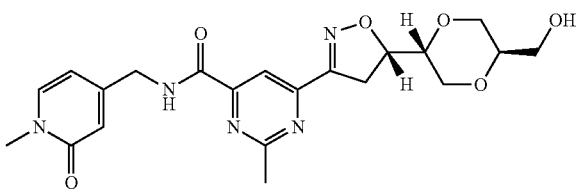 [SMILES: Cc1nc(C(=O)NCc2ccn(C)c(=O)c2)cc(C2=NO[C@H]([C@H]3CO[C@H](CO)CO3)C2)n1] |

| | | | |
|---|---|---|---|
| | | 6-((R)-5-((2R,5R)-5-(hydroxymethyl)-1,4-dioxan-2-yl)-4,5-dihydroisoxazol-3-yl)-2-methyl-N-((1-methyl-2-oxo-1,2-dihydropyridin-4-yl)methyl)pyrimidine-4-carboxamide | |
| R.1.8 | Oakwood products | 6-(5-((1r,4r)-4-acetamidocyclohexyl)-4,5-dihydroisoxazol-3-yl)-2-methyl-N-(quinolin-4-ylmethyl)pyrimidine-4-carboxamide | |
| R.1.9 | Oakwood products | 6-((S)-5-((2R,5R)-5-(hydroxymethyl)-1,4-dioxan-2-yl)-4,5-dihydroisoxazol-3-yl)-2-methyl-N-(quinolin-4-ylmethyl)pyrimidine-4-carboxamide | |
| R.1.10 | Oakwood products | 6-((R)-5-((2R,5R)-5-(hydroxymethyl)-1,4-dioxan-2-yl)-4,5-dihydroisoxazol-3-yl)-2-methyl-N-(quinolin-4-ylmethyl)pyrimidine-4-carboxamide | |
| R.1.11 | WO2006/128184A2 | 6-((S)-5-((2R,5R)-5-(hydroxymethyl)-1,4-dioxan-2-yl)-4,5-dihydroisoxazol-3-yl)-2-methyl-N-((2-oxo-1,2,3,4-tetrahydroquinolin-7-yl)methyl)pyrimidine-4-carboxamide | |

TABLE R.1-continued

| | | | |
|---|---|---|---|
| R.1.12 | (structure) WO2006/128184A2 | 6-((R)-5-((2R,5R)-5-(hydroxy-methyl)-1,4-dioxan-2-yl)-4,5-dihydro-isoxazol-3-yl)-2-methyl-N-((2-oxo-1,2,3,4-tetrahydro-quinolin-7-yl)methyl)pyrimidine-4-carboxamide | (structure) |
| R.1.13 | (structure) WO2008/63671 | 2-methyl-6-(5-(1-methyl-6-oxo-1,6-dihydro-pyridin-3-yl)-4,5-dihydro-isoxazol-3-yl)-N-((3-oxo-3,4-dihydro-2H-benzo[b][1,4]oxazin-6-yl)methyl)pyrimidine-4-carboxamide | (structure) |
| R.1.14 | (structure) (preparation #AG.2) | 6-((S)-5-((2R,5R)-5-(hydroxy-methyl)-1,4-dioxan-2-yl)-4,5-dihydro-isoxazol-3-yl)-2-methyl-N-((1-methyl-6-oxo-1,6-dihydro-pyridin-3-yl)methyl)pyrimidine-4-carboxamide | (structure) |
| R.1.15 | | 6-((R)-5-((2R,5R)-5-(hydroxy-methyl)-1,4-dioxan-2-yl)-4,5-dihydro-isoxazol-3-yl)-2-methyl-N-((1-methyl-6-oxo-1,6-dihydro-pyridin-3-yl)methyl)pyrimidine-4-carboxamide | (structure) |
| R.1.16 | (structure) WO2008/63671 | 6-(5-((1S,4r)-4-((S)-2-hydroxy-propanamido)cyclohexyl)-4,5-dihydro-isoxazol-3-yl)-2-methyl-N-((3-oxo-3,4-dihydro-2H-benzo[b][1,4]oxazin-6-yl)methyl)pyrimidine-4-carboxamide | (structure) |

TABLE R.1-continued

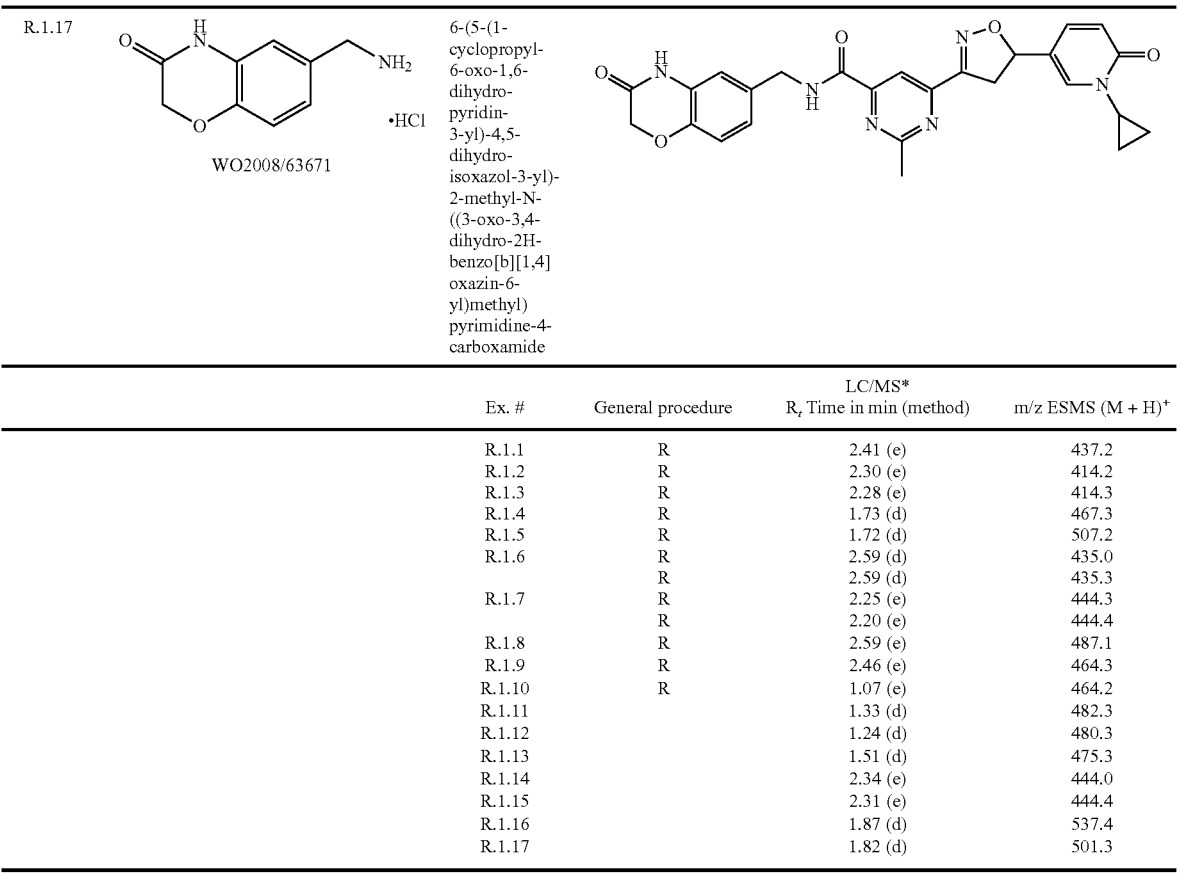

| R.1.17 | | 6-(5-(1-cyclopropyl-6-oxo-1,6-dihydro-pyridin-3-yl)-4,5-dihydro-isoxazol-3-yl)-2-methyl-N-((3-oxo-3,4-dihydro-2H-benzo[b][1,4]oxazin-6-yl)methyl)pyrimidine-4-carboxamide | |
|---|---|---|---|

WO2008/63671

| Ex. # | General procedure | LC/MS* $R_t$ Time in min (method) | m/z ESMS (M + H)+ |
|---|---|---|---|
| R.1.1 | R | 2.41 (e) | 437.2 |
| R.1.2 | R | 2.30 (e) | 414.2 |
| R.1.3 | R | 2.28 (e) | 414.3 |
| R.1.4 | R | 1.73 (d) | 467.3 |
| R.1.5 | R | 1.72 (d) | 507.2 |
| R.1.6 | R | 2.59 (d) | 435.0 |
|  | R | 2.59 (d) | 435.3 |
| R.1.7 | R | 2.25 (e) | 444.3 |
|  | R | 2.20 (e) | 444.4 |
| R.1.8 | R | 2.59 (e) | 487.1 |
| R.1.9 | R | 2.46 (e) | 464.3 |
| R.1.10 | R | 1.07 (e) | 464.2 |
| R.1.11 |  | 1.33 (d) | 482.3 |
| R.1.12 |  | 1.24 (d) | 480.3 |
| R.1.13 |  | 1.51 (d) | 475.3 |
| R.1.14 |  | 2.34 (e) | 444.0 |
| R.1.15 |  | 2.31 (e) | 444.4 |
| R.1.16 |  | 1.87 (d) | 537.4 |
| R.1.17 |  | 1.82 (d) | 501.3 |

TABLE X.1

Oxadiazole olefins prepared by General Procedure X.

| Preparation # | Olefin | Product | |
|---|---|---|---|
| X.1.1 | | | $^1$H NMR (400 MHz, CDCl$_3$): δ 8.8 (d, J = 2.0 Hz, 1H), 8.15 (d, J = 8.4 Hz, 1H), 7.92 (dd, J = 8.4 Hz, 1H), 6.8 (m, 1H), 5.97 (d, J = 18 Hz, 1H), 5.5 (d, J = 11.2 Hz, 1H) 2.5 (s, 3H), MS m/z: 188 (M + H)+. |
| X.1.2 | F.1.22 | | $^1$H NMR (400 MHz, CDCl$_3$): δ 6.92 (s, 1H), 6.61 (m, 1H), 5.83-5.73 (m, 1H), 5.43 (m, 1H), 3.98 (s, 3H), 3.93 (s, 3H), MS m/z: 191 (M + H)+. |

TABLE X.1-continued

Oxadiazole olefins prepared by General Procedure X.

| Preparation # | Olefin | Product | |
|---|---|---|---|
| X.1.3 | F.1.20 | | ¹H NMR (400 MHz, DMSO): δ 8.406-8.385 (d, J = 8.4 Hz, 1H), 8.225-8.203 (d, J = 8.4 Hz, 1H), 7.18-7.13 (m, 1H), 6.60-6.65 (m, 1H), 5.91-5.88 (m, 1H), 2.59 (s, 3H); MS m/z: 189.2 (M + H)⁺. |

Enantiomeric Separation of Example #N.1 Step 1 Product Using Chiral Preparative Hplc

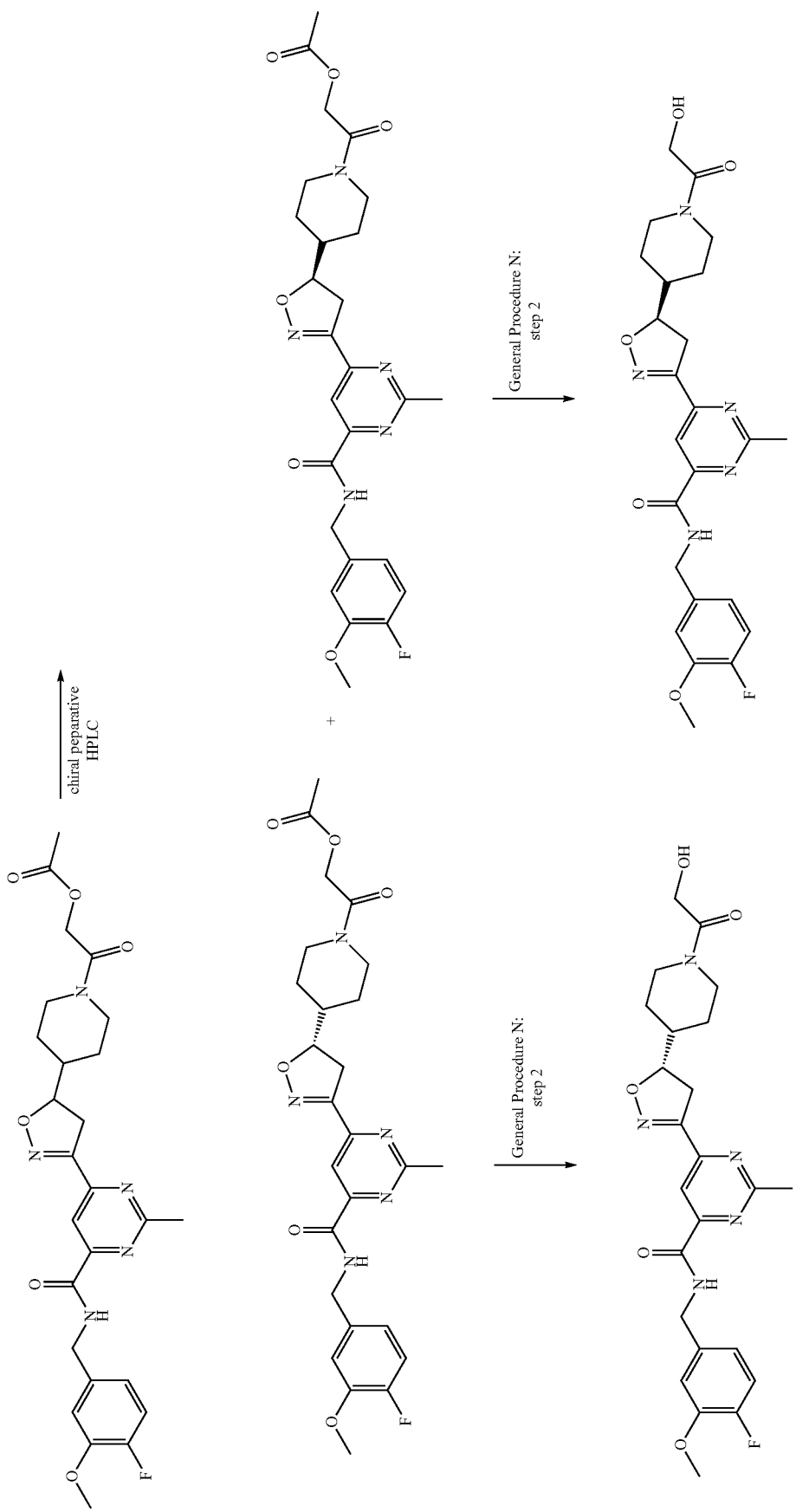

Individual enantiomers of Example #N.1 step 1 are separated using Chiral preparative HPLC (Method i, Table 2). These are subjected to base hydrolysis using the conditions that are described in General Procedure N step 2 to obtain AA.5 and AA.6

| Structure | Pure enantiomers |
|---|---|
| 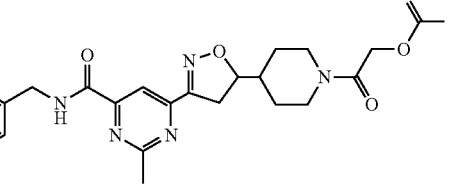<br>Example #N.1 step 1 | 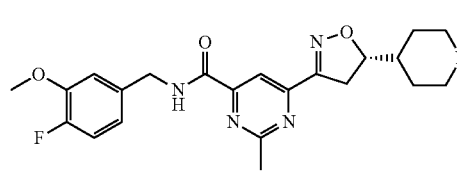<br><br>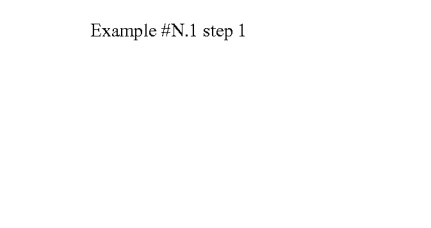 |

| Structure | m/z ESMs (M + H)+ | ee (Method-j, Table 2) |
|---|---|---|
| 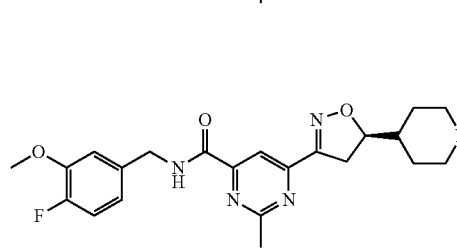<br>Example #N.1 step 1 | 528.4 | 99.58% |
|  | 528.4 | 94.68% |

| Example # | Structure | LC/MS R, Time in min (Method-e, Table 1) | m/z ESMs (M + H)+ |
|---|---|---|---|
| AA.1 | 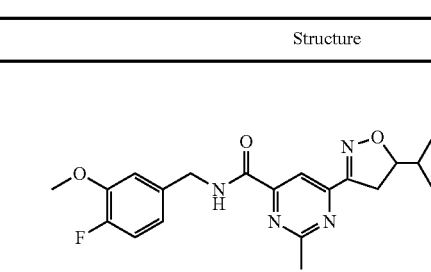 | 3.16 | 486.4 |
| AA.2 | 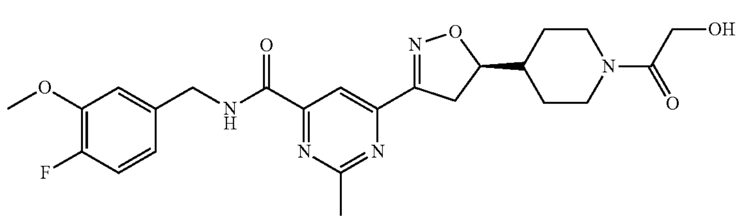 [SMILES: COc1cc(CNC(=O)c2cc(C3=NO[C@@H](C4CCN(C(=O)CO)CC4)C3)nc(C)n2)ccc1F] | 3.13 | 486.1 |

TABLE AA
Examples separated into their individual enentiomers using chiral preparative HPLC
| Example # | Structure |
|---|---|
| AA.3<br>AA.4 | 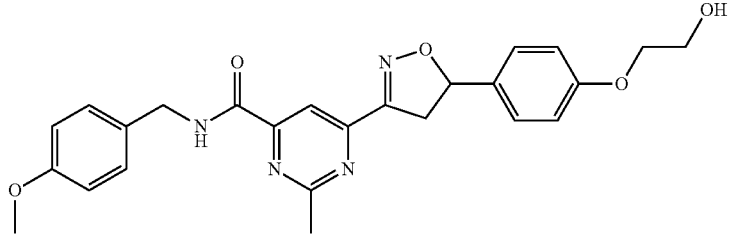 [SMILES: COc1ccc(CNC(=O)c2cc(C3=NO[C@H](c4ccc(OCCO)cc4)C3)nc(C)n2)cc1]<br>G.1.2 |
| AA.5<br>AA.6 | 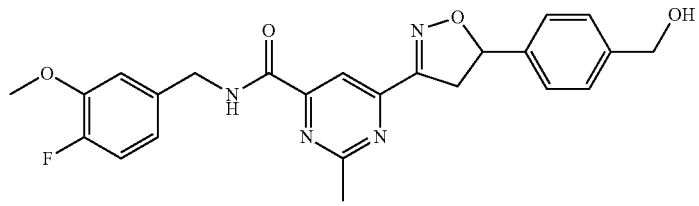<br>G.1.20 |
| AA.7<br>AA.8 | 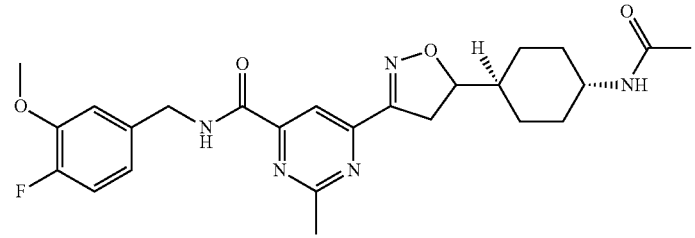<br>G.1.44 |
| AA.9<br>AA.10 | 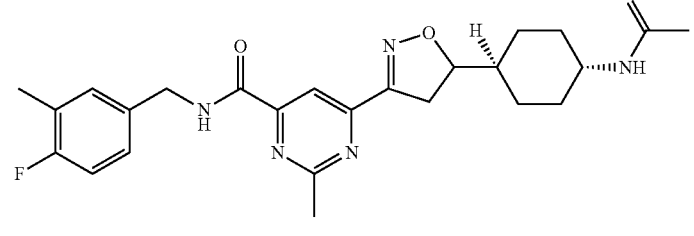<br>G.1.173 |
| AA.11<br>AA.12 | 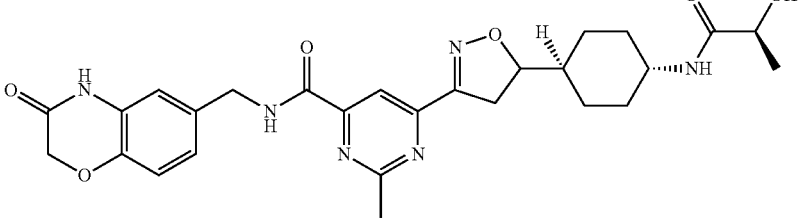<br>R.1.16 |

TABLE AA-continued
| | | |
|---|---|---|
| AA.13 AA.14 | 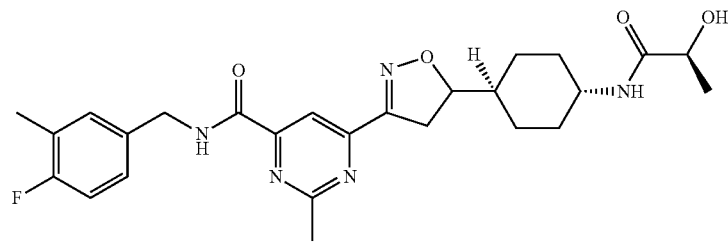 G.1.199 | |
| AA.15 AA.16 | 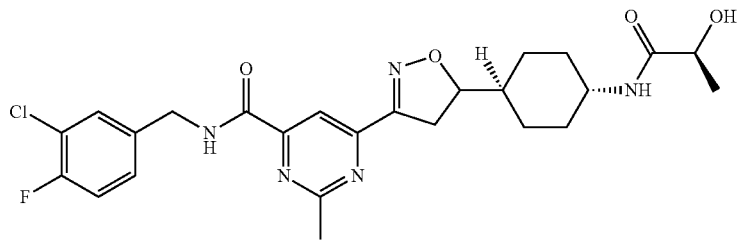 G.1.200 | |
| AA.17 AA.18 | 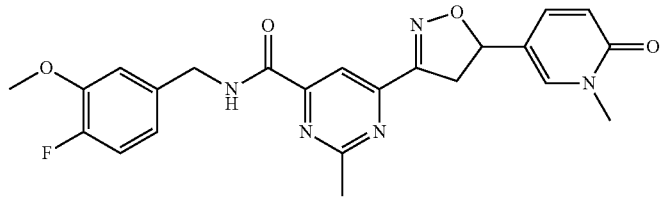 G.1.96 | |
| AA.19 AA.20 | 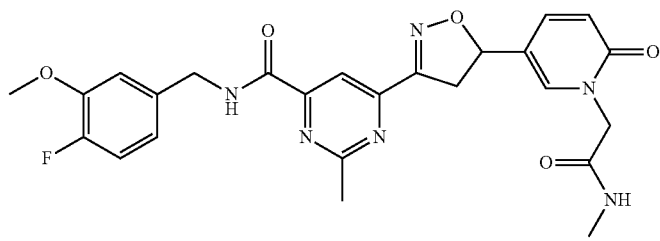 G.1.210 | |
| AA.21 AA.22 | 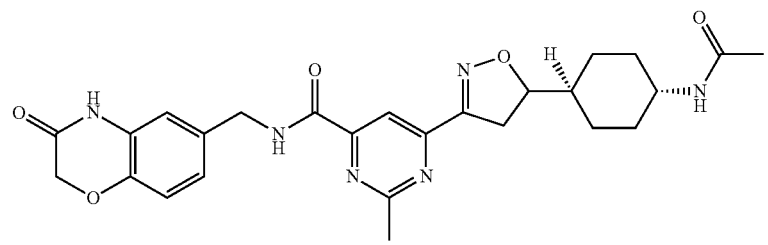 R.1.5 | |

TABLE AA-continued

| Example # | Enantiomers | Prep. HPLC method (Table 2) | LCMs R, Time in min (Method) | m/z ESMs (M + H)+ |
|---|---|---|---|---|
| AA.3 | | c-1 | 1.43 (b) | |
| AA.4 | | c-2 | 1.44 (b) | |
| AA.5 | | c-3 | 2.05 (c) | 451.3 |
| AA.6 | | c-3 | 1.98 (c) | 451.3 |
| AA.7 | | c-4 | 3.42 (d) | 484.0 |
| AA.8 | | c-4 | 3.07 (d) | 484.0 |

TABLE AA-continued

| | | | | |
|---|---|---|---|---|
| AA.9 | [structure] | c-5 | 2.970 (e) | 468.4 |
| AA.10 | [structure] | c-5 | 2.971 (e) | 468.4 |
| AA.11 | [structure] | c-14 | 1.81 (d) | 535.2 |
| AA.12 | [structure] | c-14 | 1.80 (d) | 535.3 |
| AA.13 | [structure] | c-6 | 3.124 (d) | 498.3 |
| AA.14 | [structure] | c-6 | 3.123 (d) | 498.4 |

TABLE AA-continued

| | | | | |
|---|---|---|---|---|
| AA.15 | [structure] | c-6 | 3.13 (d) | 518.2 |
| AA.16 | [structure] | c-6 | 3.137 (d) | 518.2 |
| AA.17 | [structure] | c-7 | 2.46 (d) | 452.3 |
| AA.18 | [structure] | c-7 | 2.459 (d) | 452.3 |
| AA.19 | [structure] | c-11 | 2.82 (e) | 509.3 |
| AA.20 | [structure] | c-11 | 2.76 (e) | 509.1 |

TABLE AA-continued
| | Structure | | | |
|---|---|---|---|---|
| AA.21 | 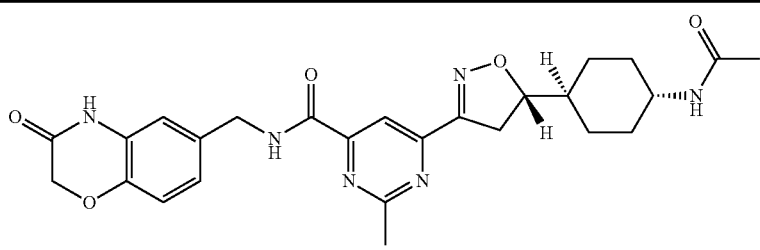 | c-13 | 1.92 (d) | 507.3 |
| AA.22 | 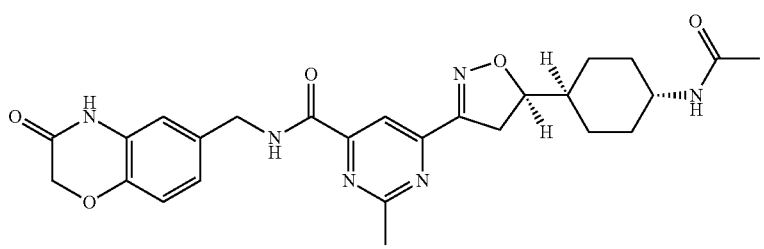 [SMILES: CC(=O)N[C@H]1CC[C@H]([C@H]2CC(c3cc(C(=O)NCc4ccc5c(c4)NC(=O)CO5)nc(C)n3)=NO2)CC1] | c-13 | 1.92 (d) | 507.3 |
MMP13 Catalytic Domain (CD) Potency of the Described Examples Determined Using Time Resolved Fluorescence Resonance Energy Transfer (FRET) Enzyme Assays:
| Structure | MMP13 (CD) IC$_{50}$ |
|---|---|
| | ** |
| | *** |
| | *** |

-continued

| Structure | MMP13 (CD) IC$_{50}$ |
|---|---|
| | ** |
| | *** |
| | *** |
| | ** |
| | ** |
| | *** |
| | ** |

-continued
| Structure | MMP13 (CD) IC$_{50}$ |
|---|---|
| 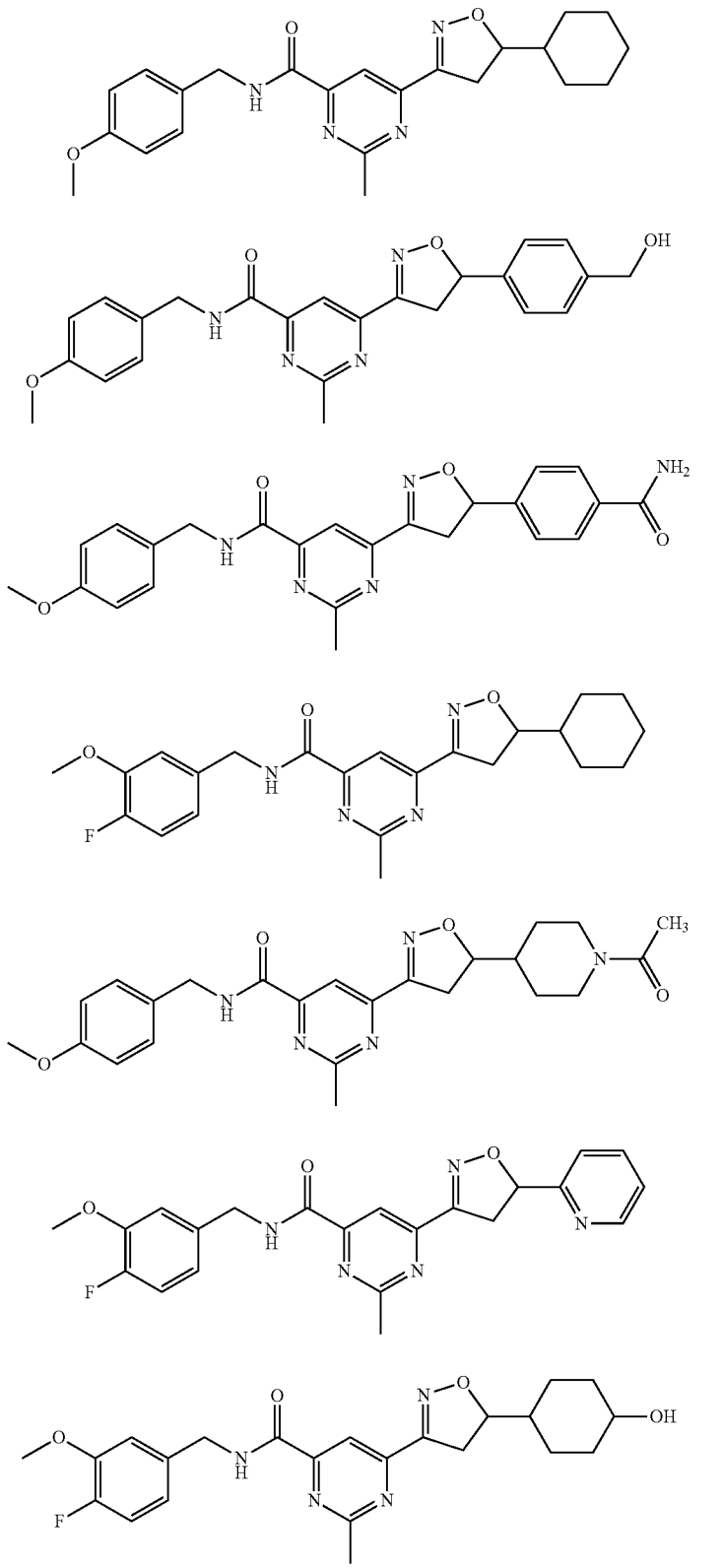 | *** |
| | *** |
| | **** |
| | **** |
| | ** |
| | *** |
| | **** |

| Structure | MMP13 (CD) IC$_{50}$ |
|---|---|
| 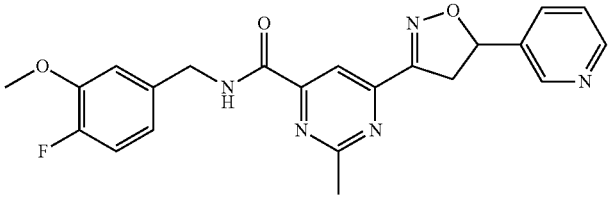 [SMILES: COc1cc(CNC(=O)c2cc(C3=NOC(c4cccnc4)C3)nc(C)n2)ccc1F] | **** |
| 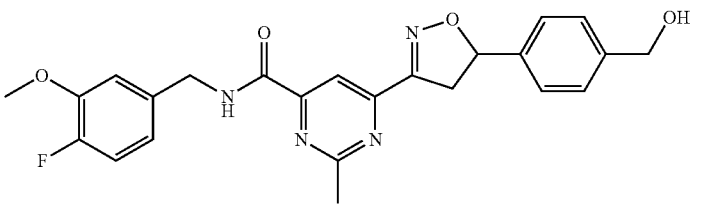 [SMILES: COc1cc(CNC(=O)c2cc(C3=NOC(c4ccc(CO)cc4)C3)nc(C)n2)ccc1F] | **** |
| 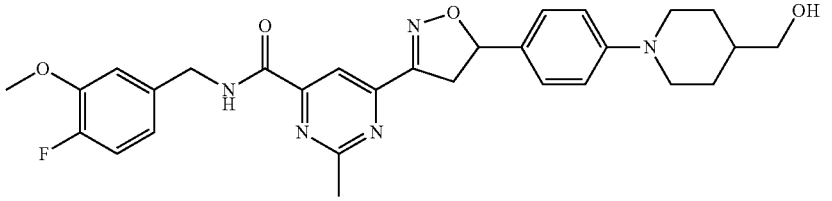 [SMILES: COc1cc(CNC(=O)c2cc(C3=NOC(c4ccc(N5CCC(CO)CC5)cc4)C3)nc(C)n2)ccc1F] | *** |
| 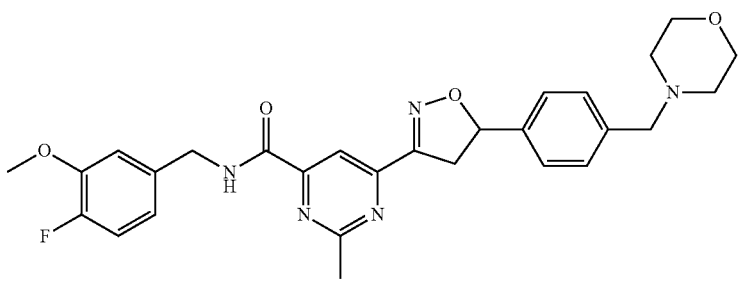 | *** |
| 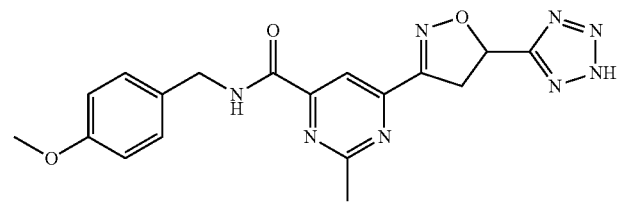 [SMILES: COc1ccc(CNC(=O)c2cc(C3=NOC(c4nn[nH]n4)C3)nc(C)n2)cc1] | * |
| 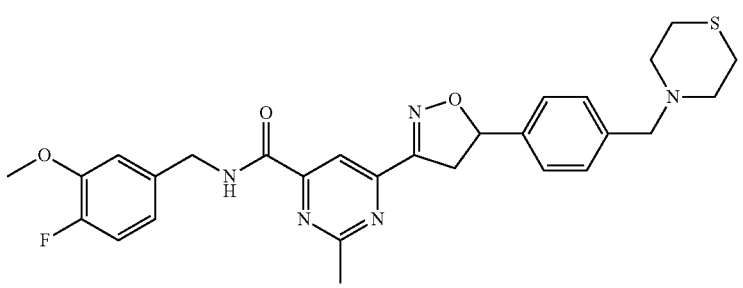 | **** |

| Structure | MMP13 (CD) IC$_{50}$ |
|---|---|
| 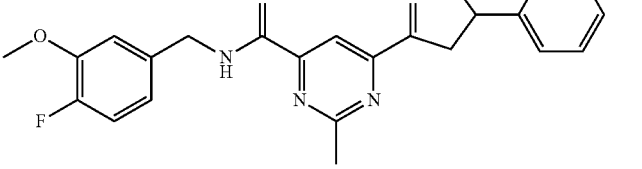 | **** |
| 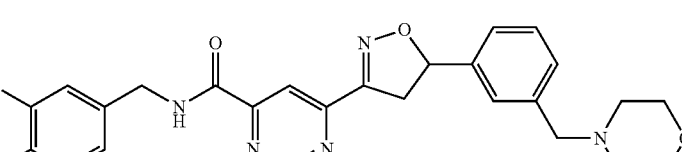 | **** |
|  | *** |
| 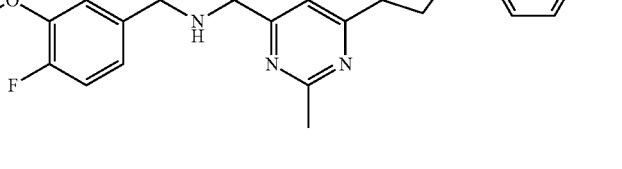 | **** |
| 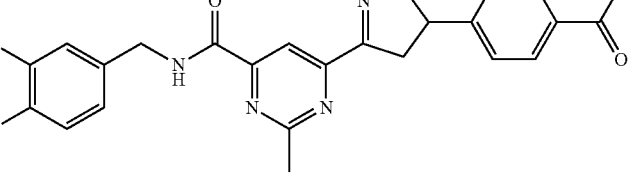 | **** |
| 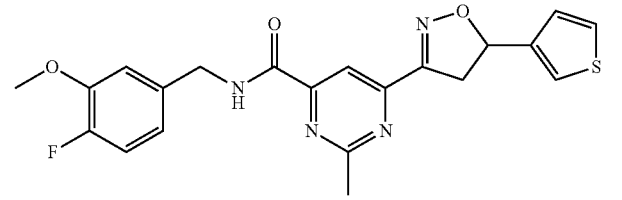 [SMILES: COc1cc(CNC(=O)c2cc(C3=NOC(c4ccsc4)C3)nc(C)n2)ccc1F] | **** |

| Structure | MMP13 (CD) IC$_{50}$ |
|---|---|
| | **** |
| | ** |
| | *** |
| | **** |
| | ** |
| | *** |

| Structure | MMP13 (CD) IC$_{50}$ |
|---|---|
| 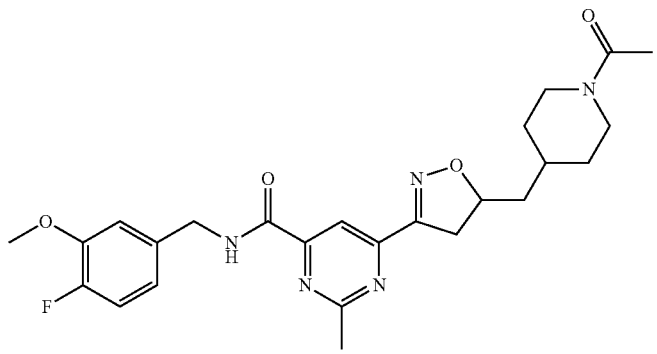 [SMILES: COc1cc(CNC(=O)c2cc(C3=NOC(CC4CCN(C(C)=O)CC4)C3)nc(C)n2)ccc1F] | *** |
| 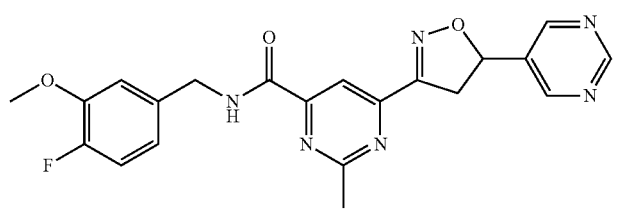 [SMILES: COc1cc(CNC(=O)c2cc(C3=NOC(c4cncnc4)C3)nc(C)n2)ccc1F] | *** |
| 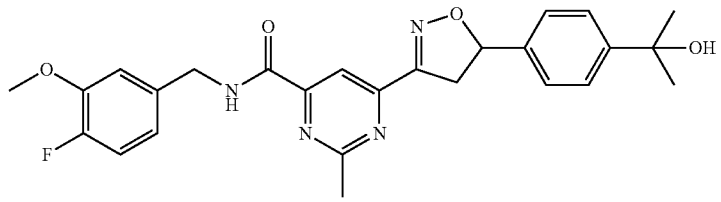 [SMILES: COc1cc(CNC(=O)c2cc(C3=NOC(c4ccc(C(C)(C)O)cc4)C3)nc(C)n2)ccc1F] | *** |
| 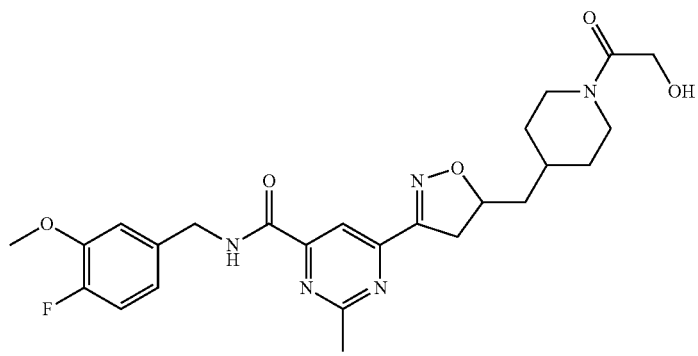 [SMILES: COc1cc(CNC(=O)c2cc(C3=NOC(CC4CCN(C(=O)CO)CC4)C3)nc(C)n2)ccc1F] | *** |
| 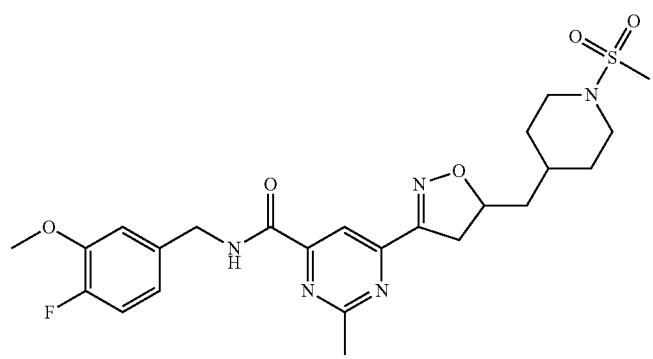 | *** |

| Structure | MMP13 (CD) IC$_{50}$ |
|---|---|
| 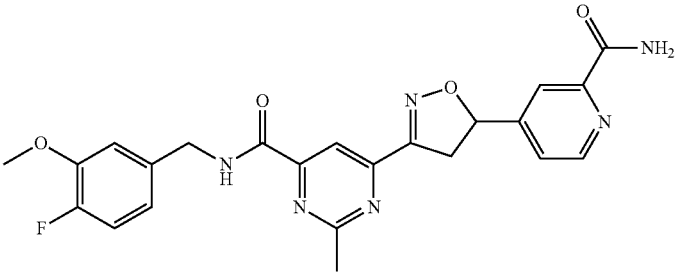 [SMILES: COc1cc(CNC(=O)c2cc(C3=NOC(c4ccnc(C(N)=O)c4)C3)nc(C)n2)ccc1F] | *** |
| 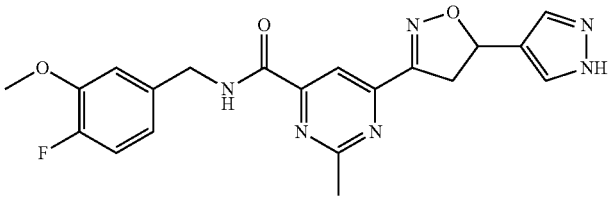 [SMILES: COc1cc(CNC(=O)c2cc(C3=NOC(c4cn[nH]c4)C3)nc(C)n2)ccc1F] | *** |
| 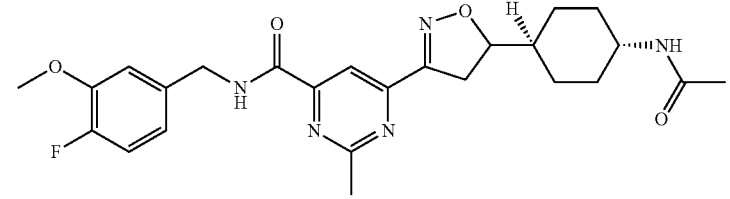 [SMILES: COc1cc(CNC(=O)c2cc(C3=NOC([C@H]4CC[C@H](NC(C)=O)CC4)C3)nc(C)n2)ccc1F] | **** |
| 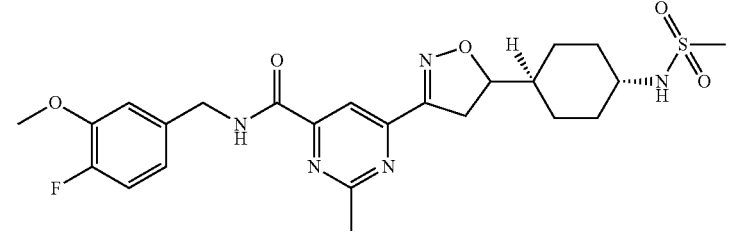 | **** |
| 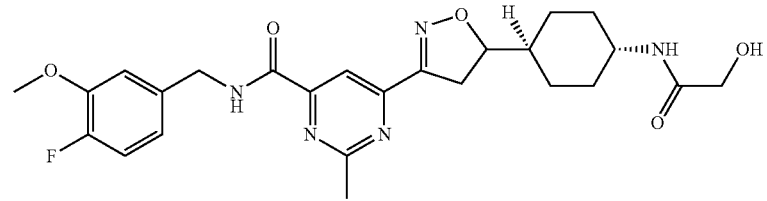 [SMILES: COc1cc(CNC(=O)c2cc(C3=NOC([C@H]4CC[C@H](NC(=O)CO)CC4)C3)nc(C)n2)ccc1F] | **** |
| 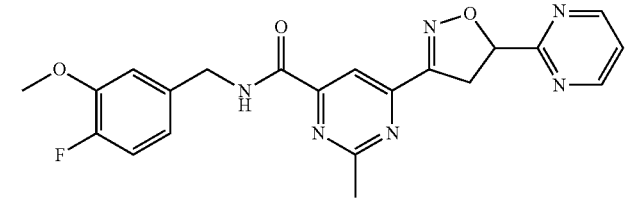 [SMILES: COc1cc(CNC(=O)c2cc(C3=NOC(c4ncccn4)C3)nc(C)n2)ccc1F] | *** |
| 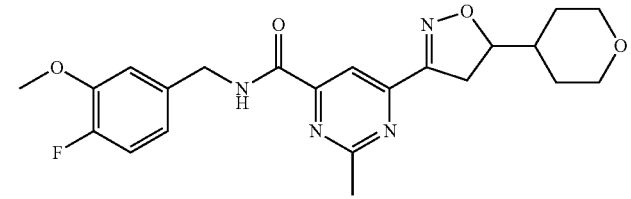 [SMILES: COc1cc(CNC(=O)c2cc(C3=NOC(C4CCOCC4)C3)nc(C)n2)ccc1F] | **** |

-continued

| Structure | MMP13 (CD) IC$_{50}$ |
|---|---|
| | *** |
| | *** |
| | **** |
| | *** |
| | *** |
| | *** |
| | *** |

-continued

| Structure | MMP13 (CD) IC$_{50}$ |
|---|---|
| | *** |
| | *** |
| | *** |
| | *** |
| | **** |
| | *** |
| | **** |

| Structure | MMP13 (CD) IC$_{50}$ |
|---|---|
| 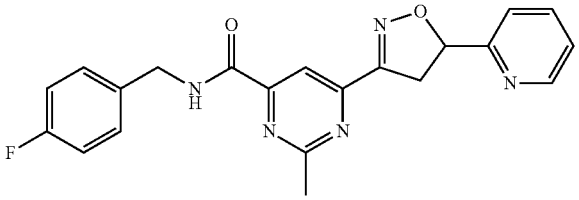 [SMILES: Cc1nc(C(=O)NCc2ccc(F)cc2)cc(C2=NOC(c3ccccn3)C2)n1] | *** |
| 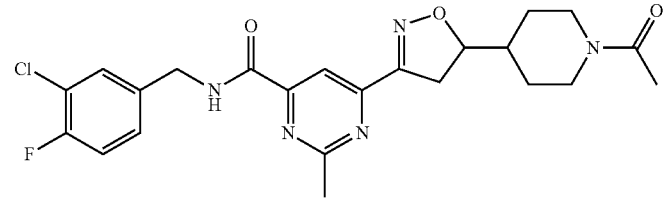 [SMILES: CC(=O)N1CCC(C2CC(c3cc(C(=O)NCc4ccc(F)c(Cl)c4)nc(C)n3)=NO2)CC1] | *** |
| 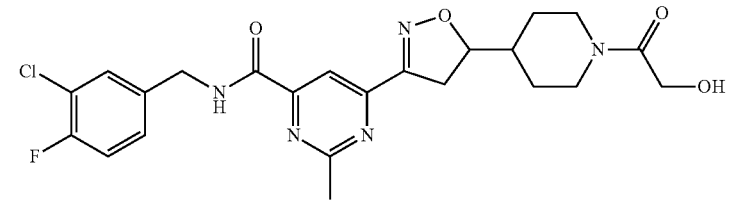 [SMILES: Cc1nc(C(=O)NCc2ccc(F)c(Cl)c2)cc(C2=NOC(C3CCN(C(=O)CO)CC3)C2)n1] | *** |
| 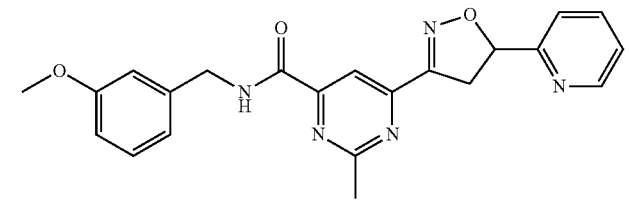 [SMILES: COc1cccc(CNC(=O)c2cc(C3=NOC(c4ccccn4)C3)nc(C)n2)c1] | *** |
| 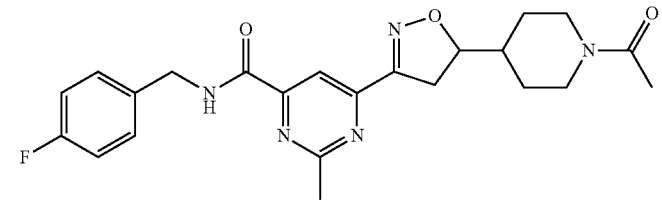 [SMILES: CC(=O)N1CCC(C2CC(c3cc(C(=O)NCc4ccc(F)cc4)nc(C)n3)=NO2)CC1] | *** |
| 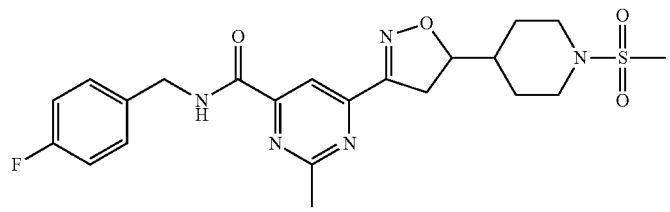 [SMILES: Cc1nc(C(=O)NCc2ccc(F)cc2)cc(C2=NOC(C3CCN(S(C)(=O)=O)CC3)C2)n1] | **** |
| 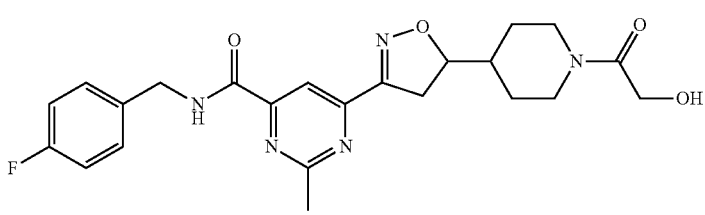 [SMILES: Cc1nc(C(=O)NCc2ccc(F)cc2)cc(C2=NOC(C3CCN(C(=O)CO)CC3)C2)n1] | *** |

| Structure | MMP13 (CD) IC$_{50}$ |
|---|---|
| 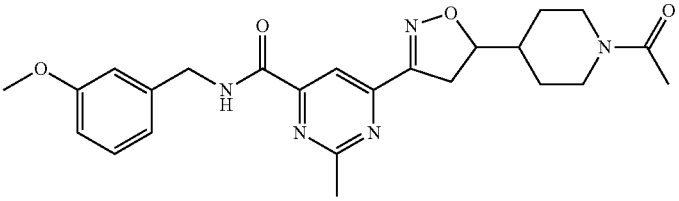 [SMILES: COc1cccc(CNC(=O)c2cc(C3=NOC(C4CCN(C(C)=O)CC4)C3)nc(C)n2)c1] | *** |
| 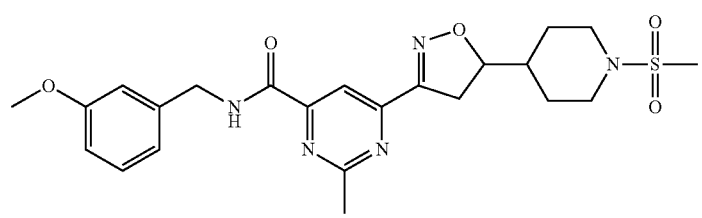 | **** |
| 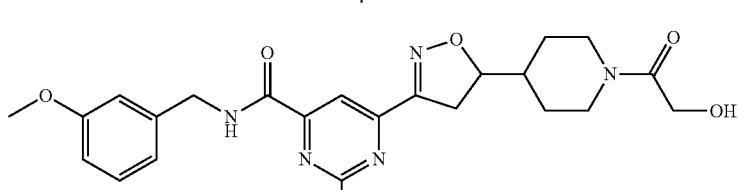 | *** |
| 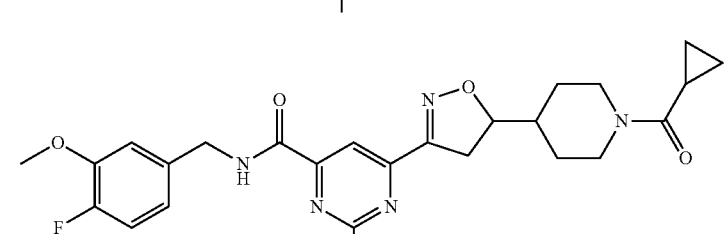 | *** |
| 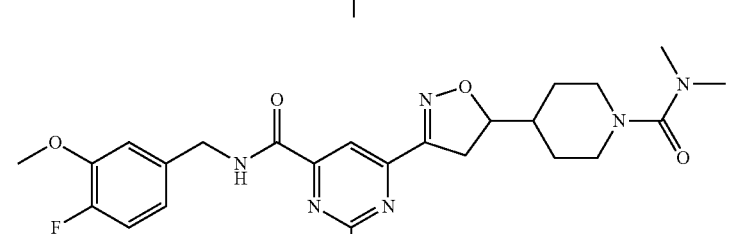 | **** |
| 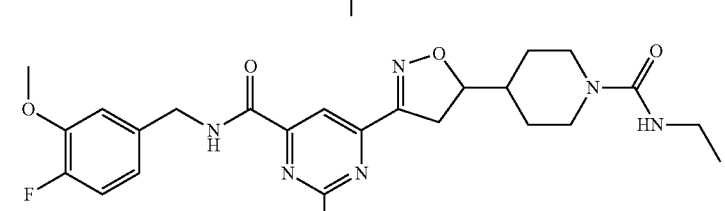 | *** |
| 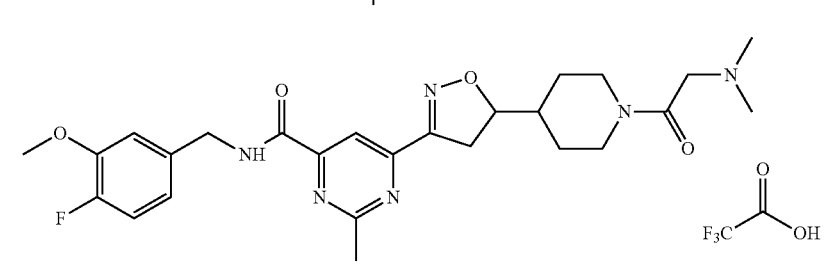 | *** |

| Structure | MMP13 (CD) IC50 |
|---|---|
| 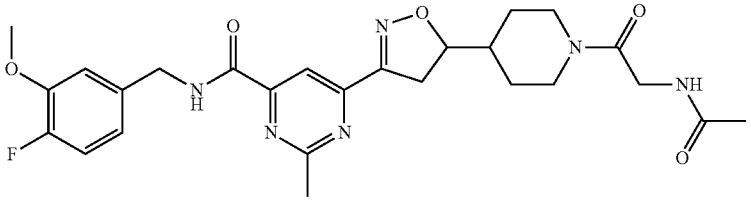 [SMILES: COc1cc(CNC(=O)c2cc(C3=NOC(C4CCN(C(=O)CNC(C)=O)CC4)C3)nc(C)n2)ccc1F] | *** |
| 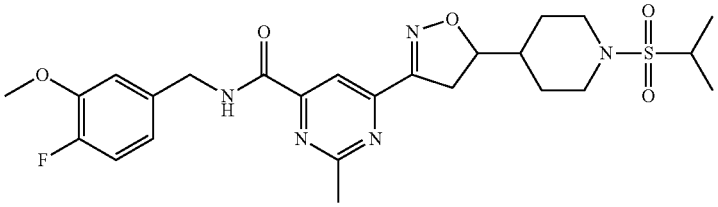 [SMILES: COc1cc(CNC(=O)c2cc(C3=NOC(C4CCN(S(=O)(=O)C(C)C)CC4)C3)nc(C)n2)ccc1F] | **** |
| 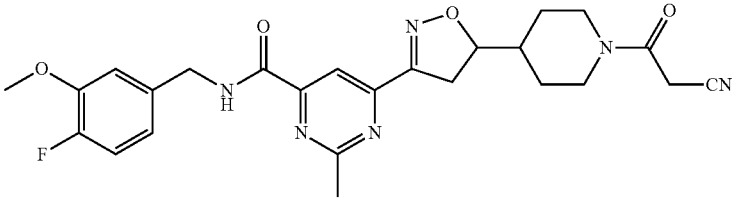 [SMILES: COc1cc(CNC(=O)c2cc(C3=NOC(C4CCN(C(=O)CC#N)CC4)C3)nc(C)n2)ccc1F] | *** |
| 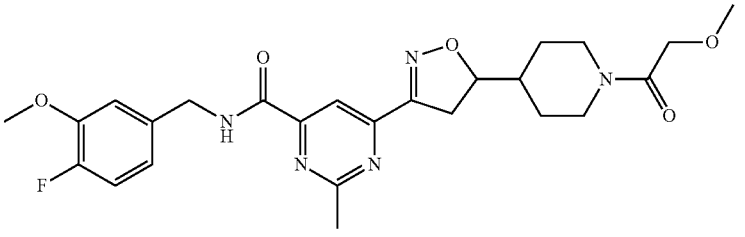 | *** |
| 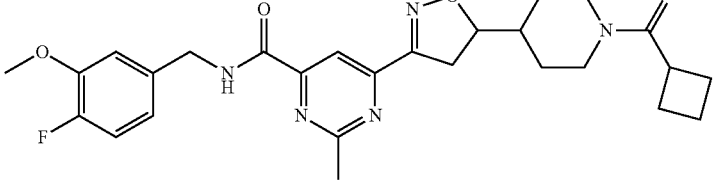 | *** |
| 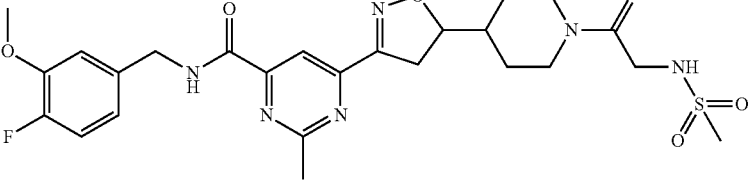 | *** |
| 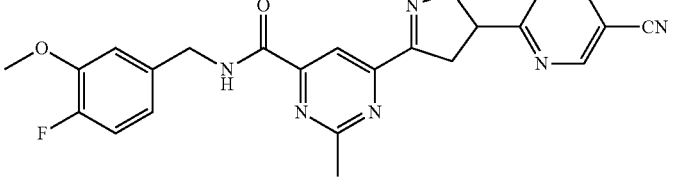 | **** |

-continued

| Structure | MMP13 (CD) IC$_{50}$ |
|---|---|
| (structure) | **** |
| (structure) | *** |
| (structure) | **** |
| (structure) | *** |
| (structure) | **** |
| (structure) | **** |
| (structure) | *** |

| Structure | MMP13 (CD) IC$_{50}$ |
|---|---|
| 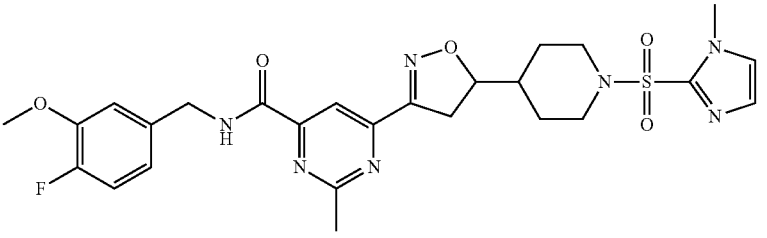 [SMILES: COc1cc(CNC(=O)c2cc(C3=NOC(C4CCN(S(=O)(=O)c5nccn5C)CC4)C3)nc(C)n2)ccc1F] | **** |
| 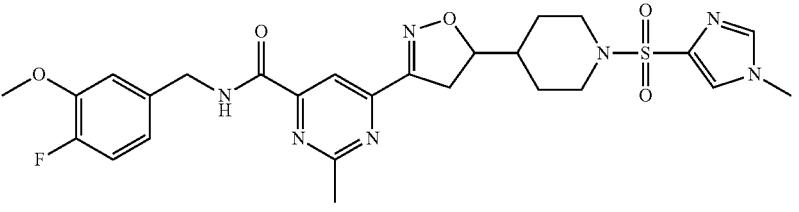 | **** |
| 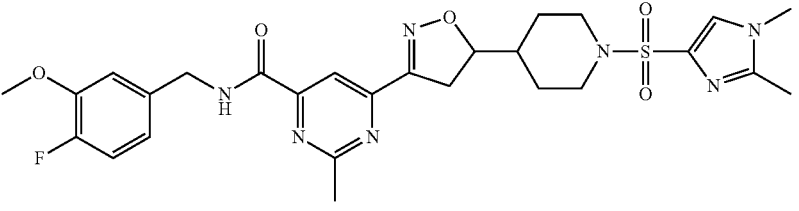 | **** |
| 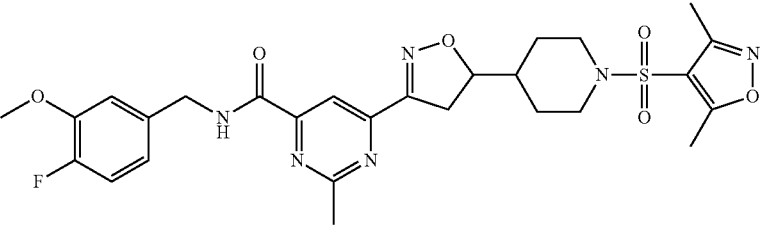 [SMILES: COc1cc(CNC(=O)c2cc(C3=NOC(C4CCN(S(=O)(=O)c5c(C)noc5C)CC4)C3)nc(C)n2)ccc1F] | **** |
| 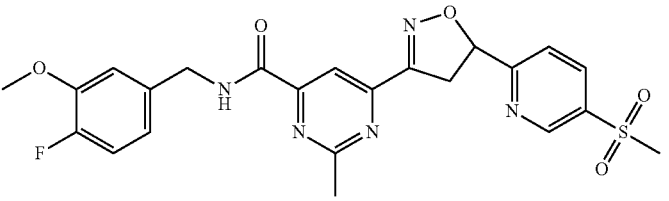 | **** |
| 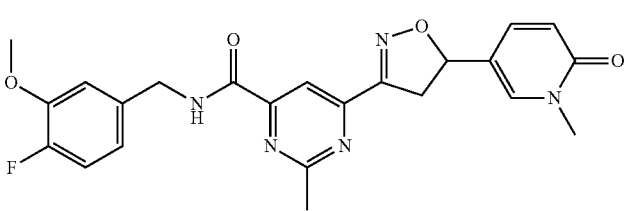 [SMILES: COc1cc(CNC(=O)c2cc(C3=NOC(c4ccc(=O)n(C)c4)C3)nc(C)n2)ccc1F] | *** |
| 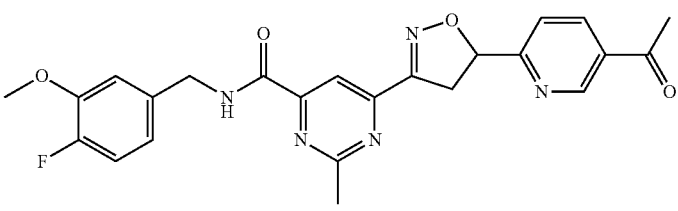 [SMILES: COc1cc(CNC(=O)c2cc(C3=NOC(c4ccc(C(C)=O)cn4)C3)nc(C)n2)ccc1F] | **** |

| Structure | MMP13 (CD) IC$_{50}$ |
|---|---|
| | **** |
| | **** |
| | ** |
| | *** |
| | * |
| | *** |
| | * |

-continued

| Structure | MMP13 (CD) IC$_{50}$ |
|---|---|
| (structure) | * |
| (structure) | *** |
| (structure) | * |
| (structure) | **** |
| (structure) | * |
| (structure) | *** |
| (structure) | ** |
| (structure) | * |

| Structure | MMP13 (CD) IC$_{50}$ |
|---|---|
| | * |
| | ** |
| | *** |
| | * |
| | *** |
| | * |
| | *** |

-continued

| Structure | MMP13 (CD) IC$_{50}$ |
|---|---|
| | * |
| | * |
| | * |
| | *** |
| | **** |
| | **** |

| Structure | MMP13 (CD) IC$_{50}$ |
|---|---|
| | *** |
| | **** |
| | **** |
| | *** |
| | **** |
| | **** |
| | *** |

| Structure | MMP13 (CD) IC$_{50}$ |
|---|---|
| 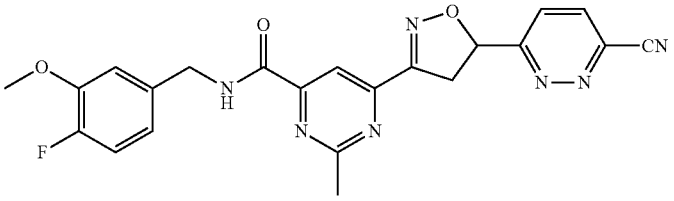 [SMILES: COc1cc(CNC(=O)c2cc(C3=NOC(c4ccc(C#N)nn4)C3)nc(C)n2)ccc1F] | **** |
| 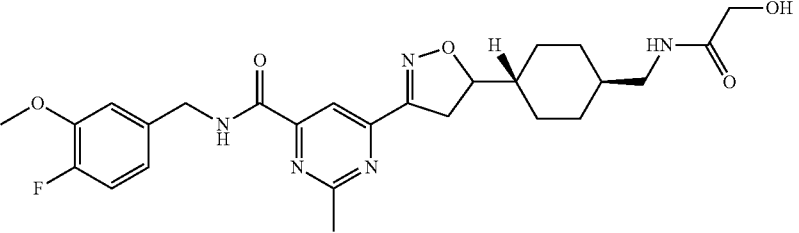 [SMILES: COc1cc(CNC(=O)c2cc(C3=NOC([C@H]4CC[C@H](CNC(=O)CO)CC4)C3)nc(C)n2)ccc1F] | **** |
| 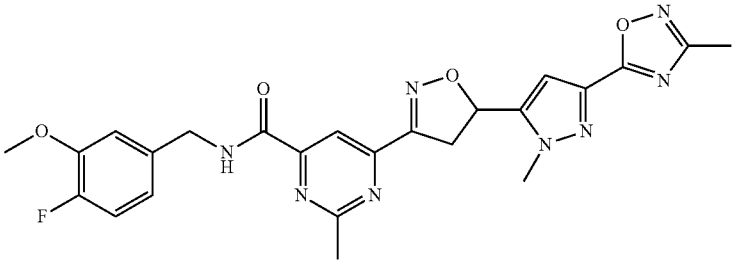 | *** |
| 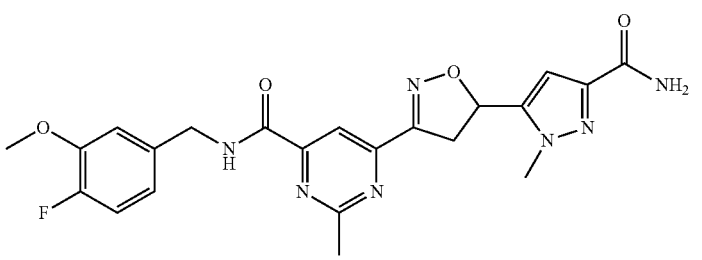 [SMILES: COc1cc(CNC(=O)c2cc(C3=NOC(c4cc(C(N)=O)nn4C)C3)nc(C)n2)ccc1F] | ** |
| 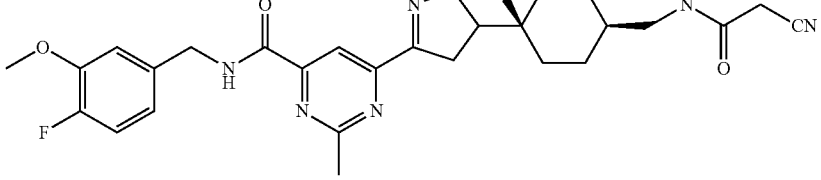 | **** |
|  | *** |

| Structure | MMP13 (CD) IC$_{50}$ |
|---|---|
| 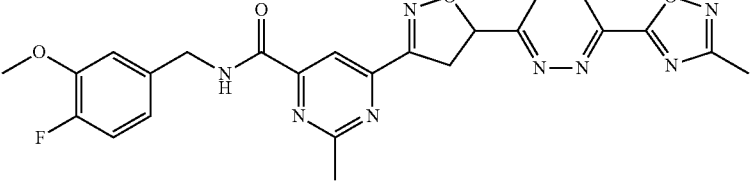 | **** |
| 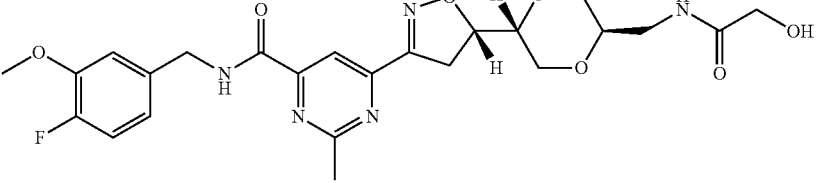 | **** |
| 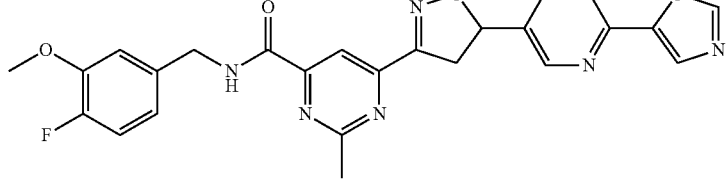 | **** |
| 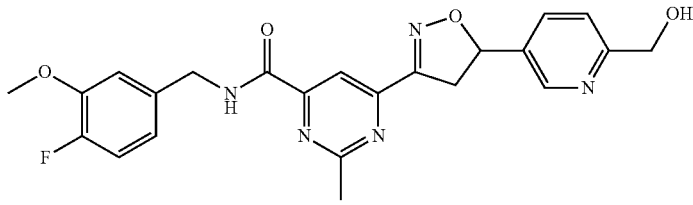 [SMILES: COc1cc(CNC(=O)c2cc(C3=NOC(c4ccc(CO)nc4)C3)nc(C)n2)ccc1F] | *** |
| 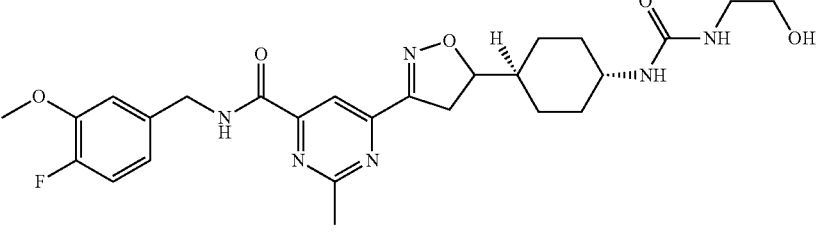 | **** |
| 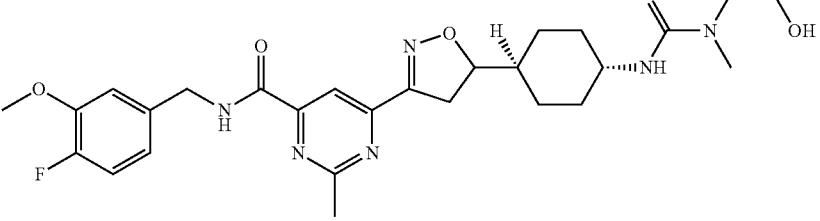 | **** |
| 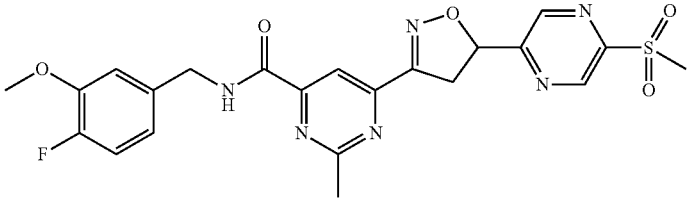 | *** |

| Structure | MMP13 (CD) IC$_{50}$ |
|---|---|
| 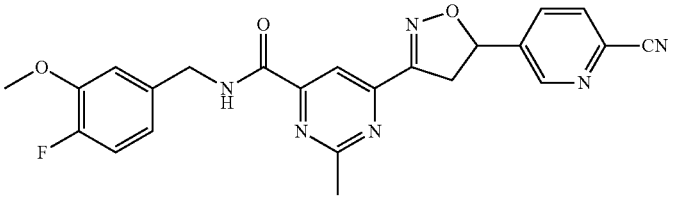 | **** |
| 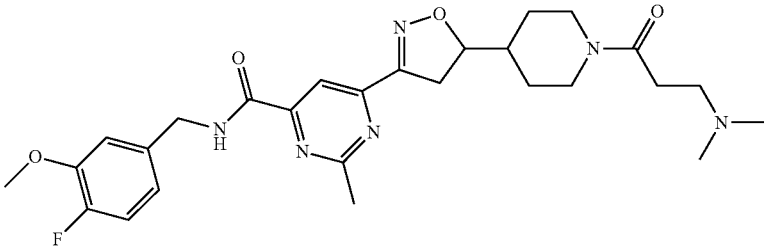 | *** |
| 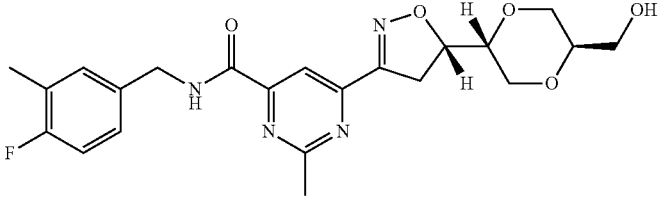 |  |
| 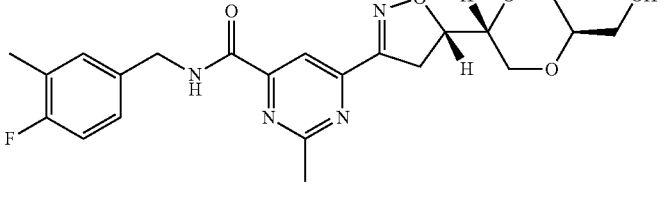 | ** |
| 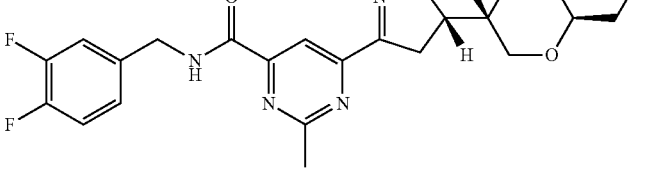 | *** |
| 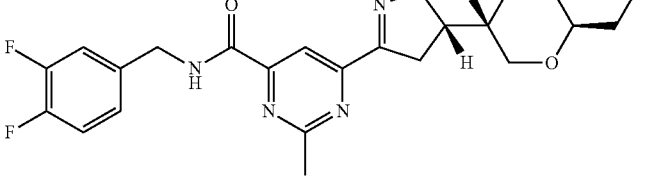 | * |
| 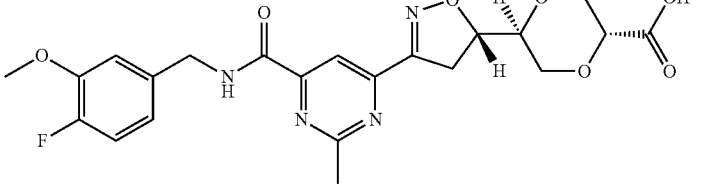 | *** |

| Structure | MMP13 (CD) IC$_{50}$ |
|---|---|
| 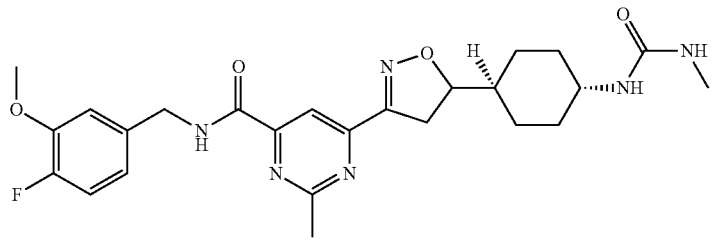 [SMILES: CNC(=O)N[C@H]1CC[C@H](C2CC(c3cc(C(=O)NCc4ccc(F)c(OC)c4)nc(C)n3)=NO2)CC1] | **** |
| 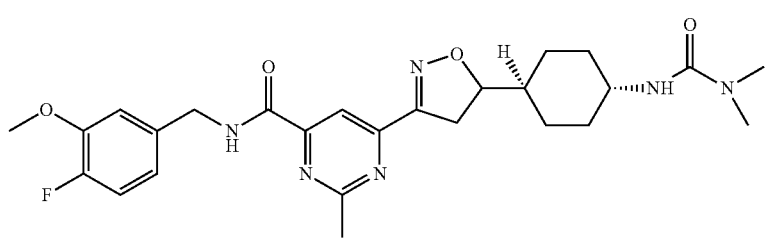 | **** |
| 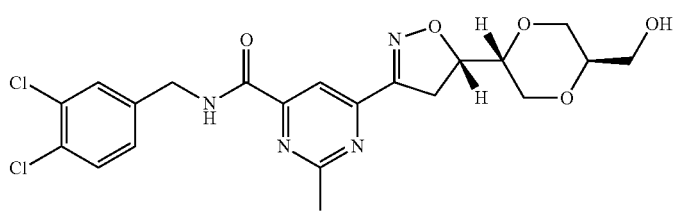 [SMILES: Cc1nc(C(=O)NCc2ccc(Cl)c(Cl)c2)cc(C2=NO[C@H]([C@H]3CO[C@H](CO)CO3)C2)n1] | * |
| 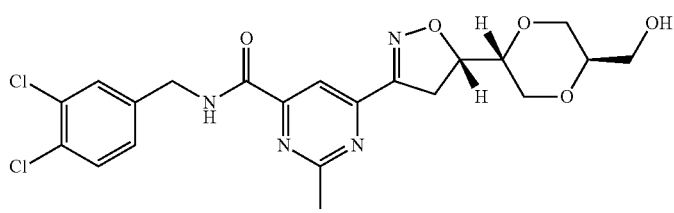 [SMILES: Cc1nc(C(=O)NCc2ccc(Cl)c(Cl)c2)cc(C2=NO[C@H]([C@H]3CO[C@H](CO)CO3)C2)n1] | * |
| 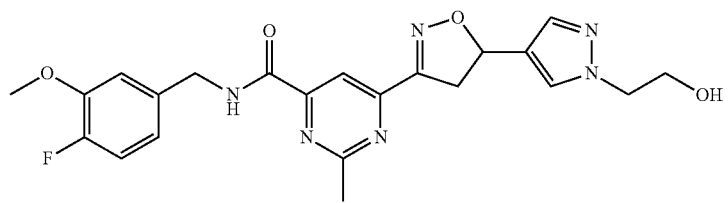 [SMILES: COc1cc(CNC(=O)c2cc(C3=NOC(c4cnn(CCO)c4)C3)nc(C)n2)ccc1F] | * |
| 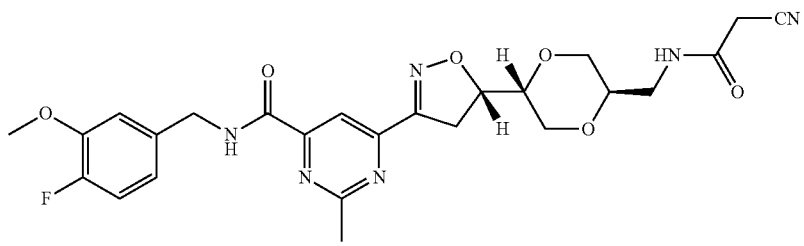 [SMILES: COc1cc(CNC(=O)c2cc(C3=NO[C@H]([C@H]4CO[C@H](CNC(=O)CC#N)CO4)C3)nc(C)n2)ccc1F] | **** |

| Structure | MMP13 (CD) IC$_{50}$ |
|---|---|
| (structure) | *** |
| (structure) | *** |
| (structure) | *** |
| (structure) | * |
| (structure) | *** |
| (structure) | *** |

-continued
| Structure | MMP13 (CD) IC$_{50}$ |
|---|---|
| 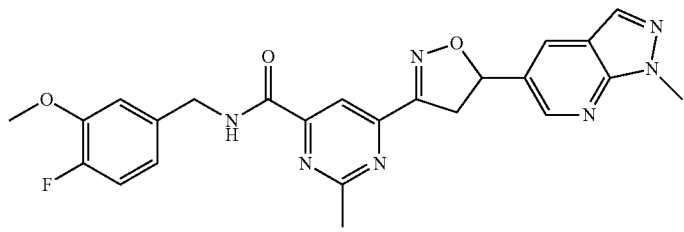 | *** |
| 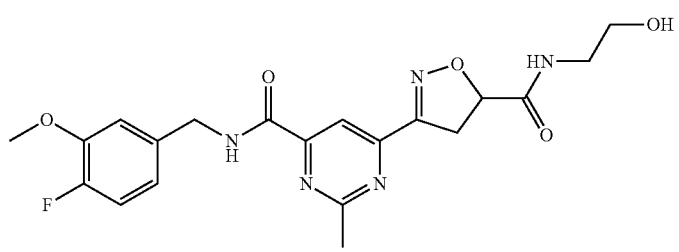 [SMILES: COc1cc(CNC(=O)c2cc(C3=NOC(C(=O)NCCO)C3)nc(C)n2)ccc1F] | ** |
| 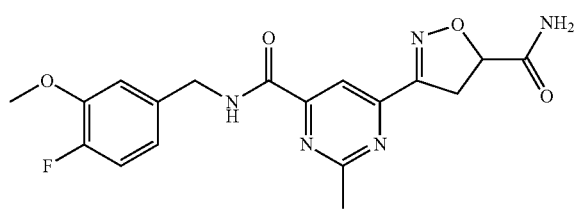 [SMILES: COc1cc(CNC(=O)c2cc(C3=NOC(C(N)=O)C3)nc(C)n2)ccc1F] | * |
| 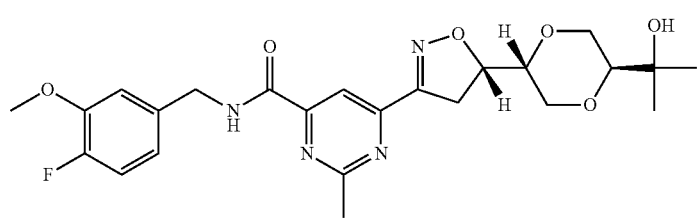 [SMILES: COc1cc(CNC(=O)c2cc(C3=NO[C@H]([C@H]4CO[C@H](C(C)(C)O)CO4)C3)nc(C)n2)ccc1F] | *** |
| 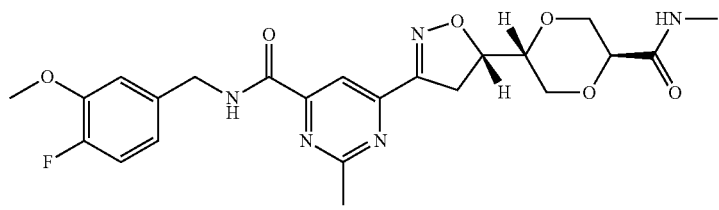 | **** |
| 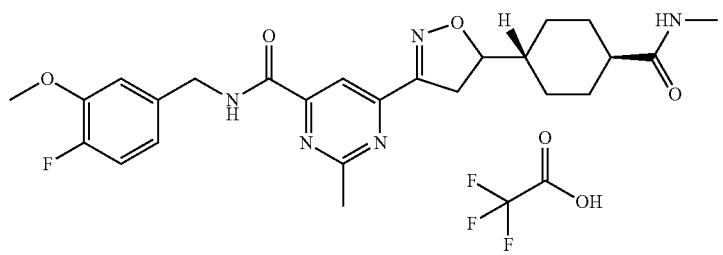 | **** |

| Structure | MMP13 (CD) IC$_{50}$ |
|---|---|
| 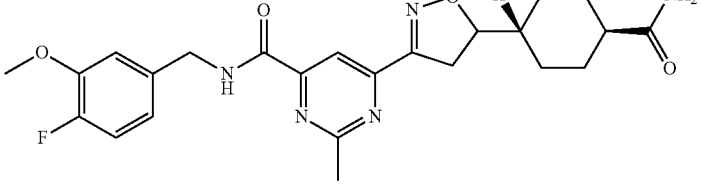 | **** |
| 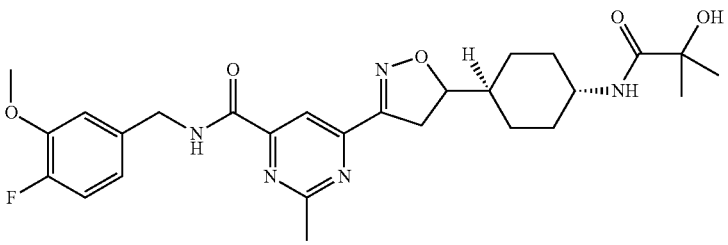 [SMILES: COc1cc(CNC(=O)c2cc(C3=NOC([C@H]4CC[C@H](NC(=O)C(C)(C)O)CC4)C3)nc(C)n2)ccc1F] | *** |
| 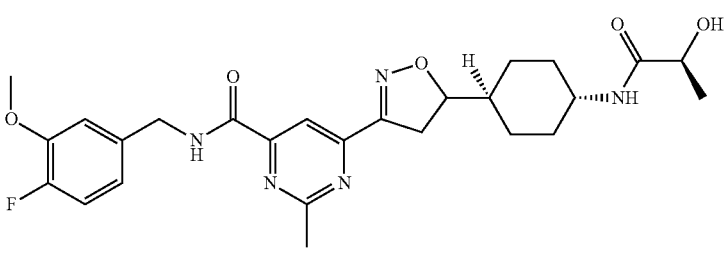 [SMILES: COc1cc(CNC(=O)c2cc(C3=NOC([C@H]4CC[C@H](NC(=O)[C@H](C)O)CC4)C3)nc(C)n2)ccc1F] | **** |
| 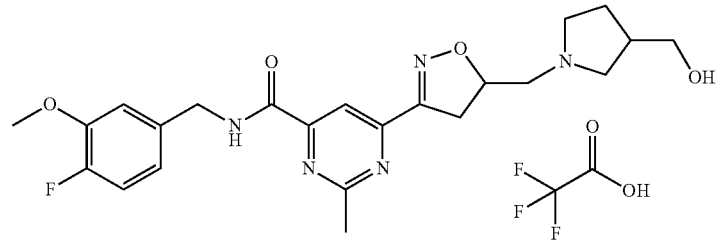 | * |
| 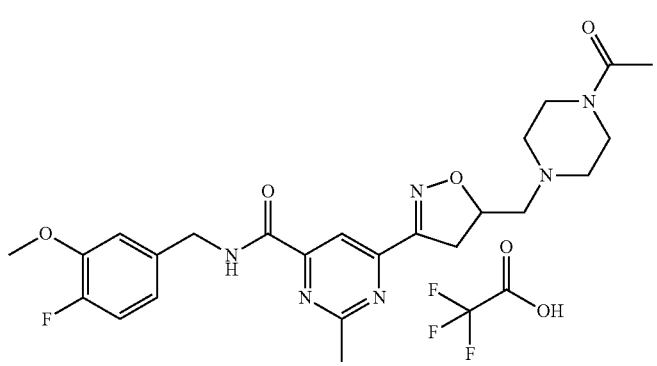 | * |
| 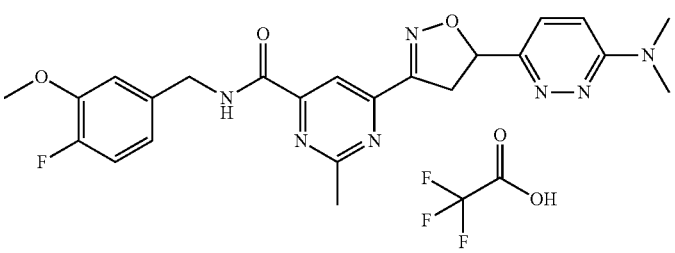 | * |

-continued

| Structure | MMP13 (CD) IC$_{50}$ |
|---|---|
| | * |
| | *** |
| | **** |
| | **** |
| | **** |
| | **** |

US 9,029,409 B2
383 384
-continued
| Structure | MMP13 (CD) IC$_{50}$ |
|---|---|
| 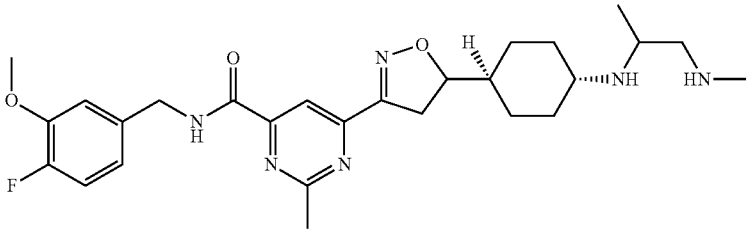 [SMILES: CNCC(C)N[C@H]1CC[C@H](C2CC(c3cc(C(=O)NCc4ccc(F)c(OC)c4)nc(C)n3)=NO2)CC1] | *** |
| 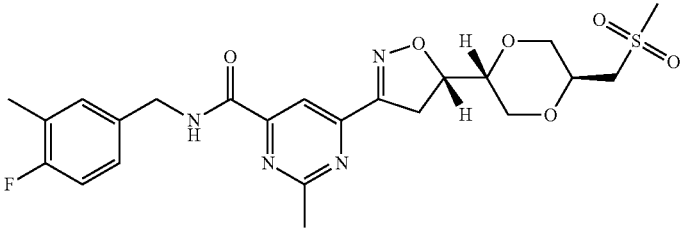 [SMILES: Cc1nc(C(=O)NCc2ccc(F)c(C)c2)cc(C2=NO[C@H]([C@H]3CO[C@H](CS(C)(=O)=O)CO3)C2)n1] | **** |
| 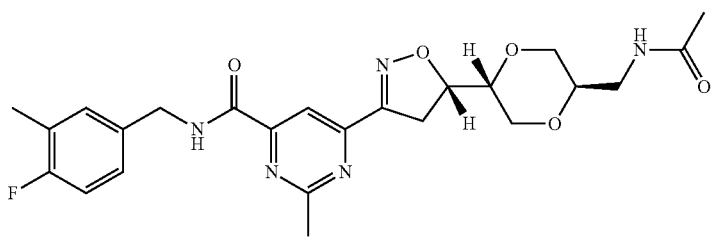 [SMILES: CC(=O)NC[C@@H]1CO[C@@H]([C@@H]2CC(c3cc(C(=O)NCc4ccc(F)c(C)c4)nc(C)n3)=NO2)CO1] | **** |
| 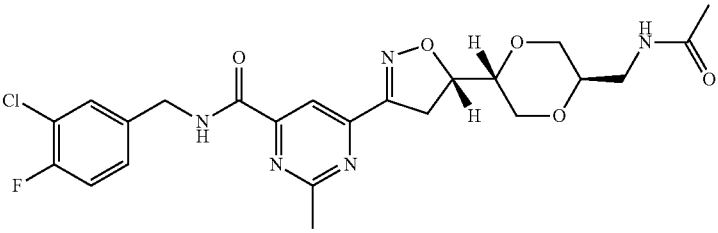 [SMILES: CC(=O)NC[C@@H]1CO[C@@H]([C@@H]2CC(c3cc(C(=O)NCc4ccc(F)c(Cl)c4)nc(C)n3)=NO2)CO1] | **** |
| 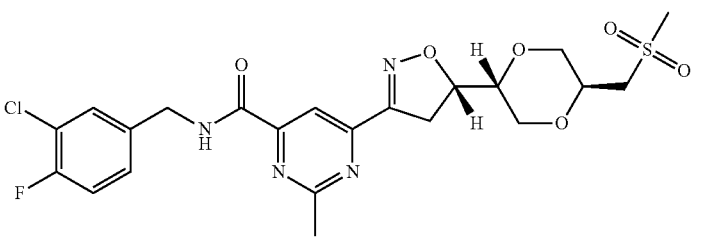 [SMILES: Cc1nc(C(=O)NCc2ccc(F)c(Cl)c2)cc(C2=NO[C@H]([C@H]3CO[C@H](CS(C)(=O)=O)CO3)C2)n1] | **** |
| 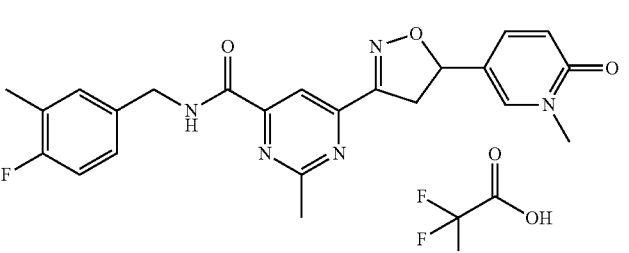 | **** |

| Structure | MMP13 (CD) IC$_{50}$ |
| --- | --- |
| | * |
| | * |
| | *** |
| | *** |
| | *** |
| | **** |

| Structure | MMP13 (CD) IC$_{50}$ |
|---|---|
| 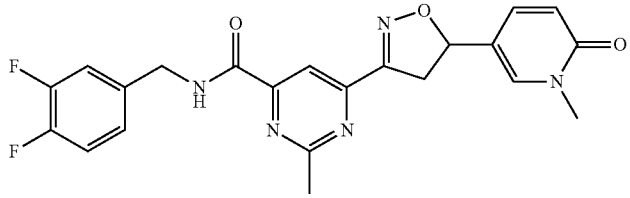 | *** |
| 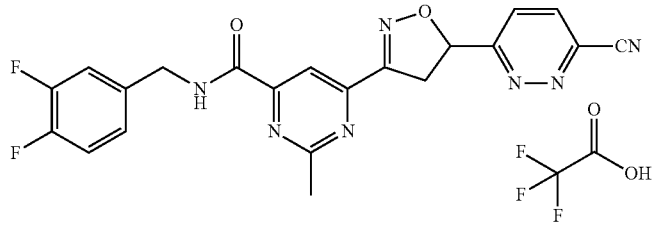 | *** |
| 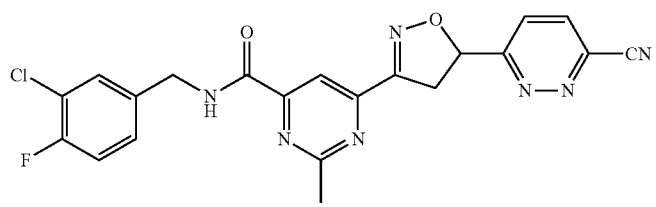 [SMILES: Cc1nc(C(=O)NCc2ccc(F)c(Cl)c2)cc(C2=NOC(c3ccc(C#N)nn3)C2)n1] | *** |
| 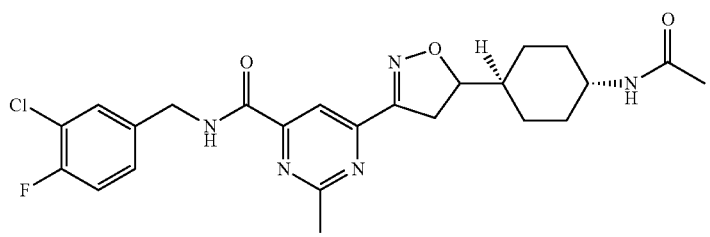 [SMILES: CC(=O)N[C@H]1CC[C@H](C2CC(c3cc(C(=O)NCc4ccc(F)c(Cl)c4)nc(C)n3)=NO2)CC1] | **** |
| 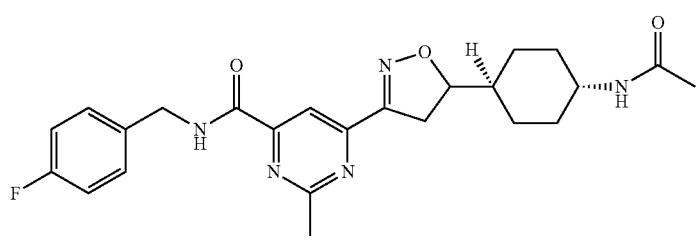 [SMILES: CC(=O)N[C@H]1CC[C@H](C2CC(c3cc(C(=O)NCc4ccc(F)cc4)nc(C)n3)=NO2)CC1] | *** |
| 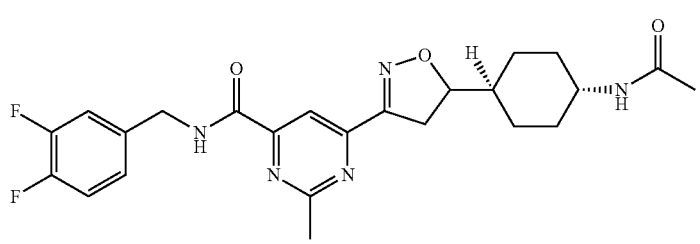 [SMILES: CC(=O)N[C@H]1CC[C@H](C2CC(c3cc(C(=O)NCc4ccc(F)c(F)c4)nc(C)n3)=NO2)CC1] | *** |
| 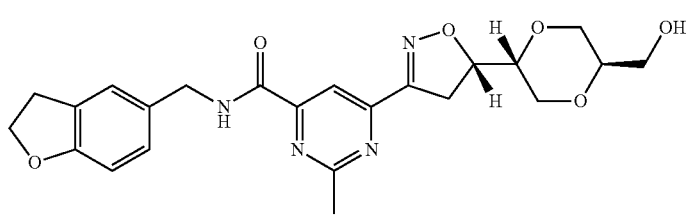 [SMILES: Cc1nc(C(=O)NCc2ccc3c(c2)CCO3)cc(C2=NO[C@H]([C@H]3CO[C@H](CO)CO3)C2)n1] | *** |

-continued

| Structure | MMP13 (CD) IC$_{50}$ |
|---|---|
| (structure) | * |
| (structure) | * |
| (structure) | *** |
| (structure) | * |
| (structure) 401 | *** |
| (structure) 402 | * |

| Structure | MMP13 (CD) IC$_{50}$ |
|---|---|
| 403 | **** |
| 404 | **** |
| (structure) | *** |
| (structure) | * |
| (structure) | *** |
| (structure) | **** |

| Structure | MMP13 (CD) IC$_{50}$ |
|---|---|
| 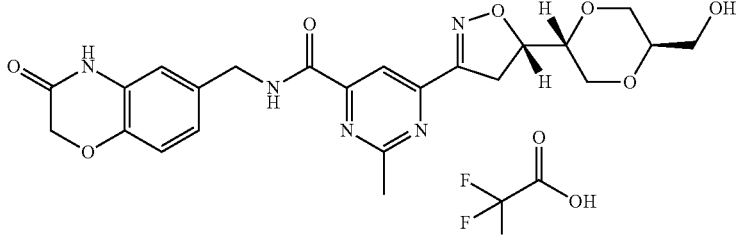 | **** |
| 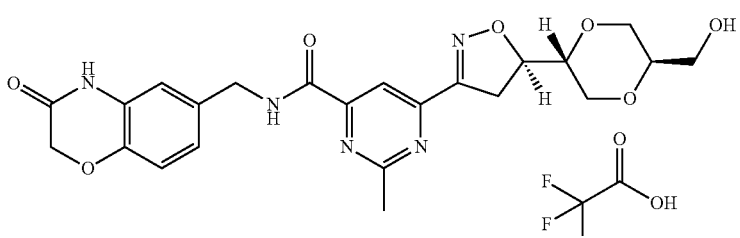 | *** |
| 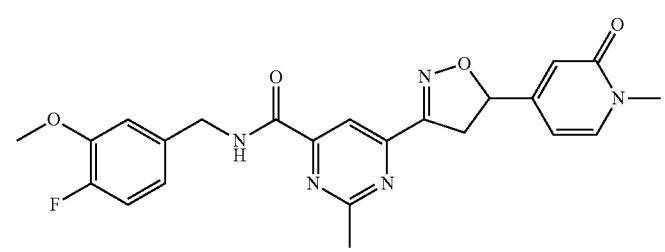 | *** |
| 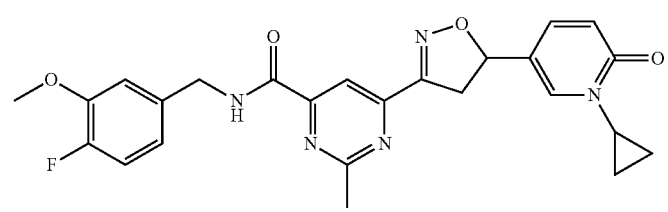 | **** |
| 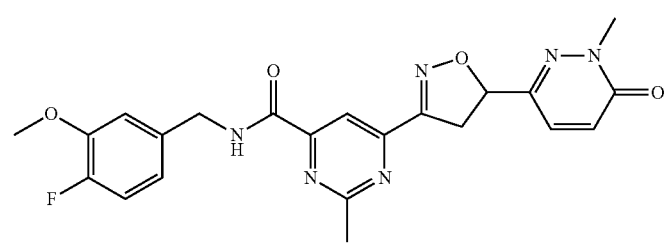 [SMILES: COc1cc(CNC(=O)c2cc(C3=NOC(c4ccc(=O)n(C)n4)C3)nc(C)n2)ccc1F] | *** |
| 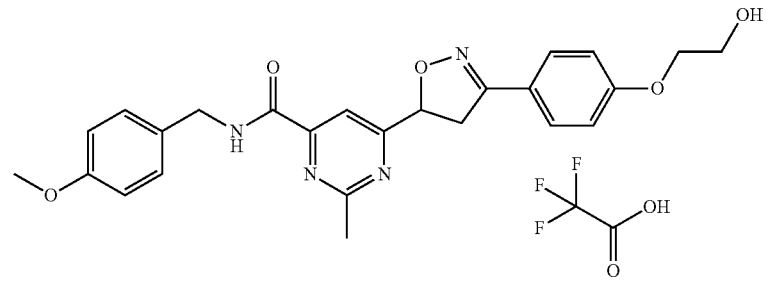 | *** |

-continued

| Structure | MMP13 (CD) IC$_{50}$ |
|---|---|
| | *** |
| | *** |
| | ** |
| | **** |
| | *** |
| | **** |
| | *** |

| Structure | MMP13 (CD) IC$_{50}$ |
|---|---|
| 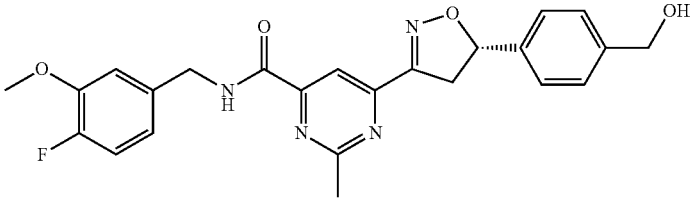 [SMILES: COc1cc(CNC(=O)c2cc(C3=NO[C@H](c4ccc(CO)cc4)C3)nc(C)n2)ccc1F] | * |
| 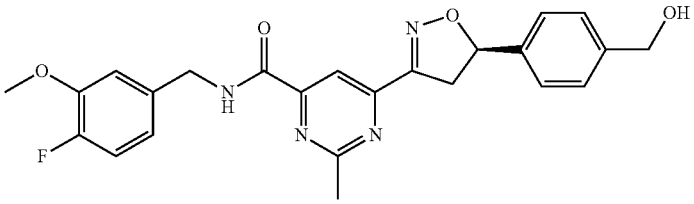 [SMILES: COc1cc(CNC(=O)c2cc(C3=NO[C@@H](c4ccc(CO)cc4)C3)nc(C)n2)ccc1F] | **** |
| 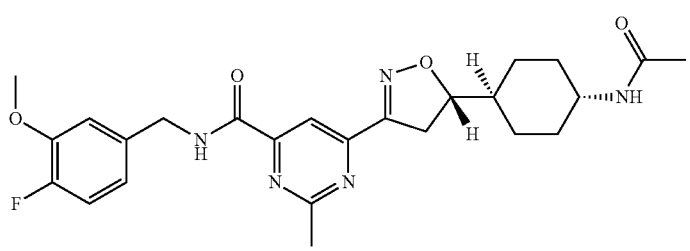 | **** |
| 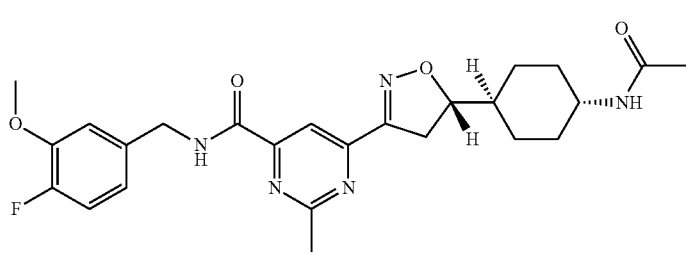 [SMILES: COc1cc(CNC(=O)c2cc(C3=NO[C@H]([C@H]4CC[C@H](NC(C)=O)CC4)C3)nc(C)n2)ccc1F] | *** |
| 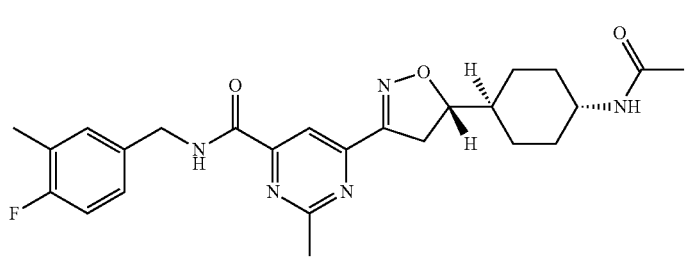 [SMILES: CC(=O)N[C@H]1CC[C@H]([C@@H]2CC(c3cc(C(=O)NCc4ccc(F)c(C)c4)nc(C)n3)=NO2)CC1] | **** |
| 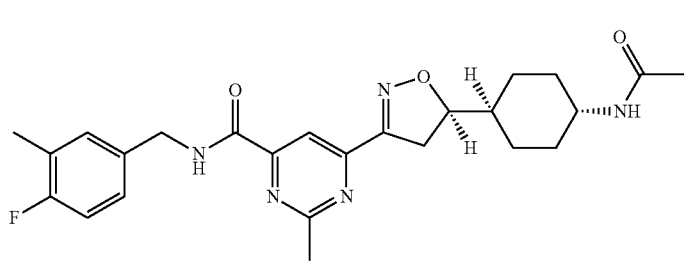 [SMILES: CC(=O)N[C@H]1CC[C@H]([C@H]2CC(c3cc(C(=O)NCc4ccc(F)c(C)c4)nc(C)n3)=NO2)CC1] | *** |

| Structure | MMP13 (CD) IC$_{50}$ |
|---|---|
| (structure) | **** |
| (structure) | *** |
| (structure) | **** |
| (structure) | *** |
| (structure) | **** |
| (structure) | *** |

-continued

| Structure | MMP13 (CD) IC$_{50}$ |
|---|---|
| | **** |
| | ** |
| | *** |
| | *** |
| | * |
| | * |
| | **** |

-continued
| Structure | MMP13 (CD) IC$_{50}$ |
|---|---|
| 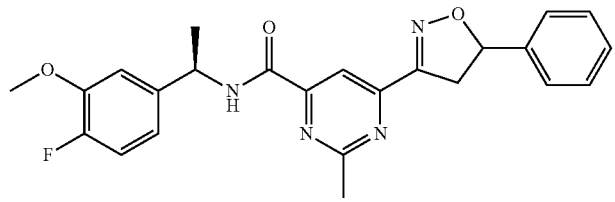 [SMILES: COc1cc([C@@H](C)NC(=O)c2cc(C3=NOC(c4ccccc4)C3)nc(C)n2)ccc1F] | * |
| 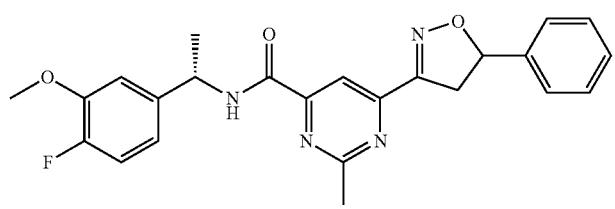 [SMILES: COc1cc([C@H](C)NC(=O)c2cc(C3=NOC(c4ccccc4)C3)nc(C)n2)ccc1F] | * |
| 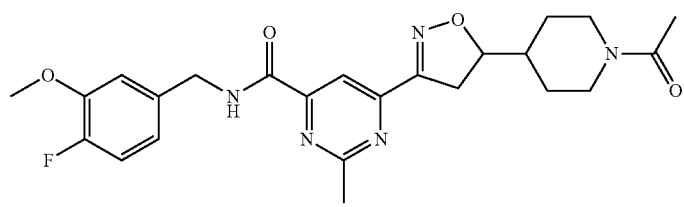 [SMILES: COc1cc(CNC(=O)c2cc(C3=NOC(C4CCN(C(C)=O)CC4)C3)nc(C)n2)ccc1F] | *** |
| 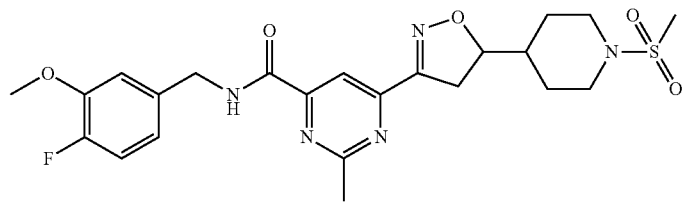 [SMILES: COc1cc(CNC(=O)c2cc(C3=NOC(C4CCN(S(C)(=O)=O)CC4)C3)nc(C)n2)ccc1F] | **** |
| 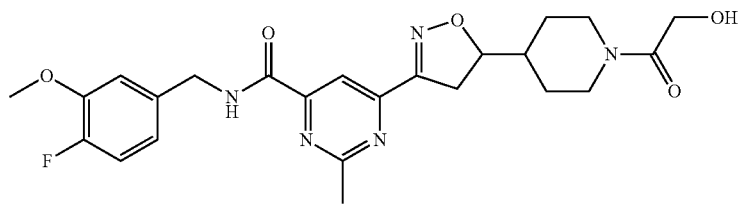 | *** |
| 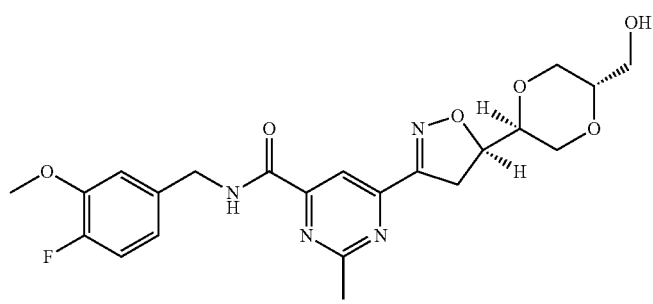 [SMILES: COc1cc(CNC(=O)c2cc(C3=NO[C@@H]([C@@H]4CO[C@@H](CO)CO4)C3)nc(C)n2)ccc1F] | ** |

-continued

| Structure | MMP13 (CD) IC$_{50}$ |
|---|---|
| | *** |
| | ** |
| | **** |
| | **** |
| | * |

-continued

| Structure | MMP13 (CD) IC$_{50}$ |
|---|---|
| | *** |
| | * |
| | **** |
| | *** |
| | *** |
| | *** |

| Structure | MMP13 (CD) IC$_{50}$ |
|---|---|
| 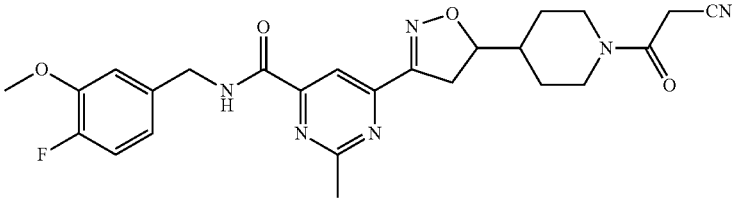 [SMILES: COc1cc(CNC(=O)c2cc(C3=NOC(C4CCN(C(=O)CC#N)CC4)C3)nc(C)n2)ccc1F] | *** |
| 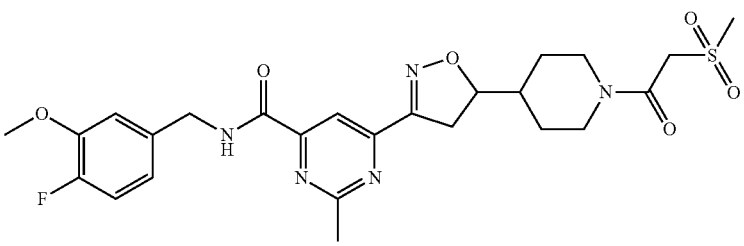 [SMILES: COc1cc(CNC(=O)c2cc(C3=NOC(C4CCN(C(=O)CS(C)(=O)=O)CC4)C3)nc(C)n2)ccc1F] | *** |
| 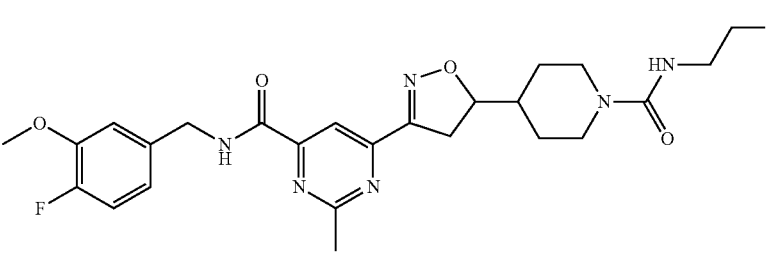 | **** |
| 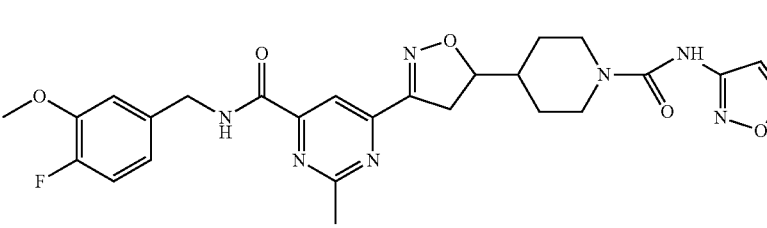 | *** |
| 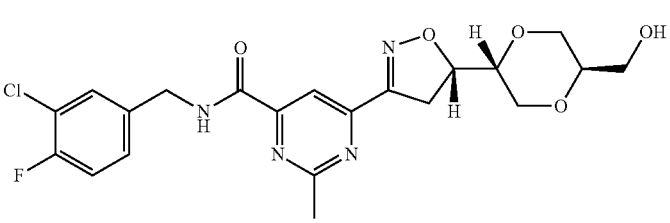 [SMILES: Cc1nc(C(=O)NCc2ccc(F)c(Cl)c2)cc(C2=NO[C@H]([C@H]3CO[C@H](CO)CO3)C2)n1] | *** |
| 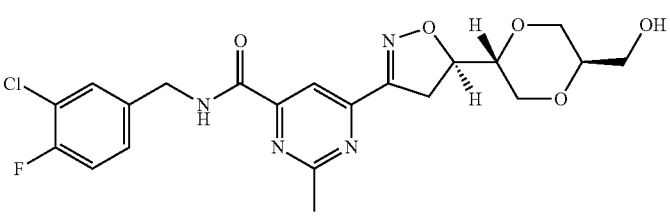 [SMILES: Cc1nc(C(=O)NCc2ccc(F)c(Cl)c2)cc(C2=NO[C@@H]([C@H]3CO[C@H](CO)CO3)C2)n1] | * |
| 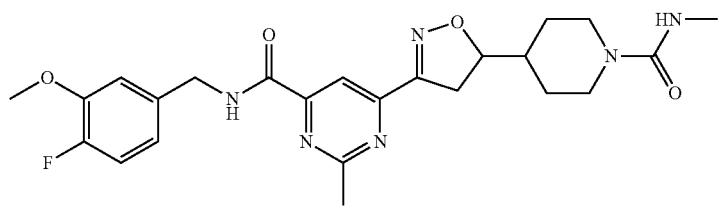 | **** |

-continued
| Structure | MMP13 (CD) IC$_{50}$ |
|---|---|
| 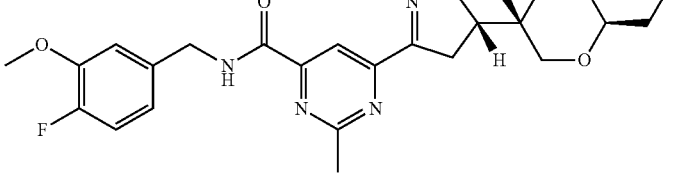 | **** |
| 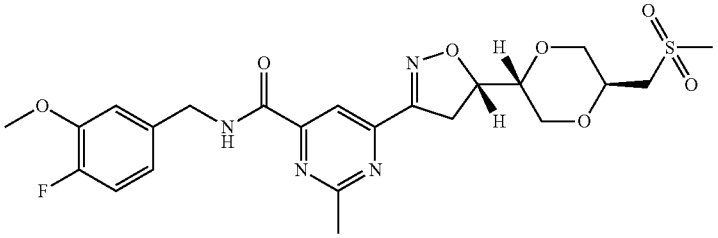 | *** |
| 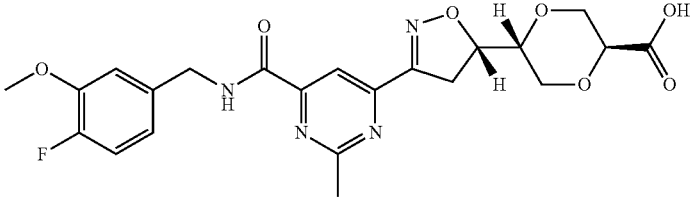 [SMILES: COc1cc(CNC(=O)c2cc(C3=NO[C@H]([C@H]4CO[C@H](C(=O)O)CO4)C3)nc(C)n2)ccc1F] | **** |
| 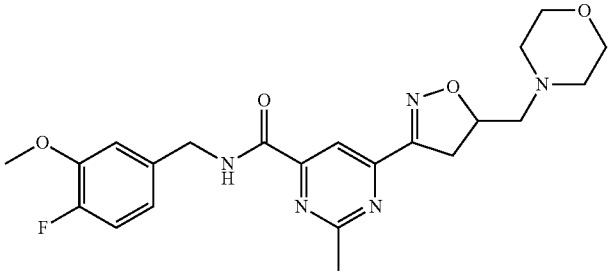 [SMILES: COc1cc(CNC(=O)c2cc(C3=NOC(CN4CCOCC4)C3)nc(C)n2)ccc1F] | * |
| 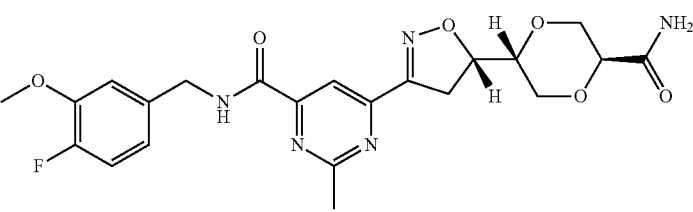 [SMILES: COc1cc(CNC(=O)c2cc(C3=NO[C@H]([C@H]4CO[C@H](C(N)=O)CO4)C3)nc(C)n2)ccc1F] | **** |
| 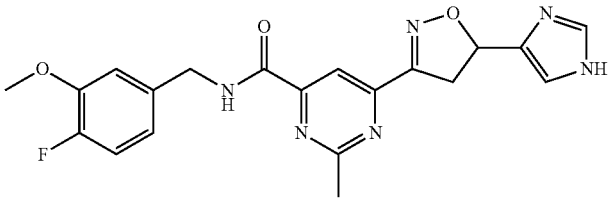 | * |

| Structure | MMP13 (CD) IC$_{50}$ |
|---|---|
| (structure) | **** |
| (structure) | **** |
| (structure) | *** |
| (structure) | **** |
| (structure) | **** |
| (structure) | ** |

-continued
| Structure | MMP13 (CD) IC$_{50}$ |
|---|---|
| 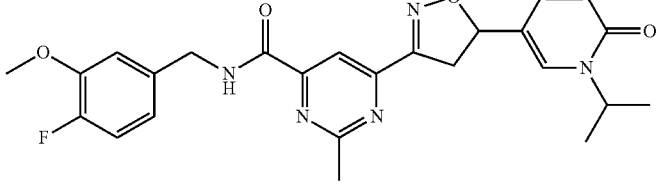 | **** |
| 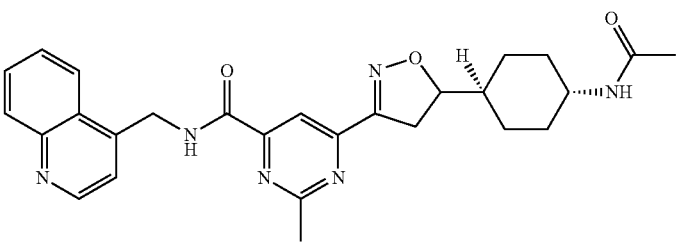 [SMILES: CC(=O)N[C@H]1CC[C@H](C2CC(c3cc(C(=O)NCc4ccnc5ccccc45)nc(C)n3)=NO2)CC1] | ** |
| 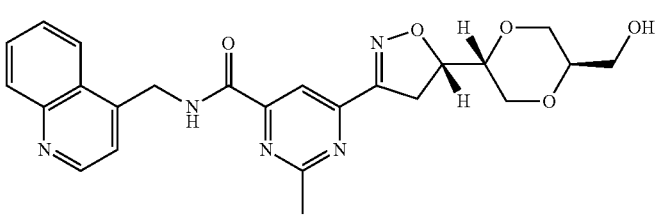 [SMILES: Cc1nc(C(=O)NCc2ccnc3ccccc23)cc(C2=NO[C@H]([C@H]3CO[C@H](CO)CO3)C2)n1] | ** |
| 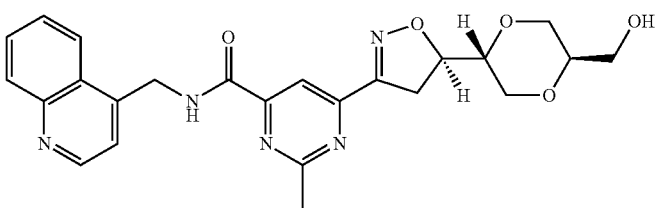 [SMILES: Cc1nc(C(=O)NCc2ccnc3ccccc23)cc(C2=NO[C@@H]([C@H]3CO[C@H](CO)CO3)C2)n1] | ** |
| 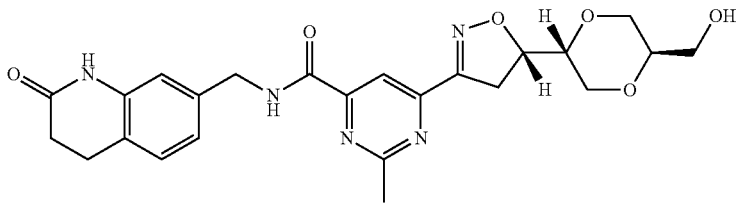 [SMILES: Cc1nc(C(=O)NCc2ccc3c(c2)NC(=O)CC3)cc(C2=NO[C@H]([C@H]3CO[C@H](CO)CO3)C2)n1] | *** |
| 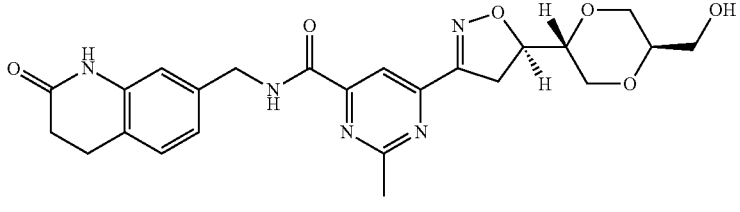 [SMILES: Cc1nc(C(=O)NCc2ccc3c(c2)NC(=O)CC3)cc(C2=NO[C@@H]([C@H]3CO[C@H](CO)CO3)C2)n1] | ** |
| 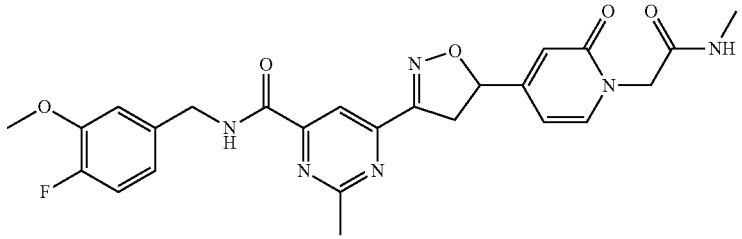 | *** |

| Structure | MMP13 (CD) IC$_{50}$ |
|---|---|
| | **** |
| | ** |
| | *** |
| | **** |
| | *** |
| | *** |
| | **** |

US 9,029,409 B2

-continued

| Structure | MMP13 (CD) IC$_{50}$ |
|---|---|
| | **** |
| | **** |
| | *** |
| | *** |
| | *** |
| | *** |

-continued

| Structure | MMP13 (CD) IC$_{50}$ |
|---|---|
| | **** |
| | **** |
| | *** |
| | *** |
| | ** |
| | *** |

-continued

| Structure | MMP13 (CD) IC$_{50}$ |
|---|---|
| | **** |
| | **** |
| | **** |
| | *** |
| | *** |
| | **** |

425 426
-continued
| Structure | MMP13 (CD) IC$_{50}$ |
|---|---|
| 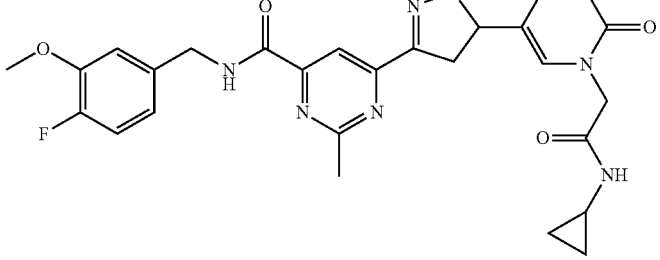 | **** |
| 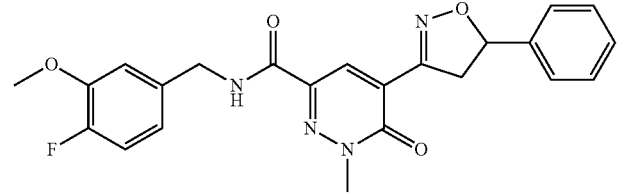 [SMILES: COc1cc(CNC(=O)c2cc(C3=NOC(c4ccccc4)C3)c(=O)n(C)n2)ccc1F] | *** |
| 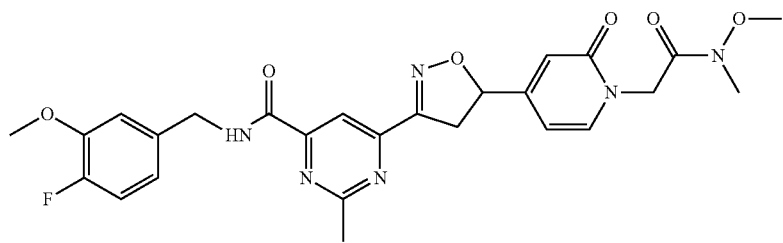 | *** |
| 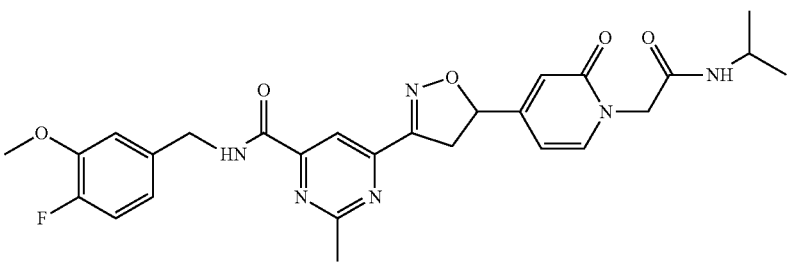 [SMILES: COc1cc(CNC(=O)c2cc(C3=NOC(c4ccn(CC(=O)NC(C)C)c(=O)c4)C3)nc(C)n2)ccc1F] | *** |
| 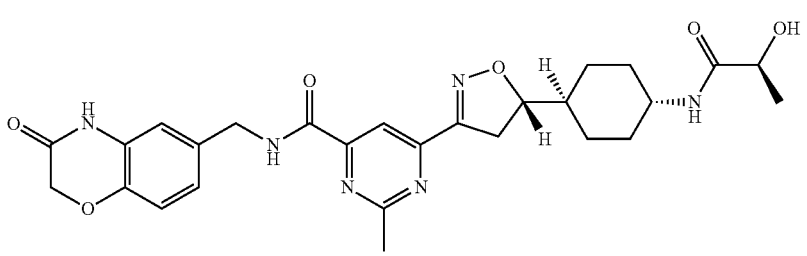 [SMILES: Cc1nc(C(=O)NCc2ccc3c(c2)NC(=O)CO3)cc(C2=NO[C@H]([C@H]3CC[C@H](NC(=O)[C@H](C)O)CC3)C2)n1] | **** |

| Structure | MMP13 (CD) IC$_{50}$ |
|---|---|
| (structure image) | **** |

MMP-13 catalytic domain IC$_{50}$: >1000 nM    *
MMP-13 catalytic domain IC$_{50}$: 100 nM-1000 nM    **
MMP-13 catalytic domain IC$_{50}$: 10 nM-100 nM    ***
MMP-13 catalytic domain IC$_{50}$: <10 nM    ****

What is claimed:
1. A compound of Formula (I)

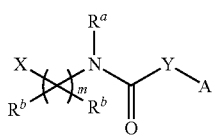

Formula (I)

stereoisomers, and pharmaceutically acceptable salts thereof wherein

A is

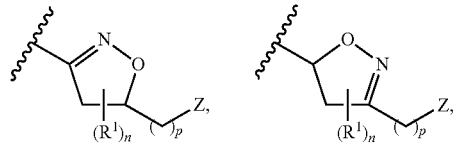

X is phenyl, benzo[1,4]oxazin-3-onyl, benzoxazolyl, 2,3-dihydrobenzo[1,4]dioxinyl, 2,3-dihydrobenzo furanyl, pyrazinonyl, pyridinyl, pyridonyl, or quinolinyl, each of which is optionally substituted with one or more substituents independently selected from Br, Cl, F, CF$_3$, CN, COOH, OCF$_3$, OH, (C$_1$-C$_6$)alkyl, or (C$_1$-C$_6$)alkoxy;

Y is pyridazinonyl, pyridinyl, or pyrimidinyl, each of which is optionally substituted by one or more substituents independently selected from CF$_3$, halogen, (C$_1$-C$_6$)alkyl, (C$_1$-C$_6$)alkoxy, Z is —C(O)NH$_2$, CN, —C(O)-morpholinyl, —C(O)-pyrrolidinyl, —C(O)—N(H)CH$_2$CH$_2$OH, (C$_3$-C$_6$)cycloalkyl, 1,4-dioxanyl, imidazolyl, morpholinyl, phenyl, piperazinyl, piperidinyl, pyrazinyl, pyrazolyl, pyrazolo[3,4-b]pyridinyl, pyridazinyl, pyridazinonyl, pyridinyl, pyridonyl, pyrimidinyl, pyrrolidinyl, tetrahydropyranyl, tetrazolyl, or thienyl, each of which is optionally substituted by one or more substituents independently selected from Br, Cl, F, CF$_3$, CN, —C(O)OH, —C(O)OCH$_3$, —C(O)CH$_3$, —C(O)CH$_2$OC(O)CH$_3$, —C(O)C(CH$_3$)$_3$, —C(O)C(H)(CH$_3$)$_2$, —C(O)CH$_2$CN, —C(O)CH$_2$OH, —C(O)CH$_2$OCH$_3$, —C(O)CH$_2$N(CH$_3$)$_2$, —C(O)C(CH$_3$)$_2$OH, —C(O)OC(CH$_3$)$_3$, —C(O)N(H)CH$_2$CH$_3$, —C(O)CH$_2$N(CH$_3$)$_2$, —C(O)CH$_2$N(H)S(O)$_2$CH$_3$, —C(O)CH$_2$N(H)C(O)CH$_3$, —C(O)CH$_2$N(H)C(O)N(H)CH$_3$, —C(O)CH$_2$OCH$_3$, —C(O)CH$_2$S(O)$_2$CH$_3$, —C(O)NH$_2$, —C(O)N(CH$_3$)$_2$, —C(O)N(H)CH$_3$, —C(O)N(H)CH$_2$CH$_3$, —C(O)N(H)CH(CH$_3$)$_2$, —C(O)N(H)CH$_2$CH$_2$OH, —C(O)N(H)-isoxazolyl, —C(O)N(H)thiazolyl, —C(O)N(CH$_3$)CH$_2$CH$_2$OH, —C(O)-cyclopropyl, —C(O)-cyclobutyl, —OCH$_2$CH$_2$OH, —OC(CH$_3$)$_3$, —NH$_2$, —N(CH$_3$)$_2$, —N(H)C(O)CH$_3$—, —N(H)C(O)CH$_2$OH, —N(H)C(O)CH$_2$CN, —N(H)C(O)C(CH$_3$)$_2$OH, —N(H)C(O)C(H)(OH)CH$_3$, —N(H)C(O)CH$_2$N(CH$_3$)$_2$, —N(H)C(O)CH$_2$N(H)CH$_3$, —N(H)C(O)(OH)CH$_3$, —N(R$^c$)C(O)N(R$^c$)(R$^c$), —N(H)C(O)N(CH$_3$)$_2$, —N(H)C(O)N(H)CH$_3$—N(H)C(O)N(H)CH$_2$CH$_2$OH, —N(H)C(O)N(H)C(H)(CH$_2$OH)$_2$, —N(H)C(O)N(CH$_3$)CH$_2$CH$_2$OH, —N(H)C(O)N(CH$_3$)CH$_2$C(H)(OH)CH$_2$OH, —N(H)C(O)O(CH$_3$)$_3$, —N(H)S(O)$_2$NH$_2$, —N(H)S(O)$_2$CH$_3$, —N(R$^c$)S(O)$_2$N(R$^c$)(R$^c$), —NO$_2$, 1,2,4-oxadiazolyl, oxo, —OH, —S(O)$_2$(R$^c$), —S(O)CH$_3$, —S(O)CH$_2$CH$_3$, —S(O)CH$_2$CH$_2$CH$_3$, —S(O)$_2$C(H)(CH$_3$)$_2$, —S(O)$_2$cyclopropyl, —S(O)$_2$-imidazolyl, —S(O)$_2$-isoxazolyl, —CH$_2$CN, —CH$_2$C(O)N(H)CH$_3$, —CH$_2$C(O)N(H)-cyclopropyl, —CH$_2$OCH$_3$, —CH$_2$OH, —CH$_2$CH$_2$OH, —CH$_2$OS(O)$_2$-phenyl, —C(CH$_3$)OH, —C(H)(CH$_2$)$_2$OH, —CH$_2$NH$_2$, —CH$_2$N(CH$_3$)$_2$, —CH$_2$N(H)C(O)CH$_3$, —CH$_2$N(H)C(O)C(H)(OH) CH$_3$, —CH$_2$N(H)C(O)CH$_2$CN, —CH$_2$N(H)C(O)CH$_2$OH, —CH$_2$N(H)C(O)C(CH$_3$)$_2$OH, —CH$_2$N(H)C(O)N(H)CH$_3$, —CH$_2$N(H)C(O)N(CH$_3$)$_2$, —CH$_2$S(O)$_2$CH$_3$, —CH$_2$-morpholinyl, —CH$_2$-thiomorpholinyl, —CH$_2$-thiomorpholinyl 1,1-dioxide, morpholinyl, oxadiazolyl, oxazolyl, piperidinyl, (C$_1$-C$_6$)alkyl, (C$_1$-C$_6$)alkoxy, or (C$_3$-C$_6$)cycloalkyl;

R$^c$ is independently H, (C$_1$-C$_3$)alkyl or (C$_3$-C$_6$)cycloalkyl;

R$^e$ is H, —C(O)R$^c$, (C$_1$-C$_6$)alkyl, (C$_1$-C$_6$)hydroxyalkyl, (C$_3$-C$_6$)cycloalkyl, heteroaryl optionally substituted with (C$_1$-C$_3$)alkyl, or heterocyclyl; or R$^a$ is independently H, (C$_1$-C$_3$)alkyl or (C$_3$-C$_6$)cycloalkyl, R$^b$ is independently H, CF$_3$, (C$_1$-C$_3$)alkyl or (C$_3$-C$_6$)cycloalkyl;

R$^1$ is independently Br, Cl, F, (C$_1$-C$_3$)alkyl or (C$_3$-C$_6$) cycloalkyl;

m is 0, 1 or 2;

n is 0; and p is 0 or 1.

2. The compound of claim 1 wherein p is 0.

3. The compound of claim 2 wherein X is phenyl, benzo[1,4]oxazin-3-onyl, benzoxazolyl, 2,3-dihydrobenzo[1,4]dioxinyl, 2,3-dihydrobenzo furanyl, pyrazinonyl, pyridinyl, or pyridonyl, each of which is optionally substituted with one or more substituents independently selected from Br, Cl, F, CF$_3$, OCF$_3$, (C$_1$-C$_6$)alkyl, (C$_1$-C$_6$)alkoxy.

4. The compound of claim 3 wherein Y is pyrimidinyl optionally substituted by one or more substituents independently selected from CF$_3$, or (C$_1$-C$_6$)alkyl.

5. The compound of claim 4 wherein Z is (C$_3$-C$_6$)cycloalkyl, 1,4-dioxanyl, morpholinyl, phenyl, piperidinyl, pyrazolyl, pyridazinyl, pyridazinonyl, pyridinyl, pyridonyl, pyrimidinyl, tetrahydropyranyl, tetrazolyl, or thienyl, each of which is optionally substituted by one or more substituents independently selected from Br, Cl, F, CF$_3$, CH$_3$, CN, —C(O)OH, —C(O)OCH$_3$, —C(O)CH$_3$, —C(O)CH$_2$OC(O)CH$_3$, —C(O)C(CH$_3$)$_3$, —C(O)C(H)(CH$_3$)$_2$, —C(O)CH$_2$CN, —C(O)CH$_2$OH, —C(O)CH$_2$OCH$_3$, —C(O)CH$_2$CH$_2$N(CH$_3$)$_2$, —C(O)C(CH$_3$)$_2$OH, —C(O)OC(CH$_3$)$_3$, —C(O)N(H)CH$_2$CH$_3$, —C(O)CH$_2$N(CH$_3$)$_2$, —C(O)CH$_2$N(H)S(O)$_2$CH$_3$, —C(O)CH$_2$N(H)C(O)CH$_3$, —C(O)CH$_2$N(H)C(O)N(H)CH$_3$, —C(O)CH$_2$S(O)$_2$CH$_3$, —C(O)NH$_2$, —C(O)N(CH$_3$)$_2$, —C(O)N(H)CH$_3$, —C(O)N(H)CH$_2$CH$_3$, —C(O)N(H)CH(CH$_3$)$_2$, —C(O)N(H)CH$_2$CH$_2$OH, —C(O)N(H)-isoxazolyl, —C(O)N(H)thiazolyl, —C(O)N(CH$_3$)CH$_2$CH$_2$OH, —C(O)-cyclopropyl, —C(O)-cyclobutyl, —OCH$_3$, —OCH$_2$CH$_2$OH, —OC(CH$_3$)$_3$, —NH$_2$, —N(CH$_3$)$_2$, —N(H)C(O)CH$_3$—, —N(H)C(O)CH$_2$OH, —N(H)C(O)CH$_2$CN, —N(H)C(O)C(CH$_3$)$_2$OH, —N(H)C(O)C(H)(OH)CH$_3$, —N(H)C(O)CH$_2$N(CH$_3$)$_2$, —N(H)C(O)CH$_2$N(H)CH$_3$, —N(H)C(O)(OH)CH$_3$, —N(H)C(O)N(CH$_3$)$_2$, —N(H)C(O)N(H)CH$_3$—N(H)C(O)N(H)CH$_2$CH$_2$OH, —N(H)C(O)N(H)C(H)(CH$_2$OH)$_2$, —N(H)C(O)N(CH$_3$)CH$_2$CH$_2$OH, —N(H)C(O)N(CH$_3$)CH$_2$C(H)(OH)CH$_2$OH, —N(H)C(O)O(CH$_3$)$_3$, —N(H)S(O)$_2$NH$_2$, —N(H)S(O)$_2$CH$_3$, —NO$_2$, 1,2,4-oxadiazolyl, oxo, —OH, —S(O)CH$_3$, —S(O)CH$_2$CH$_3$, —S(O)CH$_2$CH$_2$CH$_3$, —S(O)$_2$CH$_3$, —S(O)$_2$C(H)(CH$_3$)$_2$, —S(O)$_2$cyclopropyl, —S(O)$_2$-imidazolyl, —S(O)$_2$-isoxazolyl, —CH$_2$CN, —CH$_2$C(O)N(H)CH$_3$, —CH$_2$C(O)N(H)-cyclopropyl, —CH$_2$OCH$_3$, —CH$_2$OH, —CH$_2$CH$_2$OH, —CH$_2$OS(O)$_2$-phenyl, —C(CH$_3$)$_2$OH, —C(H)(CH$_2$)$_2$OH, —CH$_2$NH$_2$, —CH$_2$N(CH$_3$)$_2$, —CH$_2$N(H)C(O)CH$_3$, —CH$_2$N(H)S(O)$_2$CH$_3$, —CH$_2$N(H)C(O)C(H)(OH)CH$_3$, —CH$_2$N(H)C(O)CH$_2$CN, —CH$_2$N(H)C(O)CH$_2$OH, —CH$_2$N(H)C(O)C(CH$_3$)$_2$OH, —CH$_2$N(H)C(O)N(H)CH$_3$, —CH$_2$N(H)C(O)N(CH$_3$)$_2$, —CH$_2$S(O)$_2$CH$_3$, —CH$_2$-morpholinyl, —CH$_2$-thiomorpholinyl, —CH$_2$-thiomorpholinyl 1,1-dioxide, morpholinyl, oxadiazolyl, oxazolyl, piperidinyl, or (C$_3$-C$_6$) cycloalkyl.

6. The compound of claim 5, wherein
X is phenyl, benzo[1,4]oxazin-3-onyl, benzoxazolyl, 2,3-dihydrobenzo[1,4]dioxinyl, 2,3-dihydrobenzo furanyl, pyrazinonyl, or pyridinyl, each of which is optionally substituted with one or more substituents independently selected from Br, Cl, F, CF$_3$, OCF$_3$, (C$_1$-C$_6$)alkyl, (C$_1$-C$_6$)alkoxy;
Y is 2-methylpyrimidinyl; and
Z is cyclohexyl, 1,4-dioxanyl, phenyl, pyridonyl, piperidinyl, or pyridinyl, each of which is optionally substituted by one or more substituents independently selected from Br, Cl, F, CF$_3$, CH$_3$, CN, —C(O)OH, —C(O)OCH$_3$, —C(O)CH$_3$, —C(O)CH$_2$OC(O)CH$_3$, —C(O)C(CH$_3$)$_3$, —C(O)C(H)(CH$_3$)$_2$, —C(O)CH$_2$CN, —C(O)CH$_2$OH, —C(O)CH$_2$OCH$_3$, —C(O)CH$_2$CH$_2$N(CH$_3$)$_2$, —C(O)C(CH$_3$)$_2$OH, —C(O)OC(CH$_3$)$_3$, —C(O)N(H)CH$_2$CH$_3$, —C(O)CH$_2$N(CH$_3$)$_2$, —C(O)CH$_2$N(H)S(O)$_2$CH$_3$, —C(O)CH$_2$N(H)C(O)CH$_3$, —C(O)CH$_2$N(H)C(O)N(H)CH$_3$, —C(O)CH$_2$S(O)$_2$CH$_3$, —C(O)NH$_2$, —C(O)N(CH$_3$)$_2$, —C(O)N(H)CH$_3$, —C(O)N(H)CH$_2$CH$_3$, —C(O)N(H)CH(CH$_3$)$_2$, —C(O)N(H)CH$_2$CH$_2$OH, —C(O)N(H)-isoxazolyl, —C(O)N(H)thiazolyl, —C(O)N(CH$_3$)CH$_2$CH$_2$OH, —C(O)-cyclopropyl, —C(O)-cyclobutyl, —OCH$_3$, —OCH$_2$CH$_2$OH, —OC(CH$_3$)$_3$, —NH$_2$, —N(CH$_3$)$_2$, —N(H)C(O)CH$_3$—, —N(H)C(O)CH$_2$OH, —N(H)C(O)CH$_2$CN, —N(H)C(O)C(CH$_3$)$_2$OH, —N(H)C(O)C(H)(OH)CH$_3$, —N(H)C(O)CH$_2$N(CH$_3$)$_2$, —N(H)C(O)CH$_2$N(H)CH$_3$, —N(H)C(O)(OH)CH$_3$, —N(H)C(O)N(CH$_3$)$_2$, —N(H)C(O)N(H)CH$_3$—N(H)C(O)N(H)CH$_2$CH$_2$OH, —N(H)C(O)N(H)C(H)(CH$_2$OH)$_2$, —N(H)C(O)N(CH$_3$)CH$_2$CH$_2$OH, —N(H)C(O)N(CH$_3$)CH$_2$C(H)(OH)CH$_2$OH, —N(H)C(O)O(CH$_3$)$_3$, —N(H)S(O)$_2$NH$_2$, —N(H)S(O)$_2$CH$_3$, —NO$_2$, 1,2,4-oxadiazolyl, oxo, —OH, —S(O)CH$_3$, —S(O)CH$_2$CH$_3$, —S(O)CH$_2$CH$_2$CH$_3$, —S(O)$_2$CH$_3$, —S(O)$_2$C(H)(CH$_3$)$_2$, —S(O)$_2$cyclopropyl, —S(O)$_2$-imidazolyl, —S(O)$_2$-isoxazolyl, —CH$_2$CN, —CH$_2$C(O)N(H)CH$_3$, —CH$_2$C(O)N(H)-cyclopropyl, —CH$_2$OCH$_3$, —CH$_2$OH, —CH$_2$CH$_2$OH, —CH$_2$OS(O)$_2$-phenyl, —C(CH$_3$)$_2$OH, —C(H)(CH$_2$)$_2$OH, —CH$_2$NH$_2$, —CH$_2$N(CH$_3$)$_2$, —CH$_2$N(H)C(O)CH$_3$, —CH$_2$N(H)S(O)$_2$CH$_3$, —CH$_2$N(H)C(O)C(H)(OH)CH$_3$, —CH$_2$N(H)C(O)CH$_2$CN, —CH$_2$N(H)C(O)CH$_2$OH, —CH$_2$N(H)C(O)C(CH$_3$)$_2$OH, —CH$_2$N(H)C(O)N(H)CH$_3$, —CH$_2$N(H)C(O)N(CH$_3$)$_2$, —CH$_2$S(O)$_2$CH$_3$, —CH$_2$-morpholinyl, —CH$_2$-thiomorpholinyl, —CH$_2$-thiomorpholinyl 1,1-dioxide, morpholinyl, oxadiazolyl, oxazolyl, piperidinyl, or (C$_3$-C$_6$)cycloalkyl.

7. A compound selected from the group consisting of:

6-(5-(1-Acetylpiperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-(methylsulfonyl)piperidin-4-yl)-4,5-dihydroisoxazol-3-yl)pyrimidine-4-carboxamide;

N-(4-fluoro-3-methoxybenzyl)-6-(5-(1-(2-hydroxyacetyl)piperidin-4-yl)-4,5-dihydroisoxazol-3-yl)-2-methylpyrimidine-4-carboxamide;

N-(4-fluoro-3-methoxybenzyl)-6-((5)-5-((2S,5S)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-6-((R)-5-((2S,5S)-5-(hydroxymethyl)-1,4-dioxan-2-yl)-4,5-dihydroisoxazol-3-yl)-2-methylpyrimidine-4-carboxamide;

N-(4-Fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-(5-(4-Carbamoylphenyl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(morpholine-4-carbonyl)-4,5-dihydroisoxazol-3-yl)pyrimidine-4-carboxamide;

N-(4-fluoro-3-methoxybenzyl)-6-(5-(2-(2-hydroxypropan-2-yl)pyridin-4-yl)-4,5-dihydroisoxazol-3-yl)-2-methylpyrimidine-4-carboxamide;

6-(5-(2H-tetrazol-5-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(piperidin-4-yl)-4,5-dihydroisoxazol-3-yl)pyrimidine-4-carboxamide hydrochloride;

6-(5-(1-(ethylcarbamoyl)piperidin-4-yl)-4,5-dihydroisoxazol-3-yl)-N-(4-fluoro-3-methoxybenzyl)-2-methylpyrimidine-4-carboxamide;

6-(5-(1-(cyclopropanecarbonyl)piperidin-4-yl)-4,5-dihydroisoxazol-3-yl)-N-(4-fluoro-3-methoxybenzyl)-2-methylpyrimidine-4-carboxamide;

6-(5-(1-(2-acetamidoacetyl)piperidin-4-yl)-4,5-dihydroisoxazol-3-yl)-N-(4-fluoro-3-methoxybenzyl)-2-methylpyrimidine-4-carboxamide;

6-(5-(1-(2-cyanoacetyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-(2-(methylsulfonyl)acetyl)piperidin-4-yl)-4,5-dihydroisoxazol-3-yl)pyrimidine-4-carboxamide;

N-(4-fluoro-3-methoxybenzyl)-6-(5-(1-(2-hydroxy ethyl carbamoyl)piperidin-4-yl)-4,5-dihydroisoxazol-3-yl)-2-methylpyrimidine-4-carboxamide;

N-(4-fluoro-3-methoxybenzyl)-6-(5-(1-(isoxazol-3-ylcarbamoyl)piperidin-4-yl)-4,5-dihydroisoxazol-3-yl)-2-methylpyrimidine-4-carboxamide;

N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-2-methyl-6-(5-(1-(methylcarbamoyl)piperidin-4-yl)-4,5-dihydroisoxazol-3-yl)pyrimidine-4-carboxamide;

6-((S)-5-((2R,5R)-5-(cyanomethyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;

(2S,5R)-5-((S)-3-(6-((4-fluoro-3-methoxybenzyl)carbamoyl)-2-methylpyrimidin-4-yl)-4,5-dihydroisoxazol-5-yl)-1,4-dioxane-2-carboxylic acid;

N-(4-fluoro-3-methoxybenzyl)-2-methyl-6-(5-(morpholinomethyl)-4,5-dihydroisoxazol-3-yl)pyrimidine-4-carboxamide;

6-((S)-5-((2R,5S)-5-Carbamoyl-1,4-dioxan-2-yl)-4,5-dihydroisoxazol-3-yl)-N-(4-fluoro-3-methoxybenzyl)-2-methylpyrimidine-4-carboxamide;

6-(5-(1H-imidazol-4-yl)-4,5-dihydroisoxazol-3-yl)-N-(4-fluoro-3-methoxybenzyl)-2-methylpyrimidine-4-carboxamide;

6-(5-(4-(2-hydroxyethoxy)phenyl)-5-methyl-4,5-dihydroisoxazol-3-yl)-N-(4-methoxybenzyl)-2-methylpyrimidine-4-carboxamide 2,2,2-trifluoroacetate;

6-(5-(4-(2-hydroxyethoxy)phenyl)-4,5-dihydroisoxazol-3-yl)-N-(4-methoxybenzyl)-2-methylpyrimidine-4-carboxamide;

N-(4-methoxybenzyl)-2-methyl-6-(5-phenyl-4,5-dihydroisoxazol-3-yl)pyrimidine-4-carboxamide;

6-(5-(4-(hydroxymethyl)phenyl)-5-methyl-4,5-dihydroisoxazol-3-yl)-N-(4-methoxybenzyl)-2-methylpyrimidine-4-carboxamide;

N-(4-methoxybenzyl)-6-(5-(4-methoxyphenyl)-4,5-dihydroisoxazol-3-yl)-2-methylpyrimidine-4-carboxamide;

N-(4-methoxybenzyl)-2-methyl-6-(5-(4-morpholinophenyl)-4,5-dihydroisoxazol-3-yl)pyrimidine-4-carboxamide;

N-(4-methoxybenzyl)-2-methyl-6-(5-(4-(piperidin-1-yl)phenyl)-4,5-dihydroisoxazol-3-yl)pyrimidine-4-carboxamide;

6-(5-(4-(dimethylamino)phenyl)-4,5-dihydroisoxazol-3-yl)-N-(4-methoxybenzyl)-2-methylpyrimidine-4-carboxamide;

6-(5-(3-(2-hydroxyethoxy)phenyl)-4,5-dihydroisoxazol-3-yl)-N-(4-methoxybenzyl)-2-methylpyrimidine-4-carboxamide;

N-(4-methoxybenzyl)-2-methyl-6-(5-(pyridin-2-yl)-4,5-dihydroisoxazol-3-yl)pyrimidine-4-carboxamide;

6-(5-cyclohexyl-4,5-dihydroisoxazol-3-yl)-N-(4-methoxybenzyl)-2-methylpyrimidine-4-carboxamide;

6-(5-cyclohexyl-4,5-dihydroisoxazol-3-yl)-N-(4-methoxybenzyl)-2-methylpyrimidine-4-carboxamide;

6-(5-(4-(hydroxymethyl)phenyl)-4,5-dihydroisoxazol-3-yl)-N-(4-methoxybenzyl)-2-methylpyrimidine-4-carboxamide;

6-(5-(4-carbamoylphenyl)-4,5-dihydroisoxazol-3-yl)-N-(4-methoxybenzyl)-2-methylpyrimidine-4-carboxamide;

6-(5-cyclohexyl-4,5-dihydroisoxazol-3-yl)-N-(4-fluoro-3-methoxybenzyl)-2-methylpyrimidine-4-carboxamide;

6-(5-(1-acetylpiperidin-4-yl)-4,5-dihydroisoxazol-3-yl)-N-(4-methoxybenzyl)-2-methylpyrimidine-4-carboxamide;

N-(4-fluoro-3-methoxybenzyl)-2-methyl-6-(5-(pyridin-2-yl)-4,5-dihydroisoxazol-3-yl)pyrimidine-4-carboxamide;

N-(4-fluoro-3-methoxybenzyl)-6-(5-(4-hydroxycyclohexyl)-4,5-dihydroisoxazol-3-yl)-2-methylpyrimidine-4-carboxamide;

tert-butyl 4-(3-(6-((4-fluoro-3-methoxybenzylcarbamoyl)-2-methylpyrimidin-4-yl)-4,5-dihydroisoxazol-5-yl)piperidine-1-carboxylate;

N-(4-fluoro-3-methoxybenzyl)-2-methyl-6-(5-(pyridin-3-yl)-4,5-dihydroisoxazol-3-yl)pyrimidine-4-carboxamide;

N-(4-fluoro-3-methoxybenzyl)-6-(5-(4-(hydroxymethyl)phenyl)-4,5-dihydroisoxazol-3-yl)-2-methylpyrimidine-4-carboxamide;

N-(4-fluoro-3-methoxybenzyl)-6-(5-(4-(4-(hydroxymethyl)piperidin-1-yl)phenyl)-4,5-dihydroisoxazol-3-yl)-2-methylpyrimidin-4-carboxamide;

N-(4-fluoro-3-methoxybenzyl)-2-methyl-6-(5-(4-(morpholinomethyl)phenyl)-4,5-dihydroisoxazol-3-yl)pyrimidine-4-carboxamide;

6-(5-cyano-4,5-dihydroisoxazol-3-yl)-N-(4-methoxybenzyl)-2-methylpyrimidine-4-carboxamide;

N-(4-fluoro-3-methoxybenzyl)-2-methyl-6-(5-(4-(thiomorpholinomethyl)phenyl)-4,5-dihydroisoxazol-3-yl)pyrimidine-4-carboxamide;

6-(5-cyano-4,5-dihydroisoxazol-3-yl)-N-(4-fluoro-3-methoxybenzyl)-2-methylpyrimidine-4-carboxamide;

6-(5-(3-carbamoylphenyl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(3-(morpholinomethyl)phenyl)-4,5-dihydroisoxazol-3-yl)pyrimidine-4-carboxamide;

N-(4-fluoro-3-methoxybenzyl)-2-methyl-6-(5-(3-(methylcarbamoyl)phenyl)-4,5-dihydroisoxazol-3-yl)pyrimidine-4-carboxamide;

methyl 4-(3-(6-((4-fluoro-3-methoxybenzylcarbamoyl)-2-methylpyrimidin-4-yl)-4,5-dihydroisoxazol-5-yl)benzoate;

N-(4-fluoro-3-methoxybenzyl)-2-methyl-6-(5-(4-(methylcarbamoyl)phenyl)-4,5-dihydroisoxazol-3-yl)pyrimidine-4-carboxamide;

N-(4-fluoro-3-methoxybenzyl)-2-methyl-6-(5-(thiophen-3-yl)-4,5-dihydroisoxazol-3-yl)pyrimidine-4-carboxamide;

N-(4-fluoro-3-methoxybenzyl)-2-methyl-6-(5-(pyridin-4-yl)-4,5-dihydroisoxazol-3-yl)pyrimidine-4-carboxamide;

6-{5-[4-(1,1,1,-Dioxo-thiomorpholine-4-ylmethyl)phenyl]-4,5-dihydro-isoxazol-3-yl}-2-methyl pyrimidine-4-carboxylate;

N-(4-fluoro-3-methoxybenzyl)-6-((R)-5-((2S,5S)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-6-((S)-5-((2S,5S)-5-(hydroxymethyl)-1,4-dioxan-2-yl)-4,5-dihydroisoxazol-3-yl)-2-methylpyrimidine-4-carboxamide;

N-(4-Fluoro-3-methoxybenzyl)-6-((S)-5-((2S,5S)-5-(hydroxymethyl)-1,4-dioxan-2-yl)-4,5-dihydro-isoxazol-3-yl)-2-methylpyrimidine-4-carboxamide;

6-(5-((1r,4r)-4-(2-cyanoacetamido)cyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-((1r,4r)-4-(sulfamoylamino)cyclohexyl)-4,5-dihydroisoxazol-3-yl)pyrimidine-4-carboxamide;

N-(4-fluoro-3-methoxybenzyl)-2-methyl-6-(5-(pyridin-3-yl)-4,5-dihydro-1H-pyrazol-3-yl)pyrimidine-4-carboxamide;

6-(3-(4-(2-hydroxyethoxy)phenyl)-4,5-dihydroisoxazol-5-yl)-N-(4-methoxybenzyl)-2-methylpyrimidine-4-carboxamide 2,2,2-trifluoroacetate;

N-(4-fluoro-3-methoxybenzyl)-2-methyl-6-(3-phenyl-4,5-dihydroisoxazol-5-yl)pyrimidine-4-carboxamide;

N-(4-fluoro-3-methoxybenzyl)-6-(3-(4-(2-hydroxyethoxy)phenyl)-4,5-dihydroisoxazol-5-yl)-2-methylpyrimidine-4-carboxamide;

N-(4-methoxybenzyl)-2-methyl-6-(3-phenyl-4,5-dihydroisoxazol-5-yl)pyrimidine-4-carboxamide;

N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-6-(5-(4-(2-hydroxyethylcarbamoyl)phenyl)-4,5-dihydroisoxazol-3-yl)-2-methylpyrimidine-4-carboxamide;

6-(5-((1-acetylpiperidin-4-yl)methyl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(pyrimidin-5-yl)-4,5-dihydroisoxazol-3-yl)pyrimidine-4-carboxamide;

N-(4-fluoro-3-methoxybenzyl)-6-(5-(4-(2-hydroxypropan-2-yl)phenyl)-4,5-dihydroisoxazol-3-yl)-2-methylpyrimidine-4-carboxamide;

N-(4-fluoro-3-methoxybenzyl)-6-(5-((1-(2-hydroxyacetyl)piperidin-4-yl)methyl)-4,5-dihydroisoxazol-3-yl)-2-methylpyrimidine-4-carboxamide;

N-(4-fluoro-3-methoxybenzyl)-2-methyl-6-(5-((1-(methylsulfonyl)piperidin-4-yl)methyl)-4,5-dihydroisoxazol-3-yl)pyrimidine-4-carboxamide;

6-(5-(2-carbamoylpyridin-4-yl)-4,5-dihydroisoxazol-3-yl)-N-(4-fluoro-3-methoxybenzyl)-2-methylpyrimidine-4-carboxamide;

6-(5-(1H-pyrazol-4-yl)-4,5-dihydroisoxazol-3-yl)-N-(4-fluoro-3-methoxybenzyl)-2-methylpyrimidine-4-carboxamide;

6-((R)-5-((1r,4R)-4-acetamidocyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-((R)-5-((1r,4R)-4-(methylsulfonamido)cyclohexyl)-4,5-dihydroisoxazol-3-yl)pyrimidine-4-carboxamide;

N-(4-fluoro-3-methoxybenzyl)-6-((R)-5-((1r,4R)-4-(2-hydroxyacetamido)cyclohexyl)-4,5-dihydroisoxazol-3-yl)-2-methylpyrimidine-4-carboxamide;

N-(4-fluoro-3-methoxybenzyl)-2-methyl-6-(5-(pyrimidin-2-yl)-4,5-dihydroisoxazol-3-yl)pyrimidine-4-carboxamide;

N-(4-fluoro-3-methoxybenzyl)-2-methyl-6-(5-(tetrahydro-2H-pyran-4-yl)-4,5-dihydroisoxazol-3-yl)pyrimidine-4-carboxamide;

6-(5-((1r,4r)-4-acetamidocyclohexyl)-4,5-dihydroisoxazol-3-yl)-N-(4-fluoro-3-methoxybenzyl)-2-methylpyrimidine-4-carboxamide;

N-(4-Fluoro-3-methoxybenzyl)-2-methyl-6-(5-((1r,4r)-4-(methylsulfonamido)cyclohexyl)-4,5-dihydroisoxazol-3-yl)pyrimidine-4-carboxamide;

N-(4-Fluoro-3-methoxybenzyl)-6-(5-((1r,4r)-4-(2-hydroxyacetamido)cyclohexyl)-4,5-dihydroisoxazol-3-yl)-2-methylpyrimidine-4-carboxamide;

N-(4-fluoro-3-methylbenzyl)-2-methyl-6-(5-(pyridin-2-yl)-4,5-dihydroisoxazol-3-yl)pyrimidine-4-carboxamide;

6-(5-(1-acetylpiperidin-4-yl)-4,5-dihydroisoxazol-3-yl)-N-(4-fluoro-3-methylbenzyl)-2-methylpyrimidine-4-carboxamide;

N-(4-fluoro-3-methylbenzyl)-2-methyl-6-(5-(1-(methylsulfonyl)piperidin-4-yl)-4,5-dihydroisoxazol-3-yl)pyrimidine-4-carboxamide;

N-(4-fluoro-3-methylbenzyl)-6-(5-(1-(2-hydroxyacetyl)piperidin-4-yl)-4,5-dihydroisoxazol-3-yl)-2-methylpyrimidine-4-carboxamide;

N-(4-fluoro-3-methoxybenzyl)-2-methyl-6-(5-(pyrazin-2-yl)-4,5-dihydroisoxazol-3-yl)pyrimidine-4-carboxamide;

N-(4-fluoro-3-methoxybenzyl)-6-(5-(1-(2-hydroxy-2-methylpropanoyl)piperidin-4-yl)-4,5-dihydroisoxazol-3-yl)-2-methylpyrimidine-4-carboxamide;

6-(5-(1-(cyclopropylsulfonyl)piperidin-4-yl)-4,5-dihydroisoxazol-3-yl)-N-(4-fluoro-3-methoxybenzyl)-2-methylpyrimidine-4-carboxamide;

N-(3,4-difluorobenzyl)-2-methyl-6-(5-(pyridin-2-yl)-4,5-dihydroisoxazol-3-yl)pyrimidine-4-carboxamide;

6-(5-(1-acetylpiperidin-4-yl)-4,5-dihydroisoxazol-3-yl)-N-(3,4-difluorobenzyl)-2-methylpyrimidine-4-carboxamide;

N-(3,4-difluorobenzyl)-2-methyl-6-(5-(1-(methylsulfonyl)piperidin-4-yl)-4,5-dihydroisoxazol-3-yl)pyrimidine-4-carboxamide;

N-(3,4-difluorobenzyl)-6-(5-(1-(2-hydroxyacetyl)piperidin-4-yl)-4,5-dihydroisoxazol-3-yl)-2-methylpyrimidine-4-carboxamide;

6-(5-(1-(ethylsulfonyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-(1-isobutyrylpiperidin-4-yl)-4,5-dihydroisoxazol-3-yl)-2-methylpyrimidine-4-carboxamide;

N-(4-fluoro-3-methoxybenzyl)-2-methyl-6-(5-(1-(propylsulfonyl)piperidin-4-yl)-4,5-dihydroisoxazol-3-yl)pyrimidine-4-carboxamide;

N-(4-fluorobenzyl)-2-methyl-6-(5-(pyridin-2-yl)-4,5-dihydroisoxazol-3-yl)pyrimidine-4-carboxamide;

6-(5-(1-acetylpiperidin-4-yl)-4,5-dihydroisoxazol-3-yl)-N-(3-chloro-4-fluorobenzyl)-2-methylpyrimidine-4-carboxamide;

N-(3-chloro-4-fluorobenzyl)-6-(5-(1-(2-hydroxyacetyl)piperidin-4-yl)-4,5-dihydroisoxazol-3-yl)-2-methylpyrimidine-4-carboxamide;

N-(3-methoxybenzyl)-2-methyl-6-(5-(pyridin-2-yl)-4,5-dihydroisoxazol-3-yl)pyrimidine-4-carboxamide;

6-(5-(1-acetylpiperidin-4-yl)-4,5-dihydroisoxazol-3-yl)-N-(4-fluorobenzyl)-2-methylpyrimidine-4-carboxamide;

N-(4-fluorobenzyl)-2-methyl-6-(5-(1-(methylsulfonyl)piperidin-4-yl)-4,5-dihydroisoxazol-3-yl)pyrimidine-4-carboxamide;

N-(4-fluorobenzyl)-6-(5-(1-(2-hydroxyacetyl)piperidin-4-yl)-4,5-dihydroisoxazol-3-yl)-2-methylpyrimidine-4-carboxamide;

6-(5-(1-acetylpiperidin-4-yl)-4,5-dihydroisoxazol-3-yl)-N-(3-methoxybenzyl)-2-methylpyrimidine-4-carboxamide;

N-(3-methoxybenzyl)-2-methyl-6-(5-(1-(methylsulfonyl)piperidin-4-yl)-4,5-dihydroisoxazol-3-yl)pyrimidine-4-carboxamide;

6-(5-(1-(2-hydroxyacetyl)piperidin-4-yl)-4,5-dihydroisoxazol-3-yl)-N-(3-methoxybenzyl)-2-methylpyrimidine-4-carboxamide;

6-(5-(1-(cyclopropanecarbonyl)piperidin-4-yl)-4,5-dihydroisoxazol-3-yl)-N-(4-fluoro-3-methoxybenzyl)-2-methylpyrimidine-4-carboxamide;

6-(5-(1-(dimethylcarbamoyl)piperidin-4-yl)-4,5-dihydroisoxazol-3-yl)-N-(4-fluoro-3-methoxybenzyl)-2-methylpyrimidine-4-carboxamide;

6-(5-(1-(ethylcarbamoyl)piperidin-4-yl)-4,5-dihydroisoxazol-3-yl)-N-(4-fluoro-3-methoxybenzyl)-2-methylpyrimidine-4-carboxamide;

6-(5-(1-(2-(dimethylamino)acetyl)piperidin-4-yl)-4,5-dihydroisoxazol-3-yl)-N-(4-fluoro-3-methoxybenzyl)-2-methylpyrimidine-4-carboxamide;

6-(5-(1-(2-acetamidoacetyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-(1-(isopropylsulfonyl)piperidin-4-yl)-4,5-dihydroisoxazol-3-yl)-2-methylpyrimidine-4-carboxamide;

6-(5-(1-(2-cyanoacetyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-(1-(2-methoxyacetyl)piperidin-4-yl)-4,5-dihydroisoxazol-3-yl)-2-methylpyrimidine-4-carboxamide;

6-(5-(1-(cyclobutanecarbonyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-(2-(methylsulfonamido)acetyl)piperidin-4-yl)-4,5-dihydroisoxazol-3-yl)pyrimidine-4-carboxamide;

6-(5-(5-cyanopyridin-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-(5-(hydroxymethyl)pyridin-2-yl)-4,5-dihydroisoxazol-3-yl)-2-methylpyrimidine-4-carboxamide;

N-(4-fluoro-3-methoxybenzyl)-2-methyl-6-(5-(5-(methylcarbamoyl)pyridin-2-yl)-4,5-dihydroisoxazol-3-yl)pyrimidine-4-carboxamide;

N-(4-fluoro-3-methoxybenzyl)-6-(5-(1-(2-hydroxyethylcarbamoyl)piperidin-4-yl)-4,5-dihydroisoxazol-3-yl)-2-methylpyrimidine-4-carboxamide;

N-(4-fluoro-3-methoxybenzyl)-2-methyl-6-(5-(1-(2-(3-methylureido)acetyl)piperidin-4-yl)-4,5-dihydroisoxazol-3-yl)pyrimidine-4-carboxamide;

N-(4-fluoro-3-methoxybenzyl)-6-(5-(5-(1-hydroxyethyl)pyridin-2-yl)-4,5-dihydroisoxazol-3-yl)-2-methylpyrimidine-4-carboxamide;

N-(4-fluoro-3-methoxybenzyl)-6-(5-(1-(2-hydroxyethyl)(methyl)carbamoyl)piperidin-4-yl)-4,5-dihydroisoxazol-3-yl)-2-methylpyrimidine-4-carboxamide;

N-(4-fluoro-3-methoxybenzyl)-6-(5-(1-(isopropylcarbamoyl)piperidin-4-yl)-4,5-dihydroisoxazol-3-yl)-2-methylpyrimidine-4-carboxamide;

N-(4-fluoro-3-methoxybenzyl)-2-methyl-6-(5-(1-(1-methyl-1H-imidazol-2-ylsulfonyl)piperidin-4-yl)-4,5-dihydroisoxazol-3-yl)pyrimidine-4-carboxamide;

N-(4-fluoro-3-methoxybenzyl)-2-methyl-6-(5-(1-(1-methyl-1H-imidazol-4-ylsulfonyl)piperidin-4-yl)-4,5-dihydroisoxazol-3-yl)pyrimidine-4-carboxamide;

6-(5-(1-(1,2-dimethyl-1H-imidazol-4-ylsulfonyl)piperidin-4-yl)-4,5-dihydroisoxazol-3-yl)-N-(4-fluoro-3-methoxybenzyl)-2-methylpyrimidine-4-carboxamide;

6-(5-(1-(3,5-dimethylisoxazol-4-ylsulfonyl)piperidin-4-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(5-(methylsulfonyl)pyridin-2-yl)-4,5-dihydroisoxazol-3-yl)pyrimidine-4-carboxamide;

N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide;

6-(5-(5-acetylpyridin-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(5-(3-methyl-1,2,4-oxadiazol-5-yl)pyridin-2-yl)-4,5-dihydroisoxazol-3-yl)pyrimidine-4-carboxamide 2,2,2-trifluoroacetate;

((2S,5R)-5-(3-(6-(3-chloro-4-fluorobenzylcarbamoyl)-2-methylpyrimidin-4-yl)-4,5-dihydroisoxazol-5-yl)-1,4-dioxan-2-yl)methyl 4-methylbenzenesulfonate;

N-(3-chloro-4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-chloro-4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(3-chloro-4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-chloro-4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-N-(4-methoxybenzyl)-2-methylpyrimidine-4-carboxamide;

6-((R)-5-((2R,5R)-5-(hydroxymethyl)-1,4-dioxan-2-yl)-4,5-dihydroisoxazol-3-yl)-N-(4-methoxybenzyl)-2-methylpyrimidine-4-carboxamide;

6-(5-((2R,5R)-5-(hydroxymethyl)-1,4-dioxan-2-yl)-4,5-dihydroisoxazol-3-yl)-N-(3-methoxybenzyl)-2-methylpyrimidine-4-carboxamide;
((2S,5R)-5-((S)-3-(6-(4-fluoro-3-methoxybenzylcarbamoyl)-2-methylpyrimidin-4-yl)-4,5-dihydroisoxazol-5-yl)-1,4-dioxan-2-yl)methyl 4-methylbenzenesulfonate;
methyl 4-(3-(2-(3-methoxybenzylcarbamoyl)pyridin-4-yl)-4,5-dihydroisoxazol-5-yl)benzoate;
N-(3-methoxybenzyl)-4-(5-(4-methoxyphenyl)-4,5-dihydroisoxazol-3-yl)picolinamide;
4-(5-(4-chlorophenyl)-5-methyl-4,5-dihydroisoxazol-3-yl)-N-(3-methoxybenzyl)picolinamide;
4-(3-(2-(3-methoxybenzylcarbamoyl)pyridin-4-yl)-4,5-dihydroisoxazol-5-yl)benzoic acid;
4-(5-(4-((dimethylamino)methyl)phenyl)-4,5-dihydroisoxazol-3-yl)-N-(4-methoxybenzyl)picolinamide;
4-(3-(2-(4-methoxybenzylcarbamoyl)pyridin-4-yl)-4,5-dihydroisoxazol-5-yl)benzoic acid;
4-(5-(4-chlorophenyl)-5-methyl-4,5-dihydroisoxazol-3-yl)-N-(4-methoxybenzyl)picolinamide;
N-(4-methoxybenzyl)-4-(5-(pyrazin-2-yl)-4,5-dihydroisoxazol-3-yl)picolinamide;
N-(4-methoxybenzyl)-4-(5-(4-methoxyphenyl)-4,5-dihydroisoxazol-3-yl)picolinamide;
6-((S)-5-((2R,5R)-5-(hydroxymethyl)-1,4-dioxan-2-yl)-4,5-dihydroisoxazol-3-yl)-N-(3-methoxybenzyl)-2-methylpyrimidine-4-carboxamide;
6-((R)-5-((2S,5S)-5-(hydroxymethyl)-1,4-dioxan-2-yl)-4,5-dihydroisoxazol-3-yl)-N-(3-methoxybenzyl)-2-methylpyrimidine-4-carboxamide;
6-((S)-5-((2S,5S)-5-(hydroxymethyl)-1,4-dioxan-2-yl)-4,5-dihydroisoxazol-3-yl)-N-(3-methoxybenzyl)-2-methylpyrimidine-4-carboxamide;
N-(4-fluorobenzyl)-6-((R)-5-((2S,5S)-5-(hydroxymethyl)-1,4-dioxan-2-yl)-4,5-dihydroisoxazol-3-yl)-2-methylpyrimidine-4-carboxamide;
N-(4-fluorobenzyl)-6-((S)-5-((2S,5S)-5-(hydroxymethyl)-1,4-dioxan-2-yl)-4,5-dihydroisoxazol-3-yl)-2-methylpyrimidine-4-carboxamide;
6-((R)-5-((2S,5S)-5-(hydroxymethyl)-1,4-dioxan-2-yl)-4,5-dihydroisoxazol-3-yl)-N-(4-methoxybenzyl)-2-methylpyrimidine-4-carboxamide;
6-((S)-5-((2S,5S)-5-(hydroxymethyl)-1,4-dioxan-2-yl)-4,5-dihydroisoxazol-3-yl)-N-(4-methoxybenzyl)-2-methylpyrimidine-4-carboxamide;
N-(3-chloro-4-fluorobenzyl)-6-((R)-5-((2S,5S)-5-(hydroxymethyl)-1,4-dioxan-2-yl)-4,5-dihydroisoxazol-3-yl)-2-methylpyrimidine-4-carboxamide;
N-(3-chloro-4-fluorobenzyl)-6-((S)-5-((2S,5S)-5-(hydroxymethyl)-1,4-dioxan-2-yl)-4,5-dihydroisoxazol-3-yl)-2-methylpyrimidine-4-carboxamide;
6-((S)-5-((2R,5R)-5-(acetamidomethyl)-1,4-dioxan-2-yl)-4,5-dihydroisoxazol-3-yl)-N-(4-fluoro-3-methoxybenzyl)-2-methylpyrimidine-4-carboxamide;
N-(4-fluoro-3-methoxybenzyl)-2-methyl-6-((S)-5-((2R,5R)-5-(methylsulfonamidomethyl)-1,4-dioxan-2-yl)-4,5-dihydroisoxazol-3-yl)pyrimidine-4-carboxamide;
N-(4-fluoro-3-methoxybenzyl)-2-methyl-6-(5)-5-((2R,5S)-5-(methylsulfonylmethyl)-1,4-dioxan-2-yl)-4,5-dihydroisoxazol-3-yl)pyrimidine-4-carboxamide;
N-(4-fluoro-3-methoxybenzyl)-2-methyl-6-(5-(1-(thiazol-2-ylcarbamoyl)piperidin-4-yl)-4,5-dihydroisoxazol-3-yl)pyrimidine-4-carboxamide;
6-(5-((1r,4r)-4-(Acetamidomethyl)cyclohexyl)-4,5-dihydroisoxazol-3-yl)-N-(4-fluoro-3-methoxybenzyl)-2-methylpyrimidine-4-carboxamide;
6-((R)-5-((1r,4R)-4-(acetamidomethyl)cyclohexyl)-4,5-dihydroisoxazol-3-yl)-N-(4-fluoro-3-methoxybenzyl)-2-methylpyrimidine-4-carboxamide;
N-(4-fluoro-3-methoxybenzyl)-2-methyl-6-(5-(5-(oxazol-5-yl)pyridin-2-yl)-4,5-dihydroisoxazol-3-yl)pyrimidine-4-carboxamide;
N-(4-fluoro-3-methoxybenzyl)-2-methyl-6-(5-(6-(methylsulfonyl)pyridazin-3-yl)-4,5-dihydroisoxazol-3-yl)pyrimidine-4-carboxamide;
N-(4-fluoro-3-methoxybenzyl)-2-methyl-6-(5-(6-(3-methyl-1,2,4-oxadiazol-5-yl)pyridin-3-yl)-4,5-dihydroisoxazol-3-yl)pyrimidine-4-carboxamide;
6-(5-(6-acetylpyridin-3-yl)-4,5-dihydroisoxazol-3-yl)-N-(4-fluoro-3-methoxybenzyl)-2-methylpyrimidine-4-carboxamide;
6-(3-(6-(4-fluoro-3-methoxybenzylcarbamoyl)-2-methylpyrimidin-4-yl)-4,5-dihydroisoxazol-5-yl)pyridazine-3-carboxamide 2,2,2-trifluoroacetate;
6-(5-(6-cyanopyridazin-3-yl)-4,5-dihydroisoxazol-3-yl)-N-(4-fluoro-3-methoxybenzyl)-2-methylpyrimidine-4-carboxamide;
N-(4-fluoro-3-methoxybenzyl)-6-((R)-5-((1r,4R)-4-((2-hydroxyacetamido)methyl)cyclohexyl)-4,5-dihydroisoxazol-3-yl)-2-methylpyrimidine-4-carboxamide;
N-(4-fluoro-3-methoxybenzyl)-6-(5-((1r,4r)-4-((2-hydroxyacetamido)methyl)cyclohexyl)-4,5-dihydroisoxazol-3-yl)-2-methylpyrimidine-4-carboxamide;
N-(4-fluoro-3-methoxybenzyl)-2-methyl-6-(5-(1-methyl-3-(3-methyl-1,2,4-oxadiazol-5-yl)-1H-pyrazol-5-yl)-4,5-dihydroisoxazol-3-yl)pyrimidine-4-carboxamide;
6-(5-(3-carbamoyl-1-methyl-1H-pyrazol-5-yl)-4,5-dihydroisoxazol-3-yl)-N-(4-fluoro-3-methoxybenzyl)-2-methylpyrimidine-4-carboxamide;
6-(5-((1r,4r)-4-((2-cyanoacetamido)methyl)cyclohexyl)-4,5-dihydroisoxazol-3-yl)-N-(4-fluoro-3-methoxybenzyl)-2-methylpyrimidine-4-carboxamide;
6-(3-(6-((4-fluoro-3-methoxybenzyl)carbamoyl)-2-methylpyrimidin-4-yl)-4,5-dihydroisoxazol-5-yl)-N-methylpyridazine-3-carboxamide;
N-(4-fluoro-3-methoxybenzyl)-2-methyl-6-(5-(6-(3-methyl-1,2,4-oxadiazol-5-yl)pyridazin-3-yl)-4,5-dihydroisoxazol-3-yl)pyrimidine-4-carboxamide;
N-(4-fluoro-3-methoxybenzyl)-6-((S)-5-((2R,5R)-5-((2-hydroxyacetamido)methyl)-1,4-dioxan-2-yl)-4,5-dihydroisoxazol-3-yl)-2-methylpyrimidine-4-carboxamide;
N-(4-fluoro-3-methoxybenzyl)-2-methyl-6-(5-(6-(oxazol-5-yl)pyridin-3-yl)-4,5-dihydroisoxazol-3-yl)pyrimidine-4-carboxamide;
N-(4-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;
N-(4-fluoro-3-methoxybenzyl)-6-(5-(6-(hydroxymethyl)pyridin-3-yl)-4,5-dihydroisoxazol-3-yl)-2-methylpyrimidine-4-carboxamide;
N-(4-fluoro-3-methoxybenzyl)-6-(5-((1r,4r)-4-(3-(2-hydroxyethyl)ureido)cyclohexyl)-4,5-dihydroisoxazol-3-yl)-2-methylpyrimidine-4-carboxamide;
N-(4-fluoro-3-methoxybenzyl)-6-(5-((1r,4r)-4-(3-(2-hydroxyethyl)-3-methylureido)cyclohexyl)-4,5-dihydroisoxazol-3-yl)-2-methylpyrimidine-4-carboxamide;
N-(4-fluoro-3-methoxybenzyl)-2-methyl-6-(5-(5-(methylsulfonyl)pyrazin-2-yl)-4,5-dihydroisoxazol-3-yl)pyrimidine-4-carboxamide;
6-(5-(6-cyanopyridin-3-yl)-4,5-dihydroisoxazol-3-yl)-N-(4-fluoro-3-methoxybenzyl)-2-methylpyrimidine-4-carboxamide;

6-(5-(1-(3-(dimethylamino)propanoyl)piperidin-4-yl)-4,5-dihydroisoxazol-3-yl)-N-(4-fluoro-3-methoxybenzyl)-2-methylpyrimidine-4-carboxamide;

N-(4-fluoro-3-methylbenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methylbenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(3,4-difluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3,4-difluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

5S)-5-((S)-3-(6-((4-fluoro-3-methoxybenzyl)carbamoyl)-2-methylpyrimidin-4-yl)-4,5-dihydroisoxazol-5-yl)-1,4-dioxane-2-carboxylic acid;

N-(4-fluoro-3-methoxybenzyl)-2-methyl-6-(5-((1r,4r)-4-(3-methylureido)cyclohexyl)-4,5-dihydroisoxazol-3-yl)pyrimidine-4-carboxamide;

6-(5-((1r,4r)-4-(3,3-dimethylureido)cyclohexyl)-4,5-dihydroisoxazol-3-yl)-N-(4-fluoro-3-methoxybenzyl)-2-methylpyrimidine-4-carboxamide;

N-(3,4-dichlorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3,4-dichlorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-((2-cyanoacetamido)methyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((S)-5-((2R,5R)-5-((2-hydroxy-2-methylpropanamido)methyl)-1,4-dioxan-2-yl)-4,5-dihydroisoxazol-3-yl)-2-methylpyrimidine-4-carboxamide;

N-(4-fluoro-3-methoxybenzyl)-2-methyl-6-((S)-5-((2R,5R)-5-((3-methylureido)methyl)-1,4-dioxan-2-yl)-4,5-dihydroisoxazol-3-yl)pyrimidine-4-carboxamide;

6((S)-5-((2R,5R)-5-((3,3-dimethylureido)methyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(pyrrolidine-1-carbonyl)-4,5-dihydroisoxazol-3-yl)pyrimidine-4-carboxamide;

6-(5-((1r,4r)-4-(2-(dimethylamino)acetamido)cyclohexyl)-4,5-dihydroisoxazol-3-yl)-N-(4-fluoro-3-methoxybenzyl)-2-methylpyrimidine-4-carboxamide;

6-(5-(1H-pyrazolo[3,4-b]pyridin-5-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-methyl-1H-pyrazolo[3,4-b]pyridin-5-yl)-4,5-dihydroisoxazol-3-yl)pyrimidine-4-carboxamide;

6-(5-(bromomethyl)-4,5-dihydroisoxazol-3-yl)-N-(4-fluoro-3-methoxybenzyl)-2-methylpyrimidine-4-carboxamide;

3-(6-((4-fluoro-3-methoxybenzyl)carbamoyl)-2-methylpyrimidin-4-yl)-N-(2-hydroxyethyl)-4,5-dihydroisoxazole-5-carboxamide;

3-(6-((4-fluoro-3-methoxybenzyl)carbamoyl)-2-methylpyrimidin-4-yl)-4,5-dihydroisoxazole-5-carboxamide;

methyl 3-(6-((4-fluoro-3-methoxybenzyl)carbamoyl)-2-methylpyrimidin-4-yl)-4,5-dihydroisoxazole-5-carboxylate;

N-(4-fluoro-3-methoxybenzyl)-6-((S)-5-((2R,5S)-5-(2-hydroxypropan-2-yl)-1,4-dioxan-2-yl)-4,5-dihydroisoxazol-3-yl)-2-methylpyrimidine-4-carboxamide;

N-(4-fluoro-3-methoxybenzyl)-2-methyl-6-((S)-5-((2R,5S)-5-(methylcarbamoyl)-1,4-dioxan-2-yl)-4,5-dihydroisoxazol-3-yl)pyrimidine-4-carboxamide;

N-(4-fluoro-3-methoxybenzyl)-2-methyl-6-(5-((1r,4r)-4-(methylcarbamoyl)cyclohexyl)-4,5-dihydroisoxazol-3-yl)pyrimidine-4-carboxamide 2,2,2-trifluoroacetate;

6-(5-((1r,4r)-4-carbamoylcyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-((1r,4r)-4-(2-hydroxy-2-methylpropanamido)cyclohexyl)-4,5-dihydroisoxazol-3-yl)-2-methylpyrimidine-4-carboxamide;

N-(4-fluoro-3-methoxybenzyl)-6-(5-((4-((S)-2-hydroxypropanamido)cyclohexyl)-4,5-dihydroisoxazol-3-yl)-2-methylpyrimidine-4-carboxamide;

N-(4-fluoro-3-methoxybenzyl)-6-(5-((3-(hydroxymethyl)pyrrolidin-1-yl)methyl)-4,5-dihydroisoxazol-3-yl)-2-methylpyrimidine-4-carboxamide 2,2,2-trifluoroacetate;

6-(5-((4-acetylpiperazin-1-yl)methyl)-4,5-dihydroisoxazol-3-yl)-N-(4-fluoro-3-methoxybenzyl)-2-methylpyrimidine-4-carboxamide 2,2,2-trifluoroacetate;

6-(5-(6-(dimethylamino)pyridazin-3-yl)-4,5-dihydroisoxazol-3-yl)-N-(4-fluoro-3-methoxybenzyl)-2-methylpyrimidine-4-carboxamide 2,2,2-trifluoroacetate;

N-(4-fluoro-3-methoxybenzyl)-2-methyl-6-(5-(6-(pyrrolidin-1-yl)pyridazin-3-yl)-4,5-dihydroisoxazol-3-yl)pyrimidine-4-carboxamide 2,2,2-trifluoroacetate;

6-(5-((1r,4r)-4-(3-(1,3-dihydroxypropan-2-yl)ureido)cyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-((1r,4r)-4-((2-hydroxyethyl)carbamoyl)cyclohexyl)-4,5-dihydroisoxazol-3-yl)-2-methylpyrimidine-4-carboxamide;

6-(5-((1r,4r)-4-(3-(2,3-dihydroxypropyl)-3-methylureido)cyclohexyl)-4,5-dihydroisoxazol-3-yl)-N-(4-fluoro-3-methoxybenzyl)-2-methylpyrimidine-4-carboxamide;

6-(5-((1r,4r)-4-Acetamidocyclohexyl)-4,5-dihydroisoxazol-3-yl)-N-(4-fluoro-3-methylbenzyl)-2-methylpyrimidine-4-carboxamide;

6-(5-(6-cyanopyridazin-3-yl)-4,5-dihydroisoxazol-3-yl)-N-(4-fluoro-3-methylbenzyl)-2-methylpyrimidine-4-carboxamide;

N-(4-fluoro-3-methoxybenzyl)-2-methyl-6-(5-((1r,4r)-4-(2-(methylamino)acetamido)cyclohexyl)-4,5-dihydroisoxazol-3-yl)pyrimidine-4-carboxamide;

N-(4-fluoro-3-methylbenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;

6-((S)-5-((2R,5R)-5-(acetamidomethyl)-1,4-dioxan-2-yl)-4,5-dihydroisoxazol-3-yl)-N-(4-fluoro-3-methylbenzyl)-2-methylpyrimidine-4-carboxamide;

6-((S)-5-((2R,5R)-5-(acetamidomethyl)-1,4-dioxan-2-yl)-4,5-dihydroisoxazol-3-yl)-N-(3-chloro-4-fluorobenzyl)-2-methylpyrimidine-4-carboxamide;

N-(3-chloro-4-fluorobenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;

N-(4-fluoro-3-methylbenzyl)-2-methyl-6-(5-(1-methyl-6-oxo-1,6-dihydropyridin-3-yl)-4,5-dihydroisoxazol-3-yl)pyrimidine-4-carboxamide 2,2,2-trifluoroacetate;

6-((S)-5-((2R,5R)-5-(hydroxymethyl)-1,4-dioxan-2-yl)-4,5-dihydroisoxazol-3-yl)-2-methyl-N-(3-methylbenzyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-(3-methylbenzyl)pyrimidine-4-carboxamide;

6-(5-(6-cyanopyridazin-3-yl)-4,5-dihydroisoxazol-3-yl)-N-(4-fluorobenzyl)-2-methylpyrimidine-4-carboxamide;

N-(4-fluorobenzyl)-2-methyl-6-(5-(1-methyl-6-oxo-1,6-dihydropyridin-3-yl)-4,5-dihydroisoxazol-3-yl)pyrimidine-4-carboxamide 2,2,2-trifluoroacetate;

N-(4-fluoro-3-methoxybenzyl)-6-(5-(1-(2-hydroxyethyl)-6-oxo-1,6-dihydropyridin-3-yl)-4,5-dihydroisoxazol-3-yl)-2-methylpyrimidine-4-carboxamide 2,2,2-trifluoroacetate;

N-(3-chloro-4-fluorobenzyl)-2-methyl-6-(5-(1-methyl-6-oxo-1,6-dihydropyridin-3-yl)-4,5-dihydroisoxazol-3-yl)pyrimidine-4-carboxamide;

N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

6-(5-(6-cyanopyridazin-3-yl)-4,5-dihydroisoxazol-3-yl)-N-(3,4-difluorobenzyl)-2-methylpyrimidine-4-carboxamide 2,2,2-trifluoroacetate;

N-(3-chloro-4-fluorobenzyl)-6-(5-(6-cyanopyridazin-3-yl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-N-(3-chloro-4-fluorobenzyl)-2-methylpyrimidine-4-carboxamide;

6-(5-((1r,4r)-4-acetamidocyclohexyl)-4,5-dihydroisoxazol-3-yl)-N-(4-fluorobenzyl)-2-methylpyrimidine-4-carboxamide;

6-(5-((1r,4r)-4-acetamidocyclohexyl)-4,5-dihydroisoxazol-3-yl)-N-(3,4-difluorobenzyl)-2-methylpyrimidine-4-carboxamide;

N-((2,3-dihydrobenzofuran-5-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-fluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-2-methyl-N-((2-methylbenzo[d]oxazol-5-yl)methyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-((2-methylbenzo[d]oxazol-5-yl)methyl)pyrimidine-4-carboxamide;

N-(4-fluoro-3-methoxybenzyl)-6-((S)-5-((2R,5R)-5-(methoxymethyl)-1,4-dioxan-2-yl)-4,5-dihydroisoxazol-3-yl)-2-methylpyrimidine-4-carboxamide;

N-(4-fluoro-3-methoxybenzyl)-6-((R)-5-((2R,5R)-5-(methoxymethyl)-1,4-dioxan-2-yl)-4,5-dihydroisoxazol-3-yl)-2-methylpyrimidine-4-carboxamide;

N-(4-fluoro-3-methoxybenzyl)-6-((S)-5-((2R,5R)-5-(((S)-2-hydroxypropanamido)methyl)-1,4-dioxan-2-yl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-N-(3,4-difluorobenzyl)-2-methylpyrimidine-4-carboxamide;

N-(3-chloro-4-fluorobenzyl)-6-(5-((1S,4r)-4-((S)-2-hydroxypropanamido)cyclohexyl)-4,5-dihydroisoxazol-3-yl)-2-methylpyrimidine-4-carboxamide;

N-((2,3-dihydrobenzo[b][1,4]dioxin-6-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-((2,3-dihydrobenzo[b][1,4]dioxin-6-yl)methyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methylbenzyl)-2-methyl-6-(5-(1-methyl-6-oxo-1,6-dihydropyridin-3-yl)-4,5-dihydroisoxazol-3-yl)pyrimidine-4-carboxamide;

6-((S)-5-((2R,5R)-5-(hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide 2,2,2-trifluoroacetate;

6-((R)-5-((2R,5R)-5-(hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide 2,2,2-trifluoroacetate;

N-(4-fluoro-3-methoxybenzyl)-2-methyl-6-(5-(1-methyl-2-oxo-1,2-dihydropyridin-4-yl)-4,5-dihydroisoxazol-3-yl)pyrimidine-4-carboxamide;

6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-methyl-6-oxo-1,6-dihydropyridazin-3-yl)-4,5-dihydroisoxazol-3-yl)pyrimidine-4-carboxamide;

tert-butyl ((1r,4r)-4-(3-(6-((4-fluoro-3-methoxybenzyl)carbamoyl)-2-methylpyrimidin-4-yl)-4,5-dihydroisoxazol-5-yl)cyclohexyl)carbamate;

N-(4-fluoro-3-methoxybenzyl)-2-methyl-6-(5-(1-(2-(methylamino)-2-oxoethyl)-6-oxo-1,6-dihydropyridin-3-yl)-4,5-dihydroisoxazol-3-yl)pyrimidine-4-carboxamide;

N-(4-fluoro-3-methoxybenzyl)-6-(5-(1-isopropyl-6-oxo-1,6-dihydropyridin-3-yl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-2-methyl-N-(pyridin-4-ylmethyl)pyrimidine-4-carboxamide;

6-((S)-5-((2R,5R)-5-(hydroxymethyl)-1,4-dioxan-2-yl)-4,5-dihydroisoxazol-3-yl)-2-methyl-N-(pyridin-4-ylmethyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-(pyridin-4-ylmethyl)pyrimidine-4-carboxamide;

6 6-(5-((1r,4r)-4-acetamidocyclohexyl)-4,5-dihydroisoxazol-3-yl)-2-methyl-N-((1-methyl-2-oxo-1,2-dihydropyridin-4-yl)methyl)pyrimidine-4-carboxamide;

6-(5-((1r,4r)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

N—((R)-1-(4-fluoro-3-methoxyphenyl)ethyl)-2-methyl-6-(5-phenyl-4,5-dihydroisoxazol-3-yl)pyrimidine-4-carboxamide;

N—((S)-1-(4-fluoro-3-methoxyphenyl)ethyl)-2-methyl-6-(5-phenyl-4,5-dihydroisoxazol-3-yl)pyrimidine-4-carboxamide;

6-((S)-5-((2R,5R)-5-(hydroxymethyl)-1,4-dioxan-2-yl)-4,5-dihydroisoxazol-3-yl)-2-methyl-N-((1-methyl-2-oxo-1,2-dihydropyridin-4-yl)methyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-((1-methyl-2-oxo-1,2-dihydropyridin-4-yl)methyl)pyrimidine-4-carboxamide;

6-(5-((1r,4r)-4-acetamidocyclohexyl)-4,5-dihydroisoxazol-3-yl)-2-methyl-N-(quinolin-4-ylmethyl)pyrimidine-4-carboxamide;

(S)—N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide;

N-(4-fluoro-3-methoxybenzyl)-2-methyl-6-(5-(1-methyl-2-oxo-1,2-dihydropyridin-4-yl)-4,5-dihydroisoxazol-3-yl)pyrimidine-4-carboxamide;

6-((S)-5-((1r,4S)-4-acetamidocyclohexyl)-4,5-dihydroisoxazol-3-yl)-N-(4-fluoro-3-methylbenzyl)-2-methylpyrimidine-4-carboxamide;

6-((S)-5-((2R,5R)-5-(hydroxymethyl)-1,4-dioxan-2-yl)-4,5-dihydroisoxazol-3-yl)-2-methyl-N-(quinolin-4-ylmethyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-(quinolin-4-ylmethyl)pyrimidine-4-carboxamide;

N-(4-fluoro-3-methoxybenzyl)-6-((S)-5-((2R,5R)-5-((2-hydroxy-2-methylpropanamido)methyl)-1,4-dioxan-2-yl)-4,5-dihydroisoxazol-3-yl)-2-methylpyrimidine-4-carboxamide;

6-((S)-5-((2R,5R)-5-(acetamidomethyl)-1,4-dioxan-2-yl)-4,5-dihydroisoxazol-3-yl)-N-(3-chloro-4-fluorobenzyl)-2-methylpyrimidine-4-carboxamide;

6-(5-(6-cyanopyridazin-3-yl)-4,5-dihydroisoxazol-3-yl)-N-(3,4-difluorobenzyl)-2-methylpyrimidine-4-carboxamide 2,2,2-trifluoroacetate;

6-((S)-5-((1r,4S)-4-acetamidocyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(4-fluoro-3-methoxybenzyl)-6-((R)-5-((1S,4R)-4-((S)-2-hydroxypropanamido)cyclohexyl)-4,5-dihydroisoxazol-3-yl)-2-methylpyrimidine-4-carboxamide;

N-(4-Fluorobenzyl)-6-(5-(((1S,4r)-4-((S)-2-hydroxypropanamido)cyclohexyl)-4,5-dihydroisoxazol-3-yl)-2-methylpyrimidine-4-carboxamide;

N-(4-fluoro-3-methylbenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(4-fluoro-3-methylbenzyl)-6-((R)-5-((1S,4R)-4-((S)-2-hydroxypropanamido)cyclohexyl)-4,5-dihydroisoxazol-3-yl)-2-methylpyrimidine-4-carboxamide;

N-(3-chloro-4-fluorobenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(3-chloro-4-fluorobenzyl)-6-((R)-5-((1S,4R)-4-((S)-2-hydroxypropanamido)cyclohexyl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-N-((2-oxo-1,2,3,4,4a,8a-hexahydroquinolin-7-yl)methyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-((2-oxo-1,2,3,4-tetrahydroquinolin-7-yl)methyl)pyrimidine-4-carboxamide;

N-(4-fluoro-3-methoxybenzyl)-2-methyl-6-(5-(1-(2-(methylamino)-2-oxoethyl)-2-oxo-1,2-dihydropyridin-4-yl)-4,5-dihydroisoxazol-3-yl)pyrimidine-4-carboxamide;

N-(3,4-difluorobenzyl)-2-methyl-6-(5-(1-methyl-2-oxo-1,2-dihydropyridin-4-yl)-4,5-dihydroisoxazol-3-yl)pyrimidine-4-carboxamide;

(S)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

(R)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

N-(4-fluoro-3-methoxybenzyl)-6-(5-(6-methoxypyridazin-3-yl)-4,5-dihydroisoxazol-3-yl)-2-methylpyrimidine-4-carboxamide;

N-(4-fluoro-3-methoxybenzyl)-6-(5-(6-methoxypyridazin-3-yl)-4,5-dihydroisoxazol-3-yl)-2-methylpyrimidine-4-carboxamide;

(S)—N-(4-fluoro-3-methoxybenzyl)-2-methyl-6-(5-(1-(2-(methylamino)-2-oxoethyl)-6-oxo-1,6-dihydropyridazin-3-yl)-4,5-dihydroisoxazol-3-yl)pyrimidine-4-carboxamide;

(R)—N-(4-fluoro-3-methoxybenzyl)-2-methyl-6-(5-(1-(2-(methylamino)-2-oxoethyl)-6-oxo-1,6-dihydropyridazin-3-yl)-4,5-dihydroisoxazol-3-yl)pyrimidine-4-carboxamide;

2-methyl-6-(5-(1-methyl-6-oxo-1,6-dihydropyridin-3-yl)-4,5-dihydroisoxazol-3-yl)-N-((3-oxo-3,4-dihydro-2H-benzo[b][1,4]oxazin-6-yl)methyl)pyrimidine-4-carboxamide;

N-(4-fluoro-3-methoxybenzyl)-6-(5-(1-(2-(methoxy(methylamino)-2-oxoethyl)-6-oxo-1,6-dihydropyridin-3-yl)-4,5-dihydroisoxazol-3-yl)-2-methylpyrimidine-4-carboxamide;

6-(5-(5-chloro-1-(2-(methylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-(6-methoxy-5,6-dihydropyridin-2-yl)-4,5-dihydroisoxazol-3-yl)-2-methylpyrimidine-4-carboxamide;

6-(5-(1-cyclopropyl-6-oxo-1,6-dihydropyridazin-3-yl)-4,5-dihydroisoxazol-3-yl)-N-(4-fluoro-3-methoxybenzyl)-2-methylpyrimidine-4-carboxamide;

6-(5-(1-cyclopropyl-2-oxo-1,2-dihydropyridin-4-yl)-4,5-dihydroisoxazol-3-yl)-N-(4-fluoro-3-methoxybenzyl)-2-methylpyrimidine-4-carboxamide;

6-(5-(1-(2-(dimethylamino)-2-oxoethyl)-2-oxo-1,2-dihydropyridin-4-yl)-4,5-dihydroisoxazol-3-yl)-N-(4-fluoro-3-methoxybenzyl)-2-methylpyrimidine-4-carboxamide;

6-((S)-5-((1s,4R)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-((R)-5-((1r,4R)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

N-(4-fluoro-3-methoxybenzyl)-2-methyl-6-(5-(1-(2-(methylamino)-2-oxoethyl)-6-oxo-1,6-dihydropyridazin-3-yl)-4,5-dihydroisoxazol-3-yl)pyrimidine-4-carboxamide;

6-((S)-5-((2R,5R)-5-(hydroxymethyl)-1,4-dioxan-2-yl)-4,5-dihydroisoxazol-3-yl)-2-methyl-N-((1-methyl-6-oxo-1,6-dihydropyridin-3-yl)methyl)pyrimidine-4-carboxamide;

N-(4-fluoro-3-methoxybenzyl)-6-(5-(1-(2-(isopropylamino)-2-oxoethyl)-6-oxo-1,6-dihydropyridin-3-yl)-4,5-dihydroisoxazol-3-yl)-2-methylpyrimidine-4-carboxamide;

6-(5-((1S,4r)-4-((S)-2-hydroxypropanamido)cyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-(5-(3-chloro-5-cyclopropyl-4-oxocyclohexyl)-4,5-dihydroisoxazol-3-yl)-N-(4-fluoro-3-methoxybenzyl)-2-methylpyrimidine-4-carboxamide;

(S)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

(R)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

(R)-6-(5-(1-cyclopropyl-6-oxo-1,6-dihydropyridazin-3-yl)-4,5-dihydroisoxazol-3-yl)-N-(4-fluoro-3-methoxybenzyl)-2-methylpyrimidine-4-carboxamide;

6-(5-(1-cyclopropyl-6-oxo-1,6-dihydropyridin-3-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-(5-(1-(2-(cyclopropylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-1-methyl-6-oxo-5-(5-phenyl-4,5-dihydroisoxazol-3-yl)-1,6-dihydropyridazine-3-carboxamide;

N-(4-fluoro-3-methoxybenzyl)-6-(5-(1-(1-methoxyethyl)-2-oxo-1,2-dihydropyridin-4-yl)-4,5-dihydroisoxazol-3-yl)-2-methylpyrimidine-4-carboxamide; and N-(4-fluoro-3-methoxybenzyl)-6-(5-(1-(2-(isopropylamino)allyl)-2-oxo-1,2-dihydropyridin-4-yl)-4,5-dihydroisoxazol-3-yl)-2-methylpyrimidine-4-carboxamide; or a pharmaceutically acceptable salt thereof.

8. The compound according to claim 7 wherein the compound is

N-(4-Fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-6-((S)-5-((2S,5S)-5-(hydroxymethyl)-1,4-dioxan-2-yl)-4,5-dihydroisoxazol-3-yl)-2-methylpyrimidine-4-carboxamide;

6-((R)-5-((1r,4R)-4-acetamidocyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((R)-5-((1r,4R)-4-(2-hydroxyacetamido)cyclohexyl)-4,5-dihydroisoxazol-3-yl)-2-methylpyrimidine-4-carboxamide;

N-(3-chloro-4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide;

N-(4-fluoro-3-methoxybenzyl)-2-methyl-6-((S)-5-((2R,5S)-5-(methylsulfonylmethyl)-1,4-dioxan-2-yl)-4,5-dihydroisoxazol-3-yl)pyrimidine-4-carboxamide;

N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-(acetamidomethyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-((S)-5-((2R,5R)-5-(methylsulfonamidomethyl)-1,4-dioxan-2-yl)-4,5-dihydroisoxazol-3-yl)pyrimidine-4-carboxamide;

6-((R)-5-((1r,4R)-4-(acetamidomethyl)cyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(6-(methylsulfonyl)pyridazin-3-yl)-4,5-dihydroisoxazol-3-yl)pyrimidine-4-carboxamide;

(S)—N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide;

6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(1-methyl-6-oxo-1,6-dihydropyridazin-3-yl)-4,5-dihydroisoxazol-3-yl)pyrimidine-4-carboxamide;

6-(5-((1r,4r)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

N-(4-fluoro-3-methoxybenzyl)-2-methyl-6-(5-(1-(2-(methylamino)-2-oxoethyl)-6-oxo-1,6-dihydropyridin-3-yl)-4,5-dihydroisoxazol-3-yl)pyrimidine-4-carboxamide;

N-(4-fluoro-3-methylbenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(3,4-difluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3,4-difluorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

(2R,5S)-5-((S)-3-(6-((4-fluoro-3-methoxybenzyl)carbamoyl)-2-methylpyrimidin-4-yl)-4,5-dihydroisoxazol-5-yl)-1,4-dioxane-2-carboxylic acid;

N-(4-fluoro-3-methoxybenzyl)-2-methyl-6-(5-((1r,4r)-4-(3-methylureido)cyclohexyl)-4,5-dihydroisoxazol-3-yl)pyrimidine-4-carboxamide;

6-(5-((1r,4r)-4-(3,3-dimethylureido)cyclohexyl)-4,5-dihydroisoxazol-3-yl)-N-(4-fluoro-3-methoxybenzyl)-2-methylpyrimidine-4-carboxamide;

N-(3,4-dichlorobenzyl)-6-((R)-5-((2R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-((2-cyanoacetamido)methyl)-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-((S)-5-((2R,5R)-5-((3-methylureido)methyl)-1,4-dioxan-2-yl)-4,5-dihydroisoxazol-3-yl)pyrimidine-4-carboxamide;

5R)-5-((S)-3-(6-((4-fluoro-3-methoxybenzyl)carbamoyl)-2-methylpyrimidin-4-yl)-4,5-dihydroisoxazol-5-yl)-1,4-dioxane-2-carboxylic acid;

6-((S)-5-((2R,5R)-5-((3,3-dimethylureido)methyl)-1,4-dioxan-2-yl)-4,5-dihydroisoxazol-3-yl)-N-(4-fluoro-3-methoxybenzyl)-2-methylpyrimidine-4-carboxamide;

6-(5-((1r,4r)-4-(2-(dimethylamino)acetamido)cyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((S)-5-((2R,5S)-5-(2-hydroxypropan-2-yl)-1,4-dioxan-2-yl)-4,5-dihydroisoxazol-3-yl)-2-methylpyrimidine-4-carboxamide;

N-(4-fluoro-3-methoxybenzyl)-2-methyl-6-((S)-5-((2R,5S)-5-(methylcarbamoyl)-1,4-dioxan-2-yl)-4,5-dihydroisoxazol-3-yl)pyrimidine-4-carboxamide;

N-(4-fluoro-3-methoxybenzyl)-2-methyl-6-(5-((1r,4r)-4-(methylcarbamoyl)cyclohexyl)-4,5-dihydroisoxazol-3-yl)pyrimidine-4-carboxamide 2,2,2-trifluoroacetate;

6-(5-((1r,4r)-4-carbamoylcyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-(5-((4-((S)-2-hydroxypropanamido)cyclohexyl)-4,5-dihydroisoxazol-3-yl)-2-methylpyrimidine-4-carboxamide;

N-(4-fluoro-3-methoxybenzyl)-6-(5-((1r,4r)-4-(2-hydroxy-2-methylpropanamido)cyclohexyl)-4,5-dihydroisoxazol-3-yl)-2-methylpyrimidine-4-carboxamide;

6-(5-((1r,4r)-4-(3-(1,3-dihydroxypropan-2-yl)ureido)cyclohexyl)-4,5-dihydroisoxazol-3-yl)-N-(4-fluoro-3-methoxybenzyl)-2-methylpyrimidine-4-carboxamide;

6-(5-((1r,4r)-4-(2-cyanoacetamido)cyclohexyl)-4,5-dihydroisoxazol-3-yl)-N-(4-fluoro-3-methoxybenzyl)-2-methylpyrimidine-4-carboxamide;

6-((S)-5-((2R,5S)-5-Carbamoyl-1,4-dioxan-2-yl)-4,5-dihydroisoxazol-3-yl)-N-(4-fluoro-3-methoxybenzyl)-2-methylpyrimidine-4-carboxamide;

N-(4-fluoro-3-methoxybenzyl)-2-methyl-6-(5-(pyridin-3-yl)-4,5-dihydro-1H-pyrazol-3-yl)pyrimidine-4-carboxamide;

N-(4-fluoro-3-methoxybenzyl)-6-(5-((1r,4r)-4-((2-hydroxyethyl)carbamoyl)cyclohexyl)-4,5-dihydroisoxazol-3-yl)-2-methylpyrimidine-4-carboxamide;

6-(5-((1r,4r)-4-(3-(2,3-dihydroxypropyl)-3-methylureido)cyclohexyl)-4,5-dihydroisoxazol-3-yl)-N-(4-fluoro-3-methoxybenzyl)-2-methylpyrimidine-4-carboxamide;

6-(5-((1r,4r)-4-Acetamidocyclohexyl)-4,5-dihydroisoxazol-3-yl)-N-(4-fluoro-3-methylbenzyl)-2-methylpyrimidine-4-carboxamide;

6-(5-(6-cyanopyridazin-3-yl)-4,5-dihydroisoxazol-3-yl)-N-(4-fluoro-3-methylbenzyl)-2-methylpyrimidine-4-carboxamide;

N-(4-fluoro-3-methoxybenzyl)-2-methyl-6-(5-((1r,4r)-4-(2-(methylamino)acetamido)cyclohexyl)-4,5-dihydroisoxazol-3-yl)pyrimidine-4-carboxamide;

N-(4-fluoro-3-methylbenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;

6-((S)-5-((2R,5R)-5-(acetamidomethyl)-1,4-dioxan-2-yl)-4,5-dihydroisoxazol-3-yl)-N-(4-fluoro-3-methylbenzyl)-2-methylpyrimidine-4-carboxamide;

N-(3-chloro-4-fluorobenzyl)-2-methyl-6-((S)-5-((2R,5S)-5-((methylsulfonyl)methyl)-1,4-dioxan-2-yl)-4,5-dihydroisoxazol-3-yl)pyrimidine-4-carboxamide;

N-(4-fluoro-3-methylbenzyl)-2-methyl-6-(5-(1-methyl-6-oxo-1,6-dihydropyridin-3-yl)-4,5-dihydroisoxazol-3-yl)pyrimidine-4-carboxamide 2,2,2-trifluoroacetate;

6-((S)-5-((2R,5R)-5-(hydroxymethyl)-1,4-dioxan-2-yl)-4,5-dihydroisoxazol-3-yl)-2-methyl-N-(3-methylbenzyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-(3-methylbenzyl)pyrimidine-4-carboxamide;

6-(5-(6-cyanopyridazin-3-yl)-4,5-dihydroisoxazol-3-yl)-N-(4-fluorobenzyl)-2-methylpyrimidine-4-carboxamide;

N-(4-fluorobenzyl)-2-methyl-6-(5-(1-methyl-6-oxo-1,6-dihydropyridin-3-yl)-4,5-dihydroisoxazol-3-yl)pyrimidine-4-carboxamide 2,2,2-trifluoroacetate;

N-(4-fluoro-3-methoxybenzyl)-6-(5-(1-(2-hydroxyethyl)-6-oxo-1,6-dihydropyridin-3-yl)-4,5-dihydroisoxazol-3-yl)-2-methylpyrimidine-4-carboxamide 2,2,2-trifluoroacetate;

N-(3-chloro-4-fluorobenzyl)-2-methyl-6-(5-(1-methyl-6-oxo-1,6-dihydropyridin-3-yl)-4,5-dihydroisoxazol-3-yl)pyrimidine-4-carboxamide;

N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

N-(3-chloro-4-fluorobenzyl)-6-(5-(6-cyanopyridazin-3-yl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-N-(3-chloro-4-fluorobenzyl)-2-methylpyrimidine-4-carboxamide;

6-(5-((1r,4r)-4-acetamidocyclohexyl)-4,5-dihydroisoxazol-3-yl)-N-(4-fluorobenzyl)-2-methylpyrimidine-4-carboxamide;

6-(5-((1r,4r)-4-acetamidocyclohexyl)-4,5-dihydroisoxazol-3-yl)-N-(3,4-difluorobenzyl)-2-methylpyrimidine-4-carboxamide;

N-((2,3-dihydrobenzofuran-5-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-fluorobenzyl)-6-((S)-5-((2R,5R)-5-(hydroxymethyl)-1,4-dioxan-2-yl)-4,5-dihydroisoxazol-3-yl)-2-methylpyrimidine-4-carboxamide;

N-(3-fluorobenzyl)-6-((R)-5-42R,5R)-5-(hydroxymethyl)-1,4-dioxan-2-yl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-2-methyl-N-((2-methylbenzo[d]oxazol-5-yl)methyl)pyrimidine-4-carboxamide;

6-((R)-5-((2R,5R)-5-(hydroxymethyl)-1,4-dioxan-2-yl)-4,5-dihydroisoxazol-3-yl)-2-methyl-N-((2-methylbenzo[d]oxazol-5-yl)methyl)pyrimidine-4-carboxamide;

6-((S)-5-((1r,4S)-4-acetamidocyclohexyl)-4,5-dihydroisoxazol-3-yl)-N-(4-fluoro-3-methoxybenzyl)-2-methylpyrimidine-4-carboxamide;

N-(4-fluoro-3-methoxybenzyl)-6-((S)-5-((2R,5R)-5-(methoxymethyl)-1,4-dioxan-2-yl)-4,5-dihydroisoxazol-3-yl)-2-methylpyrimidine-4-carboxamide;

N-(4-fluoro-3-methoxybenzyl)-6-((R)-5-((2R,5R)-5-(methoxymethyl)-1,4-dioxan-2-yl)-4,5-dihydroisoxazol-3-yl)-2-methylpyrimidine-4-carboxamide;

N-(4-fluoro-3-methoxybenzyl)-6-((S)-5-((2R,5R)-5-(((S)-2-hydroxypropanamido)methyl)-1,4-dioxan-2-yl)-4,5-dihydroisoxazol-3-yl)-2-methylpyrimidine-4-carboxamide;

N-(4-fluoro-3-methoxybenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(4-fluoro-3-methoxybenzyl)-6-((R)-5-((1S,4R)-4-((S)-2-hydroxypropanamido)cyclohexyl)-4,5-dihydroisoxazol-3-yl)-2-methylpyrimidine-4-carboxamide;

6-(5-((1r,4r)-4-acetamidocyclohexyl)-4,5-dihydroisoxazol-3-yl)-N-(3,4-difluorobenzyl)-2-methylpyrimidine-4-carboxamide;

N-(3-chloro-4-fluorobenzyl)-6-(5-((1S,4r)-4-((S)-2-hydroxypropanamido)cyclohexyl)-4,5-dihydroisoxazol-3-yl)-2-methylpyrimidine-4-carboxamide;

N-((2,3-dihydrobenzo[b][1,4]dioxin-6-yl)methyl)-6-((S)-5-((2R,5R)-5-(hydroxymethyl)-1,4-dioxan-2-yl)-4,5-dihydroisoxazol-3-yl)-2-methylpyrimidine-4-carboxamide;

N((2,3-dihydrobenzo[b][1,4]dioxin-6-yl)methyl)-6-((R)-5-((2R,5R)-5-(hydroxymethyl)-1,4-dioxan-2-yl)-4,5-dihydroisoxazol-3-yl)-2-methylpyrimidine-4-carboxamide;

N-(4-Fluorobenzyl)-6-(5-((1S,4r)-4-((S)-2-hydroxypropanamido)cyclohexyl)-4,5-dihydroisoxazol-3-yl)-2-methylpyrimidine-4-carboxamide;

N-(4-fluoro-3-methylbenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(4-fluoro-3-methylbenzyl)-6-((R)-5-((1S,4R)-4-((S)-2-hydroxypropanamido)cyclohexyl)-4,5-dihydroisoxazol-3-yl)-2-methylpyrimidine-4-carboxamide;

N-(3-chloro-4-fluorobenzyl)-6-((S)-5-((1S,4S)-4-((S)-2-hydroxypropanamido)cyclohexyl)-4,5-dihydroisoxazol-3-yl)-2-methylpyrimidine-4-carboxamide;

N-(3-chloro-4-fluorobenzyl)-6-((R)-5-((1S,4R)-4-((S)-2-hydroxypropanamido)cyclohexyl)-4,5-dihydroisoxazol-3-yl)-2-methylpyrimidine-4-carboxamide;

6-((S)-5-((2R,5R)-5-(hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide 2,2,2-trifluoroacetate;

6-((R)-5-((2R,5R)-5-(hydroxymethyl)-1,4-dioxan-2-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide 2,2,2-trifluoroacetate;

(S)—N-(4-fluoro-3-methoxybenzyl)-2-methyl-6-(5-(1-methyl-6-oxo-1,6-dihydropyridin-3-yl)-4,5-dihydroisoxazol-3-yl)pyrimidine-4-carboxamide;

N-(4-fluoro-3-methoxybenzyl)-2-methyl-6-(5-(1-methyl-2-oxo-1,2-dihydropyridin-4-yl)-4,5-dihydroisoxazol-3-yl)pyrimidine-4-carboxamide;

6-((S)-5-((1r,4S)-4-acetamidocyclohexyl)-4,5-dihydroisoxazol-3-yl)-N-(4-fluoro-3-methylbenzyl)-2-methylpyrimidine-4-carboxamide;

(S)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

(R)—N-(3,4-difluorobenzyl)-2-methyl-6-(5-(1-methyl-6-oxo-1,6-dihydropyridin-3-yl)-4,5-dihydroisoxazol-3-yl)pyrimidine-4-carboxamide;

N-(4-fluoro-3-methoxybenzyl)-6-(5-(6-methoxypyridazin-3-yl)-4,5-dihydroisoxazol-3-yl)-2-methylpyrimidine-4-carboxamide;

(S)—N-(4-fluoro-3-methoxybenzyl)-2-methyl-6-(5-(1-(2-(methylamino)-2-oxoethyl)-6-oxo-1,6-dihydropyridazin-3-yl)-4,5-dihydroisoxazol-3-yl)pyrimidine-4-carboxamide;

2-methyl-6-(5-(1-methyl-6-oxo-1,6-dihydropyridin-3-yl)-4,5-dihydroisoxazol-3-yl)-N-((3-oxo-3,4-dihydro-2H-benzo[b][1,4]oxazin-6-yl)methyl)pyrimidine-4-carboxamide;

N-(4-fluoro-3-methoxybenzyl)-6-(5-(1-(2-(methoxy(methyl)amino)-2-oxoethyl)-6-oxo-1,6-dihydropyridin-3-yl)-4,5-dihydroisoxazol-3-yl)-2-methylpyrimidine-4-carboxamide;

6-(5-(5-chloro-1-(2-(methylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide;

6-((S)-5-((1s,4R)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-((R)-5-((1r,4R)-4-acetamidocyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

N-(4-fluoro-3-methoxybenzyl)-6-(5-(1-(2-(isopropylamino)-2-oxoethyl)-6-oxo-1,6-dihydropyridin-3-yl)-4,5-dihydroisoxazol-3-yl)-2-methylpyrimidine-4-carboxamide;

6-(5-((1S,4r)-4-((S)-2-hydroxypropanamido)cyclohexyl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-(5-(3-chloro-5-cyclopropyl-4-oxocyclohexyl)-4,5-dihydroisoxazol-3-yl)-N-(4-fluoro-3-methoxybenzyl)-2-methylpyrimidine-4-carboxamide;

(S)-6-(5-(1-cyclopropyl-6-oxo-1,6-dihydropyridin-3-yl)-4,5-dihydroisoxazol-3-yl)-N-(4-fluoro-3-methoxybenzyl)-2-methylpyrimidine-4-carboxamide;

(R)-6-(5-(1-cyclopropyl-6-oxo-1,6-dihydropyridazin-3-yl)-4,5-dihydroisoxazol-3-yl)-N-(4-fluoro-3-methoxybenzyl)-2-methylpyrimidine-4-carboxamide;

6-(5-(1-cyclopropyl-6-oxo-1,6-dihydropyridin-3-yl)-4,5-dihydroisoxazol-3-yl)-2-methyl-N-((3-oxo-3,4-dihydro-2H-benzo[b][1,4]oxazin-6-yl)methyl)pyrimidine-4-carboxamide;

6-(5-(1-(2-(cyclopropylamino)-2-oxoethyl)-6-oxo-1,6-dihydropyridin-3-yl)-4,5-dihydroisoxazol-3-yl)-N-(4-fluoro-3-methoxybenzyl)-2-methylpyrimidine-4-carboxamide;

N-(4-fluoro-3-methoxybenzyl)-1-methyl-6-oxo-5-(5-phenyl-4,5-dihydroisoxazol-3-yl)-1,6-dihydropyridazine-3-carboxamide; or N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide; or a pharmaceutically acceptable salt thereof.

9. A pharmaceutical composition comprising a compound of claim 1, stereoisomer, or pharmaceutically acceptable salt thereof and a pharmaceutically acceptable carrier or excipient.

10. A kit comprising a pharmaceutical composition of claim 9, packaging and instructions for use.

11. A method of treating a disease or condition selected from the group consisting of osteoarthritis, a traumatic joint injury, a degenerative joint disease, and a cardiovascular disorder; the method comprising administering to a subject in need thereof a therapeutically effective amount of a compound of claim 1.

12. The method of claim 11, wherein the traumatic joint injury is anterior cruciate ligament tear or meniscal tear.

13. The method of claim 11, wherein the cardiovascular disorder is acute myocardial infarction, acute coronary syndrome, chronic heart failure, myocardial infarction, or atherosclerosis.

14. The compound of claim 6, wherein $R^a$ is H; $R^b$ is H; and m is 1.

15. The compound of claim 14, wherein Z is 1,4-dioxanyl, phenyl, pyridonyl, or piperidinyl, each of which is optionally substituted by one or more substituents independently selected from Br, Cl, F, —CF₃, —CH₃, CN, —C(O)OH, —C(O)OCH₃, —C(O)CH₃, —C(O)C(H)(CH₃)₂, —C(O)-cyclopropyl, —C(O)-cyclobutyl, —C(O)CH₂CN, —C(O)CH₂OH, —C(O)C(CH₃)₂OH, —C(O)CH₂OCH₃, —C(O)N(H)CH₂CH₃, —C(O)CH₂N(CH₃)₂, —C(O)CH₂CH₂N(CH₃)₂, —C(O)CH₂N(H)C(O)CH₃, —C(O)CH₂N(H)C(O)N(H)CH₃, —C(O)CH₂S(O)₂CH₃, —C(O)NH₂, —C(O)N(CH₃)₂, —C(O)N(H)CH₃, —C(O)N(H)CH₂CH₃, —C(O)N(H)CH(CH₃)₂, —C(O)N(H)CH₂CH₂OH, —C(O)N(CH₃)CH₂CH₂OH, —OCH₃, —OCH₂CH₂OH, —NH₂, —N(CH₃)₂, —N(H)C(O)CH₃, —N(H)C(O)C(H)(OH)CH₃, —N(H)C(O)CH₂N(H)CH₃, —N(H)C(O)N(CH₃)₂, —N(H)C(O)N(H)CH₃, —N(H)C(O)N(H)CH₂CH₂OH, —N(H)C(O)N(H)C(H)(CH₂OH)₂, —N(H)C(O)N(CH₃)CH₂CH₂OH, —N(H)C(O)N(CH₃)CH₂C(H)(OH)CH₂OH, —N(H)S(O)₂CH₃, —OH, —S(O)₂CH₃, —S(O)₂C(H)(CH₃)₂, —CH₂CN, —CH₂C(O)N(H)CH₃, —CH₂C(O)N(H)-cyclopropyl, —CH₂OCH₃, —CH₂OH, —CH₂CH₂OH, —C(H)(CH₃)₂OH, —CH₂NH₂, —CH₂N(CH₃)₂, —CH₂N(H)C(O)CH₃, —CH₂N(H)C(O)N(H)CH₃, —CH₂N(H)C(O)N(CH₃)₂, —CH₂N(H)C(O)CH₂OH, —CH₂N(H)S(O)₂CH₃, —CH₂N(H)C(O)C(H)(OH)CH₃, —CH₂N(H)C(O)C(CH₃)₂OH, —CH₂N(H)C(O)CH₂CN, —CH₂S(O)₂CH₃, —CH₂-morpholinyl, or cyclopropyl.

16. The compound of claim 14, wherein Z is 1,4-dioxanyl or piperidinyl, each of which is optionally substituted by one or more substituents independently selected from Br, Cl, F, —CF₃, —CH₃, CN, —C(O)OH, —C(O)OCH₃, —C(O)CH₃, —C(O)C(H)(CH₃)₂, —C(O)-cyclopropyl, —C(O)-cyclobutyl, —C(O)CH₂CN, —C(O)CH₂OH, —C(O)C(CH₃)₂OH, —C(O)CH₂OCH₃, —C(O)N(H)CH₂CH₃, —C(O)CH₂N(CH₃)₂, —C(O)CH₂CH₂N(CH₃)₂, —C(O)CH₂N(H)C(O)CH₃, —C(O)CH₂N(H)C(O)N(H)CH₃, —C(O)CH₂S(O)₂CH₃, —C(O)NH₂, —C(O)N(CH₃)₂, —C(O)N(H)CH₃, —C(O)N(H)CH₂CH₃, —C(O)N(H)CH(CH₃)₂, —C(O)N(H)CH₂CH₂OH, —C(O)N(CH₃)CH₂CH₂OH, —S(O)₂CH₃, —S(O)₂C(H)(CH₃)₂, —CH₂CN, —CH₂OCH₃, —CH₂OH, —CH₂CH₂OH, —C(H)(CH₃)₂OH, —CH₂NH₂, —CH₂N(CH₃)₂, —CH₂N(H)C(O)CH₃, —CH₂N(H)C(O)N(H)CH₃, —CH₂N(H)C(O)N(CH₃)₂, —CH₂N(H)S(O)₂CH₃, —CH₂N(H)C(O)CH₂OH, —CH₂N(H)C(O)C(CH₃)₂OH, —CH₂N(H)C(O)C(H)(OH)CH₃, —CH₂N(H)C(O)CH₂CN, or —CH₂S(O)₂CH₃.

17. A compound or a pharmaceutically acceptable salt thereof, wherein the compound is N-(4-fluoro-3-methoxybenzyl)-6-((S)-5-((2R,5R)-5-(hydroxymethyl)-1,4-dioxan-2-yl)-4,5-dihydroisoxazol-3-yl)-2-methylpyrimidine-4-carboxamide.

* * * * *